(12) United States Patent
Hisamichi et al.

(10) Patent No.: US 10,532,048 B2
(45) Date of Patent: *Jan. 14, 2020

(54) TETRAHYDROISOQUINOLIN-1-ONE DERIVATIVE OR SALT THEREOF

(71) Applicant: Seldar Pharma Inc., Bridgewater, NJ (US)

(72) Inventors: Hiroyuki Hisamichi, Tokyo (JP); Itsuro Shimada, Tokyo (JP); Tsukasa Ishihara, Tokyo (JP); Tomofumi Takuwa, Tokyo (JP); Takafumi Shimizu, Tokyo (JP); Noriko Ishikawa, Tokyo (JP); Kyoichi Maeno, Tokyo (JP); Norio Seki, Tokyo (JP)

(73) Assignee: Seldar Pharma Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/027,988

(22) Filed: Jul. 5, 2018

(65) Prior Publication Data

US 2019/0000832 A1    Jan. 3, 2019

Related U.S. Application Data

(60) Continuation of application No. 15/350,427, filed on Nov. 14, 2016, now Pat. No. 10,016,410, which is a
(Continued)

(30) Foreign Application Priority Data

May 28, 2007  (JP) ................. 2007-140097

(51) Int. Cl.
| | | |
|---|---|---|
| *A61K 31/4725* | (2006.01) |
| *A61K 31/435* | (2006.01) |
| *C07D 217/26* | (2006.01) |
| *A61K 31/445* | (2006.01) |
| *A61K 31/439* | (2006.01) |
| *C07D 401/04* | (2006.01) |
| *C07D 401/06* | (2006.01) |
| *C07D 401/12* | (2006.01) |
| *C07D 401/14* | (2006.01) |
| *C07D 405/04* | (2006.01) |
| *C07D 405/06* | (2006.01) |
| *C07D 405/14* | (2006.01) |
| *C07D 409/12* | (2006.01) |
| *C07D 413/12* | (2006.01) |
| *C07D 417/12* | (2006.01) |
| *C07D 453/02* | (2006.01) |
| *C07D 471/04* | (2006.01) |
| *A61K 31/472* | (2006.01) |
| *A61K 31/496* | (2006.01) |
| *A61K 31/497* | (2006.01) |
| *A61K 31/501* | (2006.01) |

(Continued)

(52) U.S. Cl.
CPC ........ *A61K 31/4725* (2013.01); *A61K 31/435* (2013.01); *A61K 31/439* (2013.01); *A61K 31/445* (2013.01); *A61K 31/472* (2013.01); *A61K 31/496* (2013.01); *A61K 31/497* (2013.01); *A61K 31/501* (2013.01); *A61K 31/506* (2013.01); *A61K 31/5377* (2013.01); *A61K 31/695* (2013.01); *C07D 217/26* (2013.01); *C07D 401/04* (2013.01); *C07D 401/06* (2013.01); *C07D 401/12* (2013.01); *C07D 401/14* (2013.01); *C07D 405/04* (2013.01); *C07D 405/06* (2013.01); *C07D 405/14* (2013.01); *C07D 409/12* (2013.01); *C07D 413/12* (2013.01); *C07D 417/12* (2013.01); *C07D 453/02* (2013.01); *C07D 471/04* (2013.01)

(58) Field of Classification Search
CPC . A61K 31/4725; A61K 31/435; C07D 217/26
See application file for complete search history.

(56) References Cited

U.S. PATENT DOCUMENTS

| 2005/0049240 A1 | 3/2005 | Gribenow et al. |
| 2005/0124614 A1 | 6/2005 | Grangloff et al. |

(Continued)

FOREIGN PATENT DOCUMENTS

| EP | 1 872 795 | 1/2008 |
| JP | 2005-510475 | 4/2005 |

(Continued)

OTHER PUBLICATIONS

Chatzistamou, et al., "Inhibition of growlh of OV-1063 human epithelial ovarian cancers and c-jun and c-fos oncogene expression by bombesin antagonists", British Journal of Cancer, vol. 83, No. 7 (2000) 906-13.

(Continued)

*Primary Examiner* — Yong S. Chong
(74) *Attorney, Agent, or Firm* — Foley & Lardner LLP

(57) ABSTRACT

To provide a pharmaceutical, in particular a compound which can be used as a therapeutic agent for irritable bowel syndrome (IBS). It was found that a tetrahydroisoquinolin-1-one derivative having an amide group at the 4-position or a pharmaceutically acceptable salt thereof has an excellent bombesin 2 (BB2) receptor antagonistic action. It is also found that the tetrahydroisoquinolin-1-one derivative is highly effective on bowel movement disorders. From the above, the tetrahydroisoquinolin-1-one derivative of the present invention is useful as a therapeutic agent for diseases associated with a BB2 receptor, in particular IBS.

14 Claims, No Drawings

Related U.S. Application Data continuation of application No. 14/836,228, filed on Aug. 26, 2015, now Pat. No. 9,526,719, which is a division of application No. 13/942,158, filed on Jul. 15, 2013, now Pat. No. 9,150,541, which is a division of application No. 12/600,894, filed as application No. PCT/JP2008/059621 on May 26, 2008, now Pat. No. 8,486,970.

(51) Int. Cl.
   *A61K 31/506*     (2006.01)
   *A61K 31/5377*    (2006.01)
   *A61K 31/695*     (2006.01)

(56) References Cited

U.S. PATENT DOCUMENTS

| | | |
|---|---|---|
| 2009/0163545 A1 | 6/2009 | Goldfarb |
| 2009/0306130 A1 | 12/2009 | Weber et al. |

FOREIGN PATENT DOCUMENTS

| | | |
|---|---|---|
| WO | WO 2004/004727 | 1/2004 |
| WO | WO 2006/045096 | 4/2006 |
| WO | WO 2006/097323 | 9/2006 |
| WO | WO 2006/115135 | 11/2006 |
| WO | WO 2007/105989 | 9/2007 |
| WO | WO 2007/133108 | 11/2007 |
| WO | WO 2008/112715 | 9/2008 |

OTHER PUBLICATIONS

Foloppe, et al., "Discovery and functional evaluation of diverse novel human CB1 receptor ligands", Bioorganic & Medicinal Chemistry Letters, vol. 19 (2009) 4183-90.

Fukudo, et al., "Impact of corticotropin-releasing hormone on gastrointestinal motility and adrenocorticotropic hormone in normal controls and patients with irritable bowel syndrome", Gut, vol. 42 (1998) 845-49.

Garrido, et al., "Gastrin-releasing peptide mediated regulation of 5-HT neuronal activity in the hypothalamic paraventricular nucleus under basal and restraint stress conditions", Life Sciences, vol. 70 (2002) 2953-66.

Ishikawa, "A Clinical Study of Regulation of Motility of Digestive Tract by Gastrointestinal Hormones", Jap. J. Med., vol. 14, No. 1 (1975) 21-5.

Kahan, et al., "Inhibition of Grow1h of MDA-MB-468 Estrogen-Independent Human Breast Carcinoma by Bombesinl Gastrin-Releasing Peptide Antagonists RC-3095 and RC-3940-1I", Cancer, vol. 88, No. 6 (2000) 1384-92.

Koppan, et al., "Bombesin/Gastrin-Releasing Peptide Antagonists RC-3095 and RC-3940-IIInhibit Tumor Growth and Decrease the Levels and mRNA Expression of Epidermal Grow1h Factor Receptors in H-69 Small Cell Lung Carcinoma", Cancer, vol. 83, No. 7 (1998) 1335-43.

Martins, et al., "Non-associative learning and anxiety in rats treated with a single systemic administration of the gastrin-releasing peptide receptor antagonist RC-3095", Peptides, vol. 26, No. 12 (2005) 2525-29.

Merali, et al., "Aversive and Appetitive Events Evoke the Release of Corticotropin-Releasing Hormone and Bombesin-Like Peptides at the Central Nucleus of the Amygdala", The Journal of Neuroscience, vol. 18, No. 12 (1998) 4758-66.

Murata, et al., "Irritable bowel syndrome", Sogo Rinsho, vol. 51 Supplementary Issue (2002) 1416-19 (English Abstract).

Pinski, et al., "High potency of a new bombesin antagonist (RC-3095) in inhibiting serum gastrin levels; comparison of . . . ", Regulatory Peptides, No. 41 (1992) 185-93.

STN Registry, 902607-43-6 (2006).

STN Registry, 931315-65-0 (2007).

STN Registry, 931939-66-1 (2007).

Suzuki, et al., "Synergistic Interaction Between VIP-Related Peptides and Bombesin on Ion Transport in Guinea Pig Distal Colonic Mucosa", Annals of the New York Academy of Science, vol. 921 (2000) 420-24.

Talley, "Pharmacological Therapy for the Irritable Bowel Syndrome", The American Journal of Gastroenterology, vol. 98, No. 4 (2003) 750-58.

Vadokas, et al., "Effects of gastrin-releasing peptide (GRP) on the mechanical activity of the human ileocaecal region in vitro", Neurogastroenterol. Mot., vol. 9 (1997) 265-70.

Valentine, et al., CP-70,030 and CP-75,998: The First Non-Peptide Antgaonists of Bombesin and Gastrin Releasing Peptide, Bioorganic & Medicinal Chemistry Letters, vol. 2, No. 4 (1992) 333-38.

Yagi, et al., "Perinatal Changes in Bombesin-Stimulated Muscle Contraction in Rabbit Stomach and Colon", Gastroenterology, vol. 100 (1991) 980-85.

TETRAHYDROISOQUINOLIN-1-ONE DERIVATIVE OR SALT THEREOF

This application is a Continuation of U.S. patent application Ser. No. 15/350,427, filed Nov. 14, 2016, which is a Continuation of U.S. patent application Ser. No. 14/836,228, filed Aug. 26, 2015, which is a Divisional of U.S. patent application Ser. No. 13/942,158, filed Jul. 15, 2013, which is a Divisional of U.S. patent application Ser. No. 12/600,894, filed Nov. 19, 2009, which is the U.S. National Phase of PCT/JP2008/059621, filed Mar. 26, 2008, which claims priority from Japanese Patent Application No. P2007-140097, filed May 28, 2007, all of which are incorporated herein by reference in entirety.

TECHNICAL FIELD

The present invention relates to a pharmaceutical, in particular, a tetrahydroisoquinolin-1-one derivative or a salt thereof, which is useful as a therapeutic agent for irritable bowel syndrome.

BACKGROUND ART

Irritable bowel syndrome (IBS) is a syndrome which causes chronic symptoms such as abdominal pain, bloating, and the like, bowel movement disorders such as diarrhea, constipation, and the like, defecation trouble, defecation straining, and the like. It is caused by functional abnormality of the lower digestive tract, mainly the large intestine, despite the absence of organic disorders such as inflammation, tumors, and the like, and is classified based on the conditions of stool into diarrhea-predominant, constipation-predominant, and alternating IBS which alternately repeats diarrhea and constipation. IBS is a disease which has a relatively high frequency occupying from 20 to 50% of bowel disease patients who consult outpatient cares, which is predominant in females with a male to female ratio of 1:2 regardless of race, and which has a high prevalence rate in the younger generation. Since mental stress correlates strongly with the state of the disease, it is regarded as a representative stress-related somatic disease and it is said that the stress management is important for the improvement of symptoms. Actually, it is known that abnormal motility of gastrointestinal tract is significantly accelerated and the symptoms are aggravated when emotional stress is applied to IBS patients. In addition, since the symptoms continue, a vicious circle is likely to form in which increased patient anxiety further aggravates the symptoms.

As the drug therapy of IBS, an anticholinergic is used for abdominal pain, and a tricyclic antidepressant for the improvement of pain threshold value reduction in the digestive tracts, and for the improvement of abnormal bowel motility, a stegnotic, a drug for controlling intestinal function, and the like in the case of diarrhea, and a saline cathartic and the like in the case of constipation, however these are merely symptomatic therapies and their effects are not clear. As an agent from which effects can be expected for both diarrhea and constipation, there is polycarbophil calcium, which regulates the hardness of feces by gelating in the intestines, however it exerts very limited effects because not only there is a bloating at the initial stage of its administration but also it requires time to exhibit the effects. Anxiolytics and antidepressants are used when anxiety and tension are considerably increased due to stress, however they are administered at a dose lower than the dose in the psychiatric field, so that there are cases in which the mental symptoms are not improved or cases in which these are improved but they do not exhibit any effects on the bowel movement disorder. Generally, among the symptoms of IBS, anxiolytics are effective for diarrhea and abdominal pain in some cases, but they have a tendency to exhibit little effect on constipation.

There are a 5-HT3 receptor antagonist alosetron and a 5-HT4 receptor agonist tegaserod as the agents, which have been drawing attention in recent years, and they are used in the diarrhea-predominant and the constipation-predominant, respectively. These agents improve the bowel movement by regulating the movement of intestines, and exhibit an effect quickly. However, though alosetron shows a relatively high improving rate of from 40 to 60% for abdominal symptoms and diarrhea, constipation occurs in 30 to 35% of the patients and it causes ischemic colitis (including mortal cases) as a serious side effect, so that its use is limited (Non-Patent Document 1). In addition, it cannot be said that the effect of tegaserod on the constipation-predominant is sufficient, and there is a possibility of causing tachyphylaxis (a phenomenon in which resistance is generated when a drug is repeatedly administered within a short period of time).

Apropos, when the living body receives a stress, it generates a hypothalamic-pituitary-adrenal system (HPA system) reaction, in which an adrenocorticotropic hormone (ACTH) is released through the secretion of a stress-related substance from the hypothalamus and a subsequent action upon the anterior hypophysis, and the ACTH released into the blood secretes corticosterone from the adrenal cortex, and thereby shows various stress responses such as increase in the blood pressure and the like. As the stress-related substance, corticotropin releasing hormone (CRH), bombesin (BB)/gastrin releasing peptide (GRP), vasopressin, neuropeptide Y, substance P, neurotensin, and the like are known. Secretion of these substances from the hypothalamus is accelerated when a stress is applied to an animal.

Particularly regarding the CRH, it has been reported that it reinforces ACTH release and large bowel movement when administered to IBS patients (Non-Patent Document 2).

The bombesin/GRP as one of the stress-related substances is a brain-gut peptide and expresses various physiological actions via bombesin receptors. The bombesin receptor is classified into 3 subtypes of BB1, BB2 and BB3/BRS3 (bombesin receptor subtype-3), and as intrinsic ligands of mammals for the BB1 and BB2 receptors, neuromedin B and GRP have been identified respectively. It has been reported that the GRP and BB2 receptors are present ubiquitously in the brain, the digestive tracts, and the like, but GRP is markedly increased in the amygdala and hypothalamus when stress is applied to an animal (Non-Patent Document 3). In addition, it has been reported also that a BB2 receptor antagonist inhibits the increase in ACTH when administered into the cerebral ventricle in a restraint stress-added rat (Non-Patent Document 4).

As the role of the GRP/BB2 receptor in the digestive tract functions, it has been reported that it enhances the contraction in isolated human and rabbit ileum longitudinal muscle specimens (Non-Patent Documents 5 and 6), and enhances the water secretion in guinea pigs with the coexistence of a vasoactive intestinal peptide (VIP) (Non-Patent Document 7). In addition, it has been reported that BB2 receptor antagonists including RC-3095 that is a peptidic BB2 receptor antagonist, is effective for an abnormal bowel motility in a stress-induced defecation model. It has also been reported that, using an abdominal muscle contraction reaction as the index, RC-3095 is effective for an abdominal symptom in an abdominal pain model induced by large intestinal distension.

Accordingly the BB2 receptor antagonist shows excellent efficacy on both the abdominal symptom and abnormal bowel motility (Patent Document 1).

As shown above, the BB2 receptor antagonist is expected to be a therapeutic agent for IBS, showing excellent efficacy on both the abdominal symptom and abnormal bowel motility.

Furthermore, since the bombesin/GRP also has a function as a cell growth factor and the expression of the GRP/BB2 receptor is increased in various cancer cells of lung cancer, prostate cancer, and the like, the efficacy of RC-3095 has been reported in a large number of antitumor tests (Non-Patent Documents 8 to 10). From this viewpoint, the BB2 receptor antagonist can also be expected to be effective against various cancers.

The tetrahydroisoquinolin-1-one derivative has been reported in Patent Documents 2 to 4.

Patent Document 2 describes that a 3,4-dihydroisoquinolin-1-one derivative represented by the following formula (A) has a caspase activating action and an apoptosis inducing action, and is effective for cancers, autoimmune diseases, rheumatoid arthritis, inflammatory bowel syndrome, psoriasis, and the like. However, there is no description of its antagonistic action on a bombesin type 2 receptor or of its efficacy regarding IBS.

[Chem. 1]

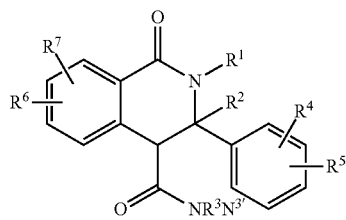

(A)

(for the symbols in the formula, refer to the publication)

Patent Document 3 describes that a tetrahydroisoquinolin-1-one derivative represented by the following formula (B) is a ligand of an HDM2 protein, has an apoptosis inducing activity and a proliferation inhibitory activity, and is effective against cancers. However, there is no description of its antagonistic action on a bombesin type 2 receptor or of its efficacy regarding IBS.

[Chem. 2]

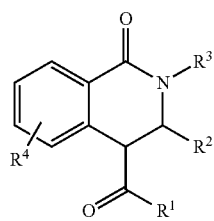

(B)

(for the symbols in the formula, refer to the publication)

Patent Document 4 describes that a tetrahydroisoquinolin-1-one derivative represented by the following formula (C) is a neurotensin-2 (NT-2) receptor antagonist and is effective against pain. However, for $R^5$ corresponding to $R^1$ of the present invention, there is no description on the $R^1$ group of the present invention. In addition, there is no description of its antagonistic action on a bombesin type 2 receptor or of its efficacy regarding IBS.

[Chem. 3]

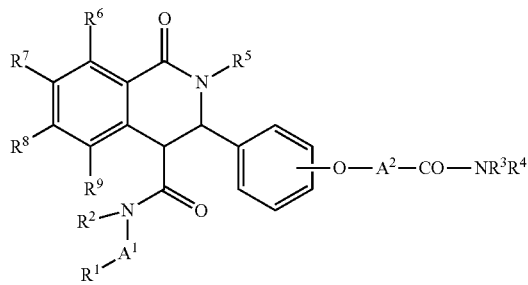

(C)

(wherein $R^5$ means ($C_1$-$C_8$) alkyl which is optionally substituted with a group selected from trifluoromethyl, halogen, saturated or partially unsaturated ($C_3$-$C_8$) cycloalkyl, and ($C_6$-$C_{10}$) aryl. For the other symbols, refer to the publication.)

The compounds described in the following Tables 1 to 11 below are reported as Catalog Compounds. However, there is no description of the antagonistic action on a bombesin type 2 receptor and the efficacy for IBS, of these compounds. Further, in the following Tables, the abbreviations below are used. Me: Methyl, Et: Ethyl, iPr: Isopropyl, nBu: Normal Butyl, Ph: Phenyl.

TABLE 1

| CAS Registry No. | $R^a R^b N$— |
|---|---|
| 931939-66-1 | |
| 931315-65-0 | |
| 902607-43-6 | $Me_2N$— |
| 902450-09-3 | Ph—$(CH_2)_2$—NH— |
| 891914-00-4 | $PhCH_2$—NH— |
| 891913-84-1 | |

TABLE 1-continued
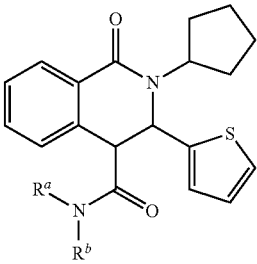
| CAS Registry No. | $R^aR^bN-$ |
|---|---|
| 891913-76-1 | 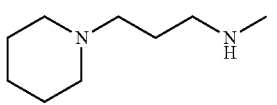 |
| 891913-68-1 | 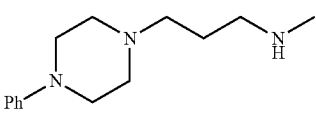 |
| 891913-28-3 | 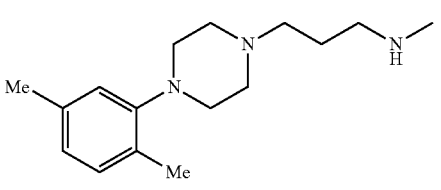 |
| 891913-04-5 | 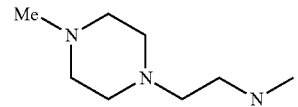 |
| 891912-88-2 | EtNH— |
| 891912-80-4 | 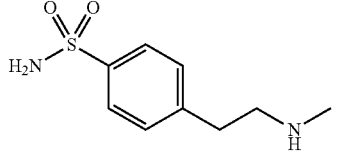 |
TABLE 2
| 891912-64-4 | 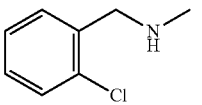 |
|---|---|
| 891912-56-4 | 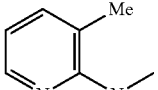 |
| 891912-48-4 | 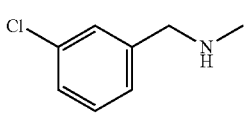 |
| 891912-40-6 | 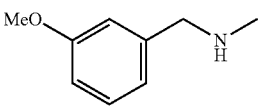 |
| 891912-16-6 | 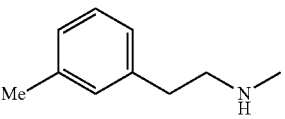 |
| 891912-08-6 | 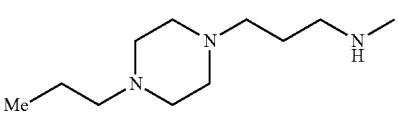 |
| 891912-00-8 | 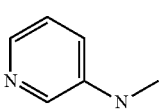 |
| 891911-84-5 | 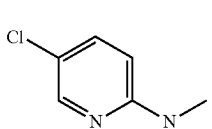 |
| 891911-60-7 | 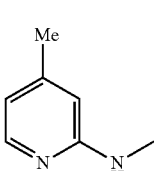 |
| 891911-52-7 | 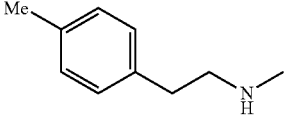 |
| 891911-44-7 | 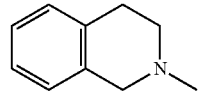 |
| 891911-36-7 | 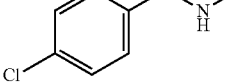 |
TABLE 3
| 891911-29-8 | 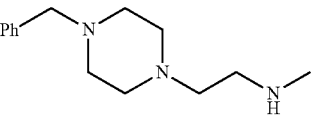 [SMILES: CNCCN1CCN(Cc2ccccc2)CC1] |
|---|---|
| 891911-22-1 | 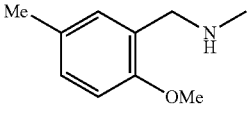 |
| 891911-07-2 | 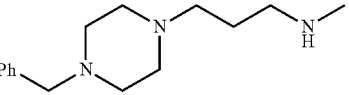 |

TABLE 3-continued

| ID | Structure |
|---|---|
| 891910-93-3 | 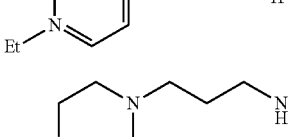 1,2,3,4-tetrahydroisoquinolin-2-yl-CH₂CH₂CH₂-NHMe |
| 891910-86-4 | 4-Me-C₆H₄-CH₂-NHMe |
| 891910-72-8 | 3-Me-C₆H₄-CH₂-N(piperidin-4-yl-CH₂-NHMe) |
| 891910-65-9 | 3-Me-C₆H₄-CH₂-NHMe |
| 891910-58-0 | 4-F-C₆H₄-piperazin-1-yl-CH₂CH₂CH₂-NHMe |
| 891910-23-9 | 2-OEt-C₆H₄-CH₂-NHMe |
| 891910-07-9 | 4-MeO-C₆H₄-piperazin-1,4-diyl-CH₂CH₂-NHMe |
| 891909-99-2 | 4-MeO-C₆H₄-CH₂-NHMe |
| 891909-91-4 | EtO—(CH₂)₃—NH— |
| 891909-83-4 | 4-Cl-C₆H₄-CH₂CH₂-NHMe |

TABLE 4

| ID | Structure |
|---|---|
| 891909-75-4 | benzo[1,3]dioxol-5-yl-CH₂-NHMe |
| 891909-67-4 | thiophen-2-yl-CH₂-NHMe |
| 891909-59-4 | iPrO—(CH₂)₃—NH— |
| 891909-51-6 | 3,4-(EtO)₂-C₆H₃-CH₂CH₂-NHMe |
| 891909-27-6 | PhN(Et)—(CH₂)₃—NH— |
| 891909-11-8 | 4-Et-piperazin-1-yl-CH₂CH₂CH₂-NHMe (pyrazine) |
| 891909-03-8 | 4-Me-piperazin-1-yl-CH₂CH₂CH₂-NHMe |
| 891908-95-5 | 3-Me-C₆H₄-N(Et)-CH₂CH₂CH₂-NHMe |
| 891908-55-7 | Et₂N— |
| 891907-99-6 | pyridin-3-yl-CH₂-NHMe |
| 891907-91-8 | pyridin-2-yl-CH₂-NHMe |
| 891907-83-8 | 3,4-Me₂-C₆H₃-CH₂CH₂-NHMe |
| 891907-75-8 | morpholin-4-yl-CH₂CH₂-NHMe |
| 891907-43-0 | MeO—(CH₂)₃—NH— |
| 891907-35-0 | nBuNH— |
| 891907-27-0 | iPrNH— |
| 891907-19-0 | furan-2-yl-CH₂-NHMe |
| 891907-11-2 | MeO—(CH₂)₂—NH— |

TABLE 5

| ID | Structure |
|---|---|
| 891907-03-2 | 4-F-C₆H₄-CH₂-NHMe |
| 891906-95-9 | morpholin-4-yl-CH₂CH₂CH₂-NHMe |

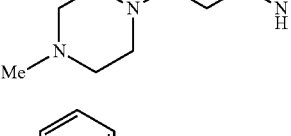
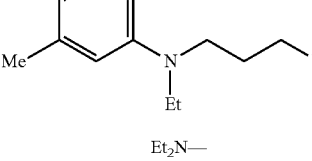
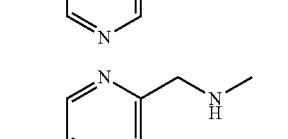
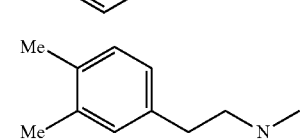
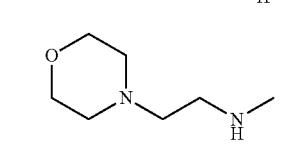
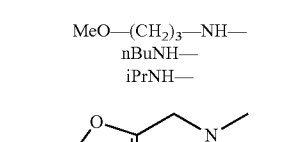
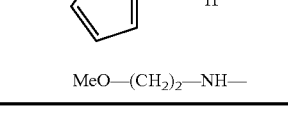

TABLE 5-continued
| CAS Registry No. | Structure |
|---|---|
| 891906-87-9 | 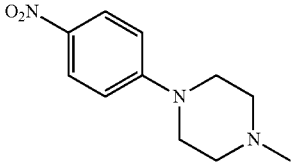 [SMILES: CN1CCN(c2ccc([N+](=O)[O-])cc2)CC1] |
| 891906-79-9 | 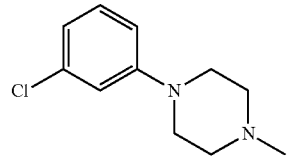 |
| 891906-71-1 | 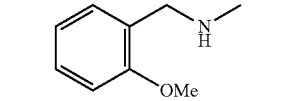 |
| 891906-55-1 | 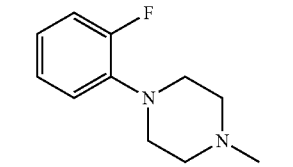 |
| 891906-39-1 | 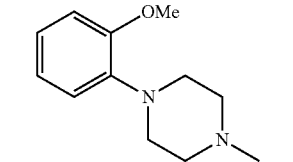 |
| 891905-75-2 | 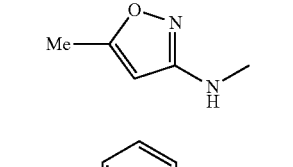 |
| 891904-87-3 | 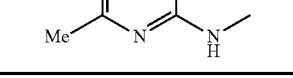 |
TABLE 6
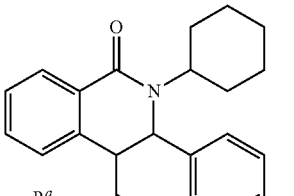
| CAS Registry No. | $R^aR^bN-$ |
|---|---|
| 685520-62-1 | 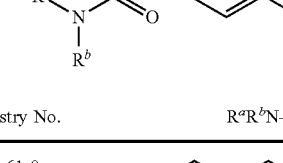 |
TABLE 6-continued
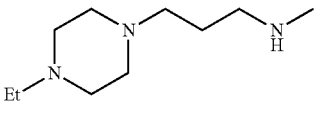
| CAS Registry No. | $R^aR^bN-$ |
|---|---|
| 685520-61-0 | 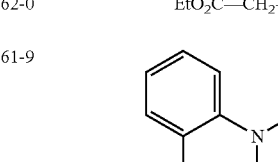 |
| 442858-62-0 | EtO$_2$C—CH$_2$—NH— |
| 442858-61-9 | 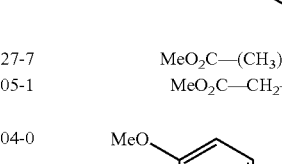 |
| 442858-27-7 | MeO$_2$C—(CH$_3$)$_2$—NH— |
| 442858-05-1 | MeO$_2$C—CH$_2$—NH— |
| 442858-04-0 | 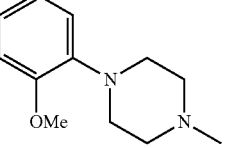 |
| 442857-76-3 | 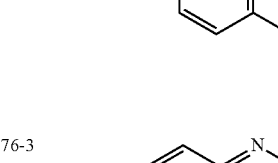 |
| 442857-73-0 | 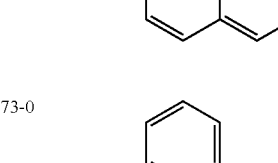 |
| 442856-86-2 | 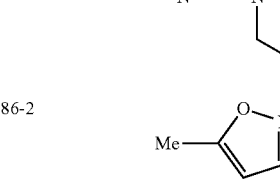 |
| 442856-85-1 | 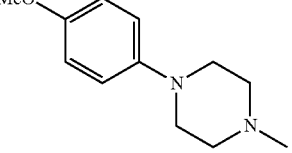 |
| 442856-80-6 | Et$_2$N— |

TABLE 7
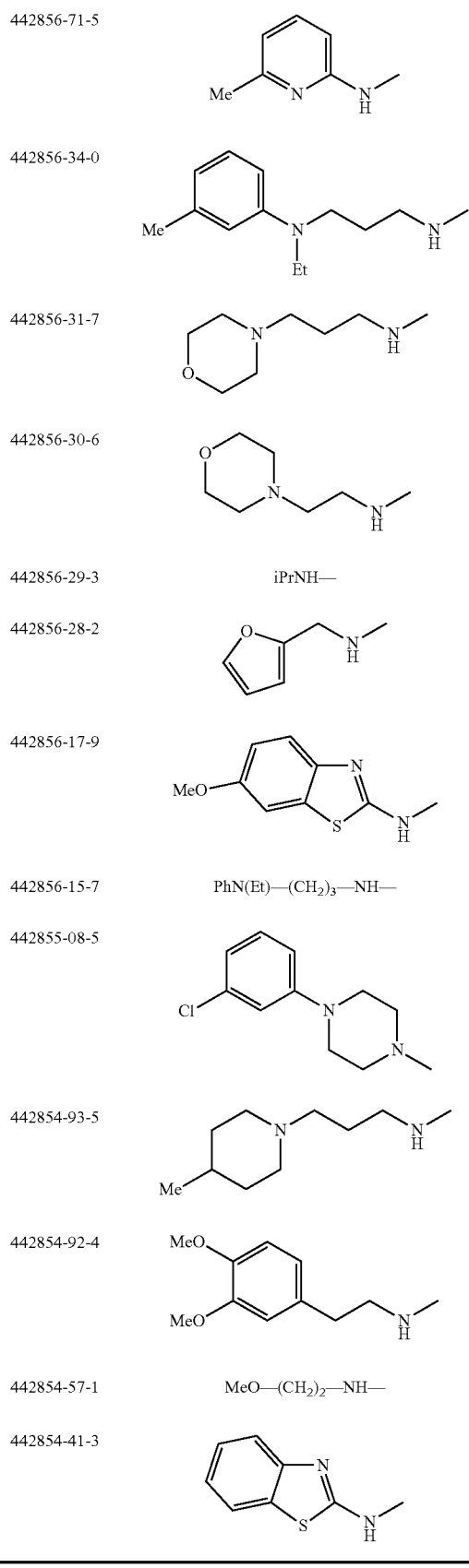
TABLE 8
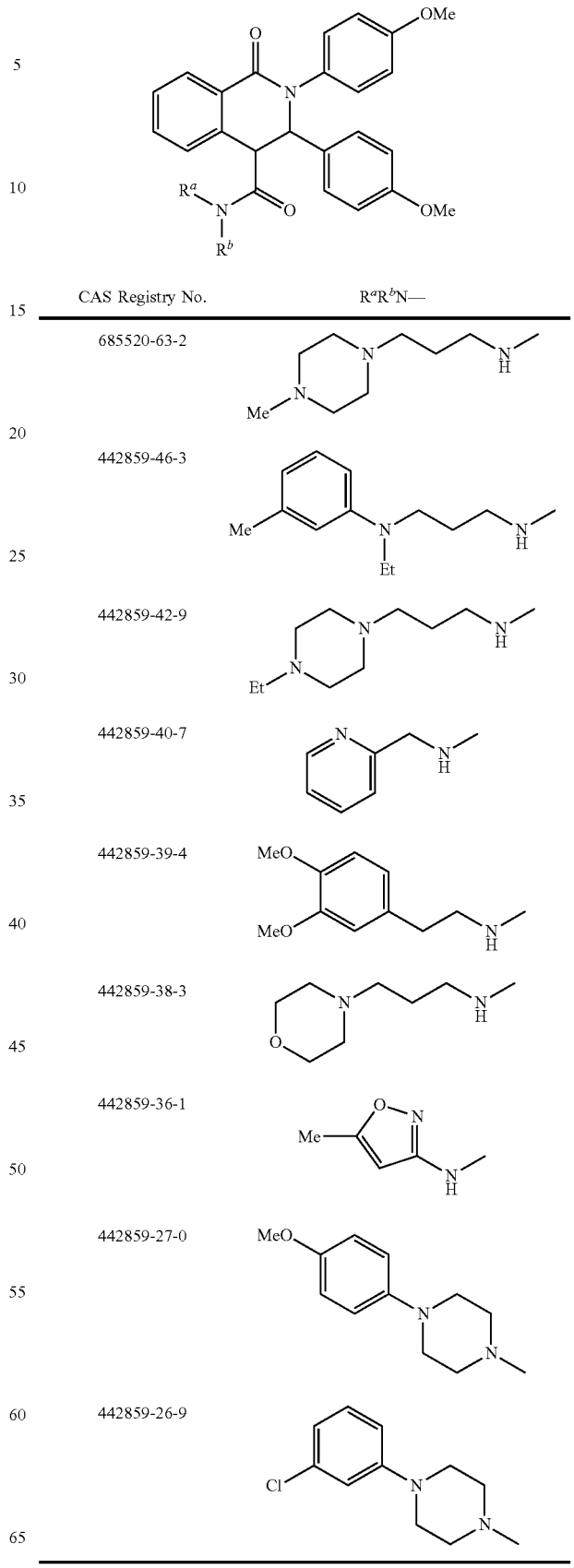

TABLE 9
| CAS Registry No. | Structure |
|---|---|
| 442859-25-8 | 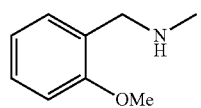 |
| 442859-20-3 | Et₂N— |
| 442859-13-4 | 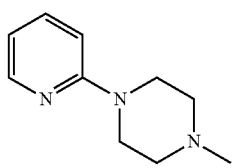 |
| 442859-12-3 | 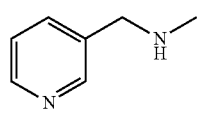 |
| 442859-11-2 | MeO—(CH₂)₃—NH— |
| 442859-09-8 | nBuN(Et)— |
| 442859-06-5 | 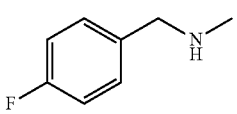 |
| 442859-05-4 | nBuNH— |
| 442859-03-2 | 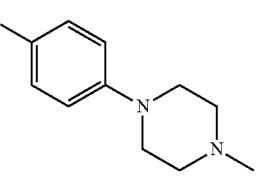 |
| 442859-02-1 | EtO₂C—CH₂—NH— |
| 442859-01-0 | MeO—(CH₂)₂—NH— |
| 442858-99-3 | nBuN(Me)NH— |
| 442858-98-2 | 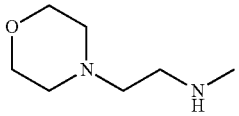 |
| 442858-93-7 | 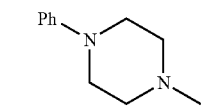 |
| 442858-91-5 | PhCH₂N(Me)— |
| 442858-86-8 | 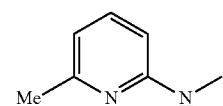 |
| 442858-79-9 | 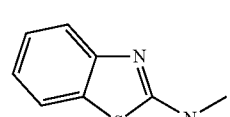 |
TABLE 10
| CAS Registry No. | Structure |
|---|---|
| 442858-77-7 | 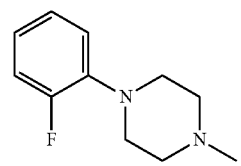 |
| 442858-76-6 | 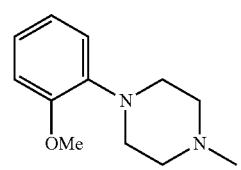 |
| 442858-72-2 | 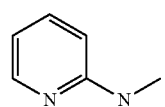 |
| 442858-67-5 | 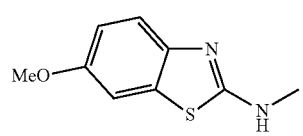 |
| 442858-56-2 | iPrNH— |
| 442858-55-1 | 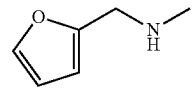 |
TABLE 11
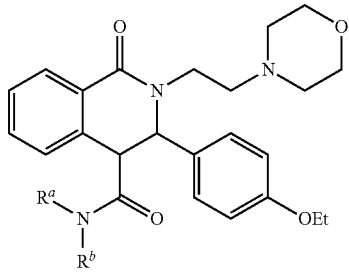
| CAS Registry No. | RᵃRᵇN— |
|---|---|
| 442888-72-4 | 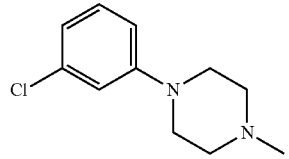 |
| 442888-70-2 | 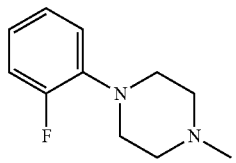 |
| 442888-60-0 | 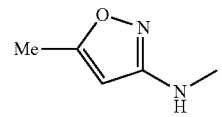 |

TABLE 11-continued

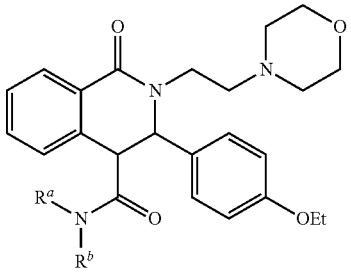

| CAS Registry No. | $R^aR^bN-$ |
|---|---|
| 442888-49-5 | 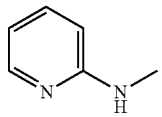 |
| 442888-41-7 | 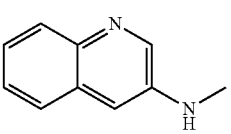 |
| 442888-39-3 | 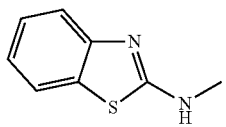 |
| 442888-37-1 | 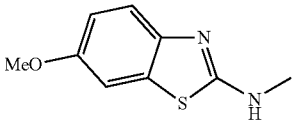 |
| 442888-35-9 | 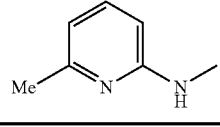 |

Non-Patent Document 1: "American Journal of Gastroenterology", (USA), 2003, vol. 98, p. 750-758
Non-Patent Document 2: "Gut", (England), 1998, vol. 42, p. 845-849
Non-Patent Document 3: "The Journal of Neuroscience", (USA), 1998, vol. 18, p. 4758-4766
Non-Patent Document 4: "Life Sciences", (Holland), 2002, vol. 70, p. 2953-2966
Non-Patent Document 5: "Gastroenterology", (USA), 1991, vol. 100, p. 980-985
Non-Patent Document 6: "Neurogastroenterology and Motility", (England), 1997, vol. 9, p. 265-270
Non-Patent Document 7: "Annals of the New York Academy of Science", (USA), 2000, vol. 921, p. 420-424
Non-Patent Document 8: "Cancer", (USA), 1998, vol. 83, p. 1335-1343
Non-Patent Document 9: "British Journal of Cancer", 2000, vol. 83, p. 906-913,
Non-Patent Document 10: "Cancer", (USA), 2000, vol. 88, p. 1384-1392
Patent Document 1: Pamphlet of International Publication No. 2006/115135
Patent Document 2: Pamphlet of International Publication No. 2004/04727
Patent Document 3: Pamphlet of International Publication No. 2006/97323
Patent Document 4: Pamphlet of International Publication No. 03/29221

DISCLOSURE OF THE INVENTION

Problem that the Invention is to Solve

It is an object of the present invention to provide a novel pharmaceutical having a BB2 receptor antagonistic action, in particular, a novel compound which is useful as a therapeutic agent for IBS.

Means for Solving the Problems

The present inventors have conducted extensive studies on BB2 receptor antagonists, and as a result, we have found that a novel tetrahydroisoquinolin-1-one derivative having an amide group as a substituent at the 4-position has an excellent BB2 receptor antagonistic action, thus completing the present invention.

Namely the present invention relates to a tetrahydroisoquinolin-1-one derivative represented by the general formula (I) or a pharmaceutically acceptable salt thereof:

[Chem. 4]

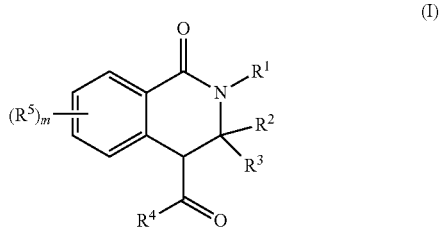

(I)

[the symbols in the formula represent the following meanings:
$R^1$: lower alkylene-OH, lower alkylene-N($R^0$)($R^6$), lower alkylene-$CO_2R^0$, cycloalkyl, cycloalkenyl, aryl, heterocyclic group, -(lower alkylene substituted with —O$R^0$)-aryl or lower alkylene-heterocyclic group,
wherein the lower alkylene, cycloalkyl, cycloalkenyl, aryl and heterocyclic group in $R^1$ may each be substituted,
$R^0$: the same as or different from each other, each representing —H or lower alkyl,
$R^6$: $R^0$, —C(O)—$R^0$, —$CO_2$-lower alkyl or —S(O)$_2$-lower alkyl,
$R^2$: lower alkyl, lower alkylene-O$R^0$, lower alkylene-aryl, lower alkylene-heterocyclic group, lower alkylene-N($R^0$)CO-aryl, lower alkylene-O-lower alkylene-aryl, —$CO_2R^0$, —C(O)N($R^0$)$_2$, —C(O)N($R^0$)-aryl, —C(O)N($R^0$)-lower alkylene-aryl, aryl or heterocyclic group,
wherein the aryl and heterocyclic group in $R^2$ may each be substituted,
$R^3$: —H or lower alkyl,
or $R^2$ and $R^3$ may be combined to form $C_{2-6}$ alkylene,
$R^4$: —N($R^7$)($R^8$), —N($R^0$)—OH, —N($R^{10}$)—$OR^7$, —N($R^0$)—N($R^0$)($R^7$), —N($R^0$)—S(O)$_2$-aryl, or —N($R^0$)—S(O)$_2$—$R^7$,
wherein the aryl in $R^4$ may be substituted,
$R^7$: lower alkyl, halogeno-lower alkyl, lower alkylene-CN, lower alkylene-O$R^0$, lower alkylene-$CO_2R^0$, lower alkylene-C(O)N($R^0$)$_2$, lower alkylene-C(O)N($R^0$)N($R^0$)$_2$, lower alkylene-C(=NH)NH$_2$, lower alkylene-C(=NOH) NH$_2$, heteroaryl, lower alkylene-X-aryl, or lower alkylene-X-heterocyclic group, wherein the lower alkylene, aryl, heteroaryl, and heterocyclic group in R$^7$ may each be substituted, X: single bond, —O—, —C(O)—, —N(R$^0$)—, —S(O)$_p$—, or *—C(O)N(R$^0$)—, wherein * in X represents a bond to lower alkylene, m: an integer of 0 to 3, p: an integer of 0 to 2, R$^8$: —H or lower alkyl, or R$^7$ and R$^8$ may be combined to form lower alkylene-N(R$^9$)-lower alkylene, lower alkylene-CH(R$^9$)-lower alkylene, lower alkylene-arylene-lower alkylene, or lower alkylene-arylene-C(O)—, R$^9$: aryl and heteroaryl which may each be substituted, R$^{10}$: —H, lower alkyl, or —C(O)R$^0$, R$^5$: lower alkyl, halogeno-lower alkyl, halogen, nitro, —OR$^0$, —O-halogeno-lower alkyl, —N(R$^0$)$_2$, —O-lower alkylene-CO$_2$R$^0$, or —O-lower alkylene-aryl, wherein the aryl in R$^5$ may be substituted, provided that, when R$^4$ is —N(R$^7$)(R$^8$), (1) a compound wherein R$^1$ is unsubstituted cyclopentyl and R$^2$ is unsubstituted 2-thienyl;

(2) a compound wherein R$^1$ is unsubstituted cyclohexyl and R$^2$ is 4-methoxyphenyl;

(3) a compound wherein R$^1$ is 4-methoxyphenyl and R$^2$ is 4-methoxyphenyl; and (4) a compound wherein R$^1$ is (morpholin-4-yl)ethyl and R$^2$ is 4-ethoxyphenyl are excluded, furthermore, 2,3-bis(4-chlorophenyl)-N-(2-methoxyethyl)-1-oxo-1,2,3,4-tetrahydroisoquinoline-4-carboxamide, 3-(4-chlorobenzyl)-2-(4-chlorophenyl)-N-(2-methoxyethyl)-1-oxo-1,2,3,4-tetrahydroisoquinoline-4-carboxamide, 3-[3,5-bis(trifluoromethyl)phenyl]-2-cyclopropyl-N-(2-furylmethyl)-1-oxo-1,2,3,4-tetrahydroisoquinoline-4-carboxamide, 3-[3,5-bis(trifluoromethyl)phenyl]-2-cyclopropyl-N-(2-methoxyethyl)-1-oxo-1,2,3,4-tetrahydroisoquinoline-4-carboxamide, ethyl 3-{3-[3,5-bis(trifluoromethyl)phenyl]-4-{[2-(4-methoxyphenyl)ethyl]carbamoyl}-1-oxo-3,4-dihydroisoquinolin-2(1H)-yl}propanoate, N-benzyl-3-[3,5-bis(trifluoromethyl)phenyl]-1-oxo-2-(tetrahydrofuran-2-ylmethyl)-1,2,3,4-tetrahydroisoquinoline-4-carboxamide, 3-[3,5-bis(trifluoromethyl)phenyl]-N-(2-methoxyethyl)-2-(2-morpholin-4-ylethyl)-1-oxo-1,2,3,4-tetrahydroisoquinoline-4-carboxamide, 3-[3,5-bis(trifluoromethyl)phenyl]-2-(2-furylmethyl)-N-(2-methoxyethyl)-1-oxo-1,2,3,4-tetrahydroisoquinoline-4-carboxamide, 3-[3,5-bis(trifluoromethyl)phenyl]-N-(2-furylmethyl)-2-(2-morpholin-4-ylethyl)-1-oxo-1,2,3,4-tetrahydroisoquinoline-4-carboxamide, and (4-chlorophenyl)[3-(4-chlorophenyl)-4-[(2-methoxyethyl)carbamoyl]-1-oxo-3,4-dihydroisoquinolin-2(1H)-yl]acetic acid are excluded.

The symbols hereinafter represent the same meanings].

Further, the present application relates to a pharmaceutical comprising a tetrahydroisoquinolin-1-one derivative represented by the general formula (I) or a salt thereof as an active ingredient, in particular a BB2 receptor antagonist, a therapeutic agent for irritable bowel syndrome or a therapeutic agent for cancers.

Furthermore, the present application relates to the use of the compound represented by the formula (I) or a pharmaceutically acceptable salt thereof for the manufacture of a BB2 receptor antagonist, a therapeutic agent for irritable bowel syndrome, or a therapeutic agent for cancers, and to a method for treating irritable bowel syndrome or cancers, comprising administering to a patient an effective amount of the compound represented by the formula (I) or a pharmaceutically acceptable salt thereof.

Namely, the present application relates to: (1) a pharmaceutical composition comprising the compound described in the general formula (I) or a pharmaceutically acceptable salt thereof, and a pharmaceutically acceptable carrier, (2) the pharmaceutical composition as described in (1), which is a BB2 receptor antagonist, (3) the pharmaceutical composition as described in (1), which is a therapeutic agent for irritable bowel syndrome, (4) the pharmaceutical composition as described in (1), which is a therapeutic agent for cancers, (5) use of the compound as described in the general formula (I) or a pharmaceutically acceptable salt thereof for the manufacture of a BB2 receptor antagonist, a therapeutic agent for irritable bowel syndrome, or a therapeutic agent for cancers, and (6) a method for treating irritable bowel syndrome or cancers, comprising administering to a patient a therapeutically effective amount of the compound as described in the general formula (I) or a pharmaceutically acceptable salt thereof.

Effects of the Invention

The compound of the present invention is useful as a therapeutic agent for IBS since it has an excellent antagonistic action on a BB2 receptor.

Best Mode for Carrying Out the Invention

The present invention will be described in more detail as follows.

The "lower alkyl" is preferably a linear or branched alkyl having 1 to 6 carbon atoms (which is hereinafter simply referred to as $C_{1-6}$), and specifically, it includes methyl, ethyl, n-propyl, isopropyl, n-butyl, isobutyl, sec-butyl, tert-butyl, n-pentyl, n-hexyl group, and the like. More preferably, it is $C_{1-4}$ alkyl, and more preferably, it includes methyl, ethyl, n-propyl, and isopropyl.

The "lower alkylene" is preferably a linear or branched $C_{1-6}$ alkylene, and specifically, it includes methylene, ethylene, trimethylene, tetramethylene, pentamethylene, hexamethylene, propylene, methylmethylene, ethylethylene, 1,2-dimethylethylene, 1,1,2,2-tetramethylethylene group, and the like. Preferably, it is $C_{1-4}$ alkylene, and more preferably, it includes methylene, ethylene, and trimethylene.

The "halogen" means F, Cl, Br, or I.

The "halogeno-lower alkyl" refers to $C_{1-6}$ alkyl substituted with one or more halogens. It is preferably lower alkyl substituted with 1 to 5 halogens, and more preferably trifluoromethyl.

The "halogeno-lower alkylene" refers to $C_{1-6}$ alkylene substituted with one or more halogens. It is preferably lower alkylene substituted with 1 to 5 halogens, and more preferably, it includes difluoromethylene and difluoroethylene.

The "cycloalkyl" refers to a $C_{3-10}$ saturated hydrocarbon ring group, which may have a bridge. Specifically, it includes cyclopropyl, cyclobutyl, cyclopentyl, cyclohexyl, cycloheptyl, cyclooctyl, adamantyl group, and the like. It is preferably $C_{3-8}$ cycloalkyl, and more preferably $C_{3-6}$ cycloalkyl, and even more preferably, it includes cyclopentyl and cyclohexyl.

The "cycloalkenyl" refers to $C_{3-15}$ cycloalkenyl, which may have a bridge, and it includes a ring group condensed with a benzene ring at a double bond site. Specifically, it includes cyclopentenyl, cyclopentadienyl, cyclohexenyl, cyclohexadienyl, 1-tetrahydronaphthyl, 1-indenyl, 9-fluorenyl group, and the like. Preferably, it is $C_{5-10}$ cycloalkenyl, and more preferably, it includes cyclopentenyl and cyclohexenyl.

The "aryl" refers to a $C_{6-14}$ monocyclic to tricyclic aromatic hydrocarbon ring group, and preferably, it includes phenyl and naphthyl, and more preferably phenyl.

The "arylene" refers to a divalent group formed by removing an arbitrary hydrogen atom from aryl, and it is preferably phenylene, and more preferably orthophenylene.

The "heteroaryl" means a ring group consisting of i) monocyclic 5- to 6-membered heteroaryl containing 1 to 4 hetero atoms selected from O, S, and N, and ii) bicyclic a 8- to 10-membered heterocycle and a tricyclic 11- to 14-membered heterocycle, each containing 1 to 5 hetero atoms selected from O, S, and N, which are formed by condensation of the monocyclic heteroaryl, and one or two rings selected from the group consisting of monocyclic heteroaryl and a benzene ring. The ring atom S or N may be oxidized to form an oxide or a dioxide.

The "heteroaryl" preferably includes pyrrolyl, imidazolyl, pyrazolyl, triazolyl, tetrazolyl, pyridyl, pyrimidinyl, pyrazinyl, furyl, thienyl, oxazolyl, oxadiazolyl, thiazolyl, thiadiazolyl, indolyl, indazolyl, benzoimidazolyl, imidazopyridyl, quinolyl, quinazolyl, quinoxalinyl, naphthylidinyl, benzofuranyl, benzothienyl, benzoxazolyl, benzothiazolyl, and carbazolyl, and more preferably pyrrolyl, pyridyl, furyl, thienyl, and thiazolyl.

The "heterocyclic group" means a ring group consisting of i) a monocyclic 3- to 8-membered (preferably 5- to 7-membered) heterocycle containing 1 to 4 hetero atoms selected from O, S, and N, and ii) a bicyclic 8- to 14-membered (preferably 9- to 11-membered) heterocycle and a tricyclic 11- to 20-membered (preferably 12- to 15-membered) heterocycle, each containing 1 to 5 hetero atoms selected from O, S, and N, which are formed by the condensation of the monocyclic heterocycle, and one or two rings selected from the group consisting of a monocyclic heterocycle, a benzene ring, $C_{5-8}$ cycloalkane, and $C_{5-8}$ cycloalkene. The ring atom S or N may be oxidized to form an oxide or a dioxide, or may have a bridge.

The "heterocyclic group" preferably includes aziridinyl, azetidinyl, pyrrolidinyl, piperidinyl, piperazinyl, homopiperazinyl, oxiranyl, oxetanyl, tetrahydrofuranyl, tetrahydropyranyl, morpholinyl, homomorpholinyl, tetrahydrothienyl, tetrahydrothiopyranyl, thiomorpholinyl, pyrrolyl, imidazolyl, pyrazolyl, triazolyl, tetrazolyl, pyridyl, pyrimidinyl, pyrazinyl, furyl, thienyl, oxazolyl, oxadiazolyl, thiazolyl, thiadiazolyl, indolyl, indazolyl, benzimidazolyl, imidazopyridyl, quinolyl, quinazolyl, quinoxalinyl, naphthylidinyl, benzofuranyl, benzothienyl, benzoxazolyl, benzothiazolyl, dihydroindolyl, dihydrobenzimidazolyl, dihydrobenzofuranyl, tetrahydroquinolyl, benzodioxolyl, dihydrobenzodioxynyl, dihydrobenzoxazinyl, tetrahydronaphthylidinyl, carbazolyl, and quinuclidinyl, and more preferably pyrrolidyl, piperidyl, tetrahydrofuryl, tetrahydropyranyl, pyrrolyl, pyridyl, furyl, thienyl, and thiazolyl.

The expression "which may be substituted" means "which is not substituted" or "which is substituted with 1 to 5 substituents which may be the same as or different from each other". The expression "which is substituted" refers to "which is substituted with 1 to 5 substituents which are the same as or different from each other". Further, if a plurality of substituents are contained, the substituents may be the same as or different from each other.

The substituent for the "lower alkylene" which may be substituted in $R^1$ is preferably a group selected from Group $G^1$, and more preferably —OH or phenyl.

Group $G^1$: halogen, —OR$^O$, —N(R$^O$)(R$^6$), and aryl.

Provided that, the "aryl" in Group $G^1$ may be substituted with a group selected from the group consisting of halogen, lower alkyl, halogeno-lower alkyl, —OR$^O$, and —O-halogeno-lower alkyl.

The substituent for the "cycloalkyl", "cycloalkenyl", and "heterocyclic group" which may be each substituted in $R^1$ is preferably a group selected from Group $G^2$, more preferably —OR$^O$, —CO$_2$R$^O$, —N(R$^O$)$_2$, —N(R$^O$)C(O)R$^O$, —N(R$^O$)C(O)-lower alkylene-OR$^O$, or —N(R$^O$)S(O)$_2$-lower alkyl, and even more preferably —OR$^O$, —N(R$^O$)C(O)R$^O$, or —N(R$^O$)S(O)$_2$-lower alkyl.

Group $G^2$: halogen, lower alkyl, halogeno-lower alkyl, lower alkylene-OR$^O$, —OR$^O$, —O-halogeno-lower alkyl, —N(R$^O$)$_2$, —N(R$^O$)-lower alkylene-OR$^O$, —N(R$^O$)-lower alkylene-CO$_2$R$^O$, —N(R$^O$)C(O)R$^O$, —N(R$^O$)C(O)OR$^O$, —N(R$^O$)C(O)-aryl, —N(R$^O$)C(O)-lower alkylene-OR$^O$, —N(R$^O$)C(O)-lower alkylene-N(R$^O$)$_2$, —N(R$^O$)C(O)N(R$^O$)$_2$, —N(R$^O$)C(=NR$^O$)-lower alkyl, —N(R$^O$)S(O)$_2$-lower alkyl, —N(lower alkylene-OR$^O$)—S(O)$_2$-lower alkyl, —N(lower alkylene-CO$_2$R$^O$)—S(O)$_2$-lower alkyl, —N(R$^O$)S(O)$_2$-lower alkylene-CO$_2$R$^O$, —N(R$^O$)S(O)$_2$-lower alkylene-S(O)$_2$-lower alkyl, —N(R$^O$)S(O)$_2$-aryl, —N(R$^O$)S(O)$_2$N(R$^O$)$_2$, —S(O)$_2$-lower alkyl, —CO$_2$R$^O$, —CO$_2$-lower alkylene-Si (lower alkyl)$_3$, —C(O)N(R$^O$)$_2$, —C(O)N(R$^O$)-lower alkylene-OR$^O$, —C(O)N(R$^O$)-lower alkylene-N(R$^O$)$_2$, —C(O)N(R$^O$)-lower alkylene-CO$_2$R$^O$, —C(O)N(R$^O$)—O-lower alkylene-heterocyclic group, heterocyclic group, —C(O)R$^O$, —C(O)-lower alkylene-OR$^O$, —C(O)-lower alkylene-N(R$^O$)$_2$, —C(O)-heterocyclic group, and oxo.

Provided that the "aryl" and the "heterocyclic group" in Group $G^2$ may be each substituted with a group selected from the group consisting of halogen, lower alkyl, halogeno-lower alkyl, —OR$^O$, —O-halogeno-lower alkyl, and oxo.

The substituent for the "aryl" which may be substituted in $R^1$ is preferably a group selected from Group $G^3$, and more preferably —OR$^O$ or lower alkylene-OR$^O$.

Group $G^3$: halogen, lower alkyl, halogeno-lower alkyl, —OR$^O$, —O-halogeno-lower alkyl, lower alkylene-OR$^O$, and —CO$_2$R$^O$.

The substituent for the "aryl" and the "heterocyclic group" which may be substituted in $R^2$ is preferably a group selected from Group $G^4$, more preferably halogen, lower alkyl, or —OR$^O$, and even more preferably halogen.

Group $G^4$: halogen, —CN, nitro, lower alkyl, halogeno-lower alkyl, —OR$^O$, —N(R$^O$)$_2$, —CO$_2$R$^O$, —C(O)N(R$^O$)$_2$, —OS(O)$_2$-lower alkyl, and oxo.

The substituent for the "lower alkylene" which may be substituted in $R^7$ is preferably a group selected from Group $G^5$, more preferably halogen.

Group $G^5$: halogen, —OR$^O$, —N(R$^O$)$_2$, and aryl.

Provided that the "aryl" in Group $G^5$ may be substituted with a group selected from the group consisting of halogen, lower alkyl, halogeno-lower alkyl, —OR$^O$, and —O-halogeno-lower alkyl.

The substituent for the "aryl" and the "heterocyclic group" which may each be substituted in $R^7$ is preferably a group selected from Group $G^6$, and more preferably halogen, —OR⁰, lower alkylene-OR⁰, —CO₂R⁰, lower alkylene-CO₂R⁰, —O-lower alkylene-CO₂R⁰, or oxo.

Group G⁶: halogen, lower alkyl which may be substituted with —OR⁰, halogeno-lower alkyl which may be substituted with —OR⁰, —OR⁰, —CN, —N(R⁰)₂, —CO₂R⁰, —CO₂-lower alkylene-aryl, —C(O)N(R⁰)₂, lower alkylene-OC(O)R⁰, lower alkylene-OC(O)aryl, lower alkylene-CO₂R⁰, halogeno-lower alkylene-CO₂R⁰, lower alkylene-CO₂-lower alkylene-aryl, lower alkylene-C(O)N(R⁰)₂, halogeno-lower alkylene-C(O)N(R⁰)₂, —O-lower alkylene-CO₂R⁰, —O-lower alkylene-CO₂-lower alkylene-aryl, —O-lower alkylene-C(O)N(R⁰)₂, —O-halogeno-lower alkylene-CO₂R⁰, —O-halogeno-lower alkylene-C(O)N(R⁰)₂, —C(O)N(R⁰)S(O)₂-lower alkyl, lower alkylene-C(O)N(R⁰)S(O)₂-lower alkyl, —S(O)₂-lower alkyl, —S(O)₂N(R⁰)₂, heterocyclic group, —C(=NH)NH₂, —C(—NH)=NO—C(O)O—C₁₋₁₀ alkyl, —C(=NOH)NH₂, —C(O)N=C(N(R⁰)₂)₂, —N(R⁰)C(O)R⁰, —N(R⁰)C(O)-lower alkylene-OR⁰, —N(R⁰)C(O)OR⁰, —N(R⁰)S(O)₂-lower alkyl, —C(aryl)₃, and oxo.

Provided that the "aryl" and the "heterocyclic group" in Group G⁶ may each be substituted with a group selected from the group consisting of halogen, lower alkyl, halogeno-lower alkyl, —OR⁰, —O-halogeno-lower alkyl, oxo, and thioxo (=S).

The substituent for the "aryl" which may be substituted in R⁴; and the substituent for the "heteroaryl" which may be substituted in R⁷ are preferably a group selected from the group consisting of halogen, lower alkyl, halogeno-lower alkyl, —OR⁰, and —O-halogeno-lower alkyl.

The substituent for the "aryl" and "heteroaryl" which may be each substituted in R⁹ is preferably a group selected from the group consisting of halogen, lower alkyl, halogeno-lower alkyl, —OR⁰, and —O-halogeno-lower alkyl.

The substituent for the "aryl" which may each be substituted in R⁵ is preferably a group selected from the group consisting of halogen, lower alkyl, halogeno-lower alkyl, —OR⁰, and —O-halogeno-lower alkyl.

Preferred embodiments of the present invention will be described below.

(a) R¹ is preferably -(lower alkylene which may be substituted)-OH, or cycloalkyl, aryl, or a heterocyclic group, which may be each substituted. More preferably, it is (lower alkylene which may be substituted)-OH, or cyclopentyl, cyclohexyl, phenyl, tetrahydrofuryl, tetrahydropyranyl, pyrrolidyl, or piperidyl, which may be each substituted. More preferably, it is (lower alkylene which may be substituted with a group selected from the group consisting of phenyl which may be substituted with halogen, lower alkyl, or —OR⁰, and —OH)—OH, or cycloalkyl substituted with a group selected from the group consisting of —OR⁰, —N(R⁰)₂, —N(R⁰)C(O)R⁰, —N(R⁰)C(O)-lower alkylene-OR⁰, —N(R⁰)S(O)₂-lower alkyl, and a heterocyclic group. Even more preferably, it is (lower alkylene which may be substituted with a group selected from the group consisting of phenyl which may be substituted with halogen, lower alkyl or —OR⁰, and —OH)—OH, or cyclopentyl or cyclohexyl, which is each substituted with a group selected from the group consisting of —OR⁰, —N(R⁰)₂, —N(R⁰)C(O)R⁰, —N(R⁰)C(O)-lower alkylene-OR⁰, —N(R⁰)S(O)₂-lower alkyl and a heterocyclic group. Particularly preferably, it is cyclohexyl substituted with a group selected from the group consisting of —OR⁰, —N(R⁰)C(O)R⁰, and —N(R⁰)S(O)₂-lower alkyl.

(b) R² is preferably aryl which may be substituted, and more preferably phenyl which may be substituted with halogen, lower alkyl, or —OR⁰, and even more preferably phenyl substituted with halogen.

(c) R³ is preferably —H.

(d) R⁴ is preferably —N(R⁰)-lower alkylene-(aryl or heteroaryl, which may be each substituted) or —N(R⁰)—O-lower alkylene-(aryl or heteroaryl, which may be each substituted). More preferably, it is —NH-lower alkylene-(phenyl, pyridyl, N-oxidopyridyl, thienyl, or thiazolyl, which may be each substituted) or —NH—O-lower alkylene-(phenyl, pyridyl, N-oxidopyridyl, thienyl, or thiazolyl, which may be each substituted). More preferably, it is —NH-lower alkylene-(phenyl, pyridyl, N-oxidopyridyl, thienyl, or thiazolyl, which may each be substituted with a group selected from the group consisting of halogen, —OR⁰, lower alkylene-OR⁰, —CO₂R⁰, lower alkylene-CO₂R⁰, and —O-lower alkylene-CO₂R⁰) or —NH—O-lower alkylene-(phenyl, pyridyl, N-oxidopyridyl, thienyl, or thiazolyl, which may each be substituted with a group selected from the group consisting of halogen, —OR⁰, lower alkylene-OR⁰, —CO₂R⁰, lower alkylene-CO₂R⁰, and —O-lower alkylene-CO₂R⁰). Even more preferably, it is —NH-lower alkylene-(phenyl which may be substituted with a group selected from the group consisting of halogen, —OR⁰, lower alkylene-OR⁰, —CO₂R⁰, lower alkylene-CO₂R⁰, and —O-lower alkylene-CO₂R⁰) or —NH—O-lower alkylene-(phenyl which may be substituted with a group selected from the group consisting of halogen, —OR⁰, lower alkylene-OR⁰, —CO₂R⁰, lower alkylene-CO₂R⁰, and —O-lower alkylene-CO₂R⁰).

(e) R⁵ is preferably halogen or —OR⁰.

(f) m is preferably 0 or 1, and more preferably 0.

In further preferred embodiments, the compounds having any combination of each of the preferable groups as described in (a) to (f) above are preferred.

Furthermore, other preferred embodiments for the compound of the present invention represented by the general formula (I) are shown below.

(1) A compound represented by the general formula (I), wherein R³ is —H.

(2) The compound as described in (1), wherein R² is phenyl which may be substituted with halogen, lower alkyl, or —OR⁰.

(3) The compound as described in (2), wherein R⁴ is —N(R⁰)-lower alkylene-(aryl or heteroaryl, which may each be substituted), or —N(R⁰)—O-lower alkylene-(aryl or heteroaryl, which may each be substituted).

(4) The compound as described in (3), wherein R¹ is (lower alkylene which may be substituted with a group selected from the group consisting of phenyl which may be substituted with halogen, lower alkyl or —OR⁰, and —OH)—OH; or cycloalkyl substituted with a group selected from the group consisting of —OR⁰, —N(R⁰)₂, —N(R⁰)C(O)R⁰, —N(R⁰)-lower alkylene-OR⁰, —N(R⁰)S(O)₂-lower alkyl, and a heterocyclic group.

(5) A compound represented by the general formula (I) selected from the group consisting of:

(3R,4R)-3-(2,4-dichlorophenyl)-2-{(1S,2S)-2-[(methylsulfonyl)amino]cyclohexyl}-1-oxo-N-(pyridin-2-ylmethoxy)-1,2,3,4-tetrahydroisoquinoline-4-carboxamide, (3R,4R)-3-(2,4-dichlorophenyl)-2-{(1S,2S)-2-[(methylsulfonyl)amino]cyclohexyl}-N-[(1-oxidopyridin-2-yl)methoxy]-1-oxo-1,2,3,4-tetrahydroisoquinoline-4-carboxamide, 3-{[({[(3R,4R)-3-(2,4-dichlorophenyl)-2-{(1S,2S)-2-[(methylsulfonyl)amino]cyclohexyl}-1-oxo-1,2,3,4-tetrahydroisoquinolin-4-yl]carbonyl}amino)oxy]methyl}benzoic acid, (4-{[({[(3R,4R)-3-(2,4-dichlorophenyl)-2-{(1S,2S)-2-[(methylsulfonyl)amino]cyclohexyl}-1-oxo-1,2,3,4-tetrahydroisoquinolin-4-yl]carbonyl}amino)oxy]methyl}phenyl)acetic acid, (3-{[({[(3R,4R)-3-(2,4-dichlorophenyl-2-{(1S,2S)-2-[(methylsulfonyl)amino]cyclohexyl}-1-oxo-1,2,3,4-tetrahydroisoquinolin-4-yl]carbonyl}amino)oxy]methyl}phenoxy)acetic acid, {3-[2-({[(3R,4R)-3-(2,4-dichlorophenyl)-2-{(1S,2S)-2-[(methylsulfonyl)amino]cyclohexyl}-1-oxo-1,2,3,4-tetrahydroisoquinolin-4-yl]carbonyl}amino)ethyl]phenyl}(difluoro)acetic acid, (3R,4R)-3-(2,4-dichlorophenyl)-2-{(1S,2S)-2-[(methylsulfonyl)amino]cyclohexyl}-N-(2-{3-[(methylsulfonyl)carbamoyl]phenyl}ethyl)-1-oxo-1,2,3,4-tetrahydroisoquinoline-4-carboxamide, {4-[2-({[(3R,4R)-3-(2,4-dichlorophenyl)-2-{(1S,2S)-2-[(methylsulfonyl)amino]cyclohexyl}-1-oxo-1,2,3,4-tetrahydroisoquinolin-4-yl]carbonyl}amino)ethyl]phenyl}acetic acid, and 4-(3-{[({[(3R,4R)-3-(2,4-dichlorophenyl)-2-{(1S,2S)-2-[(methylsulfonyl)amino]cyclohexyl}-1-oxo-1,2,3,4-tetrahydroisoquinolin-4-yl]carbonyl}amino)oxy]methyl}phenoxy)butanoic acid;

or a pharmaceutically acceptable salt thereof.

Furthermore, in the present specification, the "irritable bowel syndrome" (which is hereinafter referred to as IBS) includes diarrhea type IBS, constipation type IBS, and alternating type IBS. The disease to which the therapeutic agent of the present invention is applied is preferably diarrhea type IBS or alternating type IBS, and particularly preferably diarrhea type IBS.

The compounds of the present invention may exist in the form of other tautomers or geometrical isomers depending on the kind of the substituents. In the present specification, the compound may be described in only one form of an isomer, but the present invention includes the isomers, an isolated form or a mixture of the isomers.

Furthermore, the compound (I) may have asymmetric carbons or axial asymmetries, and correspondingly, it may exist in the form of optical isomers such as an (R)-form, an (S)-form, and the like. The compound of the present invention includes both a mixture and an isolated form of these optical isomers.

In addition, a pharmaceutically acceptable prodrug of the compound (I) is also included in the present invention. The pharmaceutically acceptable prodrug refers to a compound, having a group which can be converted into an amino group, OH, $CO_2H$, and the like of the present invention, by solvolysis or under a physiological condition. Examples of the group which forms the prodrug include those as described in Prog. Med., 5, 2157-2161 (1985), or "Pharmaceutical Research and Development" (Hirokawa Publishing Company, 1990), vol. 7, Drug Design, 163-198.

Furthermore, the compound of the present invention may form an acid-addition salt or a salt with a base, depending on the kind of the substituents, and these salts are included in the present invention as long as they are pharmaceutically acceptable salts. Specifically, examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid, or the like, and salts with inorganic bases such as sodium, potassium, magnesium, calcium, aluminum, and the like, and with organic bases such as methylamine, ethylamine, ethanolamine, lysine, ornithine, and the like, ammonium salts.

In addition, the present invention also includes various hydrates and solvates, and polymorphism of the compound of the present invention and a pharmaceutically acceptable salt thereof. Furthermore, the present invention also includes the compounds that are labeled with various radioactive or non-radioactive isotopes.

(Production Process)

The compound of the present invention and a pharmaceutically acceptable salt thereof may be prepared by applying various known synthetic methods, by the use of the characteristics based on their basic backbones or the kind of the substituents. Here, depending on the kind of the functional groups, it is in some cases effective from the viewpoint of the preparation techniques to substitute the functional group with an appropriate protecting group (a group which may be easily converted into the functional group), during the steps from starting materials to intermediates. Examples of such functional groups include an amino group, a hydroxyl group, a carboxyl group, and the like, and examples of a protecting group thereof include those as described in "Protective Groups in Organic Synthesis" ($3^{rd}$ edition, 1999), edited by Greene and Wuts, which may be optionally selected and used in response to the reaction conditions. By such a method, a desired compound can be obtained by introducing the protecting group and carrying out the reaction, and then, if desired, removing the protecting group.

In addition, a prodrug of the compound (I) can be prepared by introducing a specific group during the steps from starting materials to intermediates, in the same manner as for the aforementioned protecting groups, or by carrying out the reaction using the obtained compound (I). The reaction may be carried out by employing a method known to a person skilled in the art, such as general esterification, amidation, and dehydration.

Hereinbelow, the representative production processes of the compounds of the present invention will be described. Each of the production processes can also be carried out with reference to the reference documents attached to the present description. Further, the production processes of the present invention are not limited to the examples as shown below.

(Production Process 1)

[Chem. 5]

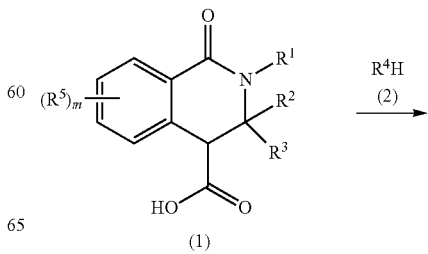

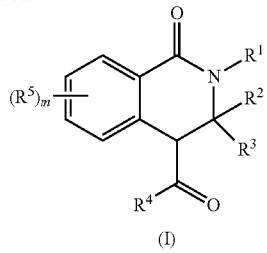

(I)

This production process is a process for obtaining the compound (I) of the present invention by subjecting a carboxylic acid compound (1) and an amine compound (2) to amidation.

The reaction can be carried out using equivalent amounts of the carboxylic acid compound (1) and the amine compound (2), or an excess amount of either, and stirring them from under cooling to under heating, preferably at −20° C. to 60° C., usually for 0.1 hour to 5 days, in a solvent which is inert to the reaction, in the presence of a condensing agent. The solvent as used herein is not particularly limited, but examples thereof include aromatic hydrocarbons such as benzene, toluene, xylene, and the like, halogenated hydrocarbons, such as dichloromethane, 1,2-dichloroethane, chloroform, and the like, ethers such as diethyl ether, tetrahydrofuran (THF), dioxane, dimethoxyethane, and the like, N,N-dimethylformamide (DMF), N,N-dimethylacetamide (DMA), N-methylpyrrolidin-2-one (NMP), dimethyl sulfoxide (DMSO), ethyl acetate, acetonitrile, water, and the like, or mixture thereof. Examples of the condensing agent include 1-(3-dimethylaminopropyl)-3-ethylcarbodiimide (WSC), dicyclohexylcarbodiimide, 1,1'-carbonyldiimidazole (CDI), diphenyl phosphoryl azide, phosphorous oxychloride, and the like, but are not limited to these. An additive (for example, 1-hydroxybenzotriazole (HOBt), and the like) may be preferable for the reaction in some cases. It may be advantageous for the smooth progress of the reaction to carry out the reaction in the presence of an organic base such as triethylamine, N,N-diisopropylethylamine, pyridine, N,N-dimethyl-4-aminopyridine (DMAP), and the like, or an inorganic base such as potassium carbonate, sodium carbonate, potassium hydroxide, and the like in some cases.

In addition, a process in which the carboxylic acid compound (1) is derived into a reactive derivative, and then reacted with the amine compound (2) can also be used. Examples of the reactive derivative of the carboxylic acid as used herein include an acid halide obtained by the reaction with a halogenating agent such as phosphorous oxychloride, thionyl chloride, and the like, a mixed acid anhydride obtained by the reaction with isobutyl chloroformate, or the like, an active ester obtained by the condensation with 1-hydroxybenzotriazole or the like, and others. The reaction of the reactive derivative and the amine compound (2) can be carried out from under cooling to under heating, preferably at −20° C. to 60° C., in a solvent which is inert to the reaction, such as halogenated hydrocarbons, aromatic hydrocarbons, ethers, and the like.

Production Process 2: Other Production Processes

Furthermore, some compounds represented by the formula (I) can also be prepared by subjecting the compound of the present invention obtained as above to any combination of the processes that are usually employed by a skilled person in the art, such as conventional amidation, hydrolysis, N-oxidation, reductive amination, sulfonylation, oxidation, reduction, N-alkylation, O-alkylation, and the like. For example, they can be prepared by the reactions as below, the methods described in Examples to be described later, a method apparent to a skilled person in the art, or a modified method thereof.

2-1: Amidation

An amide compound can be obtained by subjecting a carboxylic acid compound and an amine compound to amidation.

The amidation can be carried out in the same manner as in Production Process 1.

2-2: Hydrolysis

A compound having a carboxyl group can be prepared by hydrolyzing a compound having an ester group.

The reaction can be carried out from under cooling to under heating in a solvent such as aromatic hydrocarbons, ethers, halogenated hydrocarbons, alcohols, DMF, DMA, NMP, DMSO, pyridine, water, and the like in the presence of an acid including mineral acids such as sulfuric acid, hydrochloric acid, hydrobromic acid, and the like, and organic acids such as formic acid, acetic acid, and the like; or in the presence of a base such as lithium hydroxide, sodium hydroxide, potassium hydroxide, potassium carbonate, sodium carbonate, cesium carbonate, ammonia, and the like.

2-3: N-Oxidation

An N-oxide compound can be prepared by oxidating the nitrogen atom of a heterocycle having a nitrogen atom, such as pyridine and the like, with various oxidants.

The reaction can be carried out from under cooling, at room temperature to under heating, using an equivalent amount or excess amount of m-chloroperbenzoic acid, peracetic acid, aqueous hydrogen peroxide, and the like as an oxidant, in a solvent such as halogenated hydrocarbons, acetic acid, water, and the like.

2-4: Reductive Amination

An amine compound can be alkylated by reducing an imine compound which is prepared from a primary or secondary amine compound and a carbonyl compound.

The reaction can be carried out using equivalent amounts of an amine compound and a carbonyl compound, or an excessive amount of either thereof, in the presence of a reducing agent, in a solvent such as halogenated hydrocarbons, alcohols, ethers, and the like. As the reducing agent, sodium cyanoborohydride, sodium triacetoxyborohydride, sodium borohydride, and the like can be used. The reaction may be preferably carried out in the presence of an acid such as acetic acid, hydrochloric acid, titanium (IV) isopropoxide complexes, and the like in some cases.

2-5: Sulfonylation

A sulfonamide compound can be obtained by the sulfonylation of an amine compound.

The reaction can be carried out, for example, from under cooling, at room temperature to under heating, by using equivalent amounts of an amine compound and a sulfonyl halide, or an excessive amount of either thereof, in a solvent such as aromatic hydrocarbons, ethers, halogenated hydrocarbons, pyridine, and the like. It may be advantageous for the smooth progress of the reaction to carry out the reaction in the presence of an organic base such as triethylamine, N,N-diisopropylethylamine, pyridine, and the like, or an inorganic base such as potassium carbonate, sodium carbonate, potassium hydroxide, and the like in some cases.

(Production Processes for Starting Compounds)

The starting material used for the preparation of the compound of the present invention can be prepared, for example, by applying the methods described below, the methods described in Production Examples to be described later, a known method, a method apparent to a skilled person in the art, or a modified method thereof.
(Starting Material Synthesis 1)

[Chem. 6]

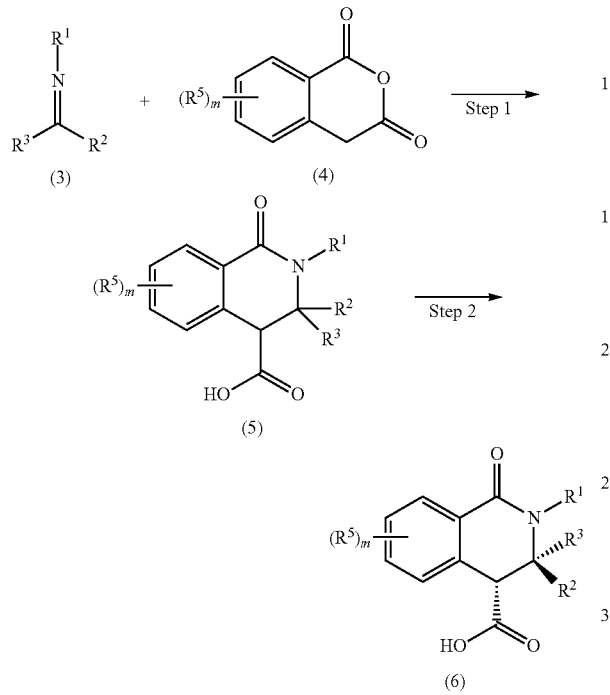

Step 1:
A compound (5) can be obtained by reacting a compound (3) with a compound (4).

The reaction can be carried out from at room temperature to under heating, using equivalent amounts of the compound (3) and the compound (4) or an excessive amount of either thereof, in a solvent such as ethers, halogenated hydrocarbons, aromatic hydrocarbons, and the like.

Step 2:
When $R^3$ is —H, a compound (6) in which the substituents at the 3- and 4-positions are trans can be obtained by isomerizing the compound (5).

The reaction can be carried out by treating the compound (5) with a base such as sodium hydroxide, potassium hydroxide, and the like, from at room temperature to under heating, in a solvent such as halogenated hydrocarbons, alcohols, water, and the like.

(Starting Material Synthesis 2)

[Chem. 7]

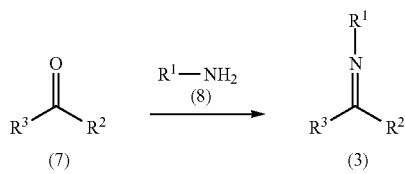

The compound (3) can be obtained by carrying out dehydration-condensation of a compound (7) with a compound (8).

The reaction can be carried out from at room temperature to under heating, using equivalent amounts of the compound (7) and the compound (8) or an excessive amount of either thereof, in a solvent such as halogenated hydrocarbons, aromatic hydrocarbons, and the like. It may be advantageous for the smooth progress of the reaction to use a dehydrating agent such as anhydrous sodium sulfate, anhydrous magnesium sulfate, Molecular Sieves, and the like in some cases.

(Starting Material Synthesis 3)

[Chem. 8]

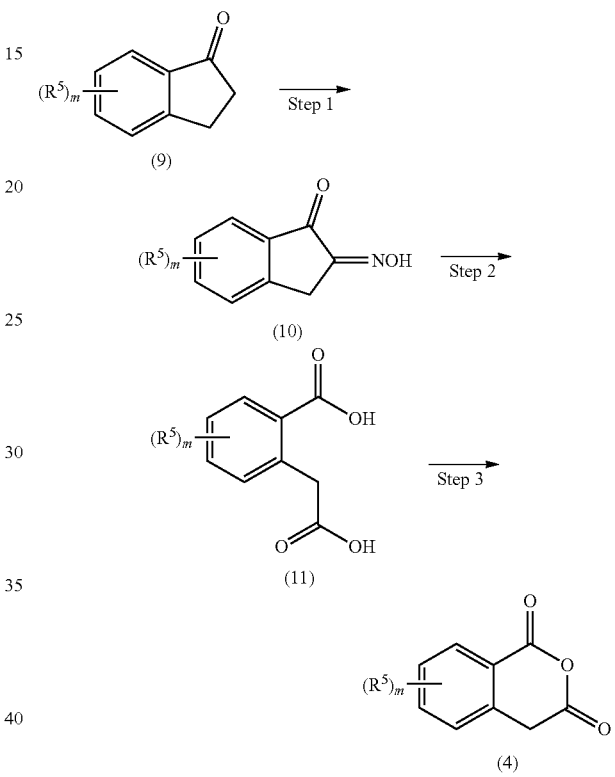

Step 1:
A compound (10) can be obtained by reacting a compound (9) with a nitrite.

The reaction can be carried out from under cooling, at room temperature to under heating in a solvent such as ethers, halogenated hydrocarbons, alcohols, and the like in the presence of a nitrite such as ethyl nitrite, butyl nitrite, isoamyl nitrite, and the like. According to the compounds, it is advantageous for the progress of the reaction to carry out the reaction in the presence of an acid such as acetic acid, hydrochloric acid, and the like, or a base such as sodium methoxide, sodium ethoxide, potassium tert-butoxide, and the like in some cases.

Step 2
A compound (11) can be prepared by subjecting the compound (10) to rearrangement and then to hydrolysis.

The rearrangement reaction can be carried out by treating the compound (10) with thionyl chloride, or the like under cooling.

The hydrolysis reaction can be carried out from at room temperature to under heating, in a solvent such as alcohols, water, and the like, using a base such as sodium hydroxide, potassium hydroxide, and the like.

Step 3

The compound (4) can be obtained by the dehydration of the compound (11).

The dehydration reaction can be carried out from at room temperature to under heating, using acetyl chloride or the like as a dehydrating agent.

The compound of the present invention is isolated and purified as a free compound, a pharmaceutically acceptable salt, hydrate, solvate, or polymorphism thereof. The pharmaceutically acceptable salt of the compound (I) of the present invention can be prepared by a salt formation reaction within a conventional technology.

The isolation and purification can be carried out by employing general chemical operations such as extraction, fractional crystallization, various types of fractional chromatography, and the like.

Various isomers can be separated by selecting an appropriate starting compound, or by making use of the difference in the physicochemical properties between isomers. For example, the optical isomer can be derived into a stereochemically pure isomer by means of general optical resolution methods (for example, fractional crystallization for inducing to diastereomeric salts with optically active bases or acids, chromatography using a chiral column, etc., and the like). In addition, the isomers can also be prepared from an appropriate optically active starting compound.

The pharmacological activity of the compound of the present invention was confirmed by the following test.

Test Example Example 1: BB2 Receptor Antagonistic Activity

A BB2 receptor binding test was carried out using a membrane sample prepared from a human prostate cancer-derived PC-3 cell. The PC-3 cell was cultured using an RPMI-1640 medium containing 5% fetal bovine serum, and then a membrane sample was prepared by the following methods. The cells detached by a trypsin treatment were added with a 50 mM Tris-HCl buffer (pH 7.4, containing 0.2 mg/ml trypsin inhibitor and 0.2 mg/ml benzamidine), and homogenized by Polytron. The cell suspension was centrifuged at 1,500 rpm for 10 minutes, and the supernatant thus obtained was subjected to 1 hour of ultracentrifugation at 37,000×g. The precipitate was suspended in the aforementioned buffer to a concentration of 0.4 mg protein/ml, and stored at −80° C.

The BB2 receptor binding test was carried out by the following method, and the receptor antagonistic activity of a compound to be tested was calculated. A 50 μl of the membrane sample, 50 μl of an assay buffer (20 mM HEPES-HBSS containing 0.1% bovine serum albumin and 0.1 mg/ml bacitracin, pH 7.4), $^{125}$I [Tyr$^4$] bombesin (0.075 nM) and 2 μl of the compound to be tested dissolved in dimethyl sulfoxide were added to a 96 well assay plate, and incubated at room temperature for 2 hours. Non-specific binding was measured using 1 μM of bombesin. After completion of the incubation, the reaction solution was filtered through a Whatman GF/B filter which had been soaked in 0.5% polyethyleneimine. The radioactivity on the filter was measured using a microplate scintillation counter (Top Count, Perkin-Elmer Co., Ltd.). The 50% binding inhibition concentrations of the representative Example Compounds are shown in Table 12. Further, Ex represents the number of the Example compound.

TABLE 12

| Ex | IC$_{50}$ (nM) |
| --- | --- |
| 61 | 12.8 |
| 62 | 18.3 |
| 236 | 3.0 |
| 542 | 4.7 |
| 560 | 4.8 |
| 589 | 5.7 |
| 631 | 4.5 |
| 700 | 6.7 |
| 701 | 7.4 |
| 709 | 8.9 |
| 712 | 6.7 |
| 856 | 6.8 |

Test Example Example 2: Restraint Stress-Induced Defecation Model

The compound to be tested of the present test was used by dissolving in water for injection containing 20% propylene glycol+20% Tween 80 or a 0.5% MC (methyl cellulose) solution.

Fifteen minutes after oral administration of the compound to be tested to a fed male Wistar rat, the animal was put into a restraint stress cage (KN-468, Natsume Seisakusho Co Ltd.). The number of feces excreted during a period from the restriction commencement to 1 hour thereafter was measured. Normal group was put into a separate cage, and number of feces excreted during 1 hour was measured in the same manner.

The inhibitory rates (%) of the representative Example Compounds when they were orally administered at a dose of 1 mg/kg are shown in Table 13. As a result, it was confirmed that the compound of the present invention exhibited an excellent action to improve the bowel movement symptom.

TABLE 13

| Ex | Inhibitory Rate (%) |
| --- | --- |
| 542 | 40.0 |
| 560 | 62.1 |
| 589 | 73.9 |
| 631 | 53.8 |
| 700 | 69.8 |
| 701 | 41.3 |
| 709 | 41.5 |
| 712 | 55.0 |
| 856 | 61.4 |

As a result of the test as described above, it was confirmed that the compound of the present invention has a BB2 receptor inhibitory action. From this point, it is obvious that the compound is useful as a therapeutic agent for the diseases associated with the BB2 receptors, in particular, IBS, cancers, functional dyspepsia, diabetic gastroparesis, reflux esophagitis, peptic ulcer, and the like.

The preparation containing one or two or more of the compound (I) of the present invention or a salt thereof as an active ingredient can be prepared in accordance with a generally used method, using a pharmaceutical carrier, an excipient, and the like, which are generally employed in the art.

The administration can be accompanied by any mode of oral administration via tablets, pills, capsules, granules, powders, liquid preparations, or the like; or parenteral administration via injections such as intraarticular, intravenous, or intramuscular injections, suppositories, eye drops, eye ointments, transdermal liquid preparations, ointments, transdermal patches, transmucosal liquid preparations, transmucosal patches, inhalations, and the like.

Regarding the solid composition for oral administration according to the present invention, tablets, powders, granules, or the like are used. In such a solid composition, one or two or more of active ingredients are mixed with at least one inactive excipient such as lactose, mannitol, glucose, hydroxypropylcellulose, microcrystalline cellulose, starch, polyvinyl pyrrolidone, and/or magnesium aluminometasilicate, and the like. According to a conventional method, the composition may contain inert additives such as a lubricant such as magnesium stearate, a disintegrator such as carboxymethyl starch sodium, a stabilizing agent, and a solubilizing agent. As necessary, tablets or pills may be coated with a sugar coating, or a film of a gastric or enteric material.

The liquid composition for oral administration includes pharmaceutically acceptable emulsions, solutions, suspensions, syrups, elixirs, or the like, and contains a generally used inert diluent such as purified water and ethanol. In addition to the inert solvent, this liquid composition may contain an auxiliary agent such as a solubilizing agent, a moistening agent, and a suspending agent, a sweetener, a flavor, an aroma, and an antiseptic.

The injections for parenteral administration include sterile aqueous or non-aqueous liquid preparations, suspensions, and emulsions. As the aqueous solvent, for example, distilled water for injection and physiological saline are included. Examples of the non-aqueous solvent include propylene glycol, polyethylene glycol, plant oils such as olive oil, alcohols such as ethanol, and Polysorbate 80 (Japanese Pharmacopeia), and the like. Such a composition may further contain a tonicity agent, an antiseptic, a moistening agent, an emulsions, a dispersant, a stabilizer, or a solubilizing agent. These are sterilized, for example, by filtration through a bacteria retaining filter, blending of a bactericide, or irradiation. In addition, these can also be used by preparing a sterile solid composition, and dissolving or suspending in sterile water or a sterile solvent for injection prior to its use.

The drug for external use includes ointments, plasters, creams, jellies, cataplasms, sprays, lotions, eye drops, eye ointments, and the like. The drug contains generally used ointment bases, lotion bases, aqueous or non-aqueous solutions, suspensions, emulsions, and the like. Examples of the ointment or lotion bases include polyethylene glycol, propylene glycol, white vaseline, bleached beeswax, polyoxyethylene hydrogenated castor oil, glyceryl monostearate, stearyl alcohol, cetyl alcohol, lauromacrogol, sorbitan sesquioleate, and the like.

Regarding a transmucosal agent such as an inhalation, a transnasal agent, and the like, those in a solid, liquid, or semi-solid state are used, and may be produced in accordance with a conventionally known method. For example, a known excipient, and in addition, a pH adjusting agent, an antiseptic, a surfactant, a lubricant, a stabilizing agent, a thickening agent, and the like may be added thereto, if desired. For their administration, an appropriate device for inhalation or blowing may be used. For example, a compound may be administered alone or as a powder of formulated mixture, or as a solution or suspension in combination with a pharmaceutically acceptable carrier, using a conventionally known device or sprayer, such as a measured administration inhalation device and the like. The dry powder inhaler or the like may be for single or multiple administration use, and a dry powder or a powder-containing capsule may be used. Alternatively, this may be in a form such as a high pressurized aerosol spray which uses an appropriate propellant, for example, a suitable gas such as chlorofluoroalkane, hydrofluoroalkane, carbon dioxide, and the like.

In the case of conventional oral administration, the daily dose may be generally from about 0.001 to 100 mg/kg, preferably from 0.1 to 30 mg/kg, and even more preferably 0.1 to 10 mg/kg, per body weight, and this is administered in one portion or in 2 to 4 divided portions. Also, in the case of intravenous administration, the daily dose is from about 0.0001 to 10 mg/kg per body weight, once a day or twice or more times a day. In addition, a transmucosal agent is administered at a dose from about 0.001 to 100 mg/kg per body weight, once a day or twice or more times a day. The dose is appropriately decided in response to an individual case by taking symptoms, age, gender, or the like into consideration.

The compound of the present invention can be used in combination with various therapeutic or prophylactic agents for the diseases, for which the compound of the present invention is considered effective. The combined preparation may be administered simultaneously, or separately and continuously or at a desired time interval. The preparations to be co-administered may be a blend, or prepared individually.

EXAMPLES

Hereinbelow, the production processes for the compound (I) of the present invention will be described in more detail with reference to Examples. The compound of the present invention is not limited to the compounds described in Examples below. Further, the production processes for the starting compounds will be described in Production Examples.

In addition, the following abbreviations are used in Examples, Production Examples, and Tables to be described later.

PEx: Production Example, Ex: Example, No: Compound No., Data: Physicochemical Data (EI+: m/z value in EI–MS (cation) (unless otherwise mentioned, (M)$^+$.), FAB+: m/z value in FAB–MS (cation) (unless otherwise mentioned, (M+H)$^+$.), FAB–: m/z value in FAB–MS (anion) (unless otherwise mentioned, (M–H)$^-$.), ESI+: m/z value in ESI–MS (cation) (unless otherwise mentioned, (M+H)$^+$.), ESI–: m/z value in ESI–MS (anion) (unless otherwise mentioned, (M–H)$^-$.), CI+: m/z value in CI–MS (cation) (unless otherwise mentioned, (M+H)$^+$.), APCI+: m/z value in APCI–MS (cation) (unless otherwise mentioned, (M+H)$^+$.), APCI–: m/z value in APCI–MS (anion) (unless otherwise mentioned, (M–H)$^-$.), NMR1: δ (ppm) of characteristic peak in δ (ppm) by $^1$H-NMR in DMSO-$d_6$), Structure: Structural Formula (a case where HCl, HBr, fum, or TFA is described in the structural formula indicates that the compound is hydrochloride, hydrobromide, fumarate, or trifluoroacetate, respectively. In the case where a numeral is attached before a salt component, the numeral means a molar ratio of the compound to the salt component. For example, a case where 2HCl is described means that the compound is dihydrochloride. Further, a case where H$_2$O is described in the structural formula indicates that the compound is a hydrate in each case.), Syn: Production Process (the numeral shows that it was prepared using a corresponding starting material, similar to the case of an Example Compound having its number as the Example No.). In the case where P is attached before the numeral, the number shows that it was produced using a corresponding starting material, similar to the case of a Production Example Compound having its number as the Production Example No. A case where a plurality of the numerals is described indicates that the compound was prepared by carrying out the reaction in order starting from the front numeral, using a corresponding starting material. Note: (the racemic mixture means a racemic mixture, the diastereo mixture means a diastero mixture, and the chiral compound means a chiral compound, in which a part of its stereochemistry is not clear. Further, less polar and more polar mean a low polarity product and a high polarity product, respectively, as compared with the corresponding diastereomers, in thin layer chromatography. Further, 3,4-trans, 1',2'-cis, and the like mean the relative configurations of the substituents or the like. Provided that the numeral which is not dashed means the position substituted in the tetrahydroisoquinolin-1-one ring, and the dashed numeral means the position substituted in the substituent at the 2-position in a tetrahydroisoquinolin-1-one ring. For example, 3,4-trans indicates that the substituents at the 3- and 4-positions in the tetrahydroisoquinolin-1-one ring are trans.) Boc: a tert-butoxycarbonyl group, DBU: 1,8-diazabicyclo[5.4.0]undec-7-ene.

In addition,

[Chem. 9]

indicates that the double bond is cis or trans, or a mixture thereof.

Production Example 1

10 g of 5-(benzyloxy)-1H-indene-1,2(3H)-dione 2-oxime was added to 20 ml of thionyl chloride at 0° C., followed by stirring for 20 minutes under the same condition. After warming to room temperature, thionyl chloride was evaporated under reduced pressure. To the residue was added 20 ml of a 40% aqueous potassium hydroxide solution, followed by heating under reflux overnight. After cooling to room temperature, and neutralizing by the addition of concentrated hydrochloric acid, the precipitated solid was collected by filtration to obtain 9.9 g of 4-(benzyloxy)-2-(carboxymethyl)benzoic acid as a dark brown powder.

Production Example 2

To a mixture of 2.01 g of diethyl [3-(1,3-dioxolan-2-yl)phenyl]malonate, 2.89 g of calcium chloride, and 50 ml of ethanol was added 2.47 g of sodium borohydride under ice-cooling, followed by stirring at the same temperature for 2 hours and at room temperature for 4 hours. To the reaction solution was added 10 ml of water at room temperature, followed by stirring for 30 minutes. The insoluble material was separated by filtration using Celite, and the filtrate was concentrated under reduced pressure to obtain 0.76 g of 2-[3-(1,3-dioxolan-2-yl)phenyl]propane-1,3-diol as a colorless oily substance.

Production Example 3

A mixture of 1.83 g of 2-[3-(1,3-dioxolan-2-yl)phenyl]propane-1,3-diyl diacetate and 60 ml of a 83% aqueous acetic acid solution was stirred at 50° C. for 2 hours. The reaction solution was concentrated under reduced pressure to obtain 1.59 g of 2-(3-formylphenyl)propane-1,3-diyl diacetate as a colorless oily substance.

Production Example 4

To a solution of 958 mg of (6-methylpyridin-3-yl)methanol, 1.3 ml of triethylamine, and 95 mg of DMAP in 40 ml of dichloromethane was added dropwise 1.08 ml of benzoyl chloride, followed by stirring at room temperature. To the reaction solution was added water, followed by carrying out an extraction operation with chloroform. The organic layer was washed with a saturated aqueous sodium chloride solution, then dried over anhydrous magnesium sulfate, and concentrated under reduced pressure. The obtained residue was purified by silica gel column chromatography (eluent: hexane-ethyl acetate) to obtain 1767 mg of (6-methylpyridin-3-yl)methyl benzoate.

Production Example 5

To a solution of 1767 mg of (6-methylpyridin-3-yl)methyl benzoate in 26.5 ml of chloroform was added 2440 mg of m-chloroperbenzoic acid under ice-cooling, followed by stirring for 1 hour. An aqueous potassium carbonate solution was added thereto to carry out a liquid separation operation, and the organic layer was washed with a saturated aqueous sodium chloride solution and then dried over anhydrous magnesium sulfate. The residue was concentrated under reduced pressure to obtain 1891 mg of (6-methyl-1-oxidopyridin-3-yl)methyl benzoate.

Production Example 6

To a solution of 1891 mg of (6-methyl-1-oxidopyridin-3-yl)methyl benzoate in 38 ml of DMF was added 11 ml of trifluoroacetic anhydride, followed by stirring at room temperature overnight. After evaporating trifluoroacetic anhydride under reduced pressure, a saturated aqueous sodium hydrogen carbonate solution was added thereto, followed by extraction with chloroform. The organic layer was dried over anhydrous magnesium sulfate and then concentrated under reduced pressure. The residue was purified by silica gel column chromatography (eluent: chloroform-methanol) to obtain 3.675 g of [6-(hydroxymethyl)pyridin-3-yl]methyl benzoate.

Production Example 7

To a solution of 858 mg of pyrazine-2,5-diyl bis(methylene) diacetate in 8.6 ml of methanol was added 600 mg of zeolite, followed by heating under reflux for 4 days. Zeolite was removed by filtration and then concentrated, and the residue was purified by silica gel column chromatography (eluent: chloroform-methanol) to obtain 209 mg of [5-(hydroxymethyl)pyrazine-2-yl]methyl acetate.

Production Example 8

To a mixture of 313 mg of 6-(hydroxymethyl)nicotinamide, 540 mg of triphenylphosphine, 503 mg of N-hydroxyphthalimide, and 4.7 ml of THF was added dropwise 0.53 ml of diisopropyl azodicarboxylate, followed by stirring overnight. After concentration, the solid thus produced was suspended in water, and ethyl acetate was added thereto. After stirring for 30 minutes, the solid was collected by filtration to obtain 292 mg of 6-{[(1,3-dioxo-1,3-dihydro-2H-isoindol-2-yl)oxy]methyl}nicotinamide.

Production Example 9

To a suspension of 292 mg of 6-{[(1,3-dioxo-1,3-dihydro-2H-isoindol-2-yl)oxy]methyl}nicotinamide in 4.4 ml of methanol was added 0.2 ml of a 40% methyl amine/methanol solution, followed by stirring at room temperature for 1 hour. The reaction solution was concentrated, ethyl acetate was added thereto, and the precipitated crystal was separated by filtration and then concentrated under reduced pressure to obtain 146 mg of 6-[(aminooxy)methyl]nicotinamide.

Production Example 10

To a mixture of 3.0 g of 6-chloronicotinic acid and 111 ml of THF was added 6.4 g of potassium tert-butoxide, followed by heating under reflux for 1 day. The reaction solution was poured into water, neutralized with citric acid, and then extracted with ethyl acetate. The organic layer was dried over anhydrous magnesium sulfate and then concentrated under reduced pressure to obtain 2.16 g of 6-tert-butoxynicotinic acid.

Production Example 11

To a mixed liquid of 2163 mg of 6-tert-butoxynicotinic acid and 32 ml of acetone were added 2297 mg of potassium carbonate and 0.97 ml of methyl iodide, followed by stirring at 35° C. overnight. Ethyl acetate and water were added thereto to carry out liquid separation, and the organic layer was dried over anhydrous magnesium sulfate and then concentrated under reduced pressure to obtain 1.191 g of methyl 6-tert-butoxynicotinate.

Production Example 12

To a mixed liquid of 1191 mg of methyl 6-tert-butoxynicotinate and 35.7 ml of ethanol was slowly added 2153 mg of sodium borohydride, followed by stirring at 50° C. for 18 hours. After the addition of methanol, water and ethyl acetate were added thereto to carry out an extraction operation. The organic layer was dried over anhydrous magnesium sulfate and then concentrated under reduced pressure to obtain 0.949 g of (6-tert-butoxypyridin-3-yl)methanol.

Production Example 13

To a mixed liquid of 1020 mg of 5-[(aminooxy)methyl]-2-tert-butoxypyridine, which had been obtained by reacting (6-tert-butoxypyridin-3-yl)methanol and N-hydroxyphthalimide in accordance with Production Example 8, and then carrying out the removal of phthalimide in accordance with Production Example 9, and 20 ml of ethyl acetate was added 1.3 ml of concentrated hydrochloric acid under ice-cooling, followed by stirring for 30 minutes. The resulting solid was separated by filtration, concentrated hydrochloric acid was further added to the filtrate, and the precipitated solid was collected by filtration to obtain 351 mg of 5-[(aminooxy)methyl]pyridin-2(1H)-one hydrochloride as a colorless solid.

Production Example 14

To a mixture of 659 mg of 1-(chloromethyl)-4-(methylsulfonyl)benzene and 10 ml of DMSO were added 525 mg of N-hydroxyphthalimide and 445 mg of potassium carbonate, followed by stirring at 50° C. for 2 hours. The reaction solution was cooled, water was then added thereto, and the precipitated crystal was collected by filtration to obtain 685 mg of 2-{[4-(methylsulfonyl)benzyl]oxy}-1H-isoindole-1,3 (2H)-dione as a white solid.

Production Example 15

To a solution of 5.08 g of tert-butyl [4-(hydroxymethyl)phenoxy]acetate and 4.6 ml of triethylamine in 30 ml of dichloromethane was added 1.98 ml of methanesulfonyl chloride under ice-cooling, followed by stirring for 1 hour under ice-cooling. The reaction solution was poured into water, followed by extraction with ethyl acetate. The organic layer was washed with saturated brine and dried over anhydrous magnesium sulfate, and the solvent was then evaporated. To a solution of the obtained residue in 40 ml of DMF was added 4.26 g of sodium azide, followed by stirring at 60° C. for 15 hours. After leaving it to be cooled, the reaction solution was poured into water, followed by extraction with ethyl acetate. The organic layer was washed with water and saturated brine, and dried over anhydrous magnesium sulfate, and the solvent was then evaporated. The residue was purified by silica gel column chromatography (eluent: ethyl acetate-hexane) to obtain 5.16 g of tert-butyl [3-(azidomethyl)phenoxy]acetate as a pale yellow oily substance.

Production Example 16

To a mixed liquid of 5.00 g of methyl 5-formylthiophene-3-carboxylate and 50 ml of THF was added 0.67 g of sodium borohydride under ice-cooling. To the reaction solution was added dropwise 5 ml of methanol, followed by stirring for 1 hour under ice-cooling. The reaction solution was added with 1 M hydrochloric acid, extracted with ethyl acetate, and washed with a saturated aqueous sodium hydrogen carbonate solution and a saturated aqueous sodium chloride solution. The organic layer was dried over anhydrous magnesium sulfate and the solvent was then evaporated to obtain 4.86 g of methyl 5-(hydroxymethyl)thiophene-3-carboxylate as a pale yellow oily substance.

Production Example 17

To a mixed liquid of 4.86 g of methyl 5-(hydroxymethyl)thiophene-3-carboxylate and 50 ml of dichloromethane was added 4.12 ml of thionyl chloride under ice-cooling, followed by stirring at room temperature for 15 hours. The reaction solution was concentrated, added with ethyl acetate, and then washed with a saturated aqueous sodium hydrogen carbonate solution and a saturated aqueous sodium chloride solution. After drying over anhydrous magnesium sulfate, the solvent was then evaporated to obtain 4.90 g of methyl 5-(chloromethyl)thiophene-3-carboxylate as a pale yellow oily substance.

Production Example 18

To a solution of 3.69 g of di-tert-butyl imidodicarbonate in 54 ml of DMF was added 1.91 g of potassium tert-butoxide at 0° C. under argon, followed by stirring at room temperature for 1 hour. A solution of 2.7 g of methyl 5-(chloromethyl)thiophene-3-carboxylate in 8.1 ml of DMF was slowly added thereto, followed by stirring at room temperature overnight. Water and ethyl acetate were added to the reaction solution, followed by carrying out an extraction operation, and the organic layer was washed with a saturated aqueous sodium chloride solution, dried over anhydrous magnesium sulfate, and then concentrated under reduced pressure. The residue was purified by silica gel column chromatography (eluent: hexane-ethyl acetate) to obtain 4.394 g of methyl 5-{[bis(tert-butoxycarbonyl)amino]methyl}thiophene-3-carboxylate.

Production Example 19

To a mixed liquid of 400 mg of ethyl difluoro(3-methylphenyl) acetate and 10 ml of carbon tetrachloride were added 349 mg of N-bromosuccinimide and 15 mg of 2,2'-azobis(isobutyronitrile), followed by heating under reflux for 2 hours. After cooling the reaction solution, the insoluble material was separated by filtration, and the filtrate was concentrated. The residue was added with hexane, washed with a saturated aqueous sodium hydrogen carbonate solution and a saturated aqueous sodium chloride solution, and dried over anhydrous magnesium sulfate. After evaporating the solvent, the residue was purified by silica gel column chromatography (eluent: hexane-ethyl acetate) to obtain 458 mg of ethyl [3-(bromomethyl)phenyl](difluoro) acetate as a colorless oily substance.

Production Example 20

To a mixed liquid of 2.89 g of ethyl 2-methyl-2-(3-methylphenyl)propionate and 90 ml of carbon tetrachloride were added 4.98 g of N-bromosuccinimide and 115 mg of 2,2'-azobis(isobutyronitrile), followed by stirring at 80° C. for 2 hours, and 4.98 g of N-bromosuccinimide and 115 mg of 2,2'-azobis(isobutyronitrile) were further added thereto, followed by stirring at 80° C. for 14 hours. After cooling the reaction solution, the insoluble material was separated by filtration, and the solvent was evaporated. To the residue was added hexane and followed by washing with a saturated aqueous sodium hydrogen carbonate solution and a saturated aqueous sodium chloride solution. The organic layer was dried over anhydrous magnesium sulfate and the solvent was then evaporated to obtain 6.0 g of a pale yellow oily substance. The obtained oily substance was dissolved in 30 ml of THF, and 21.7 ml of diethyl phosphite and 29.3 ml of diisopropylethylamine were added thereto under ice-cooling, followed by stirring at room temperature for 13 hours. The reaction solution was poured into ice water, followed by extraction with hexane. The organic layer was washed with 1 M hydrochloric acid and a saturated aqueous sodium chloride solution. After drying over anhydrous magnesium sulfate, the solvent was evaporated, and the residue was purified by silica gel column chromatography (eluent: hexane-ethyl acetate) to obtain 2.95 g of ethyl 2-[3-(dibromomethyl)phenyl]-2-methylpropionate as a pale yellow oily substance.

Production Example 21

To a mixed liquid of 2.95 g of ethyl 2-[3-(dibromomethyl)phenyl]-2-methylpropionate and 30 ml of acetic acid was added 4.77 g of potassium acetate, followed by stirring at 100° C. for 6 hours. After cooling the reaction solution, 10 ml of 6 M hydrochloric acid was added thereto, followed by stirring at room temperature for 2 hours. The reaction solution was poured into water, followed by extraction with hexane, and the organic layer was washed with water and a saturated aqueous sodium chloride solution. The organic layer was dried over anhydrous magnesium sulfate and the solvent was then evaporated to obtain 1.74 g of ethyl 2-(3-formylphenyl)-2-methylpropionate as a colorless oily substance.

Production Example 22

To a mixed liquid of 1.00 g of tert-butyl piperidin-4-ylcarbamate and 20 ml of pyridine was added 0.77 ml of methanesulfonyl chloride, followed by stirring at room temperature for 18 hours. After evaporating the pyridine under reduced pressure, ethyl acetate was added thereto, followed by washing with a 5% aqueous citric acid solution, a saturated aqueous sodium hydrogen carbonate solution, and a saturated aqueous sodium chloride solution. After drying the organic layer over anhydrous magnesium sulfate, the solvent was evaporated, and the obtained solid was washed with diethyl ether to obtain 1.19 g of t-butyl [1-(methylsulfonyl)piperidin-4-yl]carbamate as a white solid.

Production Example 23

To a solution of 1 g of tert-butyl [3-(cyanomethyl)phenoxy]acetate in 20 ml of THF and 10 ml of methanol was added dropwise a suspension of 1.31 g of cobalt chloride and 20 ml of water, and then 459 mg of sodium borohydride was portionwise added thereto at room temperature. After stirring at room temperature for 10 minutes, the insoluble material was separated by filtration over Celite, washed with methanol, and then concentrated. The obtained residue was extracted with chloroform, and dried over anhydrous magnesium sulfate, and the solvent was then evaporated. The obtained residue was purified by silica gel column chromatography (eluent: chloroform-methanol-saturated aqueous ammonia) to obtain 632 mg of tert-butyl [3-(2-aminoethyl)phenoxy]acetate as a pale yellow oily substance.

Production Example 24

To a mixed liquid of 5.16 g of t-butyl [3-(azidomethyl)phenoxy]acetate and 50 ml of THF were added 6.17 g of triphenylphosphine and 1.04 ml of water, followed by stirring at room temperature for 4 days. The solvent was evaporated and diisopropyl ether was added thereto. The precipitated solid was separated by filtration and the solvent was evaporated again. The residue was purified by silica gel column chromatography (eluent: chloroform-methanol-saturated aqueous ammonia) to obtain 4.10 g of t-butyl [3-(aminomethyl)phenoxy]acetate as a pale yellow oily substance.

Production Example 25

To a mixed liquid of 2.00 g of (1RS,2SR)-2-[(tert-butoxycarbonyl)amino]cyclohexanecarboxylic acid and 40 ml of dichloromethane were added 1.41 ml of 2-(trimethylsilyl)ethanol, 0.40 g of DMAP, and 2.21 g of WSC in this order, followed by stirring at room temperature for 60 hours. After evaporating the solvent, ethyl acetate was added thereto, followed by washing with water, a 5% aqueous citric acid solution, a saturated aqueous sodium hydrogen carbonate solution, and a saturated aqueous sodium chloride solution in this order. The organic layer was dried over anhydrous magnesium sulfate and the solvent was then evaporated to obtain 2.82 g of 2-(trimethylsilyl)ethyl (1RS,2SR)-2-[(tert-butoxycarbonyl)amino]cyclohexanecarboxylate as a colorless oily substance.

Production Example 26

To a solution of 2.82 g of 2-(trimethylsilyl)ethyl (1RS, 2SR)-2-[(t-butoxycarbonyl)amino]cyclohexanecarboxylate in 10 ml of ethyl acetate, were added 20 ml of 4 M hydrogen chloride/ethyl acetate under ice-cooling, followed by stirring at room temperature for 6 hours. The reaction solution was evaporated to obtain 2.30 g of 2-(trimethylsilyl)ethyl (1RS, 2SR)-2-aminocyclohexanecarboxylate as a colorless amorphous substance.

Production Example 27

To a mixed liquid of 4.40 g of N-[(benzyloxy)carbonyl]-3-[(methylsulfonyl)amino]-D-alanine methyl ester, 100 ml of THF, and 50 ml of ethanol was added 1.13 g of lithium chloride, and 1.01 g of sodium borohydride was further added thereto under ice-cooling. The reaction solution was stirred at room temperature for 14 hours, and the solvent was then evaporated under reduced pressure. After adding 150 ml of water, concentrated hydrochloric acid was added thereto until the pH reached 2 to 3. The solution was extracted with ethyl acetate, washed with a saturated aqueous sodium chloride solution, and dried over anhydrous magnesium sulfate. The solvent was evaporated to obtain 3.10 g of benzyl [(1R)-2-hydroxy-1-{[(methylsulfonyl)amino]methyl}ethyl]carbamate as a white solid.

Production Example 28

To a mixed liquid of 3.10 g of benzyl [(1R)-2-hydroxy-1-{[(methylsulfonyl)amino]methyl}ethyl]carbamate and 50 ml of ethanol was added 500 mg of 5% palladium/carbon, followed by stirring at room temperature for 2 hours under a hydrogen atmosphere. The palladium/carbon was separated by filtration and the solvent was then evaporated to obtain 1.72 g of N-[(2R)-2-amino-3-hydroxypropyl]methanesulfonamide as a colorless oily substance.

Production Example 29

To 700 mg of 2-(6-methoxypyridin-2-yl)ethylamine was added 10 ml of a 47% aqueous hydrogen bromide solution, followed by stirring at 80° C. for 60 hours. After evaporating the solvent, the residue was washed with diethyl ether to obtain 1.21 g of a 6-(2-aminoethyl)pyridin-2(1H)-one hydrobromide as a pale brown solid.

Production Example 30

A mixture of 3980 mg of 2-[2-(1H-tetrazol-1-yl)ethyl]-1H-isoindole-1,3(2H)-dione, 0.90 g of hydrazine monohydrate, and 80 ml of ethanol was stirred at 70° C. for 12 hours. The reaction solution was left to be cooled and the insoluble material was then collected by filtration. The filtered material was suspended in dioxane and 3.57 g of di-tert-butyl dicarbonate was added thereto at room temperature, followed by stirring for 12 hours. The insoluble material was separated by filtration and the filtrate was concentrated under reduced pressure. The obtained residue was purified by silica gel column chromatography using hexane/ethyl acetate as an eluent solvent to obtain 2210 mg of tert-butyl [2-(1H-tetrazol-1-yl)ethyl]carbamate as a colorless solid.

Production Example 31

To a solution of 2.62 g of tert-butyl 1H-pyrrole-3-carboxylate and 7.96 g of N-(2-bromoethyl)phthalimide in DMF (100 ml) was added 10.2 g of cesium carbonate at room temperature, followed by stirring for 12 hours. The reaction solution was diluted with water and extracted with ethyl acetate. The extract was washed with saturated brine and then dried over anhydrous magnesium sulfate. The organic layer was concentrated under reduced pressure. The obtained residue was purified by silica gel column chromatography using hexane/chloroform as an eluent solvent, and washed with diethyl ether to obtain 670 mg of tert-butyl 1-[2-(1,3-dioxo-1,3-dihydro-2H-isoindol-2-yl)ethyl]-1H-pyrrole-3-carboxylate as a colorless solid.

Production Example 32

A mixture of 660 mg of tert-butyl 1-[2-(1,3-dioxo-1,3-dihydro-2H-isoindol-2-yl)ethyl]-1H-pyrrole-3-carboxylate, 194 mg of hydrazine monohydrate, and 19 ml of ethanol was stirred at 70° C. for 12 hours. The reaction solution was left to be cooled and the insoluble material was then separated by filtration. The filtrate was concentrated under reduced pressure to obtain 430 mg of tert-butyl 1-(2-aminoethyl)-1H-pyrrole-3-carboxylate as a yellow oily substance.

Production Example 33

To a solution of 8.75 g of 2,4-dichlorobenzaldehyde in 100 ml of chloroform were added 5.11 g of cyclopentylamine and 5 g of Molecular Sieves 4A, followed by stirring at room temperature overnight. After removing the Molecular Sieves 4A by filtration, 6.48 g of homophthalic anhydride was added thereto, followed by stirring at room temperature overnight and then reflux for 5 hours. After concentrating under reduced pressure, ethyl acetate and a 1 M aqueous sodium hydroxide solution were added thereto to carry out a liquid separation operation. The aqueous layer was acidified by the addition of 1 M hydrochloric acid, followed by extraction with chloroform-isopropyl alcohol (3:1). The organic layer was washed with a saturated aqueous sodium chloride solution and dried over anhydrous sodium sulfate, and the solvent was then evaporated under reduced pressure. The obtained residue was added with ether and collected by filtration to obtain 4.48 g of 3,4-cis-2-cyclopentyl-3-(2,4-dichlorophenyl)-1-oxo-1,2,3,4-tetrahydroisoquinoline-4-carboxylic acid (Production Example 33-1) as a colorless crystal. The mother liquid was concentrated to obtain 6.46 g of 3,4-trans-2-cyclopentyl-3-(2,4-dichlorophenyl)-1-oxo-1,2,3,4-tetrahydroisoquinoline-4-carboxylic acid (Production Example 33-2) as a colorless amorphous substance.

Production Example 34

To a mixed solution of 2,4-dichlorobenzaldehyde in chloroform-methanol were added trans-2-aminocyclohexanol, triethylamine, and anhydrous sodium sulfate at room temperature, the reaction solution was stirred at 50° C. overnight, and homophthalic anhydride was then added thereto at room temperature, followed by stirring at room temperature overnight. After removing sodium sulfate by filtration, chloroform and a 1 M aqueous sodium hydroxide solution were added thereto to carry out a liquid separation operation, and the aqueous layer was stirred at room temperature for 2 hours. It was acidified by the addition of 1 M hydrochloric acid, and ethyl acetate was added thereto to carry out a liquid separation operation. The organic layer was washed with a saturated aqueous sodium chloride solution, dried over anhydrous sodium sulfate, and then evaporated under reduced pressure. To the residue was added diethyl ether, followed by stirring at room temperature overnight. The precipitated crystal was collected by filtration to obtain 7655 mg of 3RS,4RS-3-(2,4-dichlorophenyl)-2-(1SR,2SR-2-hydroxycyclohexyl)-1-oxo-1,2,3,4-tetrahydroisoquinoline-4-carboxylic acid (Production Example 34-1) as a colorless crystal. After concentrating the mother liquid, the residue was purified by silica gel column chromatography (eluent: chloroform:methanol) to obtain 6600 mg of 3SR,4SR-3-(2,4-dichlorophenyl)-2-(1RS,2RS-2-hydroxycyclohexyl)-1-oxo-1,2,3,4-tetrahydroisoquinoline-4-carboxylic acid (Production Example 34-2) as a colorless crystal.

Production Example 35

To 4.33 g of (3RS,4RS)-2-[(1SR,2SR)-2-aminocyclohexyl]-3-(2,4-dichlorophenyl)-1-oxo-1,2,3,4-tetrahydroisoquinoline-4-carboxylic acid were added 50 ml of ethanol and 2 ml of concentrated sulfuric acid, followed by heating under reflux overnight. Ethyl acetate and water were added thereto to carry out a liquid separation operation, and the organic layer was washed with a saturated aqueous sodium hydrogen carbonate solution and a saturated aqueous sodium chloride solution. The organic layer was dried over anhydrous sodium sulfate and then evaporated under reduced pressure. The residue was purified by silica gel column chromatography (eluent: hexane-ethyl acetate) to obtain 2.3 g of ethyl (3RS,4RS)-2-[(1SR,2SR)-2-aminocyclohexyl]-3-(2,4-dichlorophenyl)-1-oxo-1,2,3,4-tetrahydroisoquinoline-4-carboxylate as a yellow foam.

Production Example 36

To a solution of 2.25 g of ethyl (3RS,4RS)-2-[(1SR,2SR)-2-aminocyclohexyl]-3-(2,4-dichlorophenyl)-1-oxo-1,2,3,4-tetrahydroisoquinoline-4-carboxylate in 30 ml of acetonitrile were added 0.75 ml of methanesulfonyl chloride and 1.6 ml of diisopropylethylamine, followed by stirring at room temperature overnight. Ethyl acetate and water were added thereto to carry out a liquid separation operation, and the organic layer was washed with a saturated aqueous sodium chloride solution. The organic layer was dried over anhydrous sodium sulfate, and then evaporated under reduced pressure. The residue was added with diethyl ether for crystallization, and collected by filtration to obtain 2.02 g of ethyl (3RS,4RS)-3-(2,4-dichlorophenyl)-2-{(1SR,2SR)-2-[(methylsulfonyl)amino]cyclohexyl}-1-oxo-1,2,3,4-tetrahydroisoquinoline-4-carboxylate as a colorless crystal.

Production Example 37

To a solution of 1.4 g of ethyl (3RS,4RS)-3-(2,4-dichlorophenyl)-2-{(1SR,2SR)-2-[(methylsulfonyl)amino]cyclohexyl}-1-oxo-1,2,3,4-tetrahydroisoquinoline-4-carboxylate in 20 ml of DMF was added 229 mg of sodium hydride under ice-cooling, followed by stirring at the same temperature for 10 minutes, and then 0.17 ml of methyl iodide was added thereto, followed by stirring under ice-cooling for 30 minutes. Water was added thereto, followed by extraction with ethyl acetate. The organic layer was washed with a saturated aqueous sodium chloride solution and dried over anhydrous sodium sulfate, and the solvent was evaporated under reduced pressure. The residue was purified by silica gel column chromatography (eluent: chloroform-methanol) to obtain 545 mg of ethyl (3RS,4RS)-3-(2,4-dichlorophenyl)-2-{(1SR,2SR)-2-[methyl(methylsulfonyl)amino]cyclohexyl}-1-oxo-1,2,3,4-tetrahydroisoquinoline-4-carboxylate as a colorless amorphous substance.

Production Example 38

To a mixture of 2.0 g of ethyl (3RS,4RS)-3-(2,4-dichlorophenyl)-2-{(1SR,2SR)-2-[(methylsulfonyl)amino]cyclohexyl}-1-oxo-1,2,3,4-tetrahydroisoquinoline-4-carboxylate, 10 ml of methanol, and 10 ml of THF was added 10 ml of a 1 M aqueous sodium hydroxide solution, followed by stirring at room temperature for 1 hour. The solution was acidified by the addition of 1 M hydrochloric acid, and then extracted with ethyl acetate. The organic layer was washed with a saturated aqueous sodium chloride solution and dried over anhydrous sodium sulfate. The solvent was evaporated under reduced pressure to obtain 1.9 g of (3RS,4RS)-3-(2,4-dichlorophenyl)-2-{(1SR,2SR)-2-[(methylsulfonyl)amino]cyclohexyl}-1-oxo-1,2,3,4-tetrahydroisoquinoline-4-carboxylic acid as a pale yellow crystal.

Production Example 39

A mixture of 8 g of 4-(benzyloxy)-2-(carboxymethyl)benzoic acid and 30 ml of acetyl chloride was heated under reflux for 3 hours. The reaction solution was concentrated under reduced pressure, added with ether, and collected by filtration to obtain 7.50 g of 6-(benzyloxy)-1H-isochromene-1,3(4H)-dione as a dark brown solid.

Production Example 40

To 612 mg of 6-[(aminooxy)methyl]pyridin-2(1H)-one, which had been prepared by subjecting 2-[(6-oxo-1,6-dihydropyridin-2-yl)methoxy-1H-isoindole-1,3(2H)dione to removal of phthalimide in accordance with Production Example 9, was added 1.6 ml of a 4 M hydrogen chloride/ethyl acetate solution, and the precipitated solid was collected by filtration to obtain 263 mg of 6-[(aminooxy)methyl]pyridin-2(1H)-one hydrochloride as a colorless solid.

Production Example 41

To 2.04 g of (4-methyl-1H-imidazol-5-yl)methanol hydrochloride was added 20 ml of acetonitrile, and 2.1 ml of triethylamine, 3.14 g of di-tert-butyl dicarbonate, and 0.17 g of DMAP were added thereto under ice-cooling, followed by stirring at room temperature. After concentrating the reaction solution under reduced pressure, ethyl acetate and water were added thereto to carry out a liquid separation operation, and the organic layer was washed with a saturated aqueous sodium chloride solution. The organic layer was dried over anhydrous sodium sulfate, and then evaporated under reduced pressure. The obtained residue was reacted with N-hydroxyphthalimide in accordance with Production Example 14, reacted with methylamine in accordance with Production Example 9, and then subjected to deprotection of a Boc group in accordance with Production Example 26 to obtain 0.53 g of 5-[(aminooxy)methyl]-4-methyl-1H-imidazole dihydrochloride as a colorless solid.

Production Example 42

To a solution of 529 mg of (5-fluoropyridin-2-yl)methanol and 0.64 ml of triethylamine in 8 ml of dichloromethane was added 0.35 ml of methanesulfonyl chloride under ice-cooling, followed by stirring for 1 hour under ice-cooling. The reaction solution was poured into water, followed by extraction with ethyl acetate. The organic layer was washed with saturated brine and dried over anhydrous magnesium sulfate, and the solvent was then evaporated. The obtained residue was reacted with N-hydroxyphthalimide in accordance with Production Example 14 to obtain 522 mg of 2-[(5-fluoropyridin-2-yl)methoxy]-1H-isoindole-1,3(2H)-dione as a white solid.

Production Example 43

To a mixture of 2.97 g of 4-(hydroxymethyl)phenol, 4.90 g of tert-butyl bromoacetate, and 25 ml of DMF was added 4.96 g of potassium carbonate at room temperature, followed by stirring for 12 hours. To the reaction solution was added water, followed by extraction with ethyl acetate. The organic layer was washed with water and saturated brine, and dried over anhydrous magnesium sulfate, and the solvent was then evaporated. The residue was purified by silica gel column chromatography (eluent: ethyl acetate-hexane) to obtain a pale yellow oily substance. This oily substance was subjected to methanesulfonylation in accordance with Production Example 15, and then reacted with sodium azide to obtain 4.03 g of tert-butyl [4-(azidomethyl)phenoxy] acetate as a pale yellow oily substance.

Production Example 44

To a solution of 1.63 g of ethyl (3RS,4RS)-2-[(1SR,2SR)-2-{[(3-chloropropyl)sulfonyl]amino}cyclohexyl]-3-(2,4-dichlorophenyl)-1-oxo-1,2,3,4-tetrahydroisoquinoline-4-carboxylate in 20 ml of THF was added 142 mg of sodium hydride, followed by stirring at 50° C. overnight. Ethyl acetate and water were added thereto to carry out a liquid separation operation. The organic layer was washed with a saturated aqueous sodium chloride solution, dried over anhydrous sodium sulfate, and then evaporated under reduced pressure. The residue was purified by silica gel column chromatography (eluent: hexane-ethyl acetate) to obtain 466 mg of ethyl (3RS,4RS)-3-(2,4-dichlorophenyl)-2-[(1SR,2SR)-2-(1,1-dioxidoisothiazolidin-2-yl)cyclohexyl]-1-oxo-tetrahydroisoquinoline-4-carboxylate as a colorless crystal.

Production Example 45

A solution of 5.0 g of 4-bromothiophene-2-carbaldehyde, 11.4 ml of vinyltributyltin, and 3.6 g of tetrakistriphenylphosphine palladium in 100 ml of toluene was heated at 110° C. for 4 hours under a sealed tube condition. The organic layer was extracted with ethyl acetate and washed with water. In addition, the organic layer was dried over anhydrous magnesium sulfate and concentrated under reduced pressure. The residue was purified by silica gel column chromatography (eluent: hexane-ethyl acetate) to obtain 3.4 g of 4-vinylthiophene-2-carbaldehyde as a brown liquid.

Production Example 46

A solution of 5 g of methyl 1-methyl-1H-imidazole-5-carboxylate and 22.5 g of paraformaldehyde in 50 ml of methanol was heated at 140° C. for 60 hours under a sealed tube condition. The precipitate was removed by filtration and the solution was concentrated under reduced pressure. The residue was purified by silica gel column chromatography (eluent: chloroform-methanol) to obtain 4 g of methyl 2-(hydroxymethyl)-1-methyl-1H-imidazole-5-carboxylate as a white solid.

Production Example 47

7.4 ml of phosphorous oxychloride was added dropwise to 8.1 ml of DMF at 0° C., followed by warming to room temperature. To the solution was added ethyl 3-furanate, followed by warming to 126° C. and stirring for 1 hour. After cooling to room temperature, the reaction solution was poured into ice water. The organic layer was extracted with diethyl ether and washed with a saturated aqueous sodium carbonate solution. In addition, the organic layer was dried over anhydrous sodium sulfate and concentrated under reduced pressure. The residue was purified by silica gel column chromatography (eluent: hexane-ethyl acetate) to obtain 850 mg of ethyl 5-formyl-3-furnate as a yellow solid.

Production Example 48

To a mixed liquid of 1.51 g of potassium cyanide and 70 ml of acetonitrile, 6.12 g of 1,4,7,10,13,16-hexaoxacyclooctadecane was added, followed by stirring for 2 hours. Thereafter, a solution of 5.00 g of tert-butyl 3-(chloromethyl)benzoate in 30 ml of acetonitrile was added thereto, followed by stirring at room temperature for 18 hours. The reaction solution was concentrated, diluted with diethyl ether-hexane (1:1), and then washed with water and a saturated aqueous sodium chloride solution. After drying over anhydrous magnesium sulfate, the solvent was evaporated, and the residue was purified by silica gel column chromatography (eluent: hexane-ethyl acetate) to obtain 3.86 g of tert-butyl 3-(cyanomethyl)benzoate as a colorless oily substance.

Production Example 49

A solution of 2 g of (benzyloxy)acetic acid in 30 ml of DMF was cooled to 0° C., and 2.44 g of 1-(4-aminophenyl)ethanone, 294 mg of DMAP, and 3.73 g of WSC/hydrochloride were added thereto, followed by stirring at room temperature for 3 hours. Liquid separation was carried out with ethyl acetate-1 M hydrochloric acid. The organic layer was washed with a saturated aqueous sodium hydrogen carbonate solution and a saturated aqueous sodium chloride solution, dried over anhydrous magnesium sulfate, and then concentrated under reduced pressure to obtain 3.12 g of N-(4-acetylphenyl)-2-(benzyloxy)acetamide.

Production Example 50

To a solution of 1.64 g of ethyl 2-(hydroxymethyl)isonicotinate in 32.8 ml of dichloromethane were added 1.24 ml of dihydropyrane and 2.32 g of pyridinium p-toluenesulfonate, followed by stirring overnight. Ethyl acetate was added thereto, followed by washing with a saturated aqueous ammonium chloride solution and a saturated aqueous sodium chloride solution. The organic layer was dried over anhydrous magnesium sulfate and then concentrated under reduced pressure to obtain 2.4 g of ethyl 2-[(tetrahydro-2H-pyran-2-yloxy)methyl]isonicotinate.

Production Example 51

To a solution of 1.8 g of 1-[6-(hydroxymethyl)pyridin-2-yl]ethanone oxime in 36 ml of methanol was added 500 mg of 10% palladium-carbon (50% wet) under an argon atmosphere, followed by stirring for 7 hours under a hydrogen atmosphere. After filtration through Celite, the filtrate was evaporated under reduced pressure to obtain 1.5 g of [6-(1-aminoethyl)pyridin-2-yl]methanol.

Production Example 52

To a solution of 2.06 g of 3-amino-4-hydroxybenzoic acid in 20.6 ml of THF was added 4.81 g of CDI, followed by stirring at room temperature for 1 hour. The reaction mixture was added dropwise to a mixed liquid of 3.06 g of sodium borohydride in 20.6 ml of THF and 8.26 ml of water, cooled to 0° C., which had been separately prepared, followed by stirring overnight. 1 M hydrochloric acid was added thereto, followed by extracting with ethyl acetate, and washing with a saturated aqueous sodium chloride solution. The organic layer was dried over anhydrous magnesium sulfate and then concentrated under reduced pressure to obtain 1.2 g of 5-(hydroxymethyl)-1,3-benzoxazol-2(3H)-one.

Production Example 53

To 5 g of diethylpyridine-2,4-dicarboxylate were added 50 ml of ethanol and 50 ml of dichloroethane, followed by ice-cooling. 932 mg of sodium borohydride was added portionwise thereto, followed by stirring for 1 hour under ice-cooling, and further at room temperature for 15 hours. After ice-cooling the reaction solution, 5 ml of 6 M hydrochloric acid was added thereto, followed by stirring for 5 minutes and concentrating. A saturated aqueous sodium hydrogen carbonate solution was added thereto, followed by extracting with chloroform-isopropanol (10:1) and drying over anhydrous magnesium sulfate. After concentrating under reduced pressure, the residue was purified by silica gel column chromatography (eluent: chloroform-methanol) to obtain 0.7 g of ethyl 4-(hydroxymethyl)pyridine-2-carboxylate (Production Example 53-1) and 1.6 g of ethyl 2-(hydroxymethyl)isonicotinate (Production Example 53-2), respectively.

Production Example 54

To 1.6 g of 1-(6-methoxypyridin-2-yl)ethanamine was added 23.7 ml of a 47% aqueous hydrobromic acid solution, followed by stirring at 80° C. for 60 hours. After evaporating the solvent under reduced pressure, the residue was washed with diethyl ether to obtain 2.95 g of 6-(1-aminoethyl)pyridin-2(1H)-one hydrobromide as a pale brown solid.

Production Example 55

To a solution of 2.31 g of tert-butyl 1H-pyrazole-3-carboxylate and 6.98 g of N-(2-bromoethyl)phthalimide in DMF (65 mL) was added 8.95 g of cesium carbonate at room temperature, followed by stirring for 12 hours. The reaction solution was diluted with water, followed by extraction with ethyl acetate. The extract was dried over anhydrous magnesium sulfate and concentrated under reduced pressure. The obtained residue was purified by silica gel column chromatography (eluent: chloroform-hexane) to obtain 1.51 g of tert-butyl 1-[2-(1,3-dioxo-1,3-dihydro-2H-isoindol-2-yl)ethyl]-1H-pyrazole-3-carboxylate as a colorless solid.

Production Example 56

To a mixture of 2.92 g of (2-hydroxyphenyl)acetonitrile, 4.71 g of tert-butyl bromoacetate and 110 mL of DMF was added 6.06 g of potassium carbonate at room temperature, followed by stirring for 12 hours. To the reaction solution was added water, followed by extraction with ethyl acetate. The extract was dried over anhydrous magnesium sulfate and then concentrated under reduced pressure. The residue was purified by silica gel column chromatography using hexane/ethyl acetate as an eluent solvent to obtain 5.29 g of tert-butyl [2-(cyanomethyl)phenoxy]acetate as a yellow oily substance.

Production Example 57

A mixture of 1.38 g of 6-(hydroxymethyl)pyridin-2(1H)-one, 2.15 g of tert-butyl bromoacetate, 3.07 g of silver oxide, and 33 mL of DMF was stirred at room temperature for 12 hours, and then at 60° C. for 12 hours. The insoluble material was separated by filtration and the filtrate was concentrated under reduced pressure. The residue was diluted with ethyl acetate, followed by washing with a saturated aqueous sodium chloride solution. The organic layer was dried over anhydrous magnesium sulfate and then concentrated under reduced pressure. The obtained residue was purified by silica gel column chromatography (eluent: hexane-ethyl acetate) to obtain 1.92 g of tert-butyl {[6-(hydroxymethyl)pyridin-2-yl]oxy}acetate as a yellow oily substance.

Production Example 58

To a mixture of 1.00 g of 3-hydroxybenzaldehyde, 1.80 g of tert-butyl (R)-lactate, 2.58 g of triphenylphosphine, and 40 mL of THF was added 1.71 g of diethyl azodicarboxylate at room temperature, followed by stirring for 12 hours. The reaction solution was diluted with ethyl acetate, followed by washing with a 5% aqueous sodium hydrogen carbonate solution. The organic layer was dried over anhydrous magnesium sulfate and then concentrated under reduced pressure. The obtained residue was purified by silica gel column chromatography (eluent: hexane-ethyl acetate) to obtain 1.49 g of tert-butyl (2S)-2-(3-formylphenoxy)propanoate as a colorless oily substance.

To a solution of 1.48 g of tert-butyl (2S)-2-(3-formylphenoxy)propanoate in methanol(30 mL) was added 0.48 g of sodium borohydride under ice-cooling, followed by stirring for 1 hour. The reaction solution was diluted with ethyl acetate, added with water, neutralized with 1 M hydrochloric acid, and extracted with ethyl acetate. The extract was dried over anhydrous magnesium sulfate and then concentrated under reduced pressure to obtain 1.38 g of tert-butyl (2S)-2-[3-(hydroxymethyl)phenoxy]propanoate as a colorless oily substance.

Production Example 59

A solution of 2.90 g of 1,3-phenylene diacetic acid, 3.00 g of 4-methoxybenzylbromide, and 2.99 g of potassium hydrogen carbonate in 15 mL of DMF was stirred at room temperature for 36 hours. To the reaction solution was added water, followed by neutralization with 1 M hydrochloric acid. The product was extracted with ethyl acetate and the organic layer was dried over anhydrous magnesium sulfate. After concentrating under reduced pressure, 4.72 g of a colorless oily substance was obtained. A mixture of the obtained colorless oily substance (4.72 g), 2.42 g of HOBt, 2.78 g of WSC hydrochloride, 3.99 g of ammonium chloride, 7.55 g of triethylamine, and 18 mL of DMF was stirred at room temperature for 12 hours. The reaction solution was diluted with water and extracted with ethyl acetate. The organic layer was washed with saturated brine and then concentrated under reduced pressure. The obtained residue was purified by silica gel column chromatography (eluent: hexane-ethyl acetate) to obtain 4-methoxybenzyl [3-(2-amino-2-oxoethyl)phenyl]acetate as a colorless solid.

To a solution of 1.31 g of 4-methoxybenzyl [3-(2-amino-2-oxoethyl)phenyl]acetate in pyridine (20 mL) was added 718 mg of methanesulfonyl chloride under ice-cooling, followed by stirring for 2 hours. The reaction solution was concentrated under reduced pressure. The residue was diluted with ethyl acetate and washed with a 5% aqueous citric acid solution, a saturated aqueous sodium hydrogen carbonate solution, and then a saturated aqueous sodium chloride solution in this order. The organic layer was dried over anhydrous magnesium sulfate and then concentrated under reduced pressure. The obtained residue was purified by silica gel column chromatography (eluent: hexane-ethyl acetate) to obtain 1.25 g of 4-methoxybenzyl [3-(cyanomethyl)phenyl]acetate as a yellow oily substance.

Production Example 60

A mixture of 5.05 g of 5-methyl-2-furanecarboxylic acid, 7.14 g of CDI, and 40 mL of DMF was stirred at 50° C. for 2 hours. To the reaction solution were added 6.71 g of DBU and 6.53 g of 2-methyl-2-propanol at room temperature, followed by stirring at 50° C. for 48 hours. The reaction solution was concentrated under reduced pressure, and the obtained residue was diluted with diethyl ether and washed with a 5% aqueous ammonium chloride solution, a saturated aqueous sodium hydrogen carbonate solution, and then a saturated aqueous sodium chloride solution in this order. The organic layer was dried over anhydrous magnesium sulfate and then concentrated under reduced pressure. The residue was purified by silica gel column chromatography (eluent: hexane-ethyl acetate) to obtain 2.82 g of tert-butyl 5-methyl-2-furanecarboxylate as a yellow oily substance.

Production Example 61

To a solution of 1643 mg of 1-[6-(hydroxymethyl)pyridin-2-yl]ethanone in 25 ml of ethanol was added 0.72 ml of a 50% aqueous hydroxylamine solution, followed by stirring overnight. The reaction solution was concentrated under reduced pressure to obtain 1806 mg of 1-[6-(hydroxymethyl)pyridin-2-yl]ethanone oxime as an amorphous substance.

Production Example 62

To a mixture of 2.06 g of tert-butyl ({6-[(hydroxymethyl)pyridin-2-yl]oxy}acetate, 2.60 g of triphenylphosphine, 2.70 g of phthalimide, and 40 mL of THF was added 1.73 g of diethyl azodicarboxylate at room temperature, followed by stirring for 36 hours. To the reaction solution was added ethyl acetate, followed by washing with a 5% aqueous sodium hydrogen carbonate solution. The organic layer was dried over anhydrous magnesium sulfate and then concentrated under reduced pressure, and the residue was purified by silica gel column chromatography to obtain 2.33 g of ({6-[(1,3-dioxo-1,3-dihydro-2H-isoindol-2-yl)methyl]pyridin-2-yl}oxy)acetic acid as a colorless solid.

Production Example 63

To a mixture of 1266 mg of {2-[(tetrahydro-2H-pyrane-2-yloxy)methyl]pyridin-4-yl}methyl benzoate and 25 ml of methanol was added 1166 mg of pyridinium p-toluenesulfonate, followed by stirring for 2 hours. A saturated aqueous sodium hydrogen carbonate solution and chloroform were added thereto for extraction, and the organic layer was dried over anhydrous magnesium sulfate and then concentrated under reduced pressure to obtain 941 mg of [2-(hydroxymethyl)pyridin-4-yl]methyl benzoate as an amorphous substance.

Production Example Compounds 64 to 371 were prepared in the same manner as the methods of Production Examples 1 to 63 and the methods of Examples to be described later, using each of the corresponding starting materials. The structures and the physicochemical data of Production Example Compounds are shown in Tables 14 to 69.

Example 1

To a solution of 808 mg of 3,4-cis-2-cyclopentyl-3-(2,4-dichlorophenyl)-1-oxo-1,2,3,4-tetrahydroisoquinoline-4-carboxylic acid, 0.3 ml of phenylethylamine, and 405 mg of HOBt in dichloromethane (20 ml) was added 576 mg of WSC hydrochloride at room temperature, followed by stirring for 2 hours. To the reaction solution was added chloroform, and the organic layer was washed with water and a saturated aqueous sodium chloride solution in this order, dried over anhydrous sodium sulfate, and then concentrated under reduced pressure. The obtained residue was purified by silica gel column chromatography (eluent: chloroform) to obtain 902 mg of 3,4-trans-2-cyclopentyl-3-(2,4-dichlorophenyl)-1-oxo-N-phenylethyl-1,2,3,4-tetrahydroisoquinoline-4-carboxamide as a colorless crystal.

Example 2

To a mixture of 202 mg of 3,4-cis-2-cyclopentyl-3-(2,4-dichlorophenyl)-1-oxo-1,2,3,4-tetrahydroisoquinoline-4-carboxylic acid and 5 ml of dichloromethane were added 0.055 ml of oxalyl chloride and one drop of DMF under ice-cooling, followed by stirring at room temperature for 30 minutes. The reaction solution was concentrated under reduced pressure, and the obtained residue was dissolved in 5 ml of THF, and 0.13 ml of phenylethylamine and 0.07 ml of triethylamine were added thereto, followed by stirring at room temperature for 2 hours. The reaction solution was concentrated under reduced pressure, added with ethyl acetate, and washed with water and a saturated aqueous sodium chloride solution in this order. The organic layer was dried over anhydrous sodium sulfate and then concentrated under reduced pressure. The obtained residue was purified by silica gel column chromatography (eluent: chloroform), and the obtained crude product was then collected by filtration using diethyl ether to obtain 127 mg of 3,4-cis-2-cyclopentyl-3-(2,4-dichlorophenyl)-1-oxo-N-phenylethyl-1,2,3,4-tetrahydroisoquinoline-4-carboxamide as a colorless crystal.

Example 3

To a mixture of 254 mg of 3,4-trans-2-cyclopentyl-3-(2,4-dichlorophenyl)-1-oxo-N-[2-(2-pyridinyl)ethyl]-1,2,3,4-tetrahydroisoquinoline-4-carboxamide and 5 ml of dichloromethane was added 173 mg of m-chloroperbenzoic acid under ice-cooling, followed by stirring at room temperature overnight. To the reaction solution was added chloroform, washed with a 10% aqueous sodium hydrogen sulfite solution and a saturated aqueous sodium chloride solution in this order, dried over anhydrous sodium sulfate, and then concentrated under reduced pressure. The obtained residue was purified by silica gel column chromatography (eluent; chloroform-methanol) and then recrystallized from ethanol to obtain 138 mg of 3,4-trans-2-cyclopentyl-3-(2,4-dichlorophenyl)-N-[2-(1-oxidopyridin-2-yl)ethyl]-1-oxo-1,2,3,4-tetrahydroisoquinoline-4-carboxamide as a colorless crystal.

Example 4

To 654 mg of N-{[(3,4-trans-2-cyclopentyl-3-(2,4-dichlorophenyl)-1-oxo-1,2,3,4-tetrahydroisoquinolin-4-yl]carbonyl}-β-alanine ethyl ester were added 5 ml of THF, 2 ml of methanol, and 5 ml of a 1 M aqueous sodium hydroxide solution at room temperature, followed by stirring at 50° C. for 3 hours. After neutralization by the addition of 1 M hydrochloric acid, ethyl acetate was added for extraction. The organic layer was washed with water and a saturated aqueous sodium chloride solution in this order, dried over anhydrous sodium sulfate, and then evaporated under reduced pressure. The obtained white solid was recrystallized from ethyl acetate to obtain 294 mg of N-{[(3,4-trans-2-cyclopentyl-3-(2,4-dichlorophenyl)-1-oxo-1,2,3,4-tetrahydroisoquinolin-4-yl]carbonyl}-β-alanine as a colorless powdered crystal.

Example 5

To 410 mg of tert-butyl{2-[3-(2,4-dichlorophenyl)-1-oxo-4-[(2-phenylethyl)carbamoyl]-3,4-dihydroisoquinolin-2 (1H)-yl]ethyl}carbamate was added 4 ml of a 4 M hydrogen chloride/ethyl acetate solution, followed by stirring at room temperature for 2 hours. The solvent was evaporated under reduced pressure, and chloroform and a 1 M aqueous sodium hydroxide solution were then added to carry out a liquid separation operation. The organic layer was washed with a saturated aqueous sodium chloride solution, dried over anhydrous sodium sulfate, and then evaporated under reduced pressure. The obtained residue was recrystallized from ethyl acetate-hexane to obtain 192 mg of 2-(2-aminoethyl)-3-(2,4-dichlorophenyl)-1-oxo-N-(2-phenylethyl)-1,2,3,4-tetrahydroisoquinoline-4-carboxamide as a colorless powdered crystal.

Example 6

To a solution of 537 mg of 3,4-trans-2-(trans-4-aminocyclohexyl)-3-(2,4-dichlorophenyl)-1-oxo-N-(2-phenylethyl)-1,2,3,4-tetrahydroisoquinoline-4-carboxamide in 10 ml of dichloromethane were added 0.33 ml of an aqueous formalin solution and 893 mg of sodium triacetoxyborohydride, followed by stirring at room temperature overnight. To the reaction solution was added a saturated aqueous sodium hydrogen carbonate solution, followed by extraction with chloroform. The organic layer was washed with a saturated aqueous sodium chloride solution and then dried over anhydrous sodium sulfate, and the solvent was evaporated. The obtained residue was purified by silica gel column chromatography (eluent: chloroform-methanol), and the obtained white solid was recrystallized from ethyl acetate to obtain 82 mg of 3,4-trans-3-(2,4-dichlorophenyl)-2-[trans-4-(dimethylamino)cyclohexyl]-1-oxo-N-(2-phenylethyl)-1,2,3,4-tetrahydroisoquinoline-4-carboxamide as a colorless crystal.

Example 7

To a solution of 2.03 g of 3,4-trans-2-cyclopentyl-1-oxo-4-[(2-phenylethyl)carbamoyl]-1,2,3,4-tetrahydroisoquinoline-3-carboxylic acid in 20 ml of THF was added 810 mg of CDI, followed by stirring under heating at 50° C. for 1 hour. After cooling to room temperature, a mixture of 200 mg of sodium borohydride and 10 ml of water was added thereto, followed by stirring at room temperature for 4 hours. Ethyl acetate and water were added thereto to carry out a liquid separation operation, and the organic layer was washed with a saturated aqueous sodium chloride solution, dried over sodium sulfate, and then evaporated under reduced pressure. The residue was purified by silica gel column chromatography (eluent: chloroform), and the obtained solid was recrystallized from ethyl acetate to obtain 255 mg of 3,4-trans-2-cyclopentyl-3-(hydroxymethyl)-1-oxo-N-(2-phenylethyl)-1,2,3,4-tetrahydroisoquinoline-4-carboxamide as a colorless crystal.

Example 8

To 304 mg of (3RS,4RS)—N-(benzyloxy)-3-(4-methyl-3-nitrophenyl)-2-{(1SR,2SR)-2-[(methylsulfonyl)amino]cyclohexyl}-1-oxo-1,2,3,4-tetrahydroisoquinoline-4-carboxamide were added 10 ml of acetic acid and 560 mg of reduced iron, followed by stirring at 50° C. overnight. To the reaction solution was added methanol, followed by filtration through Celite, and after concentrating the mother liquid, ethyl acetate and water were added thereto to carry out a liquid separation operation. The organic layer was washed with a saturated aqueous sodium hydrogen carbonate solution and a saturated aqueous sodium chloride solution, dried over anhydrous sodium sulfate, and then evaporated under reduced pressure. The residue was purified by silica gel column chromatography (eluent: chloroform:methanol). The obtained solid was made into hydrochloride using a 4 M hydrogen chloride/ethyl acetate solution, and recrystallized from isopropyl alcohol to obtain 180 mg of (3RS,4RS)-3-(3-amino-4-methylphenyl)-N-(benzyloxy)-2-{(1SR,2SR)-2-[(methylsulfonyl)amino]cyclohexyl}-1-oxo-1,2,3,4-tetrahydroisoquinoline-4-carboxamide hydrochloride as a pale yellow powdered crystal.

Example 9

To 393 mg of 3,4-trans-2-cyclopentyl-3-(hydroxymethyl)-1-oxo-N-(2-phenylethyl)-1,2,3,4-tetrahydroisoquinoline-4-carboxamide were added 10 ml of THF and 44 mg of sodium hydride, followed by stirring at room temperature for 30 minutes. To the reaction mixture was added 161 mg of 4-chlorobenzylbromide, followed by stirring at room temperature overnight. To the reaction mixture were added ethyl acetate and water to carry out a liquid separation operation, and the organic layer was washed with a saturated aqueous sodium chloride solution. The organic layer was dried over anhydrous sodium sulfate and then evaporated under reduced pressure. The residue was purified by silica gel column chromatography (eluent: chloroform) and the obtained solid was crystallized from ether-hexane, and collected by filtration to obtain 134 mg of 3,4-trans-3-{[(4-chlorobenzyl)oxy]methyl}-2-cyclopentyl-1-oxo-N-(2-phenylethyl)-1,2,3,4-tetrahydroisoquinoline-4-carboxamide as a colorless powdered crystal.

Example 10

To a solution of 573 mg of (3RS,4RS)—N-(2-chloroethyl)-3-(2,4-dichlorophenyl)-2-{(1SR,2SR)-2-[(methylsulfonyl)amino]cyclohexyl}-1-oxo-1,2,3,4-tetrahydroisoquinoline-4-carboxamide in 10 ml of DMF were added 150 mg of sodium iodide and 340 mg of 1H-pyrazole, followed by stirring at 100° C. for 24 hours. Ethyl acetate and water were added thereto to carry out a liquid separation operation, and the organic layer was washed with a saturated aqueous sodium chloride solution, dried over anhydrous sodium sulfate, and then evaporated under reduced pressure. The residue was purified by silica gel column chromatography (eluent: chloroform-methanol) to obtain a colorless crystal. The crystal was recrystallized from ethanol to obtain 176 mg of (3RS,4RS)-3-(2,4-dichlorophenyl)-2-{(1SR,2SR)-2-[(methylsulfonyl)amino]cyclohexyl}-1-oxo-N-[2-(1H-pyrazol-1-yl)ethyl]-1,2,3,4-tetrahydroisoquinoline-4-carboxamide as a colorless powdered crystal.

Example 11

To a mixture of 270 mg of (3RS,4RS)-2-[(1SR,2SR)-2-aminocyclohexyl]-3-(2,4-dichlorophenyl)-1-oxo-N-(pyridin-2-ylmethoxy)-1,2,3,4-tetrahydroisoquinoline-4-carboxamide and 5 ml of pyridine was added 0.11 ml of acetic anhydride, followed by stirring at room temperature for 2 hours. Ethyl acetate and water were added thereto to carry out a liquid separation operation, and the organic layer was washed with a saturated aqueous sodium hydrogen carbonate solution and a saturated aqueous sodium chloride solution, dried over anhydrous sodium sulfate, and then evaporated under reduced pressure. The residue was purified by silica gel column chromatography (eluent: chloroform-methanol) to obtain a colorless crystal. The obtained crystal was added with diethyl ether and collected by filtration to obtain 55 mg of (3RS,4RS)-2-[(1SR,2SR)-2-acetamidecyclohexyl]-3-(2,4-dichlorophenyl)-1-oxo-N-(pyridin-2-ylmethoxy)-1,2,3,4-tetrahydroisoquinoline-4-carboxamide as a colorless powdered crystal.

Example 12

To a mixture of 538 mg of (3RS,4RS)-2-{(1SR,2SR)-2-aminocyclohexyl}-N-(benzyloxy)-3-(2,4-dichlorophenyl)-1-oxo-1,2,3,4-tetrahydroisoquinoline-4-carboxamide and 2.5 ml of pyridine was added 0.15 ml of methanesulfonyl chloride, followed by stirring at room temperature for 6 hours. Ethyl acetate and water were added thereto to carry out a liquid separation operation, and the organic layer was washed with a 1 M aqueous hydrochloric acid solution and a saturated aqueous sodium chloride solution, dried over anhydrous sodium sulfate, and then evaporated under reduced pressure. The residue was purified by silica gel column chromatography (eluent: chloroform) and then recrystallized from ethyl acetate-hexane to obtain 206 mg of (3RS,4RS)—N-(benzyloxy)-3-(2,4-dichlorophenyl)-2-{(1SR,2SR)-2-[(methylsulfonyl)amino]cyclohexyl}-1-oxo-1,2,3,4-tetrahydroisoquinoline-4-carboxamide as a colorless powdered crystal.

Example 13

To a mixed liquid of 200 mg of (3RS,4RS)-2-[(1SR,2SR)-2-aminocyclohexyl]-N-(benzyloxy)-3-(2,4-dichlorophenyl)-1-oxo-1,2,3,4-tetrahydroisoquinoline-4-carboxamide and 40 ml of dimethoxyethane was added 357 mg of sulfamide, followed by stirring at 80° C. for 2 days. The reaction solution was concentrated, added with chloroform, and then washed with water. The organic layer was dried over anhydrous magnesium sulfate, and the solvent was then evaporated. The residue was purified by silica gel column chromatography (eluent: chloroform-methanol), crystallized from ethyl acetate, and collected by filtration to obtain 62 mg of (3RS,4RS)-2-{(1SR,2SR)-2-[(aminosulfonyl)amino]cyclohexyl}-N-(benzyloxy)-3-(2,4-dichlorophenyl)-1-oxo-1,2,3,4-tetrahydroisoquinoline-4-carboxamide as a white crystal.

Example 14

To a mixed liquid of 269 mg of (3RS,4RS)-2-[(1SR,2SR)-2-aminocyclohexyl]-N-(benzyloxy)-3-(2,4-dichlorophenyl)-1-oxo-1,2,3,4-tetrahydroisoquinoline-4-carboxamide and 5 ml of chloroform was added 0.21 ml of dimethylsulfamoyl chloride, followed by stirring at room temperature for 15 hours, and further at 60° C. for 24 hours. In addition, 500 mg of sodium carbonate was added thereto, followed by stirring at 60° C. for 5 hours. In addition, 0.21 ml of dimethylsulfamoyl chloride was added thereto, followed by stirring at 60° C. for 5 hours. After cooling the reaction solution, a liquid separation operation was then carried out using water and chloroform. The organic layer was washed with 1 M hydrochloric acid, a saturated aqueous sodium hydrogen carbonate solution, and a saturated aqueous sodium chloride solution, and dried over anhydrous magnesium sulfate. After evaporating the solvent, the residue was purified by silica gel column chromatography (eluent: chloroform-methanol) to obtain a colorless amorphous substance. The obtained amorphous substance was crystallized with ethyl acetate to obtain 99 mg of (3RS,4RS)—N-(benzyloxy)-3-(2,4-dichlorophenyl)-2-[(1SR,2SR)-2-{[(dimethylamino)sulfonylamino]amino}cyclohexyl]-1-oxo-1,2,3,4-tetrahydroisoquinoline-4-carboxamide as a white crystal.

Example 15

To a mixed liquid of 269 mg of (3RS,4RS)-2-[(1SR,2SR)-2-aminocyclohexyl]-N-(benzyloxy)-3-(2,4-dichlorophenyl)-1-oxo-1,2,3,4-tetrahydroisoquinoline-4-carboxamide and 20 ml of ethanol was added 53 mg of nitrourea, followed by heating under reflux for 1 hour. The reaction solution was cooled and then concentrated, and the residue was purified by silica gel column chromatography (eluent: chloroform-methanol), then crystallized with acetonitrile, and collected by filtration to obtain 155 mg of (3RS,4RS)—N-(benzyloxy)-2-[(1SR,2SR)-2-(carbamoylamino)cyclohexyl]-3-(2,4-dichlorophenyl)-1-oxo-1,2,3,4-tetrahydroisoquinoline-4-carboxamide as a white crystal.

Example 16

To a mixed liquid of 269 mg of (3RS,4RS)-2-[(1SR,2SR)-2-aminocyclohexyl]-N-(benzyloxy)-3-(2,4-dichlorophenyl)-1-oxo-1,2,3,4-tetrahydroisoquinoline-4-carboxamide and 5 ml of DMF were added 58 mg of sodium carbonate and 119 mg of methyl ethanimidothioate hydrochloride, followed by stirring at 60° C. for 1 hour. Thereafter, while stirring at 60° C., 233 mg of sodium carbonate and 478 mg of methyl ethanimidothioate hydrochloride were further added in four divided portions every 1 hour. After cooling the reaction solution, water was added thereto, followed by extraction with chloroform-isopropyl alcohol (5:1). The organic layer was dried over anhydrous magnesium sulfate and then concentrated. The residue was purified by silica gel column chromatography (eluent: chloroform-methanol-aqueous ammonia) and then crystallized with ethyl acetate to obtain 113 mg of (3RS,4RS)—N-(benzyloxy)-3-(2,4- dichlorophenyl)-2-[(1SR,2SR)-2-(ethanimidoylamino)cyclohexyl]-1-oxo-1,2,3,4-tetrahydroisoquinoline-4-carboxamide as a white crystal.

Example 17

644 mg of (3RS,4RS)-3-(2,4-dichlorophenyl)-2-[(1SR,2SR)-2-hydroxycyclohexyl]-N-[2-(2-methoxy-6-methylpyridin-4-yl)ethyl]-1-oxo-1,2,3,4-tetrahydroisoquinoline-4-carboxamide and 1.92 g of pyridine hydrochloride were mixed, followed by warming from room temperature to 200° C. over 15 minutes. The molten mixture was left to be cooled and then subjected to a liquid separation operation using water and ethyl acetate. The organic layer was washed with a saturated aqueous sodium chloride solution and then dried over anhydrous magnesium sulfate, and the solvent was evaporated. The residue was purified by silica gel column chromatography (eluent: chloroform-methanol) to obtain 480 mg of a low polarity product and 146 mg of a high polarity product. The low polarity product was crystallized with ethyl acetate to obtain 277 mg of (3RS,4RS)-2-[(1SR)-cyclohex-2-en-1-yl]-3-(2,4-dichlorophenyl)-N-[2-(6-methyl-2-oxo-1,2-dihydropyridin-4-yl)ethyl]-1-oxo-1,2,3,4-tetrahydroisoquinoline-4-carboxamide (Example 17-1) as a white crystal. The high polarity product was recrystallized with ethyl acetate-ethanol to obtain 85 mg of (3RS,4RS)-3-(2,4-dichlorophenyl)-2-[(1SR,2SR)-2-hydroxycyclohexyl]-N-[2-(6-methyl-2-oxo-1,2-dihydropyridin-4-yl)ethyl]-1-oxo-1,2,3,4-tetrahydroisoquinoline-4-carboxamide (Example 17-2) as a white crystal.

Example 18

To a mixed liquid of 456 mg of (3RS,4RS)—N-[(3-cyanobenzyl)oxy]-3-(2,4-dichlorophenyl)-2-{(1SR,2SR)-2-[(methylsulfonyl)amino]cyclohexyl}-1-oxo-1,2,3,4-tetrahydroisoquinoline-4-carboxamide and 15 ml of DMF was added 139 mg of sodium azide and subsequently 114 mg of ammonium chloride at room temperature, followed by warming to 100° C. and stirring for 12 hours. The reaction solution was cooled to room temperature, then added with water, and extracted with chloroform. After drying over anhydrous magnesium sulfate, the solvent was evaporated and the residue was purified by silica gel column chromatography (eluent: chloroform-methanol). The crude purified product thus obtained was recrystallized with ethanol-water to obtain 171 mg of (3RS,4RS)-3-(2,4-dichlorophenyl)-2-{(1SR,2SR)-2-[(methylsulfonyl)amino]cyclohexyl}-1-oxo-N-{[3-(2H-tetrazol-5-yl) benzyl]oxy-1,2,3,4-tetrahydroisoquinoline-4-carboxamide as a white crystal.

Example 19

A mixture of 730 mg of tert-butyl (3-{[({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)oxy]methyl}phenoxy)acetate, 5 ml of dichloroethane, and 5 ml of trifluoroacetic acid was stirred at room temperature for 2 hours. The reaction solution was concentrated under reduced pressure, and the obtained residue was purified by silica gel column chromatography (eluent: chloroform-methanol). The crude purified product thus obtained was recrystallized from ethyl acetate to obtain 184 mg of (3-{[({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)oxy]methyl}phenoxy)acetic acid as a colorless crystal.

Example 20

To a solution of 330 mg of 3-{[({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)oxy]methyl}benzoic acid in 5 ml of DMF was added 122 mg of CDI, followed by stirring at room temperature for 30 minutes. To the reaction solution were added 71 mg of methane sulfonamide and 0.11 ml of DBU, followed by stirring at room temperature for 3 hours. To the reaction solution was added ethyl acetate, followed by washing with 1 M hydrochloric acid and a saturated aqueous sodium chloride solution. The organic layer was dried over anhydrous magnesium sulfate and the solvent was then evaporated. The residue was purified by silica gel column chromatography (eluent: chloroform-methanol) to obtain a crude purified product. This was recrystallized with acetonitrile-water to obtain 273 mg of (3RS,4RS)-3-(2,4-dichlorophenyl)-2-{(1SR,2SR)-2-[(methylsulfonyl)amino]cyclohexyl}-N-({3-[(methylsulfonyl)carbamoyl]benzyl}oxy)-1-oxo-1,2,3,4-tetrahydroisoquinoline-4-carboxamide as a white crystal.

Example 21

To a solution of 128 mg of (3RS,4RS)—N-(cyanomethoxy)-3-(2,4-dichlorophenyl)-2-{(1SR,2SR)-2-[(mesyl)amino]cyclohexyl}-1-oxo-1,2,3,4-tetrahydroisoquinoline-4-carboxamide in 1.92 ml of methanol was added 0.018 ml of a hydroxylamine solution at room temperature, followed by warming to 40° C. and stirring overnight. The reaction solution was cooled to room temperature and the precipitated crystal was then collected by filtration to obtain 26 mg of (3RS,4RS)—N-[2-amino-2-(hydroxyimino)ethoxy]-3-(2,4-dichlorophenyl)-2-{(1SR,2SR)-2-[(mesyl)amino]cyclohexyl}-1-oxo-1,2,3,4-tetrahydroisoquinoline-4-carboxamide as a white crystal.

Example 22

To a mixed liquid of 300 mg of (3RS,4RS)—N-({3-[amino(hydroxyimino)methyl]benzyl}oxy)-3-(2,4-dichlorophenyl)-2-{(1SR,2SR)-2-[(methylsulfonyl)amino]cyclohexyl}-1-oxo-1,2,3,4-tetrahydroisoquinoline-4-carboxamide and 30 ml of acetonitrile were added 132 mg of 1,1'-carbonothioyl bis(1H-imidazole) and 0.27 ml of DBU under ice-cooling, followed by stirring at room temperature for 1 hour. The reaction solution was concentrated and then added with 50 ml of water, and 1 M hydrochloric acid was added thereto until the pH reached 4 to 5. After extracting with ethyl acetate, washing with a saturated aqueous sodium chloride solution and drying over anhydrous magnesium sulfate, the solvent was evaporated. The residue was purified by silica gel column chromatography (eluent: chloroform-methanol). The crude purified product thus obtained was added with ethyl acetate and collected by filtration to obtain 61 mg of (3RS,4RS)-3-(2,4-dichlorophenyl)-2-{(1SR,2SR)-2-[(methylsulfonyl)amino]cyclohexyl}-1-oxo-N-{[3-(5-thioxo-4,5-dihydro-1,2,4-oxadiazol-3-yl)benzyl]oxy}-1,2,3,4-tetrahydroisoquinoline-4-carboxamide as a white solid.

Example 23

To a mixed liquid of 280 mg of (3RS,4RS)—N-({3-[amino(hydroxyimino)methyl]benzyl}oxy)-3-(2,4-dichlorophenyl)-2-{(1SR,2SR)-2-[(methylsulfonyl)amino]cyclohexyl}-1-oxo-1,2,3,4-tetrahydroisoquinoline-4-carboxamide and 10 ml of DMF were added 0.037 ml of pyridine and subsequently 0.084 ml of 2-ethylhexyl chloroformate under ice-cooling, followed by stirring under ice-cooling for 30 minutes. To the reaction solution was added ethyl acetate, followed by washing with water and a saturated aqueous sodium chloride solution. The organic layer was dried over anhydrous magnesium sulfate and the solvent was then evaporated under reduced pressure. The obtained residue was purified by silica gel column chromatography (eluent: chloroform-methanol) to obtain 305 mg of (3RS,4RS)—N-[(3-{amino[({[(2-ethyl hexyl)oxy]carbonyl}oxy)imino]methyl}benzyl)oxy]-3-(2,4-dichlorophenyl)-2-{(1SR,2SR)-2-[(methylsulfonyl)amino]cyclohexyl}-1-oxo-1,2,3,4-tetrahydroisoquinoline-4-carboxamide as a white amorphous substance. To 290 mg of the present compound was added 6 ml of NMP, followed by stirring at 140° C. for 3 hours. The reaction solution was cooled, and 50 ml of water was then added thereto, followed by stirring. The precipitated solid was collected by filtration. This solid was purified by silica gel column chromatography (eluent: chloroform-methanol), then crystallized with acetonitrile-water, and collected by filtration to obtain 101 mg of (3RS,4RS)-3-(2,4-dichlorophenyl)-2-{(1SR,2SR)-2-[(methylsulfonyl)amino]cyclohexyl}-1-oxo-N-{[3-(5-oxo-4,5-dihydro-1,2,4-oxadiazol-3-yl)benzyl]oxy}-1,2,3,4-tetrahydroisoquinoline-4-carboxamide as a white crystal.

Example 24

To a solution of 500 mg of (3RS,4RS)-3-(2,4-dichlorophenyl)-2-{(1SR,2SR)-2-[(methylsulfonyl)amino]cyclohexyl}-1-oxo-N-[(1-trityl-1H-1,2,4-triazol-3-yl)methoxy]-1,2,3,4-tetrahydroisoquinoline-4-carboxamide in 7.5 ml of methanol was added dropwise 0.25 ml of concentrated hydrochloric acid under ice-cooling, followed by stirring at room temperature for 4 hours. To the reaction solution was added a saturated aqueous sodium hydrogen carbonate solution, followed by extraction with chloroform. The organic layer was dried over anhydrous magnesium sulfate and then concentrated under reduced pressure. The residue was purified by silica gel column chromatography (eluent: chloroform-methanol) and recrystallized from ethyl acetate to obtain 282 mg of (3RS,4RS)-3-(2,4-dichlorophenyl)-2-{(1SR,2SR)-2-[(methylsulfonyl)amino]cyclohexyl}-1-oxo-N-(1H-1,2,4-triazol-3-ylmethoxy)-1,2,3,4-tetrahydroisoquinoline-4-carboxamide as a colorless crystal.

Example 25

A solution of 400 mg of (3RS,4RS)-6-(benzyloxy)-3-(2,4-dichlorophenyl)-2-{(1SR,2SR)-2-[(methylsulfonyl)amino]cyclohexyl}-1-oxo-N-(pyridin-2-ylmethoxy)-1,2,3,4-tetrahydroisoquinoline-4-carboxamide and 245 mg of pentamethylbenzene in 15 ml of trifluoroacetic acid was stirred at room temperature overnight. The trifluoroacetic acid was evaporated under reduced pressure, and ethyl acetate and water were added thereto to carry out a liquid separation operation. The organic layer was washed with a saturated aqueous sodium chloride solution, dried over anhydrous sodium sulfate, and then evaporated under reduced pressure. The residue was solidified with ethyl acetate-isopropyl alcohol and collected by filtration to obtain 350 mg of (3RS,4RS)-3-(2,4-dichlorophenyl)-6-hydroxy-2-{(1SR,2SR)-2-[(methylsulfonyl)amino]cyclohexyl}-1-oxo-N-(pyridin-2-ylmethoxy)-1,2,3,4-tetrahydroisoquinoline-4-carboxamide as a white solid.

Example 26

To a solution of 644 mg of (3RS,4RS)—N-[(4-tert-butoxybenzyl)oxy]-3-(2,4-dichlorophenyl)-2-{(1SR,2SR)-2-[(mesyl)amino]cyclohexyl}-1-oxo-1,2,3,4-tetrahydroisoquinoline-4-carboxamide in 8.4 ml of dichloromethane was added 0.94 ml of trifluoroacetic acid under ice-cooling, followed by stirring at room temperature for 1 hour. The solution was concentrated under reduced pressure and then recrystallized from ethyl acetate to obtain 363 mg of (3RS,4RS)-3-(2,4-dichlorophenyl)-N-hydroxy-2-{(1SR,2SR)-2-[(mesyl)amino]cyclohexyl}-1-oxo-1,2,3,4-tetrahydroisoquinoline-4-carboxamide as a colorless crystal.

Example 27

To a mixed liquid of 350 mg of ethyl 1,2-cis-2-[3,4-trans-3-(2,4-dichlorophenyl)-1-oxo-4-[(2-phenylethyl)carbamoyl]-3,4-dihydroisoquinolin-2(1H)-yl]cyclohexanecarboxylate, 25 ml of THF, and 25 ml of ethanol was added 1 ml of a 1 M aqueous sodium hydroxide solution, followed by stirring at room temperature for 60 hours, and further at 60° C. for 8 hours. After evaporating the solvent, a liquid separation operation was carried out using 1 M hydrochloric acid and chloroform. The organic layer was dried over anhydrous magnesium sulfate and the solvent was then evaporated. The residue was purified by silica gel column chromatography (eluent: chloroform-methanol). The obtained residue was washed with diisopropyl ether-ethyl acetate to obtain 144 mg of ethyl 1,2-trans-2-[3,4-trans-3-(2,4-dichlorophenyl)-1-oxo-4-[(2-phenylethyl)carbamoyl]-3,4-dihydroisoquinolin-2(1H)-yl]cyclohexanecarboxylate as a white solid.

Example 28

To a mixed liquid of 334 mg of 2-(trimethylsilylethyl) 1,2-cis-2-[3,4-trans-3-(2,4-dichlorophenyl)-1-oxo-4-[(pyridin-2-ylmethoxy)carbamoyl]-3,4-dihydroisoquinolin-2(1H)-yl]cyclohexanecarboxylate and 5 ml of THF was added 0.60 ml of a 1 M solution of tetrabutylammonium fluoride in THF, followed by stirring at room temperature for 4 hours. To the reaction solution was added 20 ml of DMF, followed by stirring at room temperature for 2 hours, then evaporating the THF under reduced pressure, and stirring again at room temperature for 20 hours. The reaction solution was warmed to 60° C. and stirred for 2 hours, and then 0.30 ml of a 1 M solution of tetrabutylammonium fluoride in THF was further added thereto, followed by stirring at 60° C. for 2 hours. After evaporating the solvent under reduced pressure, 1 M hydrochloric acid was added, and a 1 M aqueous sodium hydroxide solution was added thereto until the pH reached 2. The solution was extracted with ethyl acetate and chloroform, and dried over anhydrous magnesium sulfate, and the solvent was then evaporated. The residue was purified by silica gel column chromatography (eluent: chloroform-methanol), and the obtained residue was then washed with ethyl acetate to obtain 156 mg of 1,2-cis-2-[3,4-trans-3-(2,4-dichlorophenyl)-1-oxo-4-[(pyridin-2-ylmethoxy)carbamoyl]-3,4-dihydroisoquinolin-2(1H)-yl]cyclohexanecarboxylic acid as a white solid.

Example 29

To a solution of 1000 mg of (3RS,4RS)—N-[2-amino-2-(hydroxyimino)ethoxy]-3-(2,4-dichlorophenyl)-2-{(1SR, 2SR)-2-[(mesyl)amino]cyclohexyl}-1-oxo-1,2,3,4-tetrahydroisoquinoline-4-carboxamide in 26 ml of dichloroethane was added dropwise 0.4 ml of pyridine, and then 0.23 ml of methyl chloro(oxo)acetate was added dropwise thereto under ice-cooling, followed by stirring at 0° C. for 10 minutes, at room temperature for 20 minutes, and at 80° C. for 2 hours. The reaction solution was cooled to room temperature, washed with 0.1 M hydrochloric acid and a saturated aqueous sodium chloride solution, dried over anhydrous magnesium sulfate, and then concentrated under reduced pressure. The residue was purified by silica gel column chromatography (eluent: chloroform-methanol) to obtain 670 mg of methyl 3-{[({[(3RS,4RS)-3-(2,4-dichlorophenyl)-2-{(1SR,2SR)-2-[(mesyl)amino]cyclohexyl}-1-oxo-1,2,3,4-tetrahydroisoquinolin-4-yl]carbonyl}amino) oxy]methyl}-1,2,4-oxadiazole-5-carboxylate as a white amorphous substance.

Example 30

To 400 mg of (3RS,4RS)-3-(2,4-dichlorophenyl)-2-{(1SR,2SR)-2-[(mesyl)amino]cyclohexyl}-1-oxo-1,2,3,4-tetrahydroisoquinoline-4-carboxylic acid were added 8 ml of DMF, 243 mg of O-[3-(tetrahydro-2H-pyran-2-yl oxy) benzyl]hydroxylamine, 159 mg of HOBt, and 243 mg of WSC, followed by stirring at room temperature for 3 hours. The reaction solution was added with ethyl acetate and water to carry out a liquid separation operation, and the organic layer was washed with a saturated aqueous sodium hydrogen carbonate solution and a saturated aqueous sodium chloride solution, dried over anhydrous magnesium sulfate, and then evaporated under reduced pressure. To the residue was added methanol, and concentrated hydrochloric acid was added dropwise thereto under ice-cooling, followed by stirring under ice-cooling for 1 hour. The precipitated crystal was collected by filtration to obtain 275 mg of (3RS,4RS)-3-(2,4-dichlorophenyl)-N-[(3-hydroxybenzyl)oxy]-2-{(1SR,2SR)-2-[(mesyl)amino]cyclohexyl}-1-oxo-1,2,3,4-tetrahydroisoquinoline-4-carboxamide as a white crystal.

Example 31

To a solution of 323 mg of (3-{[({[(3RS,4RS)-3-(2,4-dichlorophenyl)-2-{(1SR,2SR)-2-[(mesyl)amino]cyclohexyl}-1-oxo-1,2,3,4-tetrahydroisoquinolin-4-yl] carbonyl}amino)oxy]methyl}-1,2,4-oxadiazol-5-yl)methyl acetate in 6.5 ml of methanol was added 66 mg of potassium carbonate, followed by stirring at room temperature for 3 hours. To the reaction solution was added ethyl acetate, followed by washing with a saturated aqueous sodium chloride solution. The organic layer was dried over anhydrous magnesium sulfate and then concentrated under reduced pressure. The residue was purified by silica gel column chromatography (eluent: chloroform-methanol) and then recrystallized from ethyl acetate to obtain 157 mg of (3RS,4RS)-3-(2,4-dichlorophenyl)-N-{[5-(hydroxymethyl)-1,2,4-oxadiazol-3-yl]methoxy}-2-{(1SR,2SR)-2-[(mesyl) amino]cyclohexyl}-1-oxo-1,2,3,4-tetrahydroisoquinoline-4-carboxamide as a white crystal.

Example 32

By condensing 4-({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)butanoic acid and ethylamine using WSC and HOBt in accordance with Example 1, (3RS,4RS)-3-(2,4-dichlorophenyl)-N-[4-(ethylamino)-4-oxobutyl]-2-{(1SR,2SR)-2-[(mesyl)amino]cyclohexyl}-1-oxo-1,2,3,4-tetrahydroisoquinoline-4-carboxamide was obtained as a colorless crystal.

Example 33

By condensing 3,4-trans-2-cyclopentyl-1-oxo-4-[(2-phenylethyl)carbamoyl]-1,2,3,4-tetrahydroisoquinoline-3-carboxylic acid and benzylamine using WSC and HOBt in accordance with Example 1, 3,4-trans-3-benzylcarbamoyl-2-cyclopentyl-1-oxo-N-(2-phenylethyl)-1,2,3,4-tetrahydroisoquinoline-4-carboxamide was obtained as a colorless crystal.

Example 34

By condensing cis-4-[3,4-trans-3-(2,4-dichlorophenyl)-1-oxo-4-[(2-phenylethyl)carbamoyl]-3,4-dihydroisoquinolin-2(1H)-yl]cyclohexanecarboxylic acid and 1-methylpiperazine using WSC and HOBt in accordance with Example 1, 3,4-trans-3-(2,4-dichlorophenyl)-2-{cis-4-[(4-methylpiperazin-1-yl)carbonyl]cyclohexyl}-1-oxo-N-(2-phenylethyl)-1,2,3,4-tetrahydroisoquinoline-4-carboxamide was obtained as a colorless crystal.

Example 35

By condensing (3RS,4RS)-2-[(1SR,2SR)-2-aminocyclohexyl]-N-(benzyloxy)-3-(2,4-dichlorophenyl)-1-oxo-1,2,3,4-tetrahydroisoquinoline-4-carboxamide and hydroxyacetic acid using WSC and HOBt in accordance with Example 1, (3RS,4RS)—N-(benzyloxy)-3-(2,4-dichlorophenyl)-2-[(1SR,2SR)-2-(glycoloylamino)cyclohexyl]-1-oxo-1,2,3,4-tetrahydroisoquinoline-4-carboxamide was obtained as a colorless crystal.

Example 36

By treating 3,4-trans-2-cyclopentyl-3-(3-pyridinyl)-1-oxo-N-phenylethyl-1,2,3,4-tetrahydroisoquinoline-4-carboxamide with m-chloroperbenzoic acid in accordance with Example 3, 3,4-trans-2-cyclopentyl-3-(1-oxidopyridin-3-yl)-1-oxo-N-phenylethyl-1,2,3,4-tetrahydroisoquinoline-4-carboxamide was obtained as a colorless crystal.

Example 37

By treating 3,4-trans-3-(2,4-dichlorophenyl)-1-oxo-N-phenylethyl-2-[2-(3-pyridinyl)ethyl]-1,2,3,4-tetrahydroisoquinoline-4-carboxamide with m-chloroperbenzoic acid in accordance with Example 3, 3,4-trans-3-(2,4-dichlorophenyl)-1-oxo-N-phenylethyl-2-[2-(1-oxidopyridin-3-yl)ethyl]-1,2,3,4-tetrahydroisoquinoline-4-carboxamide was obtained as a colorless crystal.

Example 38

By treating methyl 4-{3,4-trans-2-cyclopentyl-1-oxo-4-[(2-phenylethyl)carbamoyl]-1,2,3,4-tetrahydroisoquinolin-3-yl}benzoate with a 1 M aqueous sodium hydroxide solution in accordance with Example 4, 4-{3,4-trans-2-cyclopentyl-1-oxo-4-[(2-phenylethyl)carbamoyl]-1,2,3,4-tetrahydroisoquinolin-3-yl}benzoic acid was obtained as a colorless crystal.

Example 39

By treating ethyl 4-{3,4-trans-3-(2,4-dichlorophenyl)-1-oxo-4-[(2-phenylethyl)carbamoyl]-3,4-dihydroisoquinolin- 2(1H)-yl}propanoate with a 1 M aqueous sodium hydroxide solution in accordance with Example 4, 4-{3,4-trans-3-(2,4-dichlorophenyl)-1-oxo-4-[(2-phenylethyl)carbamoyl]-3,4-dihydroisoquinolin-2(1H)-yl}propanoic acid was obtained as a colorless crystal.

Example 40

By treating 4-{[({[(3RS,4RS)-trans-3-(2,4-dichlorophenyl)-2-[(1SR,2SR)-trans-2-hydroxycyclohexyl]-1-oxo-1,2,3,4-tetrahydroisoquinolin-4-yl]carbonyl}amino)oxy]methyl}benzoic acid with CDI and then with sodium borohydride in accordance with Example 7, (3RS,4RS)-3-(2,4-dichlorophenyl)-2-[(1SR,2SR)-1,2-trans-2-hydroxycyclohexyl]-N-{[4-(hydroxymethyl)benzyl]oxy}-1-oxo-1,2,3,4-tetrahydroisoquinoline-4-carboxamide was obtained as a colorless crystal.

Example 41

To a mixed liquid of 400 mg of (3RS,4RS)—N-[2-amino-2-(hydroxyimino)ethoxy]-3-(2,4-dichlorophenyl)-2-{(1SR,2SR)-2-[(mesyl)amino]cyclohexyl}-1-oxo-1,2,3,4-tetrahydroisoquinoline-4-carboxamide and 40 ml of acetonitrile were added 108 mg of CDI and 0.4 ml of DBU under ice-cooling, followed by stirring at room temperature overnight. After concentrating the reaction solution, a saturated aqueous ammonium chloride solution and ethyl acetate were added thereto, followed by extraction. The organic layer was washed with saturated brine and then dried over anhydrous magnesium sulfate, and the solvent was evaporated. The residue was purified by silica gel column chromatography (eluent: chloroform-methanol) and recrystallized from ethyl acetate to obtain 40 mg of (3RS,4RS)-3-(2,4-dichlorophenyl)-2-{(1SR,2SR)-2-[(mesyl)amino]cyclohexyl}-1-oxo-N-[(5-oxo-4,5-dihydro-1,2,4-oxadiazol-3-yl)methoxy]-1,2,3,4-tetrahydroisoquinoline-4-carboxamide as a colorless crystal.

Example 42

To a mixture of 300 mg of (3RS,4RS)-3-(2,4-dichlorophenyl)-2-{(1SR,2SR)-2-[(mesyl)amino]cyclohexyl}-1-oxo-1,2,3,4-tetrahydroisoquinoline-4-carboxylic acid and 6 ml of DMF were added {5-[(aminooxy)methyl]pyrazin-2-yl}methyl acetate dihydrochloride, 0.16 ml of triethylamine, 119 mg of HOBt, and 200 mg of WSC, followed by stirring at room temperature for 3 hours. Ethyl acetate and water were added thereto to carry out a liquid separation operation. The organic layer was washed with a saturated aqueous sodium hydrogen carbonate solution and saturated brine, dried over anhydrous magnesium sulfate, and then evaporated under reduced pressure. To the residue were added 4.5 ml of methanol and 2.4 ml of a 1 M aqueous sodium hydroxide solution, followed by stirring at 0° C. for 2 hours, and then 1 M hydrochloric acid was added thereto for neutralization. Chloroform was added thereto for extraction, and the organic layer was dried over anhydrous magnesium sulfate and then concentrated under reduced pressure. The residue was purified by silica gel chromatography (eluent: chloroform-methanol) and then recrystallized from ethyl acetate to obtain 73 mg of (3RS,4RS)-3-(2,4-dichlorophenyl)-N-{[5-(hydroxymethyl)pyrazin-2-yl]methoxy}-2-{(1SR,2SR)-2-[(mesyl)amino]cyclohexyl}-1-oxo-1,2,3,4-tetrahydroisoquinoline-4-carboxamide as a colorless crystal.

Example 43

To a solution of 350 mg of (3RS,4RS)—N-[2-amino-2-(hydroxyimino)ethoxy]-3-(2,4-dichlorophenyl)-2-{(1SR,2SR)-2-[(mesyl)amino]cyclohexyl}-1-oxo-1,2,3,4-tetrahydroisoquinoline-4-carboxamide in 9.2 ml of dichloroethane was added dropwise 0.15 ml of pyridine. To the reaction solution was added dropwise 0.095 ml of 2-chloro-2-oxoethyl acetate under ice-cooling, followed by stirring for 10 minutes at 0° C., 20 minutes at room temperature and then heating under reflux for 8 hours. The solution was cooled to room temperature, and ethyl acetate was added thereto, followed by washing with 0.1 M hydrochloric acid and a saturated aqueous sodium chloride solution. The organic layer was dried over anhydrous magnesium sulfate and then concentrated under reduced pressure. The residue was purified by silica gel column chromatography (eluent: chloroform-methanol) to obtain 323 mg of (3-{[({[(3RS,4RS-3-(2,4-dichlorophenyl)-2-{(1SR,2SR)-2-[(mesyl)amino]cyclohexyl}-1-oxo-1,2,3,4-tetrahydroisoquinolin-4-yl]carbonyl}amino)oxy]methyl}-1,2,4-oxadiazol-5-yl)methyl acetate.

Example 44

To a solution of 600 mg of methyl 5-{[({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)oxy]methyl}thiophene-3-carboxylate in 40 mL of THF was added 45 mg of lithium aluminum hydride at −78° C. The solution was warmed to 0° C., followed by stirring for 3 hours. Sodium sulfate decahydrate was added thereto, followed by stirring for 1 hour. After removing sodium sulfate by filtration, the organic layer was dried by adding anhydrous magnesium sulfate, and concentrated under reduced pressure. The residue was purified by silica gel column chromatography (eluent: chloroform-methanol) to obtain 162 mg of (3RS,4RS)-3-(2,4-dichlorophenyl)-N-{[4-(hydroxymethyl)-2-thienyl]methoxy}-2-{(1SR,2SR)-2-[(methylsulfonyl)amino]cyclohexyl}-1-oxo-1,2,3,4-tetrahydroisoquinoline-4-carboxamide as a white solid.

Example 45

To a solution of 500 mg of (3RS,4RS)-3-(2,4-dichlorophenyl)-2-{(1SR,2SR)-2-[(methylsulfonyl)amino]cyclohexyl}-6-nitro-1-oxo-N-(pyridin-2-ylmethoxy)-1,2,3,4-tetrahydroisoquinoline-4-carboxamide in 10 ml of methanol-dioxane(1:1) was added 500 mg of Raney nickel, followed by stirring for 30 minutes under a hydrogen atmosphere. The catalyst was removed by filtration and the solvent was concentrated under reduced pressure to obtain 300 mg of (3RS,4RS)-6-amino-3-(2,4-dichlorophenyl)-2-{(1SR,2SR)-2-[(methylsulfonyl)amino]cyclohexyl}-1-oxo-N-(pyridin-2-ylmethoxy)-1,2,3,4-tetrahydroisoquinoline-4-carboxamide as a black solid.

Example 46

To a solution of 300 mg of (3RS,4RS)-6-amino-3-(2,4-dichlorophenyl)-2-{(1SR,2SR)-2-[(methylsulfonyl)amino]cyclohexyl}-1-oxo-N-(pyridin-2-ylmethoxy)-1,2,3,4-tetrahydroisoquinoline-4-carboxamide, 213 mg of formaldehyde, and 11 mg of sulfuric acid in 5 ml of THF was added 125 mg of sodium borohydride at 0° C., followed by stirring for 2 hours. The reaction solution was poured into ice water and the organic layer was extracted with ethyl acetate. The solution was dried over anhydrous magnesium sulfate and concentrated under reduced pressure. The residue was purified by reverse-phase silica gel column chromatography (eluent: acetonitrile-water) to obtain 10 mg of (3RS,4RS)-3-(2,4-dichlorophenyl)-6-(dimethylamino)-2-{(1R,2S)-2-[(methylsulfonyl)amino]cyclohexyl}-1-oxo-N-(pyridin-2-ylmethoxy)-1,2,3,4-tetrahydroisoquinoline-4-carboxamide as a yellow solid.

Example 47

A solution of 343 mg of (3RS,4RS)-3-(2,4-dichlorophenyl)-N-(2-hydrazino-2-oxoethoxy)-2-{(1SR,2SR)-2-[(methylsulfonyl)amino]cyclohexyl}-1-oxo-1,2,3,4-tetrahydroisoquinoline-4-carboxamide in 6.9 ml of THF was cooled to 0° C., and 116 mg of 1,1'-carbonyldiimidazole and 0.12 ml of triethylamine were added thereto, followed by stirring at 0° C. for 2 hours, and then stirring at room temperature overnight. 0.1 M hydrochloric acid was added thereto, followed by extraction with ethyl acetate. The solution was washed with a saturated aqueous sodium chloride solution, dried over anhydrous magnesium sulfate, and then concentrated under reduced pressure. The residue was recrystallized from ethyl acetate to obtain 221 mg of (3RS,4RS)-3-(2,4-dichlorophenyl)-2-{(1SR,2SR)-2-[(methylsulfonyl)amino]cyclohexyl}-1-oxo-N-[(5-oxo-4,5-dihydro-1,3,4-oxadiazol-2-yl)methoxy]-1,2,3,4-tetrahydroisoquinoline-4-carboxamide as a white powder crystal.

Example 48

To a mixed liquid of 420 mg of benzyl ({6-[2-({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)ethyl]pyridin-2-yl}oxy)acetate, 5 ml of DMF, and 5 ml of ethanol was added 84 mg of 5% palladium/carbon, followed by stirring at room temperature for 15 minutes under a hydrogen atmosphere. After separating the palladium/carbon by filtration, the solvent was evaporated, and the residue was purified by silica gel column chromatography (eluent: chloroform-methanol) to obtain 78 mg of ({6-[2-({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)ethyl]pyridin-2-yl}oxy)acetic acid as a white solid.

Example 49

A solution of 480 mg of (3RS,4RS)-3-(2,4-dichlorophenyl)-N-{[6-(hydroxymethyl)pyridin-2-yl]methoxy}-2-{(1SR,2SR)-2-[(methylsulfonyl)amino]cyclohexyl}-1-oxo-1,2,3,4-tetrahydroisoquinoline-4-carboxamide in 4.8 ml of dichloromethane was cooled to 0° C., 4.5 mg of DMAP and 0.13 ml of pyridine were added, and then 0.7 ml of acetic anhydride was added dropwise, followed by stirring at room temperature overnight. To the reaction mixture was added water, followed by extraction with ethyl acetate. The organic layer was dried over anhydrous magnesium sulfate and then concentrated under reduced pressure. The residue was purified by silica gel column chromatography (eluent: chloroform-methanol) to obtain (6-{[(acetyl{[3-(2,4-dichlorophenyl)-2-{2-[(methylsulfonyl)amino]cyclohexyl}-1-oxo-1,2,3,4-tetrahydroisoquinolin-4-yl]carbonyl}amino)oxy]methyl}pyridin-2-yl)methyl acetate.

Example 50

A solution of 714 mg of (3R,4R)-3-(2,4-dichlorophenyl)-N-{1-[6-(hydroxymethyl)pyridin-2-yl]ethyl}-2-{(1S,2S)-2-[(methylsulfonyl)amino]cyclohexyl}-1-oxo-1,2,3,4-tetrahydroisoquinoline-4-carboxamide in 14.3 ml of chloroform was cooled to 0° C., and 0.23 ml of triethylamine, 0.16 ml of acetic anhydride, and 6.8 mg of DMAP were added thereto in this order, followed by stirring at room temperature for 5 hours. The reaction solution was concentrated under reduced pressure, and ethyl acetate-water was added thereto for liquid separation, followed by washing with a saturated aqueous sodium hydrogen carbonate solution and a saturated aqueous sodium chloride solution. The solution was dried over anhydrous magnesium sulfate and then concentrated under reduced pressure to obtain {6-[1-({[(3R,4R)-3-(2,4-dichlorophenyl)-2-{(1S,2S)-2-[(methylsulfonyl)amino]cyclohexyl}-1-oxo-1,2,3,4-tetrahydroisoquinolin-4-yl]carbonyl}amino)ethyl]pyridin-2-yl}methyl acetate.

Example 51

To 591 mg of [({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)oxy]acetic acid were added 8 ml of DMF, 200 mg of tert-butyl hydrazinecarboxylate, 205 mg of HOBt, and 388 mg of WSC hydrochloride, followed by stirring at room temperature for 3 hours. Ethyl acetate and water were added thereto to carry out a liquid separation operation. The organic layer was washed with a saturated aqueous sodium hydrogen carbonate solution and a saturated aqueous sodium chloride solution, dried over anhydrous magnesium sulfate, and then evaporated under reduced pressure. 7.7 ml of dichloromethane was added thereto, followed by cooling to 0° C., and 1.2 ml of trifluoroacetic acid was added thereto, followed by stirring at room temperature for 5 hours. The residue was purified by silica gel column chromatography (eluent: chloroform-methanol) and recrystallized from ethyl acetate to obtain 417 mg of (3RS,4RS)-3-(2,4-dichlorophenyl)-N-(2-hydrazino-2-oxoethoxy)-2-{(1SR,2SR)-2-[(methylsulfonyl)amino]cyclohexyl}-1-oxo-1,2,3,4-tetrahydroisoquinoline-4-carboxamide as a white powder crystal.

Example 52

A solution of 153 mg of (6-{[({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)oxy]methyl}-1-oxidopyridin-3-yl)methyl benzoate in 3 ml of ethanol was cooled to 0° C., and 32 mg of sodium hydroxide was added thereto, followed by stirring at 0° C. for 2 hours. The solution was neutralized with 1 M hydrochloric acid, and a saturated aqueous sodium hydrogen carbonate solution and chloroform were added for liquid separation. The organic layer was dried over anhydrous magnesium sulfate and then evaporated under reduced pressure. The residue was purified by silica gel column chromatography (eluent: chloroform-methanol) to obtain 24 mg of (3RS,4RS)-3-(2,4-dichlorophenyl)-N-{[5-(hydroxymethyl)-1-oxidopyridin-2-yl]methoxy}-2-{(1SR,2SR)-2-[(methylsulfonyl)amino]cyclohexyl}-1-oxo-1,2,3,4-tetrahydroisoquinoline-4-carboxamide.

Example 53

To a solution of 700 mg of (3RS,4RS)-3-(2,4-dichlorophenyl)-2-{(1SR,2SR)-2-[(methylsulfonyl)amino]cyclohexyl}-1-oxo-1,2,3,4-tetrahydroisoquinoline-4-carboxylic acid, 351 mg of 1-phenylmethanesulfonamide, and 334 mg of DMAP in 10.5 ml of DMF was added 525 mg of WSC/hydrochloride, followed by stirring at room temperature overnight. 0.1 M hydrochloric acid was added thereto, followed by extraction with ethyl acetate. The organic layer was washed with a saturated aqueous sodium chloride solution, then dried over anhydrous magnesium sulfate, and concentrated under reduced pressure. The residue was purified by silica gel column chromatography (eluent: chloroform-methanol), and ethyl acetate and a saturated aqueous sodium hydrogen carbonate solution were then added thereto for liquid separation. The organic layer was dried over anhydrous magnesium sulfate and then concentrated under reduced pressure. Ethyl acetate and diisopropyl ether were added thereto, and the precipitated solid was collected by filtration to obtain 33 mg of (3RS,4RS)—N-(benzylsulfonyl)-3-(2,4-dichlorophenyl)-2-{(1SR,2SR)-2-[(methylsulfonyl)amino]cyclohexyl}-1-oxo-1,2,3,4-tetrahydroisoquinoline-4-carboxamide as a colorless solid.

Example 54

To a solution of 566 mg of (3RS,4RS)-3-(2,4-dichlorophenyl)-N-[(2,2-dimethyl-4H-[1,3]dioxino[5,4-b]pyridin-6-yl)methoxy]-2-{(1SR,2SR)-2-[(methylsulfonyl)amino]cyclohexyl}-1-oxo-1,2,3,4-tetrahydroisoquinoline-4-carboxamide in 11.3 ml of THF was added 3.2 ml of 1 M hydrochloric acid, followed by stirring at room temperature for 2 hours. 1.6 ml of 1 M hydrochloric acid was further added, followed by stirring for 2 days. The solution was neutralized with a saturated aqueous sodium hydrogen carbonate solution and then extracted with chloroform. The organic layer was dried over anhydrous magnesium sulfate and then concentrated under reduced pressure. The residue was purified by silica gel column chromatography (eluent: chloroform-methanol) and recrystallized from ethyl acetate to obtain 196 mg of rel-(3RS,4RS)-3-(2,4-dichlorophenyl)-N-{[5-hydroxy-6-(hydroxymethyl)pyridin-2-yl]methoxy}-2-{(1SR,2SR)-2-[(methylsulfonyl)amino]cyclohexyl}-1-oxo-1,2,3,4-tetrahydroisoquinoline-4-carboxamide as a white crystal.

Example 55

To a solution of 433 mg of 6-{[(acetyl{[3-(2,4-dichlorophenyl)-2-{2-[(methylsulfonyl)amino]cyclohexyl}-1-oxo-1,2,3,4-tetrahydroisoquinolin-4-yl]carbonyl}amino)oxy]methyl}-1-oxidopyridin-2-yl)methyl acetate in 8.7 ml of methanol was added 160 mg of potassium carbonate, followed by stirring. The solution was added with 1 M hydrochloric acid and then with a saturated aqueous sodium hydrogen carbonate solution, extracted with ethyl acetate, dried over anhydrous magnesium sulfate, and then concentrated under reduced pressure. The residue was purified by silica gel column chromatography (eluent: chloroform-methanol). Ethyl acetate, ethanol, and diisopropyl ether were added thereto for solidification to obtain 164 mg of 3-(2,4-dichlorophenyl)-N-{[6-(hydroxymethyl)-1-oxidopyridin-2-yl]methoxy}-2-{2-[(methylsulfonyl)amino]cyclohexyl}-1-oxo-1,2,3,4-tetrahydroisoquinoline-4-carboxamide as a colorless solid.

Example 56

To a solution of 777 mg of {6-[1-({[(3R,4R)-3-(2,4-dichlorophenyl)-2-{(1S,2S)-2-[(methylsulfonyl)amino]cyclohexyl}-1-oxo-1,2,3,4-tetrahydroisoquinolin-4-yl]carbonyl}amino)ethyl]-1-oxidopyridin-2-yl}methyl acetate in 17 ml of methanol was added 0.21 ml of hydrazine monohydrate, followed by stirring for one week. Ethyl acetate was added thereto, followed by stirring for a while and concentrating, and the residue was purified by silica gel column chromatography (eluent: chloroform-methanol). Ethyl acetate and diisopropyl ether were used to make a powder, thereby obtaining 501 mg of (3R,4R)-3-(2,4-dichlorophenyl)-N-{1-[6-(hydroxymethyl)-1-oxidopyridin-2-yl]ethyl}-2-{(1S,2S)-2-[(methylsulfonyl)amino]cyclohexyl}-1-oxo-1,2,3,4-tetrahydroisoquinoline-4-carboxamide as a colorless solid.

Example 57

A mixture of 590 mg of 3-{[({[(3RS,4RS)-3-(2,4-dichlorophenyl)-2-{(1SR,2SR)-2-[(methylsulfonyl)amino]cyclohexyl}-1-oxo-1,2,3,4-tetrahydroisoquinolin-4-yl]carbonyl}amino)oxy]methyl}benzoic acid, 217 mg of CDI, and 9 ml of DMF was stirred at 50° C. for 1 hour, and 241 mg of guanidine carbonate was then added thereto, followed by stirring at the same temperature for 3 hours. The reaction solution was left to be cooled and the solvent was then evaporated under reduced pressure. The residue was diluted with ethyl acetate, and washed with a saturated aqueous sodium hydrogen carbonate solution and then with a saturated aqueous sodium chloride solution. The organic layer was dried over anhydrous magnesium sulfate and concentrated under reduced pressure. The obtained residue was purified by silica gel column chromatography (eluent: chloroform-methanol) and recrystallized from acetonitrile to obtain 348 mg of (3RS,4RS)—N-({3-[(diaminomethylene)carbamoyl]benzyl}oxy)-3-(2,4-dichlorophenyl)-2-{(1SR,2SR)-2-[(methylsulfonyl)amino]cyclohexyl}-1-oxo-1,2,3,4-tetrahydroisoquinoline-4-carboxamide as a colorless solid.

Example 58

To a mixture of 990 mg of 4-methoxybenzyl (3-{2-[({(3RS,4RS)-3-(2,4-dichlorophenyl)-2-[(1SR,2SR)-2-hydroxycyclohexyl]-1-oxo-1,2,3,4-tetrahydroisoquinolin-4-yl}carbonyl)amino]ethyl}phenyl)acetate and 10 ml of ethylene chloride was added 10 ml of trifluoroacetic acid at room temperature, followed by stirring for 4 hours. The reaction solution was concentrated under reduced pressure. The residue was dissolved in 20 mL of methanol, and 20 mL of a saturated aqueous sodium hydrogen carbonate solution was added thereto at room temperature, followed by stirring for 30 minutes. The organic solvent was evaporated under reduced pressure, and the residue was diluted with ethyl acetate and neutralized with 1 M hydrochloric acid. The product was extracted with ethyl acetate, and the organic layer was washed with a saturated aqueous sodium chloride solution and then dried over anhydrous magnesium sulfate. The organic layer was concentrated under reduced pressure, and the obtained residue was purified by silica gel column chromatography (eluent: chloroform-methanol) to obtain 339 mg of (3-{2-[({(3RS,4RS)-3-(2,4-dichlorophenyl)-2-[(1SR,2SR)-2-hydroxycyclohexyl]-1-oxo-1,2,3,4-tetrahydroisoquinolin-4-yl}carbonyl)amino]ethyl}phenyl)acetic acid as a colorless solid.

Example 59

To a mixture of 980 mg of (3RS,4RS)-3-(2,4-dichlorophenyl)-2-[(1SR,2SR)-2-hydroxycyclohexyl]-N-[2-(3-hydroxyphenyl)ethyl]-1-oxo-1,2,3,4-tetrahydroisoquinoline-4-carboxamide, 1160 mg of triphenylphosphine, 1080 mg of tert-butyl (2R)-2-hydroxypropanate, and 30 mL of THF was added 770 mg of diethyl azodicarboxylate at room temperature, followed by stirring for 12 hours. The reaction solution was diluted with ethyl acetate and washed with a saturated aqueous sodium hydrogen carbonate solution. The organic layer was dried over anhydrous magnesium sulfate and then concentrated under reduced pressure. The obtained residue was purified by silica gel column chromatography (eluent: chloroform-methanol) to obtain 1460 mg of tert-butyl (2S)-2-(3-{2-[({(3RS,4RS)-3-(2,4-dichlorophenyl)-2-[(1SR,2SR)-2-hydroxycyclohexyl]-1-oxo-1,2,3,4-tetrahydroisoquinolin-4-yl}carbonyl)amino]ethyl}phenoxy)propanate as a yellow solid.

The compounds of Examples 60 to 899 as shown in Tables below were prepared in the same manner as the methods of Examples 1 to 59, using each of the corresponding starting materials. The structures of each Example Compound are shown in Tables 70 to 275, and the production processes and the physicochemical data of each Example Compound are shown in Tables 276 to 300.

Furthermore, the structures of the other compounds of the present invention are shown in Tables 301 to 302. These can be easily synthesized by using the production processes as described above, the methods described in Examples, methods obvious to a skilled person in the art, or modified methods thereof.

TABLE 14

| PEx | Syn | Structure | Data | Note |
|-----|-----|-----------|------|------|
| 64 | P34 | 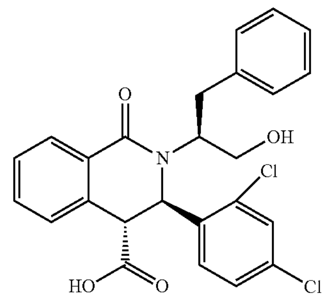 [SMILES: O=C(O)[C@@H]1c2ccccc2C(=O)N([C@H](CO)Cc2ccccc2)[C@H]1c1ccc(Cl)cc1Cl] | ESI+: 471 | |
| 65 | P34 | 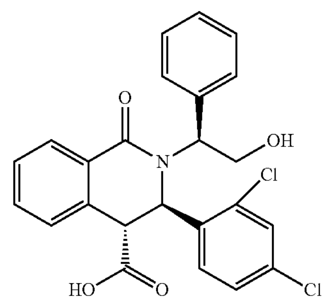 [SMILES: O=C(O)[C@@H]1c2ccccc2C(=O)N([C@H](CO)c2ccccc2)[C@H]1c1ccc(Cl)cc1Cl] | ESI+: 456 | |
| 34-2 | P34 | 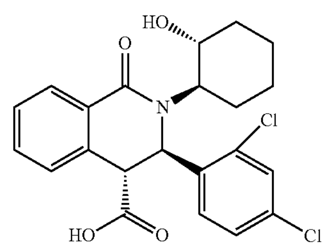 [SMILES: O=C(O)[C@@H]1c2ccccc2C(=O)N([C@@H]2CCCC[C@H]2O)[C@H]1c1ccc(Cl)cc1Cl] | ESI−: 434 | racemic mixture |
| 34-1 | P34 | 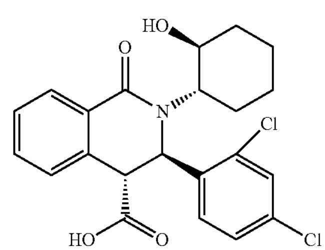 [SMILES: O=C(O)[C@@H]1c2ccccc2C(=O)N([C@H]2CCCC[C@@H]2O)[C@H]1c1ccc(Cl)cc1Cl] | ESI−: 434 | racemic mixture |

TABLE 14-continued
| PEx | Syn | Structure | Data | Note |
|---|---|---|---|---|
| 66 | P34 | 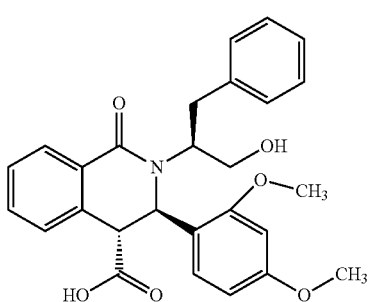 | ESI+: 430 | |
TABLE 15
| | | | | |
|---|---|---|---|---|
| 67 | P34 | | ESI+: 462 | |
| 68 | P34 | 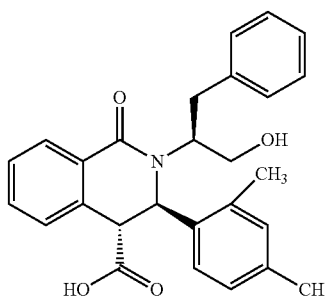 | ESI+: 430 | |
| 69 | P34 | 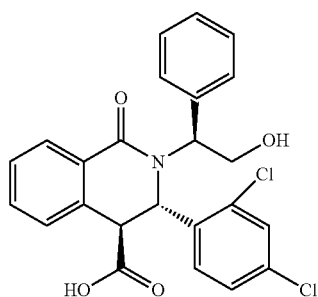 | ESI+: 456 | |

TABLE 15-continued
| 70 | P34 | 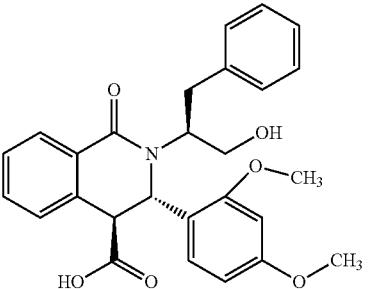 [SMILES: COc1ccc([C@@H]2[C@@H](C(=O)O)c3ccccc3C(=O)N2[C@H](CO)Cc2ccccc2)c(OC)c1] | ESI+: 462 | |
| 33-1 | P33 | 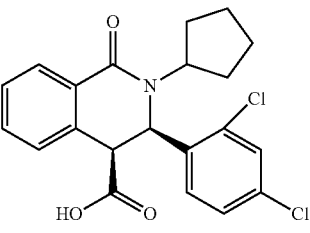 [SMILES: O=C(O)[C@H]1c2ccccc2C(=O)N(C2CCCC2)[C@H]1c1ccc(Cl)cc1Cl] | ESI+: 404 | racemic mixture |
TABLE 16
| 33-2 | P33 | 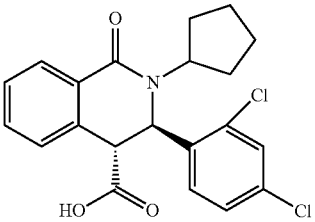 [SMILES: O=C(O)[C@@H]1c2ccccc2C(=O)N(C2CCCC2)[C@H]1c1ccc(Cl)cc1Cl] | ESI+: 404 | racemic mixture |
| 71 | P34 | 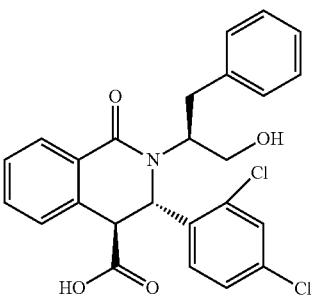 [SMILES: O=C(O)[C@H]1c2ccccc2C(=O)N([C@H](CO)Cc2ccccc2)[C@@H]1c1ccc(Cl)cc1Cl] | ESI+: 471 | |
| 72 | P33 | 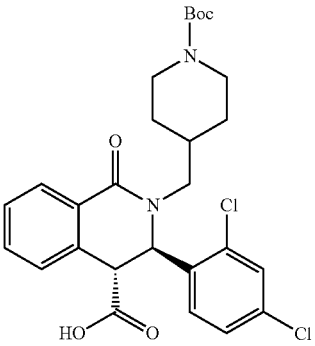 [SMILES: CC(C)(C)OC(=O)N1CCC(CN2C(=O)c3ccccc3[C@@H](C(=O)O)[C@@H]2c2ccc(Cl)cc2Cl)CC1] | FAB+: 532 | racemic mixture |

TABLE 16-continued
| 30 | P30 | 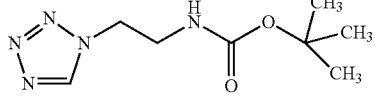 | ESI+: 214 |
| 18 | P18 | 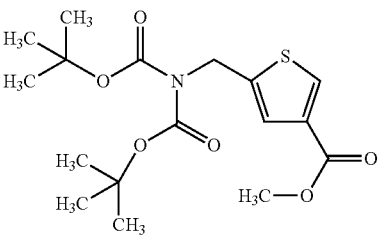 [SMILES: COC(=O)c1csc(CN(C(=O)OC(C)(C)C)C(=O)OC(C)(C)C)c1] | FAB+: 372 |
| 73 | P31 | 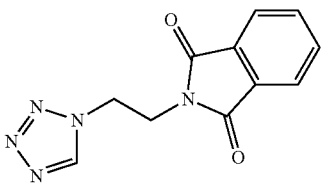 [SMILES: O=C1c2ccccc2C(=O)N1CCn1cnnn1] | ESI+: 244 |
| 74 | P31 | 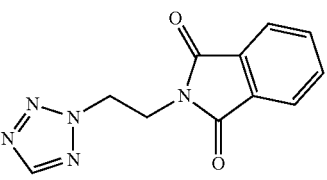 [SMILES: O=C1c2ccccc2C(=O)N1CCn1ncnn1] | ESI+: 244 |
TABLE 17
| 75 | P31 | 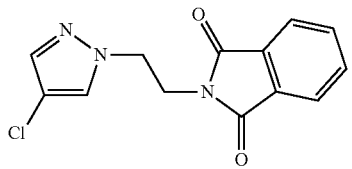 [SMILES: O=C1c2ccccc2C(=O)N1CCn1cc(Cl)cn1] | ESI+: 276 | |
| 31 | P31 | 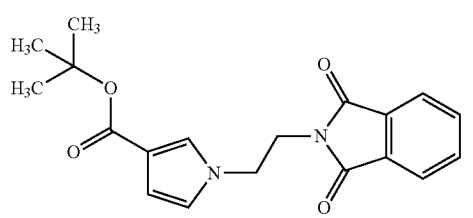 [SMILES: CC(C)(C)OC(=O)c1ccn(CCN2C(=O)c3ccccc3C2=O)c1] | FAB+: 340 | |
| 37 | P37 | 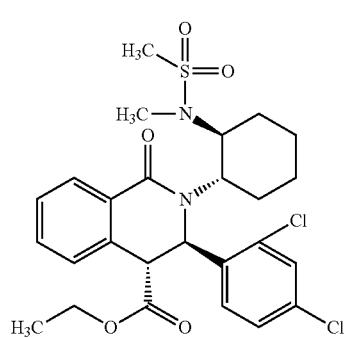 [SMILES: CCOC(=O)[C@@H]1c2ccccc2C(=O)N([C@H]2CCCC[C@@H]2N(C)S(C)(=O)=O)[C@H]1c1ccc(Cl)cc1Cl] | ESI+: 553 | racemic mixture |

TABLE 17-continued

| 5 | P5 | (structure) | FAB+: 244 |
| 76 | P17, P14 | (structure) | FAB+: 313 |
| 77 | P14 | (structure) | FAB+: 318 |
| 78 | P42 | (structure) | FAB+: 340 |

TABLE 18

| 79 | P42 | (structure) | FAB+: 340 |
| 80 | P14 | (structure) | ESI+: 330 |
| 14 | P14 | (structure) | FAB+: 332 |

TABLE 18-continued
| 81 | P14 | 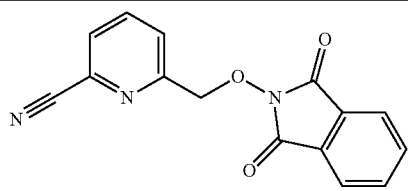 | FAB+: 280 |
| --- | --- | --- | --- |
| 82 | P14 | 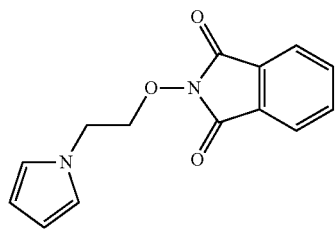 [SMILES: O=C1c2ccccc2C(=O)N1OCCn1cccc1] | FAB+: 257 |
| 83 | P14 | 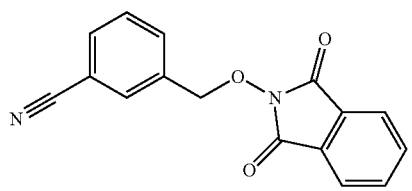 [SMILES: N#Cc1cccc(CON2C(=O)c3ccccc3C2=O)c1] | FAB+: 279 |
| 84 | P14 | 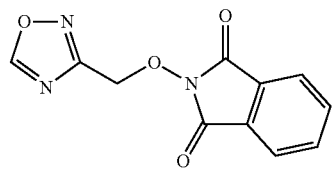 [SMILES: O=C1c2ccccc2C(=O)N1OCc1ncon1] | FAB+: 246 |
| 85 | P14 | 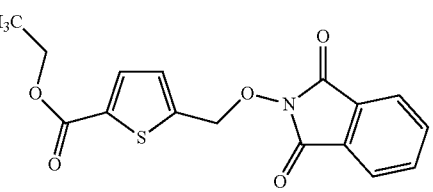 | FAB+: 332 |
TABLE 19
| 86 | P14 | 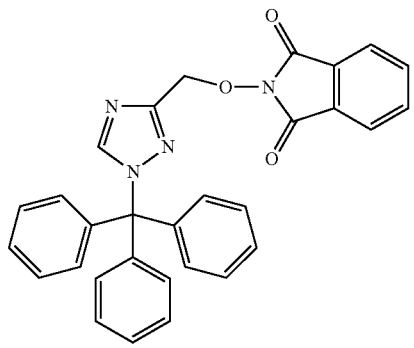 [SMILES: O=C1c2ccccc2C(=O)N1OCc1ncn(C(c2ccccc2)(c2ccccc2)c2ccccc2)n1] | FAB+: 487 |
| --- | --- | --- | --- |

TABLE 19-continued
| | | | |
|---|---|---|---|
| 87 | P14 | 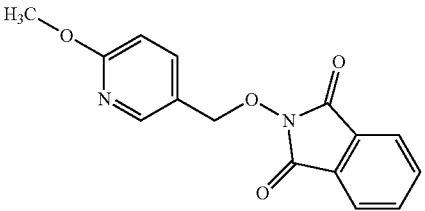 [SMILES: COc1ccc(CON2C(=O)c3ccccc3C2=O)cn1] | FAB+: 285 |
| 88 | P14 | 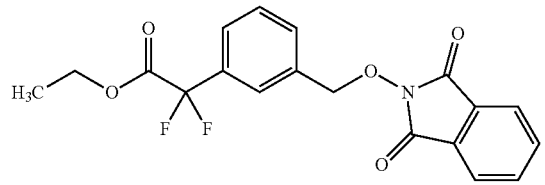 [SMILES: CCOC(=O)C(F)(F)c1cccc(CON2C(=O)c3ccccc3C2=O)c1] | FAB+: 376 |
| 89 | P42 | 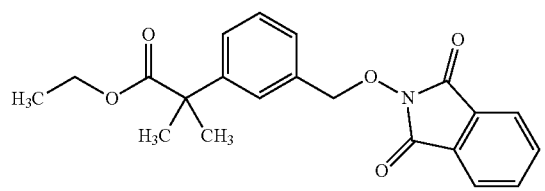 [SMILES: CCOC(=O)C(C)(C)c1cccc(CON2C(=O)c3ccccc3C2=O)c1] | FAB+: 368 |
| 90 | P14 | 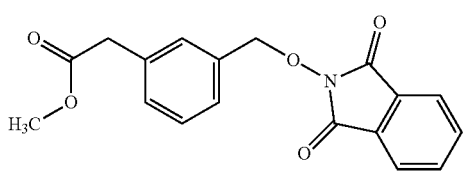 [SMILES: COC(=O)Cc1cccc(CON2C(=O)c3ccccc3C2=O)c1] | FAB+: 326 |
| 91 | P14 | 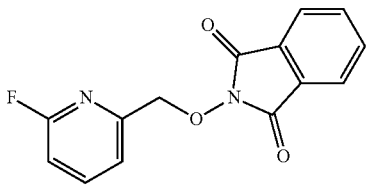 [SMILES: O=C1c2ccccc2C(=O)N1OCc1cccc(F)n1] | FAB+: 273 |
| 92 | P14 | 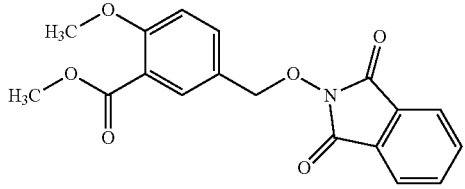 [SMILES: COC(=O)c1cc(CON2C(=O)c3ccccc3C2=O)ccc1OC] | ESI+: 342 |
TABLE 20
| | | | |
|---|---|---|---|
| 93 | P14 | 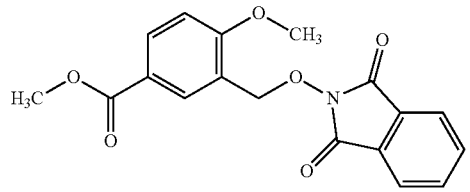 [SMILES: COC(=O)c1ccc(OC)c(CON2C(=O)c3ccccc3C2=O)c1] | ESI+: 342 |

TABLE 20-continued
| 94 | P42 | 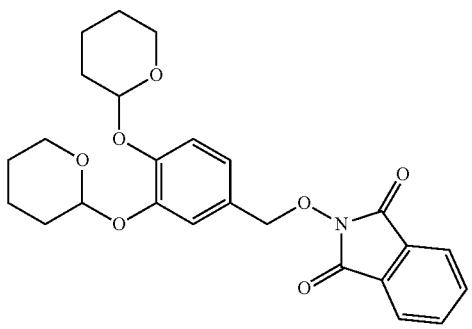 [SMILES: O=C1c2ccccc2C(=O)N1OCc1ccc(OC2CCCCO2)c(OC2CCCCO2)c1] | FAB+: 454 |
| 95 | P14 | 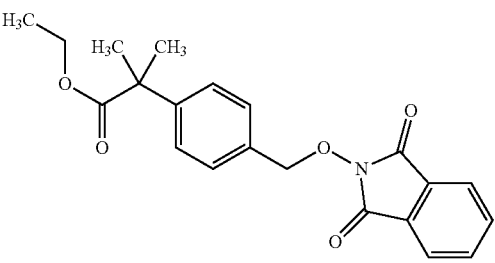 [SMILES: CCOC(=O)C(C)(C)c1ccc(CON2C(=O)c3ccccc3C2=O)cc1] | FAB+: 368 |
| 96 | P42 | 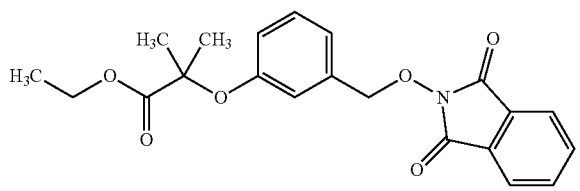 [SMILES: CCOC(=O)C(C)(C)Oc1cccc(CON2C(=O)c3ccccc3C2=O)c1] | FAB+: 384 |
| 97 | P42 | 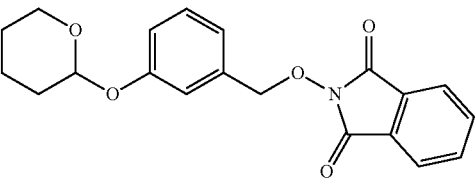 [SMILES: O=C1c2ccccc2C(=O)N1OCc1cccc(OC2CCCCO2)c1] | FAB+: 354 |
| 98 | P14 | 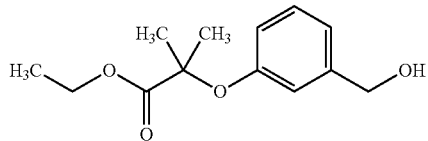 [SMILES: CCOC(=O)C(C)(C)Oc1cccc(CO)c1] | EI+: 238 |
| 99 | P42 | 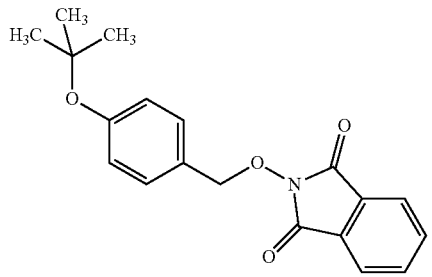 [SMILES: CC(C)(C)Oc1ccc(CON2C(=O)c3ccccc3C2=O)cc1] | FAB+: 326 |

TABLE 21

| | | | |
|---|---|---|---|
| 100 | P14 | (structure: tert-butyl ester with phenoxy and CH₂CN group) | EI+: 247 |
| 42 | P42 | (structure: 5-fluoropyridin-2-yl methyleneoxy phthalimide) | FAB+: 273 |
| 101 | P14 | (structure: 5-methyl-1,3,4-oxadiazol-2-yl methyleneoxy phthalimide) | FAB+: 260 |
| 102 | P14 | (structure: methyl 3-fluoro-5-(phthalimidooxymethyl)benzoate) | ESI+: 330 |
| 103 | P14 | (structure: 5-cyanopyridin-2-yl methyleneoxy phthalimide) | ESI+: 280 |
| 104 | P14 | (structure: 6-carbamoylpyridin-2-yl methyleneoxy phthalimide) | FAB+: 298 |
| 105 | P14 | (structure: 1-methyltetrazol-5-yl methyleneoxy phthalimide) | FAB+: 260 |
| 106 | P14 | (structure: 5-methyl-1,2,4-oxadiazol-3-yl methyleneoxy phthalimide) | FAB+: 260 |

TABLE 22
| | | | | |
|---|---|---|---|---|
| 107 | P14 | 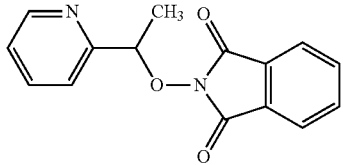 [SMILES: CC(ON1C(=O)c2ccccc2C1=O)c1ccccn1] | FAB+: 269 | |
| 108 | P14 | 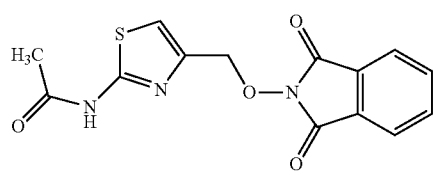 [SMILES: CC(=O)Nc1nc(CON2C(=O)c3ccccc3C2=O)cs1] | ESI+: 318 | |
| 109 | P14 | 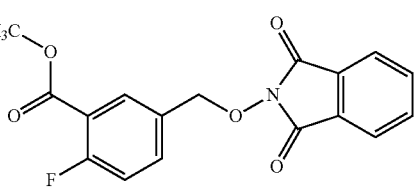 | ESI+: 330 | |
| 25 | P25 | 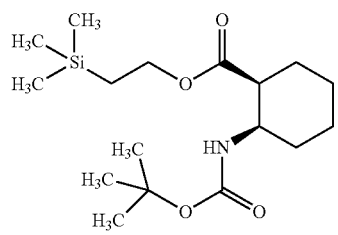 [SMILES: CC(C)(C)OC(=O)N[C@@H]1CCCC[C@@H]1C(=O)OCC[Si](C)(C)C] | FAB+: 344 | racemic mixture |
| 15 | P15 | 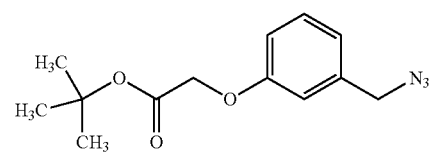 [SMILES: CC(C)(C)OC(=O)COc1cccc(CN=[N+]=[N-])c1] | FAB+: 263 | |
| 43 | P43 | 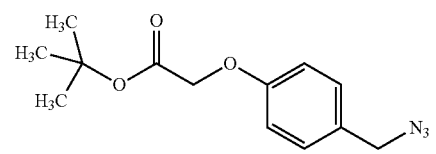 [SMILES: CC(C)(C)OC(=O)COc1ccc(CN=[N+]=[N-])cc1] | FAB+: 263 | |
| 110 | 11 | 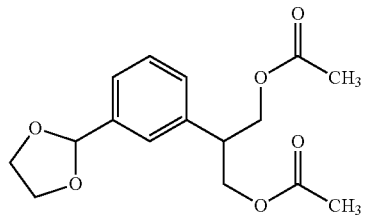 [SMILES: CC(=O)OCC(COC(C)=O)c1cccc(C2OCCO2)c1] | ESI+: 309 | |

TABLE 23
| 111 | 11 | 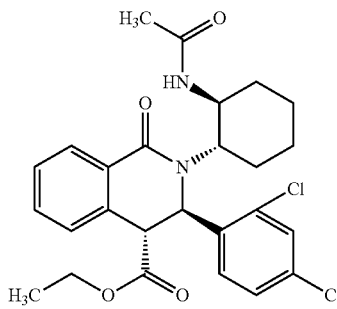 | FAB+: 503 racemic mixture |
| 112 | P34 | 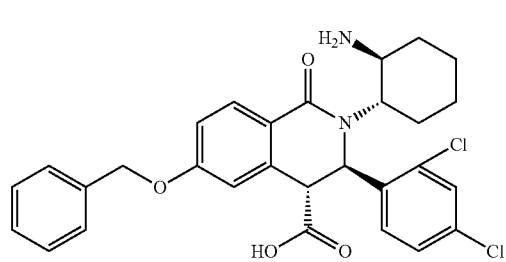 [SMILES: N[C@H]1CCCC[C@@H]1N1C(=O)c2ccc(OCc3ccccc3)cc2[C@@H](C(=O)O)[C@@H]1c1ccc(Cl)cc1Cl] | FAB+: 539 racemic mixture |
| 113 | P34 | 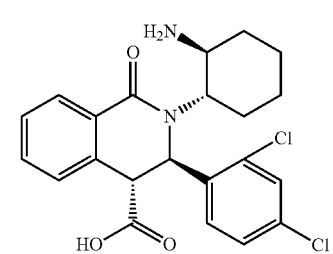 [SMILES: N[C@H]1CCCC[C@@H]1N1C(=O)c2ccccc2[C@@H](C(=O)O)[C@@H]1c1ccc(Cl)cc1Cl] | ESI+: 433 |
| 114 | P34 | 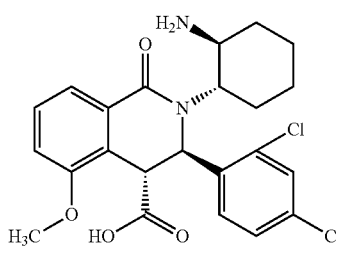 | FAB+: 463 racemic mixture |
| 115 | P34 | 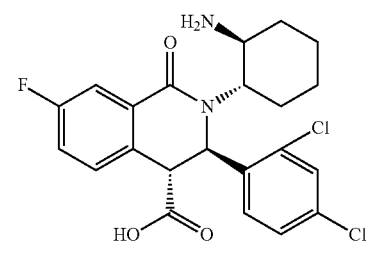 [SMILES: N[C@H]1CCCC[C@@H]1N1C(=O)c2cc(F)ccc2[C@@H](C(=O)O)[C@@H]1c1ccc(Cl)cc1Cl] | FAB+: 451 racemic mixture |
| 116 | P34 | 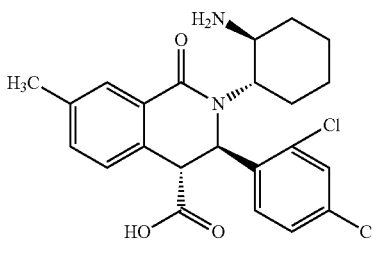 | FAB+: 447 racemic mixture |

TABLE 24
| | | | | |
|---|---|---|---|---|
| 117 | P34 | 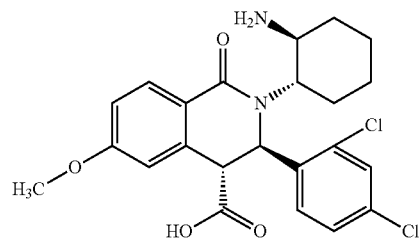 [SMILES: COc1ccc2c(c1)[C@@H](C(=O)O)[C@H](c1ccc(Cl)cc1Cl)N([C@H]1CCCC[C@@H]1N)C2=O] | ESI+: 463 | racemic mixture |
| 118 | P34 | 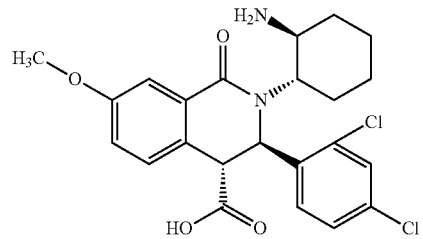 [SMILES: COc1ccc2c(c1)C(=O)N([C@H]1CCCC[C@@H]1N)[C@@H](c1ccc(Cl)cc1Cl)[C@@H]2C(=O)O] | ESI+: 463 | racemic mixture |
| 119 | P34 | 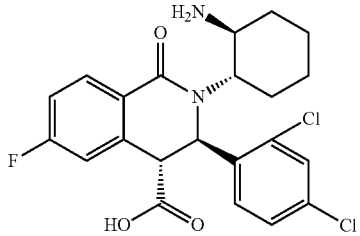 [SMILES: N[C@H]1CCCC[C@@H]1N1C(=O)c2ccc(F)cc2[C@@H](C(=O)O)[C@@H]1c1ccc(Cl)cc1Cl] | FAB+: 451 | racemic mixture |
| 120 | P34 | 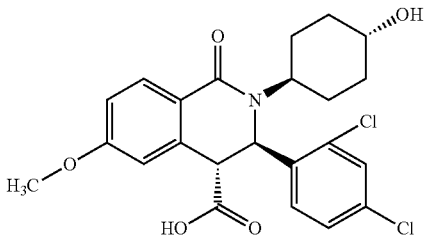 [SMILES: COc1ccc2c(c1)[C@@H](C(=O)O)[C@H](c1ccc(Cl)cc1Cl)N([C@H]1CC[C@H](O)CC1)C2=O] | ESI+: 465 | racemic mixture |
| 121 | P33 | 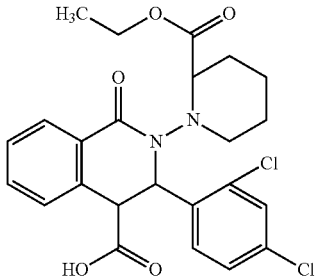 [SMILES: CCOC(=O)C1CCCCN1N1C(=O)c2ccccc2C(C(=O)O)C1c1ccc(Cl)cc1Cl] | FAB+: 491 | |
| 122 | P33 | 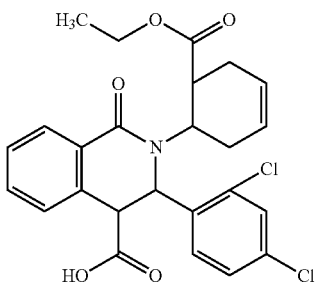 [SMILES: CCOC(=O)C1CC=CCC1N1C(=O)c2ccccc2C(C(=O)O)C1c1ccc(Cl)cc1Cl] | FAB+: 488 | 1',2'-trans |

TABLE 25

| | | | | |
|---|---|---|---|---|
| 123 | P33 | (structure) | FAB+: 562 | 1',2'-trans |
| 124 | P33 | (structure) | FAB+: 462 | 1',2'-trans |
| 125 | P33 | (structure) | FAB+: 405 | |
| 126 | P35 | (structure) | ESI+: 491 | racemic mixture |
| 127 | P34 P35 | (structure) | ESI+: 445 | 1',2'-trans, 3,4-trans, diastereo mixture |
| 35 | P35 | (structure) | ESI+: 461 | racemic mixture |

TABLE 26
| 128 | P35 | 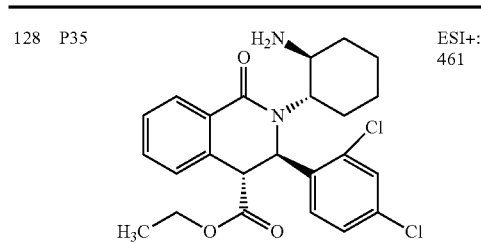 | ESI+: 461 | |
| 11 | P11 | 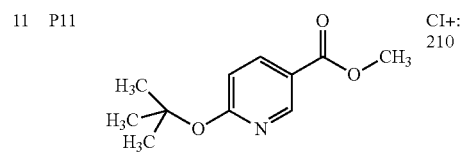 | CI+: 210 | |
| 17 | P17 | 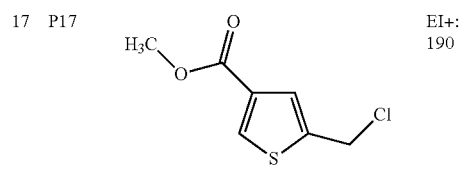 | EI+: 190 | |
| 20 | P20 | 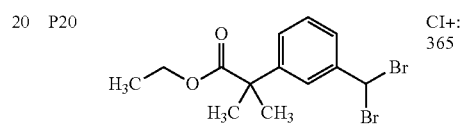 | CI+: 365 | |
| 19 | P19 | 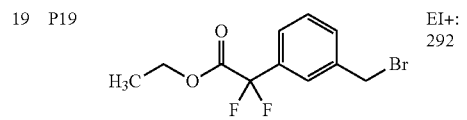 | EI+: 292 | |
| 4 | P4 | 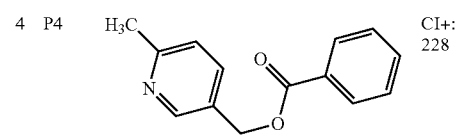 | CI+: 228 | |
| 21 | P21 | 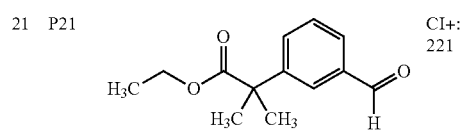 | CI+: 221 | |
| 129 | P36 | 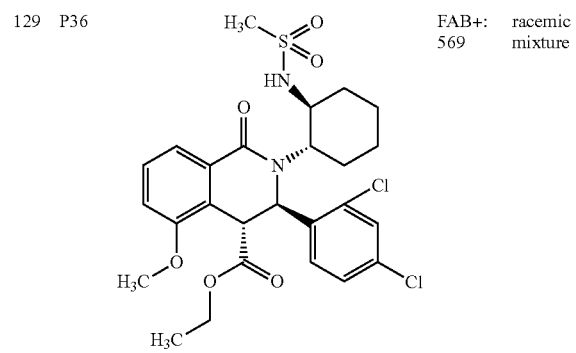 | FAB+: 569 | racemic mixture |
TABLE 27
| 130 | P36 | 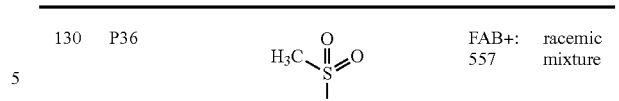 | FAB+: 557 | racemic mixture |
| 131 | P36 | 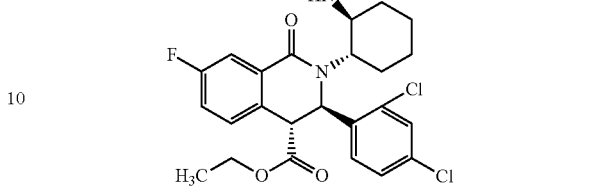 | FAB+: 557 | racemic mixture |
| 132 | P34 P35 P36 | 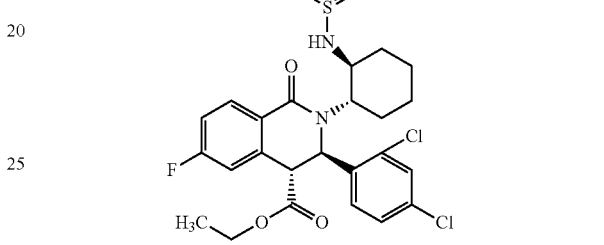 | FAB+: 569 | racemic mixture |
| 133 | P34 P35 P36 | 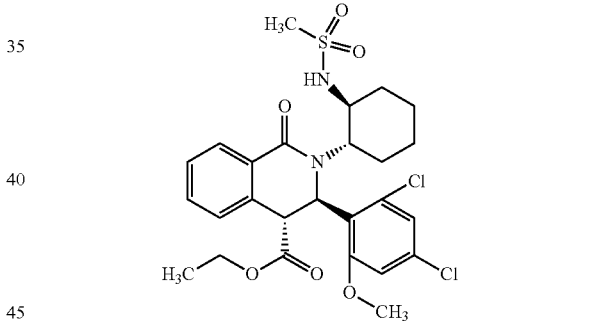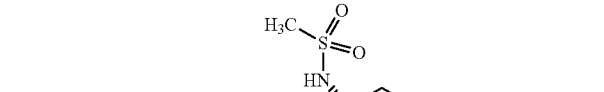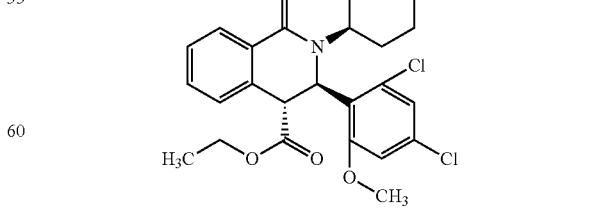 | FAB+: 569 | racemic mixture |

TABLE 28
| | | | |
|---|---|---|---|
| 134 | P34 P35 P36 | 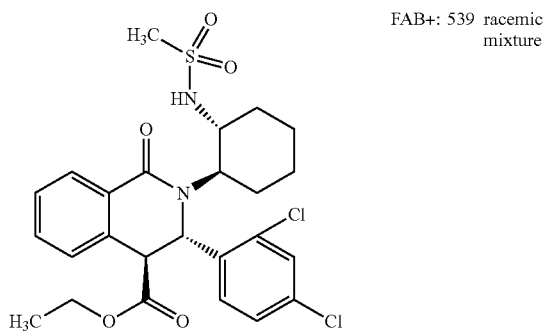 | FAB+: 539 racemic mixture |
| 135 | P34 P35 P36 | 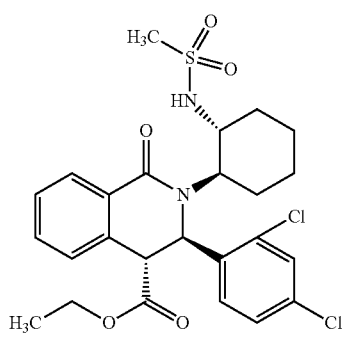 [SMILES: CCOC(=O)[C@@H]1c2ccccc2C(=O)N([C@@H]2CCCC[C@H]2NS(C)(=O)=O)[C@H]1c1ccc(Cl)cc1Cl] | FAB+: 539 racemic mixture |
| 136 | P36 | 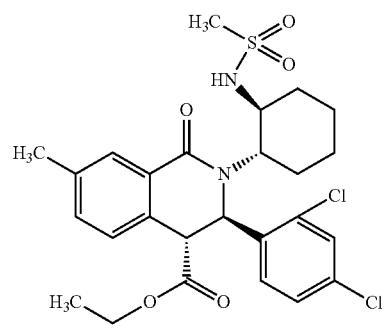 [SMILES: CCOC(=O)[C@@H]1c2ccc(C)cc2C(=O)N([C@H]2CCCC[C@@H]2NS(C)(=O)=O)[C@H]1c1ccc(Cl)cc1Cl] | ESI+: 553 racemic mixture |
| 137 | P36 | 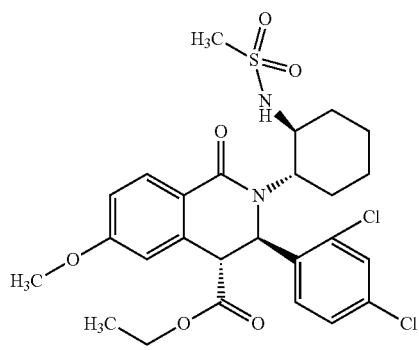 [SMILES: CCOC(=O)[C@@H]1c2cc(OC)ccc2C(=O)N([C@H]2CCCC[C@@H]2NS(C)(=O)=O)[C@H]1c1ccc(Cl)cc1Cl] | FAB+: 569 racemic mixture |

TABLE 28-continued
| | | | | |
|---|---|---|---|---|
| 138 | P36 | 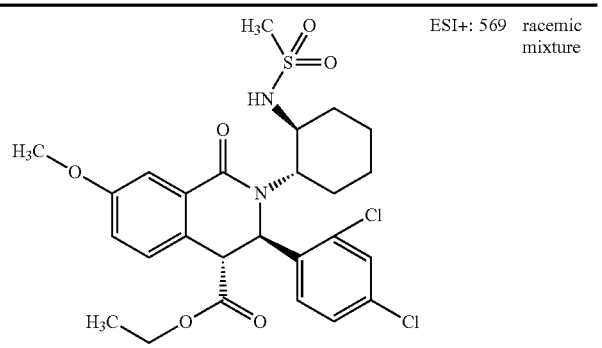 | ESI+: 569 | racemic mixture |
TABLE 29
| | | | | |
|---|---|---|---|---|
| 139 | P34 P35 P36 | 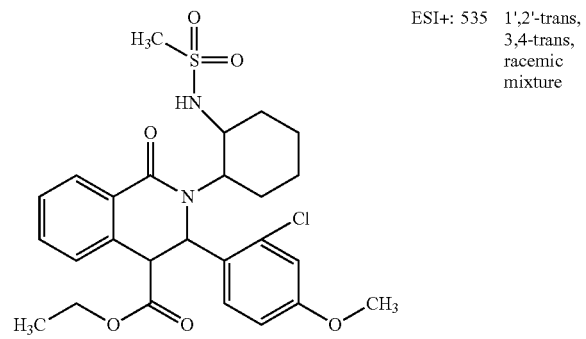 | ESI+: 535 | 1',2'-trans, 3,4-trans, racemic mixture |
| 140 | P34 P35 P36 | 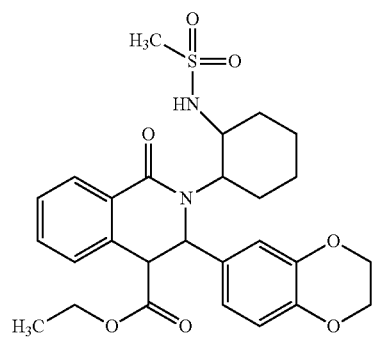 [SMILES: CCOC(=O)C1c2ccccc2C(=O)N(C2CCCCC2NS(C)(=O)=O)C1c1ccc2c(c1)OCCO2] | FAB+: 529 | 1',2'-trans, 3,4-trans, racemic mixture |
| 141 | P34 P35 P36 |  | FAB+: 513 | 1',2'-trans, 3,4-trans, racemic mixture |

TABLE 29-continued
| 142 | P36 | 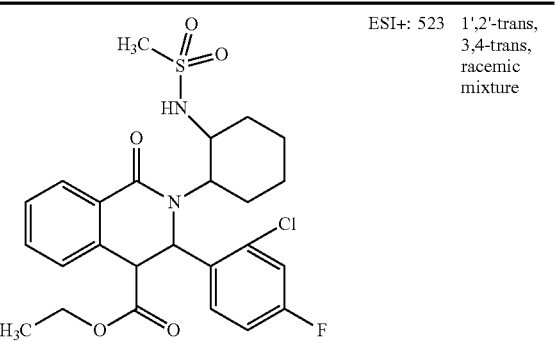 | ESI+: 523 | 1',2'-trans, 3,4-trans, racemic mixture |
TABLE 30
| 143 | P36 | 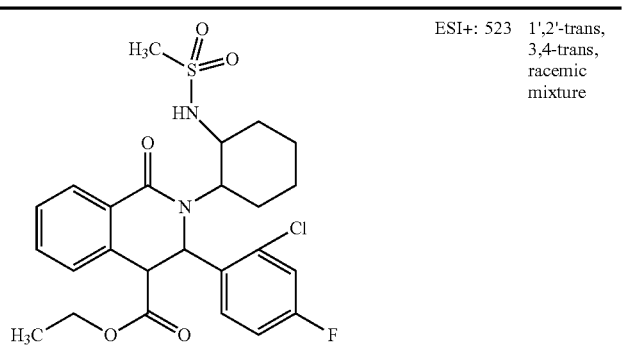 | ESI+: 523 | 1',2'-trans, 3,4-trans, racemic mixture |
| 144 | P35 P36 | 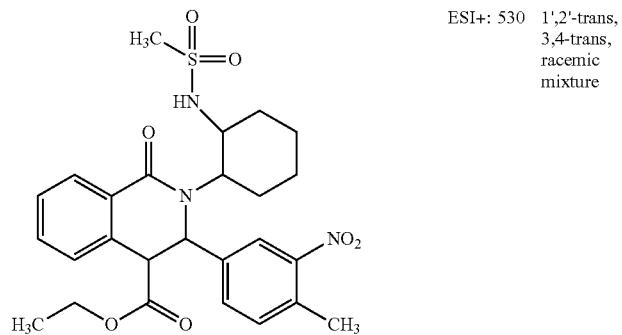 | ESI+: 530 | 1',2'-trans, 3,4-trans, racemic mixture |
| 145 | P34 P35 P36 | 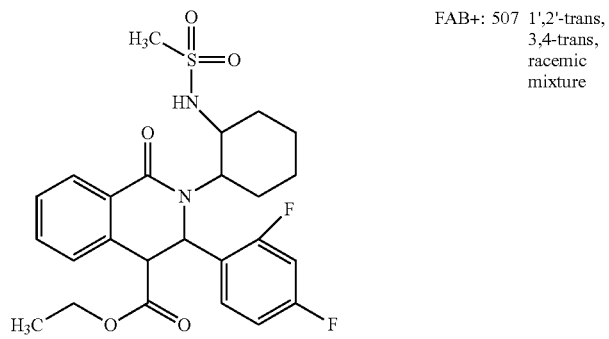 | FAB+: 507 | 1',2'-trans, 3,4-trans, racemic mixture |
| 146 | P36 | 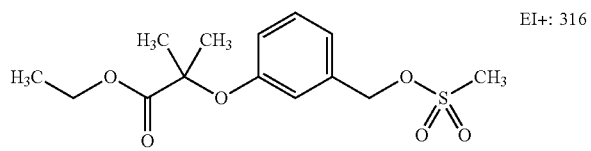 | EI+: 316 | |

TABLE 30-continued
| 147 | P36 | 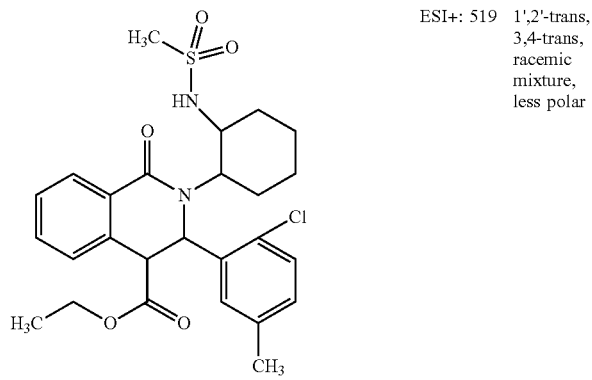 | ESI+: 519 | 1',2'-trans, 3,4-trans, racemic mixture, less polar |
TABLE 31
| 148 | P36 | 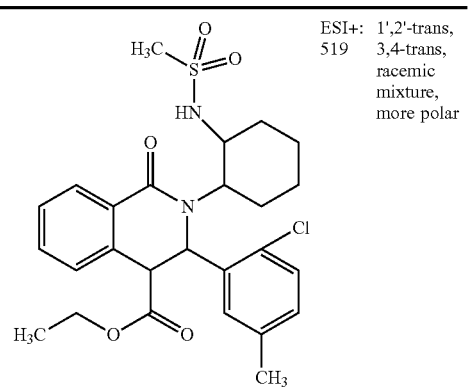 | ESI+: 519 | 1',2'-trans, 3,4-trans, racemic mixture, more polar |
| 149 | P36 | 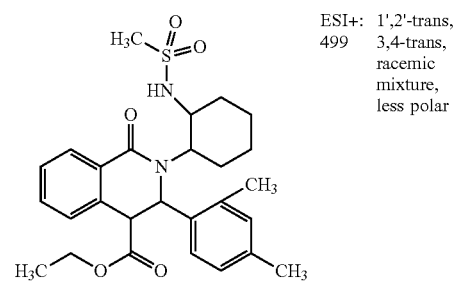 | ESI+: 499 | 1',2'-trans, 3,4-trans, racemic mixture, less polar |
TABLE 31-continued
| 150 | P36 | 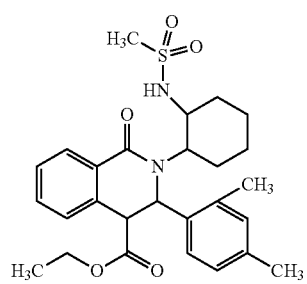 [SMILES: CCOC(=O)C1c2ccccc2C(=O)N(C2CCCCC2NS(C)(=O)=O)C1c1ccc(C)cc1C] | ESI+: 499 | 1',2'-trans, 3,4-trans, racemic mixture, more polar |
| 36 | P36 | 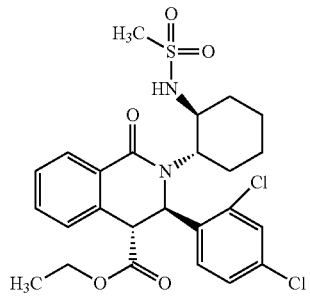 [SMILES: CCOC(=O)[C@@H]1c2ccccc2C(=O)N([C@H]2CCCC[C@@H]2NS(C)(=O)=O)[C@H]1c1ccc(Cl)cc1Cl] | ESI+: 539 | racemic mixture |
TABLE 32
| 151 | P36 | 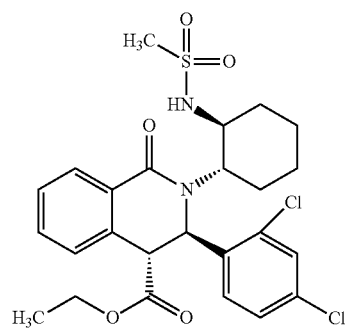 [SMILES: CCOC(=O)[C@@H]1c2ccccc2C(=O)N([C@H]2CCCC[C@@H]2NS(C)(=O)=O)[C@H]1c1ccc(Cl)cc1Cl] | ESI+: 539 |

TABLE 32-continued
| 152 | P22 | 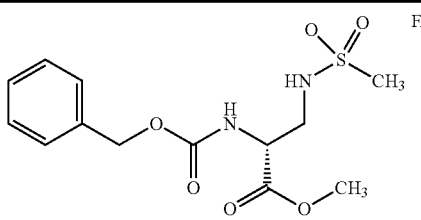 | FAB+: 331 | |
| 22 | P22 | 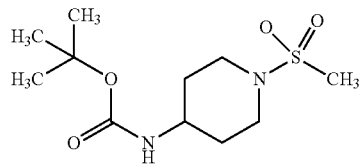 | FAB+: 279 | |
| 153 | P22 | 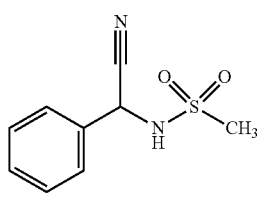 | FAB−: 209 | |
| 154 | P22 | 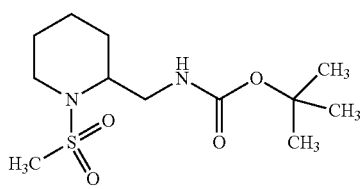 [SMILES: CC(C)(C)OC(=O)NCC1CCCCN1S(C)(=O)=O] | FAB+: 293 | |
| 155 | P34 | 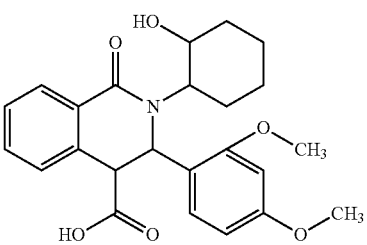 [SMILES: COc1ccc(C2C(C(=O)O)c3ccccc3C(=O)N2C2CCCCC2O)c(OC)c1] | FAB+: 426 | 1',2'-trans, 3,4-trans, racemic mixture, less polar |
TABLE 33
| 156 | P34 | 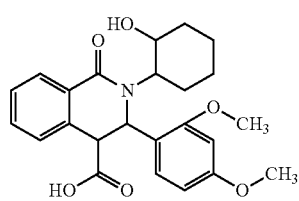 [SMILES: COc1ccc(C2C(C(=O)O)c3ccccc3C(=O)N2C2CCCCC2O)c(OC)c1] | FAB+: 426 | 1',2'-trans, 3,4-trans, racemic mixture, more polar |
| 157 | P34 | 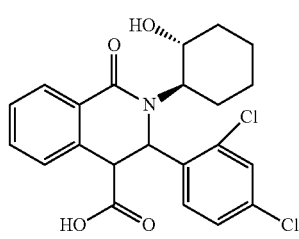 [SMILES: O=C(O)C1c2ccccc2C(=O)N([C@@H]2CCCC[C@H]2O)C1c1ccc(Cl)cc1Cl] | FAB+: 434 | 1',2'-trans, 3,4-trans, racemic mixture, less polar |
| 158 | P34 | 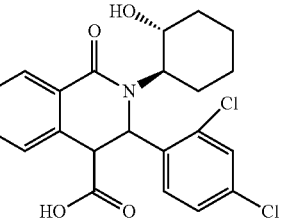 | FAB+: 434 | 1',2'-trans, 3,4-trans, racemic mixture, more polar |
| 159 | P34 | 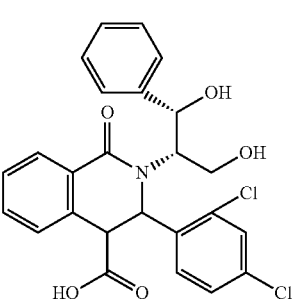 [SMILES: O=C(O)C1c2ccccc2C(=O)N([C@@H](CO)[C@@H](O)c2ccccc2)C1c1ccc(Cl)cc1Cl] | FAB+: 486 | |

TABLE 33-continued

| 160 | P34 | [structure] | ESI+: 424 | 1',2'-trans, 3,4-trans, |
| 161 | P34 | [structure] | ESI+: 511 | 3,4-trans, diastereo mixture |

TABLE 34

| 162 | P34 | [structure] | FAB+: 497 | racemic mixture |
| 163 | P34 | [structure] | ESI−: 485 | 3,4-trans, diastereo mixture |

TABLE 34-continued

| 164 | P34 | [structure] | ESI−: 485 | 3,4-trans, diastereo mixture |
| 165 | P34 | [structure] | FAB+: 533 | 3,4-trans, diastereo mixture |
| 166 | P34 | [structure] | ESI+: 422 | 1',2'-trans, 3,4-trans, racemic mixture, more polar |

TABLE 35

| 167 | P34 | [structure] | ESI+: 422 | 1',2'-trans, 3,4-trans, racemic mixture, less polar |

TABLE 35-continued
| | | | | |
|---|---|---|---|---|
| 168 | P34 | 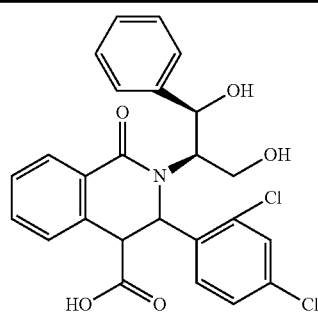 | FAB+: 486 | |
| 169 | P34 | 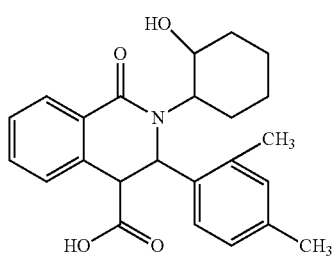 [SMILES: Cc1ccc(C2C(C(=O)O)c3ccccc3C(=O)N2C2CCCCC2O)c(C)c1] | FAB+: 394 | 1',2'-trans, 3,4-trans, racemic mixture, less polar |
| 170 | P34 | 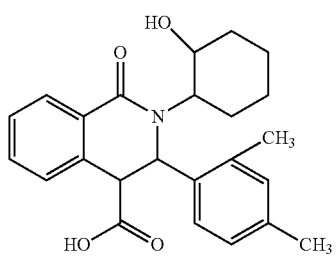 [SMILES: Cc1ccc(C2C(C(=O)O)c3ccccc3C(=O)N2C2CCCCC2O)c(C)c1] | FAB+: 394 | 1',2'-trans, 3,4-trans, racemic mixture, more polar |
| 171 | P34 | 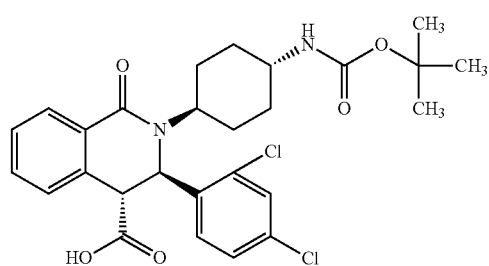 [SMILES: CC(C)(C)OC(=O)N[C@H]1CC[C@H](N2C(=O)c3ccccc3[C@@H](C(=O)O)[C@@H]2c2ccc(Cl)cc2Cl)CC1] | FAB−: 531 | racemic mixture |
TABLE 36
| | | | | |
|---|---|---|---|---|
| 172 | P34 P35 P36 P38 | 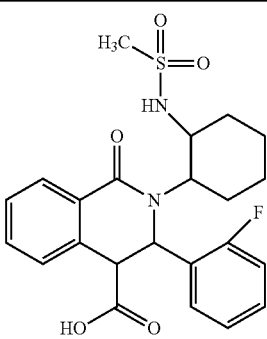 | ESI+: 461 | 1',2'-trans, 3,4-trans, racemic mixture |
TABLE 36-continued
| | | | | |
|---|---|---|---|---|
| 38 | P38 | 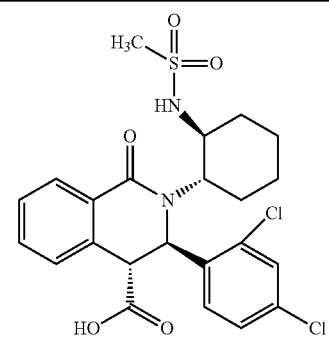 | ESI+: 512 | racemic mixture |

TABLE 36-continued
| 173 | P38 | 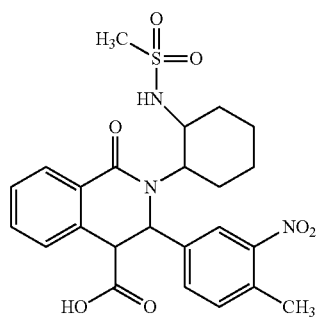 [SMILES: Cc1ccc(C2C(C(=O)O)c3ccccc3C(=O)N2C2CCCCC2NS(C)(=O)=O)cc1[N+](=O)[O-]] | ESI+: 502 | 1',2'-trans, 3,4-trans, racemic mixture |
TABLE 36-continued
| 174 | P38 | 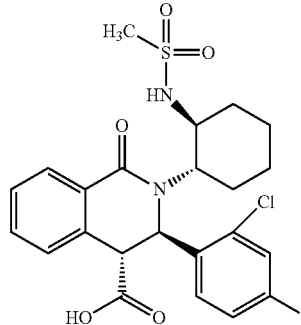 | ESI+: 511 | |
TABLE 37
| 175 | P38 | 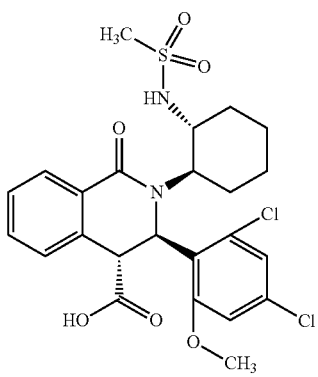 [SMILES: COc1cc(Cl)cc(Cl)c1[C@H]1[C@H](C(=O)O)c2ccccc2C(=O)N1[C@@H]1CCCC[C@H]1NS(C)(=O)=O] | FAB+: 541 racemic mixture |
| 176 | P38 | 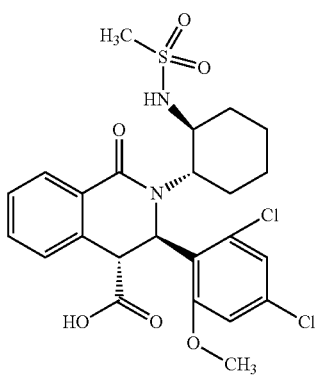 [SMILES: COc1cc(Cl)cc(Cl)c1[C@H]1[C@H](C(=O)O)c2ccccc2C(=O)N1[C@H]1CCCC[C@@H]1NS(C)(=O)=O] | FAB+: 541 racemic mixture |
| 177 | P38 | 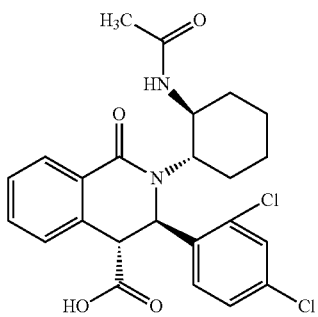 [SMILES: CC(=O)N[C@H]1CCCC[C@@H]1N1C(=O)c2ccccc2[C@@H](C(=O)O)[C@@H]1c1ccc(Cl)cc1Cl] | ESI+: 475 racemic mixture |

TABLE 37-continued
| | | | | |
|---|---|---|---|---|
| 178 | P38 | 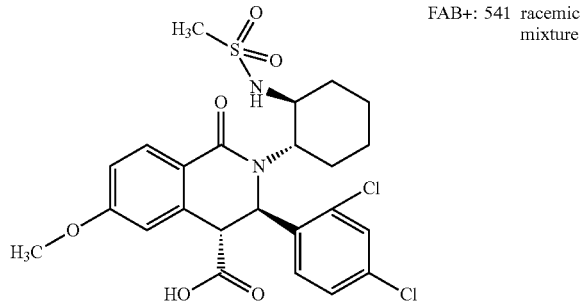 | FAB+: 541 | racemic mixture |
TABLE 38
| | | | | |
|---|---|---|---|---|
| 179 | P38 | 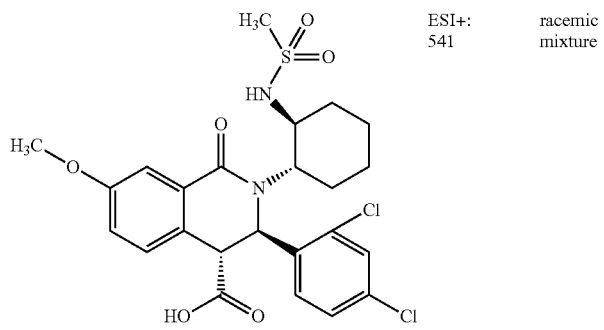 | ESI+: 541 | racemic mixture |
| 180 | P38 | 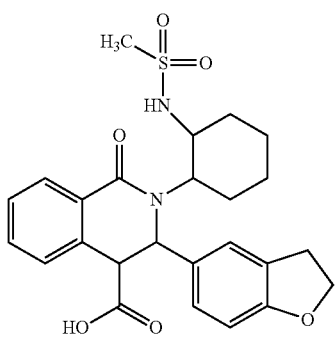 [SMILES: CS(=O)(=O)NC1CCCCC1N1C(=O)c2ccccc2C(C(=O)O)C1c1ccc2c(c1)CCO2] | ESI+: 485 | 1',2'-trans, 3,4-trans, racemic mixture |
| 181 | P38 | 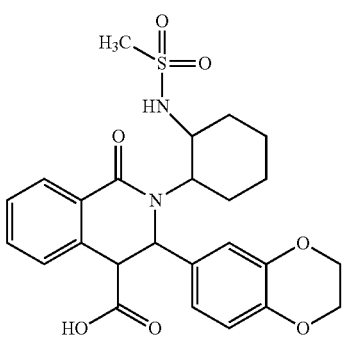 [SMILES: CS(=O)(=O)NC1CCCCC1N1C(=O)c2ccccc2C(C(=O)O)C1c1ccc2c(c1)OCCO2] | ESI+: 501 | 1',2'-trans, 3,4-trans, racemic mixture |

TABLE 38-continued
| | | | | |
|---|---|---|---|---|
| 182 | P38 | 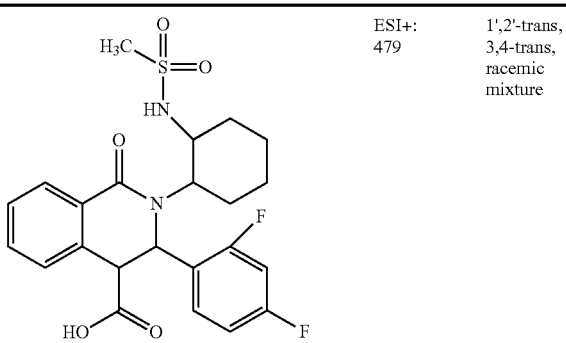 | ESI+: 479 | 1',2'-trans, 3,4-trans, racemic mixture |
| 183 | P38 | 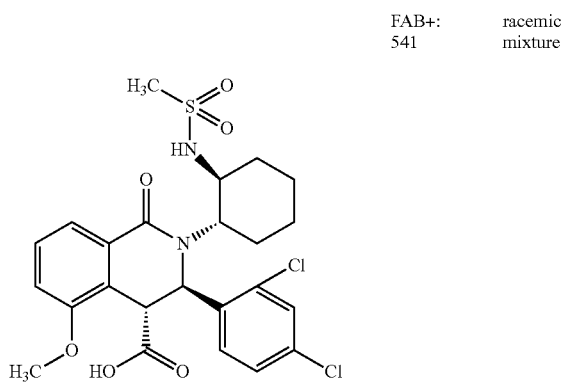 | FAB+: 541 | racemic mixture |
TABLE 39
| | | | | |
|---|---|---|---|---|
| 184 | P34 P35 P36 P38 | 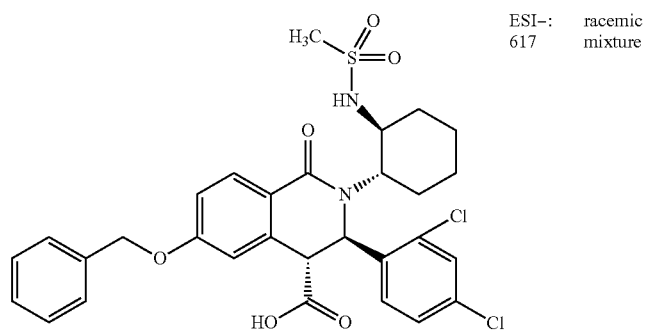 | ESI−: 617 | racemic mixture |
| 185 | P38 | 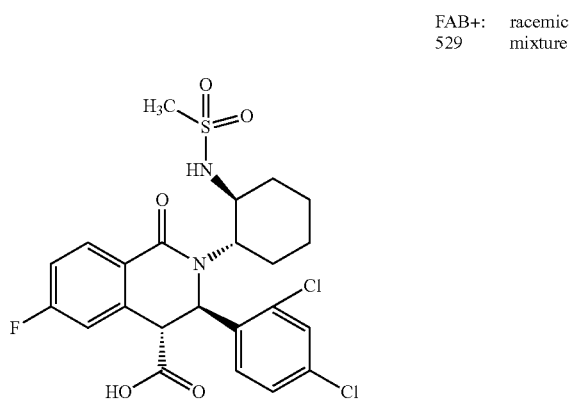 | FAB+: 529 | racemic mixture |

TABLE 39-continued
| | | | | |
|---|---|---|---|---|
| 186 | P38 | 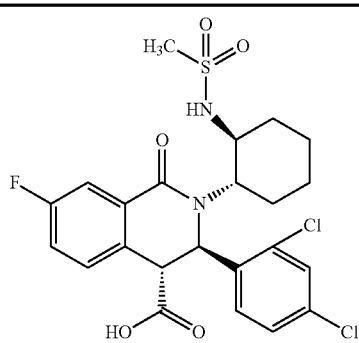 | FAB+: 529 | racemic mixture |
| 187 | P38 | 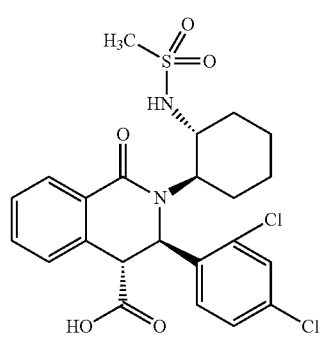 [SMILES: CS(=O)(=O)N[C@@H]1CCCC[C@H]1N1C(=O)c2ccccc2[C@@H](C(=O)O)[C@@H]1c1ccc(Cl)cc1Cl] | FAB+: 511 | |
| 188 | P38 | 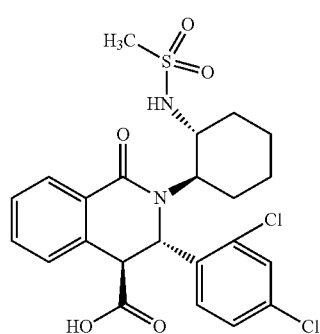 [SMILES: CS(=O)(=O)N[C@@H]1CCCC[C@H]1N1C(=O)c2ccccc2[C@H](C(=O)O)[C@H]1c1ccc(Cl)cc1Cl] | FAB+: 511 | |
TABLE 40
| | | | | |
|---|---|---|---|---|
| 189 | P38 | 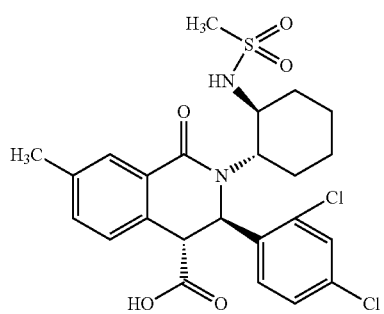 [SMILES: Cc1ccc2c(c1)C(=O)N([C@H]1CCCC[C@@H]1NS(C)(=O)=O)[C@@H](c1ccc(Cl)cc1Cl)[C@@H]2C(=O)O] | FAB+: 525 | racemic mixture |

TABLE 40-continued
| | | | |
|---|---|---|---|
| 1 | P1 | 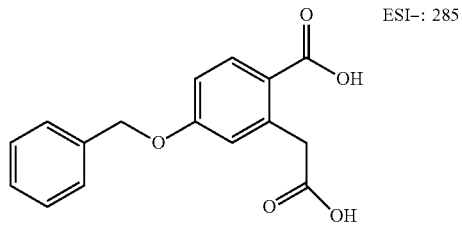 | ESI−: 285 |
| 7 | P7 | 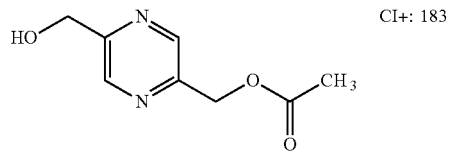 | CI+: 183 |
| 190 | P39 | 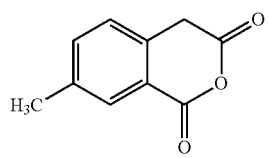 | ESI+: 177 |
| 191 | P39 | 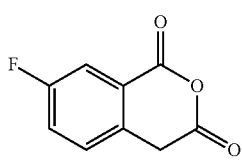 | EI+: 180 |
| 39 | P39 | 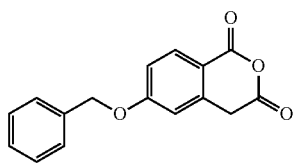 [SMILES: O=C1Cc2cc(OCc3ccccc3)ccc2C(=O)O1] | FAB+: 269 |
| 192 | P23 | 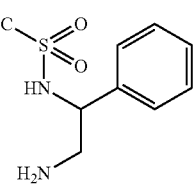 | FAB+: 215 |
| 23 | P23 | 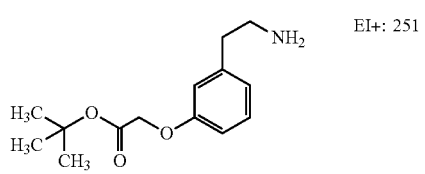 | EI+: 251 |

TABLE 41
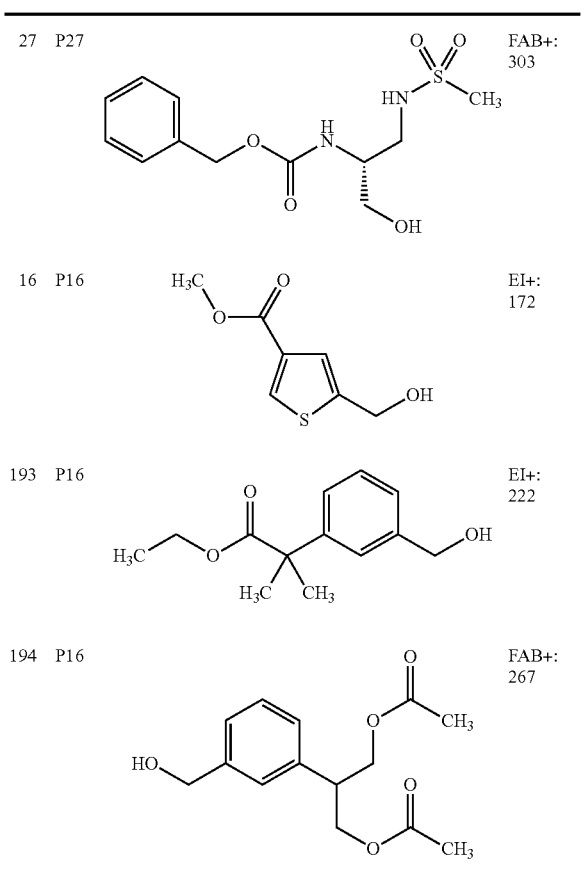
TABLE 41-continued
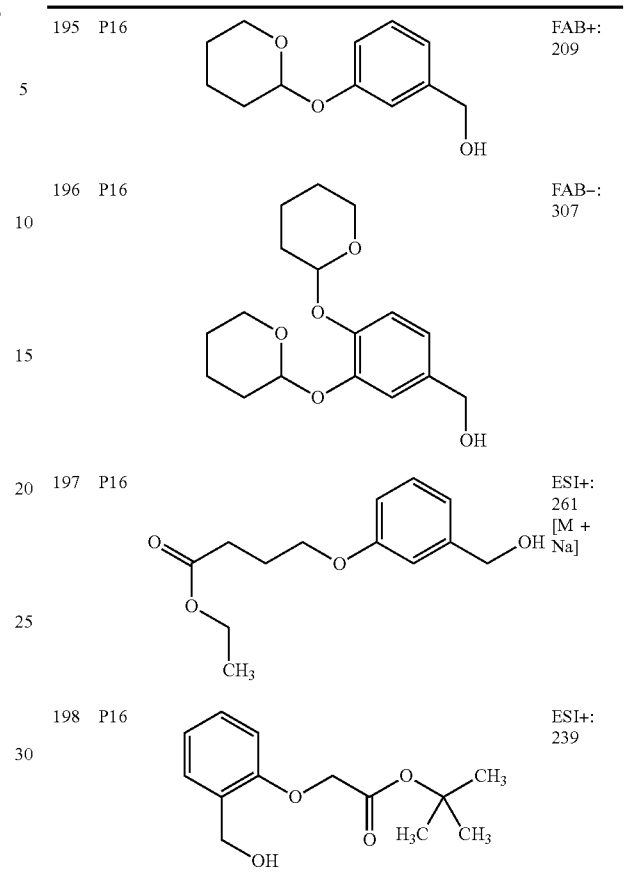
TABLE 42
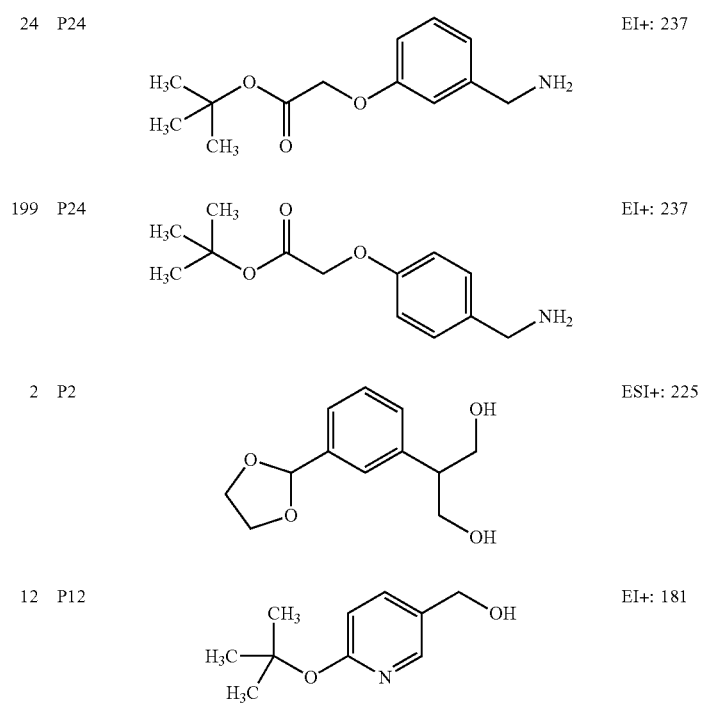

TABLE 42-continued

| | | | |
|---|---|---|---|
| 200 | P8 | (structure) | FAB+: 342 |
| 8 | P8 | (structure) | FAB+: 298 |
| 201 | P8 | (structure) | FAB+: 271 |
| 202 | P8 | (structure) | APCI+: 384 |

TABLE 43

| | | | |
|---|---|---|---|
| 203 | P8 | (structure) | ESI+: 384 |
| 204 | P8 | (structure) | ESI+: 412 |

TABLE 43-continued
| | | | |
|---|---|---|---|
| 205 | P8 | 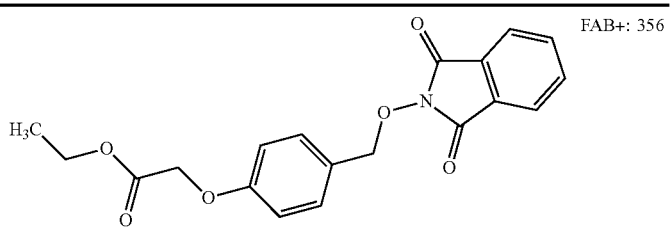 | FAB+: 356 |
| 206 | P8 | 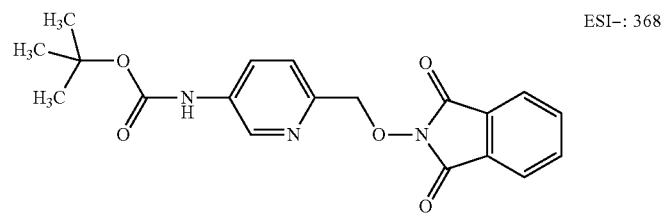 | ESI−: 368 |
| 207 | P56<br>P8 | 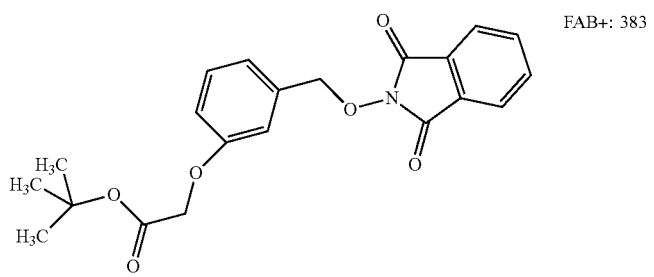 | FAB+: 383 |
| 208 | P8 | 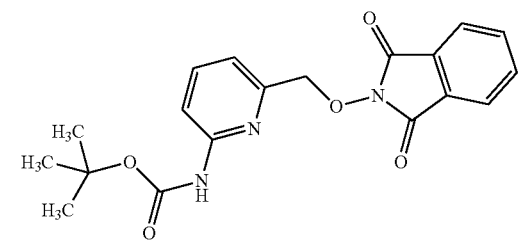 [SMILES: CC(C)(C)OC(=O)Nc1cccc(CON2C(=O)c3ccccc3C2=O)n1] | ESI+: 370 |
| 209 | P40 | 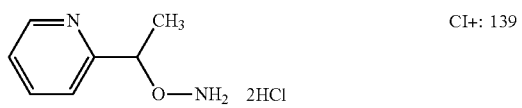 | CI+: 139 |
TABLE 44
| | | | |
|---|---|---|---|
| 210 | P40 | 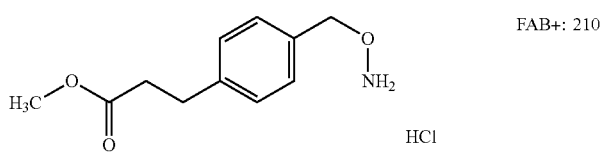 | FAB+: 210 |
| 211 | P8<br>P40 | 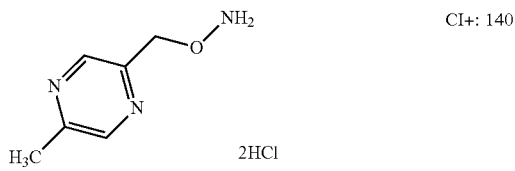 | CI+: 140 |

TABLE 44-continued

| | | | | |
|---|---|---|---|---|
| 212 | P8 P40 | (H2N-O-CH2-pyrazine-CH2-O-C(O)-CH3) 2HCl | FAB+: 198 | |
| 40 | P40 | (NH2-O-CH2-pyridin-2(1H)-one) HCl | FAB+: 141 | |
| 213 | P8 P40 | (H2N-O-CH2-pyridine-CH2-O-C(O)-Ph) 2HCl | FAB+: 259 | |
| 214 | P40 | (H3C-O-C(O)-CH2-phenyl-CH2-O-NH2) HCl | FAB+: 196 | |
| 215 | P40 | (H3C-O-pyridine-CH2-O-NH2) 2HCl | FAB+: 155 | |
| 216 | P8 P40 | (imidazo[1,2-a]pyridine-CH2-O-NH2) 2HCl | FAB+: 164 | |
| 217 | P40 | (H3C-O-C(O)-CH2CH2-phenyl-CH2-O-NH2) HCl | FAB+: 210 | |
| 218 | P8 P40 | (pyrimidine-CH2-O-NH2) 2HCl | FAB+: 126 | |

TABLE 45

| | | | | |
|---|---|---|---|---|
| 26 | P26 | ((CH3)3Si-CH2CH2-O-C(O)-cyclohexyl-NH2) HCl | FAB+: 244 | racemic mixture |
| 219 | P25 P26 | ((CH3)3Si-CH2CH2-O-C(O)-cyclohexyl-NH2) HCl | FAB+: 244 | racemic mixture |

TABLE 45-continued
| 220 | P26 | 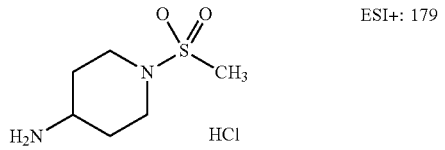 | ESI+: 179 |
| 221 | P26 | 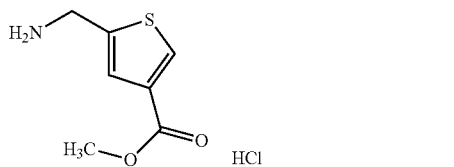 | FAB+: 172 |
| 222 | P26 | 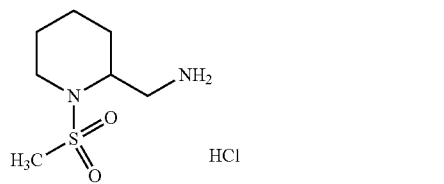 | FAB+: 193 |
| 41 | P41 | 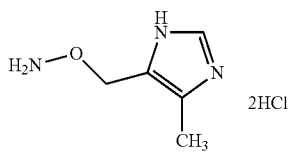 | FAB+: 128 |
| 28 | P28 | 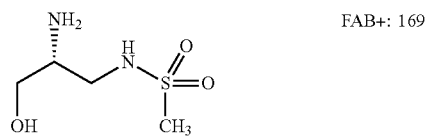 | FAB+: 169 |
| 3 | P3 | 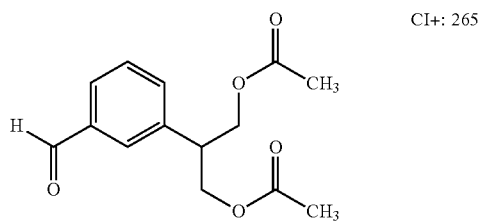 | CI+: 265 |
| 223 | P40 |  | FAB+: 202 |

TABLE 46

| | | | |
|---|---|---|---|
| 224 | P40 | methyl 6-((aminooxy)methyl)picolinate structure | FAB+: 183 2HCl |
| 225 | P40 | 3-((aminooxy)methyl)benzonitrile structure | EI+: 148 HCl |
| 226 | P14, P9 | 4-methoxy-2-((aminooxy)methyl)pyridine structure | FAB+: 155 |
| 227 | P9 | methyl 2-methoxy-5-((aminooxy)methyl)benzoate structure | CI+: 212 |
| 9 | P9 | 6-((aminooxy)methyl)nicotinamide structure | CI+: 168 |
| 228 | P40 | 6-((aminooxy)methyl)picolinamide structure | ESI+: 168 2HCl |
| 229 | P40 | 6-((aminooxy)methyl)-2-cyanopyridine structure | FAB+: 150 2HCl |
| 230 | P9 | O-(2-(1H-pyrrol-1-yl)ethyl)hydroxylamine structure | EI+: 126 |
| 231 | 28, P9 | O-((3-methyl-1,2,4-oxadiazol-5-yl)methyl)hydroxylamine structure | CI+: 130 |
| 232 | P8, P9 | O-((2-methylthiazol-5-yl)methyl)hydroxylamine structure | CI+: 145 |
| 233 | P8, P9 | O-((5-methylpyridin-2-yl)methyl)hydroxylamine structure | EI+: 138 |

TABLE 47

| | | | |
|---|---|---|---|
| 234 | P9 | ethyl 2-(3-((aminooxy)methyl)phenoxy)-2-methylpropanoate structure | EI+: 253 |
| 235 | P9 | ethyl 2-(4-((aminooxy)methyl)phenyl)-2-methylpropanoate structure | CI+: 238 |
| 236 | P9 | O-(3-((tetrahydro-2H-pyran-2-yl)oxy)benzyl)hydroxylamine structure | EI+: 223 |
| 237 | P9 | bis-THP-protected structure | FAB+: 324 |
| 238 | P9 | O-(4-tert-butoxybenzyl)hydroxylamine structure | CI+: 196 |
| 239 | P9 | methyl 4-methoxy-3-((aminooxy)methyl)benzoate structure | CI+: 212 |
| 240 | P9 | trityl-triazole (aminooxy)methyl structure | FAB+: 357 |
| 241 | P9 | O-((6-fluoropyridin-2-yl)methyl)hydroxylamine structure | CI+: 143 |

TABLE 48

| | | | |
|---|---|---|---|
| 242 | P9 | (structure: 4-methylsulfonylbenzyl aminooxy) | FAB+: 202 |
| 243 | P9 | (structure: 5-methyl-1,3,4-oxadiazol-2-yl methyl aminooxy) | CI+: 130 |
| 244 | P9 | (structure: 5-fluoropyridin-2-yl methyl aminooxy) | CI+: 143 |
| 245 | P9 | (structure: ethyl 2-(3-(aminooxymethyl)phenyl)-2-methylpropanoate) | FAB+: 238 |
| 246 | P14, P40 | (structure: methyl 2-(4-(aminooxymethyl)phenyl)acetate HCl) | FAB+: 196 |

TABLE 48-continued

| | | | |
|---|---|---|---|
| 247 | P9 | (structure: 2-(3-(aminooxymethyl)phenyl)-2,2-difluoro-N-methylacetamide) | CI+: 231 |
| 248 | P8, P9 | (structure: 6-(aminooxymethyl)benzoxazol-2(3H)-one) | CI+: 180 |
| 249 | P9 | (structure: ethyl 5-(aminooxymethyl)-2-hydroxybenzoate) | CI+: 212 |
| 250 | P9 | (structure: (1-methyl-1H-tetrazol-5-yl)methyl aminooxy) | CI+: 130 |
| 251 | P9 | (structure: (5-methyl-1,2,4-oxadiazol-3-yl)methyl aminooxy) | CI+: 130 |
| 252 | P9 | (structure: (1,2,4-oxadiazol-3-yl)methyl aminooxy) | EI+: 115 |

TABLE 49

| | | | |
|---|---|---|---|
| 253 | P40 | 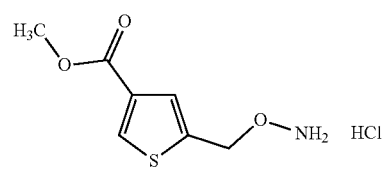 (methyl 5-(aminooxymethyl)thiophene-3-carboxylate HCl) | FAB+: 188 |
| 254 | P9 | 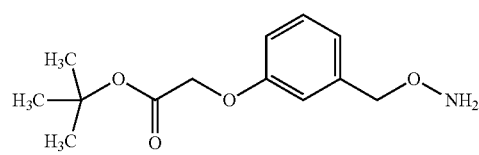 [SMILES: CC(C)(C)OC(=O)COc1cccc(CON)c1] (tert-butyl 2-(3-(aminooxymethyl)phenoxy)acetate) | ESI+: 254 |
| 255 | P9 | 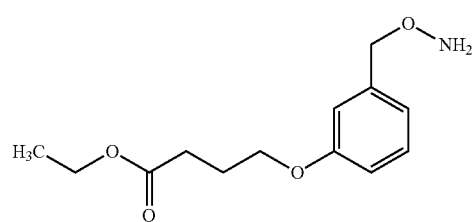 [SMILES: CCOC(=O)CCCOc1cccc(CON)c1] (ethyl 4-(3-(aminooxymethyl)phenoxy)butanoate) | ESI+: 254 |

TABLE 49-continued
| 256 | P9 | 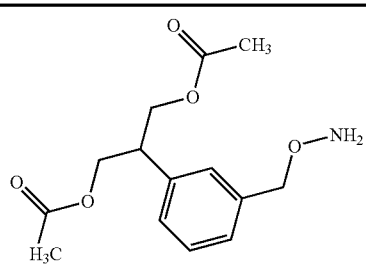 | ESI+: 282 |
| 257 | P9 | 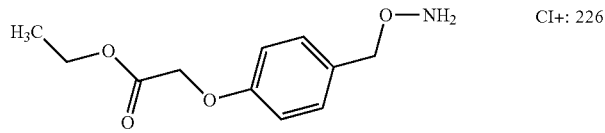 | CI+: 226 |
| 258 | P9 | 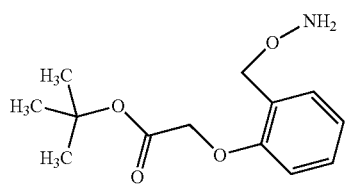 [SMILES: CC(C)(C)OC(=O)COc1ccccc1CON] | ESI+: 254 |
| 259 | P9 | 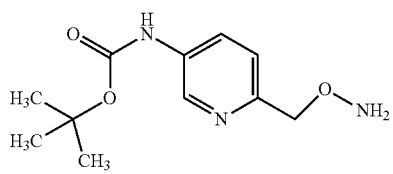 [SMILES: CC(C)(C)OC(=O)Nc1ccc(CON)nc1] | ESI+: 240 |
| 260 | P9 | 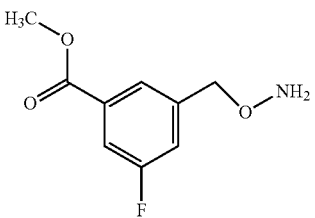 | ESI+: 200 |
TABLE 50
| 261 | P9 | 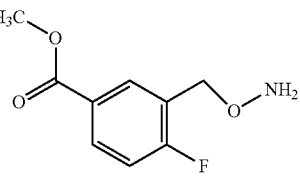 | ESI+: 200 |
| 262 | P9 | 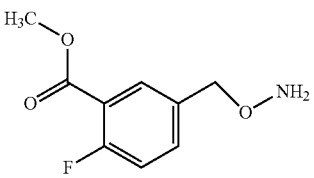 | ESI+: 200 |
| 263 | P9 | 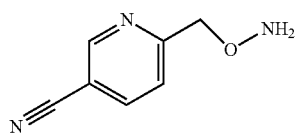 [SMILES: N#Cc1ccc(CON)nc1] | ESI+: 150 |

TABLE 50-continued
| | | | |
|---|---|---|---|
| 264 | P9 | 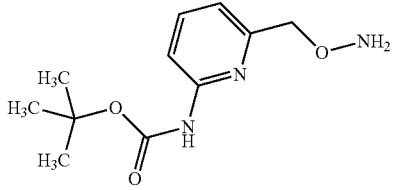 [SMILES: CC(C)(C)OC(=O)Nc1cccc(CON)n1] | ESI+: 240 |
| 265 | P32 | 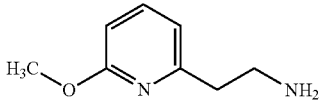 | EI+: 152 |
| 266 | P32 | 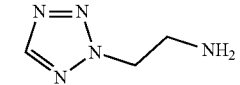 | ESI+: 114 |
| 267 | P32 | 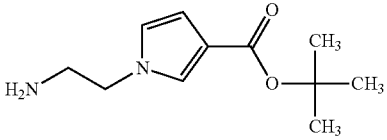 | ESI+: 146 |
| 32 | P32 | 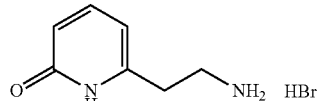 | ESI+: 211 |
| 13 | P13 | 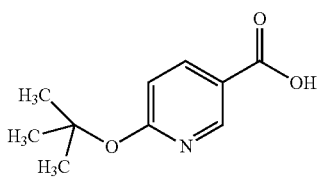 HCl | FAB+: 141 |
| 29 | P29 | 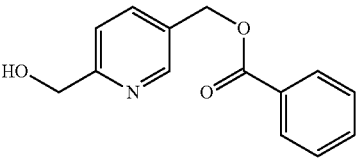 [SMILES: O=C(OCc1ccc(CO)nc1)c1ccccc1] HBr | FAB+: 139 |
TABLE 51
| | | | |
|---|---|---|---|
| 10 | P10 | | FAB+: 196 |
| 6 | P6 | | ESI−: 242 |

TABLE 51-continued
| | | | | |
|---|---|---|---|---|
| 268 | P33 | 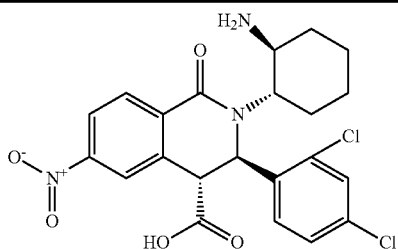 | ESI+: 478 | racemic mixture |
| 269 | P35 P36 | 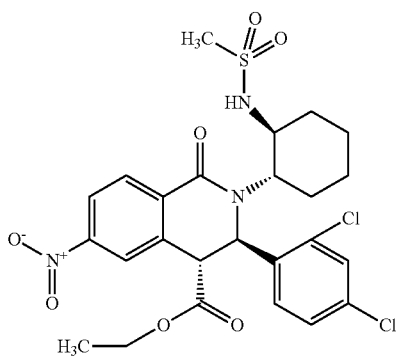 [SMILES: CCOC(=O)[C@@H]1c2cc([N+](=O)[O-])ccc2C(=O)N([C@H]2CCCC[C@@H]2NS(C)(=O)=O)[C@H]1c1ccc(Cl)cc1Cl] | ESI+: 584 | racemic mixture |
| 270 | P42 | 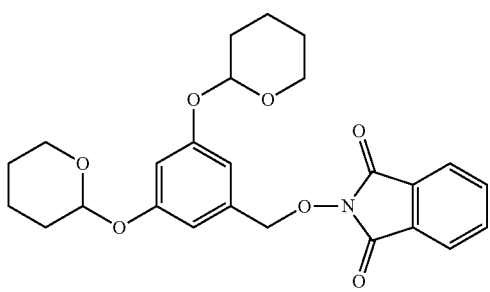 [SMILES: O=C1c2ccccc2C(=O)N1OCc1cc(OC2CCCCO2)cc(OC2CCCCO2)c1] | FAB+: 454 | |
| 271 | P38 | 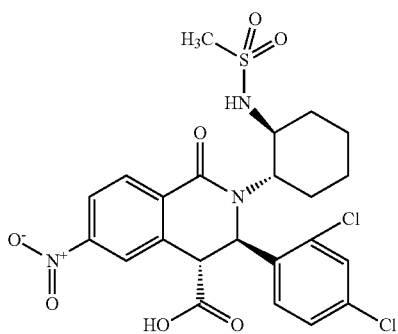 [SMILES: CS(=O)(=O)N[C@H]1CCCC[C@@H]1N1C(=O)c2ccc([N+](=O)[O-])cc2[C@@H](C(=O)O)[C@@H]1c1ccc(Cl)cc1Cl] | ESI+: 556 | racemic mixture |
TABLE 52
| | | | |
|---|---|---|---|
| 272 | P33 | 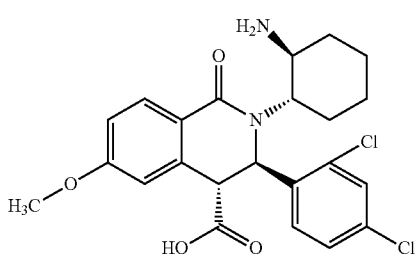 [SMILES: COc1ccc2c(c1)[C@@H](C(=O)O)[C@H](c1ccc(Cl)cc1Cl)N([C@H]1CCCC[C@@H]1N)C2=O] | ESI+: 464 |

TABLE 52-continued
| | | | |
|---|---|---|---|
| 273 | P42 | 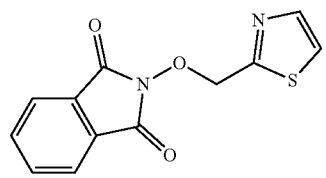 [SMILES: O=C1c2ccccc2C(=O)N1OCc1nccs1] | FAB+: 261 |
| 274 | P9 | 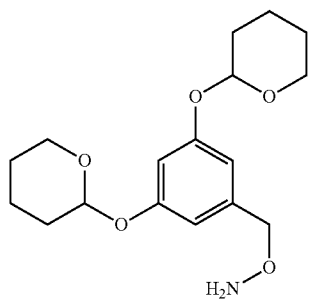 [SMILES: NOCc1cc(OC2CCCCO2)cc(OC2CCCCO2)c1] | FAB+: 324 |
| 275 | P35<br>P36 | 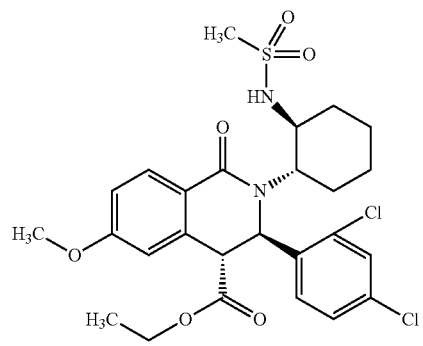 [SMILES: CCOC(=O)[C@@H]1c2cc(OC)ccc2C(=O)N([C@H]2CCCC[C@@H]2NS(C)(=O)=O)[C@H]1c1ccc(Cl)cc1Cl] | ESI+: 569 |
| 55 | P55 | 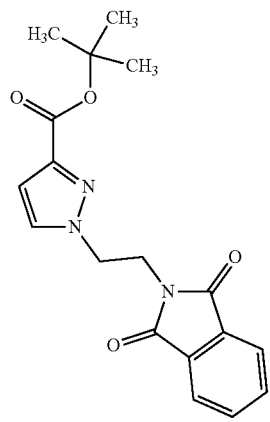 [SMILES: CC(C)(C)OC(=O)c1ccn(CCN2C(=O)c3ccccc3C2=O)n1] | ESI+: 342 |

TABLE 53
| | | | |
|---|---|---|---|
| 276 | P8 | 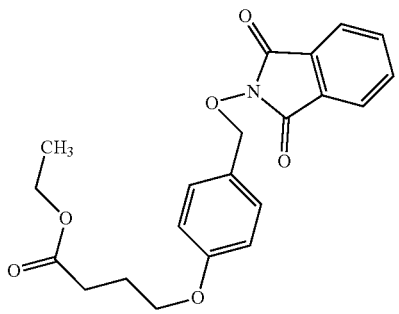 | ESI+: 342 |
| 277 | P9<br>P40 | 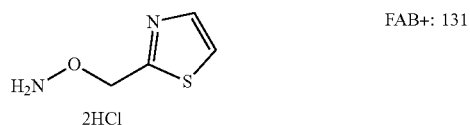     2HCl | FAB+: 131 |
| 278 | P9 | 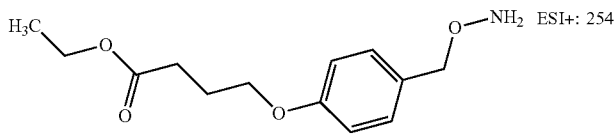 | ESI+: 254 |
| 279 | P32 | 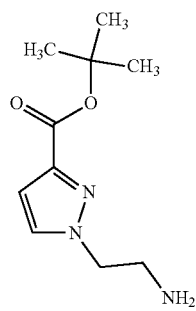 | ESI+: 212 |
| 280 | P51<br>P40 | 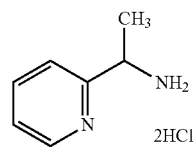     2HCl | ESI+: 123 |
| 281 | P14 | 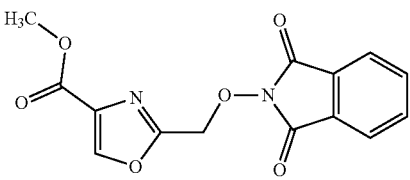 [SMILES: COC(=O)c1coc(CON2C(=O)c3ccccc3C2=O)n1] | ESI+: 303 |
| 282 | P8 | 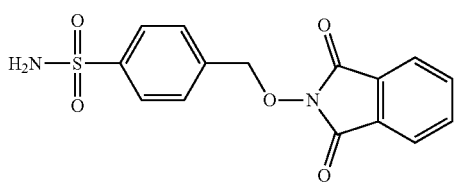 [SMILES: NS(=O)(=O)c1ccc(CON2C(=O)c3ccccc3C2=O)cc1] | ESI+: 333 |

TABLE 54
| 57 | P57 | 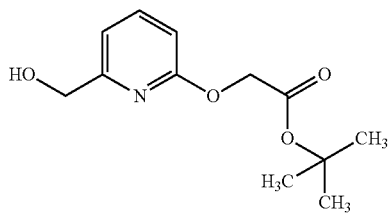 [SMILES: CC(C)(C)OC(=O)COc1cccc(CO)n1] | FAB+: 240 |
| 283 | P9 | 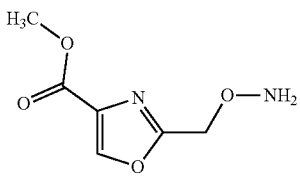 | ESI+: 173 |
| 284 | P38 | 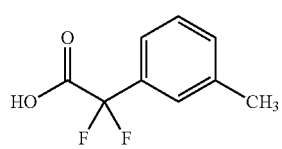 | EI+: 186 |
| 52 | P52 | 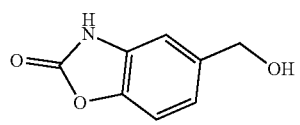 [SMILES: O=c1[nH]c2cc(CO)ccc2o1] | EI+: 165 |
| 285 | P60 | 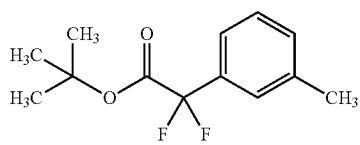 [SMILES: Cc1cccc(C(F)(F)C(=O)OC(C)(C)C)c1] | CI+: 243 |
| 286 | P9 | 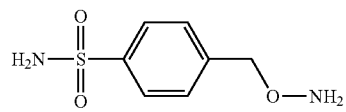 [SMILES: NOCc1ccc(S(N)(=O)=O)cc1] | FAB+: 203 |
| 62 | P62 | 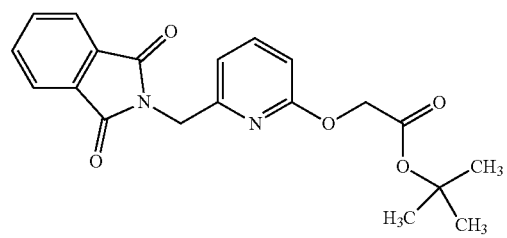 [SMILES: CC(C)(C)OC(=O)COc1cccc(CN2C(=O)c3ccccc3C2=O)n1] | ESI+: 369 |
| 287 | P32 | 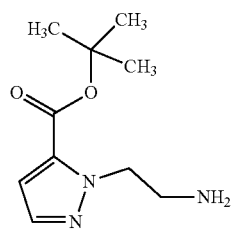 | ESI+: 212 |

TABLE 55
| 288 | 20 | 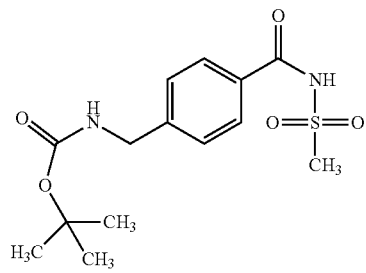 [SMILES: CC(C)(C)OC(=O)NCc1ccc(C(=O)NS(C)(=O)=O)cc1] | ESI−: 327 |
| --- | --- | --- | --- |
| 289 | P8 P9 | 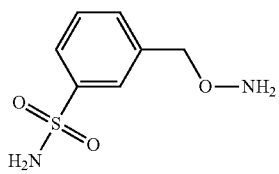 | FAB+: 203 |
| 290 | P8 P9 | 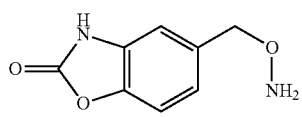 [SMILES: NOCc1ccc2oc(=O)[nH]c2c1] | FAB+: 181 |
| 291 | P19 | 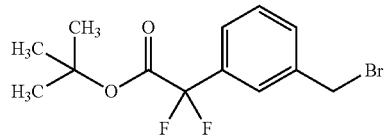 [SMILES: CC(C)(C)OC(=O)C(F)(F)c1cccc(CBr)c1] | CI+: 321 |
| 292 | P8 | 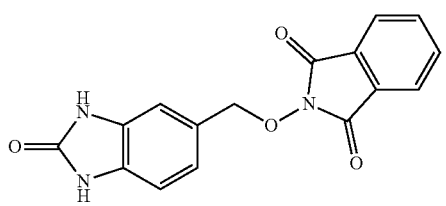 [SMILES: O=C1c2ccccc2C(=O)N1OCc1ccc2[nH]c(=O)[nH]c2c1] | ESI+: 310 |
| 293 | P26 | 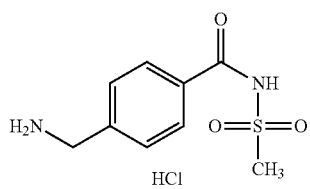 | FAB+: 229 |
| 294 | P14 | 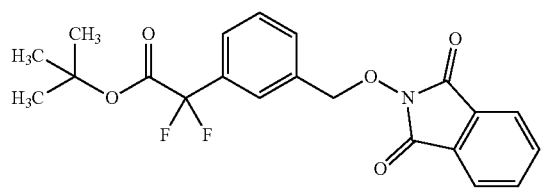 [SMILES: CC(C)(C)OC(=O)C(F)(F)c1cccc(CON2C(=O)c3ccccc3C2=O)c1] | ESI+: 402 |
| 295 | P9 | 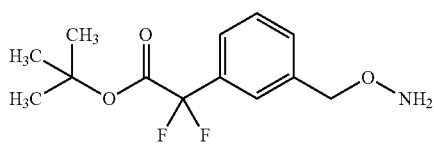 | CI+: 274 |
| 296 | P9 | 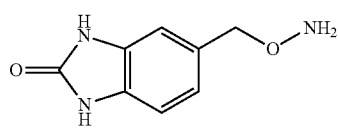 [SMILES: NOCc1ccc2[nH]c(=O)[nH]c2c1] | FAB+: 180 |

TABLE 56

| | | | | |
|---|---|---|---|---|
| 297 | 20 | (structure) | FAB−: 341 | |
| 298 | P26 | (structure) | ESI+: 243 | |
| 299 | P16 | (structure) | ESI+: 170 | |
| 300 | P8 P9 | (structure) | NMR1: 2.50 (2H, s), 4.50 (3H, s), 6.00 (2H, s), 6.13-6.16 (1H, m), 6.71-6.73 (1H, m), 11.84 (1H, s) | |
| 301 | P62 | (structure) | ESI+: 269 | |
| 302 | 12 | (structure) | ESI+: 603 | racemic mixture |

TABLE 57
| | | | | |
|---|---|---|---|---|
| 44 | P44 | 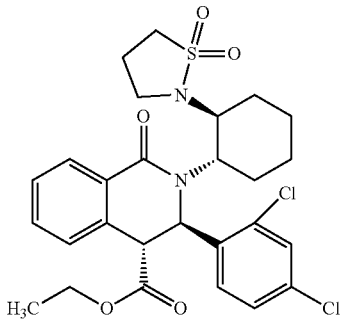 [SMILES: CCOC(=O)[C@@H]1c2ccccc2C(=O)N([C@H]2CCCC[C@@H]2N2CCCS2(=O)=O)[C@H]1c1ccc(Cl)cc1Cl] | ESI+: 565 | racemic mixture |
| 58 | P58 | 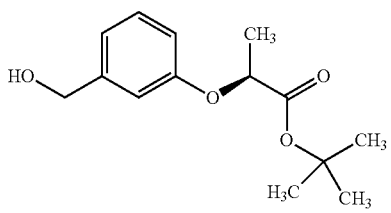 [SMILES: C[C@H](Oc1cccc(CO)c1)C(=O)OC(C)(C)C] | EI+: 252 | |
| 303 | P32 | 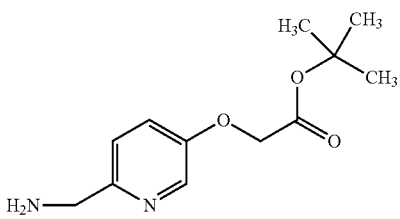 [SMILES: CC(C)(C)OC(=O)COc1ccc(CN)nc1] | ESI+: 239 | |
| 304 | P62 | 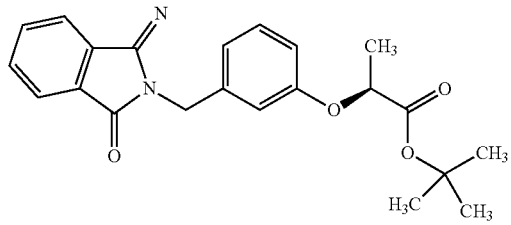 [SMILES: C[C@H](Oc1cccc(CN2C(=N)c3ccccc3C2=O)c1)C(=O)OC(C)(C)C] | FAB+: 381 | |
| 305 | P8 | 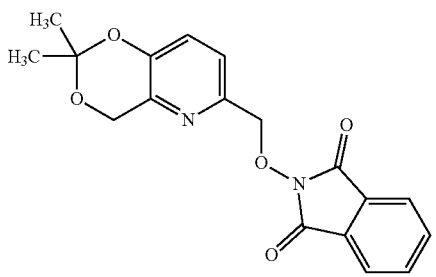 [SMILES: CC1(C)OCc2nc(CON3C(=O)c4ccccc4C3=O)ccc2O1] | FAB+: 341 | |
| 306 | P9 | 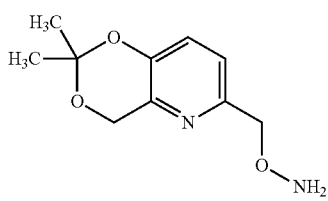 | CI+: 211 | |

TABLE 58

| | | | |
|---|---|---|---|
| 307 | P32 | (structure) | ESI+: 252 |
| 308 | P4 | (structure) | FAB+: 245 |
| 309 | P8 | (structure) | FAB+: 390 |
| 310 | P9 | (structure) | FAB+: 260 |
| 53-1 | P53 | (structure) | CI+: 182 |
| 53-2 | P53 | (structure) | EI+: 180 |
| 311 | P14 | (structure) | ESI+: 316 |

TABLE 59
| 312 | P48 | 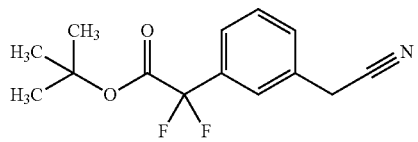 [SMILES: CC(C)(C)OC(=O)C(F)(F)c1cccc(CC#N)c1] | CI+: 268 |
| 313 | P23 | 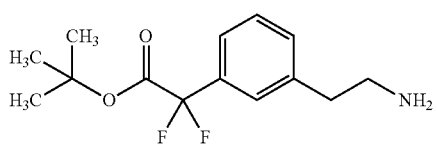 [SMILES: CC(C)(C)OC(=O)C(F)(F)c1cccc(CCN)c1] | FAB+: 272 |
| 50 | P50 | 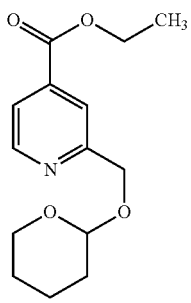 [SMILES: CCOC(=O)c1ccnc(COC2CCCCO2)c1] | FAB+: 266 |
| 314 | P12 | 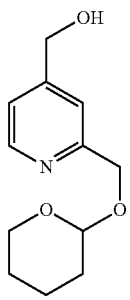 | FAB+: 244 |
| 315 | P4 | 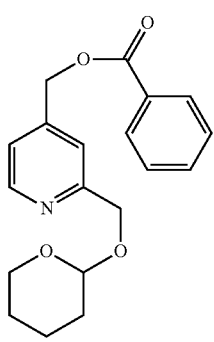 [SMILES: O=C(OCc1ccnc(COC2CCCCO2)c1)c1ccccc1] | FAB+: 328 |
| 63 | P63 | 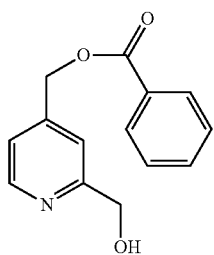 [SMILES: O=C(OCc1ccnc(CO)c1)c1ccccc1] | FAB+: 244 |

TABLE 59-continued
| 316 | P14 | 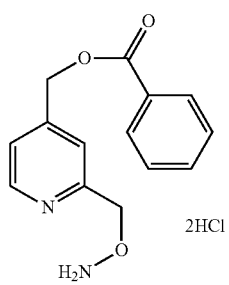 [SMILES: NOCc1cc(COC(=O)c2ccccc2)ccn1] | ESI+: 332 |
TABLE 60
| 317 | P8<br>P9<br>P40 | 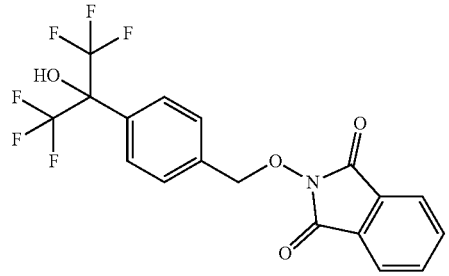 [SMILES: O=C1c2ccccc2C(=O)N1OCc1ccc(C(O)(C(F)(F)F)C(F)(F)F)cc1] | ESI+: 259 |
| 318 | P14 | | FAB+: 420 |
| 319 | P9 | 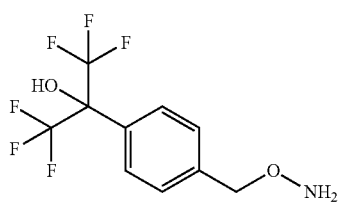 [SMILES: NOCc1ccc(C(O)(C(F)(F)F)C(F)(F)F)cc1] | CI+: 290 |
| 320 | P48 |  | FAB+: 268 |
| 321 | P14<br>P9 | 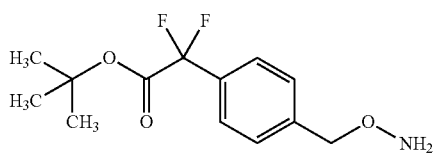 [SMILES: CC(C)(C)OC(=O)C(F)(F)c1ccc(CON)cc1] | CI+: 274 |
| 322 | P23 | 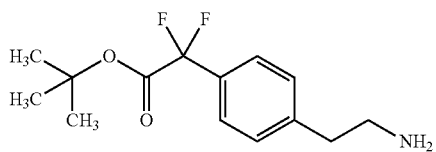 | EI+: 271 |

TABLE 60-continued

| | | Structure | MS |
|---|---|---|---|
| 61 | P61 | (pyridine with HO-N=C(CH3)- and -CH2OH substituents) | FAB+: 167 |
| 323 | P19 | (tert-butyl 4-(bromomethyl)thiophene-2-carboxylate) | CI+: 275, 277 |

TABLE 61

| | | Structure | MS |
|---|---|---|---|
| 324 | P16, P8, P9 | (ethyl 2-(5-((aminooxy)methyl)thiophen-3-yl)acetate) | ESI+: 216 |
| 46 | P46 | (methyl 2-(hydroxymethyl)-1-methyl-1H-imidazole-5-carboxylate) | ESI+: 171 |
| 51 | P51 | (2-(1-aminoethyl)-6-(hydroxymethyl)pyridine) | CI+: 153 |
| 325 | P48 | (tert-butyl 4-(cyanomethyl)thiophene-2-carboxylate) | ESI-: 222 |
| 326 | P55 | (tert-butyl 4-((1,3-dioxoisoindolin-2-yl)methyl)thiophene-2-carboxylate) | ESI-: 222 |
| 327 | P32 | (tert-butyl 4-(aminomethyl)thiophene-2-carboxylate) | APCI+: 213 |
| 328 | P8 | (methyl 2-(((1,3-dioxoisoindolin-2-yl)oxy)methyl)-1-methyl-1H-imidazole-5-carboxylate) | ESI+: 316 |

TABLE 61-continued
| 47 | P47 | 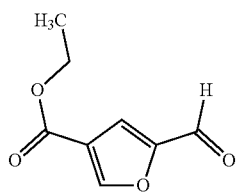 | APCI+: 169 |
| --- | --- | --- | --- |
| 329 | P9 | 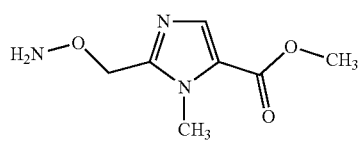 | ESI+: 186 |
TABLE 62
| 330 | P19 | 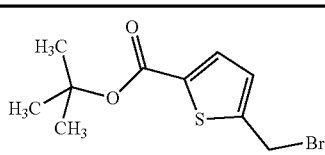 | APCI+: 279 |
| --- | --- | --- | --- |
| 331 | P30 | 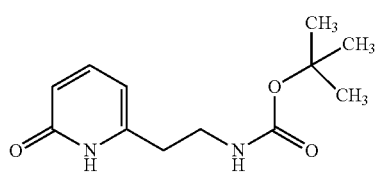 [SMILES: CC(C)(C)OC(=O)NCCc1cccc(=O)[nH]1] | FAB+: 239 |
| 332 | P55 | 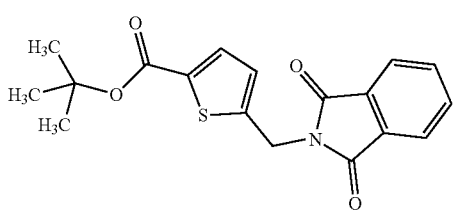 [SMILES: CC(C)(C)OC(=O)c1ccc(CN2C(=O)c3ccccc3C2=O)s1] | FAB+: 343 |
| 333 | P23 | 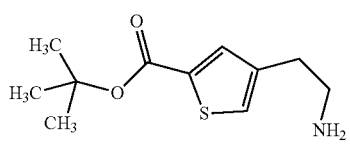 | ESI+: 228 |
| 334 | P57 | 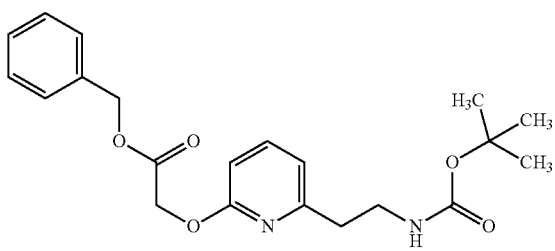 [SMILES: CC(C)(C)OC(=O)NCCc1cccc(OCC(=O)OCc2ccccc2)n1] | ESI+: 387 |
| 335 | P16 | 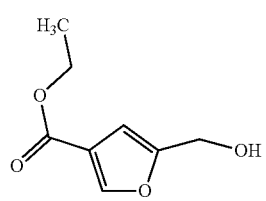 | FAB+: 171 |

TABLE 62-continued
| 336 | P32 | 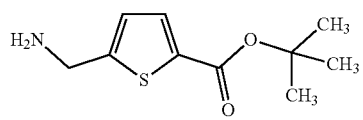 | ESI+: 214 |
| 337 | P61 P51 | 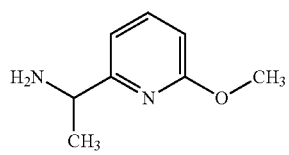 | EI+: 152 |
TABLE 63
| 338 | P61 | 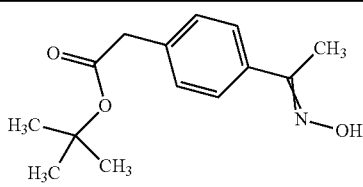 | EI+: 249 |
| 339 | P26 | 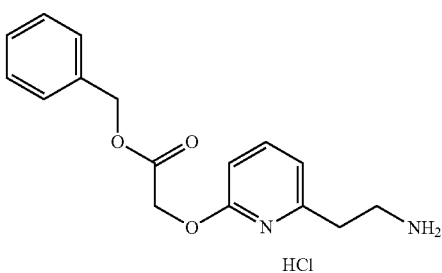 [SMILES: NCCc1cccc(OCC(=O)OCc2ccccc2)n1 ; Cl] | ESI+: 287 |
| 340 | P48 | 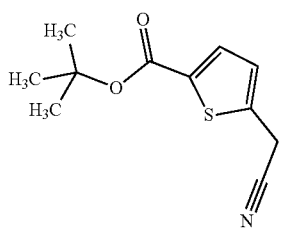 | ESI+: 214 |
| 341 | P8 | 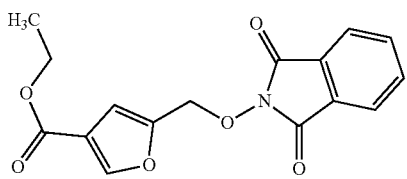 [SMILES: CCOC(=O)c1coc(CON2C(=O)c3ccccc3C2=O)c1] | APCI−: 314 |
| 342 | P51 | 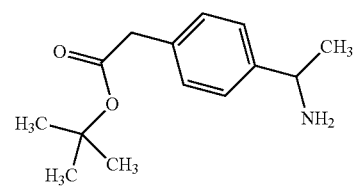 [SMILES: CC(N)c1ccc(CC(=O)OC(C)(C)C)cc1] | FAB+: 236 |
| 343 | P16 | 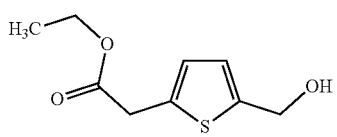 | FAB−: 199 |

TABLE 63-continued
| 344 | P56 | 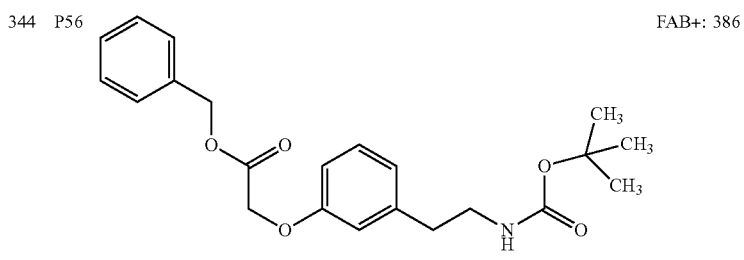 | FAB+: 386 |
TABLE 64
| 345 | P26 | 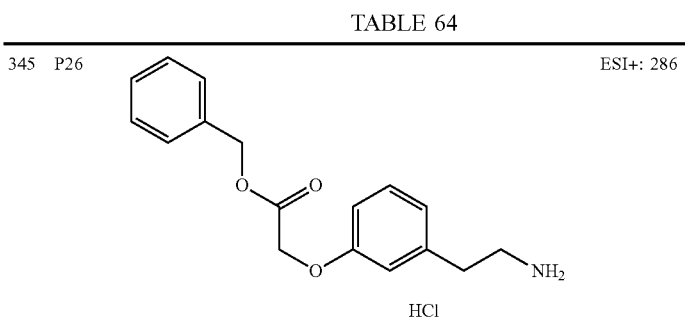 | ESI+: 286 |
| 346 | P61 P51 | 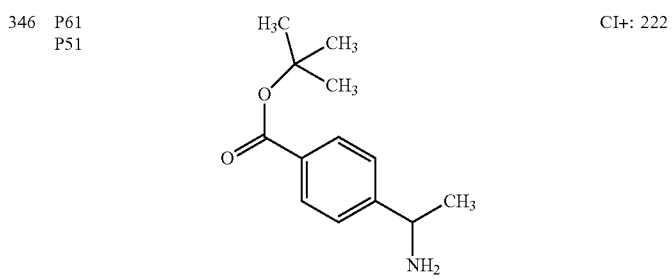 | CI+: 222 |
| 54 | P54 | 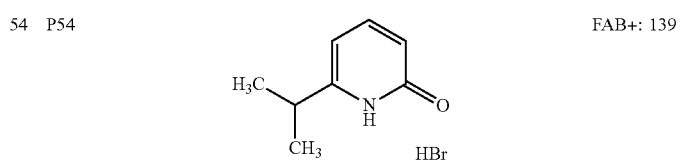 | FAB+: 139 |
| 347 | P8 | 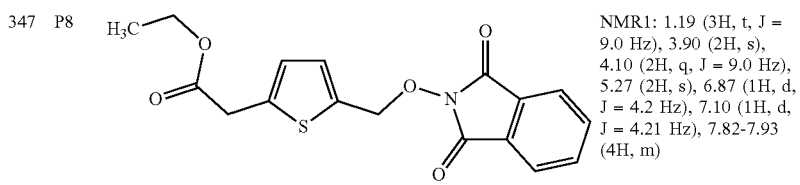 | NMR1: 1.19 (3H, t, J = 9.0 Hz), 3.90 (2H, s), 4.10 (2H, q, J = 9.0 Hz), 5.27 (2H, s), 6.87 (1H, d, J = 4.2 Hz), 7.10 (1H, d, J = 4.21 Hz), 7.82-7.93 (4H, m) |
| 48 | P48 | 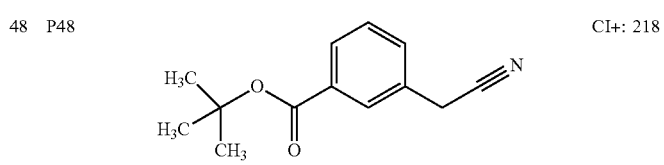 | CI+: 218 |
| 348 | P23 | 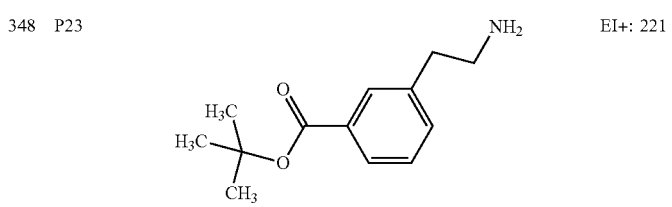 | EI+: 221 |

TABLE 65
| | | | | |
|---|---|---|---|---|
| 349 | P61 P51 | 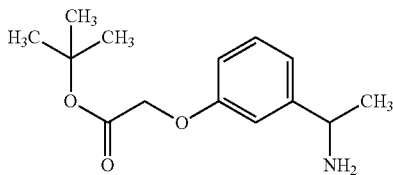 [SMILES: CC(N)c1cccc(OCC(=O)OC(C)(C)C)c1] | FAB+: 252 | |
| 350 | P36 | 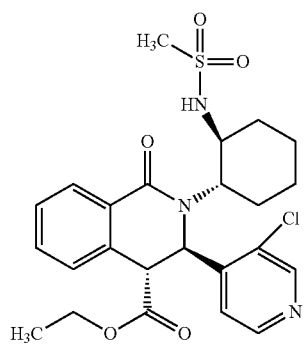 [SMILES: CCOC(=O)[C@@H]1c2ccccc2C(=O)N([C@H]2CCCC[C@@H]2NS(C)(=O)=O)[C@H]1c1ccncc1Cl] | ESI+: 506 | racemic mixture |
| 351 | P38 | 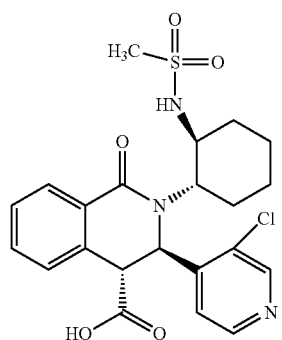 [SMILES: CS(=O)(=O)N[C@H]1CCCC[C@@H]1N1C(=O)c2ccccc2[C@@H](C(=O)O)[C@@H]1c1ccncc1Cl] | ESI+: 478 | racemic mixture |
| 49 | P49 | 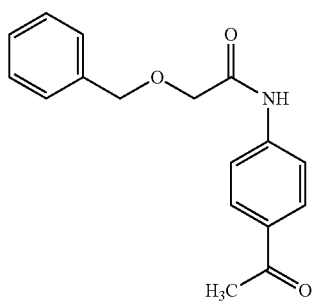 [SMILES: CC(=O)c1ccc(NC(=O)COCc2ccccc2)cc1] | CI+: 184 | |
| 352 | P61 P51 | 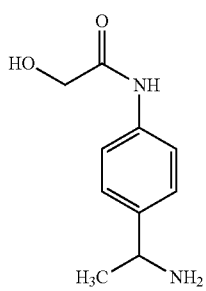 | FAB+: 195 | |

TABLE 66
| | | | |
|---|---|---|---|
| 56 | P56 | 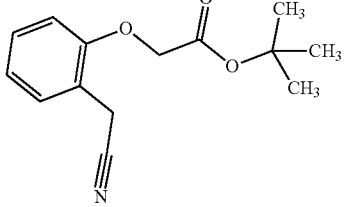 | ESI+: 248 |
| 59 | P59 | 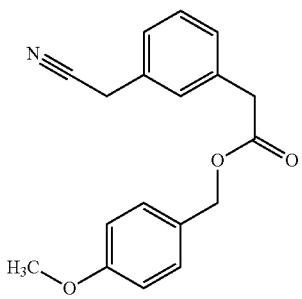 [SMILES: COc1ccc(COC(=O)Cc2cccc(CC#N)c2)cc1] | ESI+: 300 |
| 353 | P56 | 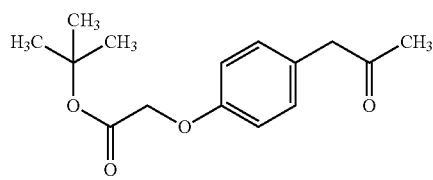 [SMILES: CC(=O)Cc1ccc(OCC(=O)OC(C)(C)C)cc1] | EI+: 264 |
| 354 | P61 P51 | 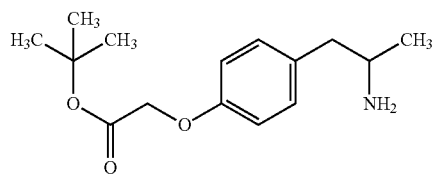 [SMILES: CC(N)Cc1ccc(OCC(=O)OC(C)(C)C)cc1] | CI+: 266 |
| 355 | P23 | 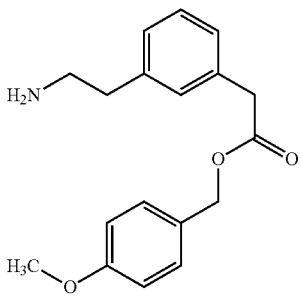 | ESI+: 296 |
| 45 | P45 | 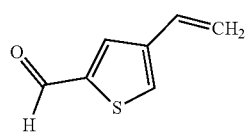 | NMR1: 5.31 (1H, d, J = 8.2 Hz), 5.79 (1H, d, J = 13.3 Hz), 6.75 (1H, dd, J = 13.3, 8.2 Hz), 8.07 (1H, s), 8.25 (1H, s), 9.92 (1H, s) |

TABLE 67

| 356 | P8 | (structure) | NMR1: 3.92 (3H, s), 5.22 (2H, s), 6.35 (1H, d, J = 3.0 Hz), 6.85 (1H, dd, J = 3.0 Hz), 7.82-7.88 (4H, m) | |
|---|---|---|---|---|
| 357 | P16 P8 | (structure) | NMR1: 5.17 (1H, d, J = 8.1 Hz), 5.62 (2H, d, J = 13.2 Hz), 6.66 (1H, dd, J = 13.2, 8.1 Hz), 7.50 (1H, s), 7.58 (1H, s), 7.83-7.89 (4H, m) | |
| 358 | P33 P34 | (structure) | ESI+: 450 | racemic mixture |
| 359 | P9 | (structure) | ESI+: 152 | |
| 360 | P48 | (structure) | ESI+: 224 | |

TABLE 68

| 361 | P8 P9 | (structure) | NMR1: 3.38-3.52 (2H, m), 4.48-4.55 (1H, m), 4.65 (2H, s), 4.66-4.71 (1H, s), 5.15 (1H, d, J = 3.9 Hz), 6.08 (2H, s), 6.98 (1H, s), 7.22 (1H, s) |
|---|---|---|---|
| 362 | P23 | (structure) | ESI+: 228 |

TABLE 68-continued
| 363 | P33 P34 | 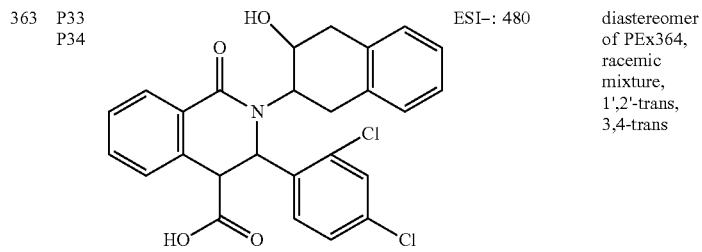 | ESI−: 480 | diastereomer of PEx364, racemic mixture, 1',2'-trans, 3,4-trans |
| --- | --- | --- | --- | --- |
| 364 | P33 P34 | 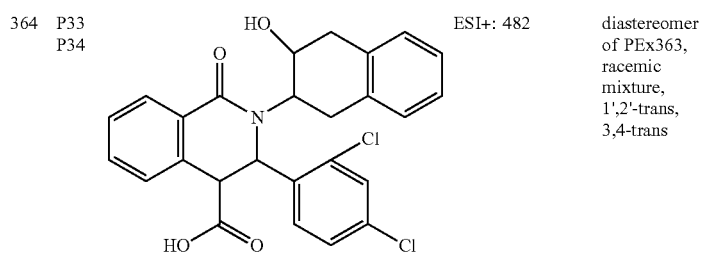 | ESI+: 482 | diastereomer of PEx363, racemic mixture, 1',2'-trans, 3,4-trans |
| 365 | P33 P34 | 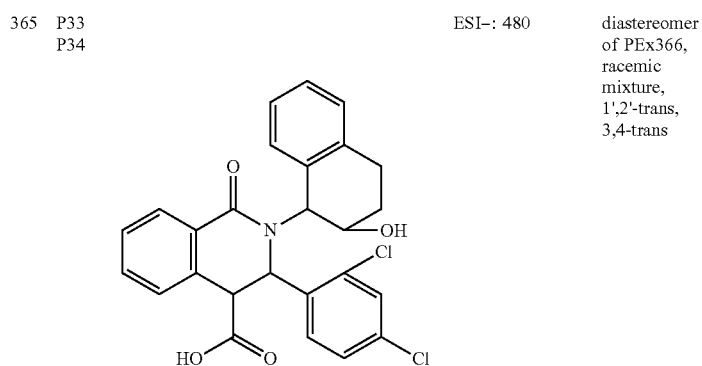 | ESI−: 480 | diastereomer of PEx366, racemic mixture, 1',2'-trans, 3,4-trans |
TABLE 69
| 366 | P33 P34 | 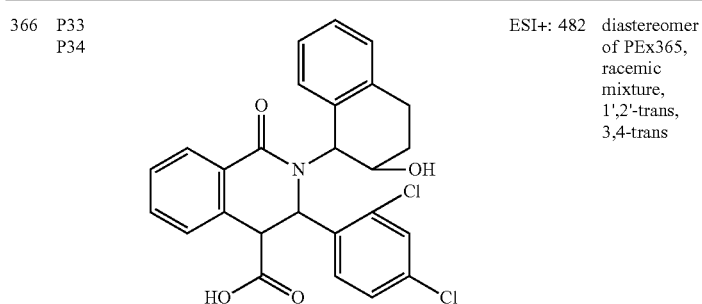 | ESI+: 482 | diastereomer of PEx365, racemic mixture, 1',2'-trans, 3,4-trans |
| --- | --- | --- | --- | --- |
| 367 | P33 P34 | 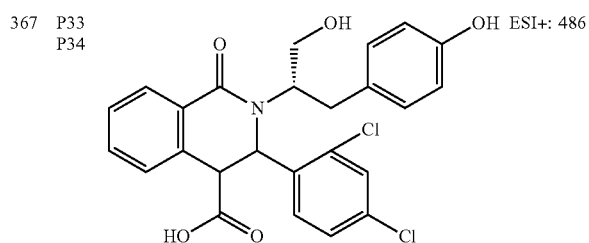 | ESI+: 486 | |

TABLE 69-continued
| 368 | P33 P34 | 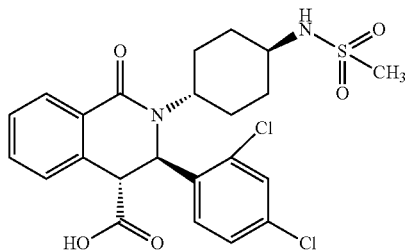 [SMILES: CS(=O)(=O)N[C@H]1CC[C@H](N2C(=O)c3ccccc3[C@@H](C(=O)O)[C@@H]2c2ccc(Cl)cc2Cl)CC1] | ESI+: 511 | racemic mixture |
| --- | --- | --- | --- | --- |
| 60 | P60 | 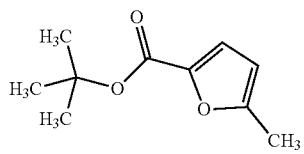 | EI+: 182 | |
| 369 | P19 | 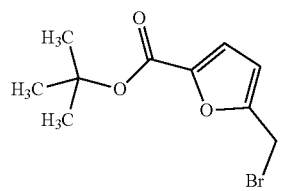 | EI+: 260, 262 | |
| 370 | P48 | 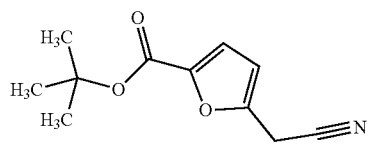 | ESI−: 206 | |
| 371 | P23 | 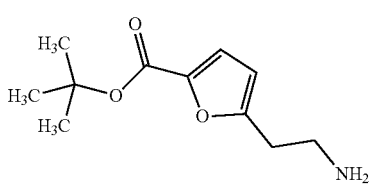 | ESI+: 212 | |
TABLE 70
| Ex | Structure | Note |
| --- | --- | --- |
| 60 | 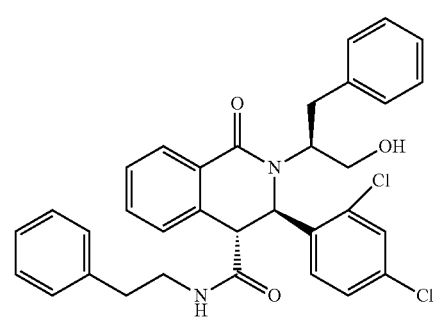 [SMILES: O=C(NCCc1ccccc1)[C@@H]1c2ccccc2C(=O)N([C@H](CO)Cc2ccccc2)[C@H]1c1ccc(Cl)cc1Cl] | |
| 61 | 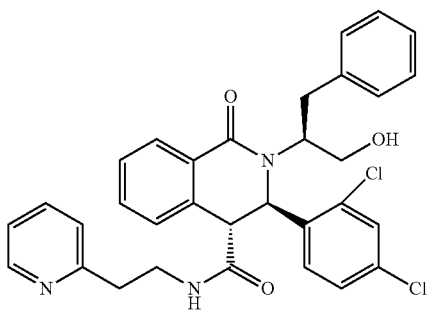 [SMILES: O=C(NCCc1ccccn1)[C@@H]1c2ccccc2C(=O)N([C@H](CO)Cc2ccccc2)[C@H]1c1ccc(Cl)cc1Cl] | |

TABLE 70-continued

| Ex | Structure | Note |
|---|---|---|
| 62 | 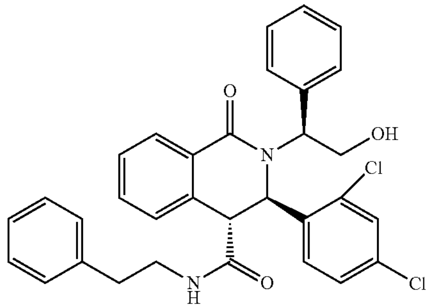 [SMILES: O=C(NCCc1ccccc1)[C@@H]1c2ccccc2C(=O)N([C@H](CO)c2ccccc2)[C@H]1c1ccc(Cl)cc1Cl] | |
| 63 | 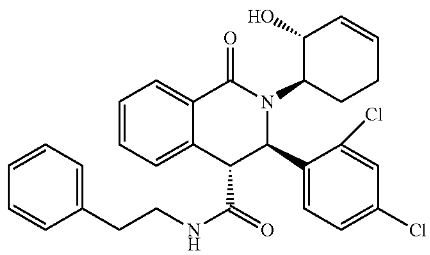 [SMILES: O=C(NCCc1ccccc1)[C@@H]1c2ccccc2C(=O)N([C@@H]2CCC=C[C@H]2O)[C@H]1c1ccc(Cl)cc1Cl] | racemic mixture |
| 64 | 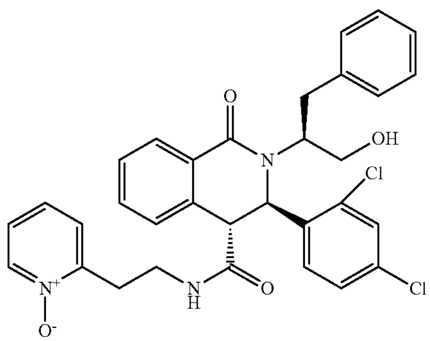 [SMILES: O=C(NCCc1cccc[n+]1[O-])[C@@H]1c2ccccc2C(=O)N([C@H](CO)Cc2ccccc2)[C@H]1c1ccc(Cl)cc1Cl] | |

TABLE 71

| 65 | | |
|---|---|---|
| 66 | | racemic mixture |
| 67 | | racemic mixture |
| 68 | | |
| 69 | | racemic mixture |

TABLE 72

| 70 | | racemic mixture |
|---|---|---|
| 71 | | |

TABLE 72-continued
| 72 | 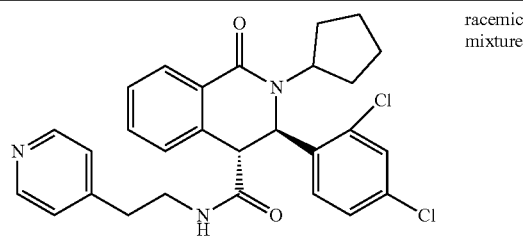 | racemic mixture |
| --- | --- | --- |
| 73 | 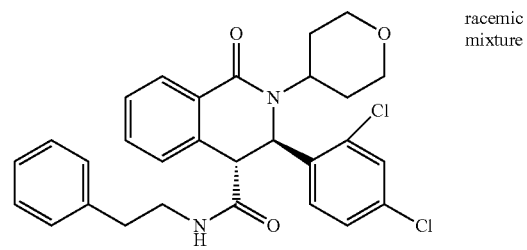 | racemic mixture |
| 74 | 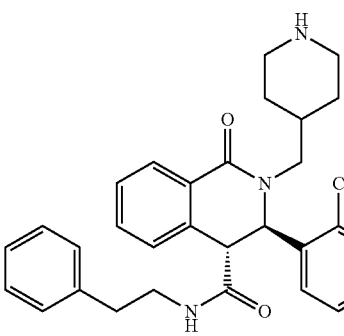 | racemic mixture |
TABLE 73
| 75 | 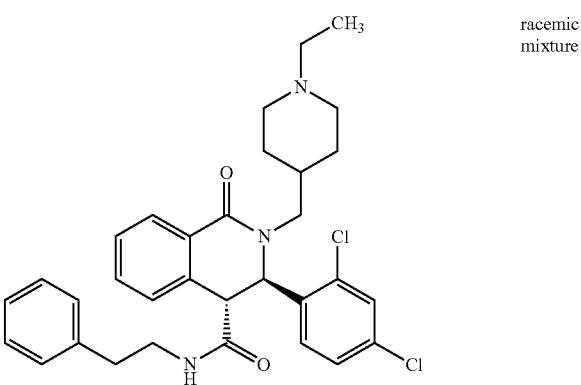 | racemic mixture |
| --- | --- | --- |
| 1 | 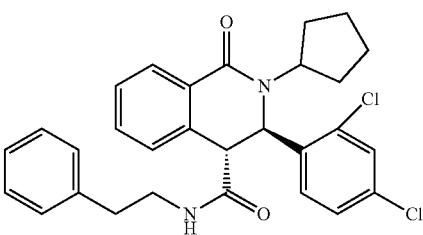 [SMILES: O=C(NCCc1ccccc1)[C@@H]1c2ccccc2C(=O)N(C2CCCC2)[C@H]1c1ccc(Cl)cc1Cl] | racemic mixture |
| 76 | 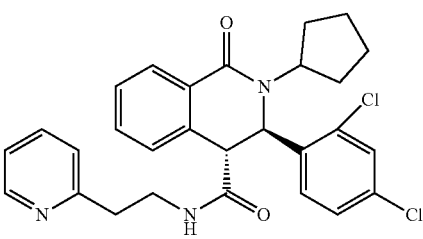 [SMILES: O=C(NCCc1ccccn1)[C@@H]1c2ccccc2C(=O)N(C2CCCC2)[C@H]1c1ccc(Cl)cc1Cl] | racemic mixture |

TABLE 73-continued
| 77 | 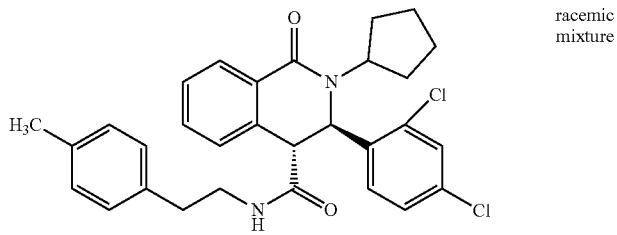 | racemic mixture |
| 78 | 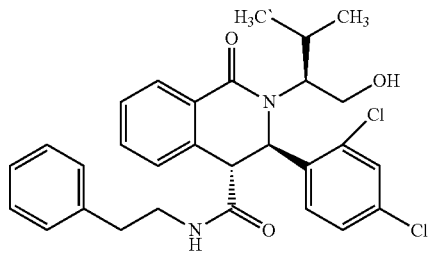 | |
TABLE 74
| 3 | 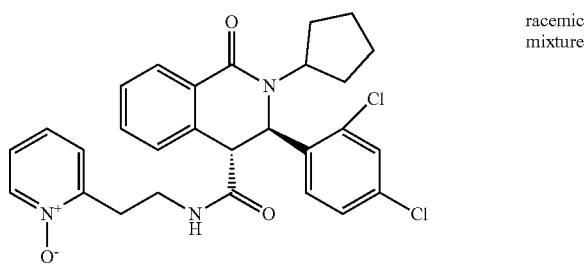 | racemic mixture |
| 79 | 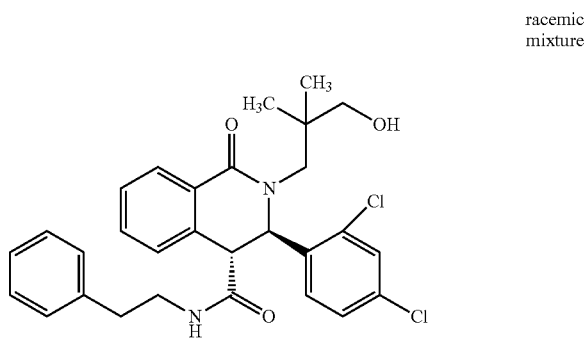 | racemic mixture |
| 80 | 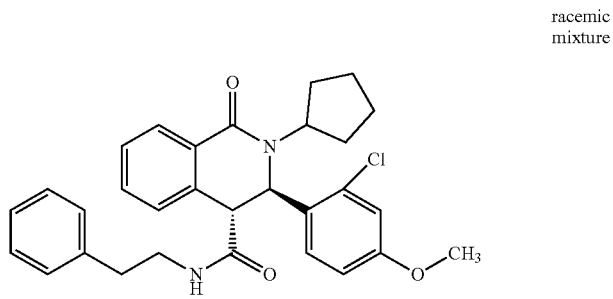 | racemic mixture |

TABLE 74-continued
81 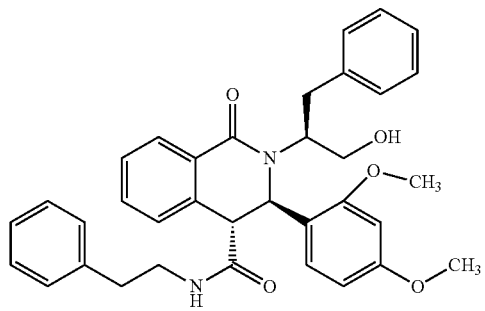 [SMILES: COc1ccc([C@H]2[C@H](C(=O)NCCc3ccccc3)c3ccccc3C(=O)N2[C@H](CO)Cc2ccccc2)c(OC)c1]
82 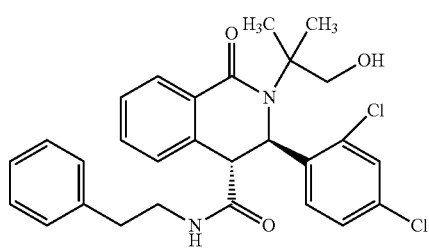 [SMILES: CC(C)(CO)N1C(=O)c2ccccc2[C@@H](C(=O)NCCc2ccccc2)[C@@H]1c1ccc(Cl)cc1Cl]
racemic mixture
TABLE 75
83 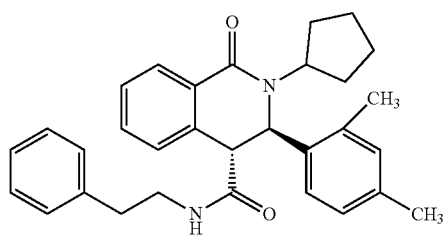 [SMILES: Cc1ccc([C@H]2[C@H](C(=O)NCCc3ccccc3)c3ccccc3C(=O)N2C2CCCC2)c(C)c1]
racemic mixture
84 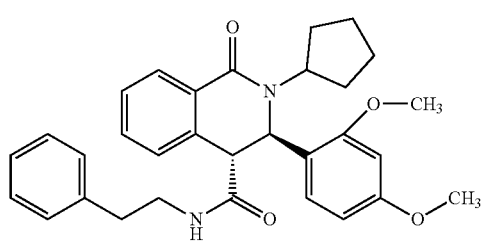 [SMILES: COc1ccc([C@H]2[C@H](C(=O)NCCc3ccccc3)c3ccccc3C(=O)N2C2CCCC2)c(OC)c1]
racemic mixture
85 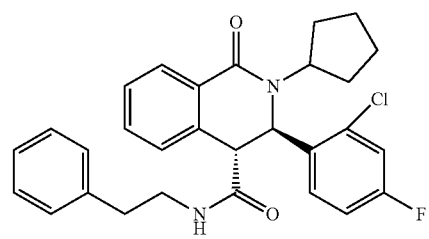 [SMILES: O=C(NCCc1ccccc1)[C@@H]1c2ccccc2C(=O)N(C2CCCC2)[C@H]1c1ccc(F)cc1Cl]
racemic mixture TABLE 75-continued
| 86 | 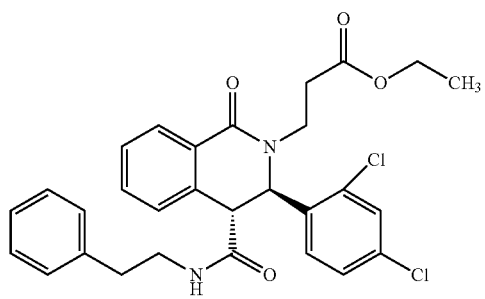 [SMILES: CCOC(=O)CCN1C(=O)c2ccccc2[C@@H](C(=O)NCCc2ccccc2)[C@@H]1c1ccc(Cl)cc1Cl] | racemic mixture |
| --- | --- | --- |
| 37 | 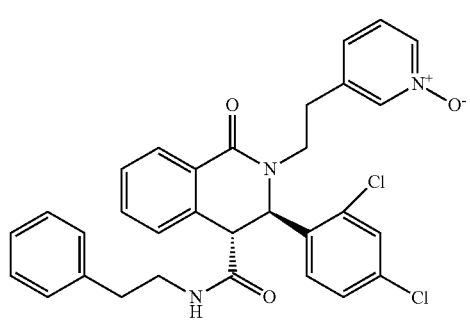 [SMILES: O=C(NCCc1ccccc1)[C@@H]1c2ccccc2C(=O)N(CCc2ccc[n+]([O-])c2)[C@H]1c1ccc(Cl)cc1Cl] | racemic mixture |
TABLE 76
| 87 | 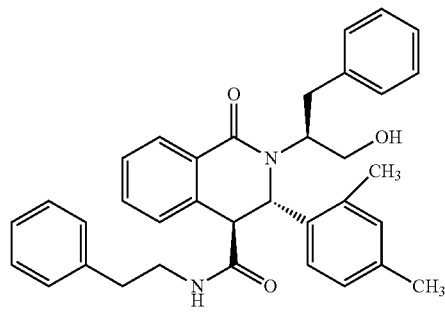 [SMILES: Cc1ccc([C@@H]2[C@@H](C(=O)NCCc3ccccc3)c3ccccc3C(=O)N2[C@H](CO)Cc2ccccc2)c(C)c1] | |
| --- | --- | --- |
| 88 | 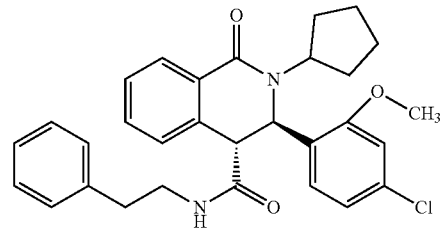 [SMILES: COc1cc(Cl)ccc1[C@H]1[C@H](C(=O)NCCc2ccccc2)c2ccccc2C(=O)N1C1CCCC1] | racemic mixture |
| 89 | 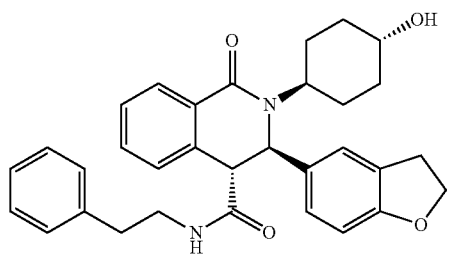 [SMILES: O=C(NCCc1ccccc1)[C@@H]1c2ccccc2C(=O)N([C@H]2CC[C@H](O)CC2)[C@H]1c1ccc2c(c1)CCO2] | racemic mixture |
TABLE 76-continued
| 90 | 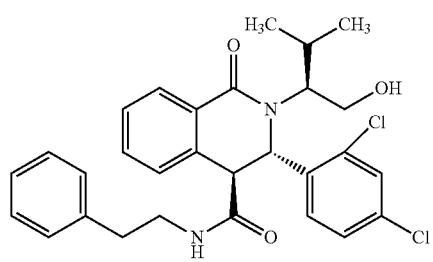 [SMILES: CC(C)[C@@H](CO)N1C(=O)c2ccccc2[C@H](C(=O)NCCc2ccccc2)[C@H]1c1ccc(Cl)cc1Cl] | |
| --- | --- | --- |
| 91 | 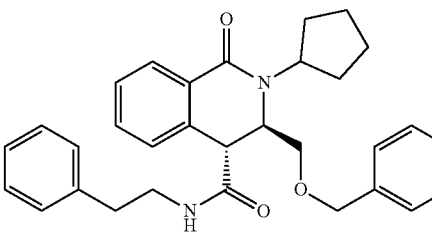 | racemic mixture |

TABLE 77
| 92 | 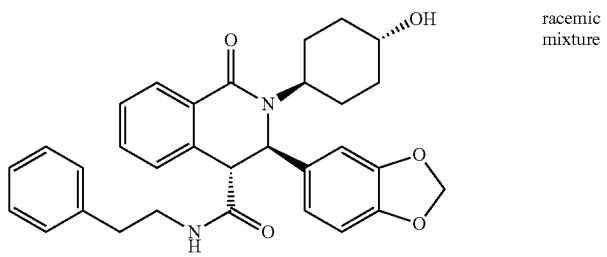 | racemic mixture |
| --- | --- | --- |
| 93 | 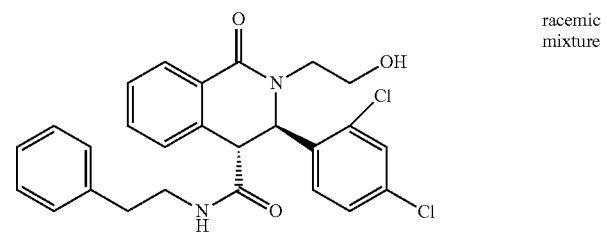 | racemic mixture |
| 94 | 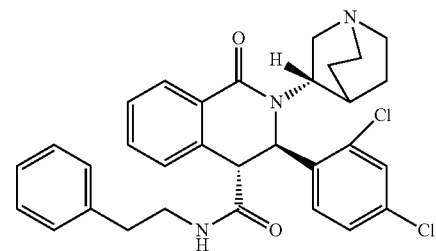 [SMILES: O=C(NCCc1ccccc1)[C@@H]1c2ccccc2C(=O)N([C@@H]2CN3CCC2CC3)[C@H]1c1ccc(Cl)cc1Cl] | racemic mixture |
| 95 | 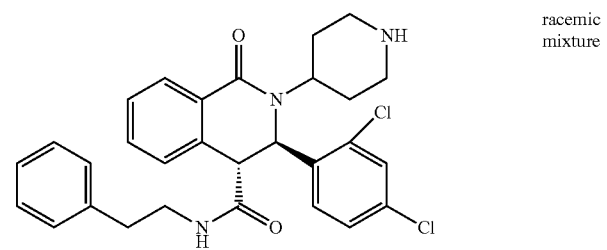 | racemic mixture |
| 96 | 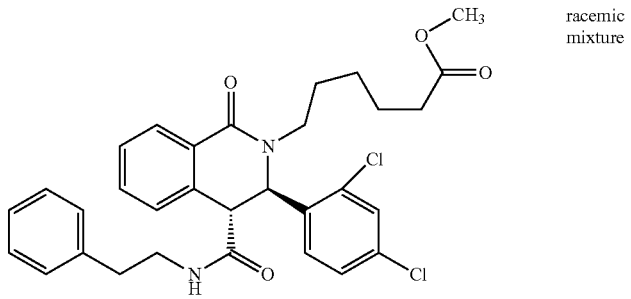 | racemic mixture |
| 97 | 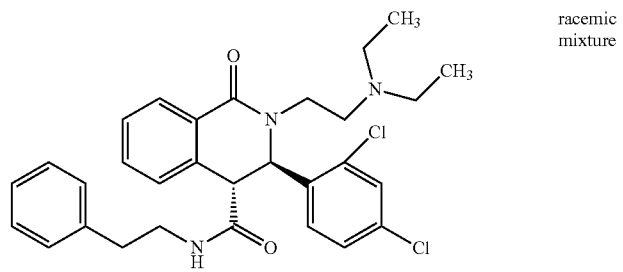 | racemic mixture |

TABLE 78
| | | | |
|---|---|---|---|
| 98 | 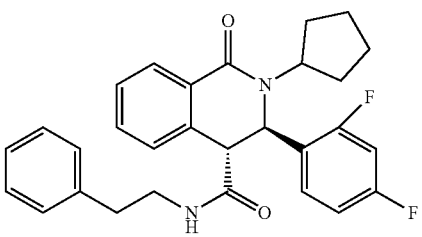 [SMILES: O=C(NCCc1ccccc1)[C@@H]1c2ccccc2C(=O)N(C2CCCC2)[C@H]1c1ccc(F)cc1F] | | racemic mixture |
| 99 | 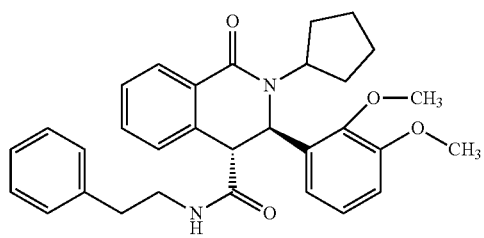 [SMILES: COc1cccc([C@H]2[C@H](C(=O)NCCc3ccccc3)c3ccccc3C(=O)N2C2CCCC2)c1OC] | | racemic mixture |
| 100 | 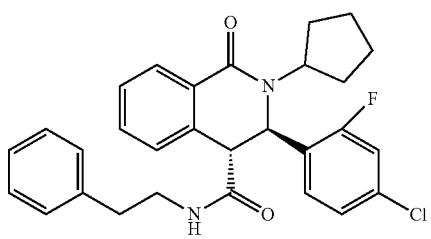 [SMILES: O=C(NCCc1ccccc1)[C@@H]1c2ccccc2C(=O)N(C2CCCC2)[C@H]1c1ccc(Cl)cc1F] | | racemic mixture |
| 101 | 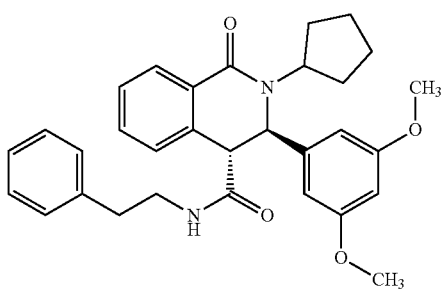 [SMILES: COc1cc(OC)cc([C@H]2[C@H](C(=O)NCCc3ccccc3)c3ccccc3C(=O)N2C2CCCC2)c1] | | racemic mixture |
| 102 | 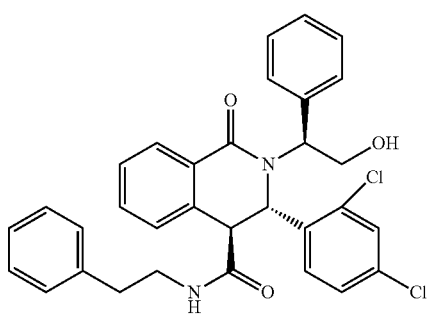 [SMILES: O=C(NCCc1ccccc1)[C@H]1c2ccccc2C(=O)N([C@H](CO)c2ccccc2)[C@@H]1c1ccc(Cl)cc1Cl] | | |
| 103 | 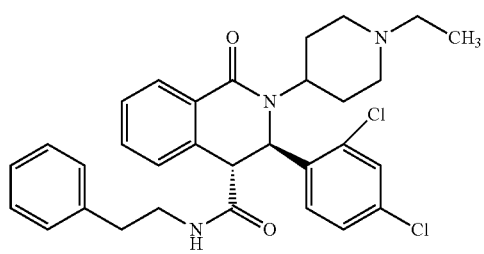 [SMILES: CCN1CCC(N2C(=O)c3ccccc3[C@@H](C(=O)NCCc3ccccc3)[C@@H]2c2ccc(Cl)cc2Cl)CC1] | | racemic mixture |

TABLE 79

| | | |
|---|---|---|
| 104 | (structure) | racemic mixture |
| 105 | (structure) | racemic mixture |
| 106 | (structure) | racemic mixture |
| 107 | (structure) | racemic mixture |
| 108 | (structure) | |
| 2 | (structure) | racemic mixture |

TABLE 80
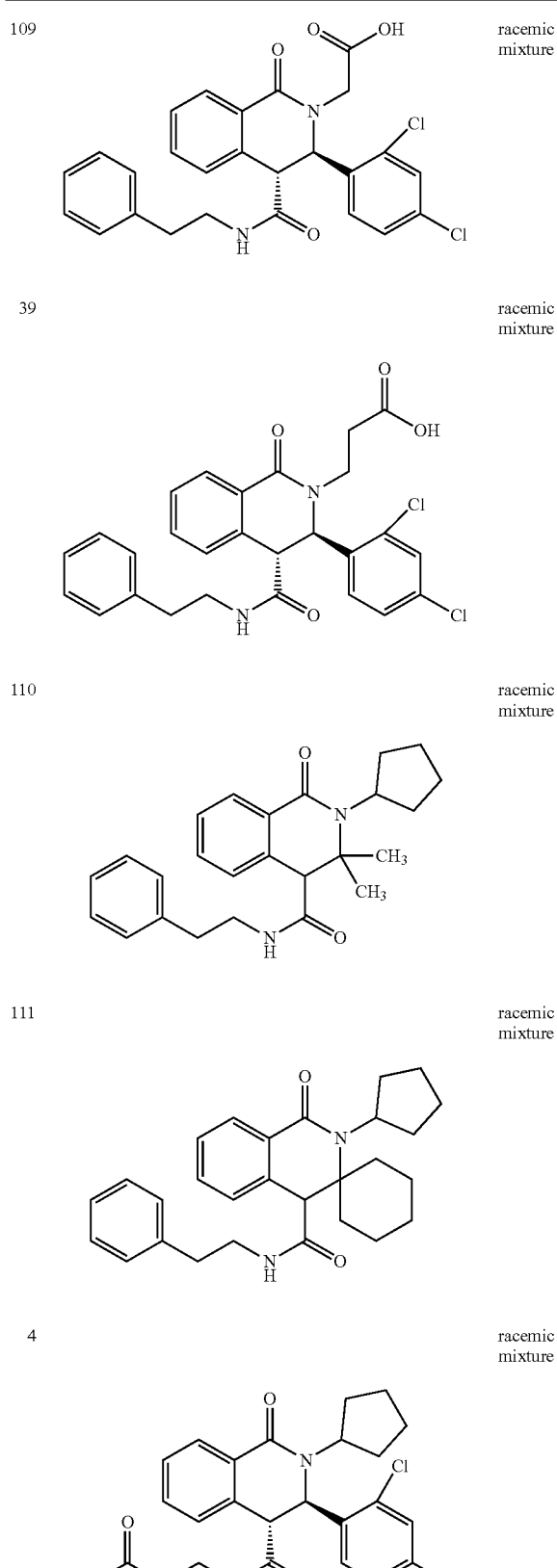
TABLE 81
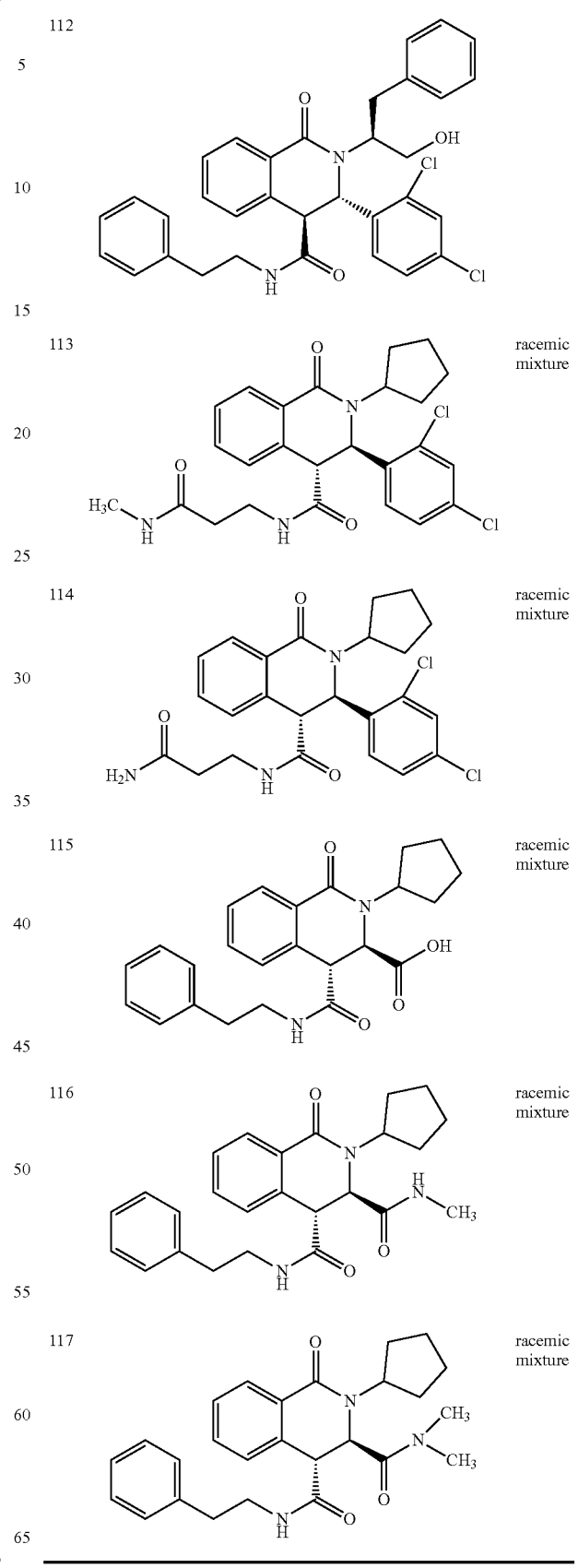

TABLE 82
| 118 | 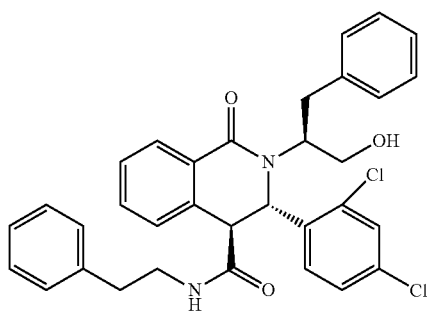 [SMILES: O=C(NCCc1ccccc1)[C@H]1c2ccccc2C(=O)N([C@H](CO)Cc2ccccc2)[C@@H]1c1ccc(Cl)cc1Cl] | |
| --- | --- | --- |
| 119 | 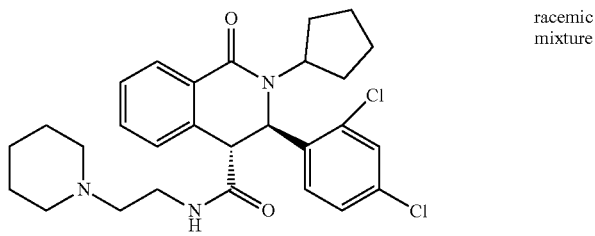 | racemic mixture |
| 120 | 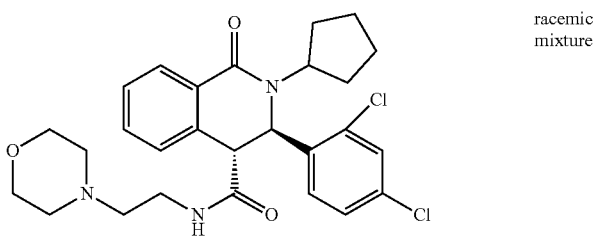 | racemic mixture |
| 121 | 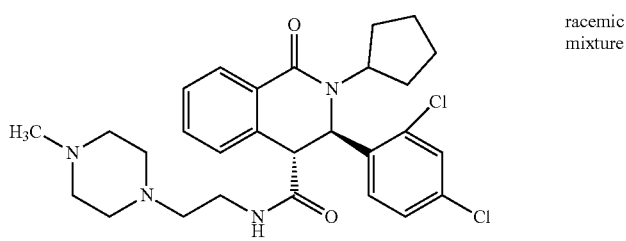 | racemic mixture |
| 122 | 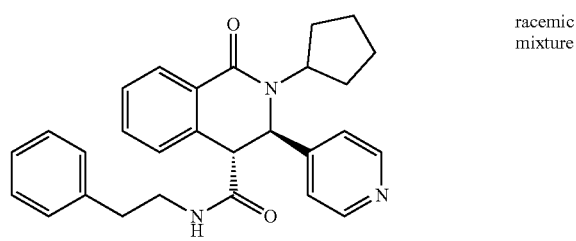 | racemic mixture |
| 123 | 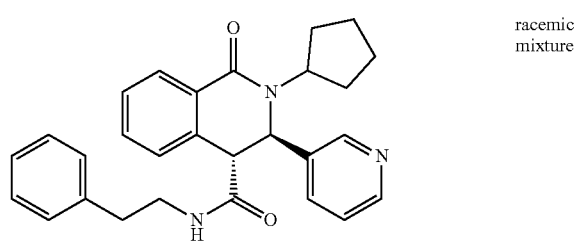 | racemic mixture |

TABLE 83
| | | |
|---|---|---|
| 124 | 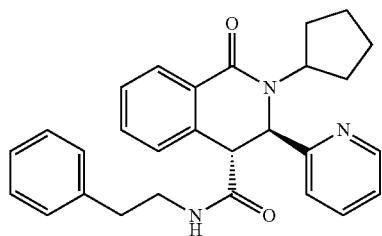 [SMILES: O=C(NCCc1ccccc1)[C@@H]1c2ccccc2C(=O)N(C2CCCC2)[C@H]1c1ccccn1] | racemic mixture |
| 36 | 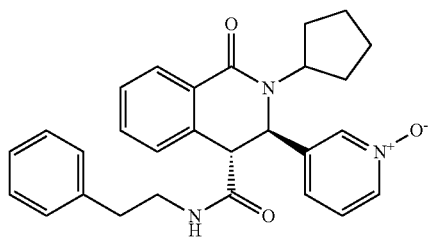 [SMILES: O=C(NCCc1ccccc1)[C@@H]1c2ccccc2C(=O)N(C2CCCC2)[C@H]1c1ccc[n+]([O-])c1] | racemic mixture |
| 125 | 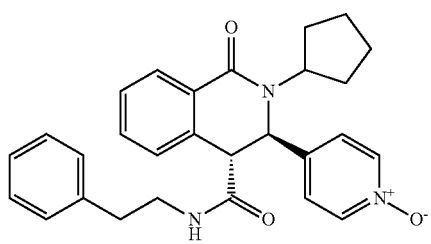 [SMILES: O=C(NCCc1ccccc1)[C@@H]1c2ccccc2C(=O)N(C2CCCC2)[C@H]1c1cc[n+]([O-])cc1] | racemic mixture |
TABLE 83-continued
| | | |
|---|---|---|
| 126 | 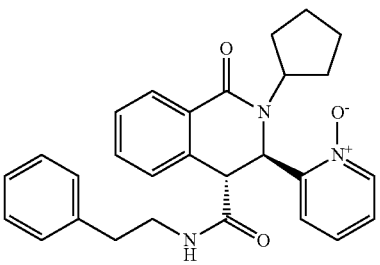 [SMILES: O=C(NCCc1ccccc1)[C@@H]1c2ccccc2C(=O)N(C2CCCC2)[C@H]1c1cccc[n+]1[O-]] | racemic mixture |
| 127 | 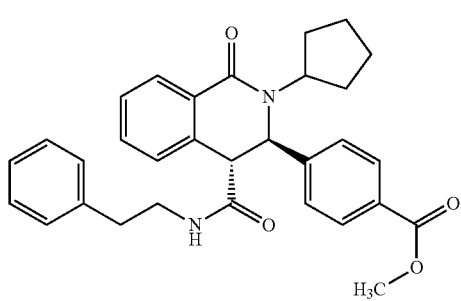 [SMILES: COC(=O)c1ccc([C@H]2[C@H](C(=O)NCCc3ccccc3)c3ccccc3C(=O)N2C2CCCC2)cc1] | racemic mixture |
| 38 | 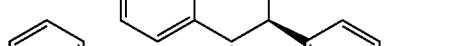 | racemic mixture |
TABLE 84
| | | |
|---|---|---|
| 128 | 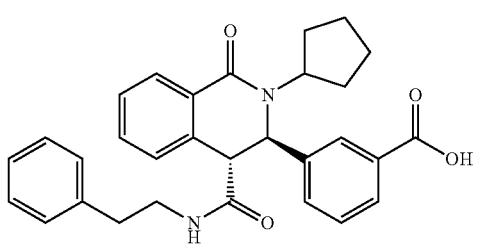 [SMILES: O=C(O)c1cccc([C@H]2[C@H](C(=O)NCCc3ccccc3)c3ccccc3C(=O)N2C2CCCC2)c1] | racemic mixture |
| 7 | 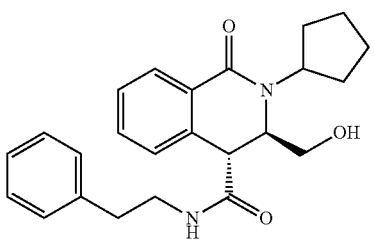 [SMILES: O=C(NCCc1ccccc1)[C@@H]1c2ccccc2C(=O)N(C2CCCC2)[C@H]1CO] | racemic mixture |

TABLE 84-continued
| 129 | 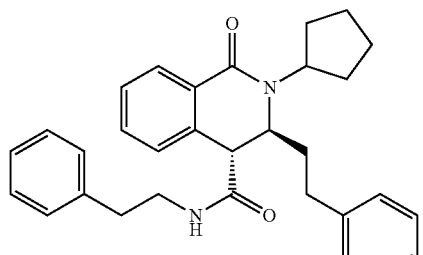 | racemic mixture |
| --- | --- | --- |
| 130 | 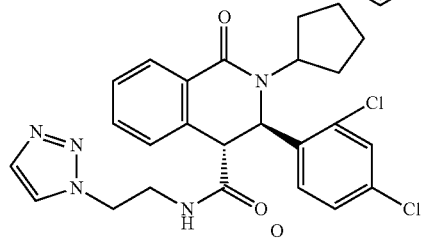 | racemic mixture |
| 10 | 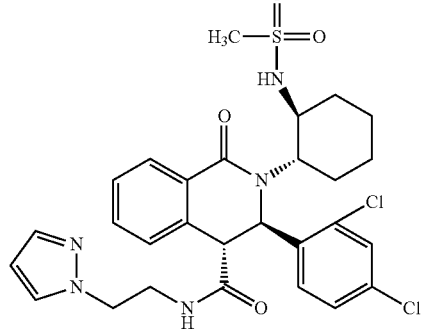 | racemic mixture |
TABLE 85
| 131 | 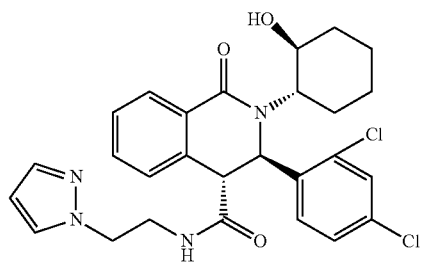 [SMILES: O=C(NCCn1cccn1)[C@@H]1c2ccccc2C(=O)N([C@H]2CCCC[C@@H]2O)[C@H]1c1ccc(Cl)cc1Cl] | racemic mixture |
| --- | --- | --- |
| 132 | 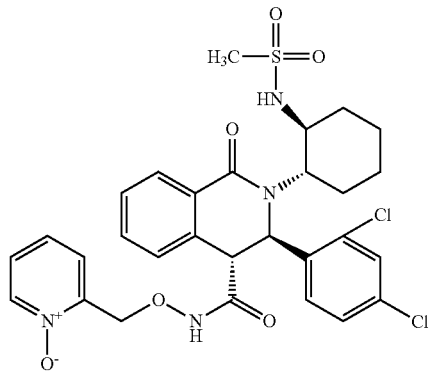 [SMILES: CS(=O)(=O)N[C@H]1CCCC[C@@H]1N1C(=O)c2ccccc2[C@@H](C(=O)NOCc2cccc[n+]2[O-])[C@@H]1c1ccc(Cl)cc1Cl] | racemic mixture |
TABLE 85-continued
| 133 | 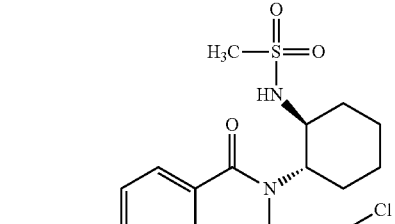 | racemic mixture |
| --- | --- | --- |
| 134 | 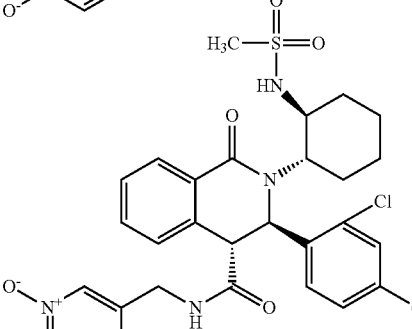 | racemic mixture |

TABLE 86
| | | |
|---|---|---|
| 135 | 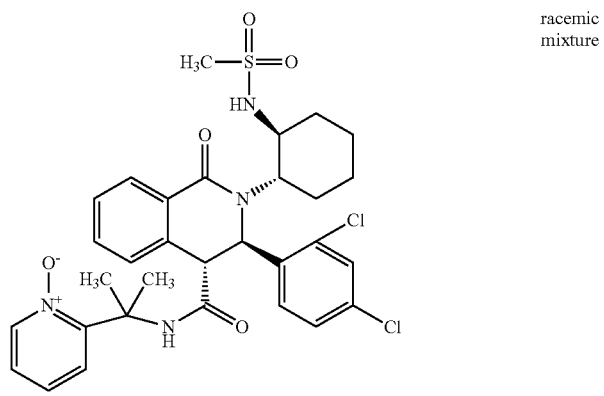 | racemic mixture |
| 136 | 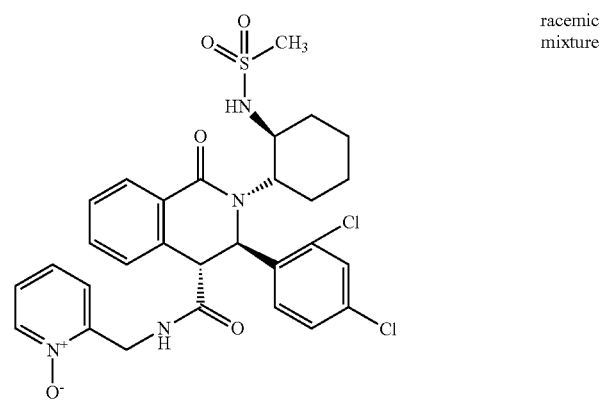 | racemic mixture |
| 137 | 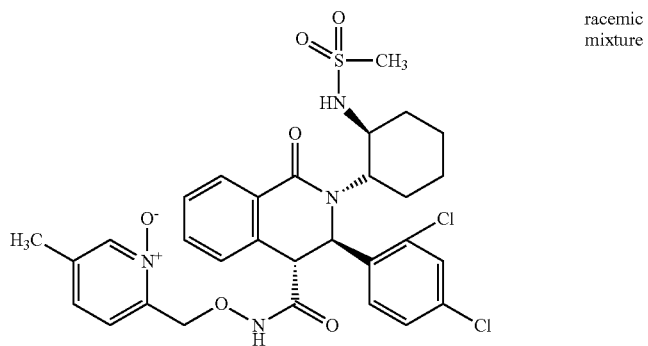 | racemic mixture |
| 138 | 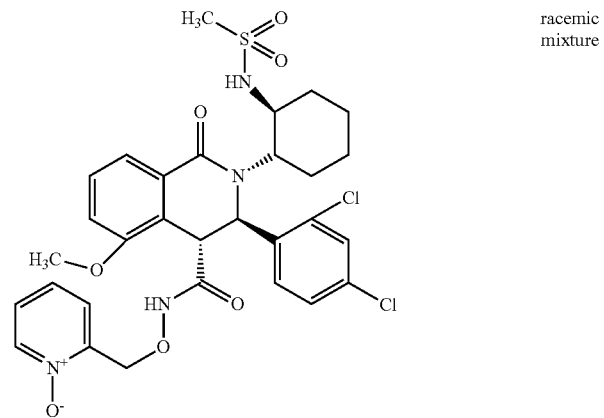 | racemic mixture |

TABLE 87
| 139 | 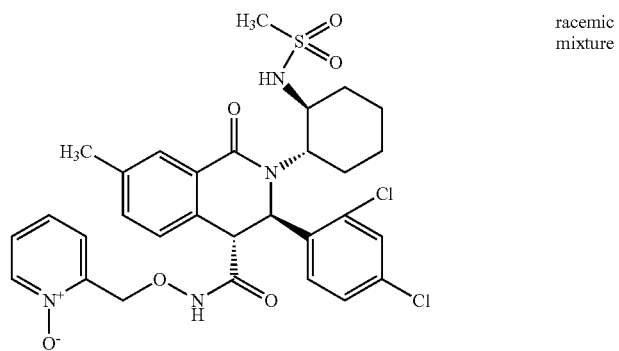 | racemic mixture |
| 140 | 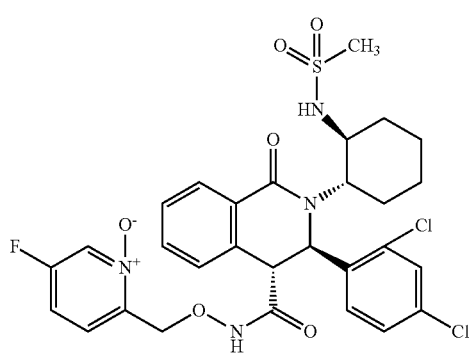 [SMILES: CS(=O)(=O)N[C@H]1CCCC[C@@H]1N1C(=O)c2ccccc2[C@@H](C(=O)NOCc2ccc(F)c[n+]2[O-])[C@@H]1c1ccc(Cl)cc1Cl] | racemic mixture |
| 141 | 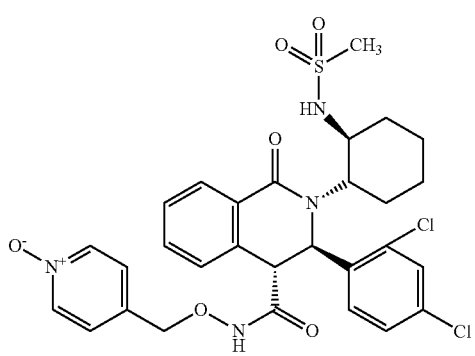 | racemic mixture |
| 142 | 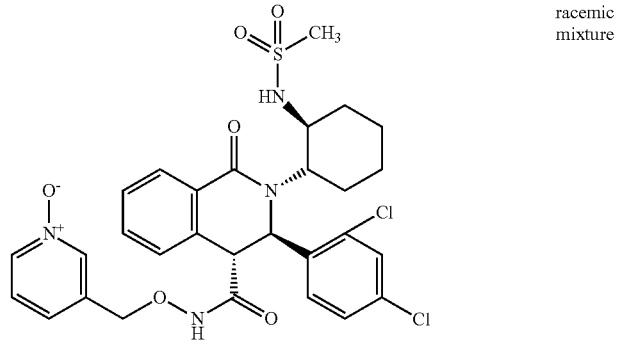 | racemic mixture |

TABLE 88
| | | |
|---|---|---|
| 143 | 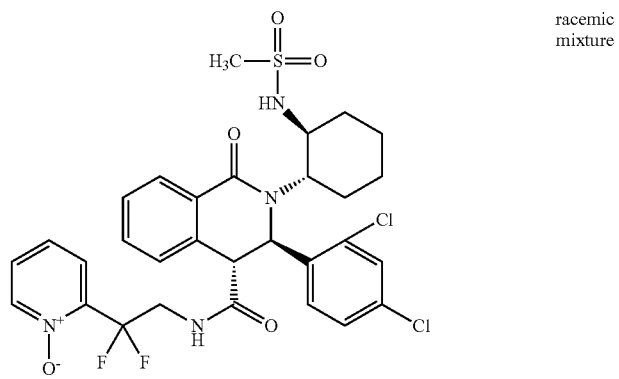 | racemic mixture |
| 144 | 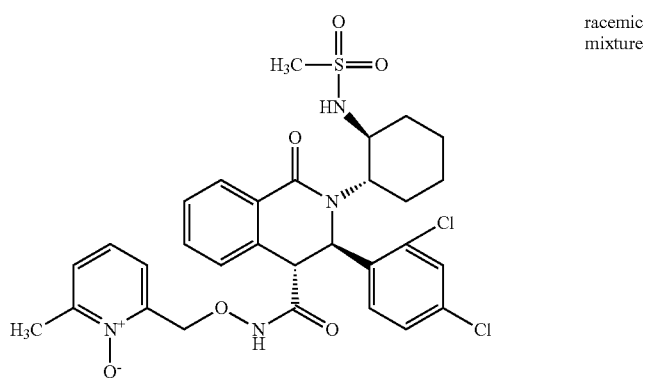 | racemic mixture |
| 145 | 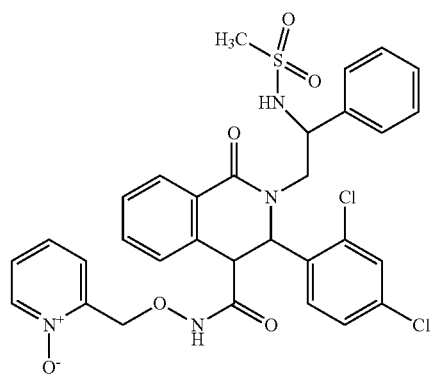 [SMILES: CS(=O)(=O)NC(CN1C(=O)c2ccccc2C(C(=O)NOCc2cccc[n+]2[O-])C1c1ccc(Cl)cc1Cl)c1ccccc1] | 3,4-trans, diastereo mixture |
| 146 | 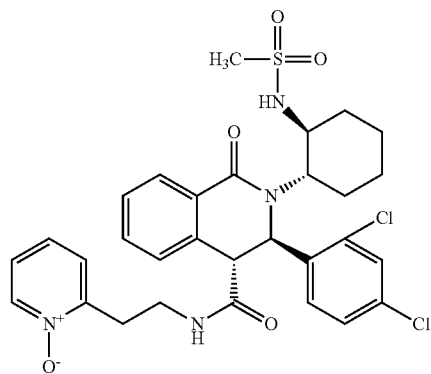 | racemic mixture |

TABLE 89
| 147 | 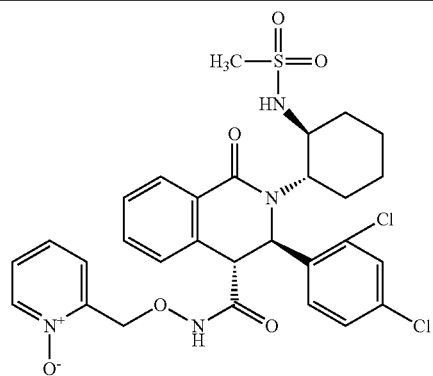 | |
| --- | --- | --- |
| | 9 | racemic mixture |
| 148 | 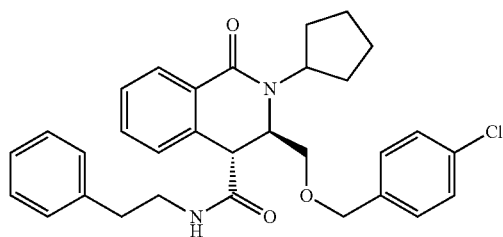 [SMILES: O=C(NCCc1ccccc1)[C@@H]1c2ccccc2C(=O)N(C2CCCC2)[C@H]1COCc1ccc(Cl)cc1] | 1',2'-3,4-trans, diastereomer of Ex 149, more polar |
| 149 | 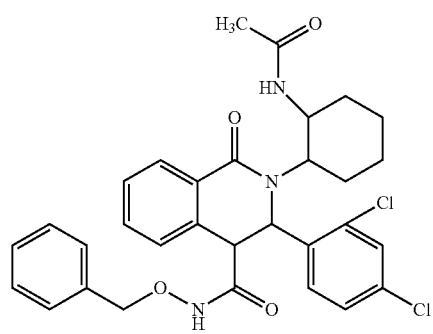 [SMILES: CC(=O)NC1CCCCC1N1C(=O)c2ccccc2C(C(=O)NOCc2ccccc2)C1c1ccc(Cl)cc1Cl] | 1',2'-3,4-trans, diastereomer of Ex 148, more polar |
| | 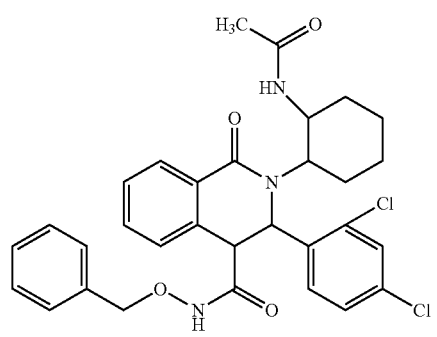 [SMILES: CC(=O)NC1CCCCC1N1C(=O)c2ccccc2C(C(=O)NOCc2ccccc2)C1c1ccc(Cl)cc1Cl] | |

TABLE 90
| | | |
|---|---|---|
| 11 | 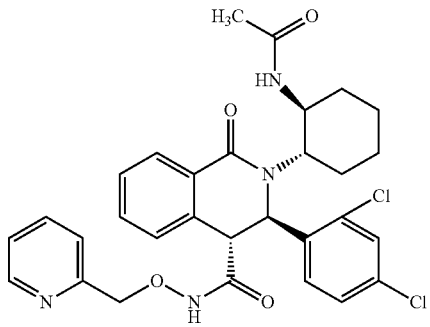 [SMILES: CC(=O)N[C@H]1CCCC[C@@H]1N1C(=O)c2ccccc2[C@@H](C(=O)NOCc2ccccn2)[C@@H]1c1ccc(Cl)cc1Cl] | racemic mixture |
| 150 | 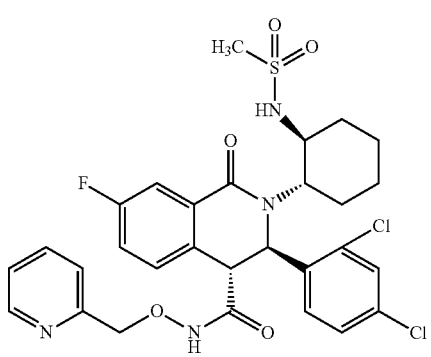 [SMILES: CS(=O)(=O)N[C@H]1CCCC[C@@H]1N1C(=O)c2cc(F)ccc2[C@@H](C(=O)NOCc2ccccn2)[C@@H]1c1ccc(Cl)cc1Cl] | racemic mixture |
| 151 | 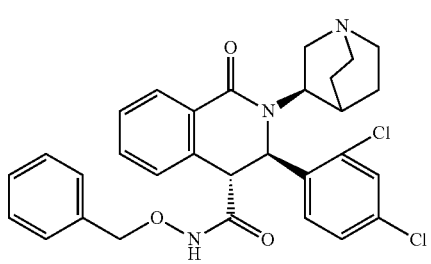 [SMILES: O=C(NOCc1ccccc1)[C@@H]1c2ccccc2C(=O)N([C@H]2CN3CCC2CC3)[C@H]1c1ccc(Cl)cc1Cl] | |
| 152 | 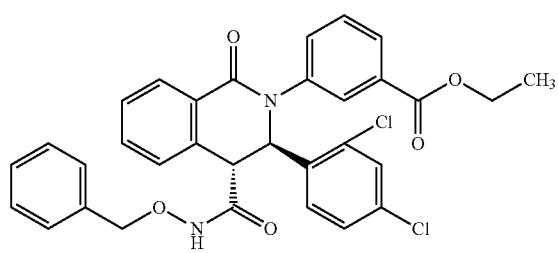 [SMILES: CCOC(=O)c1cccc(N2C(=O)c3ccccc3[C@@H](C(=O)NOCc3ccccc3)[C@@H]2c2ccc(Cl)cc2Cl)c1] | racemic mixture |
| 153 | 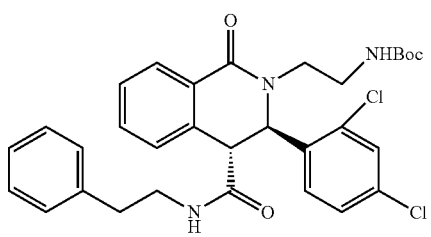 [SMILES: CC(C)(C)OC(=O)NCCN1C(=O)c2ccccc2[C@@H](C(=O)NCCc2ccccc2)[C@@H]1c1ccc(Cl)cc1Cl] | racemic mixture |

TABLE 91
| | | |
|---|---|---|
| 154 | 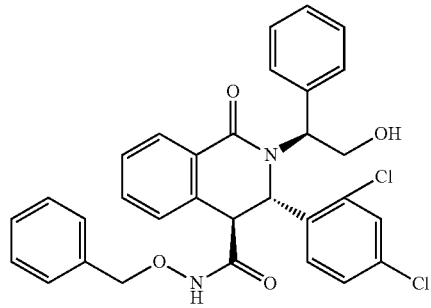 [SMILES: O=C(NOCc1ccccc1)[C@H]1c2ccccc2C(=O)N([C@H](CO)c2ccccc2)[C@@H]1c1ccc(Cl)cc1Cl] | |
| 155 | 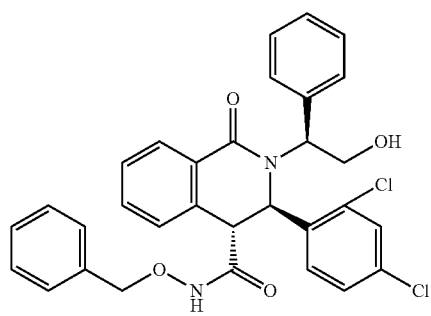 [SMILES: O=C(NOCc1ccccc1)[C@@H]1c2ccccc2C(=O)N([C@H](CO)c2ccccc2)[C@H]1c1ccc(Cl)cc1Cl] | |
| 156 | 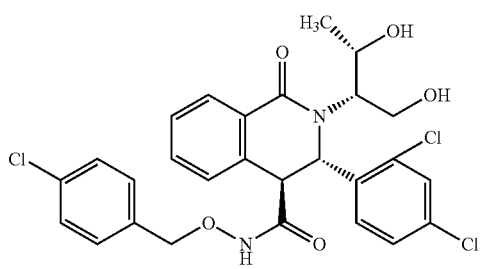 [SMILES: C[C@H](O)[C@H](CO)N1C(=O)c2ccccc2[C@H](C(=O)NOCc2ccc(Cl)cc2)[C@H]1c1ccc(Cl)cc1Cl] | |
| 157 | 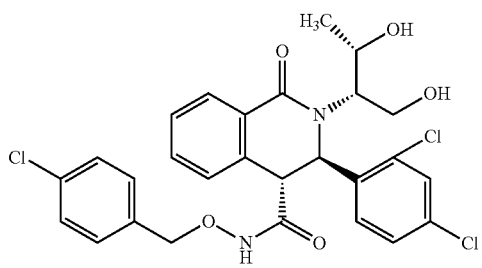 [SMILES: C[C@H](O)[C@H](CO)N1C(=O)c2ccccc2[C@@H](C(=O)NOCc2ccc(Cl)cc2)[C@@H]1c1ccc(Cl)cc1Cl] | |
| 158 | 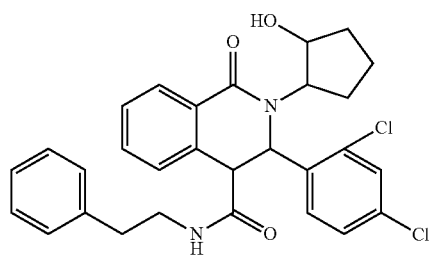 [SMILES: O=C(NCCc1ccccc1)C1c2ccccc2C(=O)N(C2CCCC2O)C1c1ccc(Cl)cc1Cl] | 1',2'-trans, 3,4-trans, diastereo mixture |

TABLE 92
| | | |
|---|---|---|
| 159 | 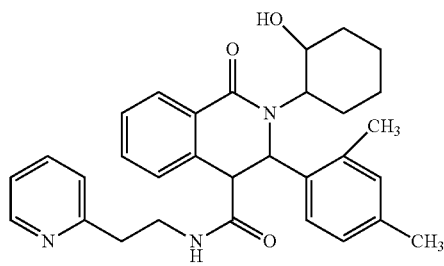 [SMILES: Cc1ccc(C2C(C(=O)NCCc3ccccn3)c3ccccc3C(=O)N2C2CCCCC2O)c(C)c1] | 1',2'-trans, 3,4-trans, diastereomer of Ex 160, less polar |
| 160 | 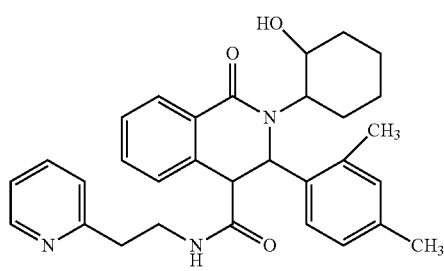 [SMILES: Cc1ccc(C2C(C(=O)NCCc3ccccn3)c3ccccc3C(=O)N2C2CCCCC2O)c(C)c1] | 1',2'-trans, 3,4-trans, diastereomer of Ex 159, more polar |
| 161 | 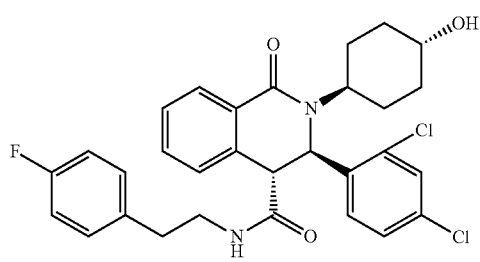 [SMILES: O=C(NCCc1ccc(F)cc1)[C@@H]1c2ccccc2C(=O)N([C@H]2CC[C@H](O)CC2)[C@H]1c1ccc(Cl)cc1Cl] | racemic mixture |
| 162 | 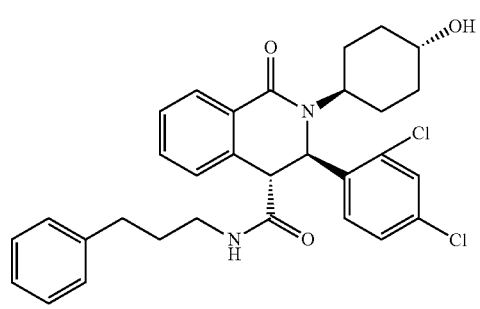 [SMILES: O=C(NCCCc1ccccc1)[C@@H]1c2ccccc2C(=O)N([C@H]2CC[C@H](O)CC2)[C@H]1c1ccc(Cl)cc1Cl] | racemic mixture |
| 163 | 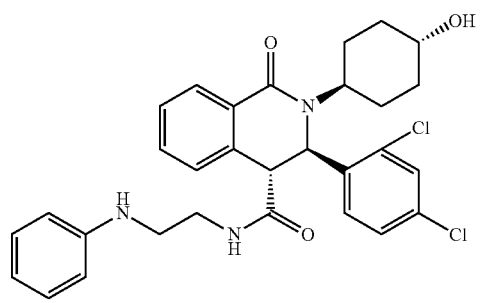 [SMILES: O=C(NCCNc1ccccc1)[C@@H]1c2ccccc2C(=O)N([C@H]2CC[C@H](O)CC2)[C@H]1c1ccc(Cl)cc1Cl] | racemic mixture |

TABLE 93
| | | |
|---|---|---|
| 164 | 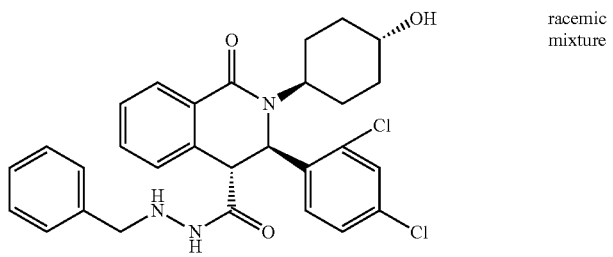 | racemic mixture |
| 165 | 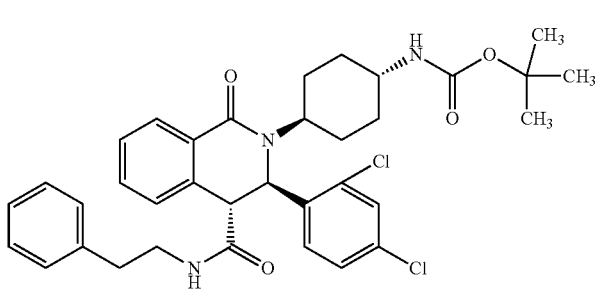 [SMILES: CC(C)(C)OC(=O)N[C@H]1CC[C@H](N2C(=O)c3ccccc3[C@@H](C(=O)NCCc3ccccc3)[C@@H]2c2ccc(Cl)cc2Cl)CC1] | racemic mixture |
| 166 | 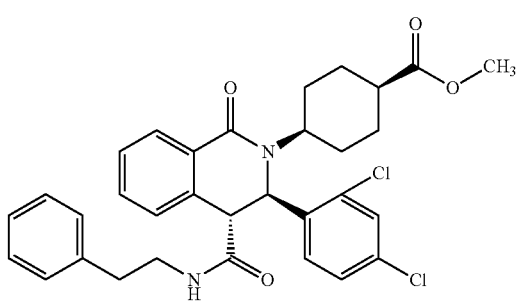 [SMILES: COC(=O)[C@H]1CC[C@@H](N2C(=O)c3ccccc3[C@@H](C(=O)NCCc3ccccc3)[C@@H]2c2ccc(Cl)cc2Cl)CC1] | racemic mixture |
| 167 | 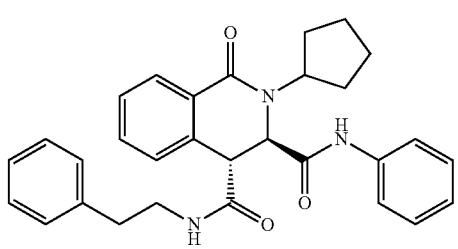 [SMILES: O=C(NCCc1ccccc1)[C@@H]1c2ccccc2C(=O)N(C2CCCC2)[C@H]1C(=O)Nc1ccccc1] | racemic mixture |
| 168 | 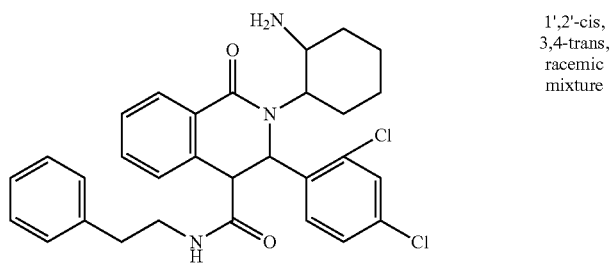 | 1',2'-cis, 3,4-trans, racemic mixture |

TABLE 94
| | | |
|---|---|---|
| 169 | 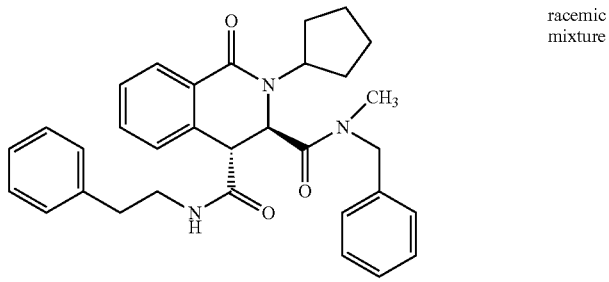 | racemic mixture |
| 170 | 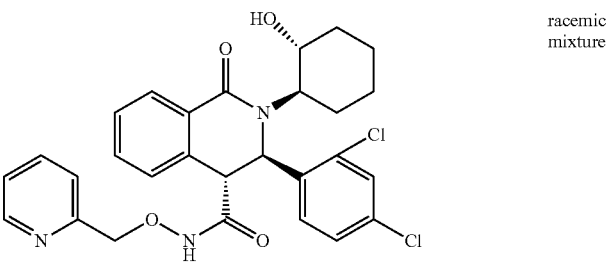 | racemic mixture |
| 171 | 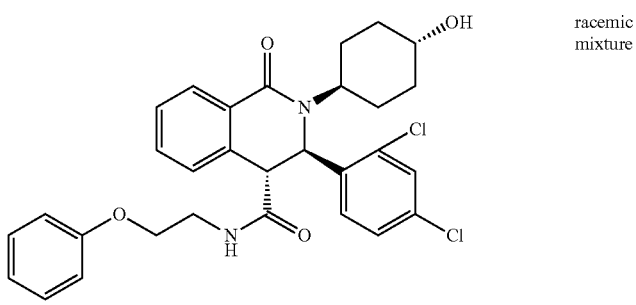 | racemic mixture |
| 172 | 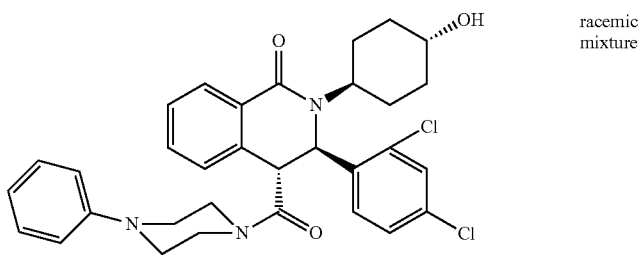 | racemic mixture |
| 173 | 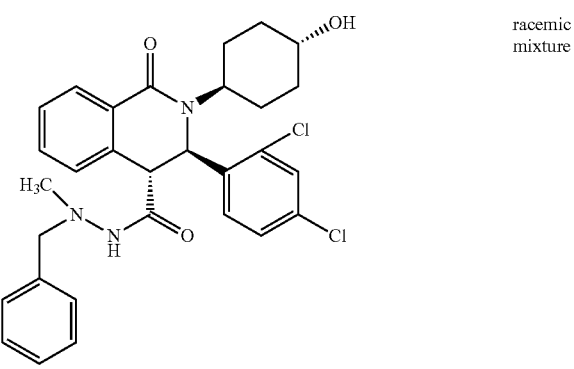 | racemic mixture |

TABLE 95
| 174 | 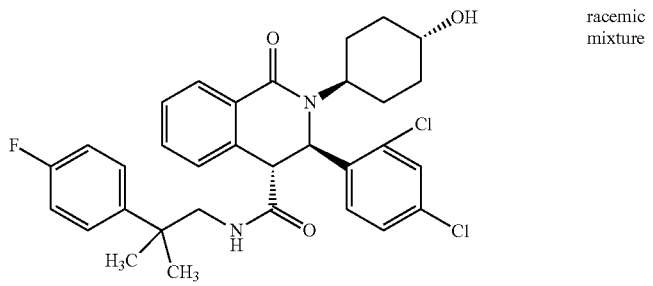 | racemic mixture |
| --- | --- | --- |
| 175 | 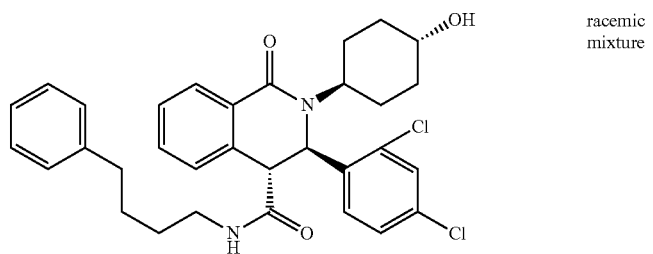 | racemic mixture |
| 176 | 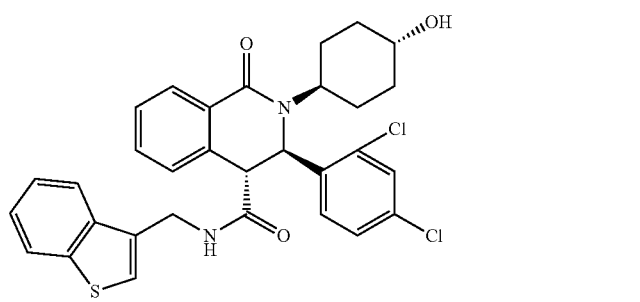 [SMILES: O=C(NCc1csc2ccccc12)[C@@H]1c2ccccc2C(=O)N([C@H]2CC[C@H](O)CC2)[C@H]1c1ccc(Cl)cc1Cl] | racemic mixture |
| 177 | 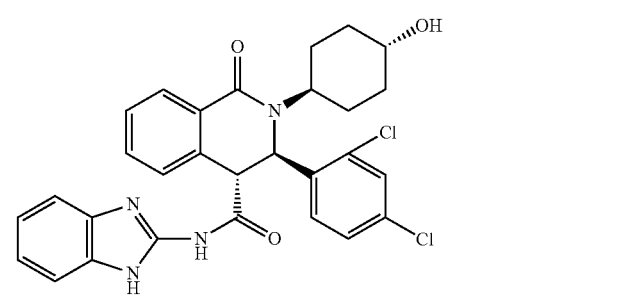 [SMILES: O=C(Nc1nc2ccccc2[nH]1)[C@@H]1c2ccccc2C(=O)N([C@H]2CC[C@H](O)CC2)[C@H]1c1ccc(Cl)cc1Cl] | racemic mixture |
| 178 | 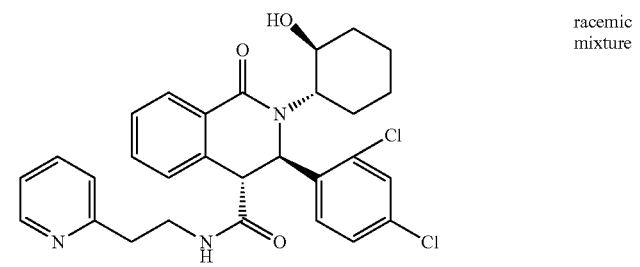 | racemic mixture |

TABLE 96
| | | |
|---|---|---|
| 34 | 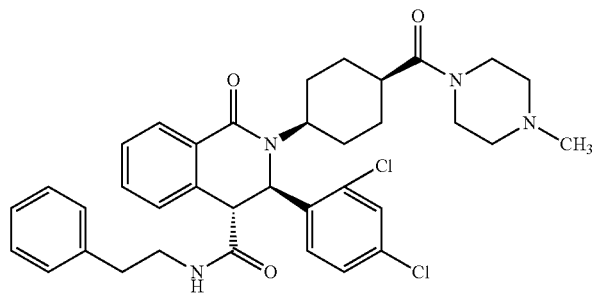 [SMILES: CN1CCN(C(=O)[C@H]2CC[C@@H](N3C(=O)c4ccccc4[C@@H](C(=O)NCCc4ccccc4)[C@@H]3c3ccc(Cl)cc3Cl)CC2)CC1] | racemic mixture |
| 179 | 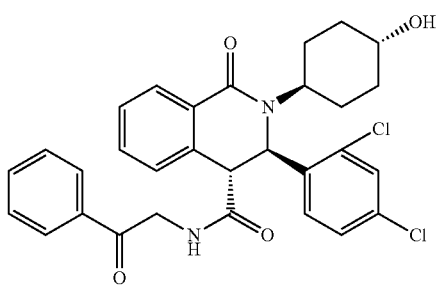 [SMILES: O=C(CNC(=O)[C@@H]1c2ccccc2C(=O)N([C@H]2CC[C@H](O)CC2)[C@H]1c1ccc(Cl)cc1Cl)c1ccccc1] | racemic mixture |
| 180 | 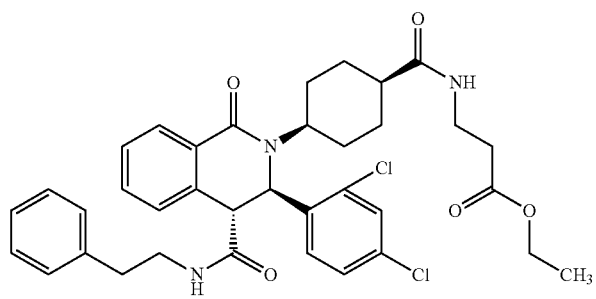 [SMILES: CCOC(=O)CCNC(=O)[C@H]1CC[C@@H](N2C(=O)c3ccccc3[C@@H](C(=O)NCCc3ccccc3)[C@@H]2c2ccc(Cl)cc2Cl)CC1] | racemic mixture |
| 181 | 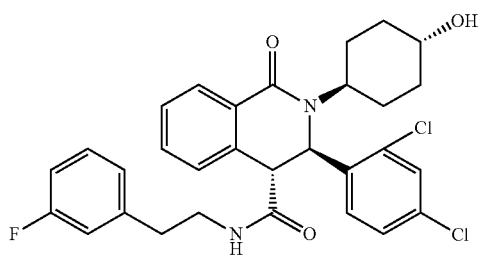 [SMILES: O=C(NCCc1cccc(F)c1)[C@@H]1c2ccccc2C(=O)N([C@H]2CC[C@H](O)CC2)[C@H]1c1ccc(Cl)cc1Cl] | racemic mixture |
| 182 | 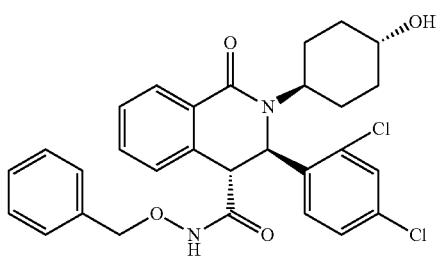 | racemic mixture |

TABLE 97
| 183 | 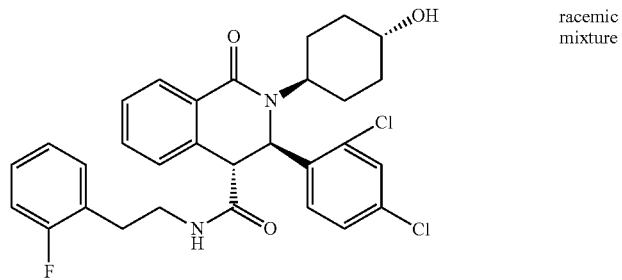 | racemic mixture |
| --- | --- | --- |
| 184 | 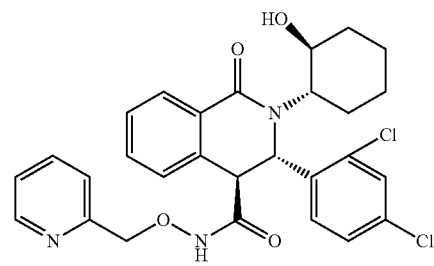 [SMILES: O=C(NOCc1ccccn1)[C@H]1c2ccccc2C(=O)N([C@H]2CCCC[C@@H]2O)[C@@H]1c1ccc(Cl)cc1Cl] | |
| 185 | 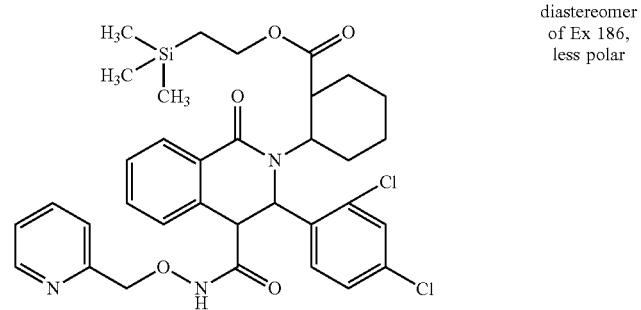 | 1',2'-trans, 3,4-trans, diastereomer of Ex 186, less polar |
| 186 | 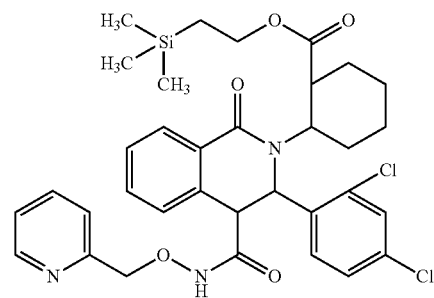 [SMILES: C[Si](C)(C)CCOC(=O)C1CCCCC1N1C(=O)c2ccccc2C(C(=O)NOCc2ccccn2)C1c1ccc(Cl)cc1Cl] | 1',2'-trans, 3,4-trans, diastereomer of Ex 185, |
| 187 | 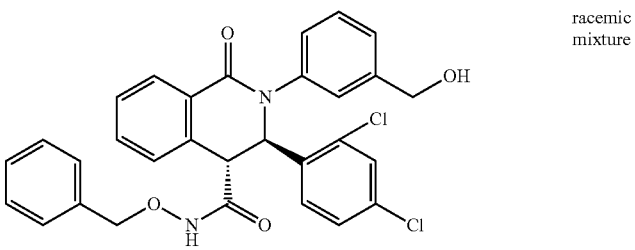 | racemic mixture |

TABLE 98

| # | Structure | Notes |
|---|---|---|
| 188 | (isoquinolinone core with (2-hydroxycyclohexyl), 2,4-dichlorophenyl, and pyridin-2-ylmethoxy-NH-C(=O)- substituents) | HCl |
| 189 | (isoquinolinone core with (2-hydroxycyclohexyl), 4-chlorophenyl, and benzyloxy-NH-C(=O)- substituents) | 1',2'-trans, 3,4-trans, diastereomer of Ex190, less polar |
| 190 | (isoquinolinone core with (2-hydroxycyclohexyl), 4-chlorophenyl, and benzyloxy-NH-C(=O)- substituents) | 1',2'-trans, 3,4-trans, diastereomer of Ex189, more polar |
| 191 | (isoquinolinone core with 2-hydroxypropyl, 2,4-dichlorophenyl, and benzyloxy-NH-C(=O)- substituents) | 3,4-trans, diastereomer of Ex192, less polar |
| 192 | (isoquinolinone core with 2-hydroxypropyl, 2,4-dichlorophenyl, and benzyloxy-NH-C(=O)- substituents) | 3,4-trans, diastereomer of Ex191, more polar |

TABLE 99

| # | Structure | Notes |
|---|---|---|
| 193 | (isoquinolinone core with 2-hydroxyphenyl, 2,4-dichlorophenyl, and benzyloxy-NH-C(=O)- substituents) | racemic mixture |

TABLE 99-continued

| # | Structure | Notes |
|---|---|---|
| 194 | (isoquinolinone core with 1,3-dihydroxybutan-2-yl, 2,4-dichlorophenyl, and 2-(pyridin-2-yl)ethyl-NH-C(=O)- substituents) |  |
| 195 | (isoquinolinone core with 1,3-dihydroxybutan-2-yl, 2,4-dichlorophenyl, and 2-(pyridin-2-yl)ethyl-NH-C(=O)- substituents) |  |
| 196 | (isoquinolinone core with 2-hydroxy-2-phenylethyl, 2,4-dichlorophenyl, and benzyloxy-NH-C(=O)- substituents) | 3,4-trans, diastereomer of Ex197, less polar |
| 197 | (isoquinolinone core with 2-hydroxy-2-phenylethyl, 2,4-dichlorophenyl, and benzyloxy-NH-C(=O)- substituents) | 3,4-trans, diastereomer of Ex196, more polar |

TABLE 100

| # | Structure | Notes |
|---|---|---|
| 198 | (isoquinolinone core with (2-hydroxycyclohexyl), 2-chlorophenyl, and benzyloxy-NH-C(=O)- substituents) | 1',2'-trans, 3,4-trans, diastereomer of Ex199, less polar |

TABLE 100-continued

| # | Structure | Notes |
|---|---|---|
| 199 | (structure) | 1',2'-trans, 3,4-trans, diastereomer of Ex198, more polar |
| 200 | (structure) | 1',2'-trans, 3,4-trans, diastereomer of Ex201, less polar |
| 201 | (structure) | 1',2'-trans, 3,4-trans, diastereomer of Ex200, more polar |
| 202 | (structure) | 3,4-trans |

TABLE 101

| # | Structure | Notes |
|---|---|---|
| 203 | (structure) | 1',2'-trans, 3,4-trans, diastereomer of Ex409 |
| 204 | (structure) | racemic mixture |
| 205 | (structure) | 1',2'-trans, 3,4-trans, distereo mixture |

TABLE 101-continued
| 206 | 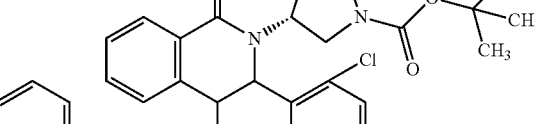 | 3,4-trans, distereo mixture |
| --- | --- | --- |
| 207 | 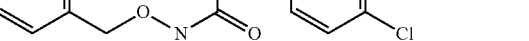 | 3,4-trans distereo mixture |
TABLE 102
| 208 | 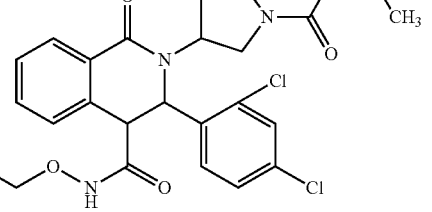 | 1',2'-trans, 3,4-trans, distereomer of Ex209 |
| --- | --- | --- |
| 209 | 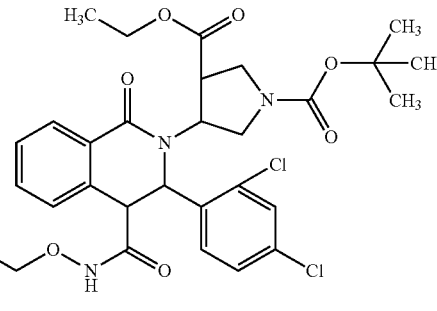 | 1',2'-trans, 3,4-trans, distereomer of Ex208 |
| 210 | 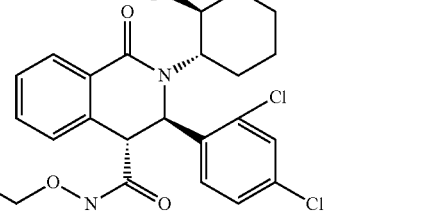 | racemic mixture |

TABLE 102-continued
| 211 | 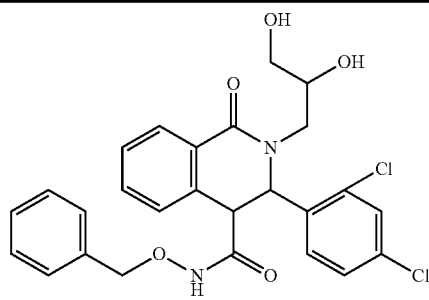 | 3,4-trans, diastereomer of Ex212, less polar |
| --- | --- | --- |
| 212 | 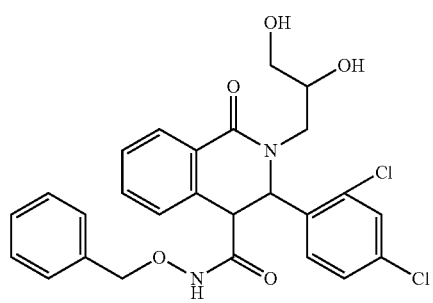 [SMILES: O=C(NOCc1ccccc1)C1c2ccccc2C(=O)N(CC(O)CO)C1c1ccc(Cl)cc1Cl] | 3,4-trans, diastereomer of Ex211, more polar |
TABLE 103
| 213 | 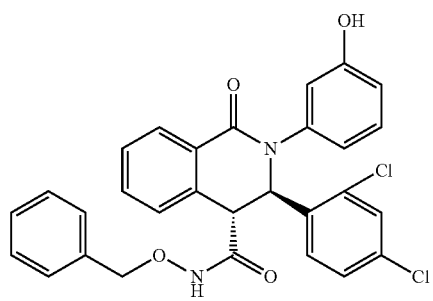 [SMILES: O=C(NOCc1ccccc1)[C@@H]1c2ccccc2C(=O)N(c2cccc(O)c2)[C@H]1c1ccc(Cl)cc1Cl] | racemic mixture |
| --- | --- | --- |
| 214 | 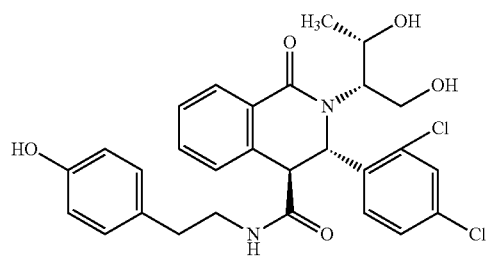 [SMILES: C[C@H](O)[C@H](CO)N1C(=O)c2ccccc2[C@H](C(=O)NCCc2ccc(O)cc2)[C@H]1c1ccc(Cl)cc1Cl] | |
| 215 | 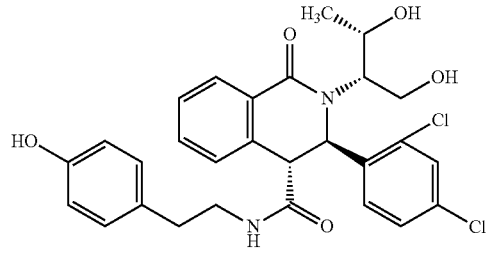 [SMILES: C[C@H](O)[C@H](CO)N1C(=O)c2ccccc2[C@@H](C(=O)NCCc2ccc(O)cc2)[C@@H]1c1ccc(Cl)cc1Cl] | |
TABLE 103-continued
| 216 | 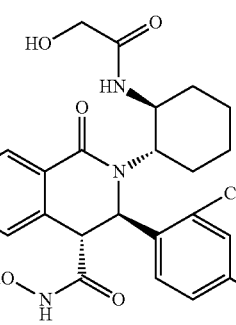 | racemic mixture |
| --- | --- | --- |
| 217 | 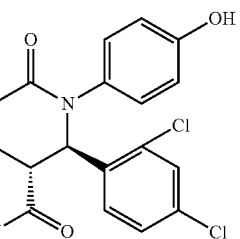 | racemic mixture |

TABLE 104
| 218 | 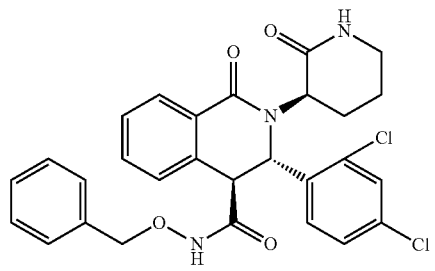 [SMILES: O=C1NCCC[C@H]1N1C(=O)c2ccccc2[C@H](C(=O)NOCc2ccccc2)[C@H]1c1ccc(Cl)cc1Cl] | |
| --- | --- | --- |
| 219 | 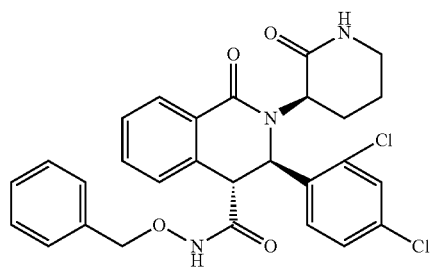 [SMILES: O=C(NOCc1ccccc1)[C@@H]1c2ccccc2C(=O)N([C@@H]2CCCNC2=O)[C@H]1c1ccc(Cl)cc1Cl] | |
| 220 | 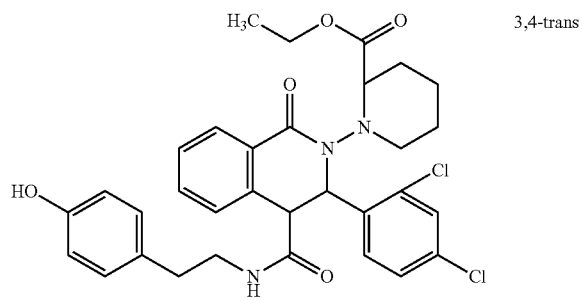 | 3,4-trans |
| 221 | 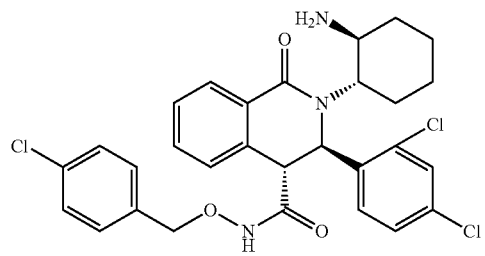 [SMILES: N[C@H]1CCCC[C@@H]1N1C(=O)c2ccccc2[C@@H](C(=O)NOCc2ccc(Cl)cc2)[C@@H]1c1ccc(Cl)cc1Cl] | racemic mixture |
| 222 | 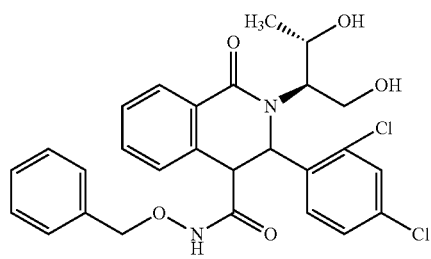 [SMILES: C[C@H](O)[C@@H](CO)N1C(=O)c2ccccc2C(C(=O)NOCc2ccccc2)C1c1ccc(Cl)cc1Cl] | 3,4-trans, diastereomer of Ex223, less polar |

TABLE 105
| 223 | 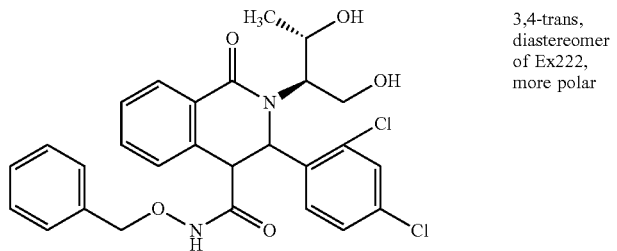 | 3,4-trans, diastereomer of Ex222, more polar |
| --- | --- | --- |
| 224 | 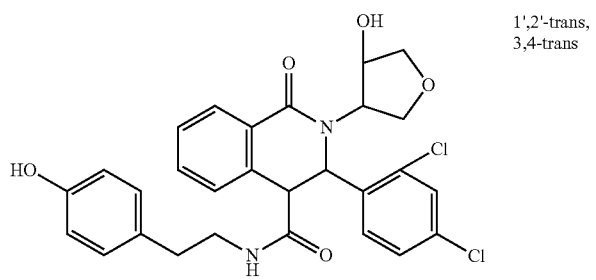 | 1',2'-trans, 3,4-trans |
| 225 | 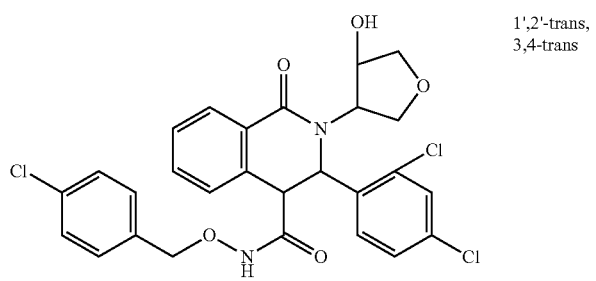 | 1',2'-trans, 3,4-trans |
| 226 | 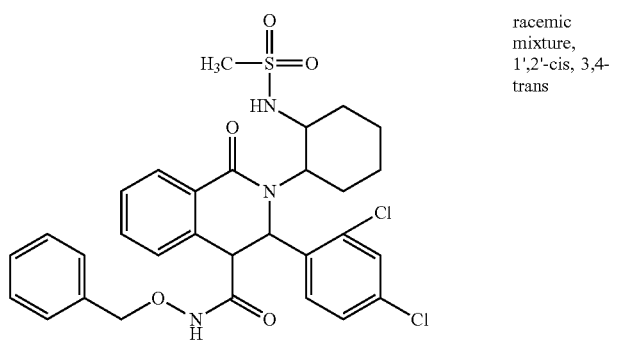 | racemic mixture, 1',2'-cis, 3,4-trans |
| 227 | 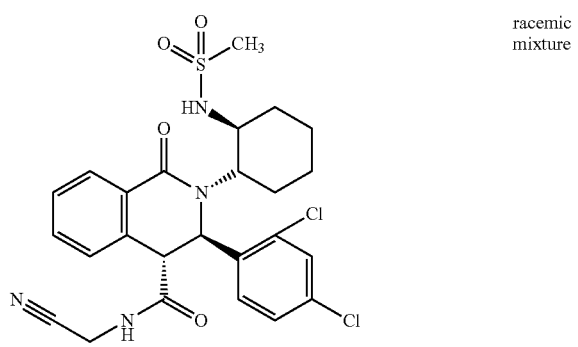 | racemic mixture |

TABLE 106
| 228 | 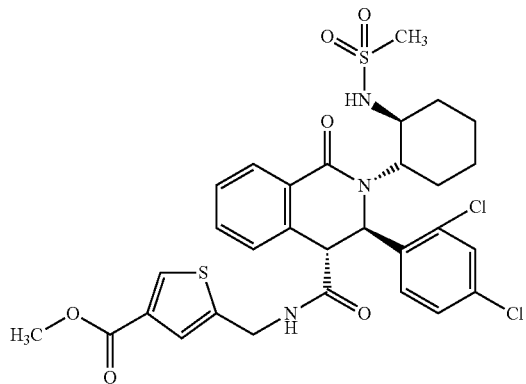 | racemic mixture |
| 229 | 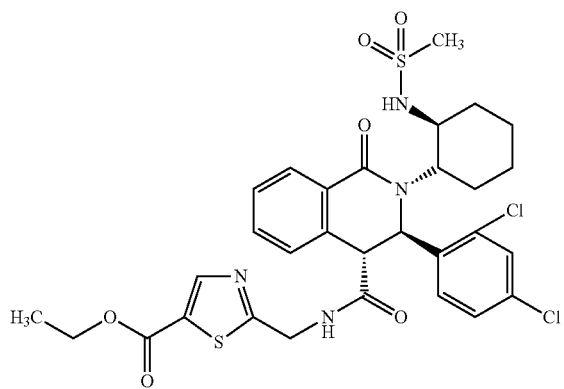 | racemic mixture |
| 230 | 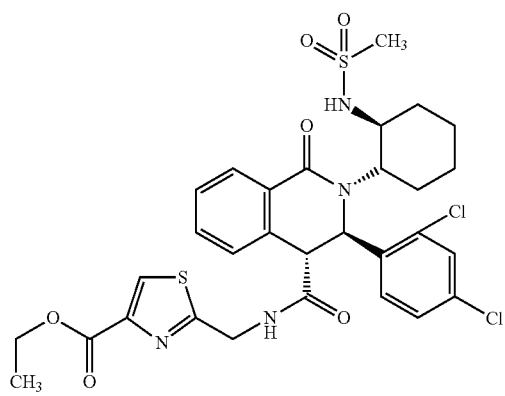 | racemic mixture |
| 231 | 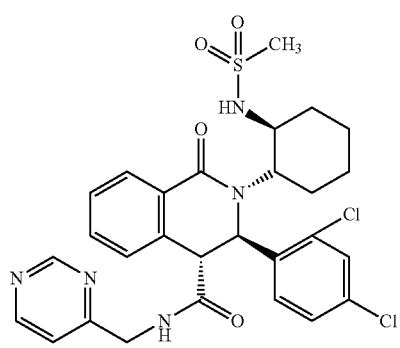 | racemic mixture |

TABLE 107
| | | |
|---|---|---|
| 232 | 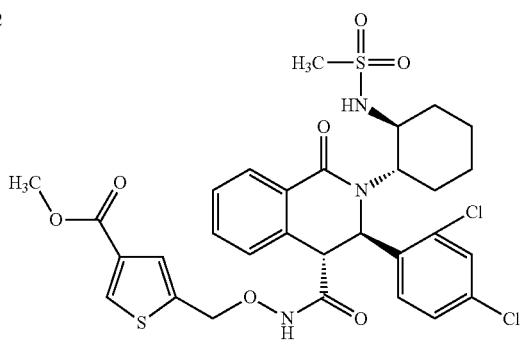 | racemic mixture |
| 233 | 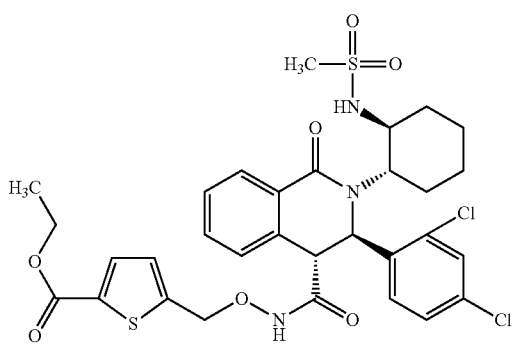 [SMILES: CCOC(=O)c1ccc(CONC(=O)[C@@H]2c3ccccc3C(=O)N([C@H]3CCCC[C@@H]3NS(C)(=O)=O)[C@H]2c2ccc(Cl)cc2Cl)s1] | racemic mixture |
| 234 | 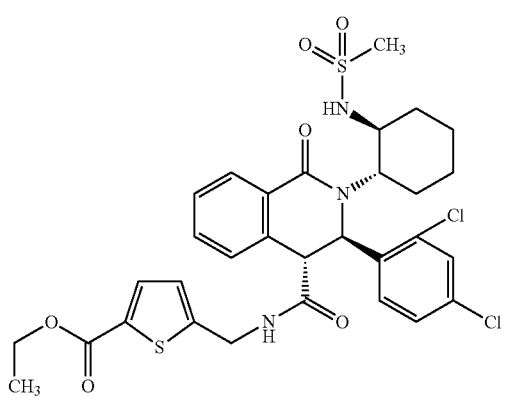 [SMILES: CCOC(=O)c1ccc(CNC(=O)[C@@H]2c3ccccc3C(=O)N([C@H]3CCCC[C@@H]3NS(C)(=O)=O)[C@H]2c2ccc(Cl)cc2Cl)s1] | racemic mixture |
| 235 | 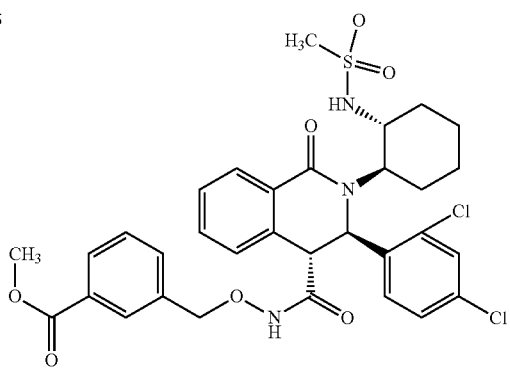 | |

TABLE 108
236 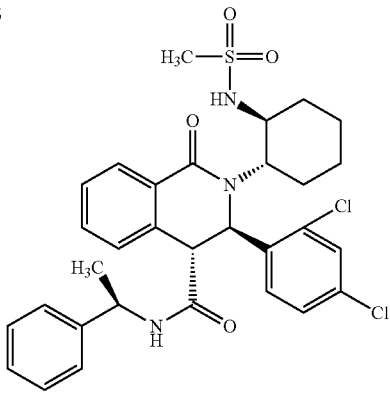
237 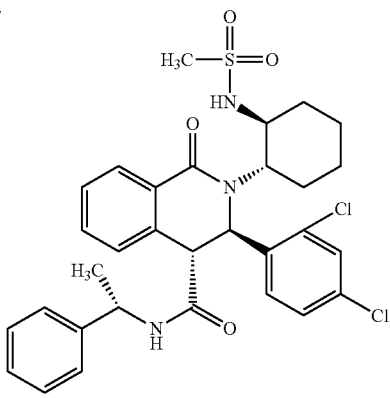
238 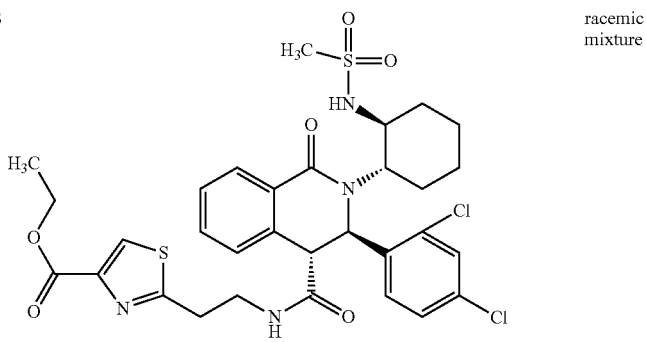   racemic mixture
239 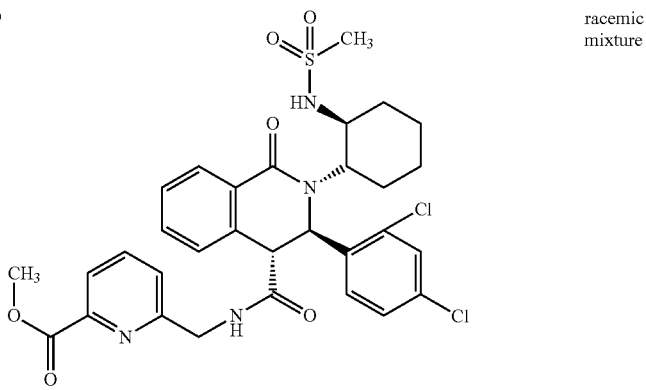   racemic mixture

TABLE 109
| | | |
|---|---|---|
| 240 | 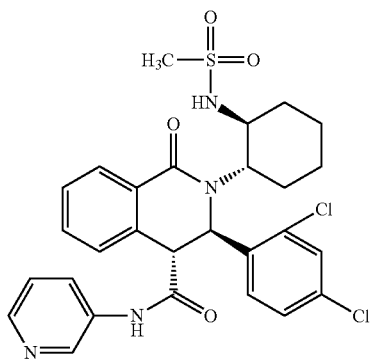 | racemic mixture |
| 241 | 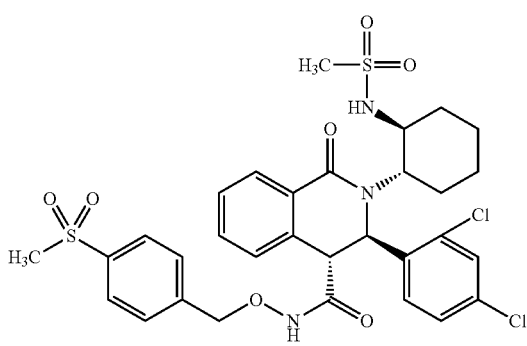 [SMILES: CS(=O)(=O)N[C@H]1CCCC[C@@H]1N1C(=O)c2ccccc2[C@@H](C(=O)NOCc2ccc(S(C)(=O)=O)cc2)[C@@H]1c1ccc(Cl)cc1Cl] | racemic mixture |
| 242 | 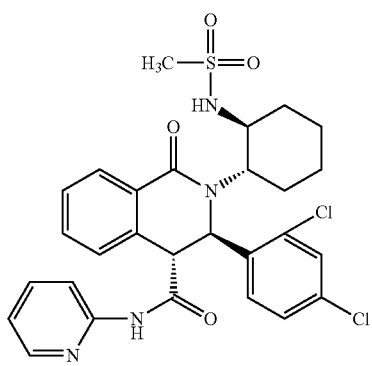 [SMILES: CS(=O)(=O)N[C@H]1CCCC[C@@H]1N1C(=O)c2ccccc2[C@@H](C(=O)Nc2ccccn2)[C@@H]1c1ccc(Cl)cc1Cl] | racemic mixture |
| 243 | 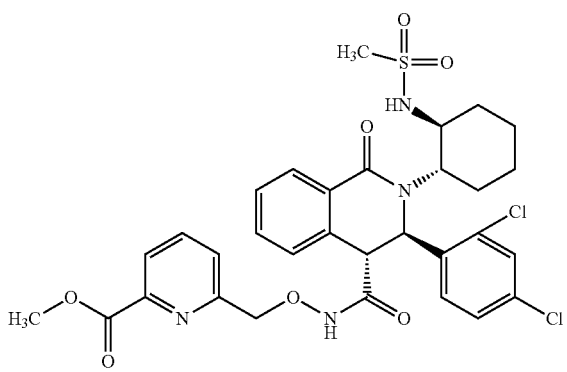 [SMILES: COC(=O)c1cccc(CONC(=O)[C@@H]2c3ccccc3C(=O)N([C@H]3CCCC[C@@H]3NS(C)(=O)=O)[C@H]2c2ccc(Cl)cc2Cl)n1] | racemic mixture |

TABLE 110
| 244 | 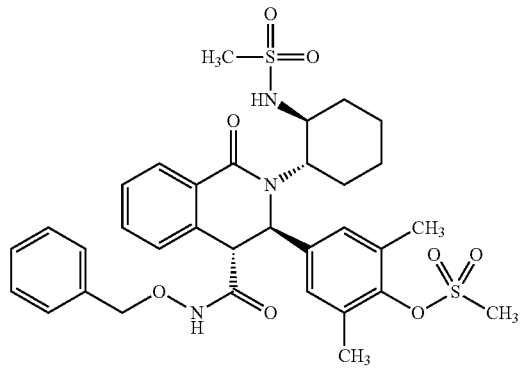 [SMILES: Cc1cc([C@H]2[C@H](C(=O)NOCc3ccccc3)c3ccccc3C(=O)N2[C@H]2CCCC[C@@H]2NS(C)(=O)=O)cc(C)c1OS(C)(=O)=O] | racemic mixture |
| 245 | 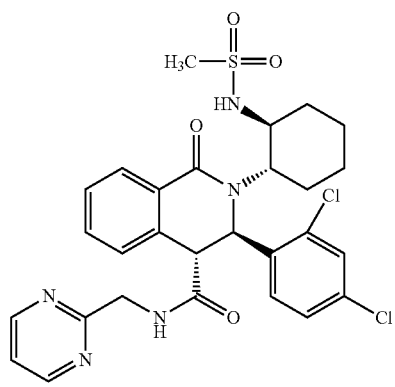 [SMILES: CS(=O)(=O)N[C@H]1CCCC[C@@H]1N1C(=O)c2ccccc2[C@@H](C(=O)NCc2ncccn2)[C@@H]1c1ccc(Cl)cc1Cl] | racemic mixture |
| 246 | 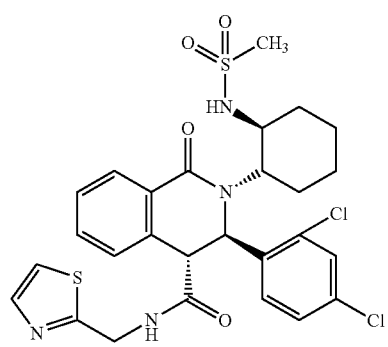 | racemic mixture |
| 247 | 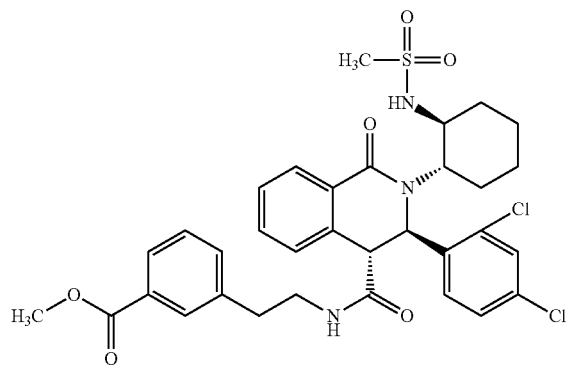 | racemic mixture |

TABLE 111
| | | |
|---|---|---|
| 248 | 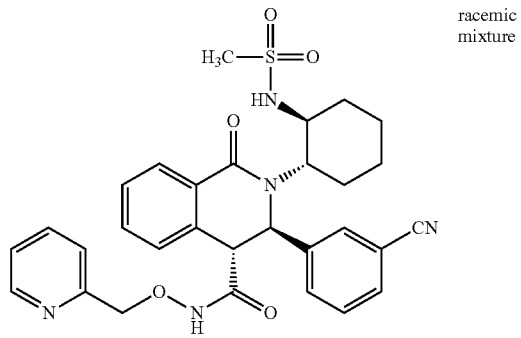 | racemic mixture |
| 249 | 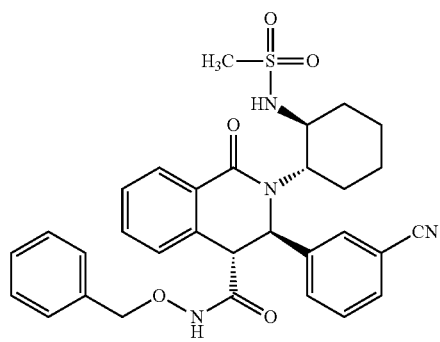 [SMILES: CS(=O)(=O)N[C@H]1CCCC[C@@H]1N1C(=O)c2ccccc2[C@@H](C(=O)NOCc2ccccc2)[C@@H]1c1cccc(C#N)c1] | racemic mixture |
| 250 | 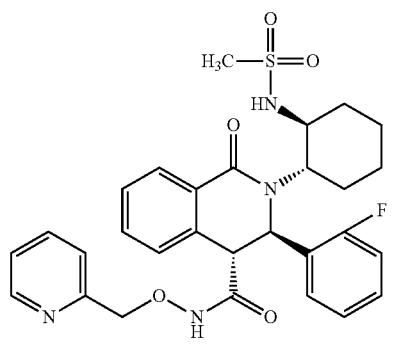 [SMILES: CS(=O)(=O)N[C@H]1CCCC[C@@H]1N1C(=O)c2ccccc2[C@@H](C(=O)NOCc2ccccn2)[C@@H]1c1ccccc1F] | racemic mixture |
| 251 | 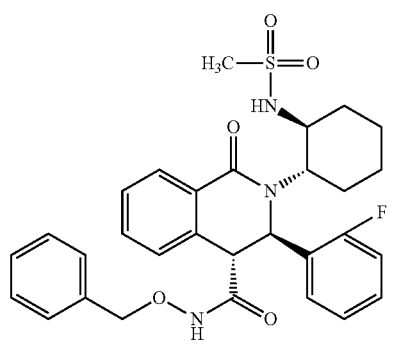 [SMILES: CS(=O)(=O)N[C@H]1CCCC[C@@H]1N1C(=O)c2ccccc2[C@@H](C(=O)NOCc2ccccc2)[C@@H]1c1ccccc1F] | racemic mixture |
TABLE 112
| | | |
|---|---|---|
| 252 | 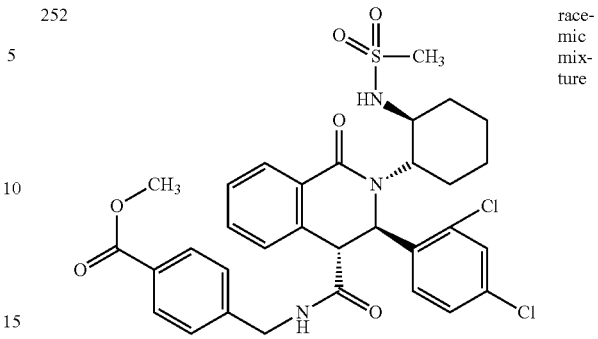 | racemic mixture |
| 253 | 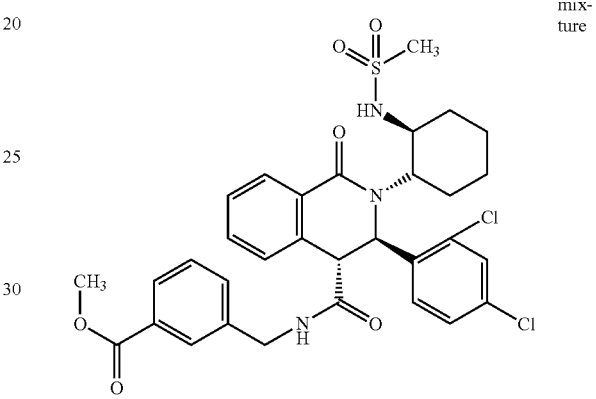 | racemic mixture |
| 254 | 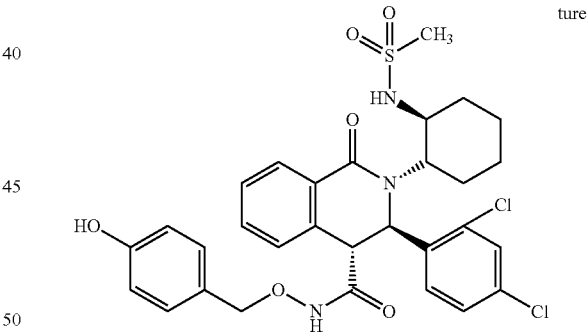 | racemic mixture |
| 255 | 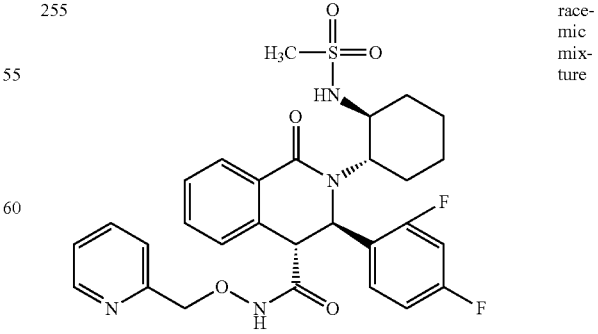 | racemic mixture |

TABLE 113
256 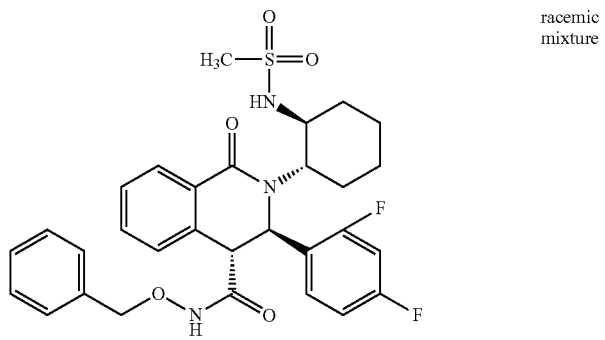 racemic mixture
257 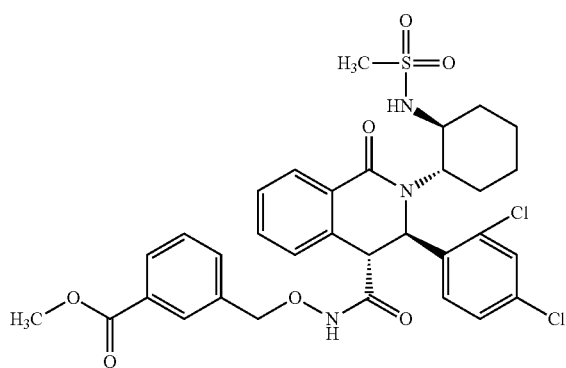 [SMILES: COC(=O)c1cccc(CONC(=O)[C@@H]2c3ccccc3C(=O)N([C@H]3CCCC[C@@H]3NS(C)(=O)=O)[C@H]2c2ccc(Cl)cc2Cl)c1]
258 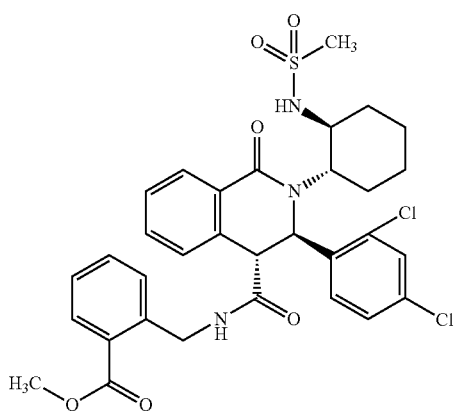 [SMILES: COC(=O)c1ccccc1CNC(=O)[C@@H]1c2ccccc2C(=O)N([C@H]2CCCC[C@@H]2NS(C)(=O)=O)[C@H]1c1ccc(Cl)cc1Cl] racemic mixture
259 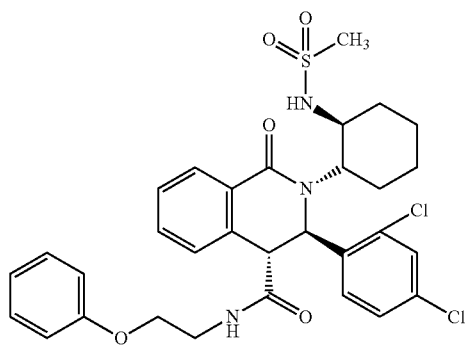 racemic mixture TABLE 114
| 260 | 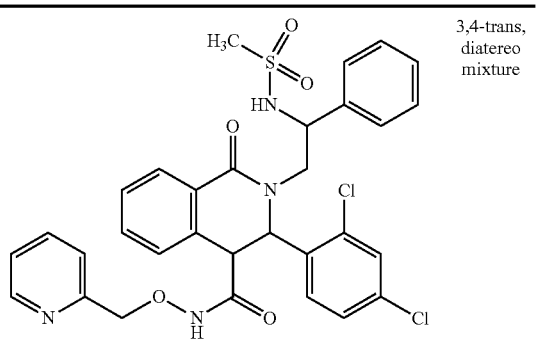 | 3,4-trans, diastereo mixture |
| --- | --- | --- |
| 261 | 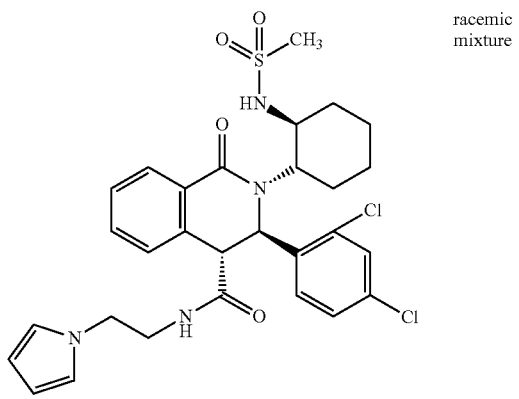 | racemic mixture |
TABLE 114-continued
| 262 | 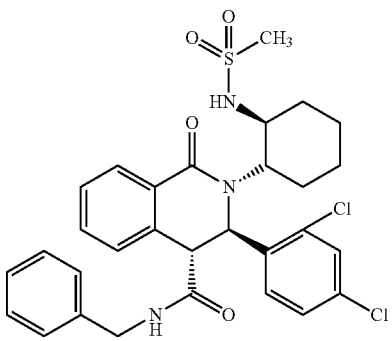 | racemic mixture |
| --- | --- | --- |
| 263 | 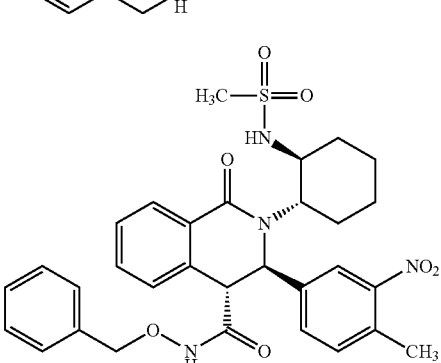 | racemic mixture |
TABLE 115
| 264 | 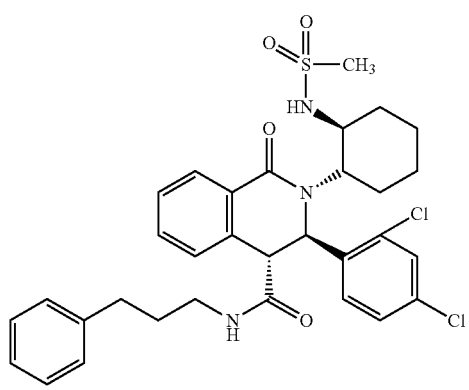 | racemic mixture |
| --- | --- | --- |
| 265 | 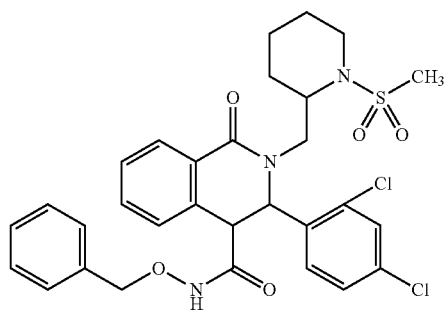 [SMILES: CS(=O)(=O)N1CCCCC1CN1C(=O)c2ccccc2C(C(=O)NOCc2ccccc2)C1c1ccc(Cl)cc1Cl] | 3,4-trans, diastereomer of Ex 266, less polar |

TABLE 115-continued
| | | |
|---|---|---|
| 266 | 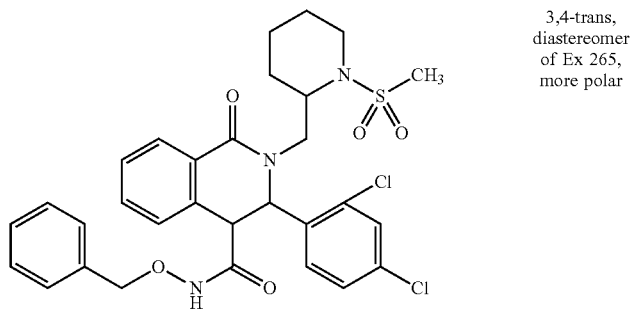 | 3,4-trans, diastereomer of Ex 265, more polar |
| 267 | 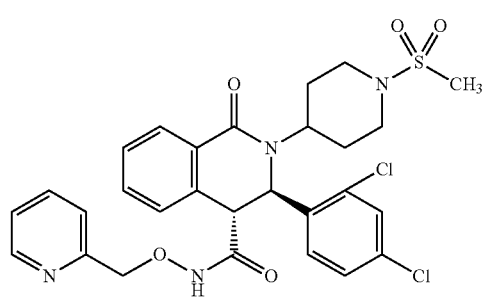 [SMILES: CS(=O)(=O)N1CCC(N2C(=O)c3ccccc3[C@@H](C(=O)NOCc3ccccn3)[C@@H]2c2ccc(Cl)cc2Cl)CC1] | racemic mixture |
| 268 | 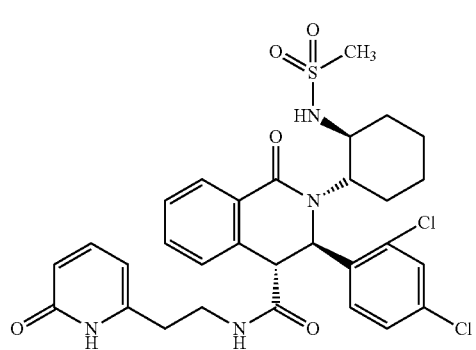 | racemic mixture |
TABLE 116
| | | |
|---|---|---|
| 269 | 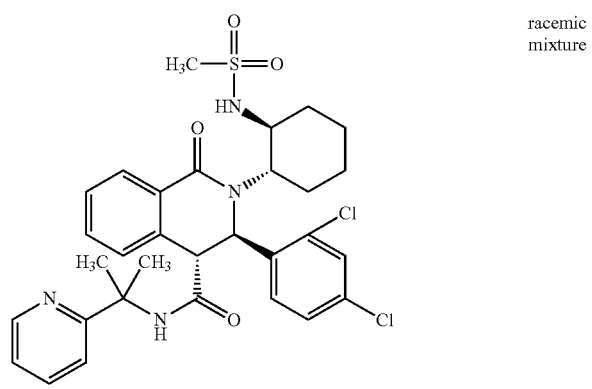 | racemic mixture |

TABLE 116-continued
| | | |
|---|---|---|
| 270 | 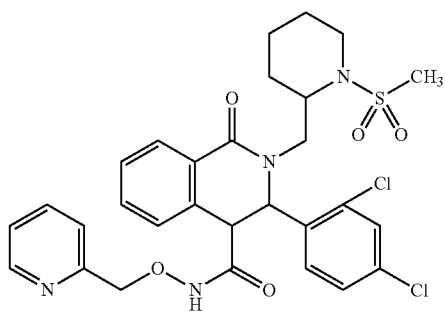 | 3,4-trans |
| 271 | 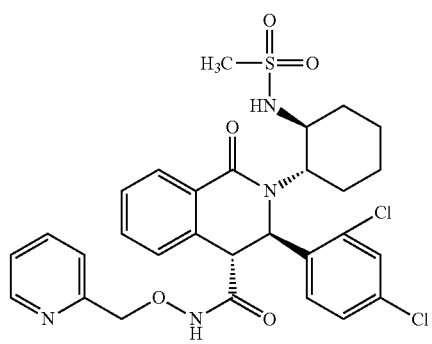 [SMILES: CS(=O)(=O)N[C@H]1CCCC[C@@H]1N1C(=O)c2ccccc2[C@@H](C(=O)NOCc2ccccn2)[C@@H]1c1ccc(Cl)cc1Cl] | diastereomer of Ex 275, more polar |
| 272 | 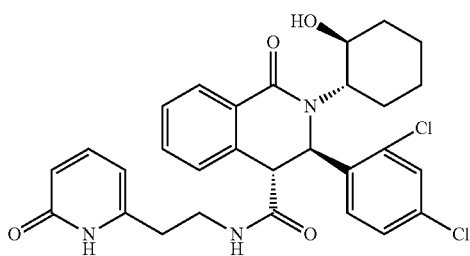 [SMILES: O=C(NCCc1cccc(=O)[nH]1)[C@@H]1c2ccccc2C(=O)N([C@H]2CCCC[C@@H]2O)[C@H]1c1ccc(Cl)cc1Cl] | racemic mixture |
TABLE 117
| | | |
|---|---|---|
| 273 | 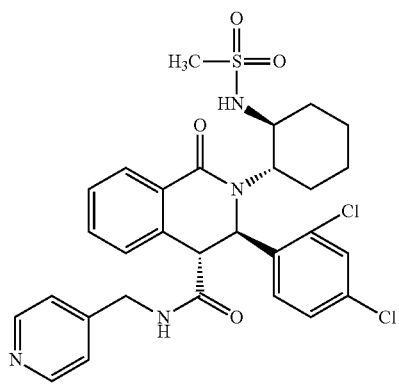 [SMILES: CS(=O)(=O)N[C@H]1CCCC[C@@H]1N1C(=O)c2ccccc2[C@@H](C(=O)NCc2ccncc2)[C@@H]1c1ccc(Cl)cc1Cl] | racemic mixture |

TABLE 117-continued
| 274 | 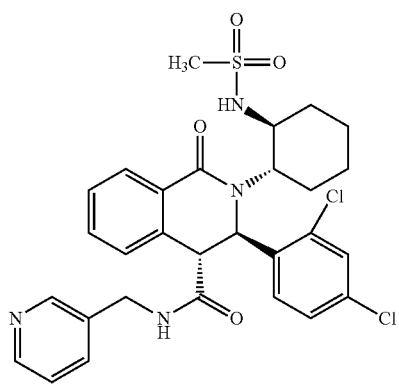 [SMILES: CS(=O)(=O)N[C@H]1CCCC[C@@H]1N1C(=O)c2ccccc2[C@@H](C(=O)NCc2cccnc2)[C@@H]1c1ccc(Cl)cc1Cl] | racemic mixture |
| --- | --- | --- |
| 275 | 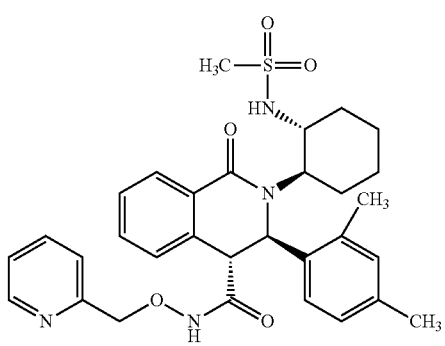 [SMILES: Cc1ccc([C@H]2[C@H](C(=O)NOCc3ccccn3)c3ccccc3C(=O)N2[C@@H]2CCCC[C@H]2NS(C)(=O)=O)c(C)c1] | diastereomer of Ex 271, less polar |
| 276 |  | racemic mixture |
| 277 |  | 2HCl |
TABLE 118
| 278 | 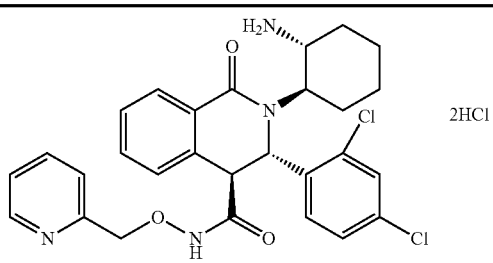 | 2HCl |
| --- | --- | --- |

TABLE 118-continued
| | | |
|---|---|---|
| 279 | 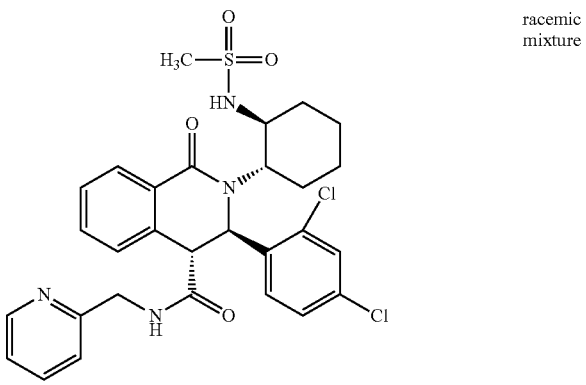 | racemic mixture |
| 280 | 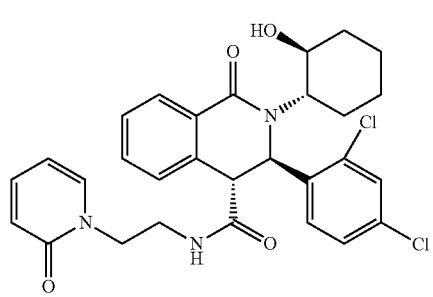 [SMILES: O=C(NCCn1ccccc1=O)[C@@H]1c2ccccc2C(=O)N([C@H]2CCCC[C@@H]2O)[C@H]1c1ccc(Cl)cc1Cl] | racemic mixture |
| 281 | 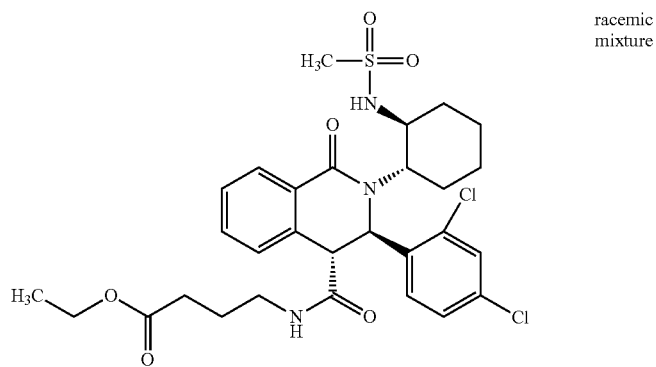 | racemic mixture |
TABLE 119
| | | |
|---|---|---|
| 282 | 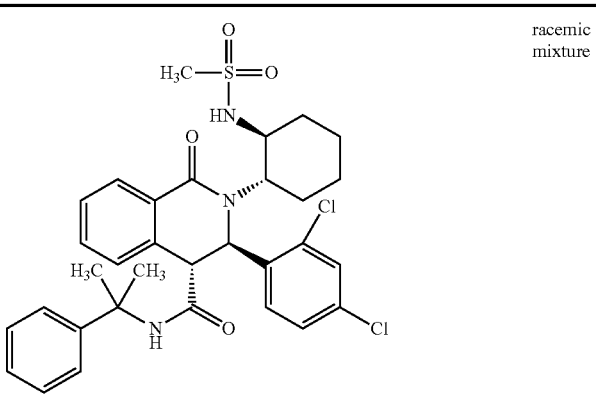 | racemic mixture |

TABLE 119-continued
| 283 | 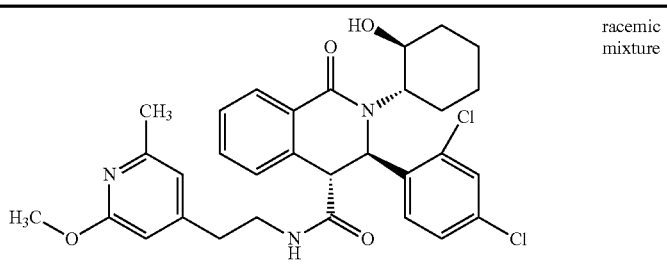 | racemic mixture |
| 284 | 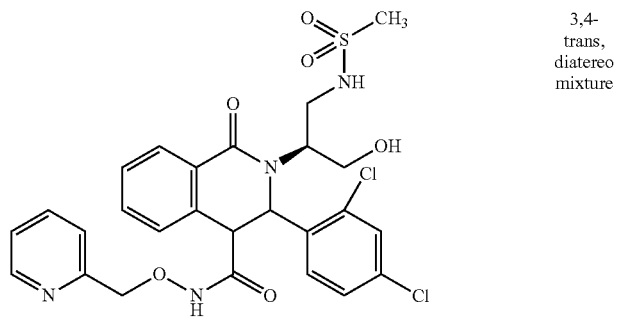 | 3,4-trans, diatereo mixture |
| 285 | 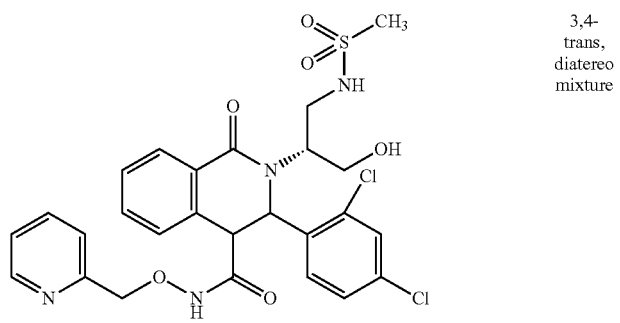 | 3,4-trans, diatereo mixture |
TABLE 120
| 286 | 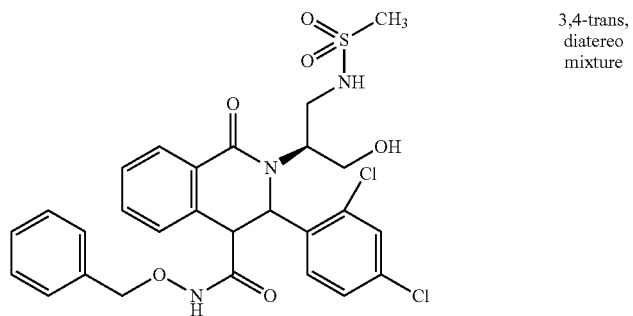 | 3,4-trans, diatereo mixture |
| 287 | 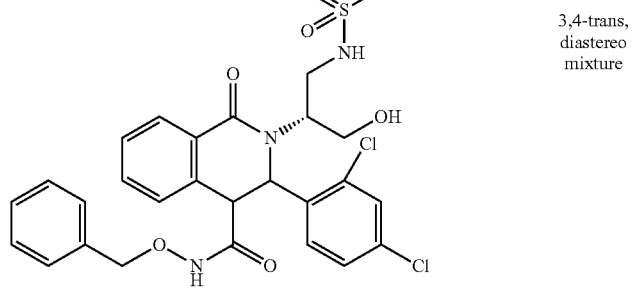 | 3,4-trans, diastereo mixture |

TABLE 120-continued
| | | |
|---|---|---|
| 288 | 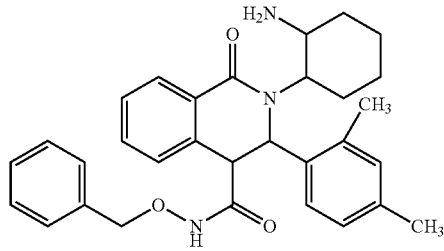 [SMILES: Cc1ccc(C2C(C(=O)NOCc3ccccc3)c3ccccc3C(=O)N2C2CCCCC2N)c(C)c1] | 1',2'-trans, 3,4-trans, diastereo mixture |
| 289 | 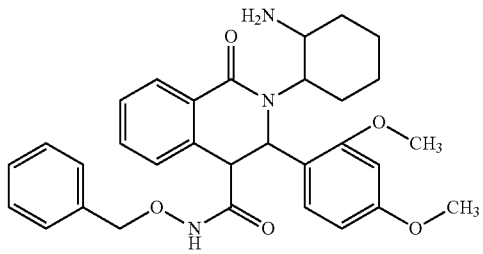 [SMILES: COc1ccc(C2C(C(=O)NOCc3ccccc3)c3ccccc3C(=O)N2C2CCCCC2N)c(OC)c1] | 1',2'-trans, 3,4-trans, diastereomer of Ex 290, more polar |
| 290 | 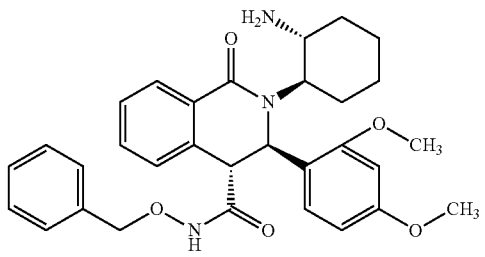 [SMILES: COc1ccc([C@H]2[C@H](C(=O)NOCc3ccccc3)c3ccccc3C(=O)N2[C@@H]2CCCC[C@H]2N)c(OC)c1] | racemic mixture, diastereomer of Ex 289, less polar |
TABLE 121
| | | |
|---|---|---|
| 291 | 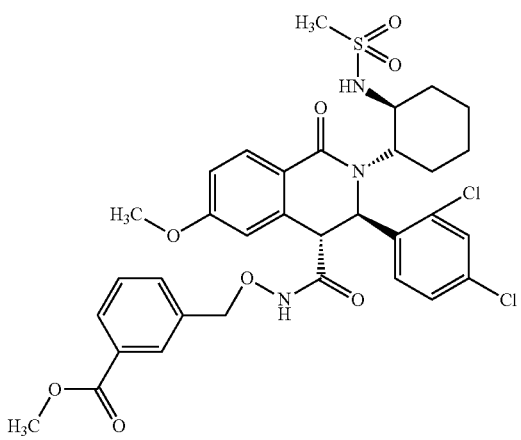 | racemic mixture |
| 292 | 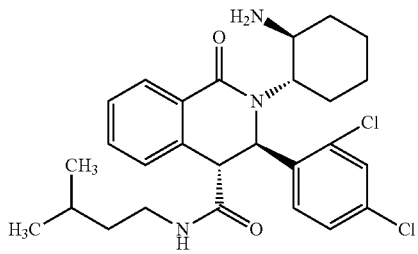 [SMILES: CC(C)CCNC(=O)[C@@H]1c2ccccc2C(=O)N([C@H]2CCCC[C@@H]2N)[C@H]1c1ccc(Cl)cc1Cl] | racemic mixture |

TABLE 121-continued
| | | |
|---|---|---|
| 293 | 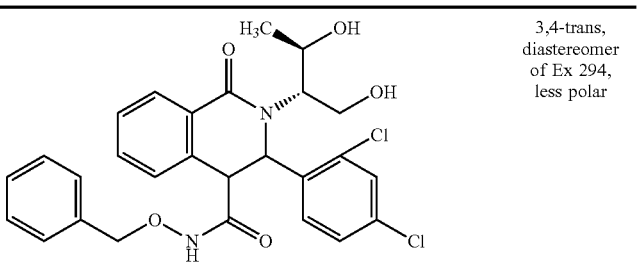 | 3,4-trans, diastereomer of Ex 294, less polar |
| 294 | 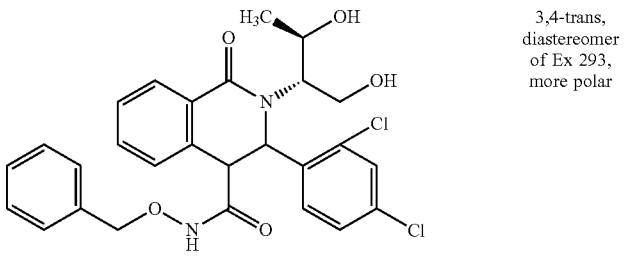 | 3,4-trans, diastereomer of Ex 293, more polar |
TABLE 122
| | | |
|---|---|---|
| 295 | 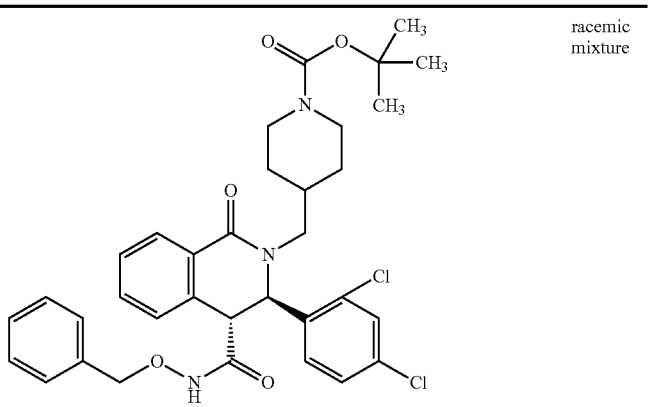 | racemic mixture |
| 296 | 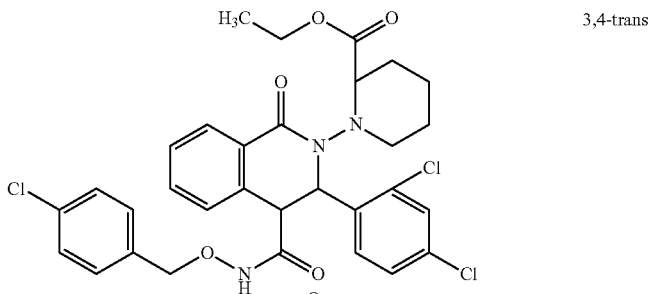 | 3,4-trans |
| 297 | 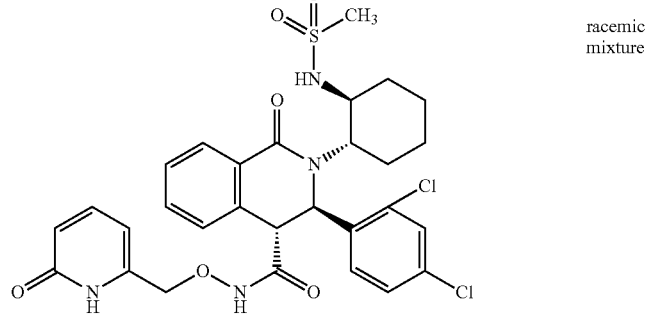 | racemic mixture |

TABLE 122-continued
| 298 | 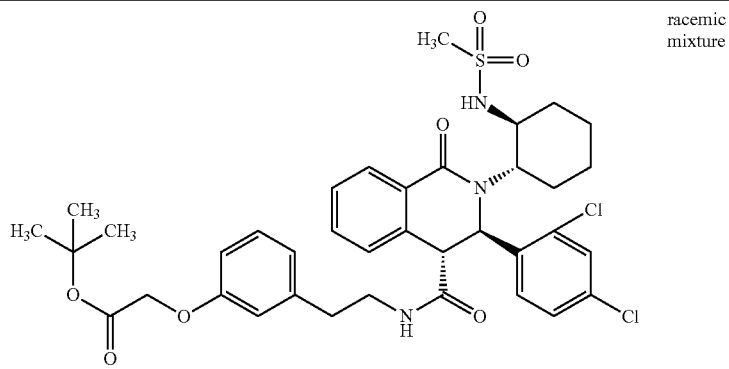 | racemic mixture |
TABLE 123
| 299 | 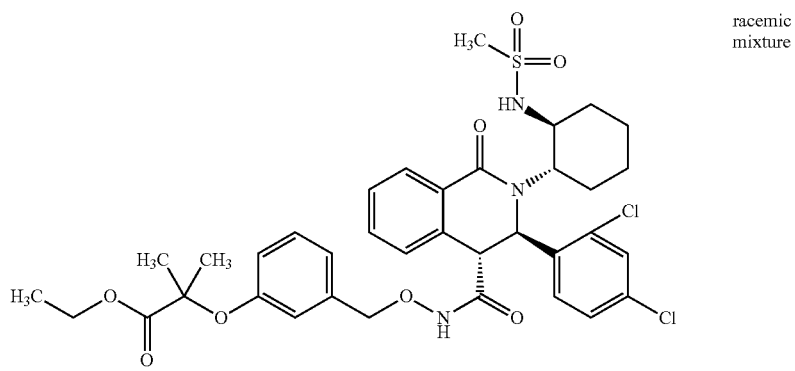 | racemic mixture |
| 300 | 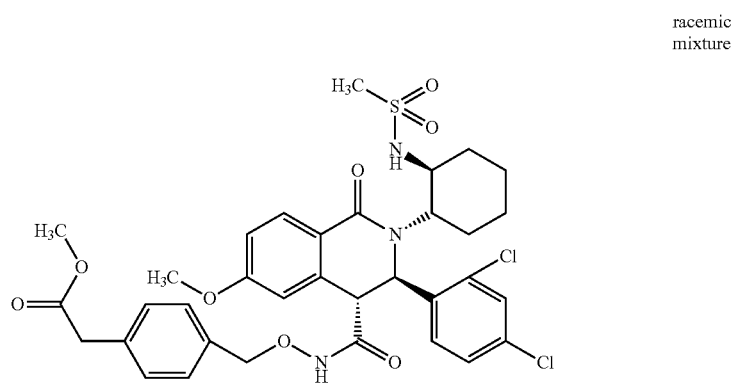 | racemic mixture |
| 301 | 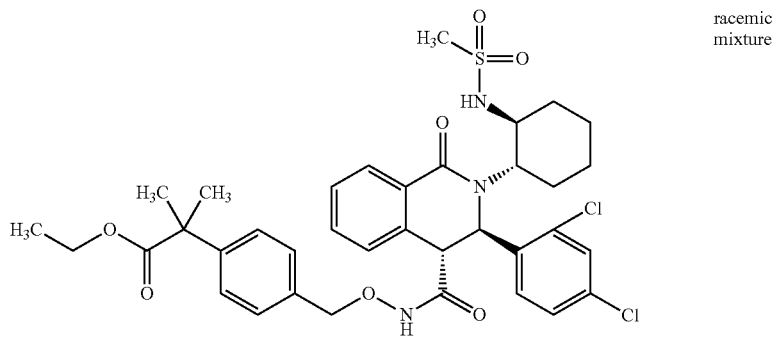 | racemic mixture |

TABLE 123-continued
| | | |
|---|---|---|
| 302 | 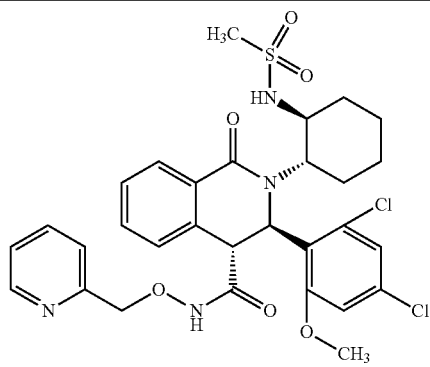 | racemic mixture, diastereomer of Ex 306, less polar |
TABLE 124
| | | |
|---|---|---|
| 303 | 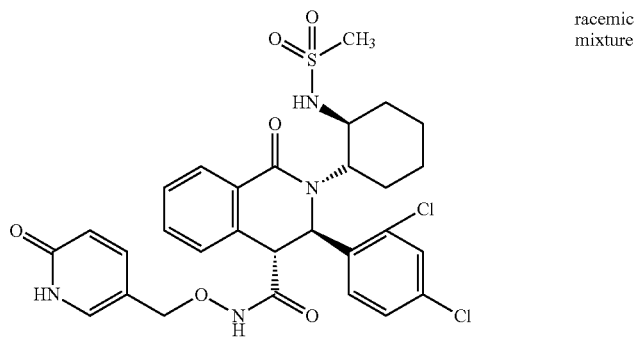 | racemic mixture |
| 304 | 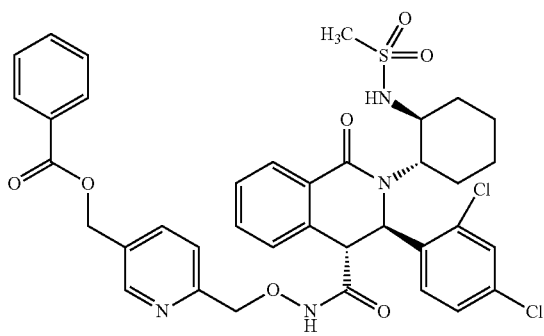 [SMILES: CS(=O)(=O)N[C@H]1CCCC[C@@H]1N1C(=O)c2ccccc2[C@@H](C(=O)NOCc2ccc(COC(=O)c3ccccc3)cn2)[C@@H]1c1ccc(Cl)cc1Cl] | racemic mixture |
| 305 | 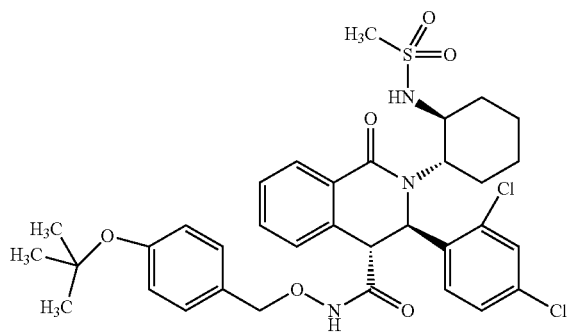 [SMILES: CC(C)(C)Oc1ccc(CONC(=O)[C@@H]2c3ccccc3C(=O)N([C@H]3CCCC[C@@H]3NS(C)(=O)=O)[C@H]2c2ccc(Cl)cc2Cl)cc1] | racemic mixture |

TABLE 124-continued
| | | |
|---|---|---|
| 306 | 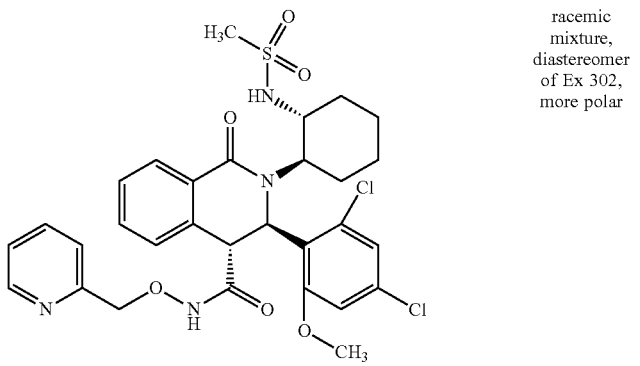 | racemic mixture, diastereomer of Ex 302, more polar |
TABLE 125
| | | |
|---|---|---|
| 307 | 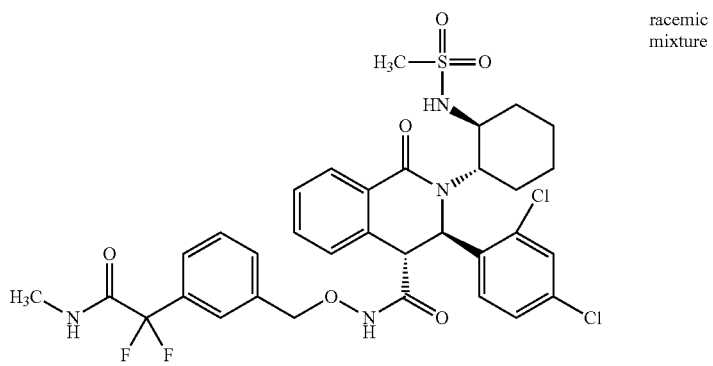 | racemic mixture |
| 308 | 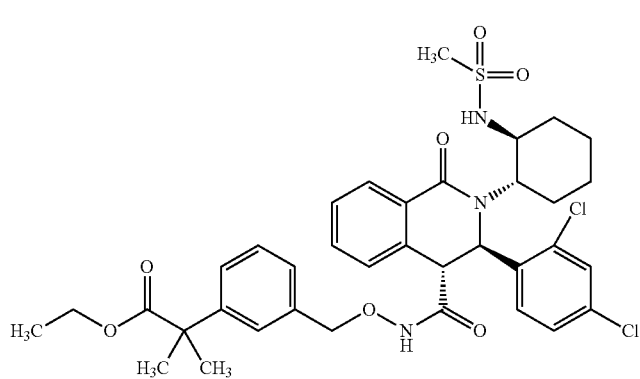 [SMILES: CCOC(=O)C(C)(C)c1cccc(CONC(=O)[C@@H]2c3ccccc3C(=O)N([C@H]3CCCC[C@@H]3NS(C)(=O)=O)[C@H]2c2ccc(Cl)cc2Cl)c1] | racemic mixture |
| 309 | 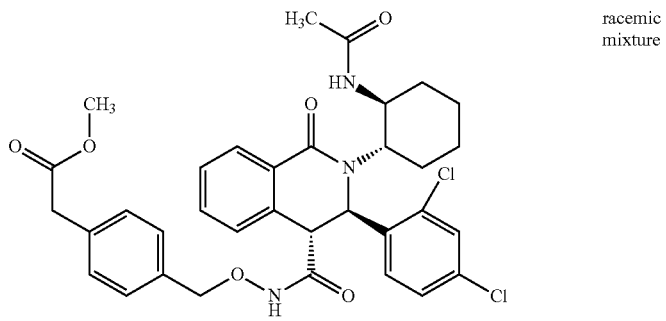 | racemic mixture |

TABLE 125-continued
| | | |
|---|---|---|
| 310 | 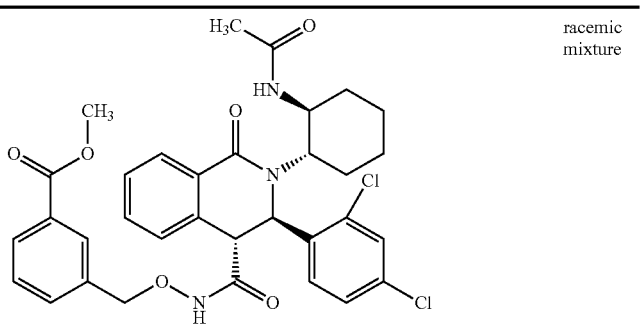 | racemic mixture |
TABLE 126
| | | |
|---|---|---|
| 311 | 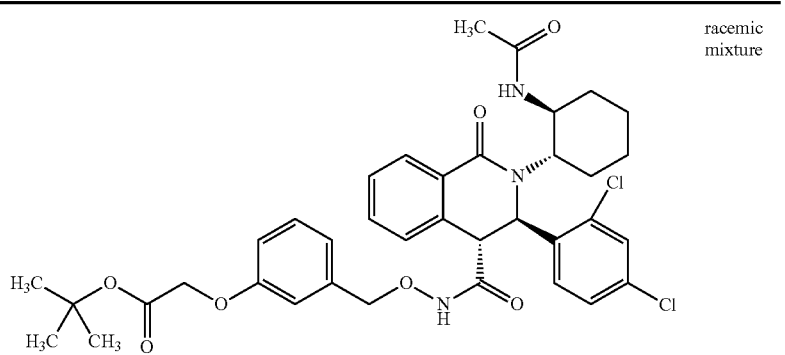 | racemic mixture |
| 312 | 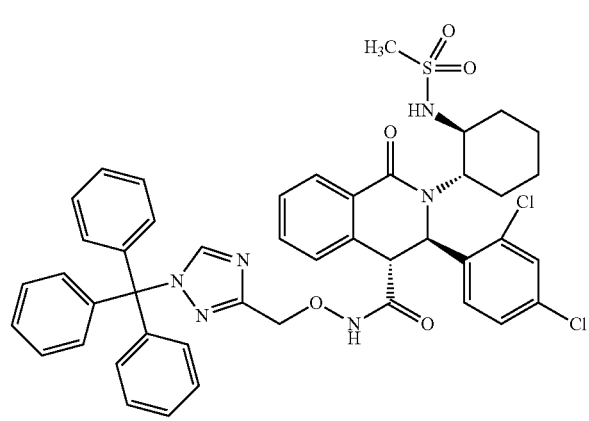 [SMILES: CS(=O)(=O)N[C@H]1CCCC[C@@H]1N1C(=O)c2ccccc2[C@@H](C(=O)NOCc2ncn(C(c3ccccc3)(c3ccccc3)c3ccccc3)n2)[C@@H]1c1ccc(Cl)cc1Cl] | racemic mixture |
| 313 | 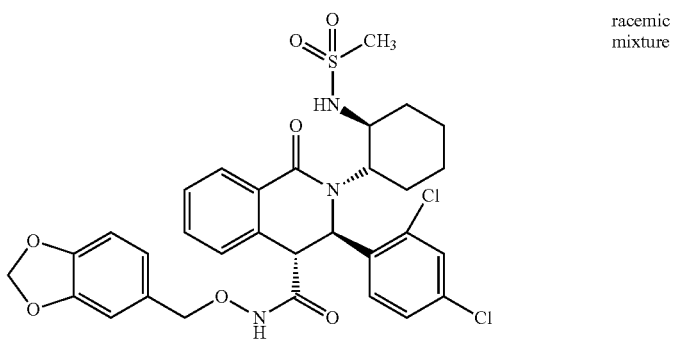 | racemic mixture |

TABLE 126-continued
| 314 | 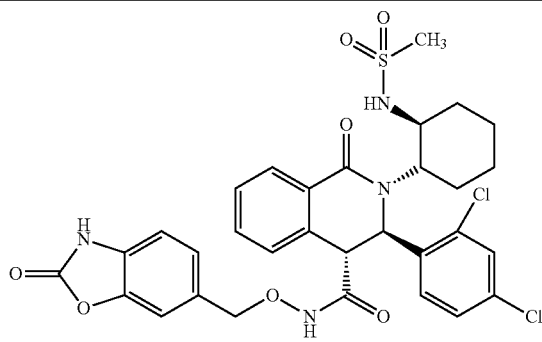 | racemic mixture |
TABLE 127
| 315 | 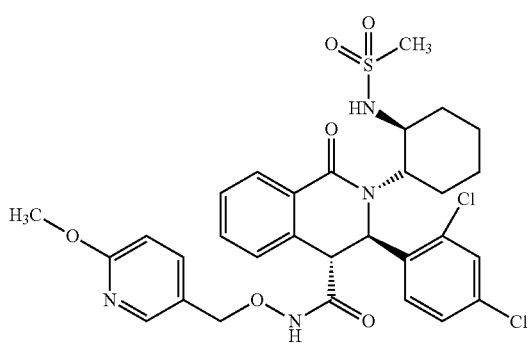 | racemic mixture |
| 316 | 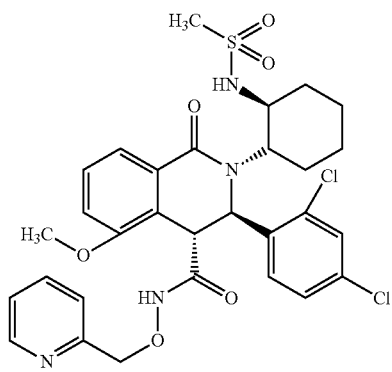 | racemic mixture |
| 317 | 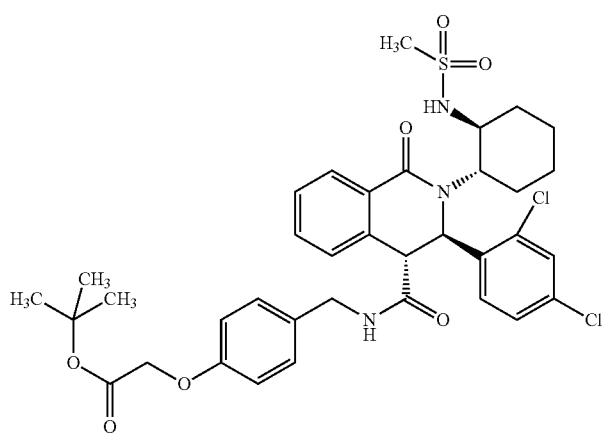 [SMILES: CC(C)(C)OC(=O)COc1ccc(CNC(=O)[C@@H]2c3ccccc3C(=O)N([C@H]3CCCC[C@@H]3NS(C)(=O)=O)[C@H]2c2ccc(Cl)cc2Cl)cc1] | racemic mixture |

TABLE 127-continued
| | | |
|---|---|---|
| 318 | 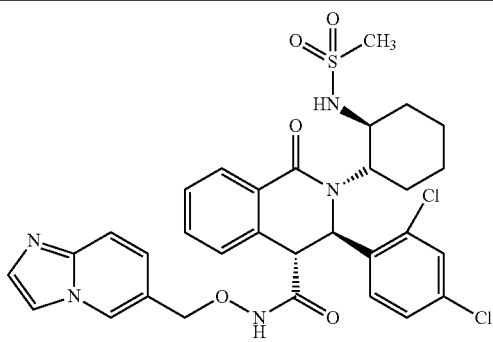 | racemic mixture |
TABLE 128
| | | |
|---|---|---|
| 319 | 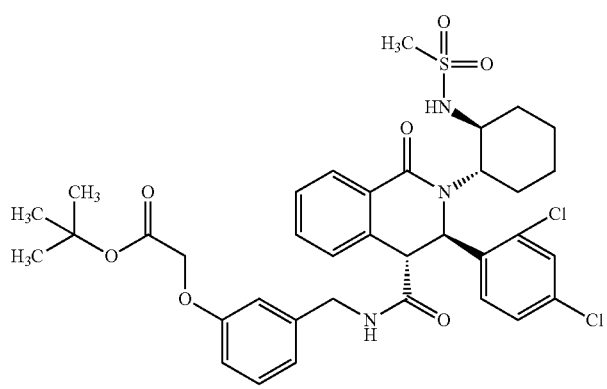 [SMILES: CC(C)(C)OC(=O)COc1cccc(CNC(=O)[C@@H]2c3ccccc3C(=O)N([C@H]3CCCC[C@@H]3NS(C)(=O)=O)[C@H]2c2ccc(Cl)cc2Cl)c1] | racemic mixture |
| 320 | 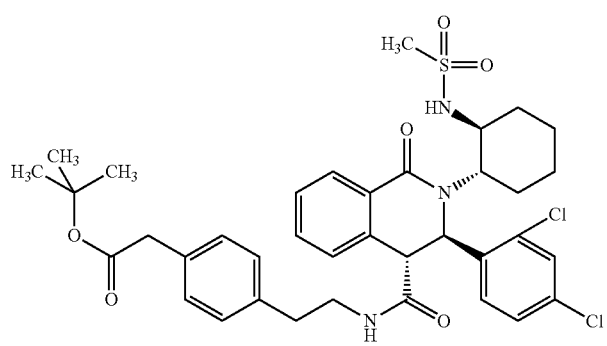 [SMILES: CC(C)(C)OC(=O)Cc1ccc(CCNC(=O)[C@@H]2c3ccccc3C(=O)N([C@H]3CCCC[C@@H]3NS(C)(=O)=O)[C@H]2c2ccc(Cl)cc2Cl)cc1] | racemic mixture |
| 321 | 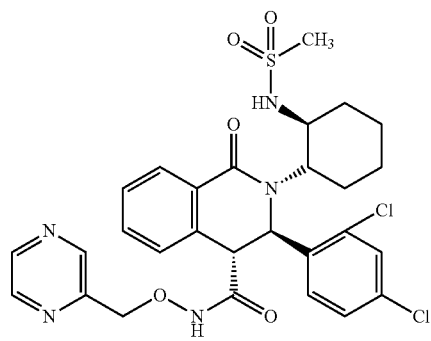 | racemic mixture |

TABLE 128-continued
| 322 | 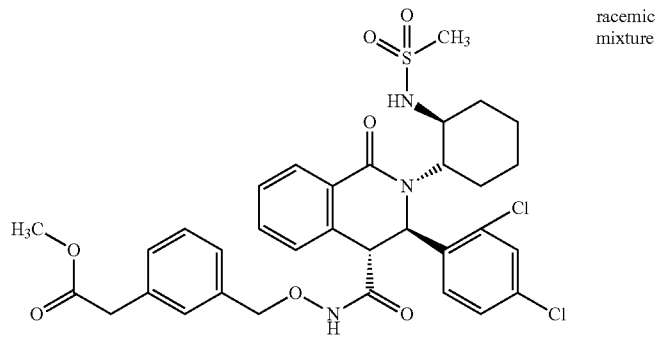 | racemic mixture |
TABLE 129
| 323 | 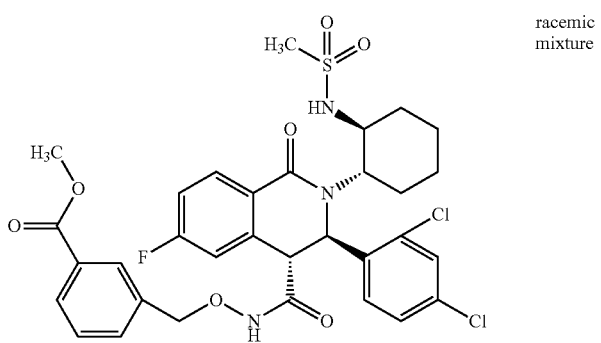 | racemic mixture |
| 324 | 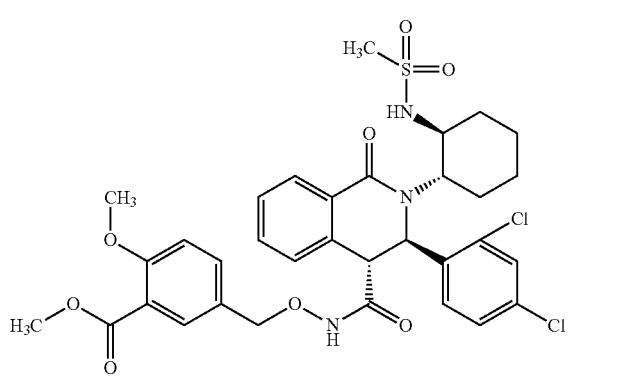 [SMILES: COC(=O)c1cc(CONC(=O)[C@@H]2c3ccccc3C(=O)N([C@H]3CCCC[C@@H]3NS(C)(=O)=O)[C@H]2c2ccc(Cl)cc2Cl)ccc1OC] | racemic mixture |
| 325 | 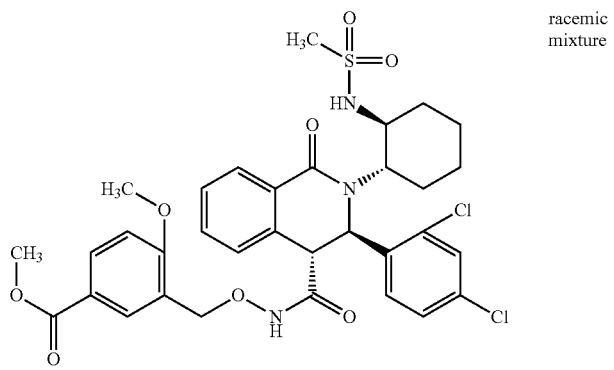 | racemic mixture |

TABLE 129-continued
| 326 | 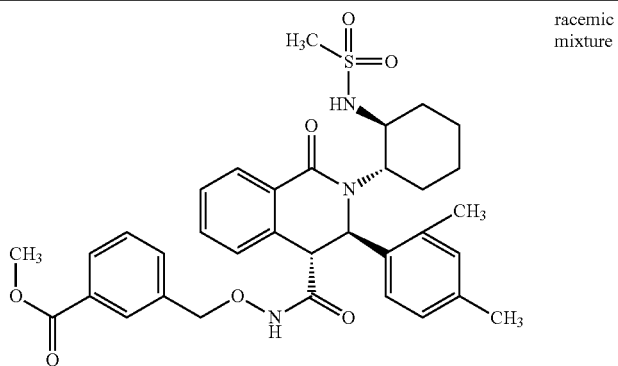 | racemic mixture |
TABLE 130
| 327 | 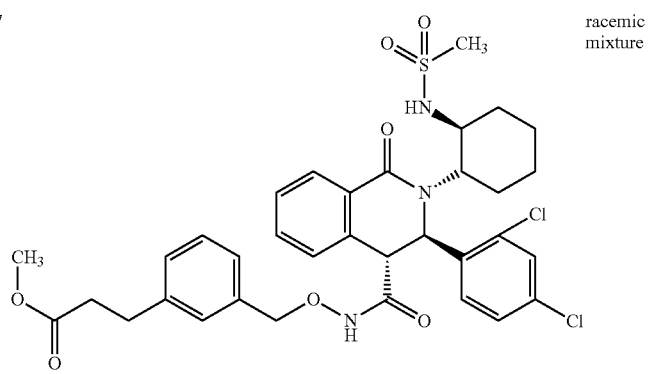 | racemic mixture |
| 328 | 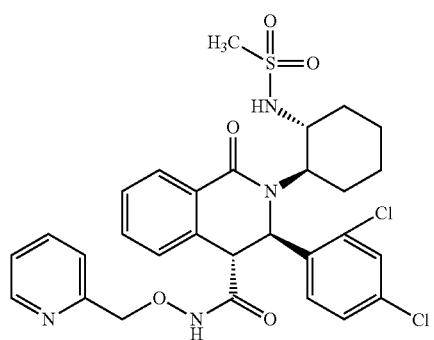 [SMILES: CS(=O)(=O)N[C@@H]1CCCC[C@H]1N1C(=O)c2ccccc2[C@@H](C(=O)NOCc2ccccn2)[C@@H]1c1ccc(Cl)cc1Cl] | |
| 329 | 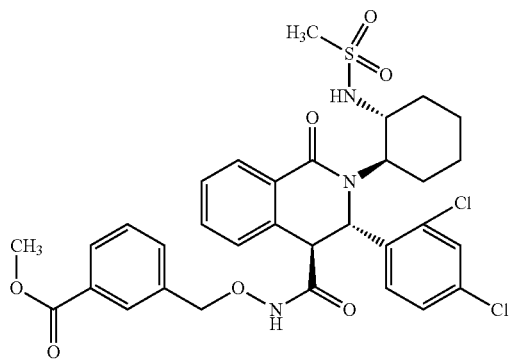 [SMILES: COC(=O)c1cccc(CONC(=O)[C@H]2c3ccccc3C(=O)N([C@@H]3CCCC[C@H]3NS(C)(=O)=O)[C@@H]2c2ccc(Cl)cc2Cl)c1] | |

TABLE 130-continued
330 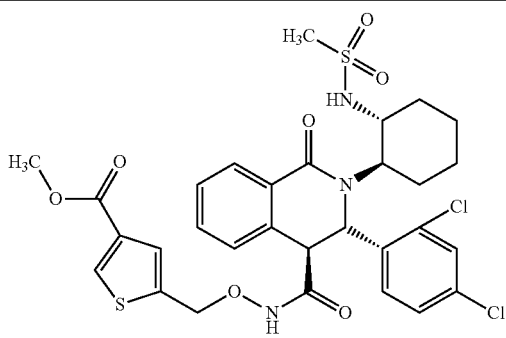
TABLE 131
331 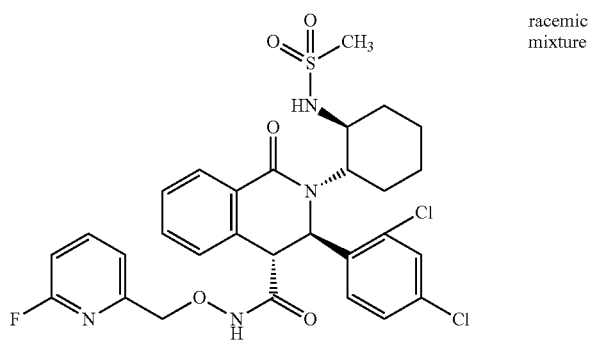 racemic mixture
332 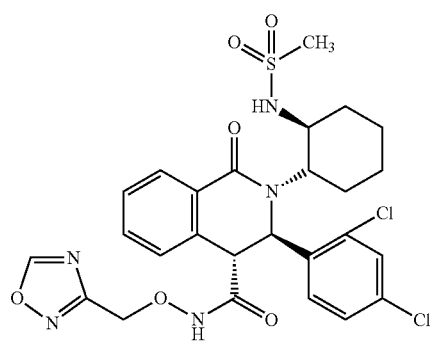
333 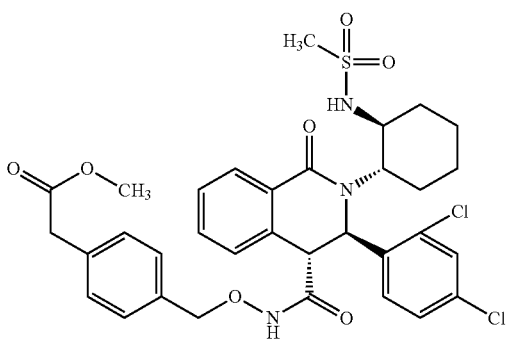 [SMILES: COC(=O)Cc1ccc(CONC(=O)[C@@H]2c3ccccc3C(=O)N([C@H]3CCCC[C@@H]3NS(C)(=O)=O)[C@H]2c2ccc(Cl)cc2Cl)cc1]

TABLE 131-continued
| 334 | 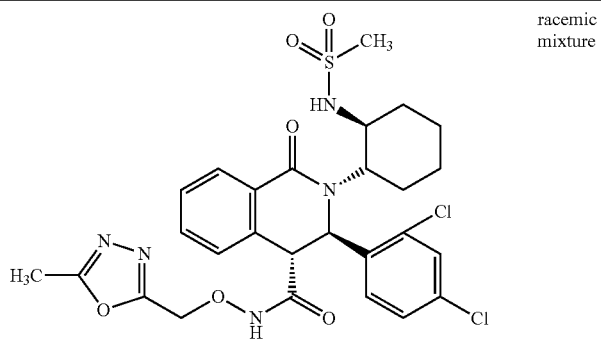 | racemic mixture |
TABLE 132
| 335 | 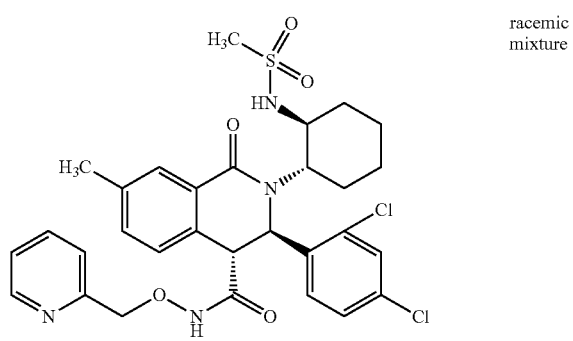 | racemic mixture |
| 336 | 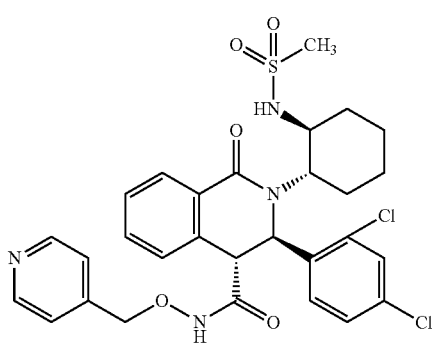 [SMILES: CS(=O)(=O)N[C@H]1CCCC[C@@H]1N1C(=O)c2ccccc2[C@@H](C(=O)NOCc2ccncc2)[C@@H]1c1ccc(Cl)cc1Cl] | racemic mixture |
| 337 | 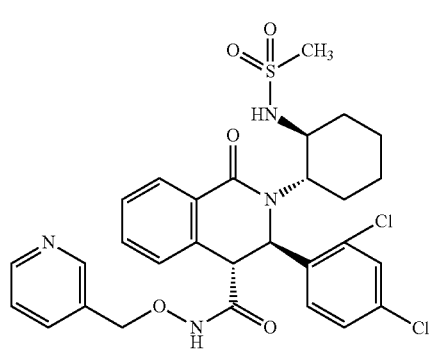 [SMILES: CS(=O)(=O)N[C@H]1CCCC[C@@H]1N1C(=O)c2ccccc2[C@@H](C(=O)NOCc2cccnc2)[C@@H]1c1ccc(Cl)cc1Cl] | racemic mixture |

TABLE 132-continued
| 338 | 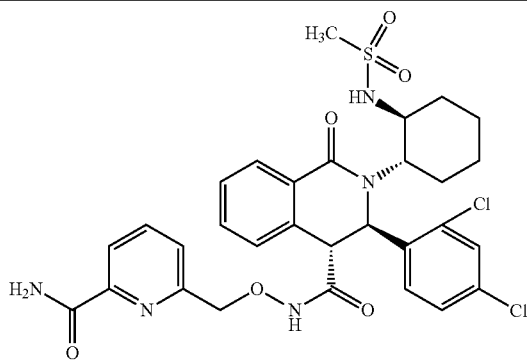 | racemic mixture |
TABLE 133
| 339 | 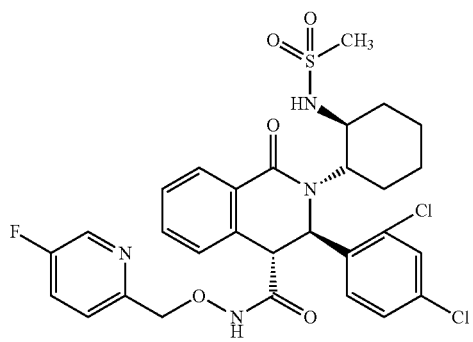 | racemic mixture |
| 340 | 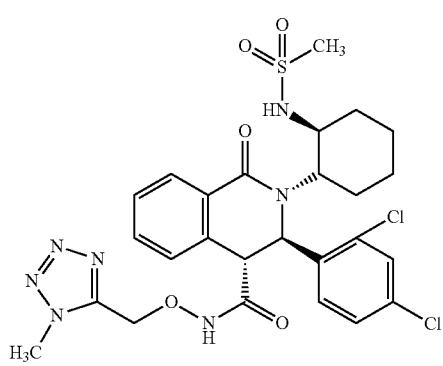 | racemic mixture |
| 341 | 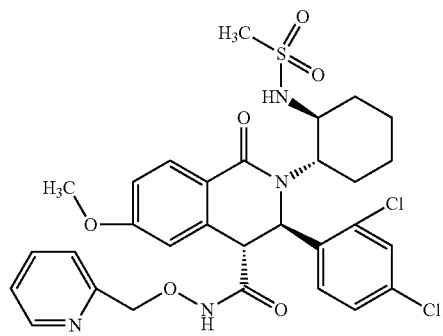 [SMILES: COc1ccc2c(c1)[C@@H](C(=O)NOCc1ccccn1)[C@H](c1ccc(Cl)cc1Cl)N([C@H]1CCCC[C@@H]1NS(C)(=O)=O)C2=O] | racemic mixture |

TABLE 133-continued
| 342 | 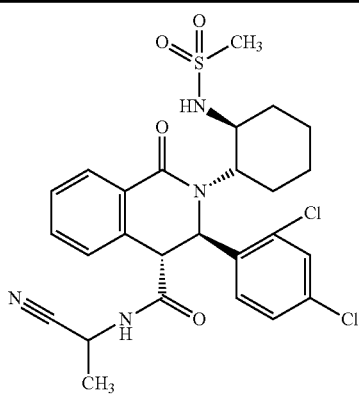 | chiral compound, diastereomer of Ex 143, less polar |
TABLE 134
| 343 | 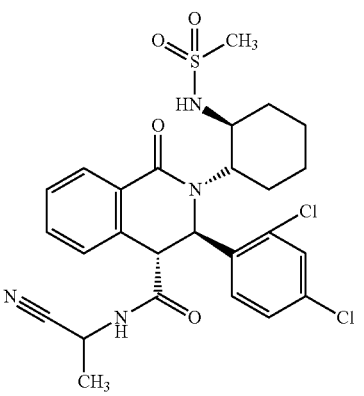 | chiral compound diastereomer of Ex 342, more polar |
| 344 | 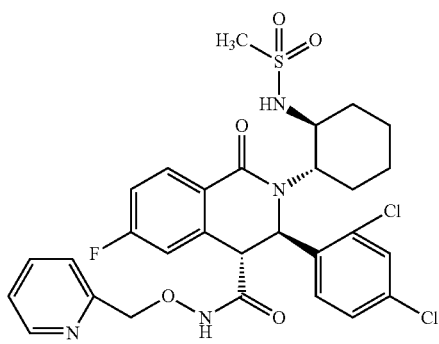 [SMILES: CS(=O)(=O)N[C@H]1CCCC[C@@H]1N1C(=O)c2ccc(F)cc2[C@@H](C(=O)NOCc2ccccn2)[C@@H]1c1ccc(Cl)cc1Cl] | racemic mixture |
| 345 | 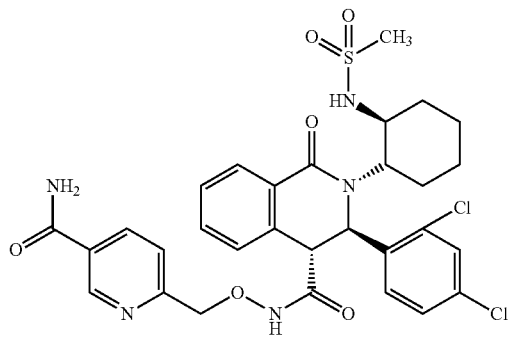 | racemic mixture |

TABLE 134-continued
| 346 | 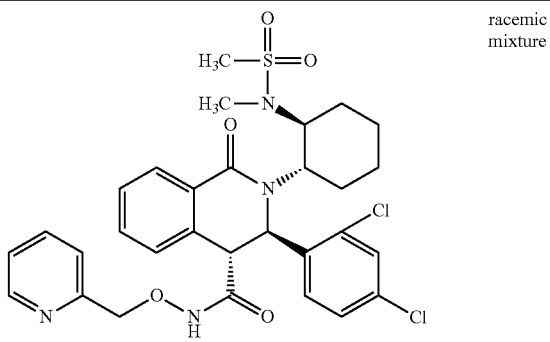 | racemic mixture |
TABLE 135
| 347 | 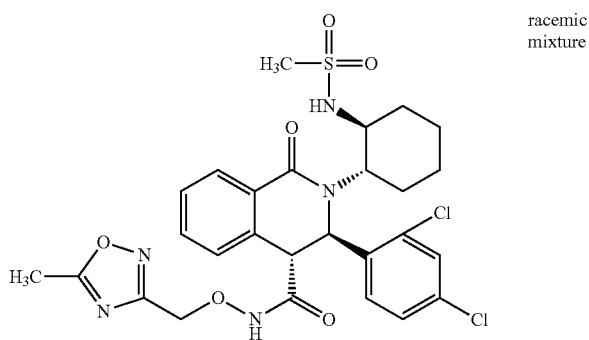 | racemic mixture |
| 348 | 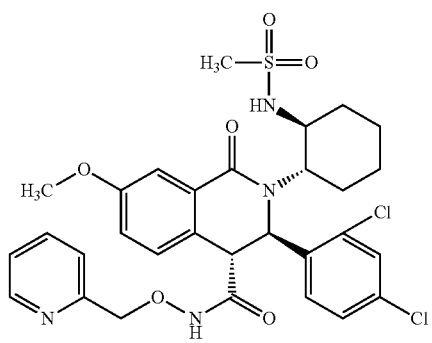 [SMILES: COc1ccc2c(c1)C(=O)N([C@H]1CCCC[C@@H]1NS(C)(=O)=O)[C@@H](c1ccc(Cl)cc1Cl)[C@@H]2C(=O)NOCc1ccccn1] | racemic mixture |
| 349 | 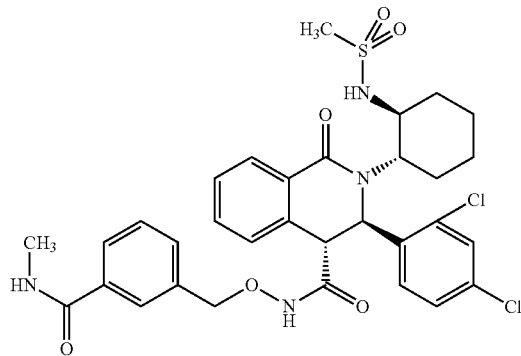 [SMILES: CNC(=O)c1cccc(CONC(=O)[C@@H]2c3ccccc3C(=O)N([C@H]3CCCC[C@@H]3NS(C)(=O)=O)[C@H]2c2ccc(Cl)cc2Cl)c1] | racemic mixture |

TABLE 135-continued
| 350 | 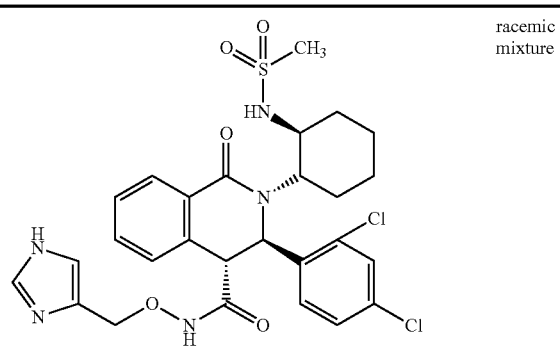 | racemic mixture |
TABLE 136
| 351 | 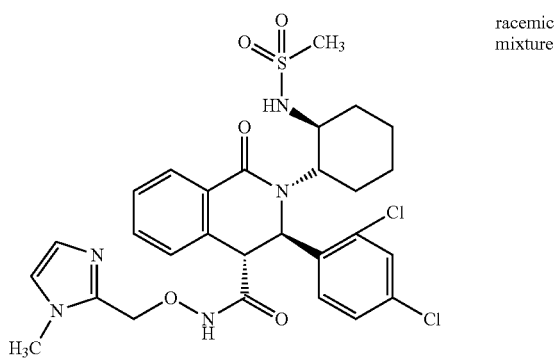 | racemic mixture |
| 352 | 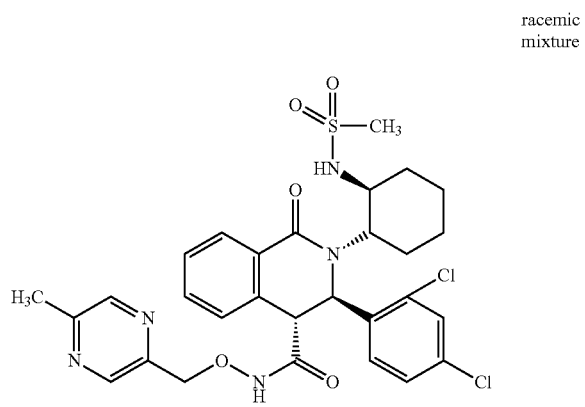 | racemic mixture |
| 353 | 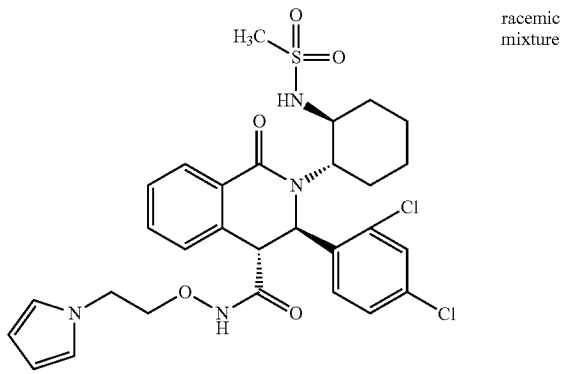 | racemic mixture |

TABLE 136-continued
| 354 | 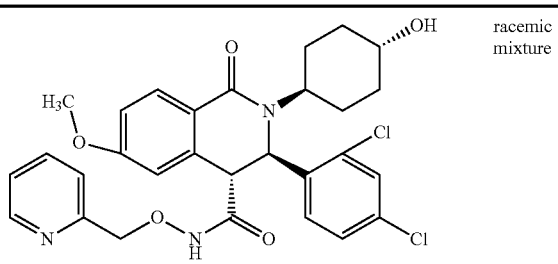 | racemic mixture |
TABLE 137
| 355 | 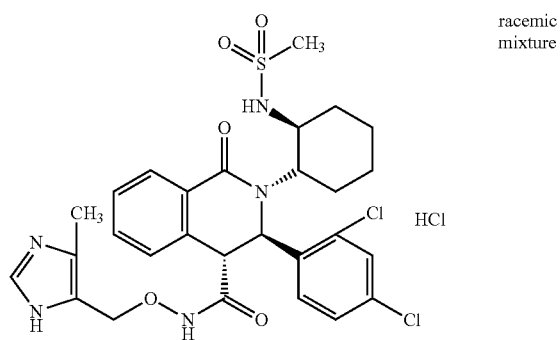 | racemic mixture HCl |
| 356 | 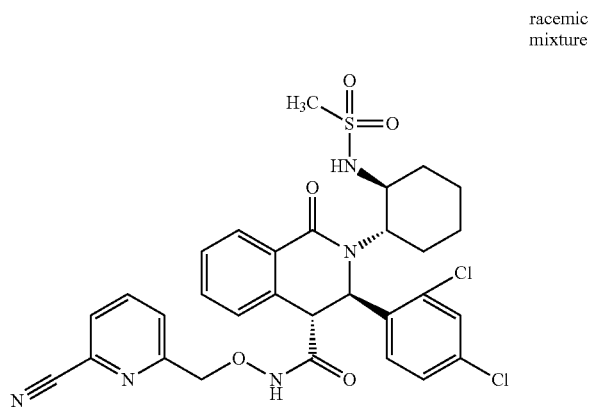 | racemic mixture |
| 357 | 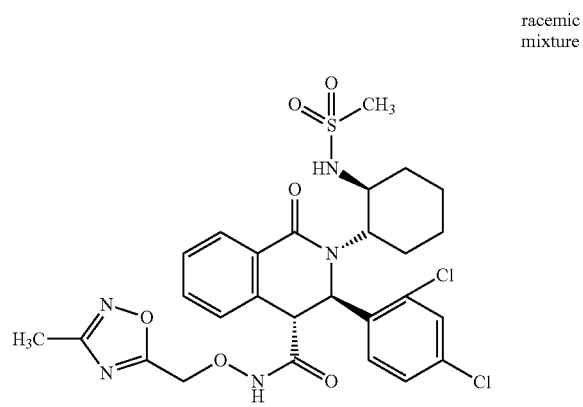 | racemic mixture |

TABLE 137-continued
| 358 | 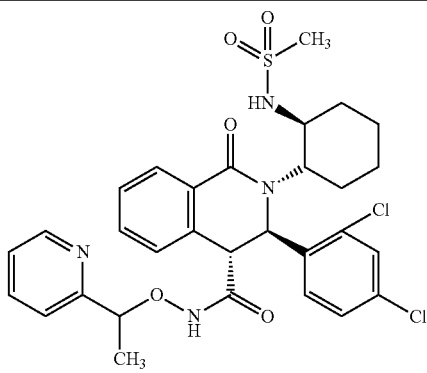 | diastereo mixture |
TABLE 138
| 359 | 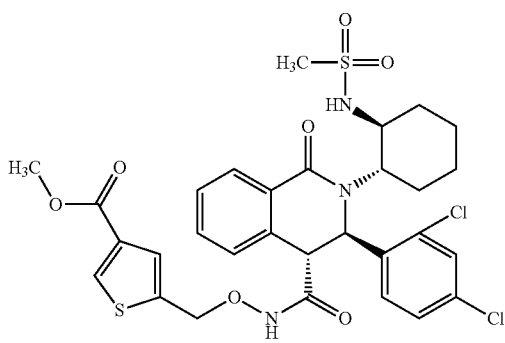 [SMILES: COC(=O)c1csc(CONC(=O)[C@@H]2c3ccccc3C(=O)N([C@H]3CCCC[C@@H]3NS(C)(=O)=O)[C@H]2c2ccc(Cl)cc2Cl)c1] | |
| 360 | 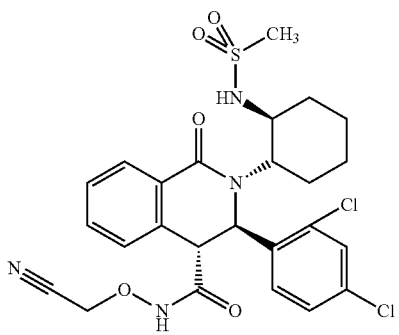 | racemic mixture |
| 361 | 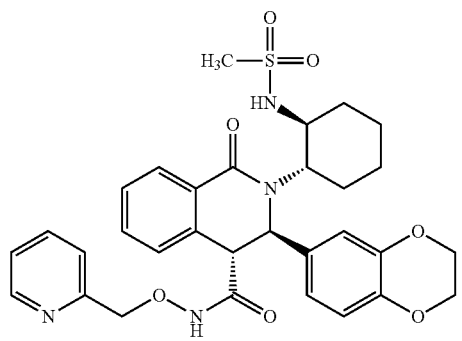 [SMILES: CS(=O)(=O)N[C@H]1CCCC[C@@H]1N1C(=O)c2ccccc2[C@@H](C(=O)NOCc2ccccn2)[C@@H]1c1ccc2c(c1)OCCO2] | racemic mixture |

TABLE 138-continued
| 362 | 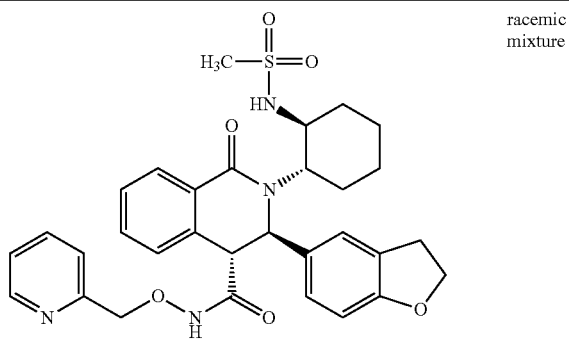 | racemic mixture |
TABLE 139
| 363 | 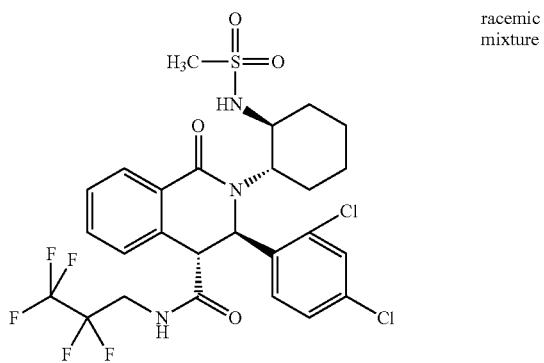 | racemic mixture |
| 364 | 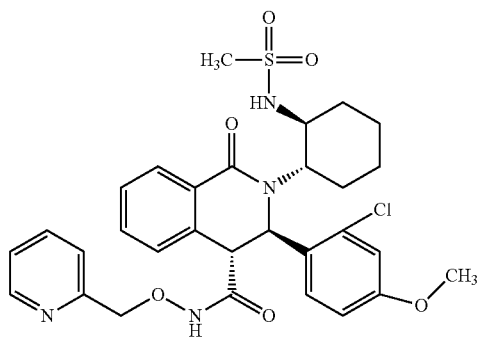 [SMILES: COc1ccc([C@H]2[C@H](C(=O)NOCc3ccccn3)c3ccccc3C(=O)N2[C@H]2CCCC[C@@H]2NS(C)(=O)=O)c(Cl)c1] | racemic mixture |
| 365 | 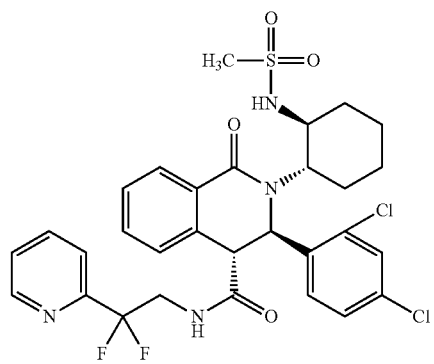 [SMILES: CS(=O)(=O)N[C@H]1CCCC[C@@H]1N1C(=O)c2ccccc2[C@@H](C(=O)NCC(F)(F)c2ccccn2)[C@@H]1c1ccc(Cl)cc1Cl] | racemic mixture |

TABLE 139-continued
| 366 | 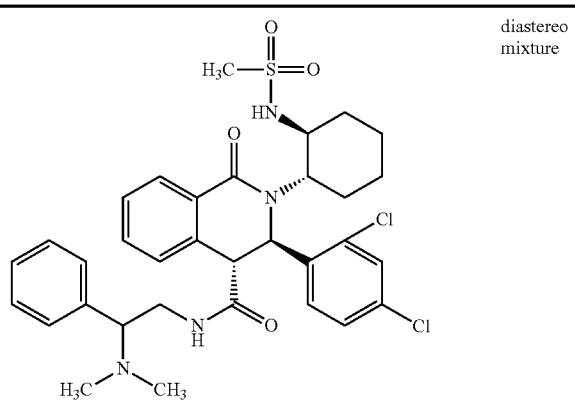 | diastereo mixture |
TABLE 140
| 367 | 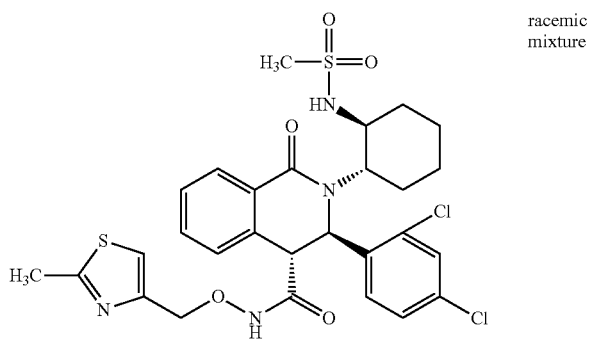 | racemic mixture |
| 368 | 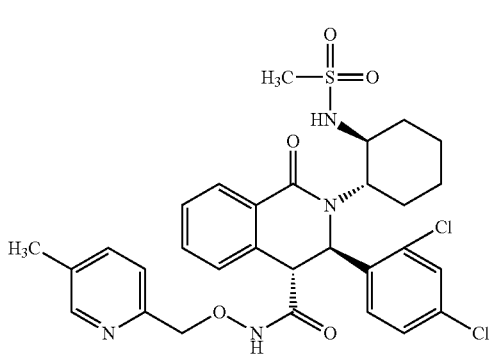 [SMILES: Cc1ccc(CONC(=O)[C@@H]2c3ccccc3C(=O)N([C@H]3CCCC[C@@H]3NS(C)(=O)=O)[C@H]2c2ccc(Cl)cc2Cl)nc1] | racemic mixture |
| 369 | 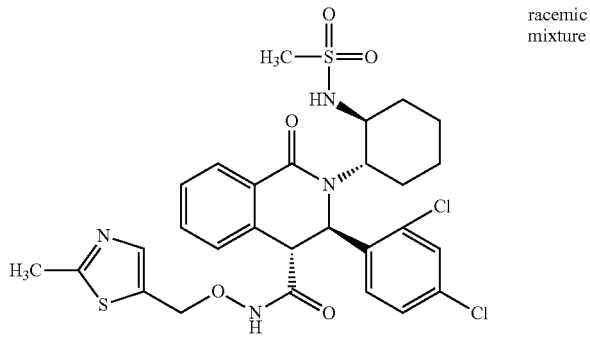 | racemic mixture |

TABLE 140-continued
| 370 | 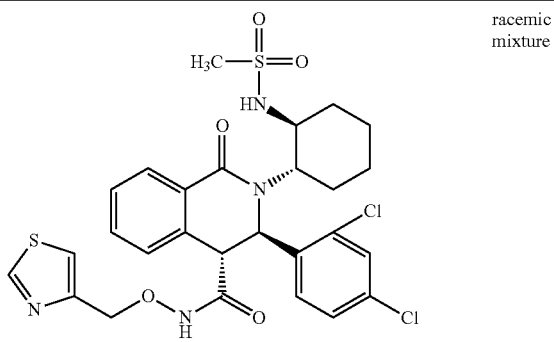 | racemic mixture |
TABLE 141
| 371 | 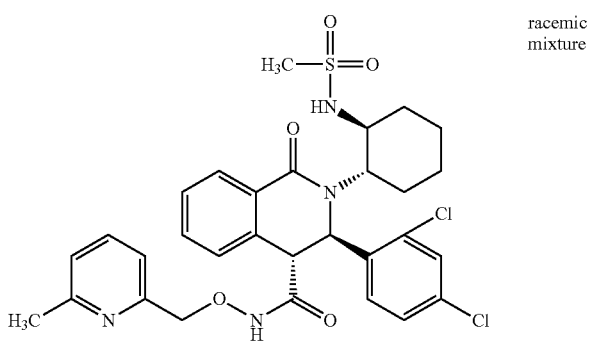 | racemic mixture |
| 372 | 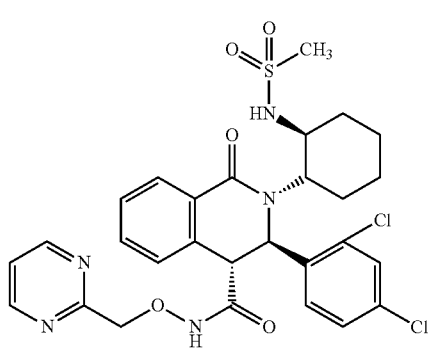 | racemic mixture |
| 373 | 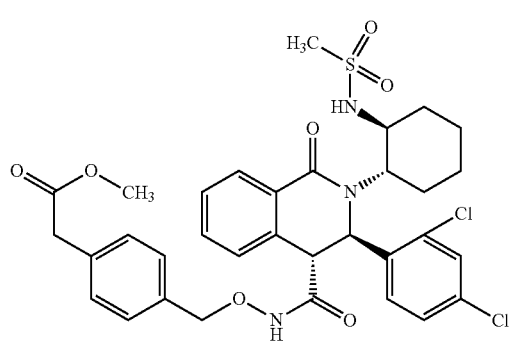 [SMILES: COC(=O)Cc1ccc(CONC(=O)[C@@H]2c3ccccc3C(=O)N([C@H]3CCCC[C@@H]3NS(C)(=O)=O)[C@H]2c2ccc(Cl)cc2Cl)cc1] | racemic mixture |

TABLE 141-continued
| 374 | 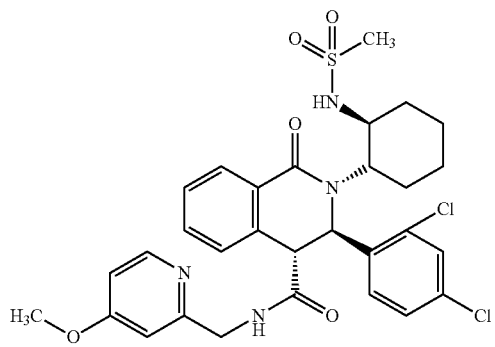 | racemic mixture |
TABLE 142
| 375 | 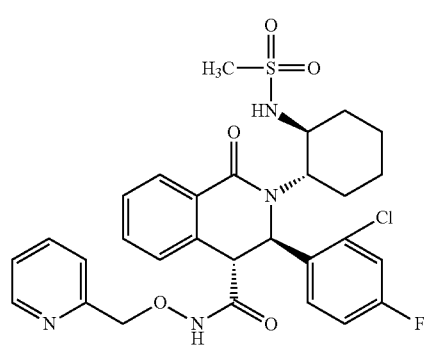 [SMILES: CS(=O)(=O)N[C@H]1CCCC[C@@H]1N1C(=O)c2ccccc2[C@@H](C(=O)NOCc2ccccn2)[C@@H]1c1ccc(F)cc1Cl] | racemic mixture, diastereomer of Ex 377, more polar |
| 376 | 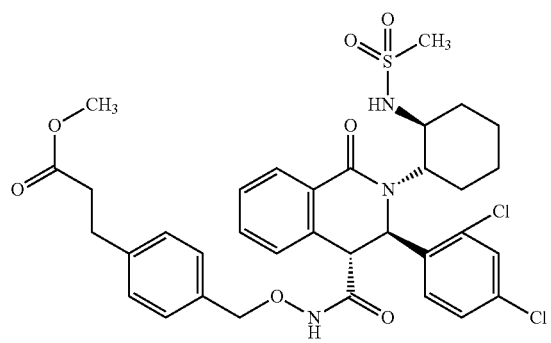 | racemic mixture |

US 10,532,048 B2
303                                                                                   304
TABLE 142-continued
| 377 | 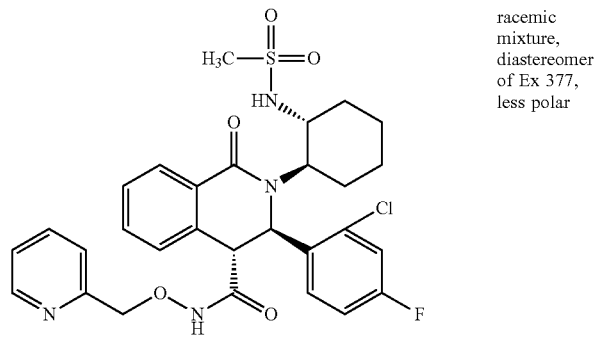 | racemic mixture, diastereomer of Ex 377, less polar |
| --- | --- | --- |
| 378 | 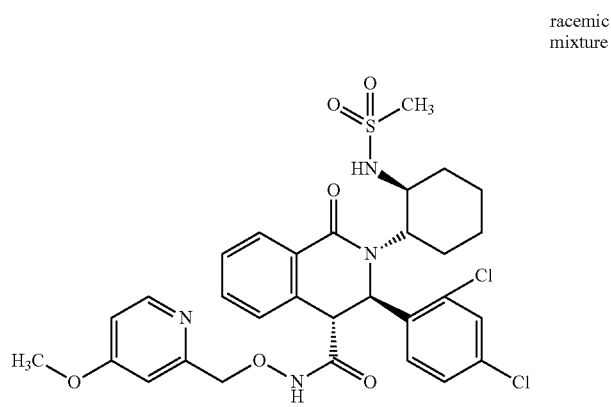 | racemic mixture |
TABLE 143
| 379 | 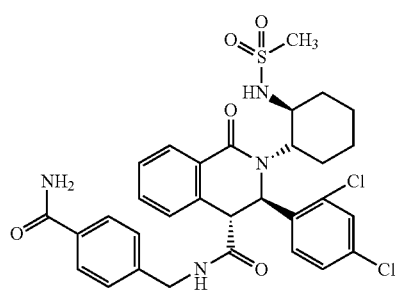 | racemic mixture |
| --- | --- | --- |
| 380 | 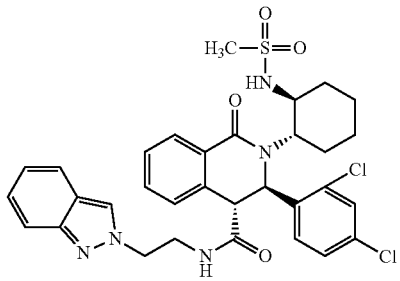 [SMILES: CS(=O)(=O)N[C@H]1CCCC[C@@H]1N1C(=O)c2ccccc2[C@@H](C(=O)NCCn2cc3ccccc3n2)[C@@H]1c1ccc(Cl)cc1Cl] | racemic mixture |
TABLE 143-continued
| 381 | 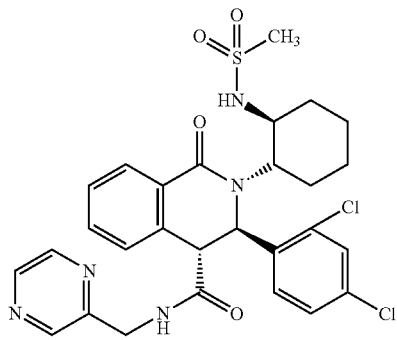 | racemic mixture |
| --- | --- | --- |
| 382 | 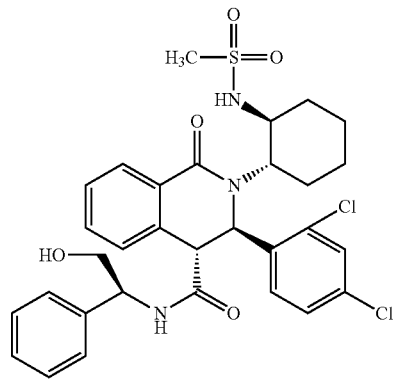 [SMILES: CS(=O)(=O)N[C@H]1CCCC[C@@H]1N1C(=O)c2ccccc2[C@@H](C(=O)N[C@H](CO)c2ccccc2)[C@@H]1c1ccc(Cl)cc1Cl] | |

TABLE 144
| | | |
|---|---|---|
| 383 | 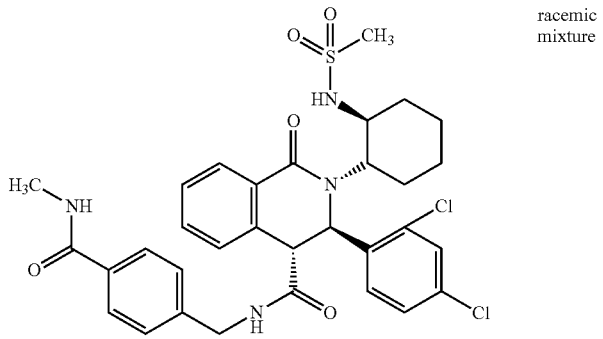 | racemic mixture |
| 384 | 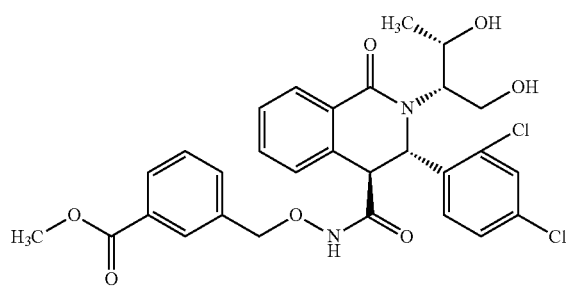 [SMILES: COC(=O)c1cccc(CONC(=O)[C@H]2c3ccccc3C(=O)N([C@@H](CO)[C@H](C)O)[C@@H]2c2ccc(Cl)cc2Cl)c1] | |
| 385 | 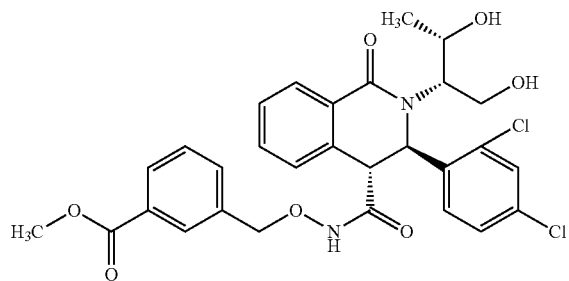 [SMILES: COC(=O)c1cccc(CONC(=O)[C@@H]2c3ccccc3C(=O)N([C@@H](CO)[C@H](C)O)[C@H]2c2ccc(Cl)cc2Cl)c1] | |
| 386 | 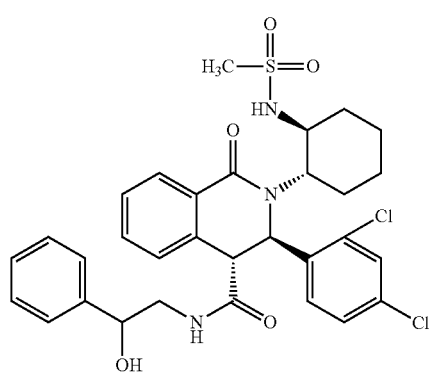 [SMILES: CS(=O)(=O)N[C@H]1CCCC[C@@H]1N1C(=O)c2ccccc2[C@@H](C(=O)NCC(O)c2ccccc2)[C@@H]1c1ccc(Cl)cc1Cl] | chiral compound, diastereomer of Ex387, less polar |

TABLE 145
| 387 | 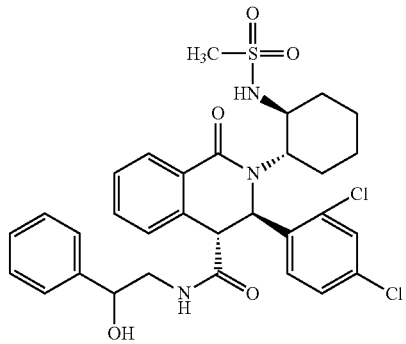 [SMILES: CS(=O)(=O)N[C@H]1CCCC[C@@H]1N1C(=O)c2ccccc2[C@@H](C(=O)NCC(O)c2ccccc2)[C@@H]1c1ccc(Cl)cc1Cl] | chiral compound, diastereomer of Ex386, more polar |
| --- | --- | --- |
| 388 | 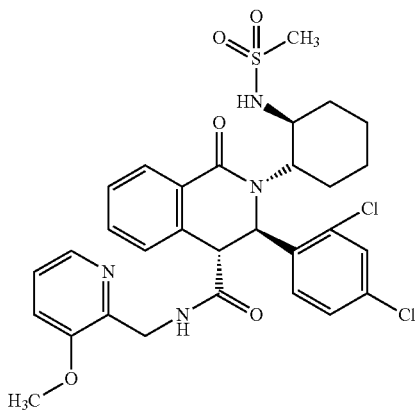 | racemic mixture |
| 389 | 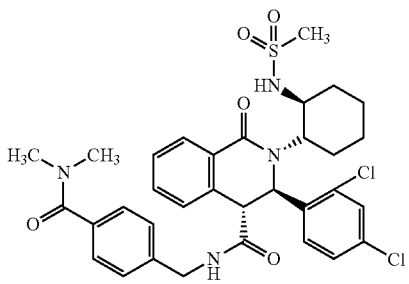 | racemic mixture |
| 390 | 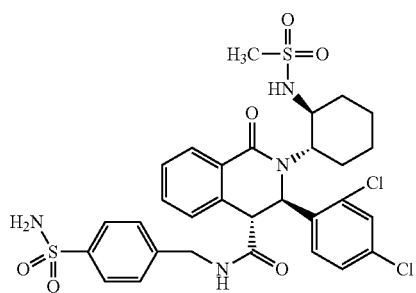 [SMILES: CS(=O)(=O)N[C@H]1CCCC[C@@H]1N1C(=O)c2ccccc2[C@@H](C(=O)NCc2ccc(S(N)(=O)=O)cc2)[C@@H]1c1ccc(Cl)cc1Cl] | racemic mixture |
TABLE 146
| 391 | 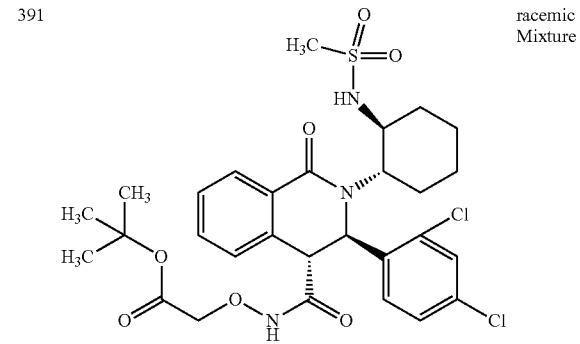 | racemic Mixture |
| --- | --- | --- |
| 392 | 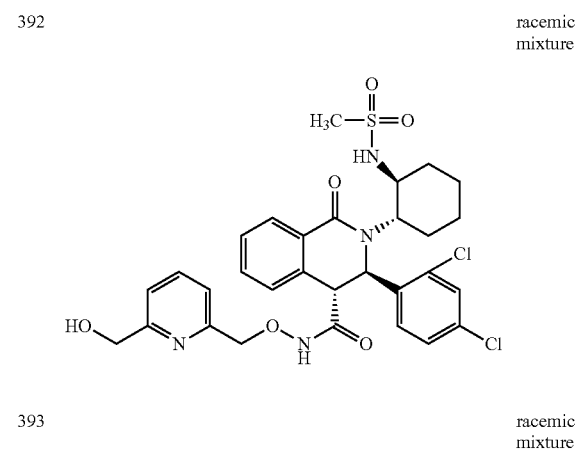 | racemic mixture |
| 393 | 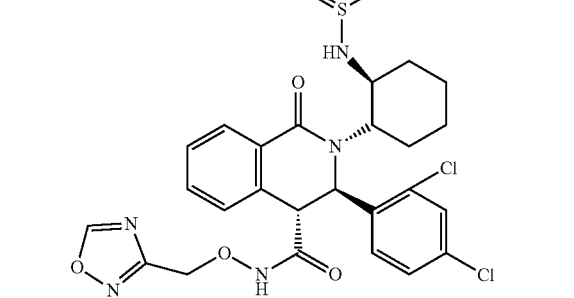 | racemic mixture |
| 394 | 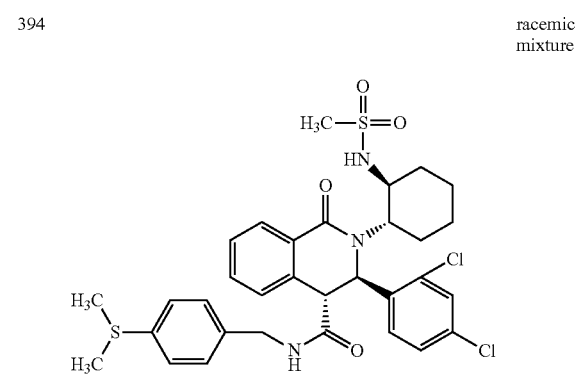 | racemic mixture |

TABLE 147
| | | |
|---|---|---|
| 395 | 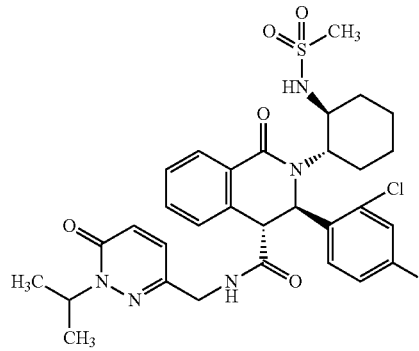 | racemic mixture |
| 396 | 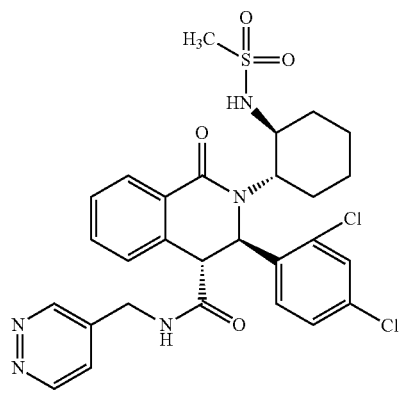 [SMILES: CS(=O)(=O)N[C@H]1CCCC[C@@H]1N1C(=O)c2ccccc2[C@@H](C(=O)NCc2ccnnc2)[C@@H]1c1ccc(Cl)cc1Cl] | racemic mixture |
| 397 | 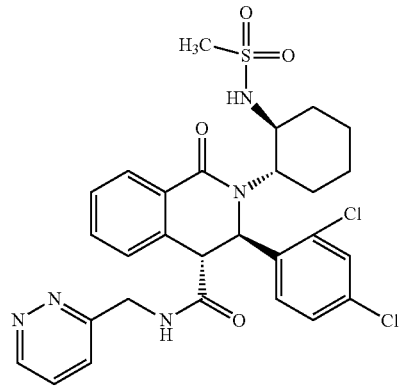 [SMILES: CS(=O)(=O)N[C@H]1CCCC[C@@H]1N1C(=O)c2ccccc2[C@@H](C(=O)NCc2cccnn2)[C@@H]1c1ccc(Cl)cc1Cl] | racemic mixture |
| 398 | 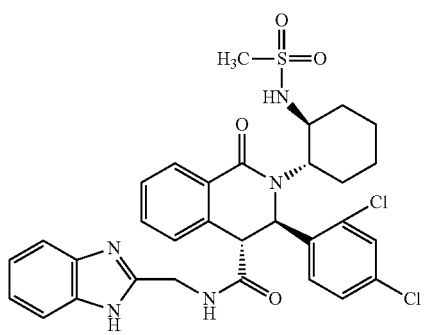 [SMILES: CS(=O)(=O)N[C@H]1CCCC[C@@H]1N1C(=O)c2ccccc2[C@@H](C(=O)NCc2nc3ccccc3[nH]2)[C@@H]1c1ccc(Cl)cc1Cl] | racemic mixture |
TABLE 148
| | | |
|---|---|---|
| 399 | 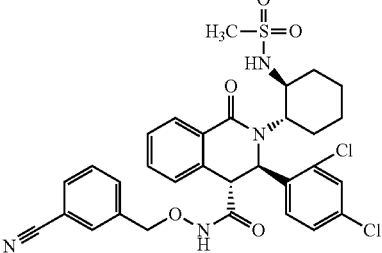 | racemic mixture |
| 400 | 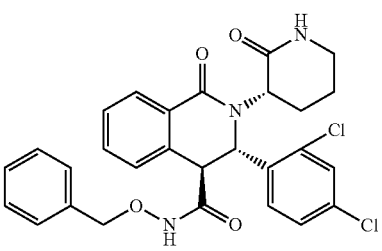 [SMILES: O=C(NOCc1ccccc1)[C@H]1c2ccccc2C(=O)N([C@H]2CCCNC2=O)[C@@H]1c1ccc(Cl)cc1Cl] | |
| 401 | 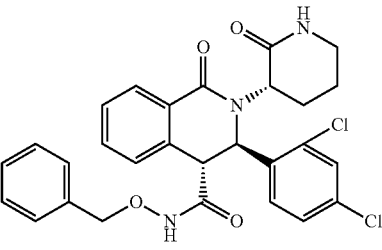 [SMILES: O=C(NOCc1ccccc1)[C@@H]1c2ccccc2C(=O)N([C@H]2CCCNC2=O)[C@H]1c1ccc(Cl)cc1Cl] | |
| 402 | 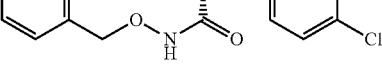 | 1',2'-trans, 3,4-trans, diastereomer of Ex404 |
| 403 | 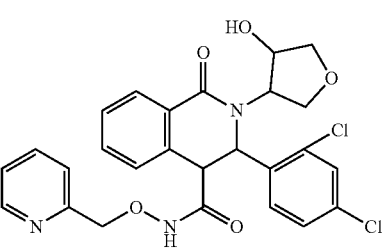 [SMILES: O=C(NOCc1ccccn1)C1c2ccccc2C(=O)N(C2COCC2O)C1c1ccc(Cl)cc1Cl] | racemic mixture |
TABLE 149
| | | |
|---|---|---|
| 404 | 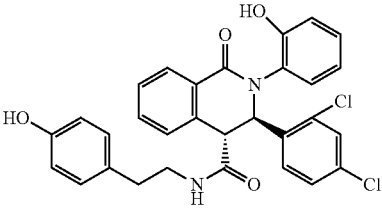 [SMILES: O=C(NCCc1ccc(O)cc1)[C@@H]1c2ccccc2C(=O)N(c2ccccc2O)[C@H]1c1ccc(Cl)cc1Cl] | 1',2'-trans, 3,4-trans, diastereomer of Ex402 |

TABLE 149-continued

| | | |
|---|---|---|
| 405 | | racemic mixture |
| 406 | | racemic mixture, HCl |
| 407 | | |
| 408 | | |

TABLE 150

| | | |
|---|---|---|
| 409 | | 1',2'-trans, 3,4-trans, diastereomer of Ex203 |
| 410 | | 1',2'-trans, 3,4-trans, diastereomer of Ex411, less polar |
| 411 | | 1',2'-trans, 3,4-trans, diastereomer of Ex410, more polar |
| 412 | | racemic mixture, 1',2'-cis, 3,4-trans, diastereomer of Ex28 |
| 413 | | |

TABLE 151

| | | |
|---|---|---|
| 414 | | 1',2'-trans, 3,4-trans |
| 415 | | |

TABLE 151-continued
| 416 | 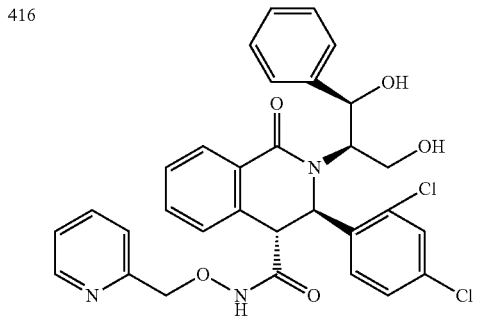 | |
| 417 | 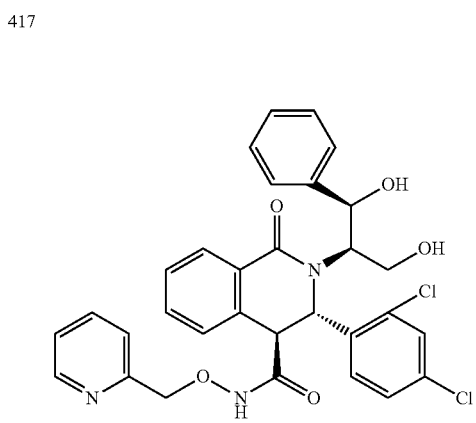 | |
| 418 | 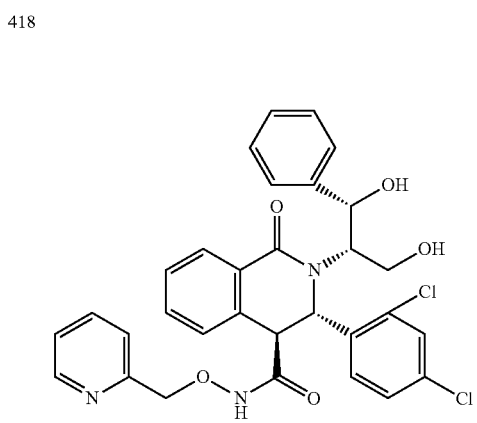 | |
TABLE 152
| 419 | 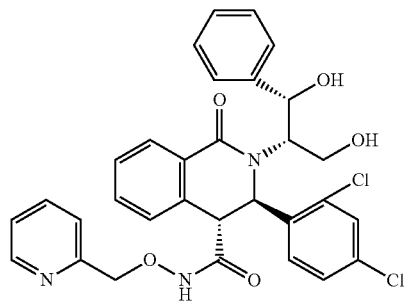 [SMILES: O=C(NOCc1ccccn1)[C@@H]1c2ccccc2C(=O)N([C@@H](CO)[C@@H](O)c2ccccc2)[C@H]1c1ccc(Cl)cc1Cl] | |
TABLE 152-continued
| 420 | 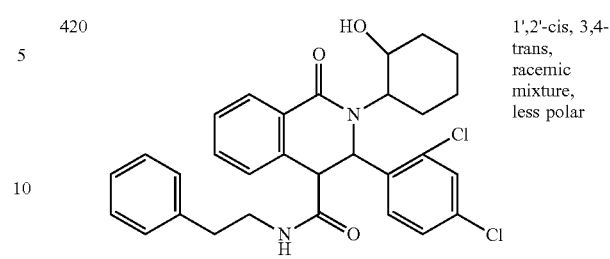 | 1',2'-cis, 3,4-trans, racemic mixture, less polar |
| 421 | 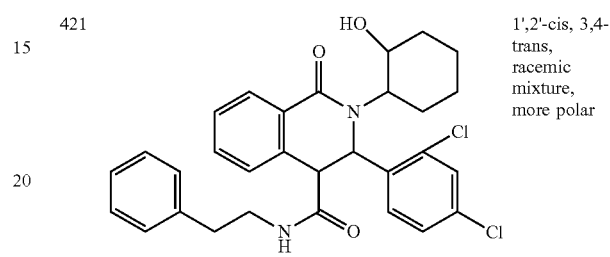 | 1',2'-cis, 3,4-trans, racemic mixture, more polar |
| 422 | 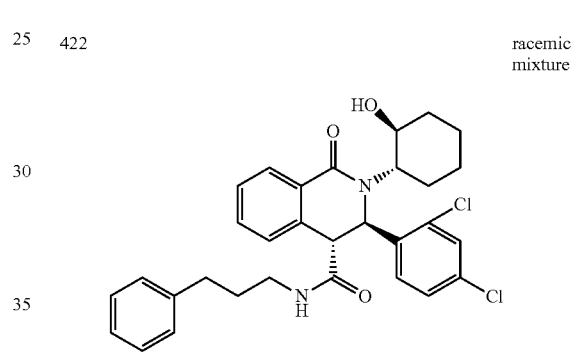 | racemic mixture |
| 423 | 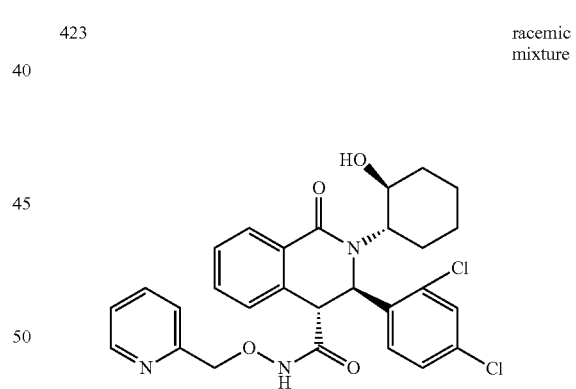 | racemic mixture |
TABLE 153
| 424 | | racemic mixture |

TABLE 153-continued
| 425 | 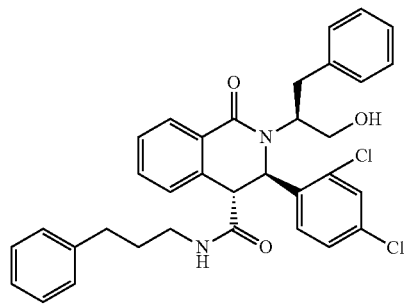 [SMILES: O=C(NCCCc1ccccc1)[C@@H]1c2ccccc2C(=O)N([C@H](CO)Cc2ccccc2)[C@H]1c1ccc(Cl)cc1Cl] |
| --- | --- |
| 426 | 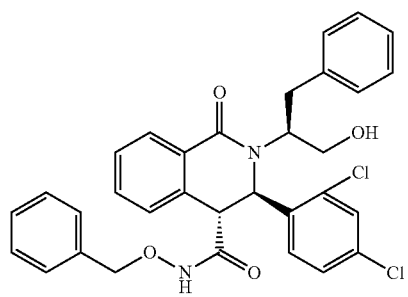 [SMILES: O=C(NOCc1ccccc1)[C@@H]1c2ccccc2C(=O)N([C@H](CO)Cc2ccccc2)[C@H]1c1ccc(Cl)cc1Cl] |
TABLE 153-continued
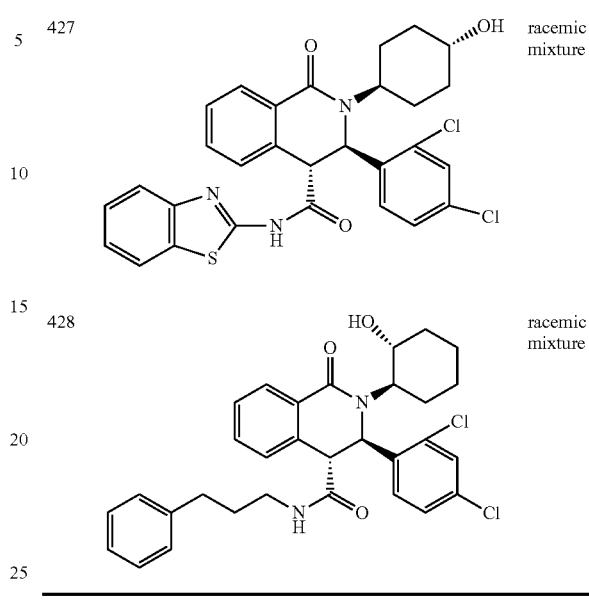
| 427 | | racemic mixture |
| 428 | | racemic mixture |
TABLE 154
| 429 | 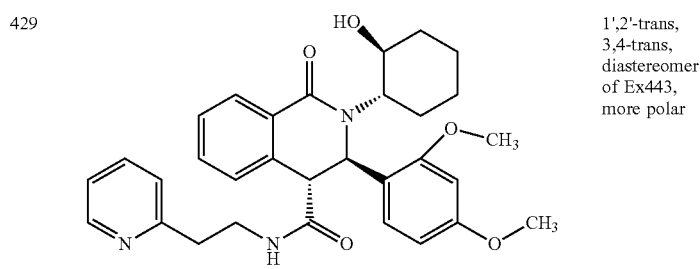 | 1',2'-trans, 3,4-trans, diastereomer of Ex443, more polar |
| --- | --- | --- |
| 430 | 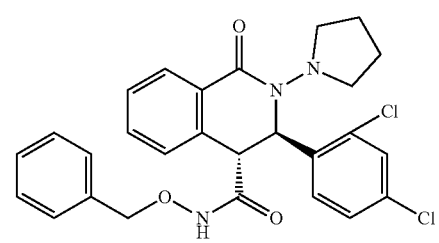 [SMILES: O=C(NOCc1ccccc1)[C@@H]1c2ccccc2C(=O)N(N2CCCC2)[C@H]1c1ccc(Cl)cc1Cl] | racemic mixture |
| 431 | 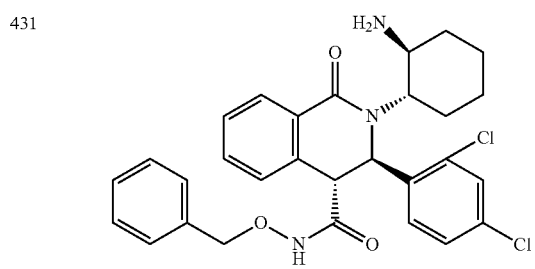 | |

TABLE 154-continued
| 432 | 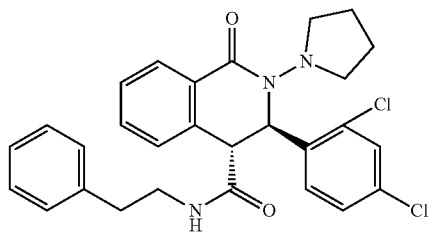 [SMILES: O=C(NCCc1ccccc1)[C@@H]1c2ccccc2C(=O)N(N2CCCC2)[C@H]1c1ccc(Cl)cc1Cl] | racemic mixture |
| --- | --- | --- |
| 433 | 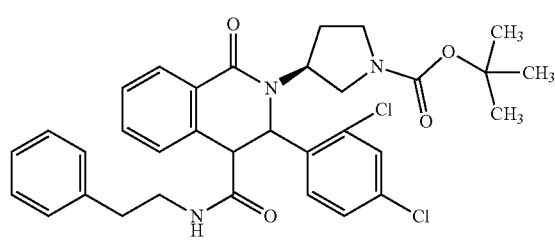 [SMILES: CC(C)(C)OC(=O)N1CC[C@H](N2C(=O)c3ccccc3C(C(=O)NCCc3ccccc3)C2c2ccc(Cl)cc2Cl)C1] | 3,4-trans, diastereo mixture |
| 434 | 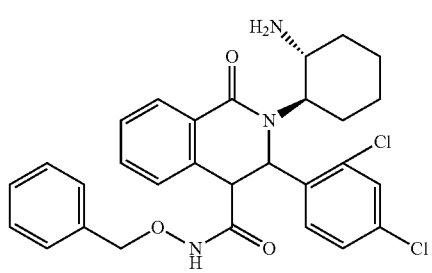 [SMILES: N[C@@H]1CCCC[C@H]1N1C(=O)c2ccccc2C(C(=O)NOCc2ccccc2)C1c1ccc(Cl)cc1Cl] | 3,4-trans, diastereo mixture |
TABLE 155
| 435 | 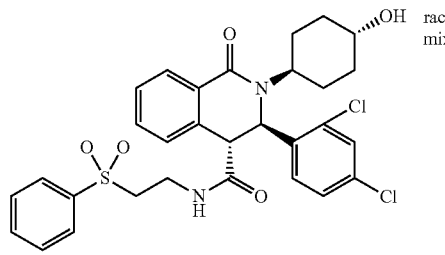 | racemic mixture |
| --- | --- | --- |
| 436 | 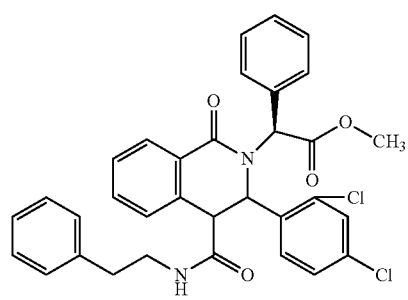 [SMILES: COC(=O)[C@H](c1ccccc1)N1C(=O)c2ccccc2C(C(=O)NCCc2ccccc2)C1c1ccc(Cl)cc1Cl] | 3,4-trans |
TABLE 155-continued
| 437 | 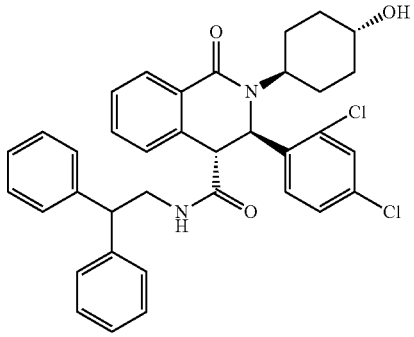 [SMILES: O=C(NCC(c1ccccc1)c1ccccc1)[C@@H]1c2ccccc2C(=O)N([C@H]2CC[C@H](O)CC2)[C@H]1c1ccc(Cl)cc1Cl] | racemic mixture |
| --- | --- | --- |
| 438 | 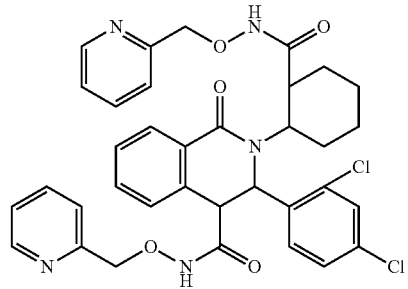 [SMILES: O=C(NOCc1ccccn1)C1CCCCC1N1C(=O)c2ccccc2C(C(=O)NOCc2ccccn2)C1c1ccc(Cl)cc1Cl] | 1',2'-trans, 3,4-trans |

TABLE 155-continued
| 439 | 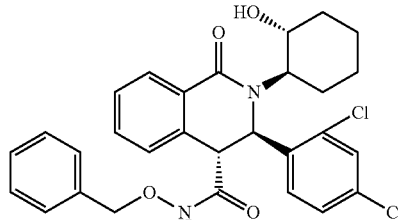 | racemic mixture |
TABLE 156
| 440 | 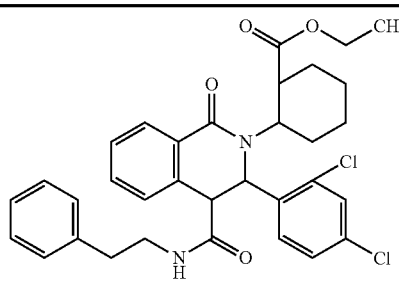 | 1',2'-cis, 3,4-trans, racemic mixture |
| 441 | 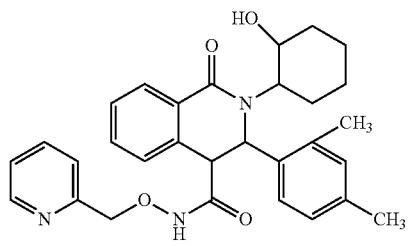 [SMILES: Cc1ccc(C2C(C(=O)NOCc3ccccn3)c3ccccc3C(=O)N2C2CCCCC2O)c(C)c1] | 1',2'-trans, 3,4-trans, racemic mixture |
| 442 | 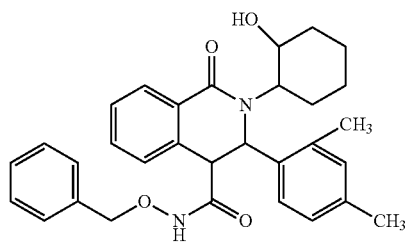 [SMILES: Cc1ccc(C2C(C(=O)NOCc3ccccc3)c3ccccc3C(=O)N2C2CCCCC2O)c(C)c1] | 1',2'-trans, 3,4-trans |
| 443 | 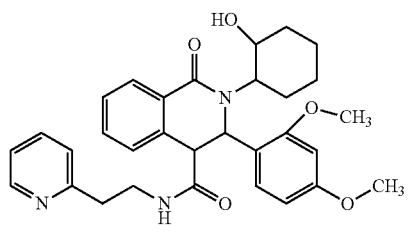 [SMILES: COc1ccc(C2C(C(=O)NCCc3ccccn3)c3ccccc3C(=O)N2C2CCCCC2O)c(OC)c1] | 1',2'-trans, 3,4-trans, diastereomer of Ex429, less polar |
| 444 | 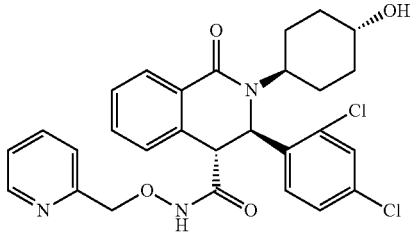 [SMILES: O=C(NOCc1ccccn1)[C@@H]1c2ccccc2C(=O)N([C@H]2CC[C@H](O)CC2)[C@H]1c1ccc(Cl)cc1Cl] | racemic mixture |
TABLE 157
| 445 | 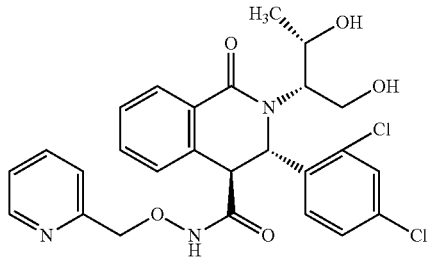 [SMILES: C[C@H](O)[C@H](CO)N1C(=O)c2ccccc2[C@H](C(=O)NOCc2ccccn2)[C@H]1c1ccc(Cl)cc1Cl] | |
| 446 | 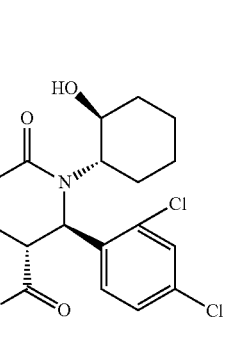 | |
| 447 | 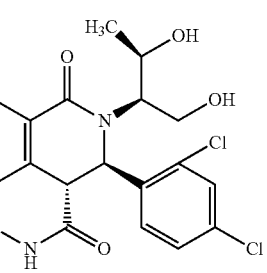 | |
| 448 | 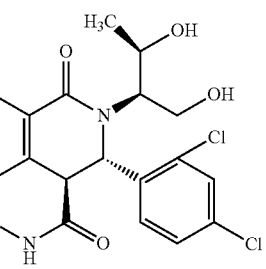 | |
| 449 | 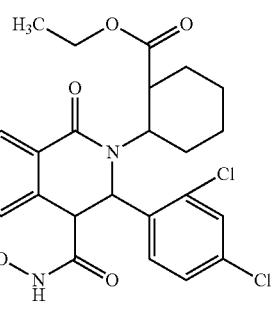 | 1',2'-trans, 3,4-trans |

TABLE 158
| | | |
|---|---|---|
| 450 | 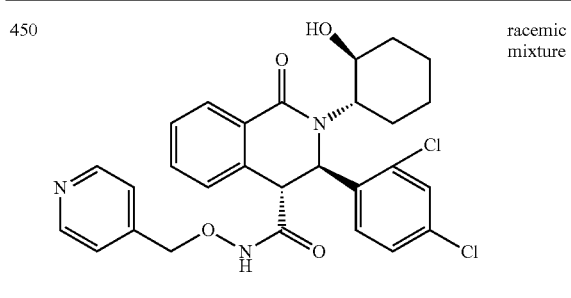 | racemic mixture |
| 451 | 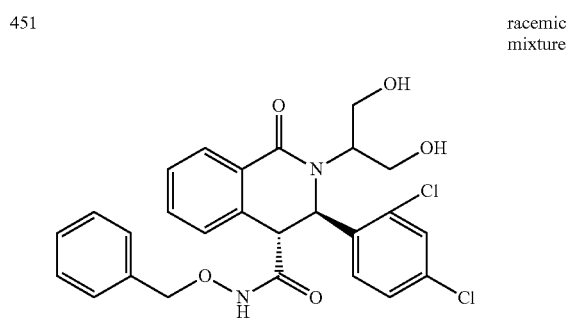 | racemic mixture |
| 452 | 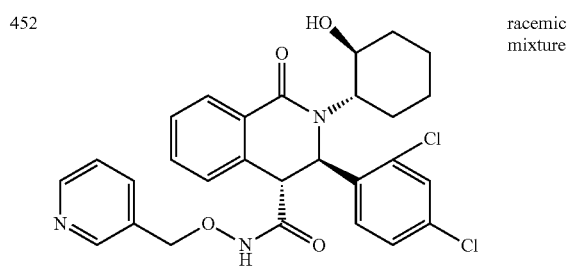 | racemic mixture |
| 453 | 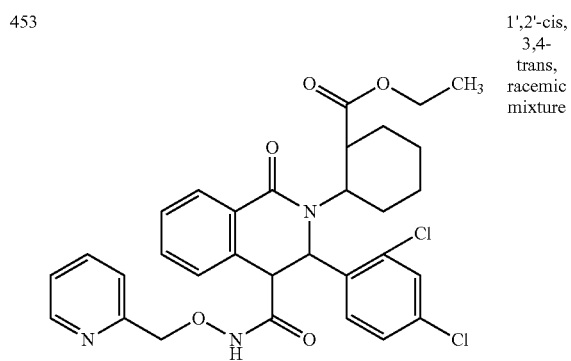 | 1',2'-cis, 3,4-trans, racemic mixture |
| 454 | 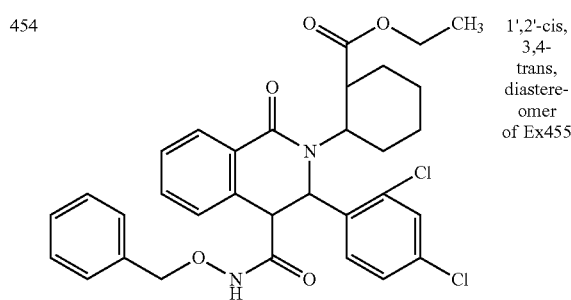 | 1',2'-cis, 3,4-trans, diastereomer of Ex455 |
TABLE 159
| | | |
|---|---|---|
| 455 | 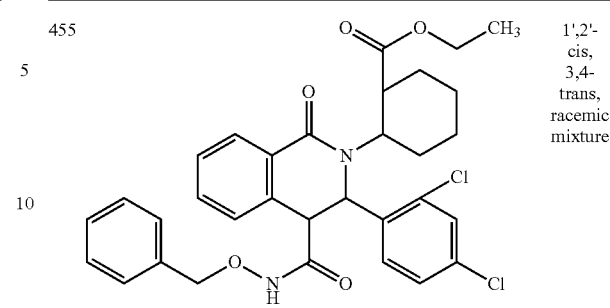 | 1',2'-cis, 3,4-trans, racemic mixture |
| 456 | 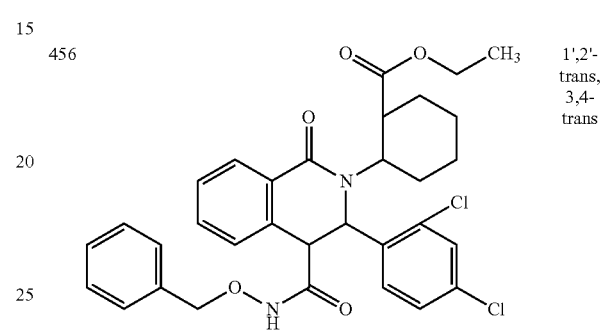 | 1',2'-trans, 3,4-trans |
| 457 | 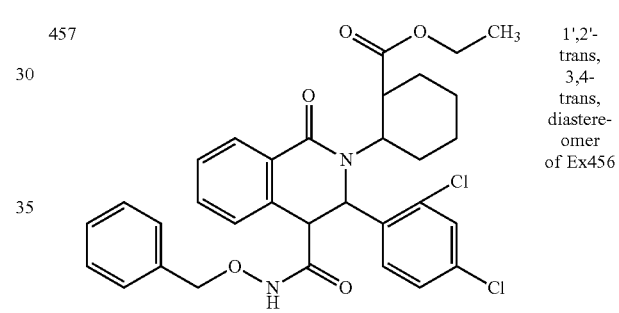 | 1',2'-trans, 3,4-trans, diastereomer of Ex456 |
| 458 | 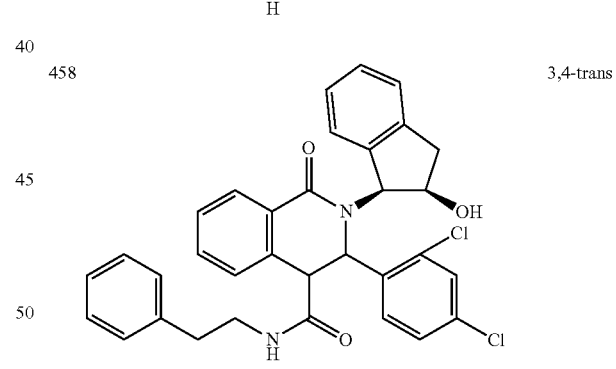 | 3,4-trans |
| 459 | 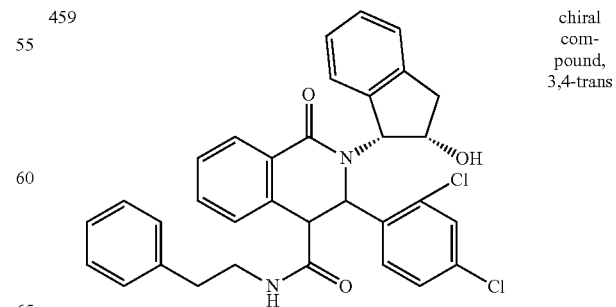 | chiral compound, 3,4-trans |

TABLE 160
| | | |
|---|---|---|
| 460 | 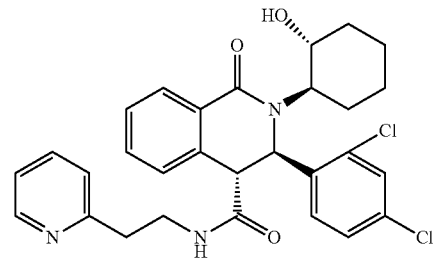 | racemic mixture |
| 461 | 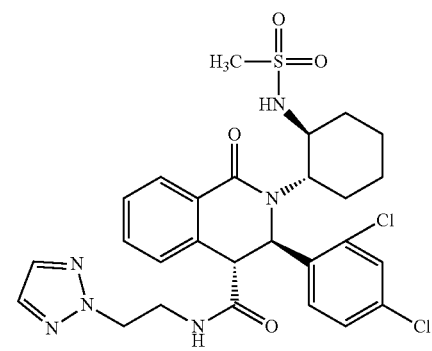 [SMILES: CS(=O)(=O)N[C@H]1CCCC[C@@H]1N1C(=O)c2ccccc2[C@@H](C(=O)NCCn2nccn2)[C@@H]1c1ccc(Cl)cc1Cl] | racemic mixture |
| 462 | 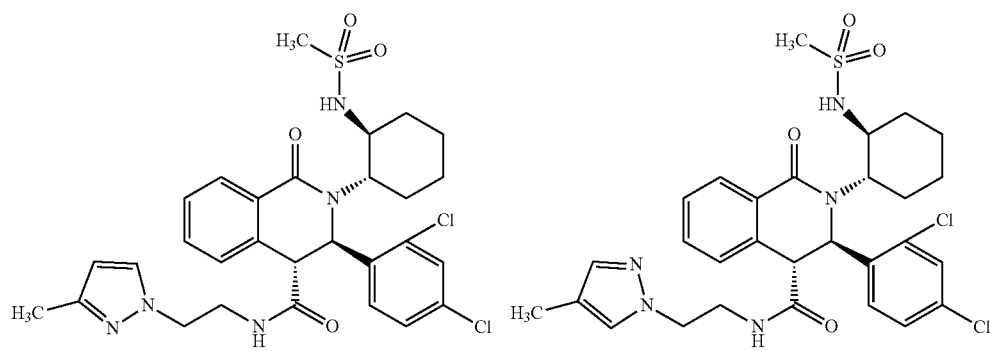<br>3:1 mixture | racemic mixture |
| 463 | 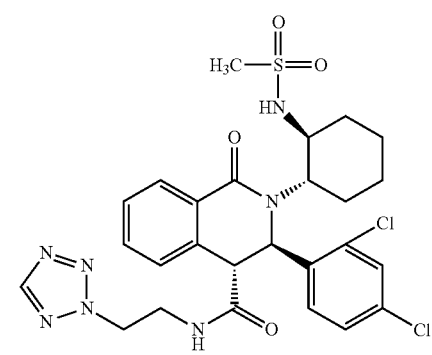 [SMILES: CS(=O)(=O)N[C@H]1CCCC[C@@H]1N1C(=O)c2ccccc2[C@@H](C(=O)NCCn2ncnn2)[C@@H]1c1ccc(Cl)cc1Cl] | racemic mixture |

TABLE 161
| 464 | 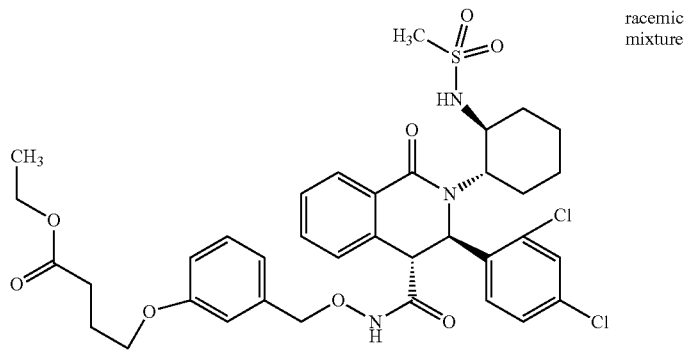 | racemic mixture |
| --- | --- | --- |
| 465 | 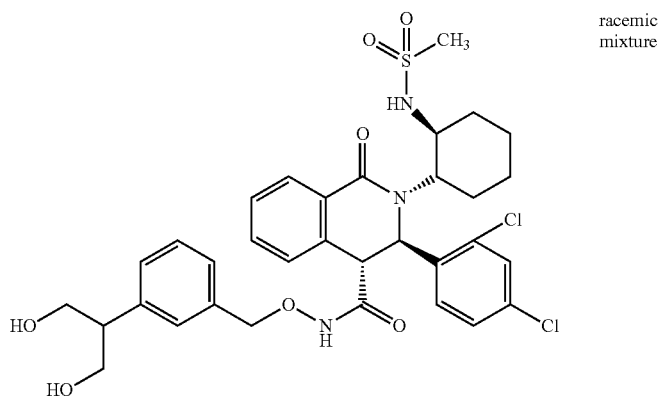 | racemic mixture |
| 466 | 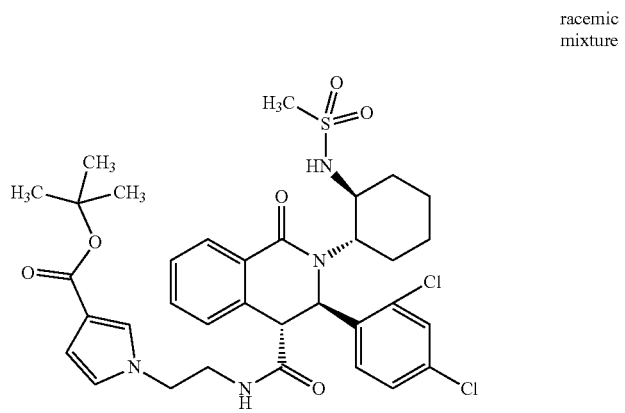 | racemic mixture |
| 467 | 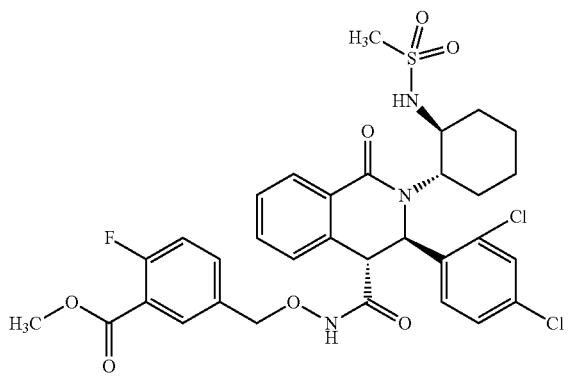 [SMILES: COC(=O)c1cc(CONC(=O)[C@@H]2c3ccccc3C(=O)N([C@H]3CCCC[C@@H]3NS(C)(=O)=O)[C@H]2c2ccc(Cl)cc2Cl)ccc1F] | |

TABLE 162
468 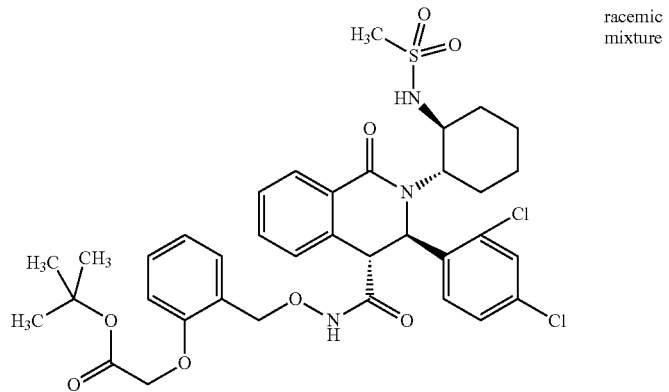 racemic mixture
469 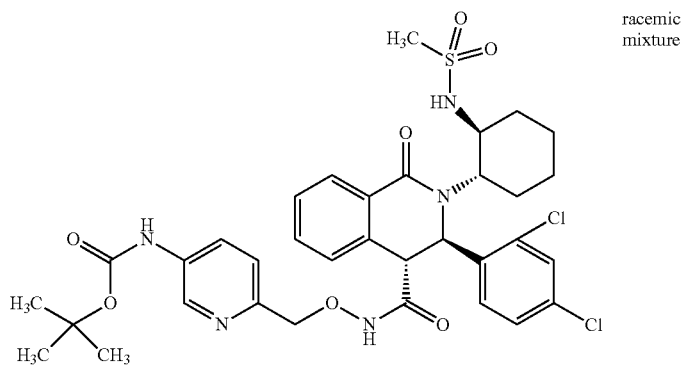 racemic mixture
470 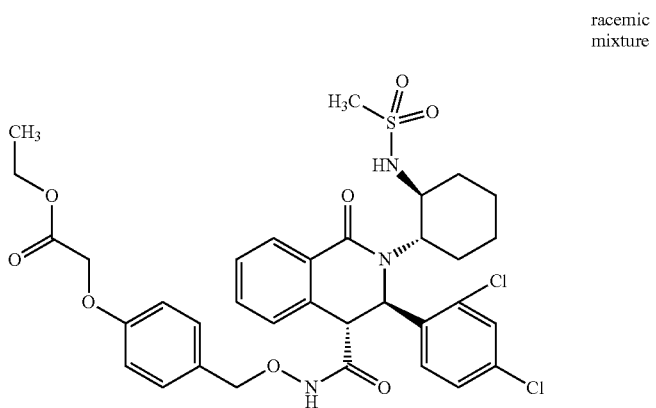 racemic mixture
471 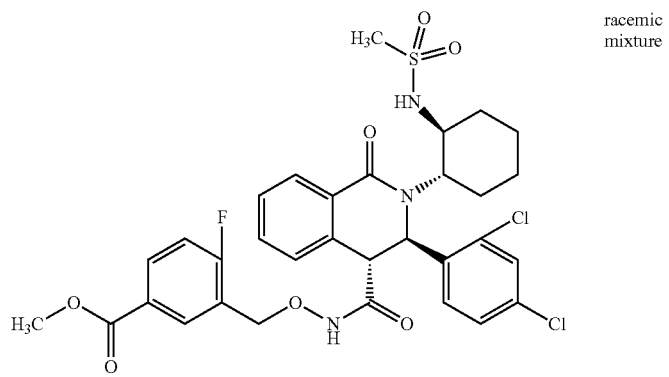 racemic mixture

TABLE 163
| | | |
|---|---|---|
| 472 | 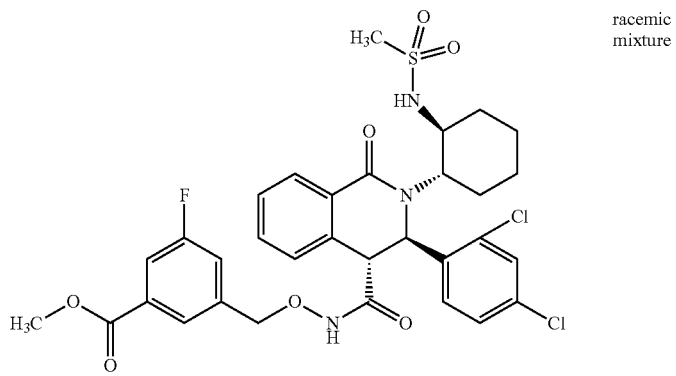 | racemic mixture |
| 473 | 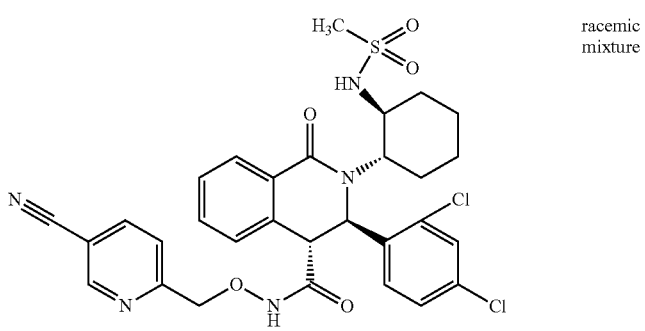 | racemic mixture |
| 474 | 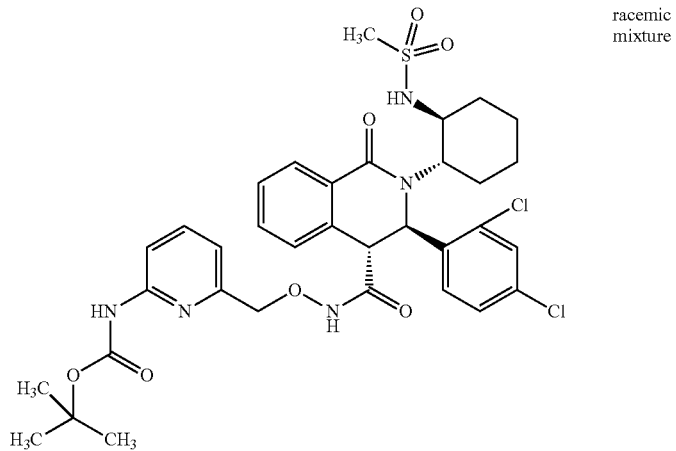 | racemic mixture |
| 475 | 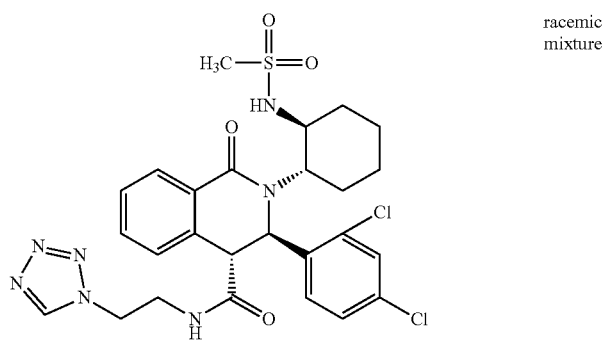 | racemic mixture |

TABLE 164
| 476 | 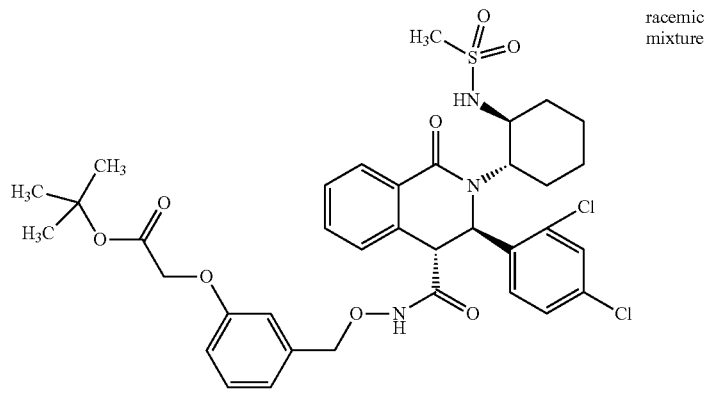 | racemic mixture |
| 477 | 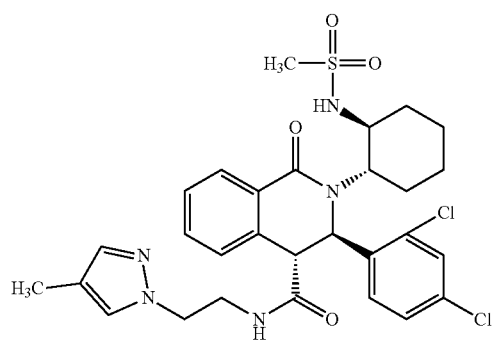 [SMILES: Cc1cnn(CCNC(=O)[C@@H]2c3ccccc3C(=O)N([C@H]3CCCC[C@@H]3NS(C)(=O)=O)[C@H]2c2ccc(Cl)cc2Cl)c1] | racemic mixture |
| 478 | 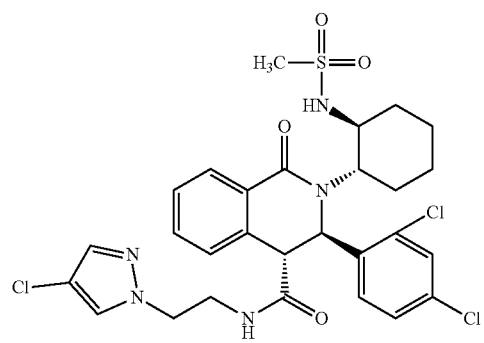 [SMILES: CS(=O)(=O)N[C@H]1CCCC[C@@H]1N1C(=O)c2ccccc2[C@@H](C(=O)NCCn2cc(Cl)cn2)[C@@H]1c1ccc(Cl)cc1Cl] | racemic mixture |
| 479 | 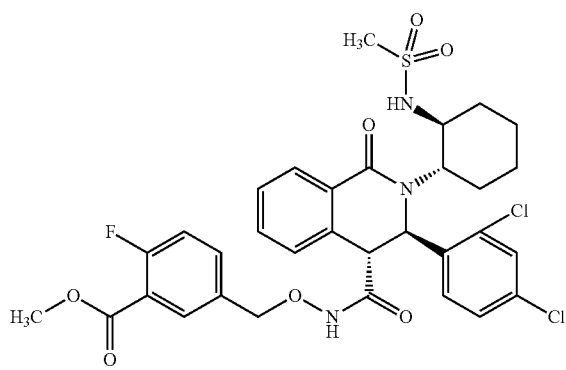 [SMILES: COC(=O)c1cc(CONC(=O)[C@@H]2c3ccccc3C(=O)N([C@H]3CCCC[C@@H]3NS(C)(=O)=O)[C@H]2c2ccc(Cl)cc2Cl)ccc1F] | racemic mixture |

US 10,532,048 B2
333                                                                  334
TABLE 165
| 480 | 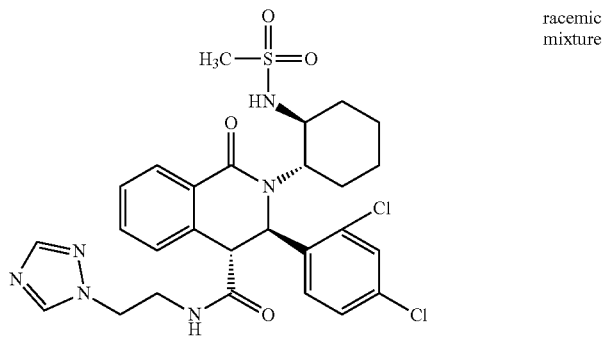 | racemic mixture |
| 481 | 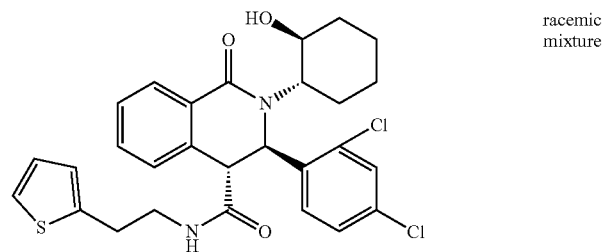 | racemic mixture |
| 482 | 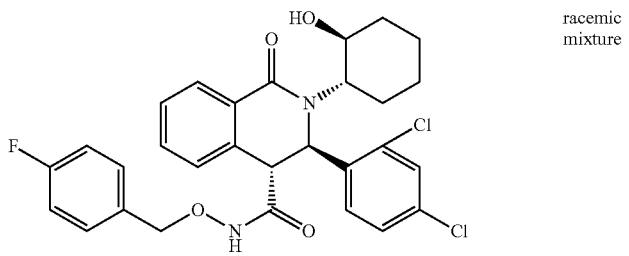 | racemic mixture |
| 483 | 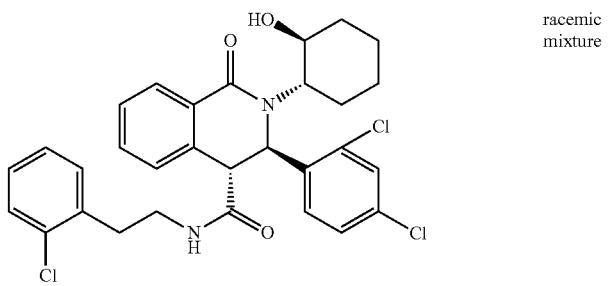 | racemic mixture |
| 484 | 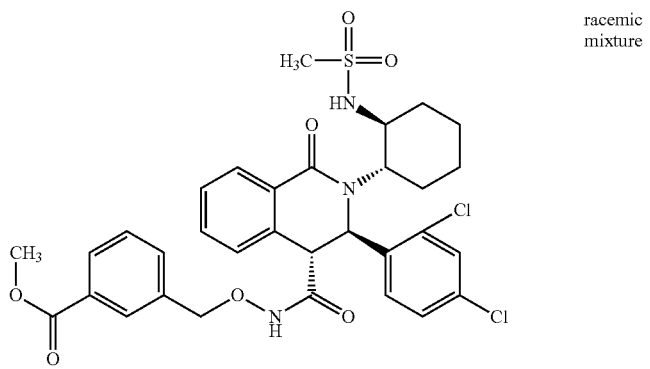 | racemic mixture |

TABLE 166
| | | |
|---|---|---|
| 485 | 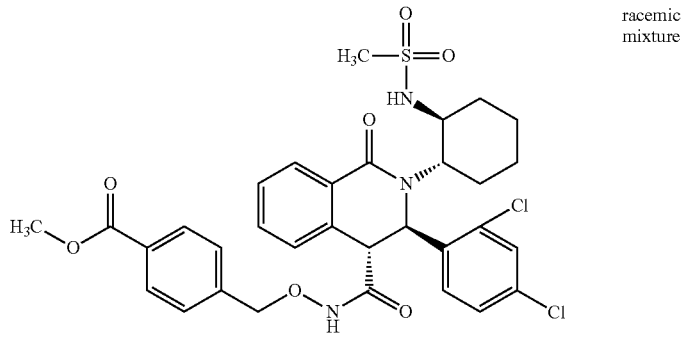 | racemic mixture |
| 486 | 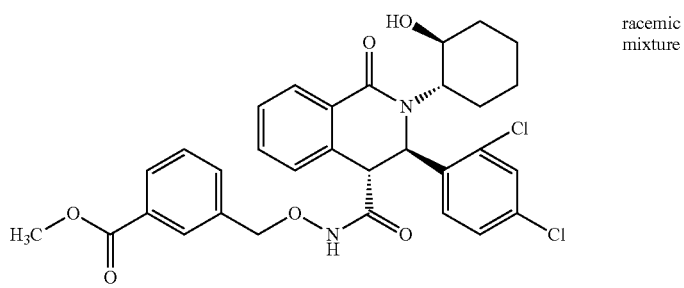 | racemic mixture |
| 487 | 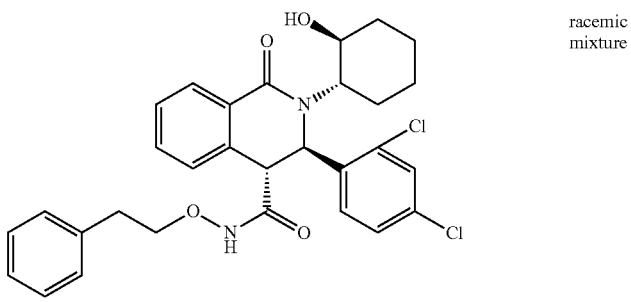 | racemic mixture |
| 488 | 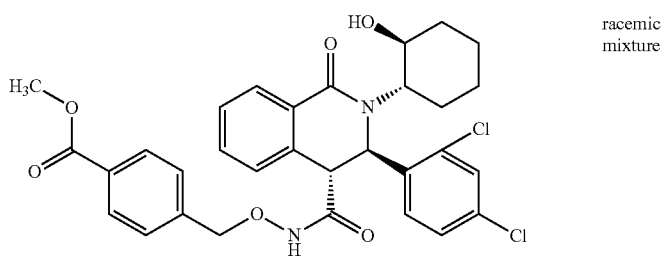 | racemic mixture |
| 489 | 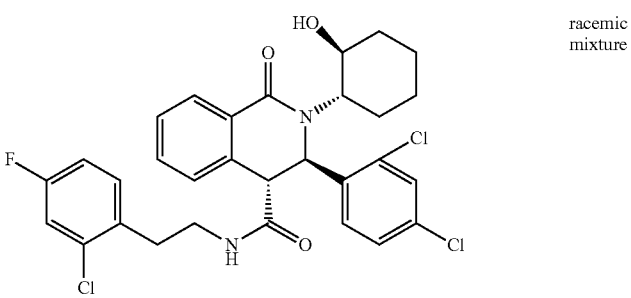 | racemic mixture |

TABLE 167
| | | |
|---|---|---|
| 490 | 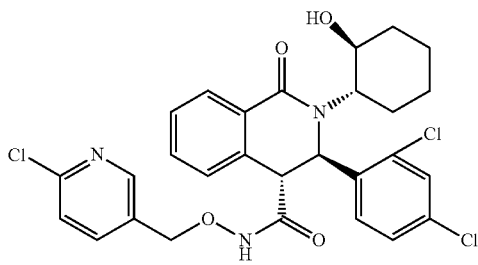 [SMILES: O=C(NOCc1ccc(Cl)nc1)[C@@H]1c2ccccc2C(=O)N([C@H]2CCCC[C@@H]2O)[C@H]1c1ccc(Cl)cc1Cl] | racemic mixture |
| 491 | 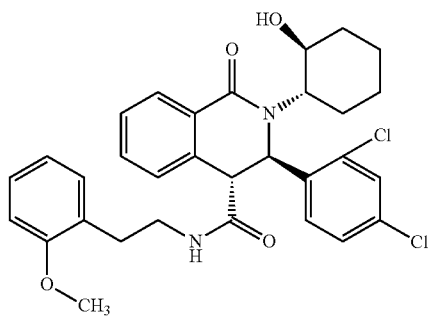 [SMILES: COc1ccccc1CCNC(=O)[C@@H]1c2ccccc2C(=O)N([C@H]2CCCC[C@@H]2O)[C@H]1c1ccc(Cl)cc1Cl] | racemic mixture |
| 492 | 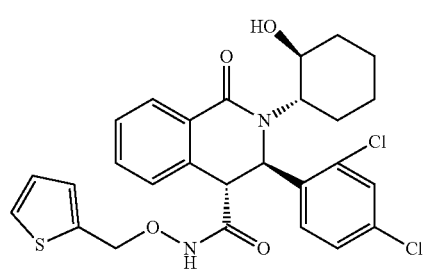 [SMILES: O=C(NOCc1cccs1)[C@@H]1c2ccccc2C(=O)N([C@H]2CCCC[C@@H]2O)[C@H]1c1ccc(Cl)cc1Cl] | racemic mixture |
| 493 | 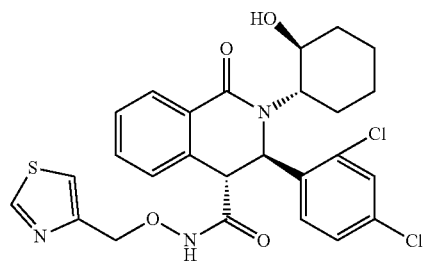 [SMILES: O=C(NOCc1cscn1)[C@@H]1c2ccccc2C(=O)N([C@H]2CCCC[C@@H]2O)[C@H]1c1ccc(Cl)cc1Cl] | racemic mixture |
| 494 | 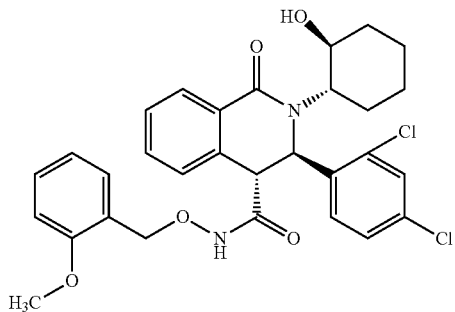 [SMILES: COc1ccccc1CONC(=O)[C@@H]1c2ccccc2C(=O)N([C@H]2CCCC[C@@H]2O)[C@H]1c1ccc(Cl)cc1Cl] | racemic mixture |

TABLE 168
| | | |
|---|---|---|
| 495 | 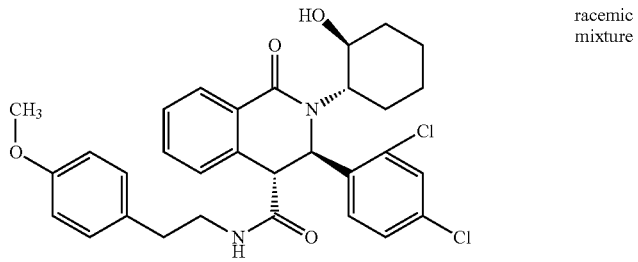 | racemic mixture |
| 496 | 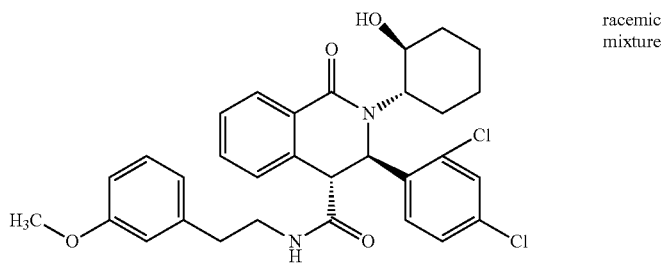 | racemic mixture |
| 497 | 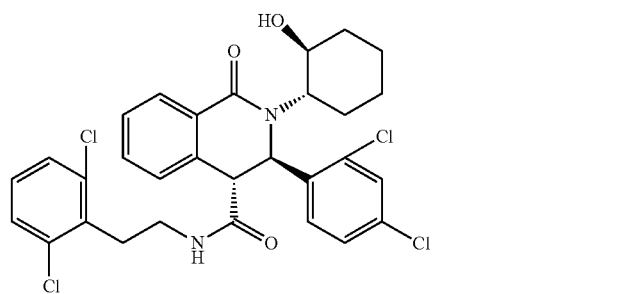 [SMILES: O=C(NCCc1c(Cl)cccc1Cl)[C@@H]1c2ccccc2C(=O)N([C@H]2CCCC[C@@H]2O)[C@H]1c1ccc(Cl)cc1Cl] | racemic mixture |
| 498 | 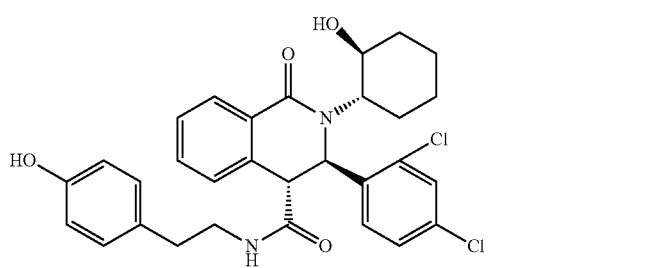 [SMILES: O=C(NCCc1ccc(O)cc1)[C@@H]1c2ccccc2C(=O)N([C@H]2CCCC[C@@H]2O)[C@H]1c1ccc(Cl)cc1Cl] | racemic mixture |
| 499 | 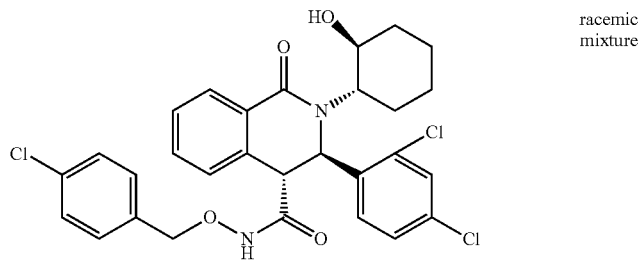 | racemic mixture |

TABLE 169
| | | |
|---|---|---|
| 500 | 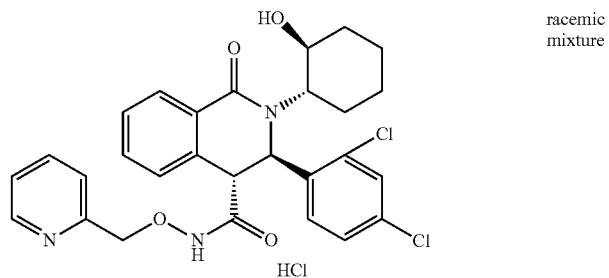 | racemic mixture |
| 501 | 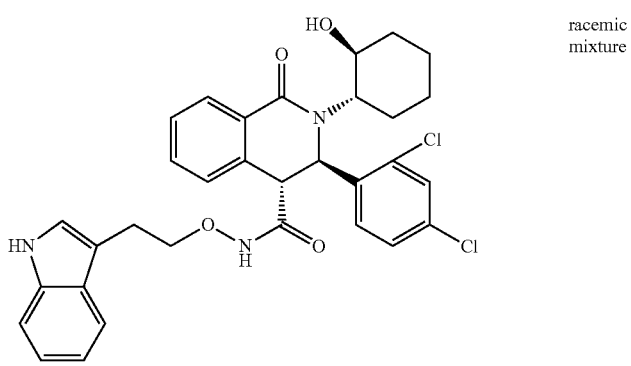 | racemic mixture |
| 502 | 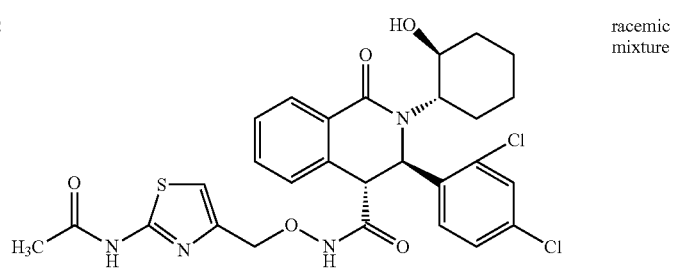 | racemic mixture |
| 503 | 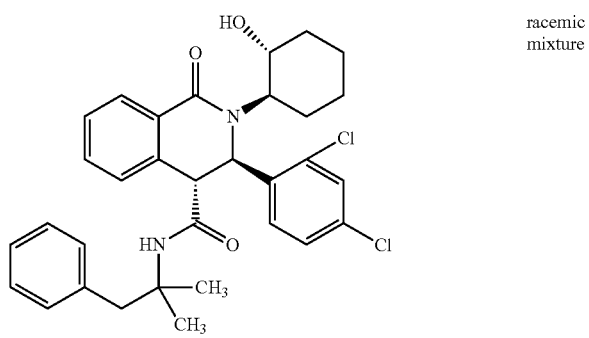 | racemic mixture |
| 504 | 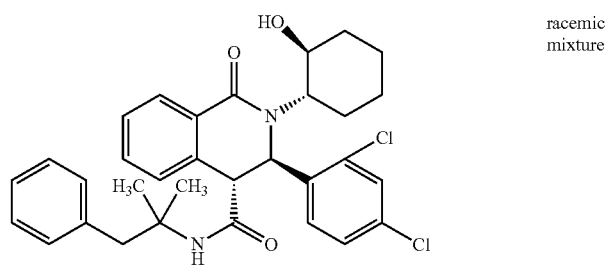 | racemic mixture |

TABLE 170
| | | |
|---|---|---|
| 505 | 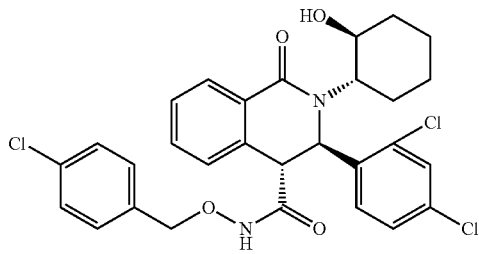 | racemic mixture |
| 506 | 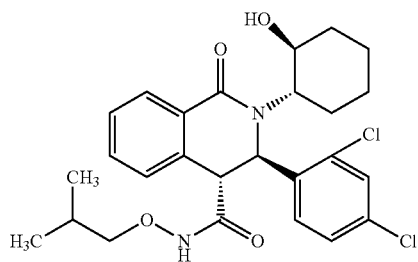 [SMILES: CC(C)CONC(=O)[C@@H]1c2ccccc2C(=O)N([C@H]2CCCC[C@@H]2O)[C@H]1c1ccc(Cl)cc1Cl] | racemic mixture |
| 507 | 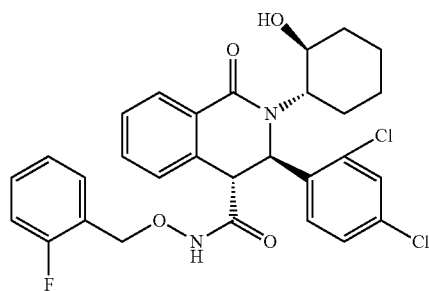 [SMILES: O=C(NOCc1ccccc1F)[C@@H]1c2ccccc2C(=O)N([C@H]2CCCC[C@@H]2O)[C@H]1c1ccc(Cl)cc1Cl] | racemic mixture |
| 32 | 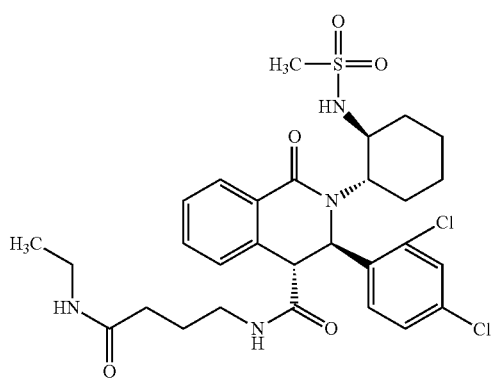 [SMILES: CCNC(=O)CCCNC(=O)[C@@H]1c2ccccc2C(=O)N([C@H]2CCCC[C@@H]2NS(C)(=O)=O)[C@H]1c1ccc(Cl)cc1Cl] | racemic mixture |

TABLE 171
| 508 | 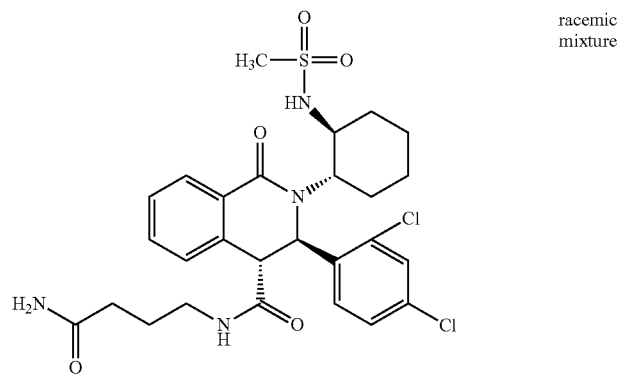 | racemic mixture |
| --- | --- | --- |
| 509 | 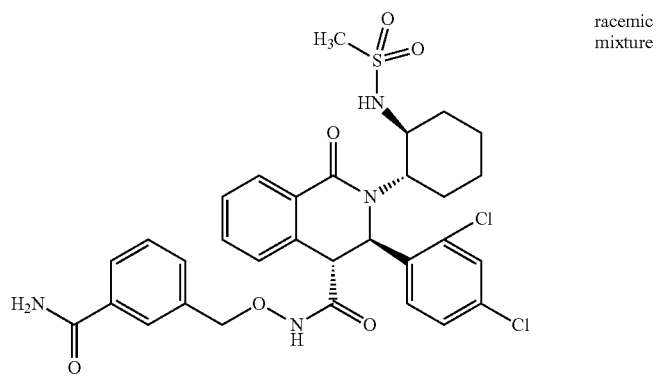 | racemic mixture |
| 510 | 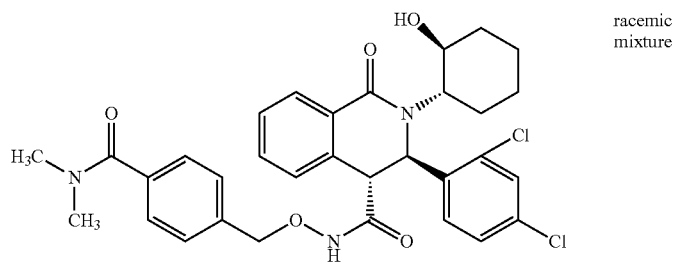 | racemic mixture |
| 511 | 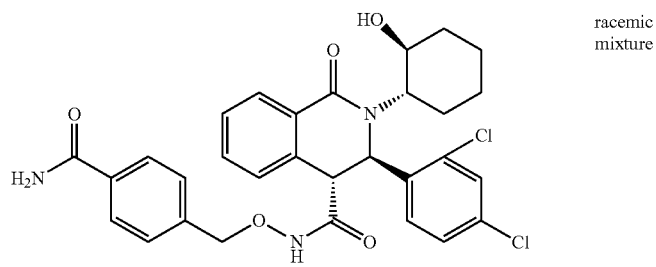 | racemic mixture |
| 512 | 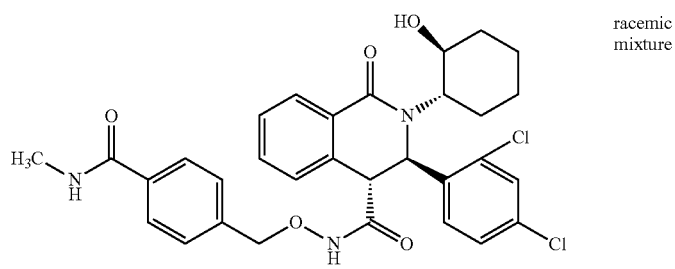 | racemic mixture |

TABLE 172
| 513 | 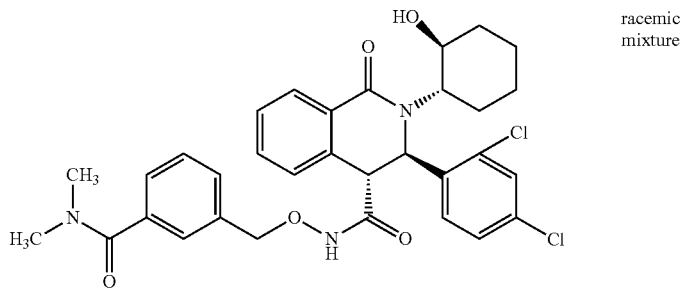 | racemic mixture |
|---|---|---|
| 514 | 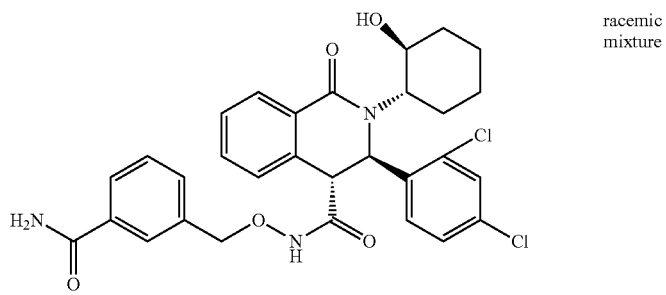 | racemic mixture |
| 515 | 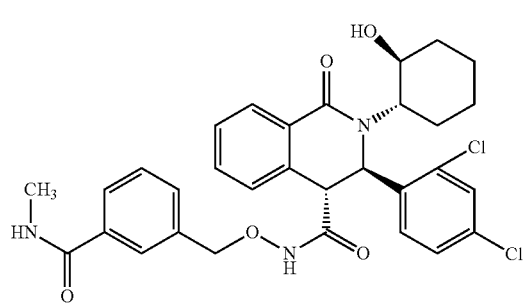 [SMILES: CNC(=O)c1cccc(CONC(=O)[C@@H]2c3ccccc3C(=O)N([C@H]3CCCC[C@@H]3O)[C@H]2c2ccc(Cl)cc2Cl)c1] | racemic mixture |
| 33 | 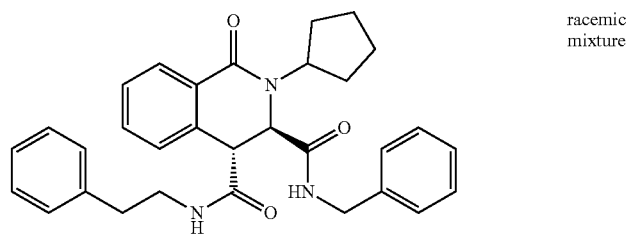 | racemic mixture |
| 516 | 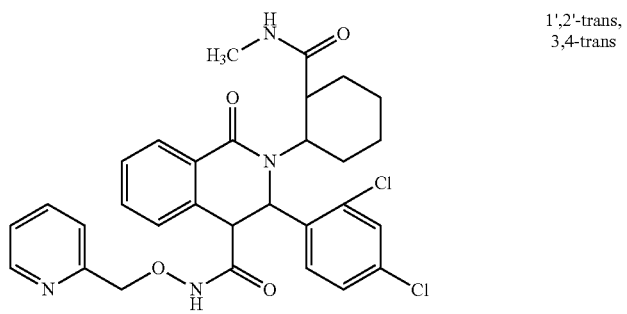 | 1',2'-trans, 3,4-trans |

TABLE 173
| | | |
|---|---|---|
| 517 | 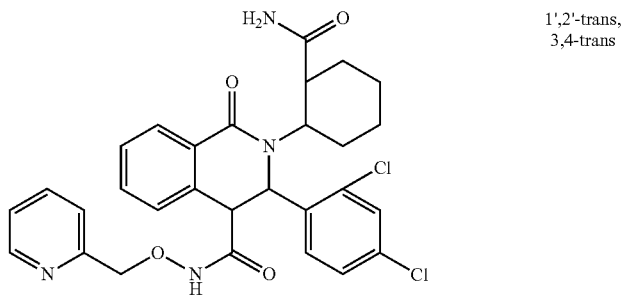 | 1',2'-trans, 3,4-trans |
| 518 | 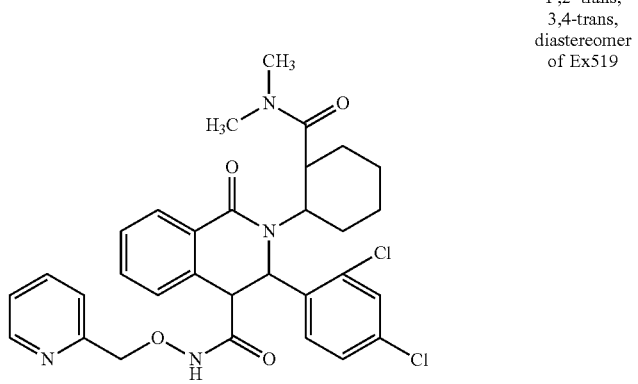 | 1',2'-trans, 3,4-trans, diastereomer of Ex519 |
| 519 | 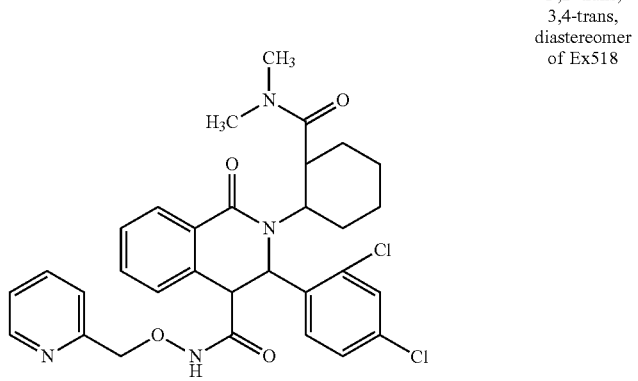 | 1',2'-trans, 3,4-trans, diastereomer of Ex518 |
| 520 | 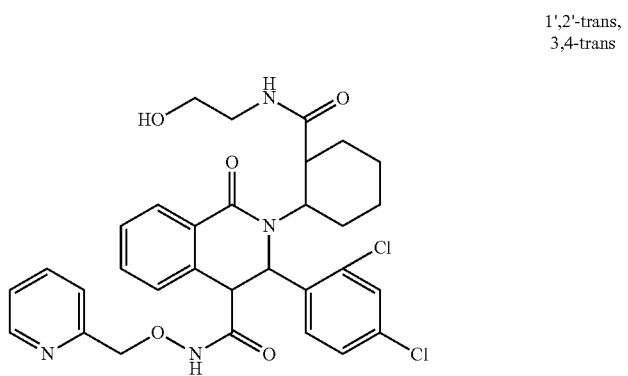 | 1',2'-trans, 3,4-trans |

TABLE 174
| | | |
|---|---|---|
| 521 | 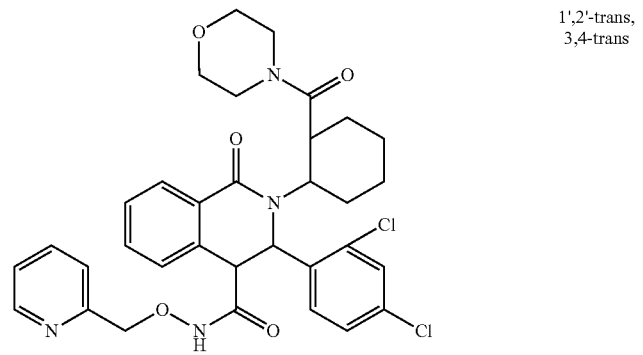 | 1',2'-trans, 3,4-trans |
| 522 | 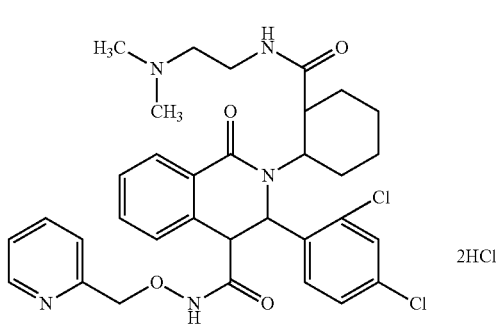 [SMILES: CN(C)CCNC(=O)C1CCCCC1N1C(=O)c2ccccc2C(C(=O)NOCc2ccccn2)C1c1ccc(Cl)cc1Cl] 2HCl | 1',2'-trans, 3,4-trans |
| 523 | 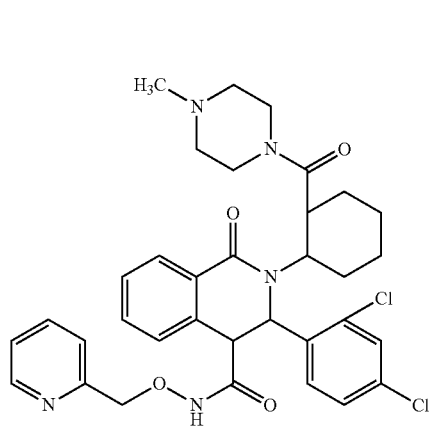 [SMILES: CN1CCN(C(=O)C2CCCCC2N2C(=O)c3ccccc3C(C(=O)NOCc3ccccn3)C2c2ccc(Cl)cc2Cl)CC1] | 1',2'-trans, 3,4-trans |
| 524 | 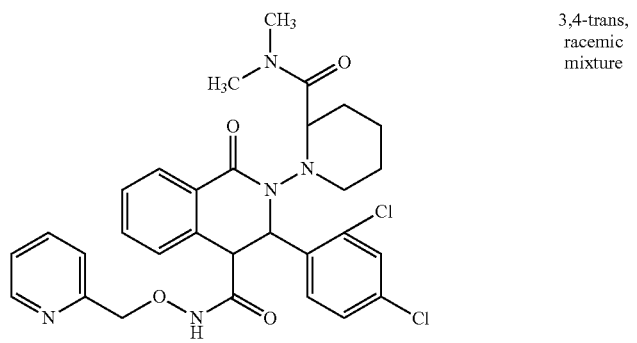 | 3,4-trans, racemic mixture |

TABLE 175
| | | |
|---|---|---|
| 525 | 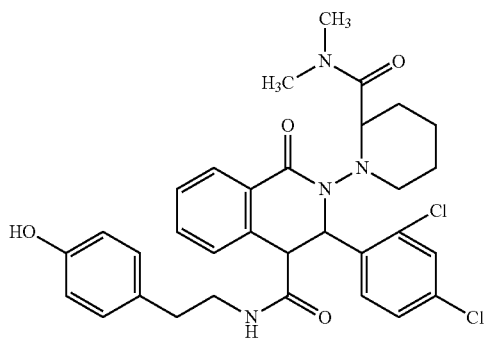 [SMILES: CN(C)C(=O)C1CCCCN1N1C(=O)c2ccccc2C(C(=O)NCCc2ccc(O)cc2)C1c1ccc(Cl)cc1Cl] | 3,4-trans |
| 526 | 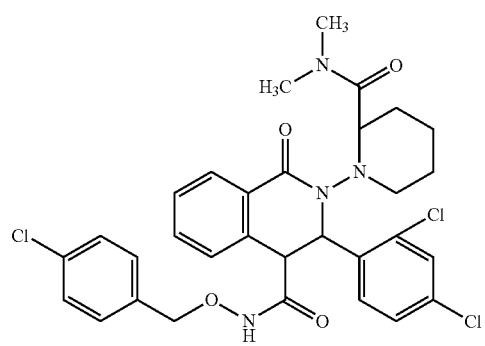 [SMILES: CN(C)C(=O)C1CCCCN1N1C(=O)c2ccccc2C(C(=O)NOCc2ccc(Cl)cc2)C1c1ccc(Cl)cc1Cl] | 3,4-trans |
| 35 | 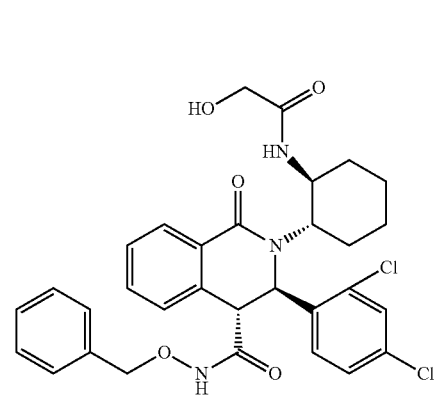 [SMILES: O=C(CO)N[C@H]1CCCC[C@@H]1N1C(=O)c2ccccc2[C@@H](C(=O)NOCc2ccccc2)[C@@H]1c1ccc(Cl)cc1Cl] | racemic mixture |
| 527 | 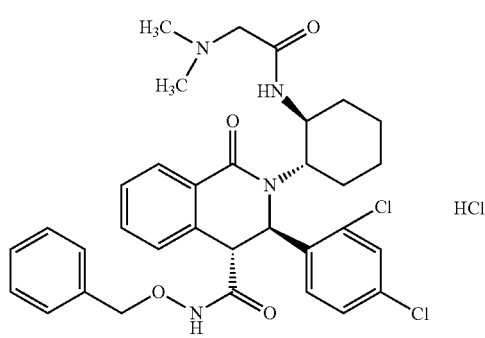 [SMILES: CN(C)CC(=O)N[C@H]1CCCC[C@@H]1N1C(=O)c2ccccc2[C@@H](C(=O)NOCc2ccccc2)[C@@H]1c1ccc(Cl)cc1Cl ; Cl] HCl | racemic mixture |

TABLE 176
528 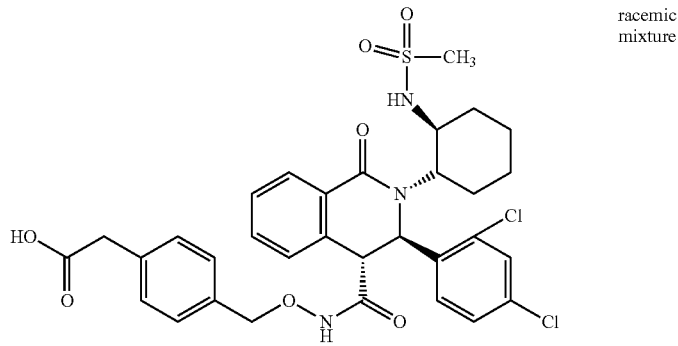 racemic mixture
529 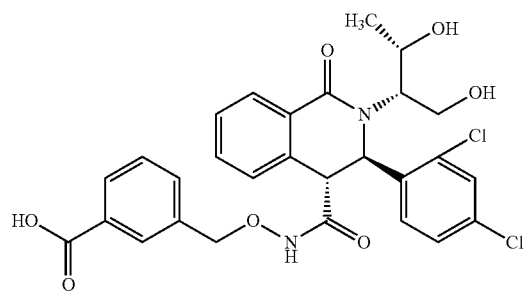 [SMILES: C[C@H](O)[C@H](CO)N1C(=O)c2ccccc2[C@@H](C(=O)NOCc2cccc(C(=O)O)c2)[C@@H]1c1ccc(Cl)cc1Cl]
530 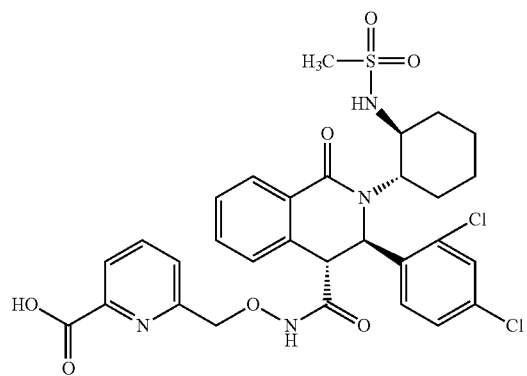 racemic mixture
531 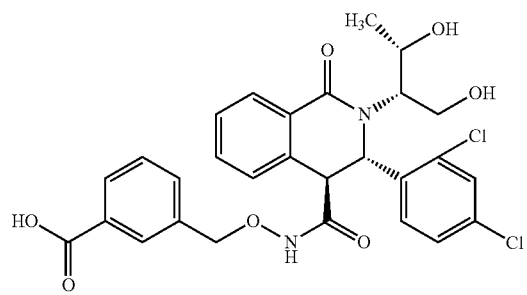 [SMILES: C[C@H](O)[C@H](CO)N1C(=O)c2ccccc2[C@H](C(=O)NOCc2cccc(C(=O)O)c2)[C@H]1c1ccc(Cl)cc1Cl]

TABLE 177
532 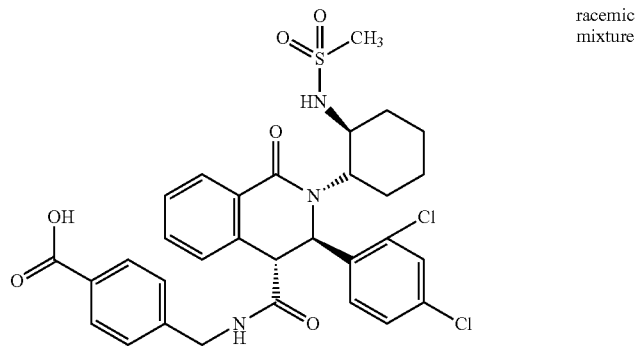 racemic mixture
533 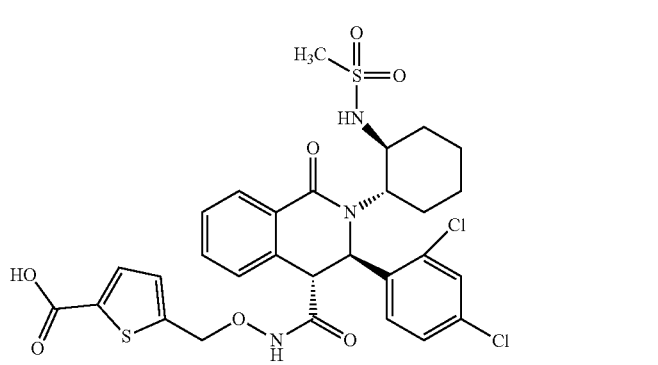 racemic mixture
534 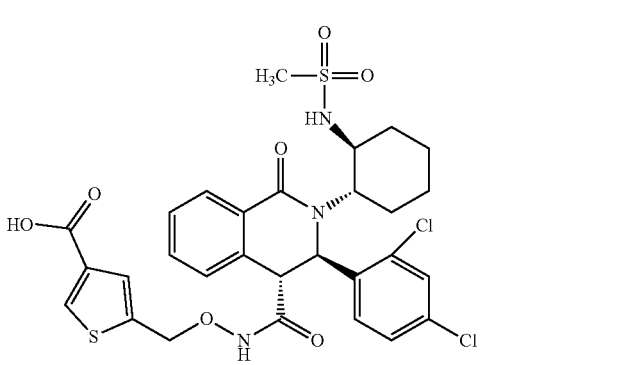 [SMILES: CS(=O)(=O)N[C@H]1CCCC[C@@H]1N1C(=O)c2ccccc2[C@@H](C(=O)NOCc2cc(C(=O)O)cs2)[C@@H]1c1ccc(Cl)cc1Cl] racemic mixture
535 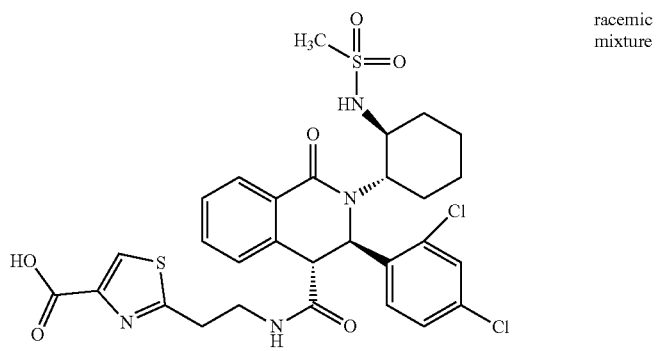 racemic mixture TABLE 178
| 536 | 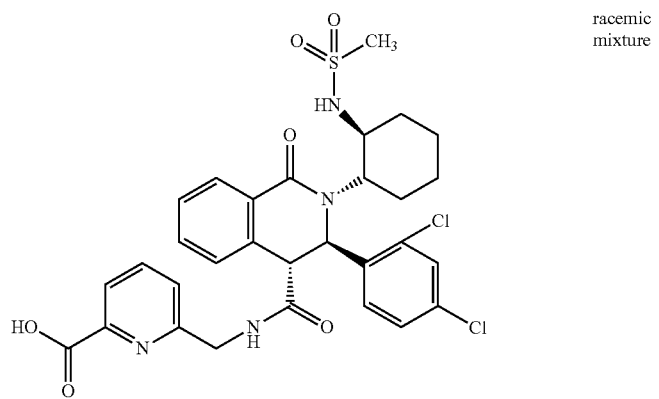 | racemic mixture |
| --- | --- | --- |
| 537 | 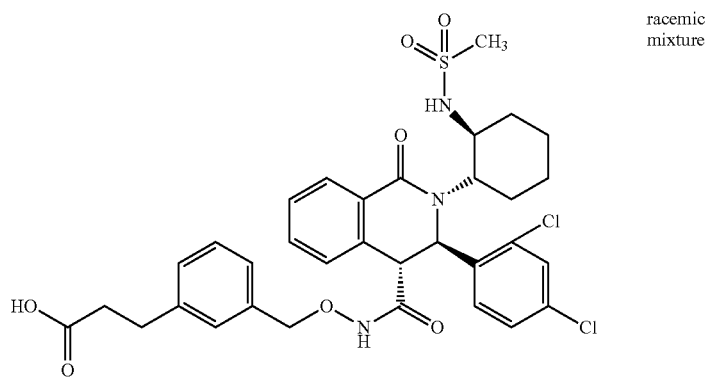 | racemic mixture |
| 538 | 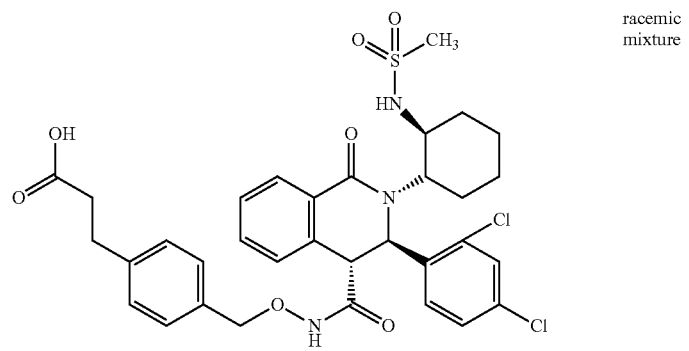 | racemic mixture |
| 539 | 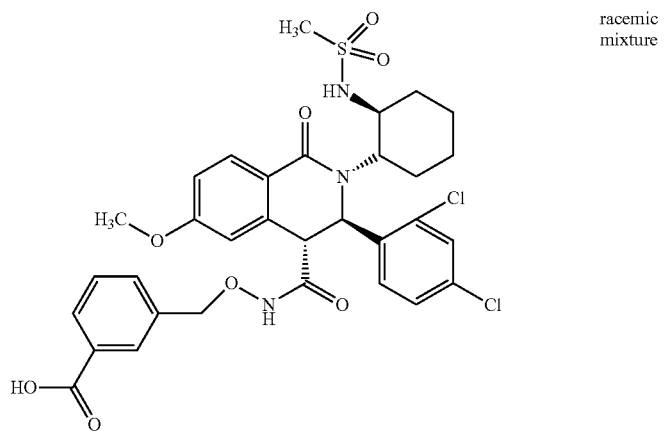 | racemic mixture |

TABLE 179
540 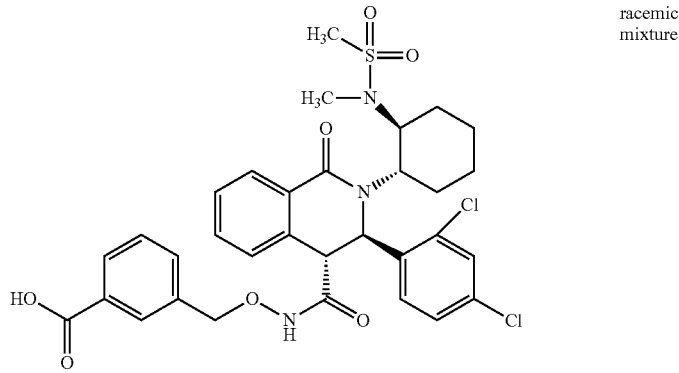 racemic mixture
541 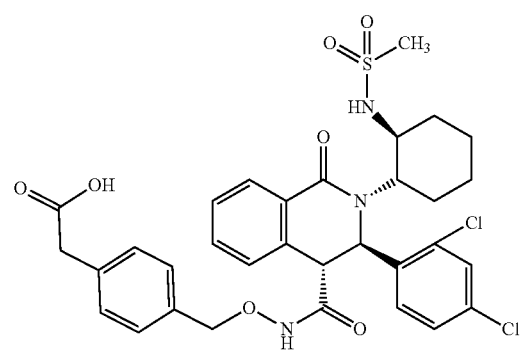
542 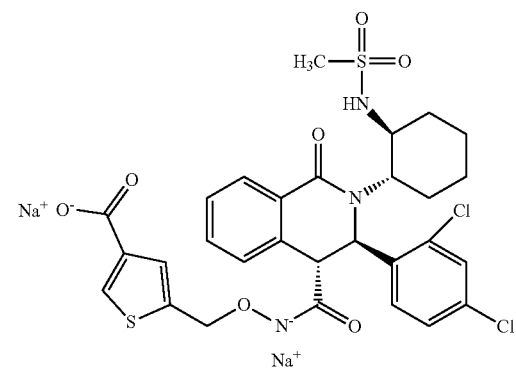 [SMILES: [Na+] ; CS(=O)(=O)N[C@H]1CCCC[C@@H]1N1C(=O)c2ccccc2[C@@H](C(=O)[N-]OCc2cc(C(=O)[O-])cs2)[C@@H]1c1ccc(Cl)cc1Cl ; [Na+]]
543 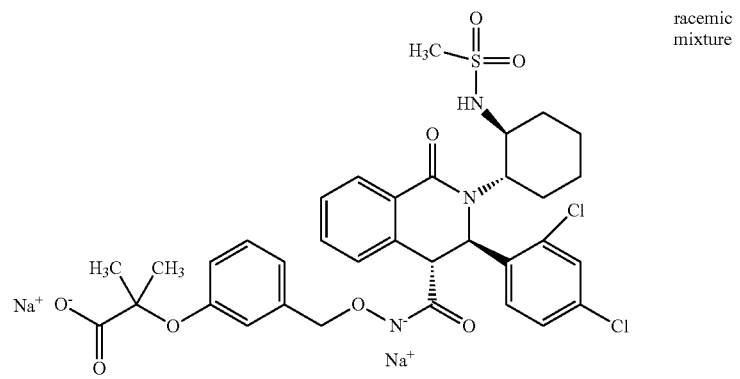 racemic mixture

TABLE 180
| | | |
|---|---|---|
| 544 | 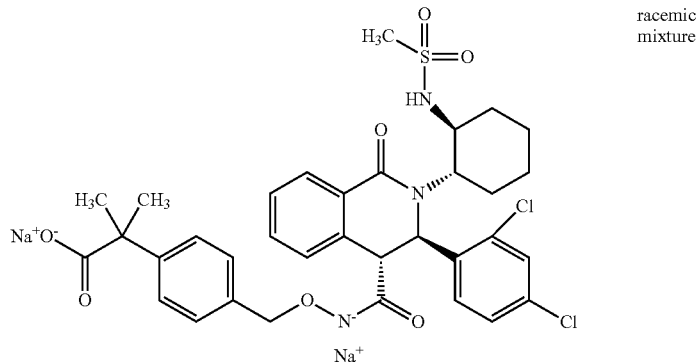 | racemic mixture |
| 545 | 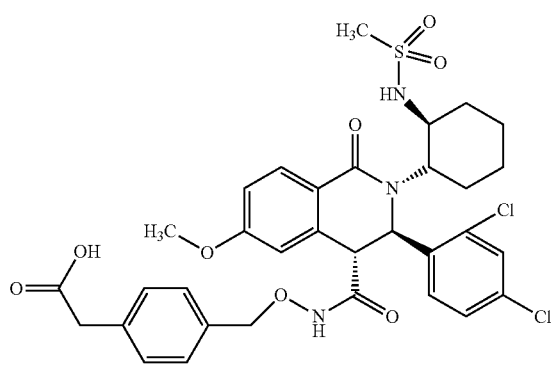 | racemic mixture |
| 546 | 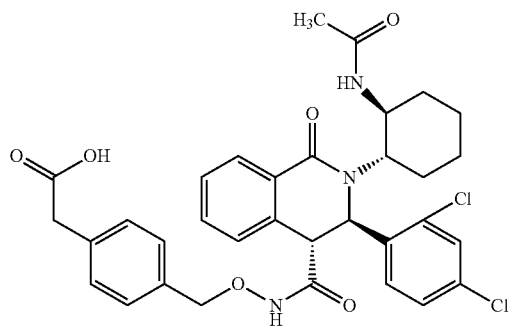 [SMILES: CC(=O)N[C@H]1CCCC[C@@H]1N1C(=O)c2ccccc2[C@@H](C(=O)NOCc2ccc(CC(=O)O)cc2)[C@@H]1c1ccc(Cl)cc1Cl] | racemic mixture |
| 547 | 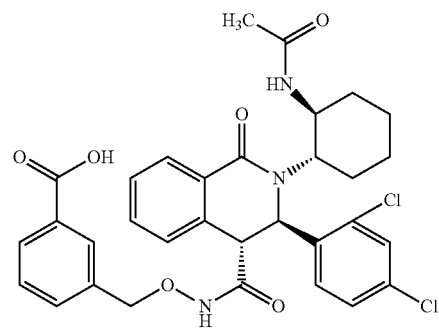 [SMILES: CC(=O)N[C@H]1CCCC[C@@H]1N1C(=O)c2ccccc2[C@@H](C(=O)NOCc2cccc(C(=O)O)c2)[C@@H]1c1ccc(Cl)cc1Cl] | racemic mixture |

TABLE 181
| 548 | 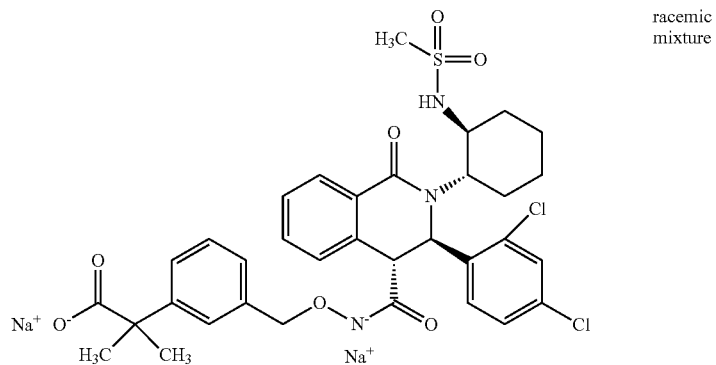 | racemic mixture |
|---|---|---|
| 549 | 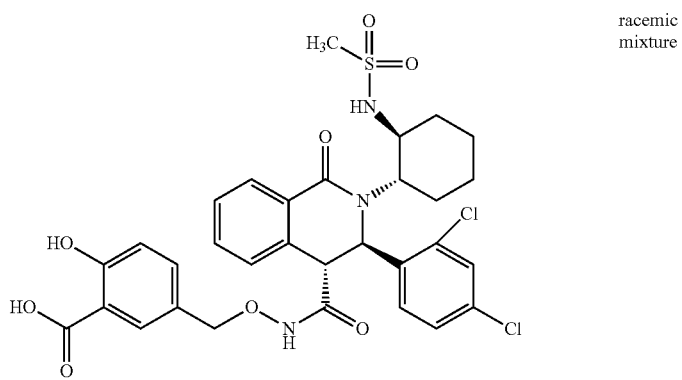 | racemic mixture |
| 550 | 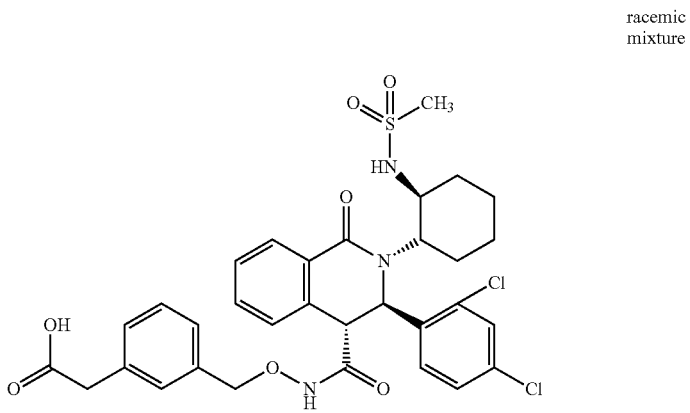 | racemic mixture |
| 551 | 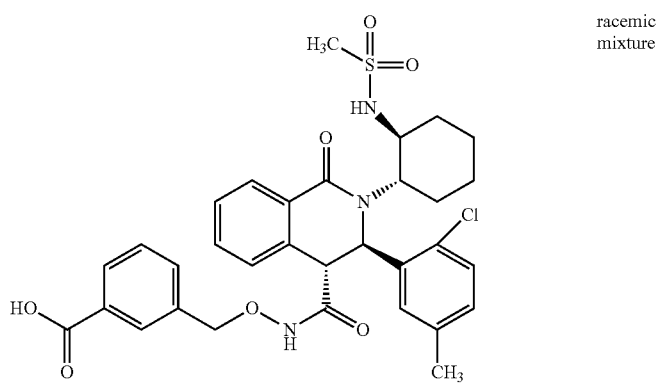 | racemic mixture |

TABLE 182
| | | |
|---|---|---|
| 552 | 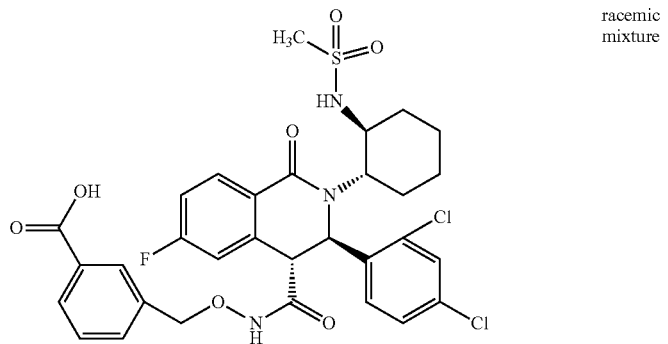 | racemic mixture |
| 553 | 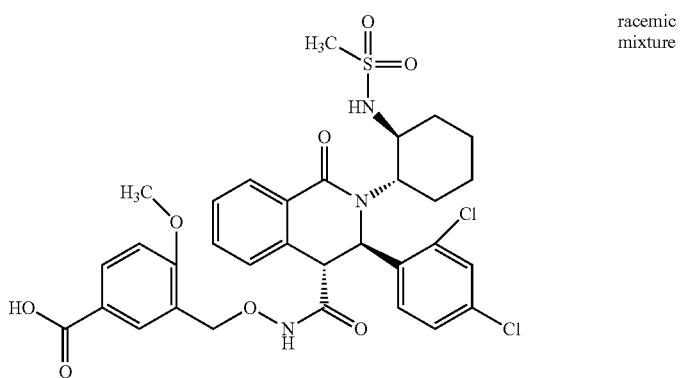 | racemic mixture |
| 554 | 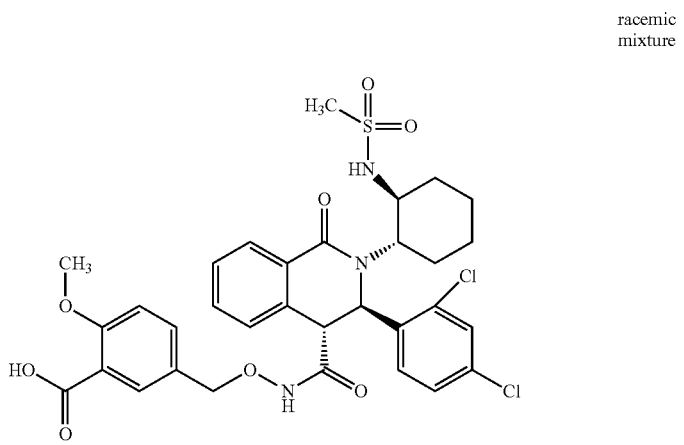 | racemic mixture |
| 555 | 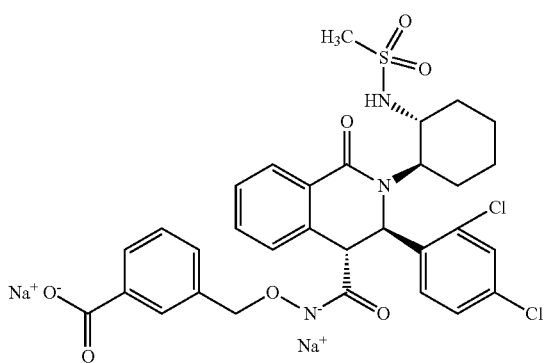 | |

TABLE 183
556 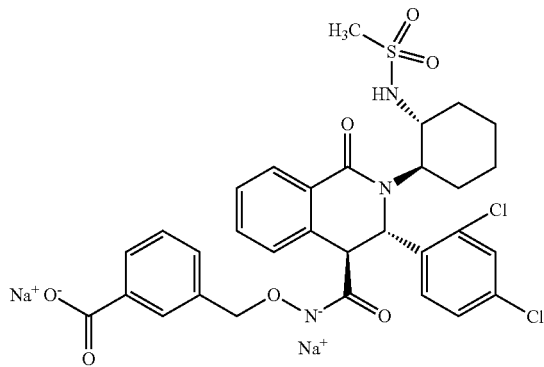
557 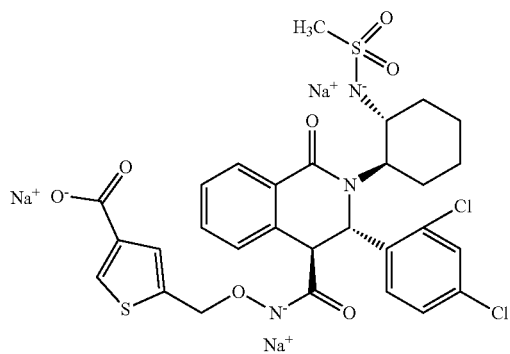 [SMILES: [Na+] ; CS(=O)(=O)[N-][C@@H]1CCCC[C@H]1N1C(=O)c2ccccc2[C@H](C(=O)[N-]OCc2cc(C(=O)[O-])cs2)[C@H]1c1ccc(Cl)cc1Cl ; [Na+] ; [Na+]]
558 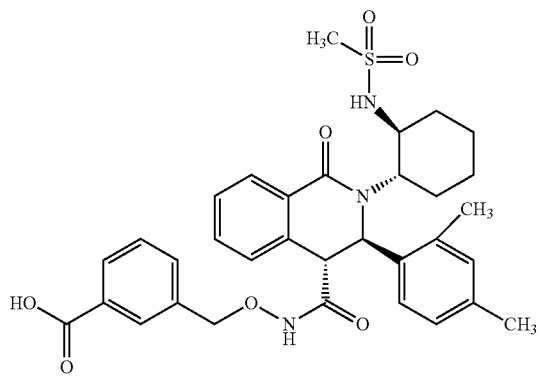 [SMILES: Cc1ccc([C@H]2[C@H](C(=O)NOCc3cccc(C(=O)O)c3)c3ccccc3C(=O)N2[C@H]2CCCC[C@@H]2NS(C)(=O)=O)c(C)c1] racemic mixture
559 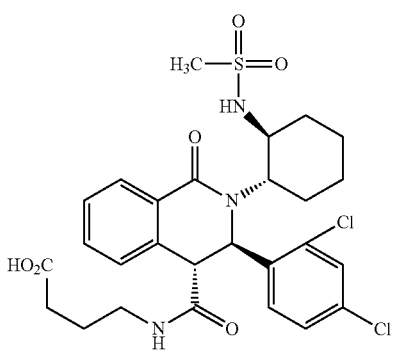 [SMILES: CS(=O)(=O)N[C@H]1CCCC[C@@H]1N1C(=O)c2ccccc2[C@@H](C(=O)NCCCC(=O)O)[C@@H]1c1ccc(Cl)cc1Cl] racemic mixture TABLE 184
560 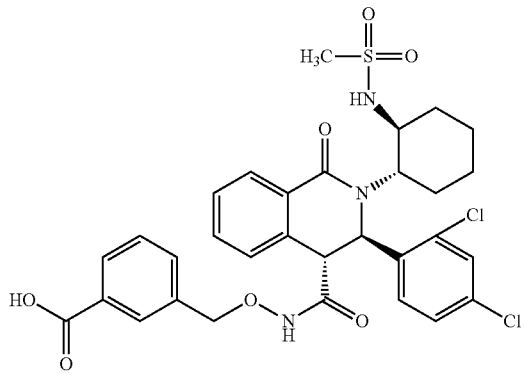 [SMILES: CS(=O)(=O)N[C@H]1CCCC[C@@H]1N1C(=O)c2ccccc2[C@@H](C(=O)NOCc2cccc(C(=O)O)c2)[C@@H]1c1ccc(Cl)cc1Cl]
561 racemic mixture
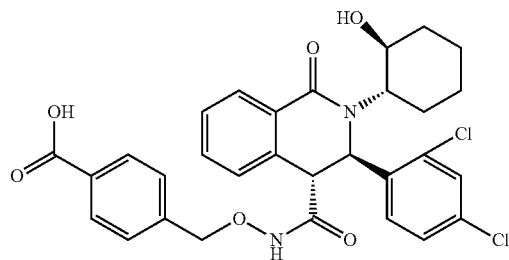 [SMILES: O=C(O)c1ccc(CONC(=O)[C@@H]2c3ccccc3C(=O)N([C@H]3CCCC[C@@H]3O)[C@H]2c2ccc(Cl)cc2Cl)cc1]
562 racemic mixture
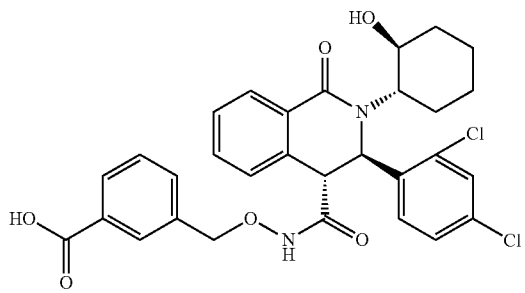 [SMILES: O=C(O)c1cccc(CONC(=O)[C@@H]2c3ccccc3C(=O)N([C@H]3CCCC[C@@H]3O)[C@H]2c2ccc(Cl)cc2Cl)c1]
563 racemic mixture
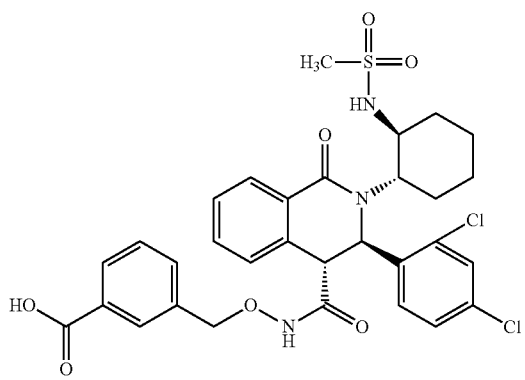 [SMILES: CS(=O)(=O)N[C@H]1CCCC[C@@H]1N1C(=O)c2ccccc2[C@@H](C(=O)NOCc2cccc(C(=O)O)c2)[C@@H]1c1ccc(Cl)cc1Cl]

TABLE 185
564 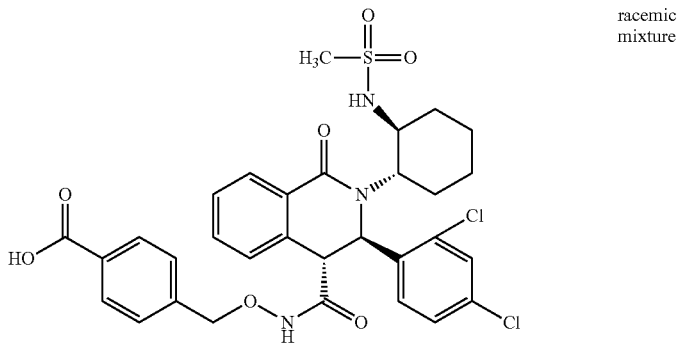 racemic mixture
565 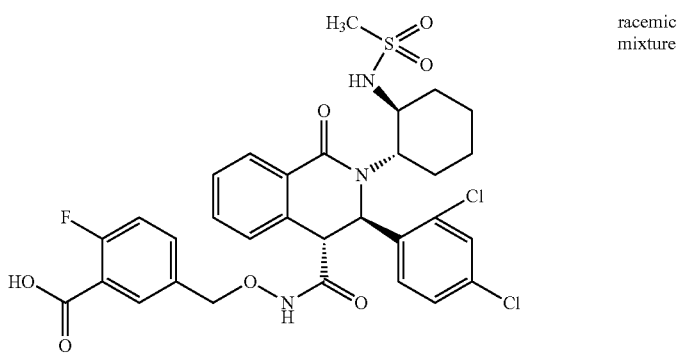 racemic mixture
566 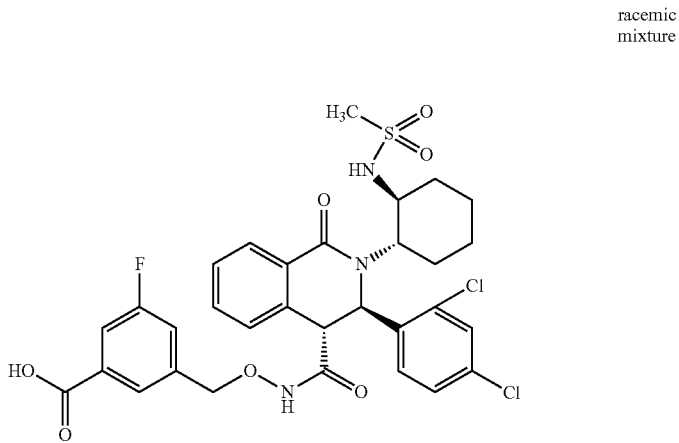 racemic mixture
567 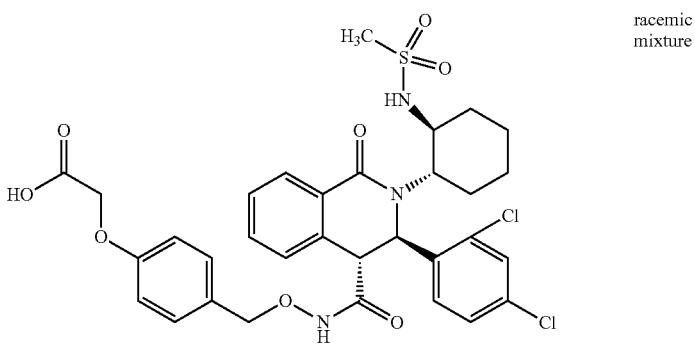 racemic mixture TABLE 186
| 568 | 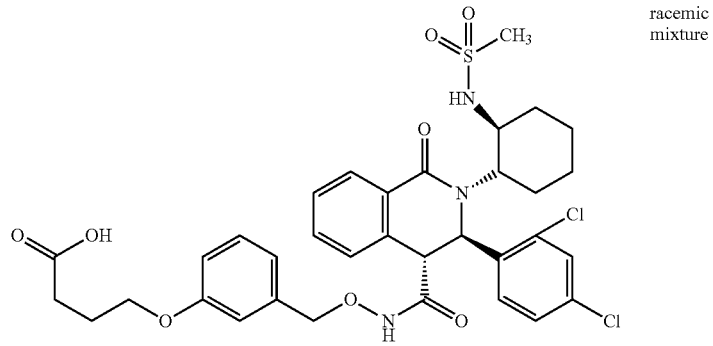 | racemic mixture |
| 569 | 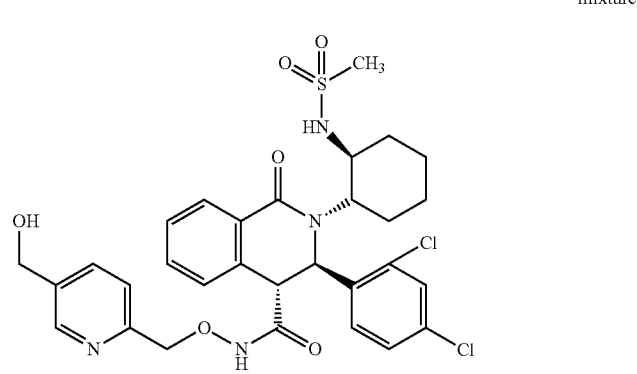 | racemic mixture |
| 570 | 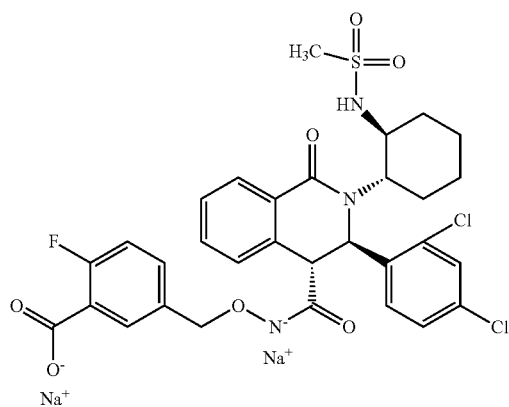 [SMILES: CS(=O)(=O)N[C@H]1CCCC[C@@H]1N1C(=O)c2ccccc2[C@@H](C(=O)[N-]OCc2ccc(F)c(C(=O)[O-])c2)[C@@H]1c1ccc(Cl)cc1Cl ; [Na+] ; [Na+]] | |
| 571 | 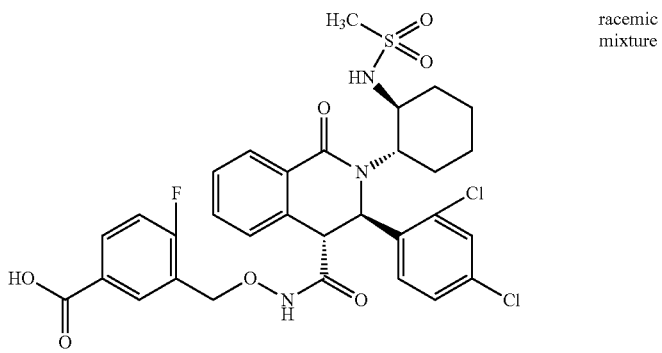 | racemic mixture |

TABLE 187
| | | |
|---|---|---|
| 572 | 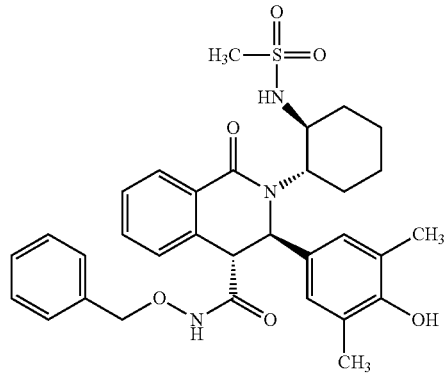 [SMILES: Cc1cc([C@H]2[C@H](C(=O)NOCc3ccccc3)c3ccccc3C(=O)N2[C@H]2CCCC[C@@H]2NS(C)(=O)=O)cc(C)c1O] | racemic mixture |
| 573 | 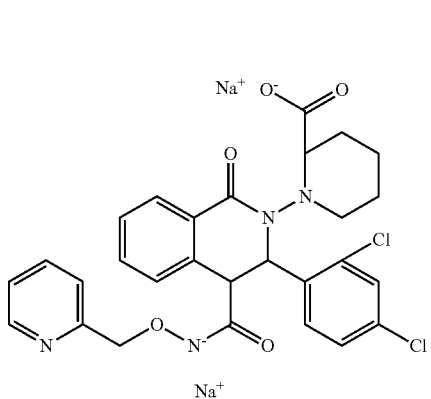 [SMILES: [Na+] ; O=C([N-]OCc1ccccn1)C1c2ccccc2C(=O)N(N2CCCCC2C(=O)[O-])C1c1ccc(Cl)cc1Cl ; [Na+]] | 3,4-trans racemic mixture |
| 574 | 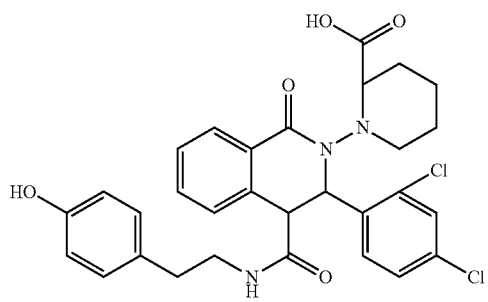 [SMILES: O=C(NCCc1ccc(O)cc1)C1c2ccccc2C(=O)N(N2CCCCC2C(=O)O)C1c1ccc(Cl)cc1Cl] | racemic mixture |
| 575 | 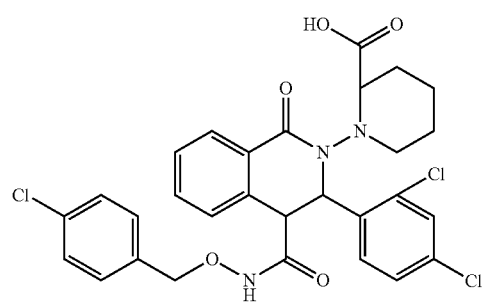 [SMILES: O=C(NOCc1ccc(Cl)cc1)C1c2ccccc2C(=O)N(N2CCCCC2C(=O)O)C1c1ccc(Cl)cc1Cl] | racemic mixture |

TABLE 188
| 576 | 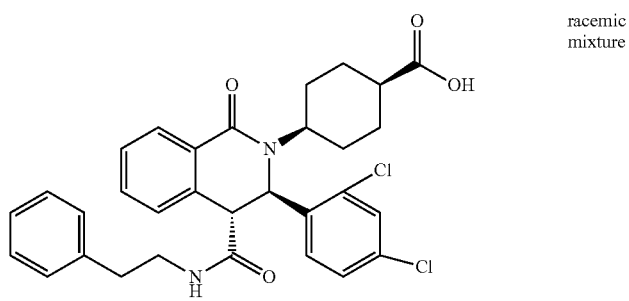 | racemic mixture |
| --- | --- | --- |
| 577 | 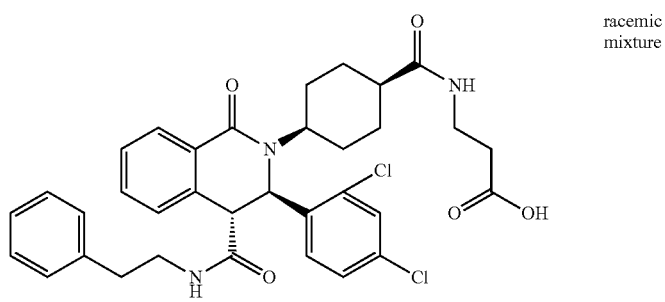 | racemic mixture |
| 578 | 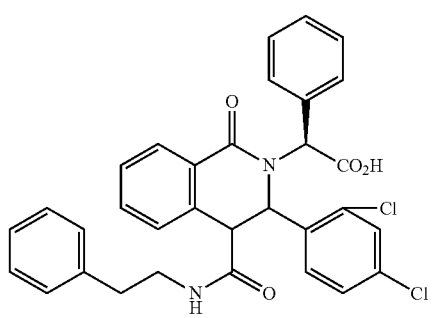 [SMILES: O=C(NCCc1ccccc1)C1c2ccccc2C(=O)N([C@H](C(=O)O)c2ccccc2)C1c1ccc(Cl)cc1Cl] | 3,4-trans |
| 16 | 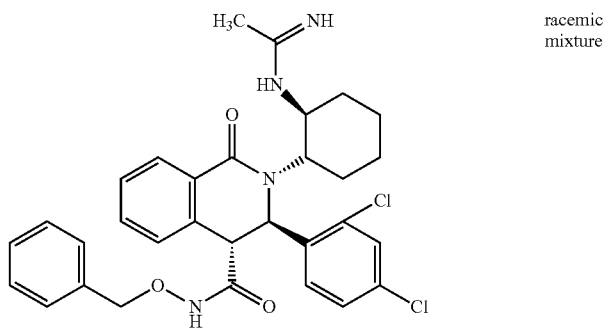 | racemic mixture |
| 15 | 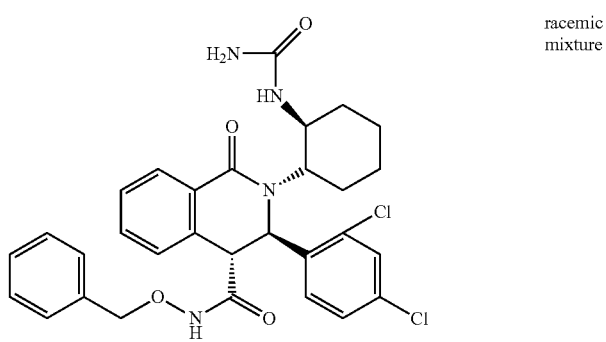 | racemic mixture |

TABLE 189
| | | |
|---|---|---|
| 22 | 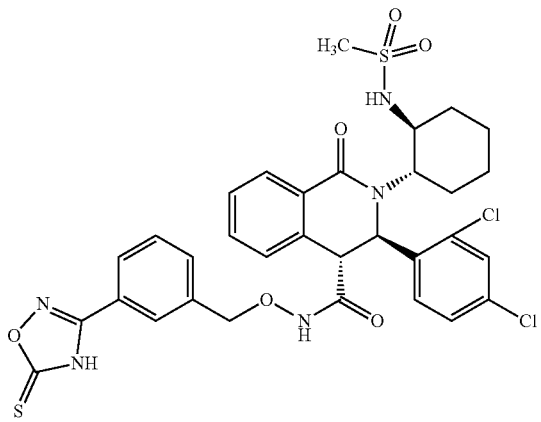 [SMILES: CS(=O)(=O)N[C@H]1CCCC[C@@H]1N1C(=O)c2ccccc2[C@@H](C(=O)NOCc2cccc(-c3noc(=S)[nH]3)c2)[C@@H]1c1ccc(Cl)cc1Cl] | racemic mixture |
| 43 | 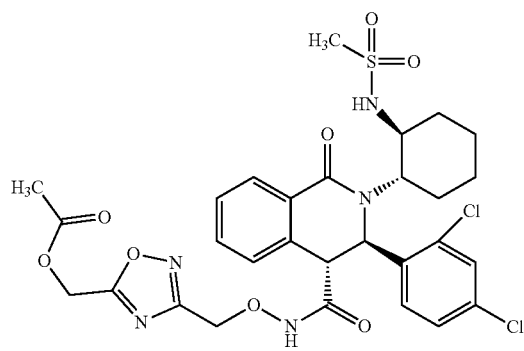 [SMILES: CC(=O)OCc1nc(CONC(=O)[C@@H]2c3ccccc3C(=O)N([C@H]3CCCC[C@@H]3NS(C)(=O)=O)[C@H]2c2ccc(Cl)cc2Cl)no1] | racemic mixture |
| 29 | 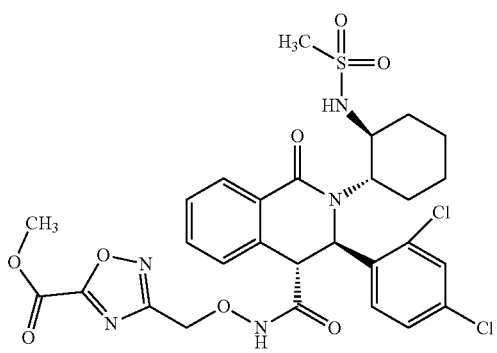 [SMILES: COC(=O)c1nc(CONC(=O)[C@@H]2c3ccccc3C(=O)N([C@H]3CCCC[C@@H]3NS(C)(=O)=O)[C@H]2c2ccc(Cl)cc2Cl)no1] | racemic mixture |

TABLE 190
| | | |
|---|---|---|
| 23 | 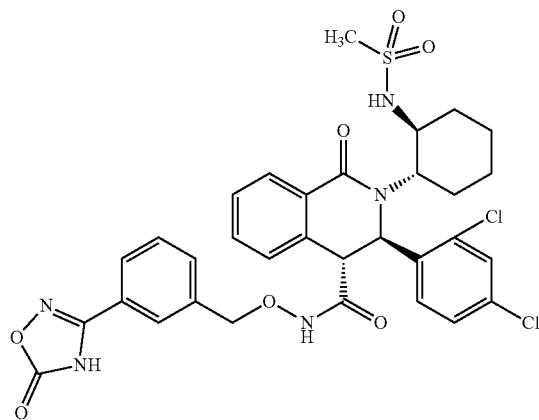 [SMILES: CS(=O)(=O)N[C@H]1CCCC[C@@H]1N1C(=O)c2ccccc2[C@@H](C(=O)NOCc2cccc(-c3noc(=O)[nH]3)c2)[C@@H]1c1ccc(Cl)cc1Cl] | racemic mixture |
| 41 | 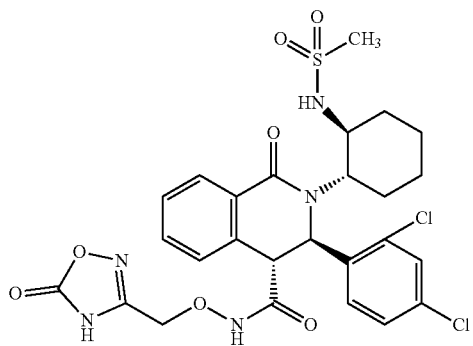 [SMILES: CS(=O)(=O)N[C@H]1CCCC[C@@H]1N1C(=O)c2ccccc2[C@@H](C(=O)NOCc2noc(=O)[nH]2)[C@@H]1c1ccc(Cl)cc1Cl] | racemic mixture |
| 579 | 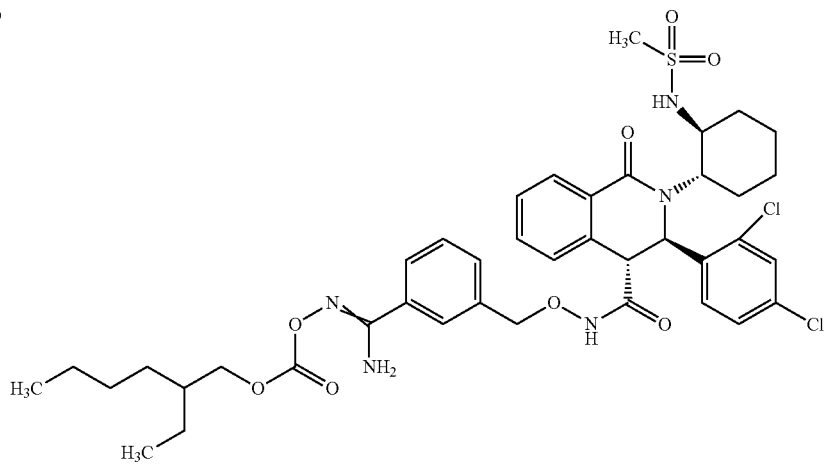 [SMILES: CCCCC(CC)COC(=O)ON=C(N)c1cccc(CONC(=O)[C@@H]2c3ccccc3C(=O)N([C@H]3CCCC[C@@H]3NS(C)(=O)=O)[C@H]2c2ccc(Cl)cc2Cl)c1] | racemic mixture |
| 13 | 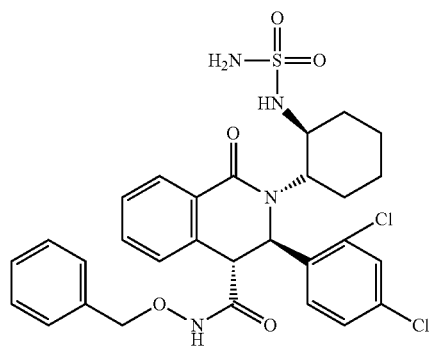 | racemic mixture |

TABLE 191
| | | |
|---|---|---|
| 580 | 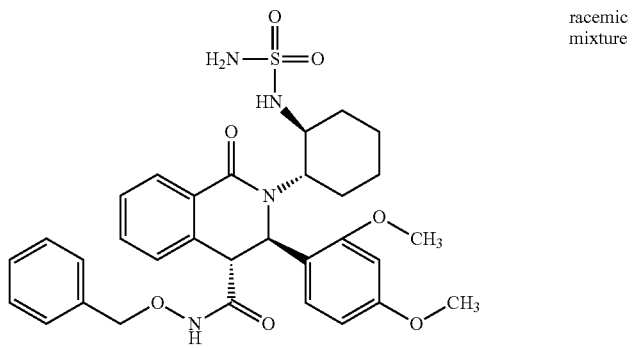 | racemic mixture |
| 581 | 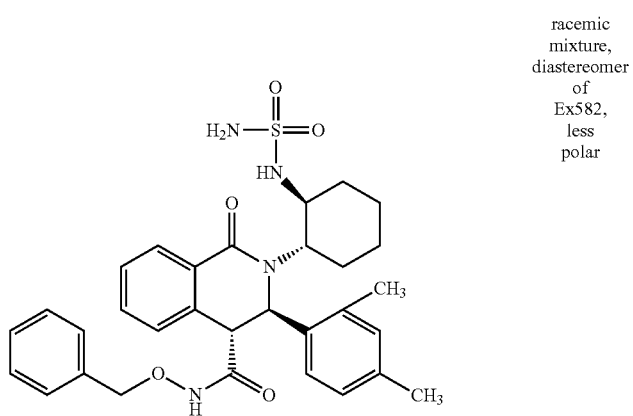 | racemic mixture, diastereomer of Ex582, less polar |
| 582 | 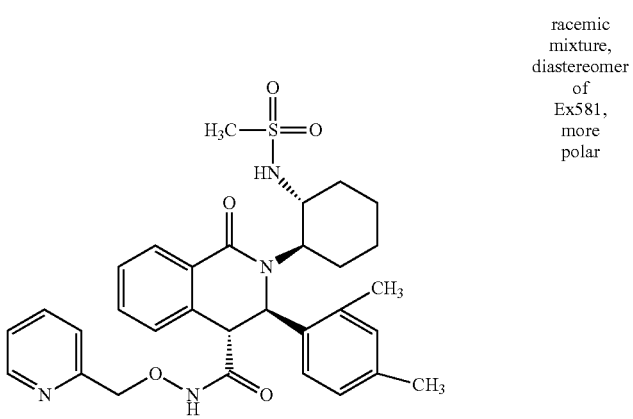 | racemic mixture, diastereomer of Ex581, more polar |
| 583 | 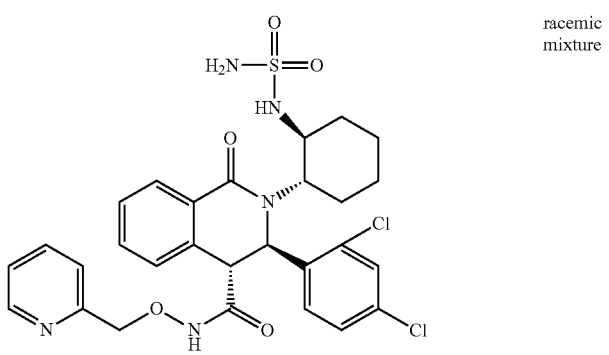 | racemic mixture |

TABLE 192
| | | |
|---|---|---|
| 14 | 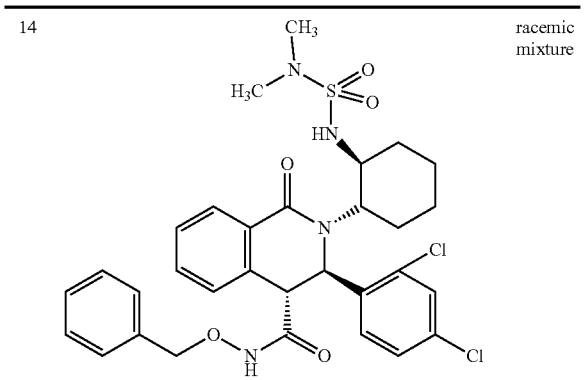 | racemic mixture |
| 584 | 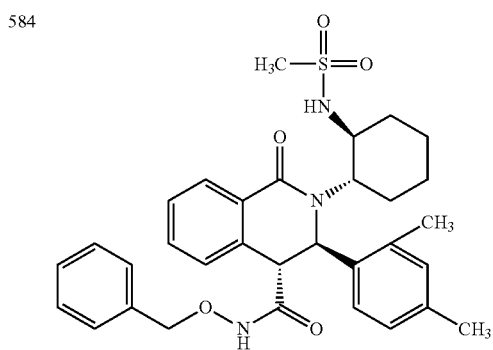 | racemic mixture |
TABLE 192-continued
| | | |
|---|---|---|
| 12 | 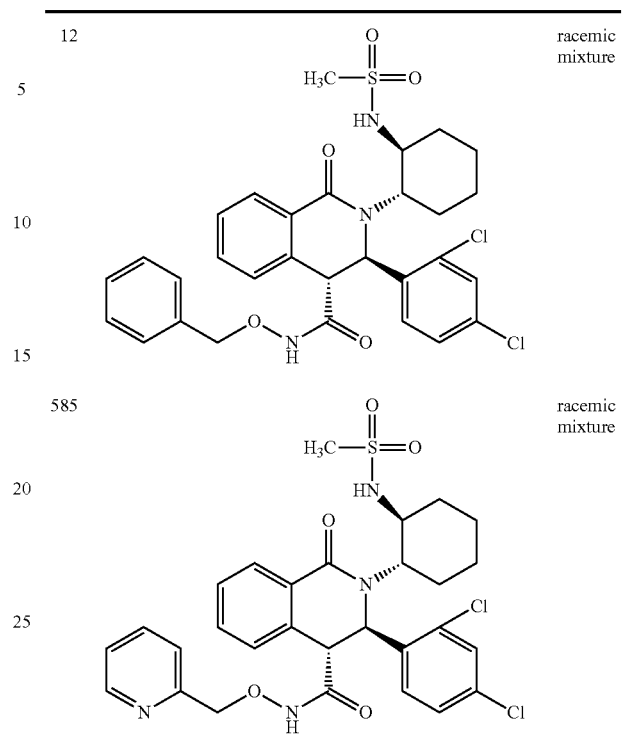 | racemic mixture |
| 585 | | racemic mixture |
TABLE 193
| | | |
|---|---|---|
| 586 | 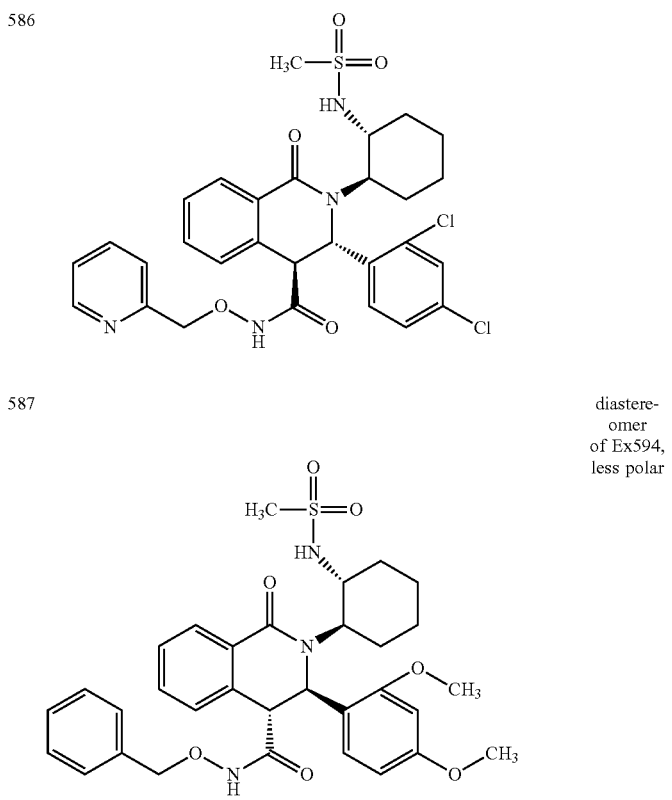 | |
| 587 | | diastereomer of Ex594, less polar |

TABLE 193-continued
| | | |
|---|---|---|
| 588 | 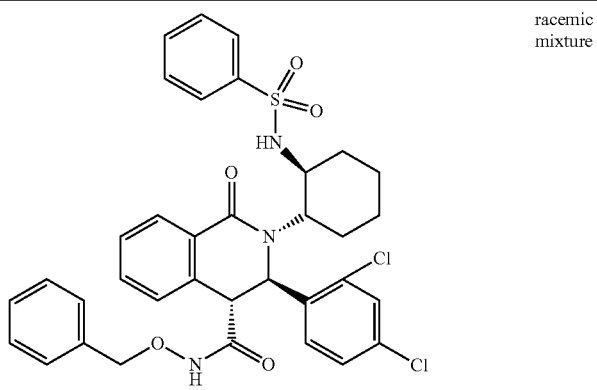 | racemic mixture |
| 589 | 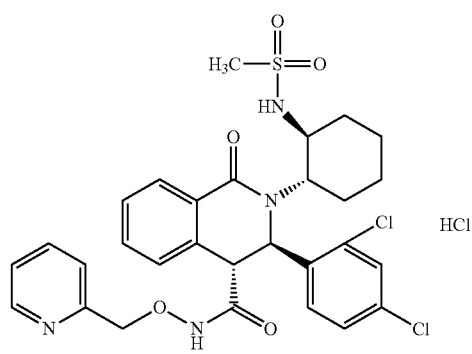 [SMILES: CS(=O)(=O)N[C@H]1CCCC[C@@H]1N1C(=O)c2ccccc2[C@@H](C(=O)NOCc2ccccn2)[C@@H]1c1ccc(Cl)cc1Cl ; Cl] | HCl |
TABLE 194
| | | |
|---|---|---|
| 590 | 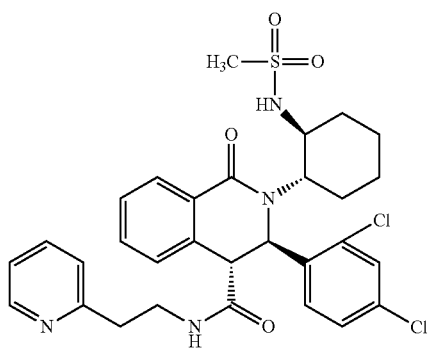 [SMILES: CS(=O)(=O)N[C@H]1CCCC[C@@H]1N1C(=O)c2ccccc2[C@@H](C(=O)NCCc2ccccn2)[C@@H]1c1ccc(Cl)cc1Cl] | racemic mixture |
| 591 | 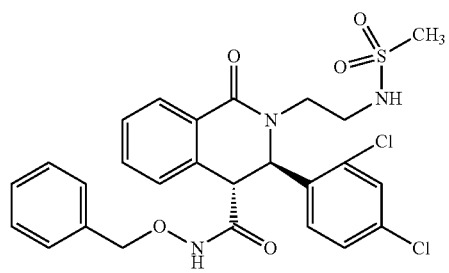 [SMILES: CS(=O)(=O)NCCN1C(=O)c2ccccc2[C@@H](C(=O)NOCc2ccccc2)[C@@H]1c1ccc(Cl)cc1Cl] | racemic mixture |
TABLE 194-continued
| | | |
|---|---|---|
| 592 | 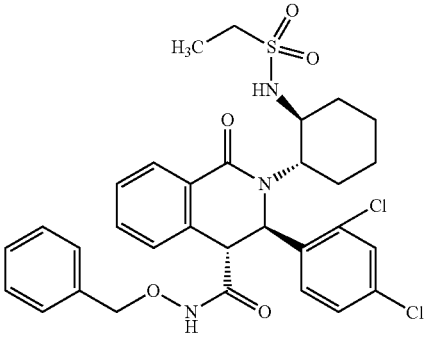 [SMILES: CCS(=O)(=O)N[C@H]1CCCC[C@@H]1N1C(=O)c2ccccc2[C@@H](C(=O)NOCc2ccccc2)[C@@H]1c1ccc(Cl)cc1Cl] | racemic mixture |
| 593 | 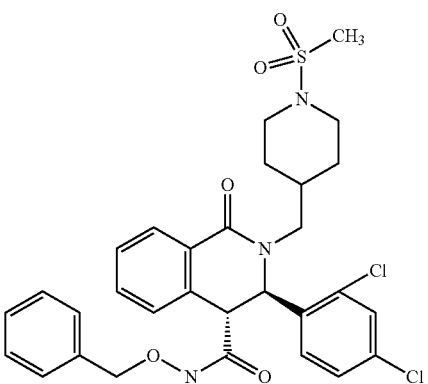 | racemic mixture |

TABLE 195
| | | |
|---|---|---|
| 594 | 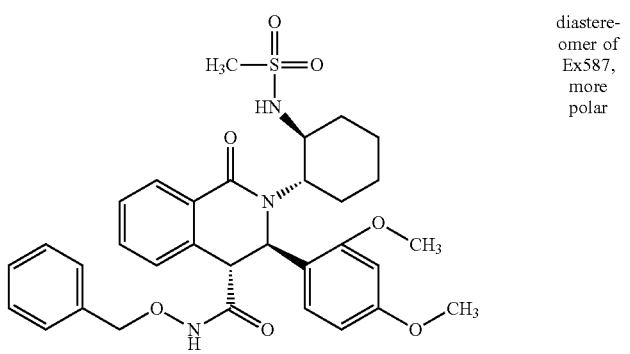 | diastereomer of Ex587, more polar |
| 595 | 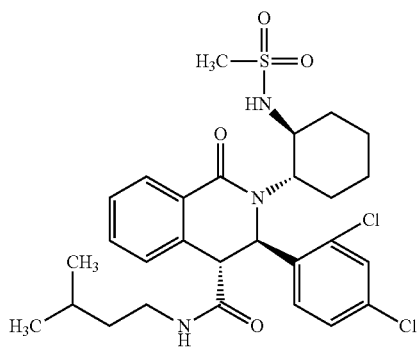 [SMILES: CC(C)CCNC(=O)[C@@H]1c2ccccc2C(=O)N([C@H]2CCCC[C@@H]2NS(C)(=O)=O)[C@H]1c1ccc(Cl)cc1Cl] | racemic mixture |
| 596 | 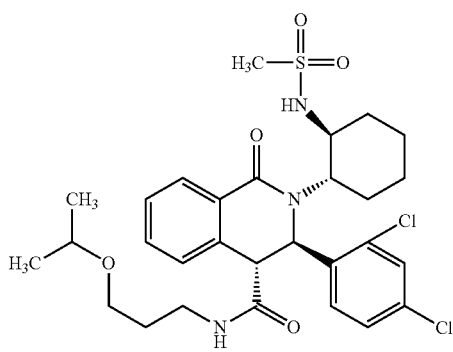 [SMILES: CC(C)OCCCNC(=O)[C@@H]1c2ccccc2C(=O)N([C@H]2CCCC[C@@H]2NS(C)(=O)=O)[C@H]1c1ccc(Cl)cc1Cl] | racemic mixture |
| 18 | 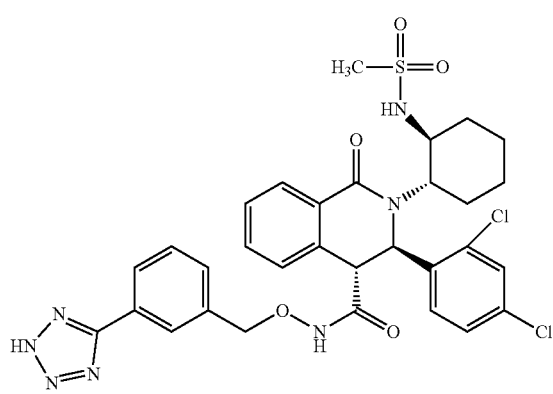 [SMILES: CS(=O)(=O)N[C@H]1CCCC[C@@H]1N1C(=O)c2ccccc2[C@@H](C(=O)NOCc2cccc(-c3nn[nH]n3)c2)[C@@H]1c1ccc(Cl)cc1Cl] | racemic mixture |

TABLE 196
| | | |
|---|---|---|
| 597 | 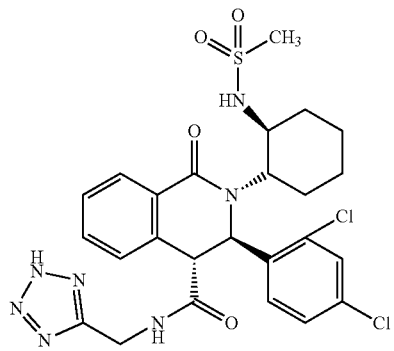 | racemic mixture |
| 598 | 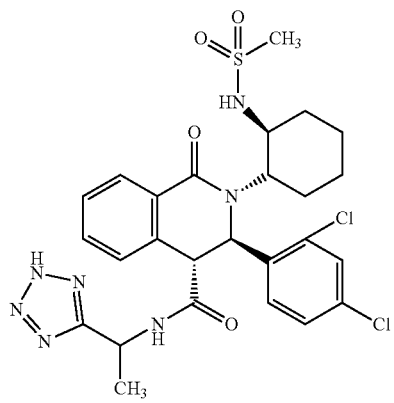 | chiral compound, diastereomer of Ex599 |
| 599 | 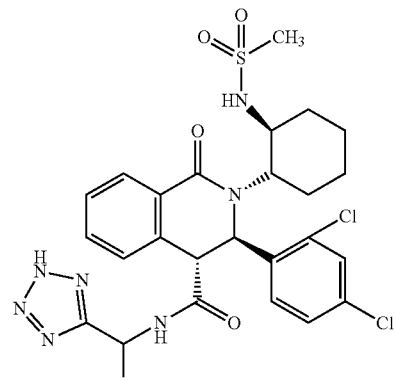 | chiral compound, diastereomer of Ex598 |
| 600 | 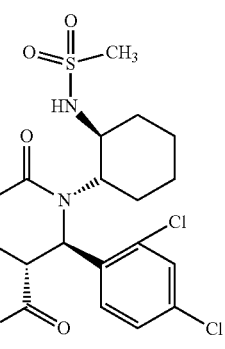 | racemic mixture |
TABLE 197
| | | |
|---|---|---|
| 21 | 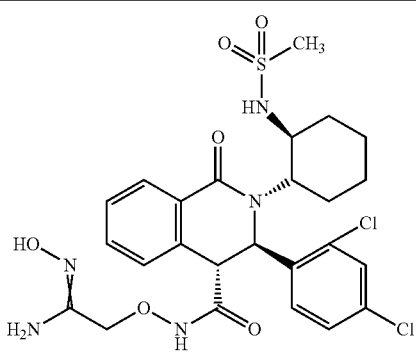 | racemic mixture |
| 601 | 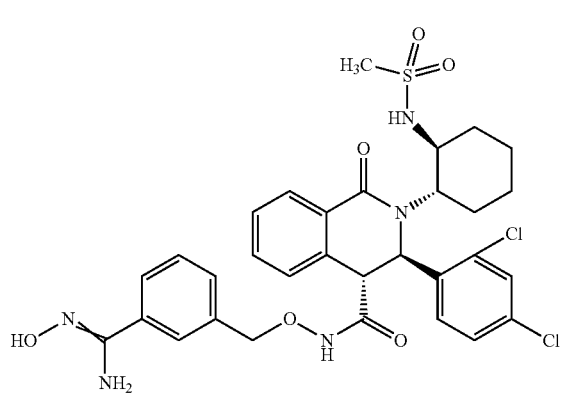 [SMILES: CS(=O)(=O)N[C@H]1CCCC[C@@H]1N1C(=O)c2ccccc2[C@@H](C(=O)NOCc2cccc(C(N)=NO)c2)[C@@H]1c1ccc(Cl)cc1Cl] | racemic mixture |

TABLE 197-continued
| 20 | 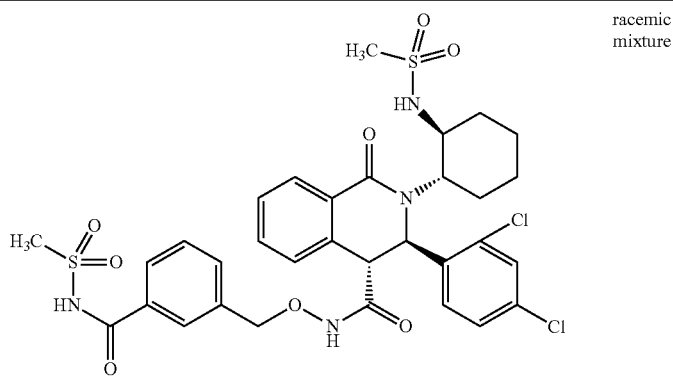 | racemic mixture |
| --- | --- | --- |
| 27 | 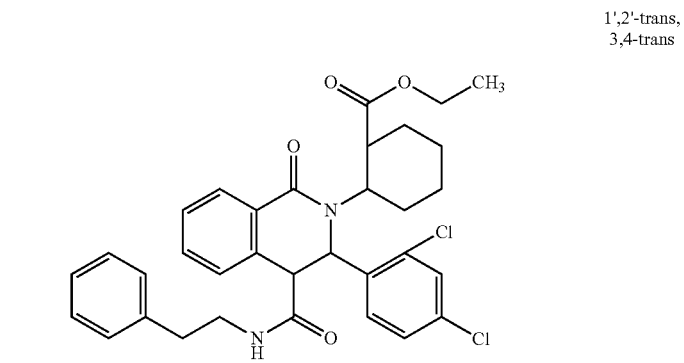 | 1',2'-trans, 3,4-trans |
TABLE 198
| 40 | 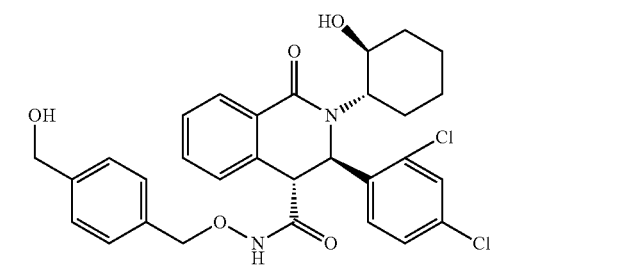 [SMILES: O=C(NOCc1ccc(CO)cc1)[C@@H]1c2ccccc2C(=O)N([C@H]2CCCC[C@@H]2O)[C@H]1c1ccc(Cl)cc1Cl] | racemic mixture |
| --- | --- | --- |
| 602 | 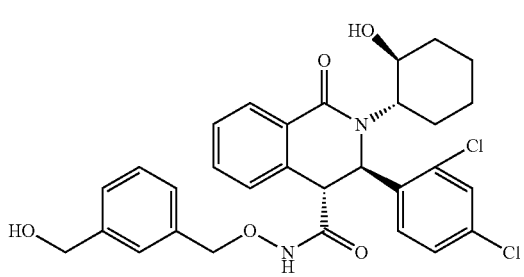 [SMILES: O=C(NOCc1cccc(CO)c1)[C@@H]1c2ccccc2C(=O)N([C@H]2CCCC[C@@H]2O)[C@H]1c1ccc(Cl)cc1Cl] | racemic mixture |

TABLE 198-continued
| | | | |
|---|---|---|---|
| 8 | 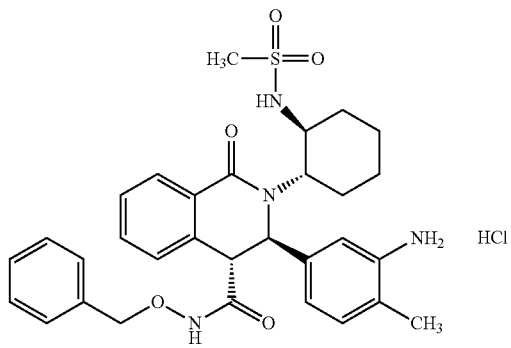 [SMILES: Cc1ccc([C@H]2[C@H](C(=O)NOCc3ccccc3)c3ccccc3C(=O)N2[C@H]2CCCC[C@@H]2NS(C)(=O)=O)cc1N ; Cl] | racemic mixture | HCl |
| 603 | 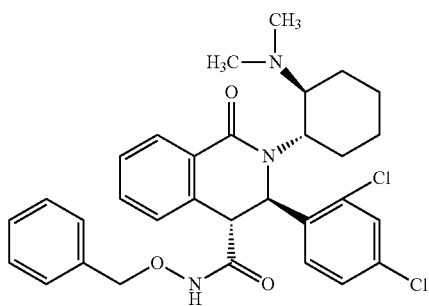 [SMILES: CN(C)[C@H]1CCCC[C@@H]1N1C(=O)c2ccccc2[C@@H](C(=O)NOCc2ccccc2)[C@@H]1c1ccc(Cl)cc1Cl] | racemic mixture | |
| 604 | 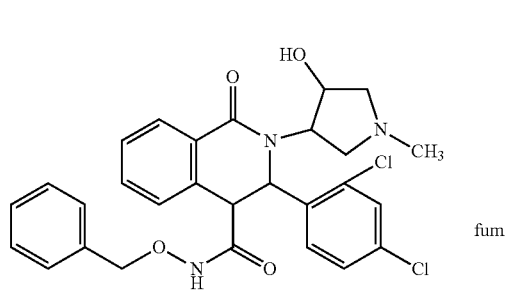 [SMILES: CN1CC(O)C(N2C(=O)c3ccccc3C(C(=O)NOCc3ccccc3)C2c2ccc(Cl)cc2Cl)C1] | 1',2'-trans, 3,4-trans, diastereomer of Ex605 | fum |
TABLE 199
| | | | |
|---|---|---|---|
| 605 | 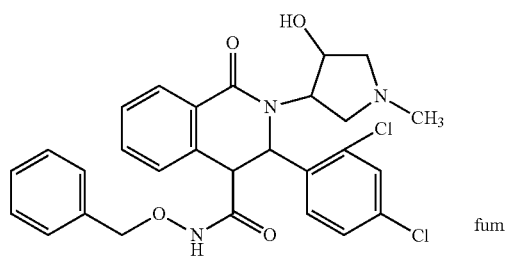 [SMILES: CN1CC(O)C(N2C(=O)c3ccccc3C(C(=O)NOCc3ccccc3)C2c2ccc(Cl)cc2Cl)C1] | 1',2'-trans, 3,4-trans, diastereomer of Ex604 | fum |
| 606 | 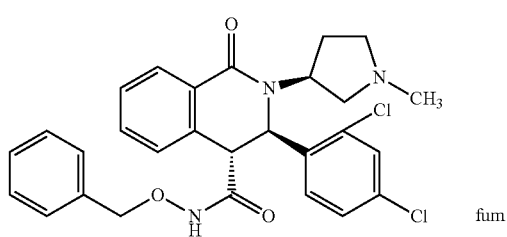 [SMILES: CN1CC[C@H](N2C(=O)c3ccccc3[C@@H](C(=O)NOCc3ccccc3)[C@@H]2c2ccc(Cl)cc2Cl)C1] | | fum |

TABLE 199-continued
| 6 | 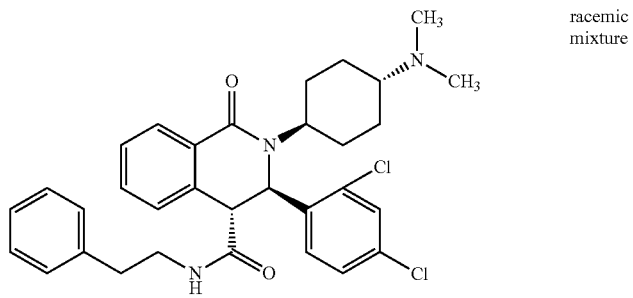 | racemic mixture |
|---|---|---|
| 607 | 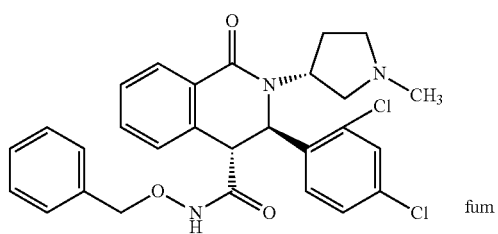 [SMILES: CN1CC[C@@H](N2C(=O)c3ccccc3[C@@H](C(=O)NOCc3ccccc3)[C@@H]2c2ccc(Cl)cc2Cl)C1] | fum |
| 42 | 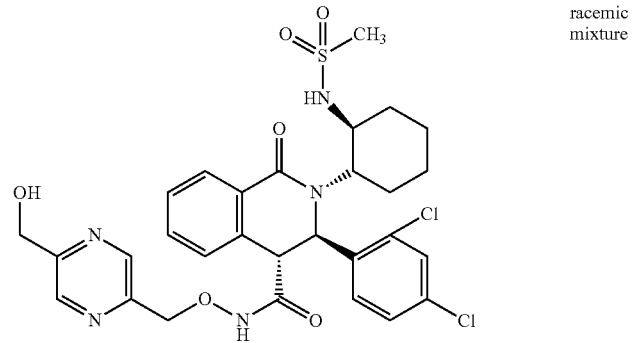 | racemic mixture |
TABLE 200
| 31 | 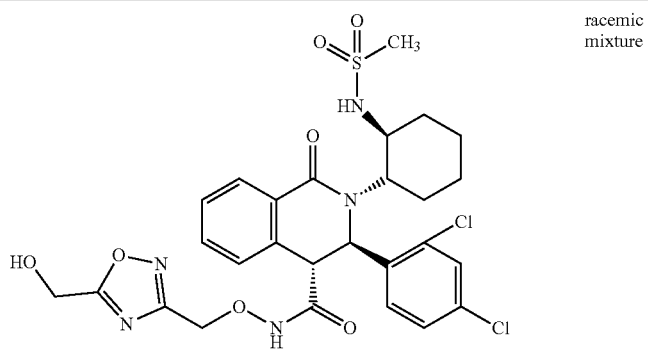 | racemic mixture |
|---|---|---|
| 608 | 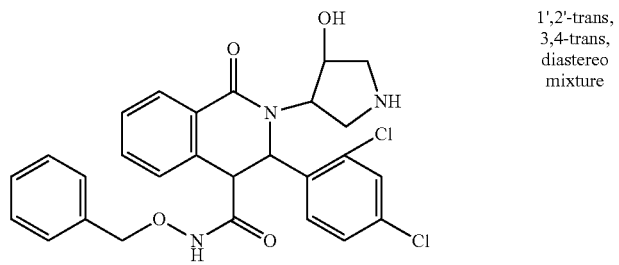 | 1',2'-trans, 3,4-trans, diastereo mixture |

TABLE 200-continued

| 609 | (structure) | racemic mixture |
| 610 | (structure) | racemic mixture, HCl |
| 611 | (structure) | 1',2'-trans, 3,4-trans, diastereomer of Ex616, fum |

TABLE 201

| 612 | (structure) | |
| 613 | (structure) | |

TABLE 201-continued
| 614 | 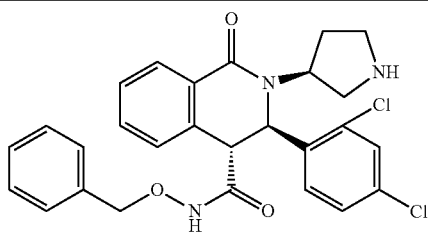 | |
| --- | --- | --- |
| 615 | 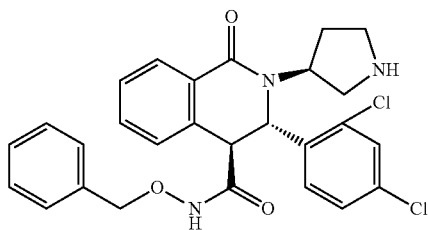 | |
| 616 | 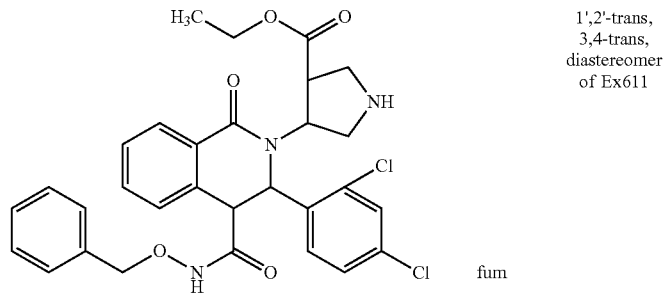 | 1',2'-trans, 3,4-trans, diastereomer of Ex611<br><br>fum |
| 617 | 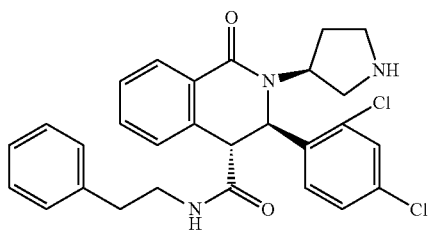 [SMILES: O=C(NOCc1ccccc1)[C@@H]1c2ccccc2C(=O)N([C@H]2CCNC2)[C@H]1c1ccc(Cl)cc1Cl] | |
TABLE 202
| 618 | 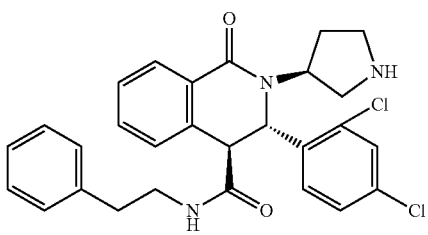 [SMILES: O=C(NCCc1ccccc1)[C@H]1c2ccccc2C(=O)N([C@H]2CCNC2)[C@@H]1c1ccc(Cl)cc1Cl] | |
| --- | --- | --- |
| 619 | 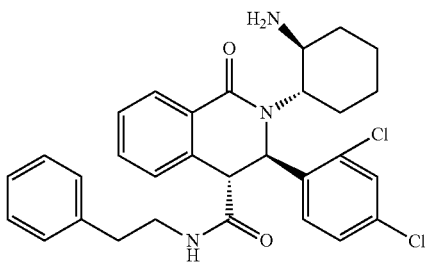 [SMILES: N[C@H]1CCCC[C@@H]1N1C(=O)c2ccccc2[C@@H](C(=O)NCCc2ccccc2)[C@@H]1c1ccc(Cl)cc1Cl] | racemic mixture |
TABLE 202-continued
| 620 | 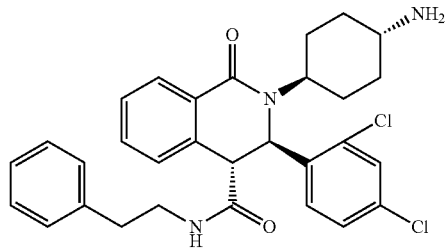 [SMILES: N[C@H]1CC[C@H](N2C(=O)c3ccccc3[C@@H](C(=O)NCCc3ccccc3)[C@@H]2c2ccc(Cl)cc2Cl)CC1] | racemic mixture |
| --- | --- | --- |

TABLE 202-continued
| 5 | 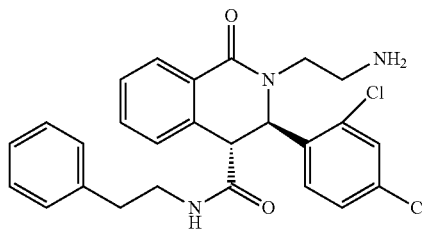 | racemic mixture |
|---|---|---|
| 621 | 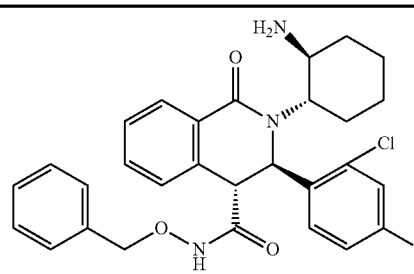 | racemic mixture |
|---|---|---|
TABLE 203
| 30 | 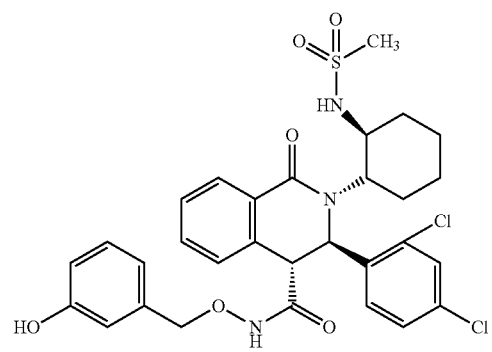 | racemic mixture |
|---|---|---|
| 622 | 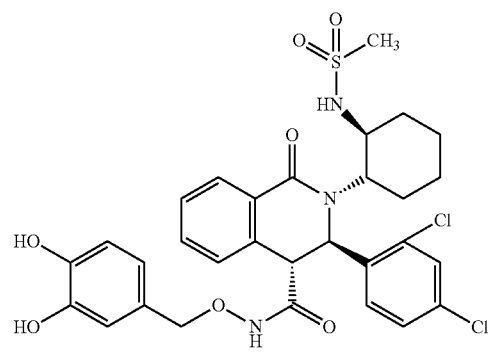 | racemic mixture |
| 623 | 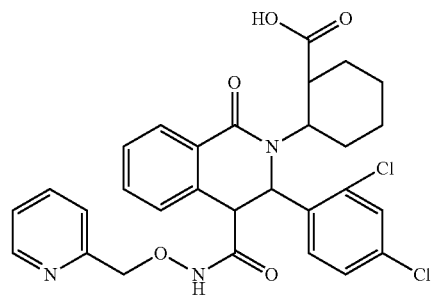 [SMILES: O=C(O)C1CCCCC1N1C(=O)c2ccccc2C(C(=O)NOCc2ccccn2)C1c1ccc(Cl)cc1Cl] | 1',2'-trans, 3,4-trans, diastereomer of Ex624 |
| 28 | 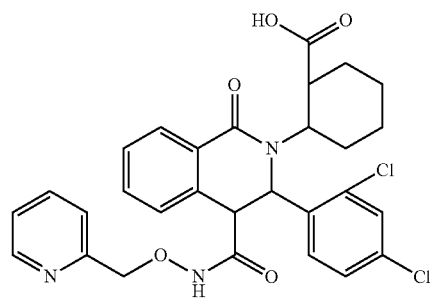 [SMILES: O=C(O)C1CCCCC1N1C(=O)c2ccccc2C(C(=O)NOCc2ccccn2)C1c1ccc(Cl)cc1Cl] | 1',2'-cis, 3,4-trans |

TABLE 203-continued
| 624 | 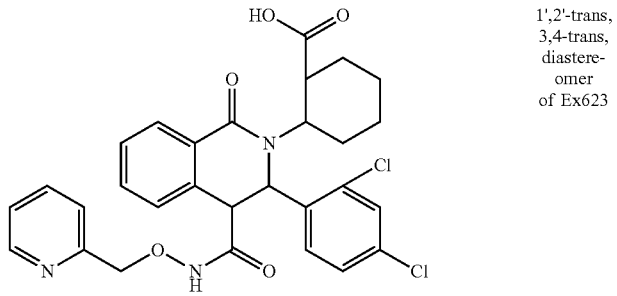 | 1',2'-trans, 3,4-trans, diastereomer of Ex623 |
TABLE 204
| 24 | 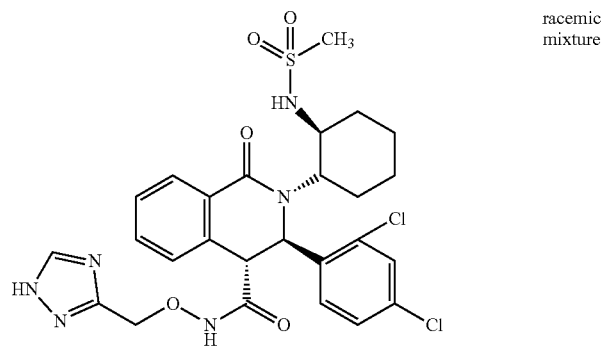 | racemic mixture |
| 625 | 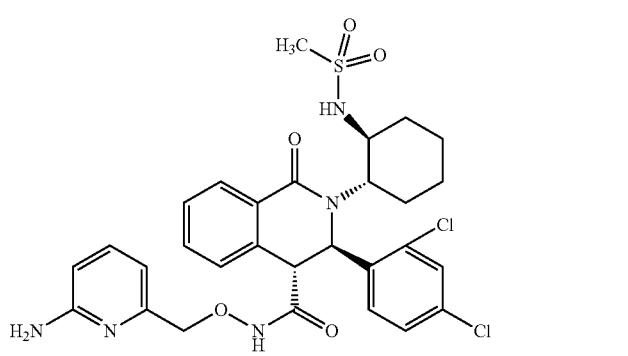 [SMILES: CS(=O)(=O)N[C@H]1CCCC[C@@H]1N1C(=O)c2ccccc2[C@@H](C(=O)NOCc2cccc(N)n2)[C@@H]1c1ccc(Cl)cc1Cl] | racemic mixture |
| 626 | 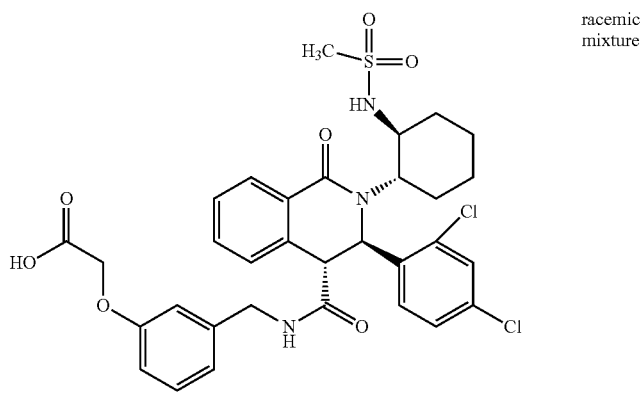 | racemic mixture |

TABLE 204-continued
| 627 | 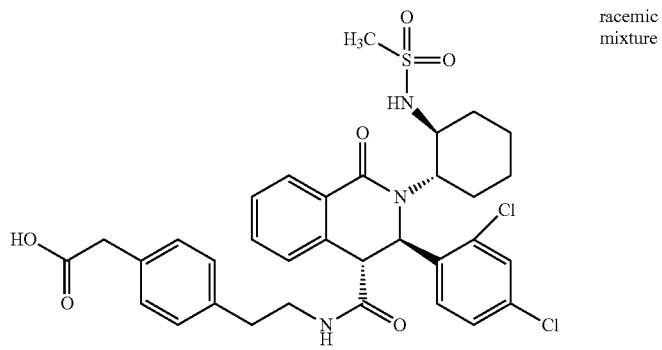 | racemic mixture |
TABLE 205
| 628 | 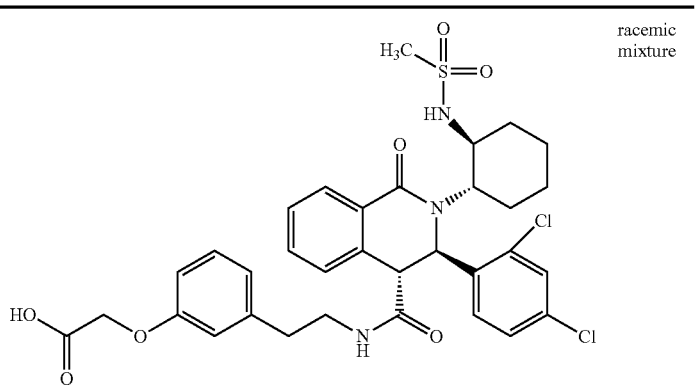 | racemic mixture |
| 629 | 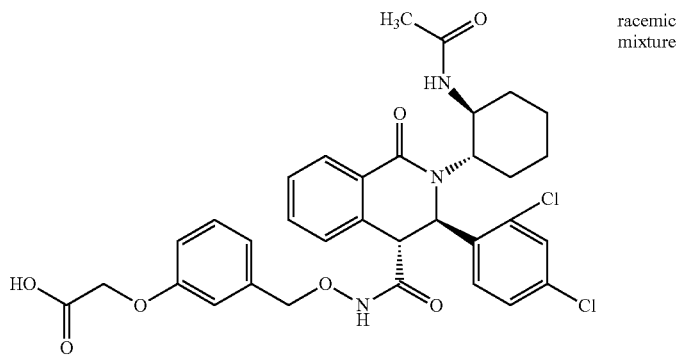 | racemic mixture |
| 630 | 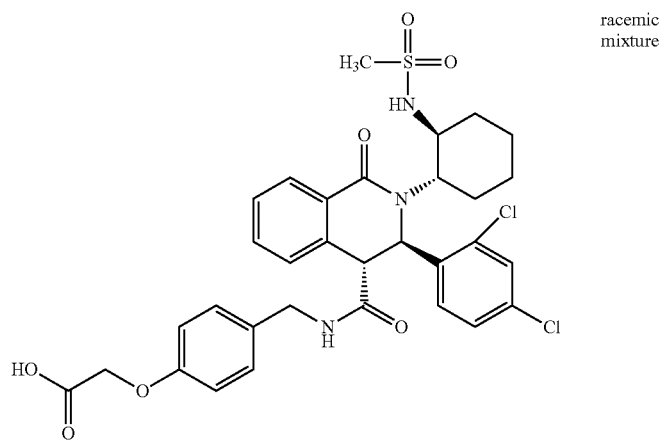 | racemic mixture |

TABLE 205-continued
| | | |
|---|---|---|
| 631 | 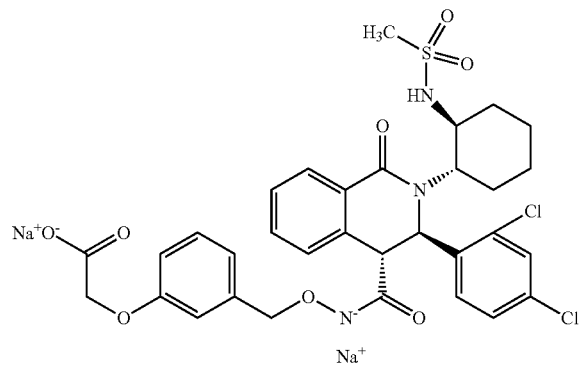 | |
TABLE 206
| | | |
|---|---|---|
| 632 | 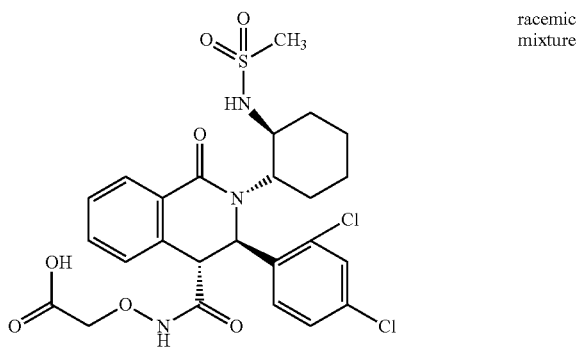 | racemic mixture |
| 633 | 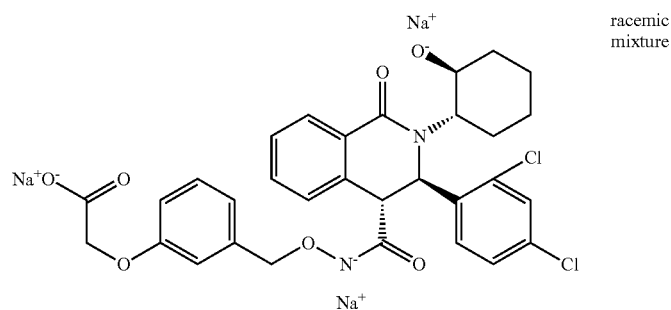 | racemic mixture |
| 19 | 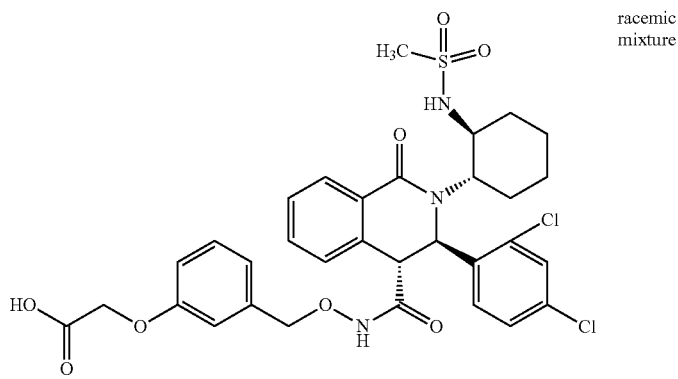 | racemic mixture |

TABLE 206-continued
| 634 | 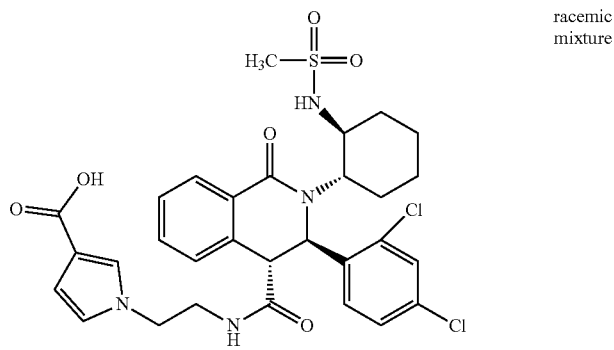 | racemic mixture |
TABLE 207
| 635 | 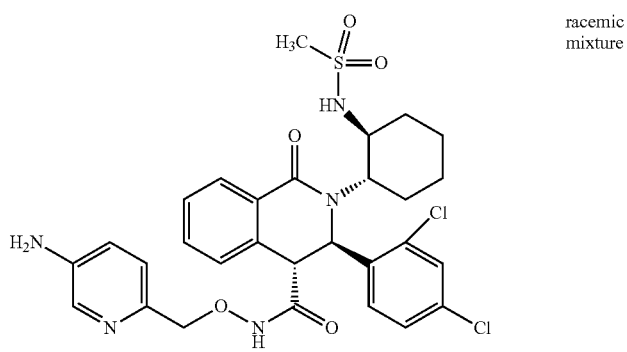 | racemic mixture |
| 636 | 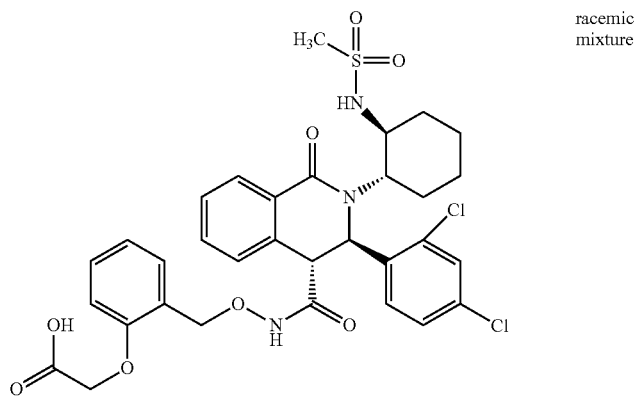 | racemic mixture |
| 25 | 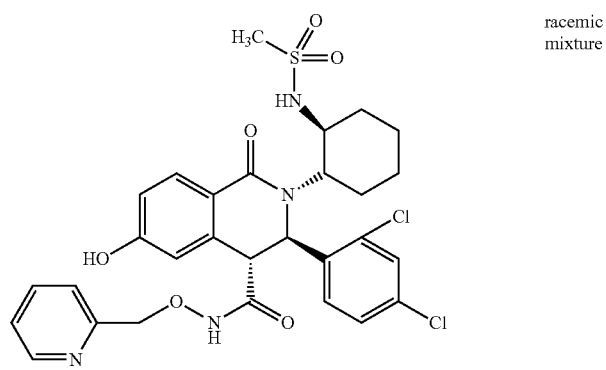 | racemic mixture |

TABLE 207-continued
| 637 | 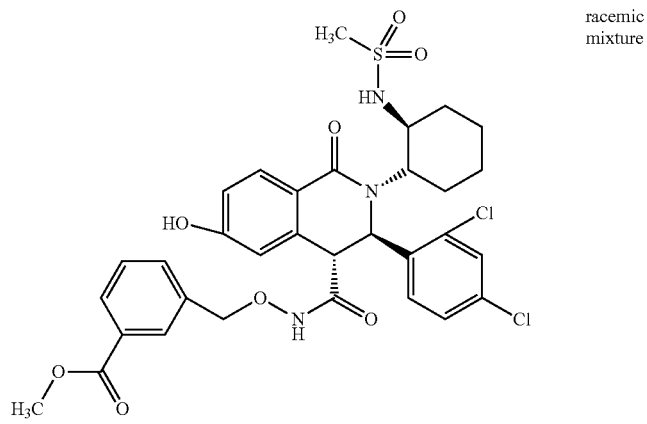 | racemic mixture |
TABLE 208
| 26 | 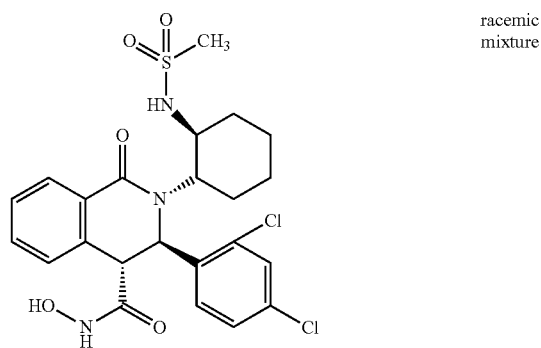 | racemic mixture |
| 17-2 | 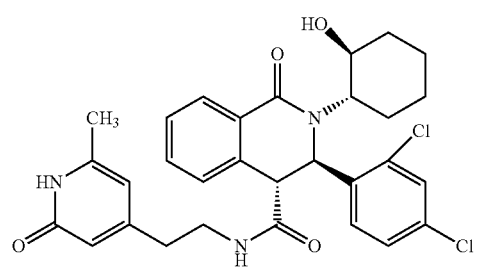 [SMILES: Cc1cc(CCNC(=O)[C@@H]2c3ccccc3C(=O)N([C@H]3CCCC[C@@H]3O)[C@H]2c2ccc(Cl)cc2Cl)cc(=O)[nH]1] | racemic mixture |
| 17-1 | 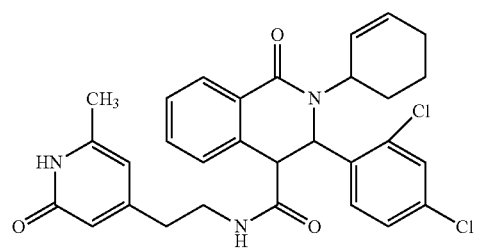 [SMILES: Cc1cc(CCNC(=O)C2c3ccccc3C(=O)N(C3C=CCCC3)C2c2ccc(Cl)cc2Cl)cc(=O)[nH]1] | 3,4-trans |

TABLE 208-continued
638
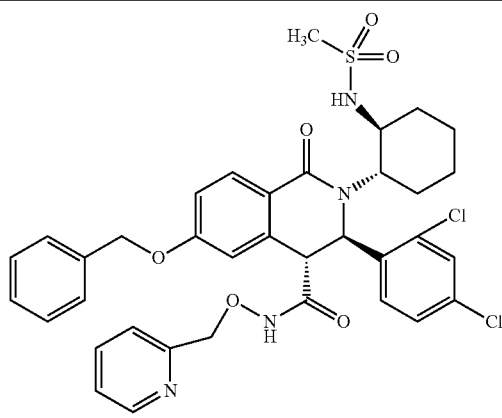
TABLE 209
639
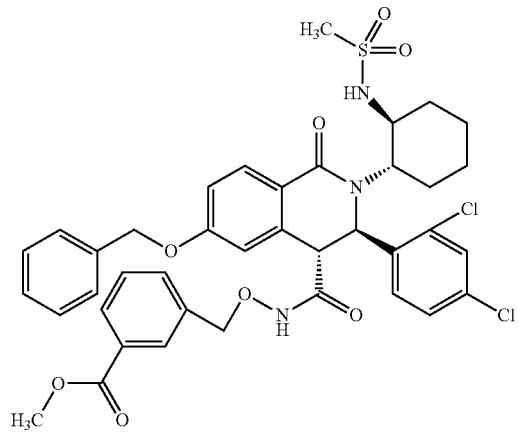 [SMILES: COC(=O)c1cccc(CONC(=O)[C@@H]2c3cc(OCc4ccccc4)ccc3C(=O)N([C@H]3CCCC[C@@H]3NS(C)(=O)=O)[C@H]2c2ccc(Cl)cc2Cl)c1]
640 racemic mixture
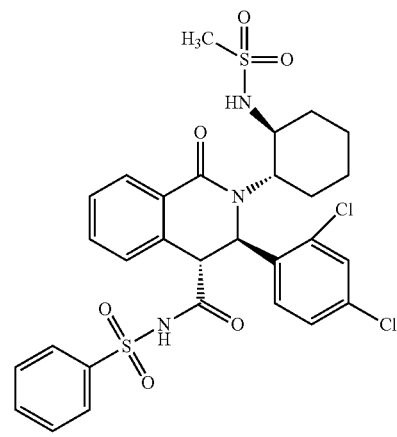 [SMILES: CS(=O)(=O)N[C@H]1CCCC[C@@H]1N1C(=O)c2ccccc2[C@@H](C(=O)NS(=O)(=O)c2ccccc2)[C@@H]1c1ccc(Cl)cc1Cl]

TABLE 209-continued
| | | |
|---|---|---|
| 53 | 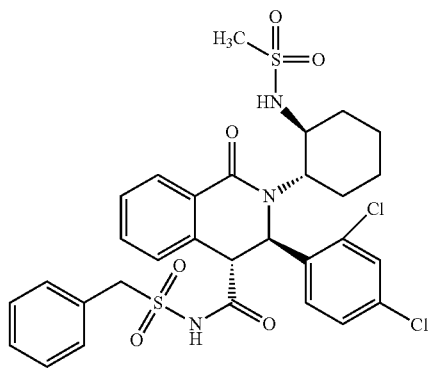 [SMILES: CS(=O)(=O)N[C@H]1CCCC[C@@H]1N1C(=O)c2ccccc2[C@@H](C(=O)NS(=O)(=O)Cc2ccccc2)[C@@H]1c1ccc(Cl)cc1Cl] | racemic mixture |
| 641 | 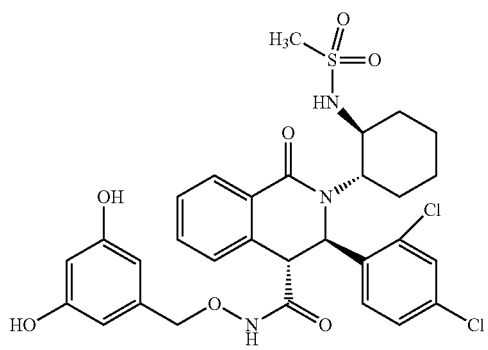 [SMILES: CS(=O)(=O)N[C@H]1CCCC[C@@H]1N1C(=O)c2ccccc2[C@@H](C(=O)NOCc2cc(O)cc(O)c2)[C@@H]1c1ccc(Cl)cc1Cl] | racemic mixture |
TABLE 210
| | | |
|---|---|---|
| 642 | 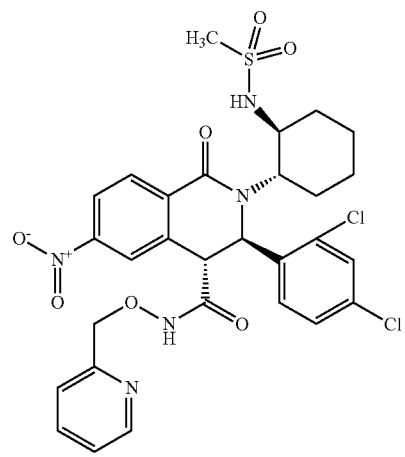 [SMILES: CS(=O)(=O)N[C@H]1CCCC[C@@H]1N1C(=O)c2ccc([N+](=O)[O-])cc2[C@@H](C(=O)NOCc2ccccn2)[C@@H]1c1ccc(Cl)cc1Cl] | racemic mixture |

TABLE 210-continued
| | | |
|---|---|---|
| 45 | 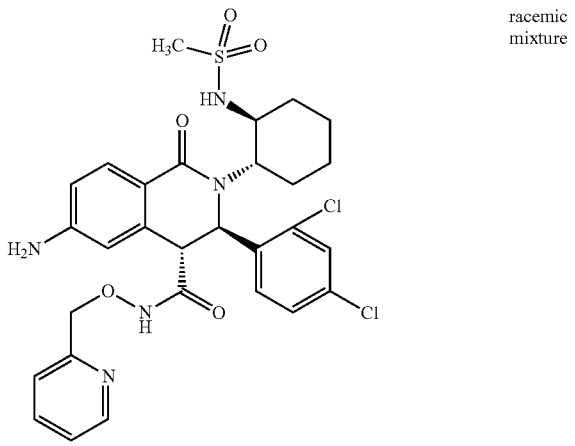 | racemic mixture |
| 643 | 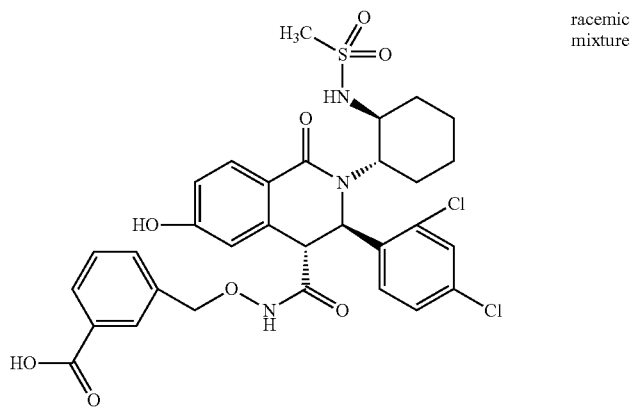 | racemic mixture |
TABLE 211
| | | |
|---|---|---|
| 644 | 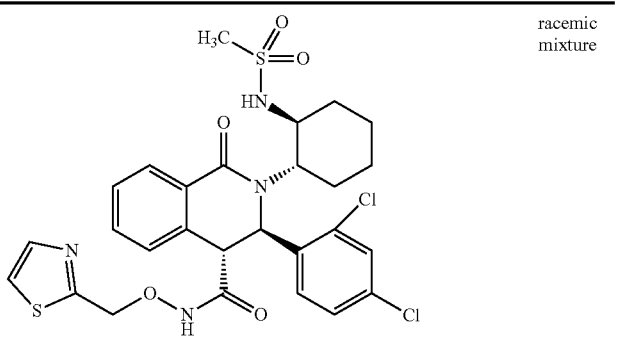 | racemic mixture |
| 645 | 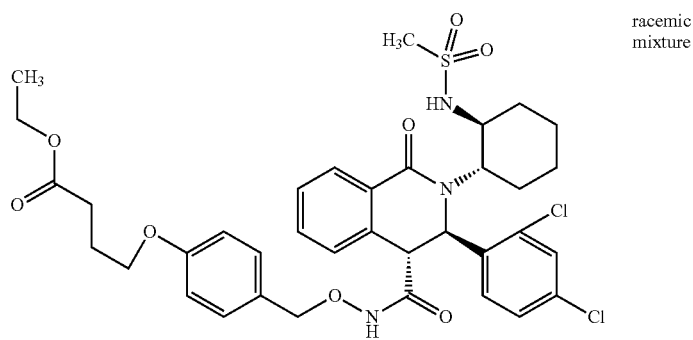 | racemic mixture |

TABLE 211-continued
646 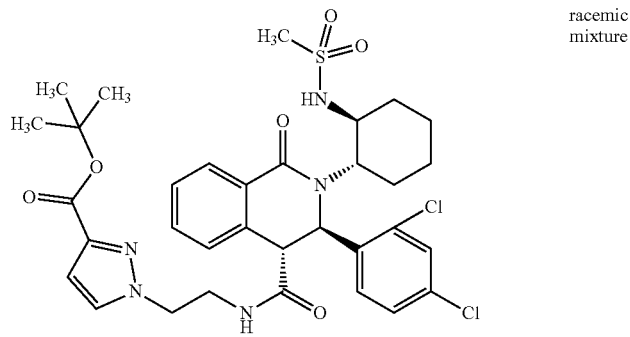 racemic mixture
647 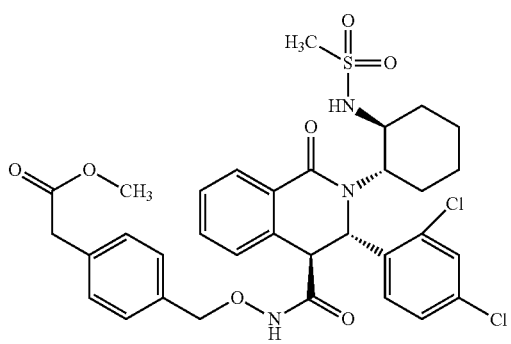 [SMILES: COC(=O)Cc1ccc(CONC(=O)[C@H]2c3ccccc3C(=O)N([C@H]3CCCC[C@@H]3NS(C)(=O)=O)[C@@H]2c2ccc(Cl)cc2Cl)cc1]
TABLE 212
648 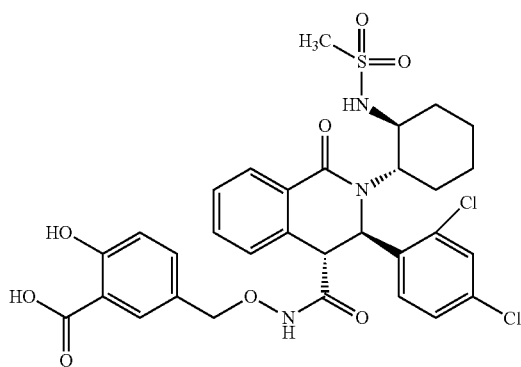 [SMILES: CS(=O)(=O)N[C@H]1CCCC[C@@H]1N1C(=O)c2ccccc2[C@@H](C(=O)NOCc2ccc(O)c(C(=O)O)c2)[C@@H]1c1ccc(Cl)cc1Cl]
649 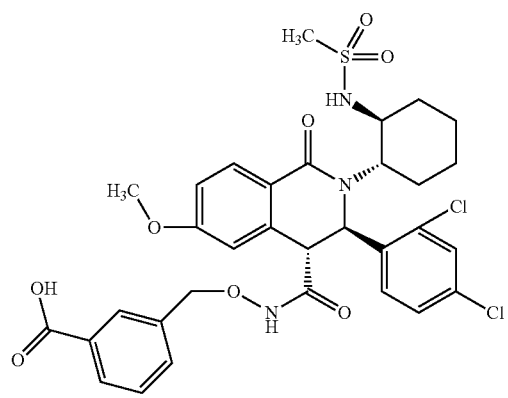 [SMILES: COc1ccc2c(c1)[C@@H](C(=O)NOCc1cccc(C(=O)O)c1)[C@H](c1ccc(Cl)cc1Cl)N([C@H]1CCCC[C@@H]1NS(C)(=O)=O)C2=O]

TABLE 212-continued
| 650 | 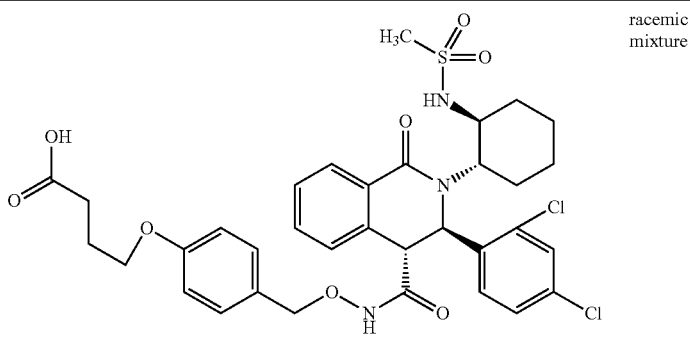 | racemic mixture |
| 651 | 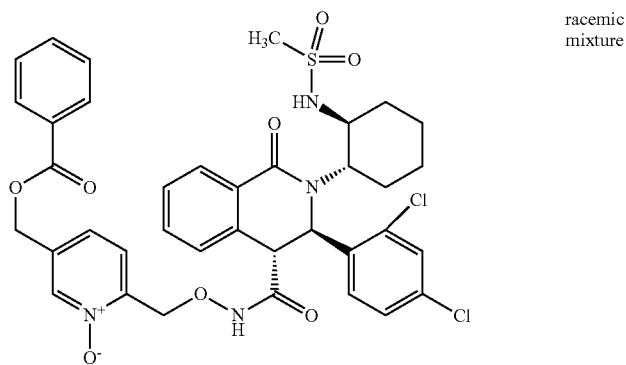 | racemic mixture |
TABLE 213
| 52 | 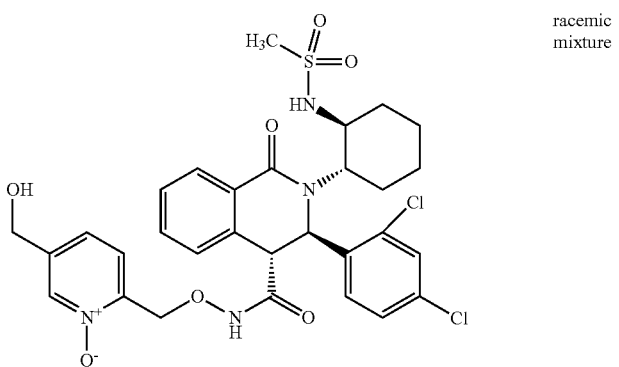 | racemic mixture |
| 652 | 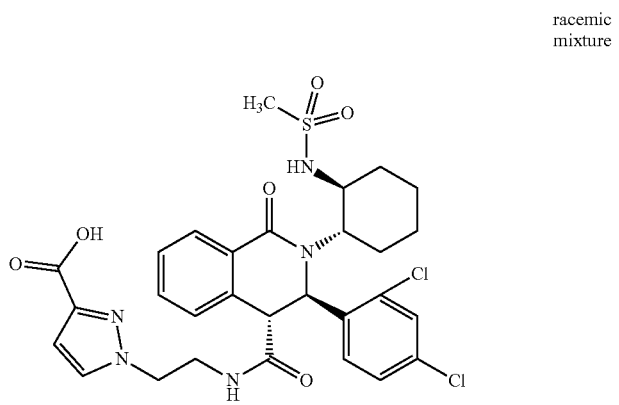 | racemic mixture |

TABLE 213-continued
| 653 | 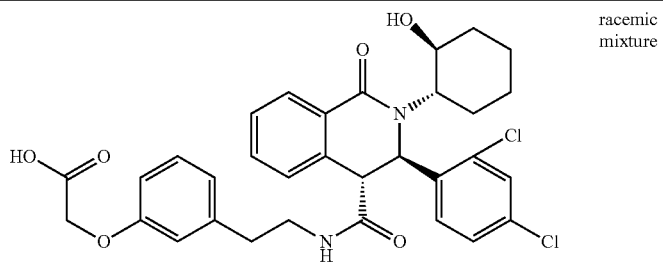 | racemic mixture |
| 654 | 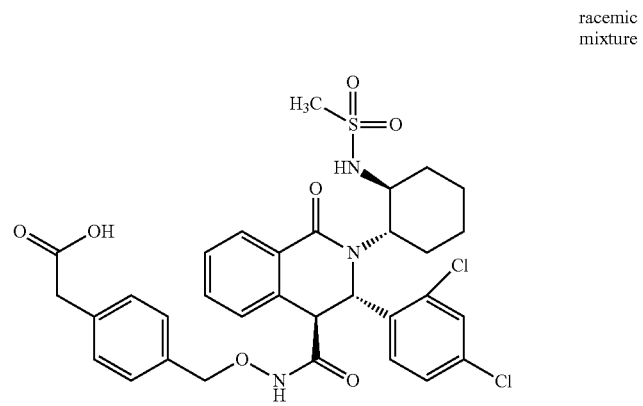 | racemic mixture |
TABLE 214
| 655 | 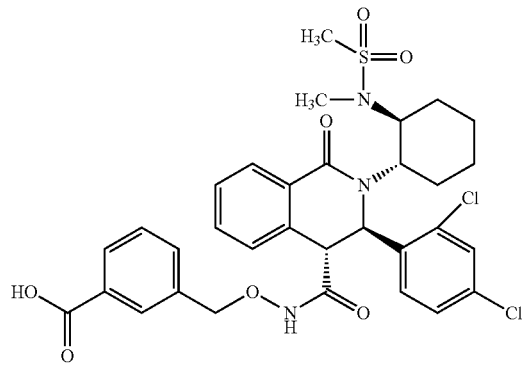 [SMILES: CN([C@H]1CCCC[C@@H]1N1C(=O)c2ccccc2[C@@H](C(=O)NOCc2cccc(C(=O)O)c2)[C@@H]1c1ccc(Cl)cc1Cl)S(C)(=O)=O] | |
| 656 | 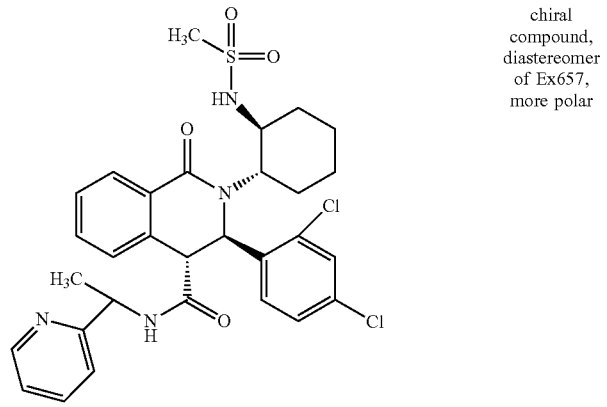 | chiral compound, diastereomer of Ex657, more polar |

TABLE 214-continued
| 657 | 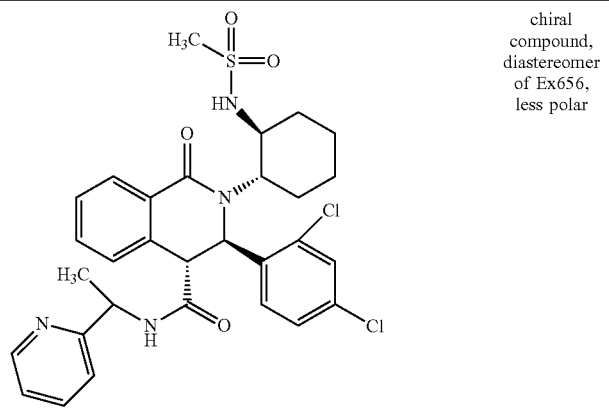 | chiral compound, diastereomer of Ex656, less polar |
| --- | --- | --- |
| 51 | 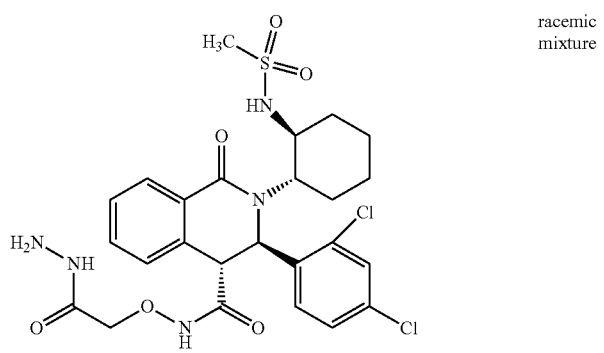 | racemic mixture |
TABLE 215
| 658 | 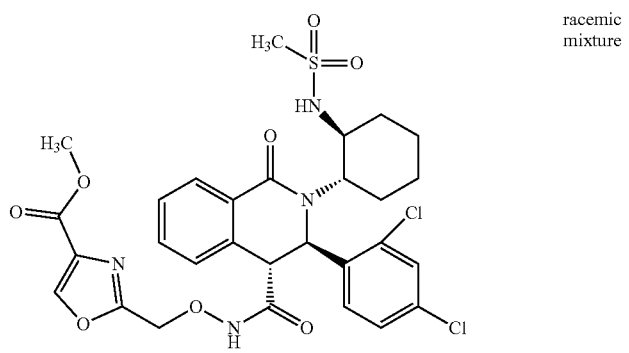 | racemic mixture |
| --- | --- | --- |
| 659 | 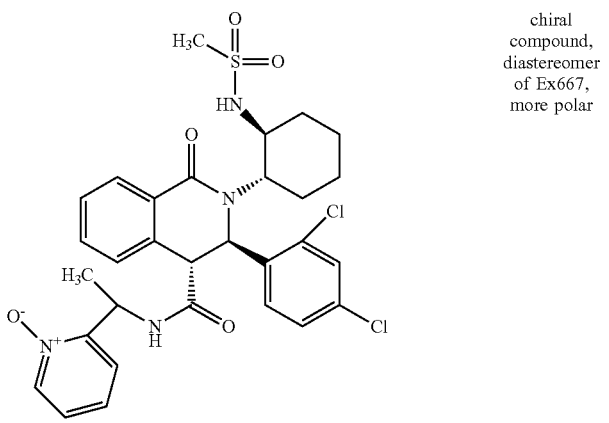 | chiral compound, diastereomer of Ex667, more polar |

TABLE 215-continued
660 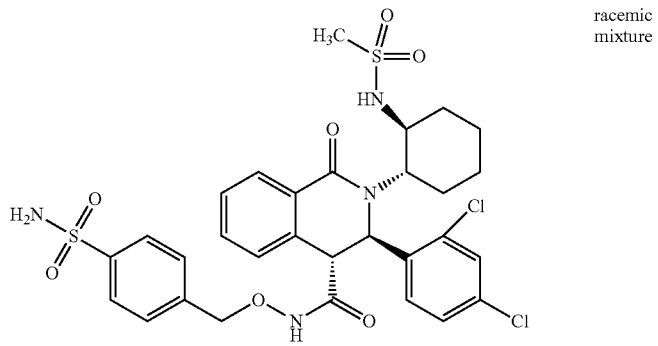 racemic mixture
661 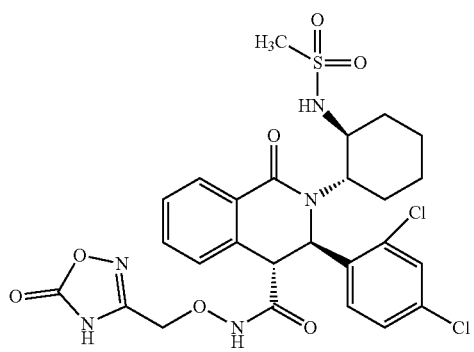 [SMILES: CS(=O)(=O)N[C@H]1CCCC[C@@H]1N1C(=O)c2ccccc2[C@@H](C(=O)NOCc2noc(=O)[nH]2)[C@@H]1c1ccc(Cl)cc1Cl]
TABLE 216
662 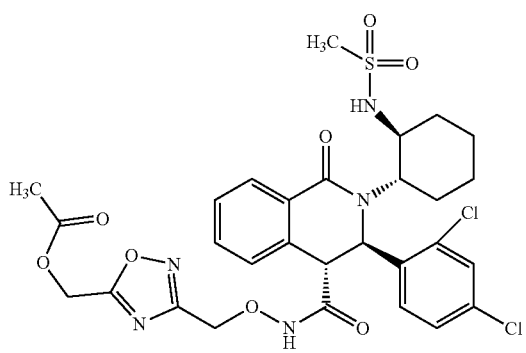 [SMILES: CC(=O)OCc1nc(CONC(=O)[C@@H]2c3ccccc3C(=O)N([C@H]3CCCC[C@@H]3NS(C)(=O)=O)[C@H]2c2ccc(Cl)cc2Cl)no1]
663 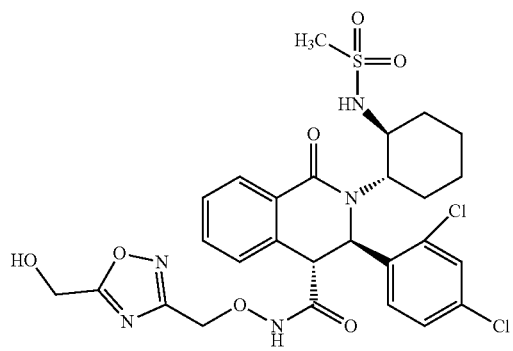 [SMILES: CS(=O)(=O)N[C@H]1CCCC[C@@H]1N1C(=O)c2ccccc2[C@@H](C(=O)NOCc2noc(CO)n2)[C@@H]1c1ccc(Cl)cc1Cl]

433
TABLE 216-continued
| 664 | | racemic mixture |
|---|---|---|
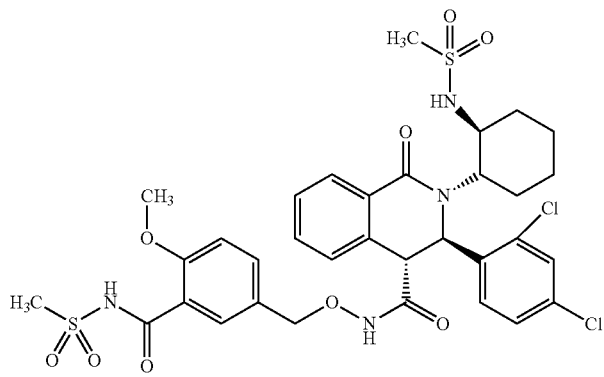
| 665 | | racemic mixture |
|---|---|---|
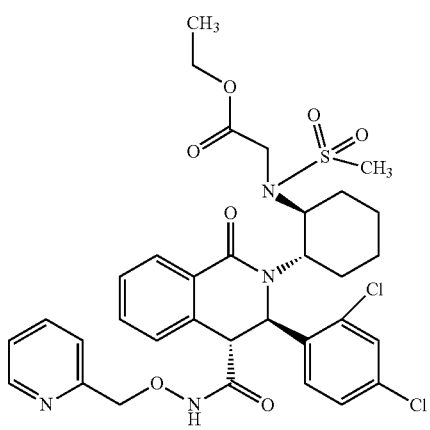 [SMILES: CCOC(=O)CN([C@H]1CCCC[C@@H]1N1C(=O)c2ccccc2[C@@H](C(=O)NOCc2ccccn2)[C@@H]1c1ccc(Cl)cc1Cl)S(C)(=O)=O]
TABLE 217
| 666 | | racemic mixture |
|---|---|---|
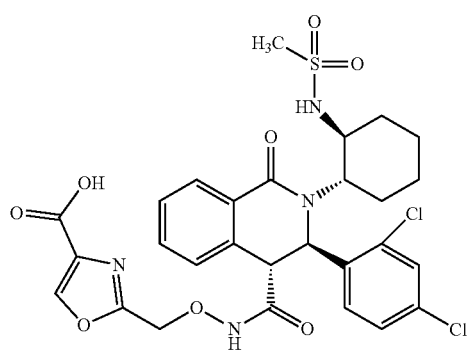

TABLE 217-continued
| | | |
|---|---|---|
| 667 | 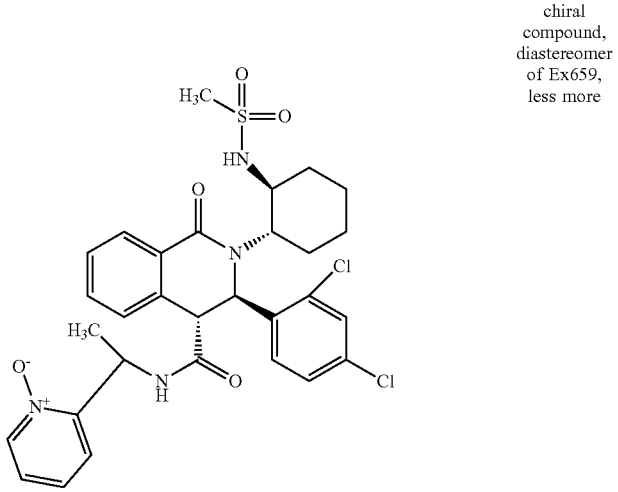 | chiral compound, diastereomer of Ex659, less more |
| 668 | 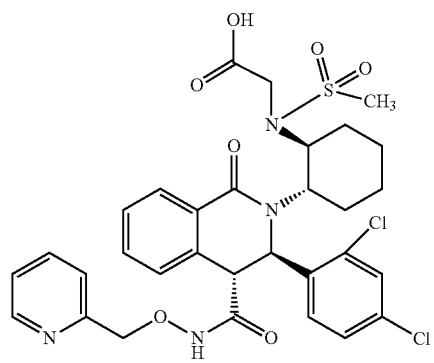 [SMILES: CS(=O)(=O)N(CC(=O)O)[C@H]1CCCC[C@@H]1N1C(=O)c2ccccc2[C@@H](C(=O)NOCc2ccccn2)[C@@H]1c1ccc(Cl)cc1Cl] | racemic mixture |
| 46 | 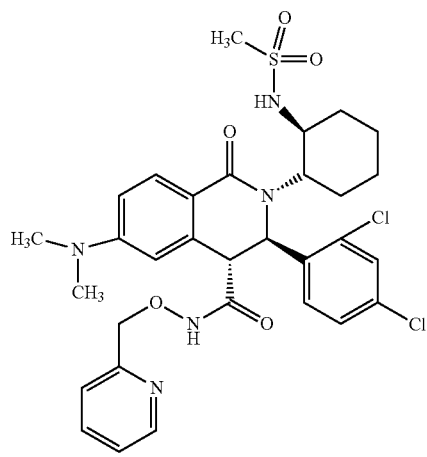 | racemic mixture |

437 438
TABLE 218
| 669 | | racemic mixture |
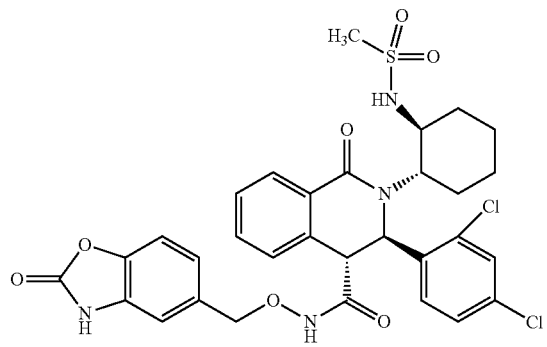 [SMILES: CS(=O)(=O)N[C@H]1CCCC[C@@H]1N1C(=O)c2ccccc2[C@@H](C(=O)NOCc2ccc3oc(=O)[nH]c3c2)[C@@H]1c1ccc(Cl)cc1Cl]
| 670 | | racemic mixture |
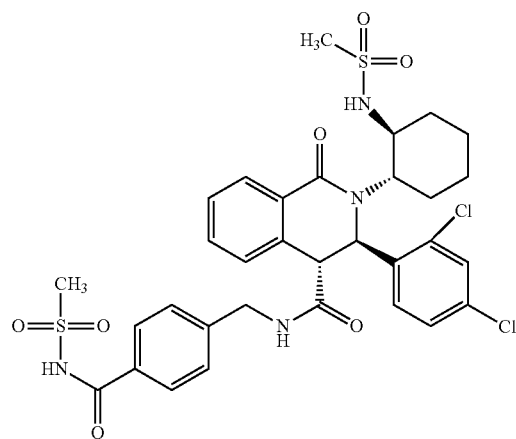 [SMILES: CS(=O)(=O)NC(=O)c1ccc(CNC(=O)[C@@H]2c3ccccc3C(=O)N([C@H]3CCCC[C@@H]3NS(C)(=O)=O)[C@H]2c2ccc(Cl)cc2Cl)cc1]
| 47 | | racemic mixture |
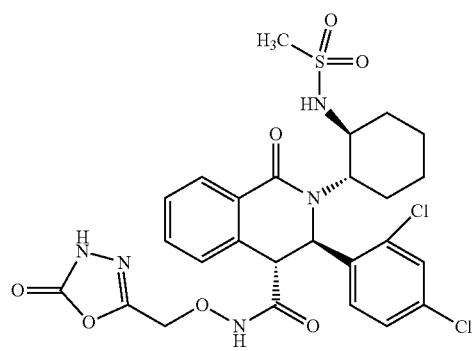 [SMILES: CS(=O)(=O)N[C@H]1CCCC[C@@H]1N1C(=O)c2ccccc2[C@@H](C(=O)NOCc2n[nH]c(=O)o2)[C@@H]1c1ccc(Cl)cc1Cl]

TABLE 219
671 racemic mixture
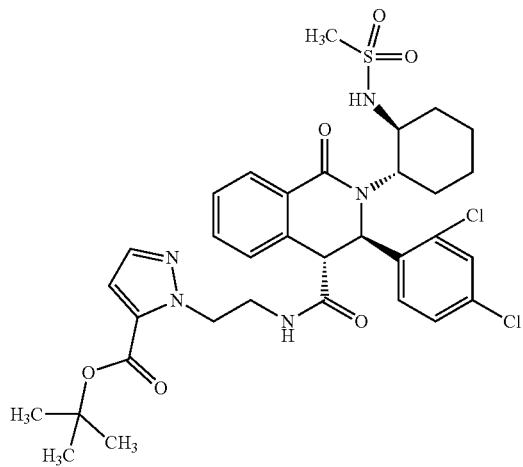 [SMILES: CC(C)(C)OC(=O)c1ccnn1CCNC(=O)[C@@H]1c2ccccc2C(=O)N([C@H]2CCCC[C@@H]2NS(C)(=O)=O)[C@H]1c1ccc(Cl)cc1Cl]
672 racemic mixture
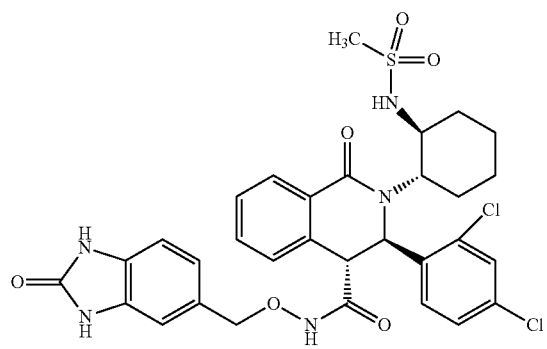 [SMILES: CS(=O)(=O)N[C@H]1CCCC[C@@H]1N1C(=O)c2ccccc2[C@@H](C(=O)NOCc2ccc3[nH]c(=O)[nH]c3c2)[C@@H]1c1ccc(Cl)cc1Cl]
673 racemic mixture
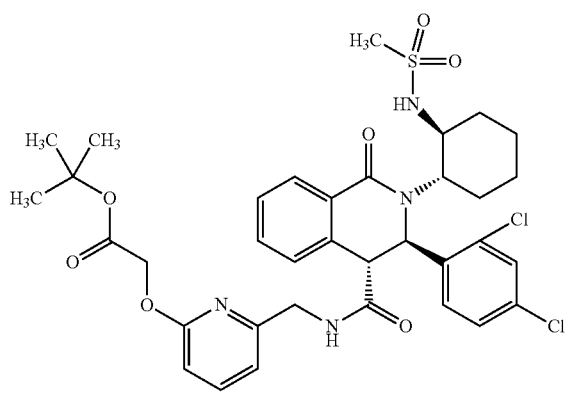 [SMILES: CC(C)(C)OC(=O)COc1cccc(CNC(=O)[C@@H]2c3ccccc3C(=O)N([C@H]3CCCC[C@@H]3NS(C)(=O)=O)[C@H]2c2ccc(Cl)cc2Cl)n1]

TABLE 220
674 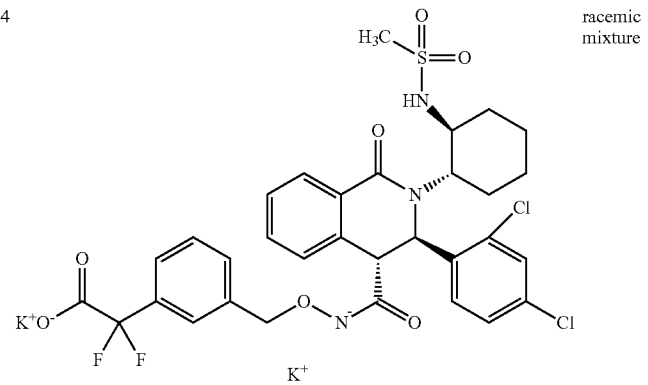 racemic mixture
675 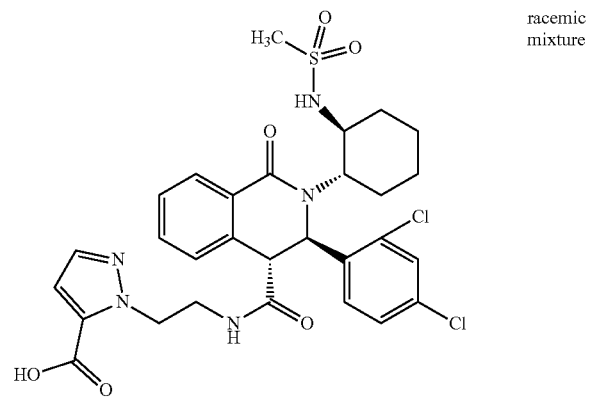 racemic mixture
676 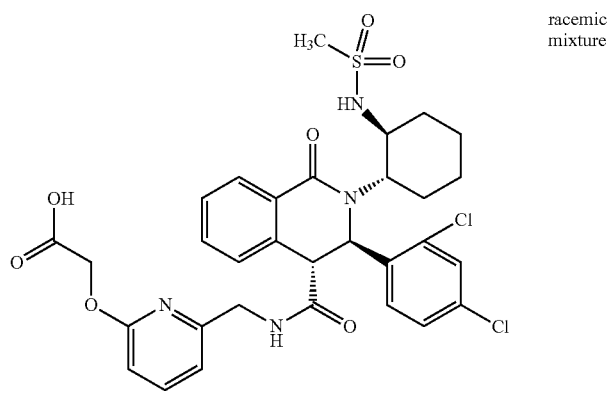 racemic mixture
677 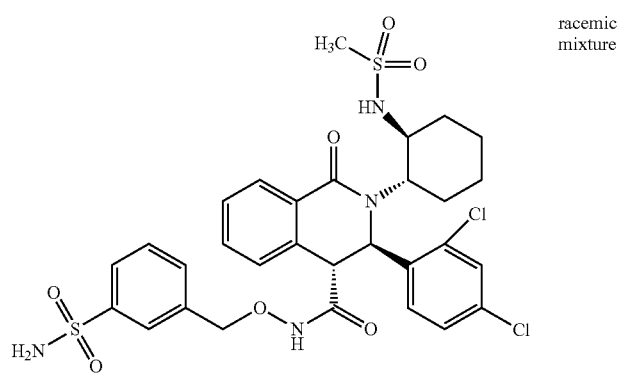 racemic mixture TABLE 221
678 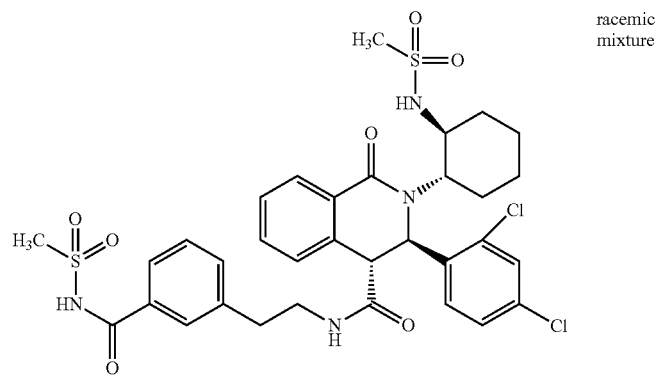 racemic mixture
679 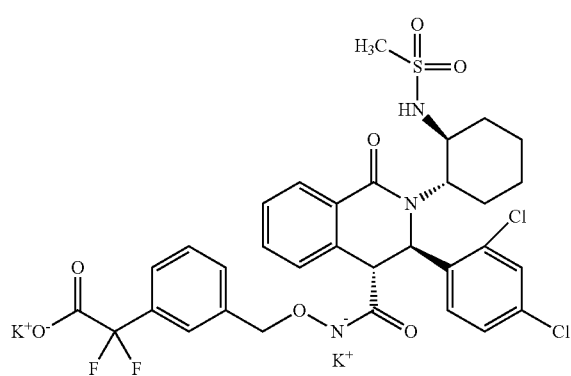
680 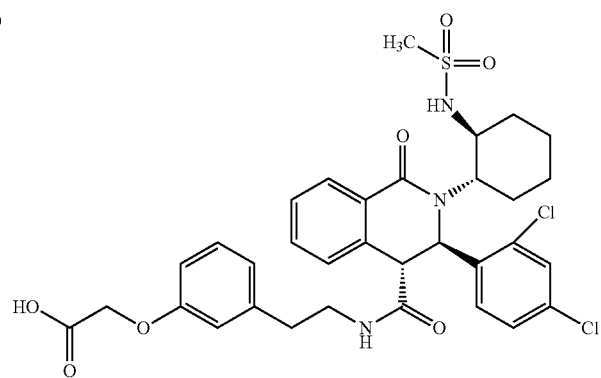
681 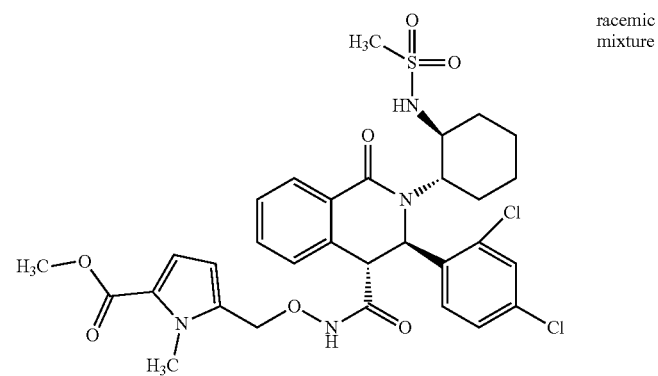 racemic mixture TABLE 222
982 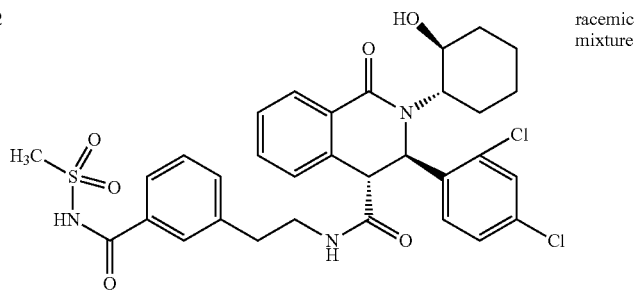 racemic mixture
683 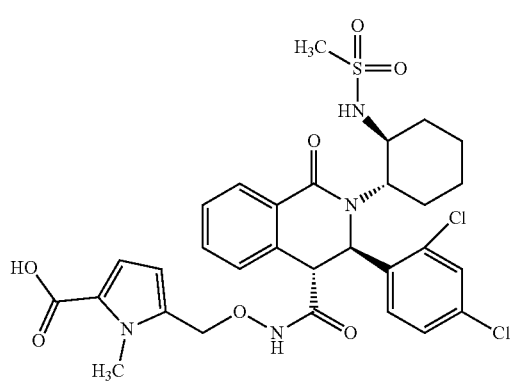 racemic mixture
684 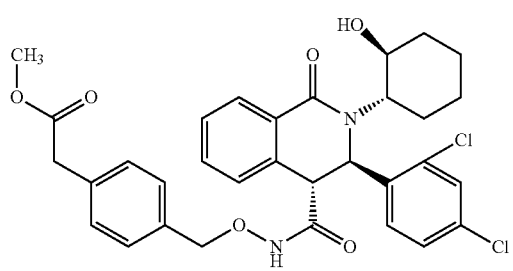 [SMILES: COC(=O)Cc1ccc(CONC(=O)[C@@H]2c3ccccc3C(=O)N([C@H]3CCCC[C@@H]3O)[C@H]2c2ccc(Cl)cc2Cl)cc1] racemic mixture
49 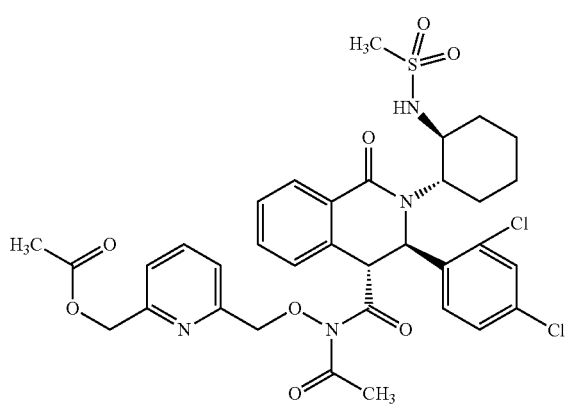 [SMILES: CC(=O)OCc1cccc(CON(C(C)=O)C(=O)[C@@H]2c3ccccc3C(=O)N([C@H]3CCCC[C@@H]3NS(C)(=O)=O)[C@H]2c2ccc(Cl)cc2Cl)n1] racemic mixture TABLE 223
685 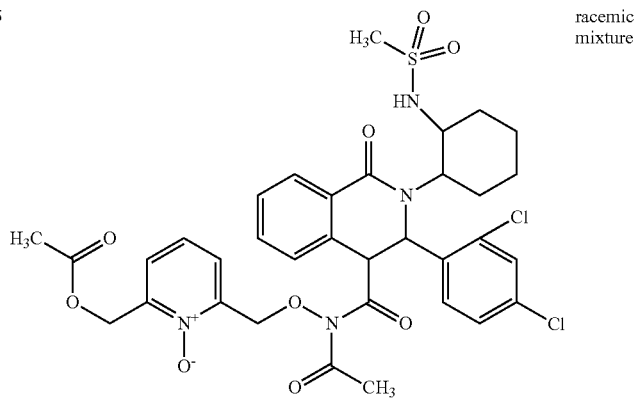 racemic mixture
686 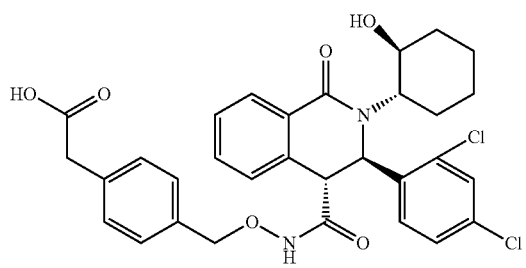 [SMILES: O=C(O)Cc1ccc(CONC(=O)[C@@H]2c3ccccc3C(=O)N([C@H]3CCCC[C@@H]3O)[C@H]2c2ccc(Cl)cc2Cl)cc1] racemic mixture
687 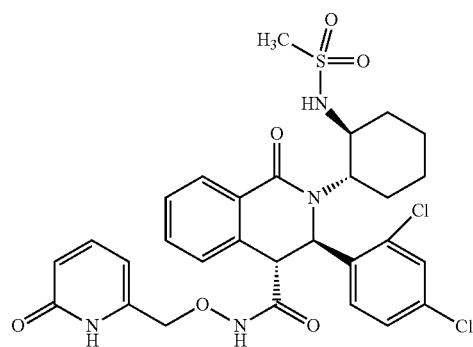 [SMILES: CS(=O)(=O)N[C@H]1CCCC[C@@H]1N1C(=O)c2ccccc2[C@@H](C(=O)NOCc2cccc(=O)[nH]2)[C@@H]1c1ccc(Cl)cc1Cl] racemic mixture
688 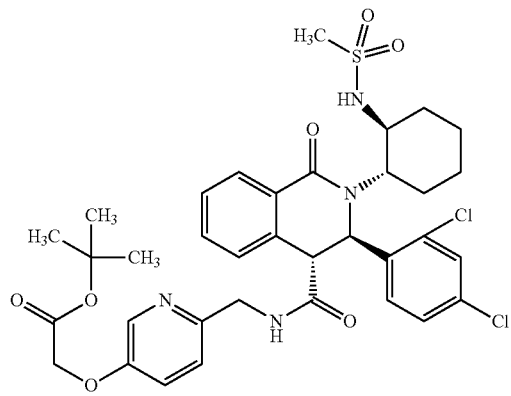 [SMILES: CC(C)(C)OC(=O)COc1ccc(CNC(=O)[C@@H]2c3ccccc3C(=O)N([C@H]3CCCC[C@@H]3NS(C)(=O)=O)[C@H]2c2ccc(Cl)cc2Cl)nc1] racemic mixture TABLE 224
55 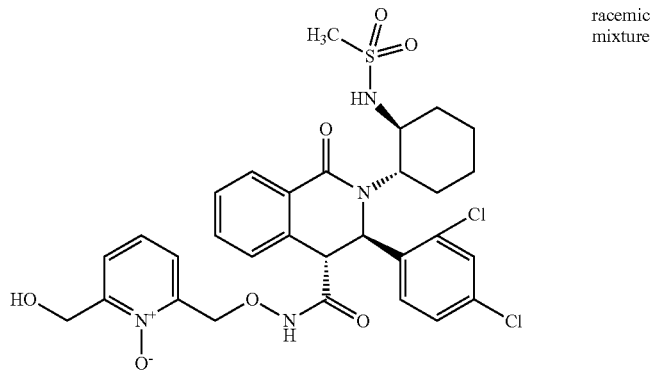 racemic mixture
689 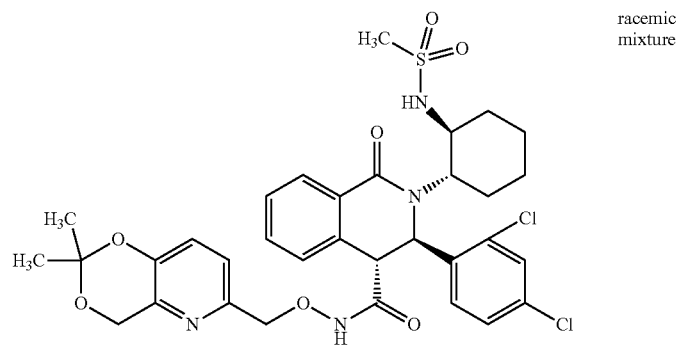 racemic mixture
690 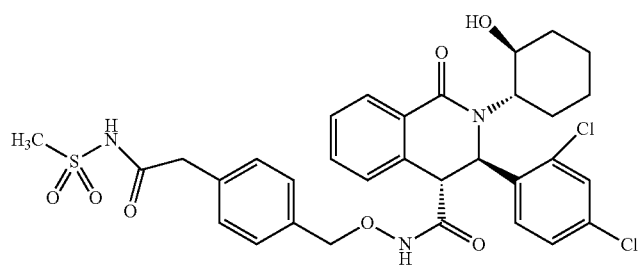 [SMILES: CS(=O)(=O)NC(=O)Cc1ccc(CONC(=O)[C@@H]2c3ccccc3C(=O)N([C@H]3CCCC[C@@H]3O)[C@H]2c2ccc(Cl)cc2Cl)cc1] racemic mixture
691 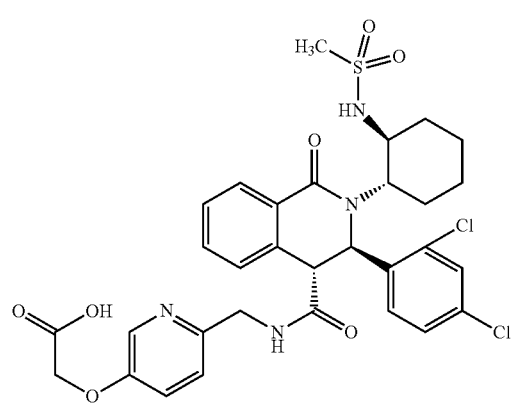 [SMILES: CS(=O)(=O)N[C@H]1CCCC[C@@H]1N1C(=O)c2ccccc2[C@@H](C(=O)NCc2ccc(OCC(=O)O)cn2)[C@@H]1c1ccc(Cl)cc1Cl] racemic mixture TABLE 225
| | | |
|---|---|---|
| 692 | 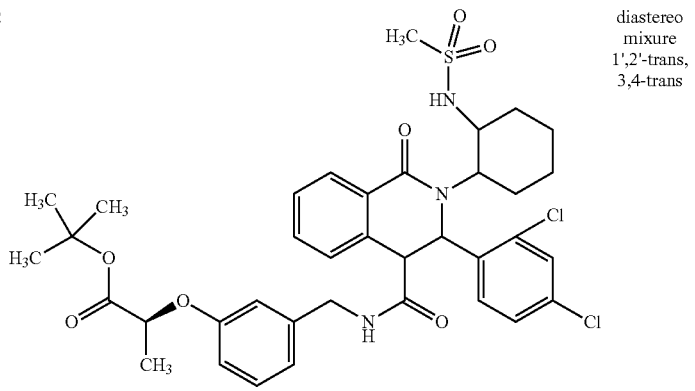 | diastereo mixure 1',2'-trans, 3,4-trans |
| 693 | 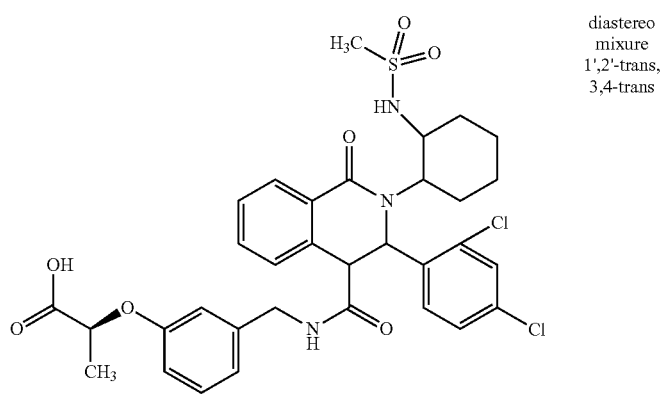 | diastereo mixure 1',2'-trans, 3,4-trans |
| 54 | 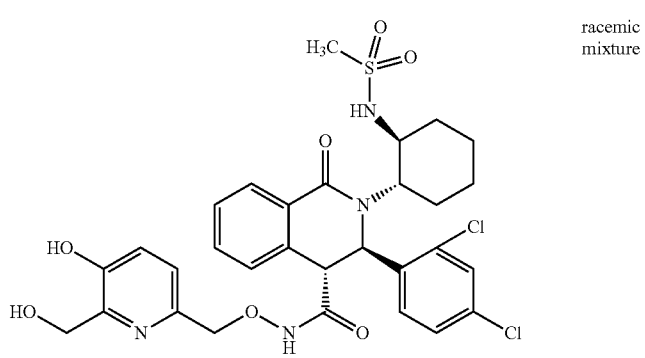 | racemic mixture |
| 694 | 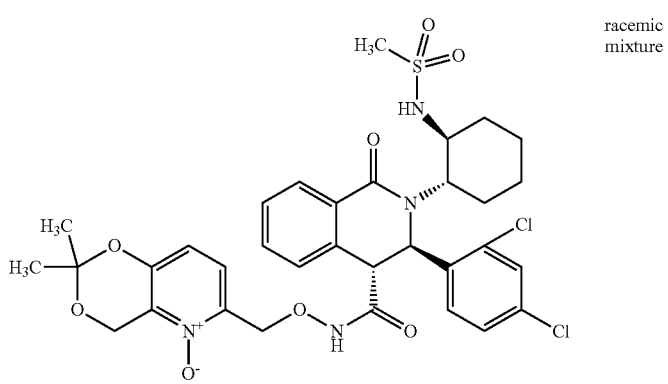 | racemic mixture |

TABLE 226
695 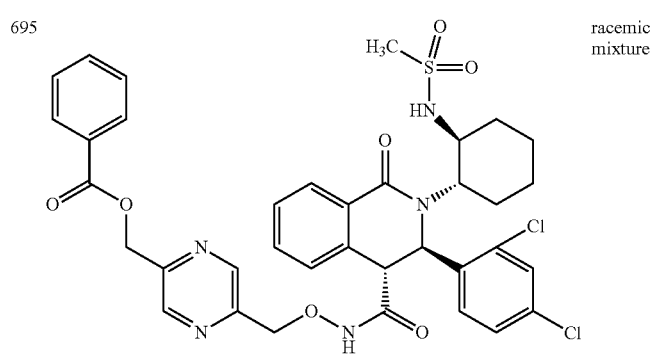 racemic mixture
696 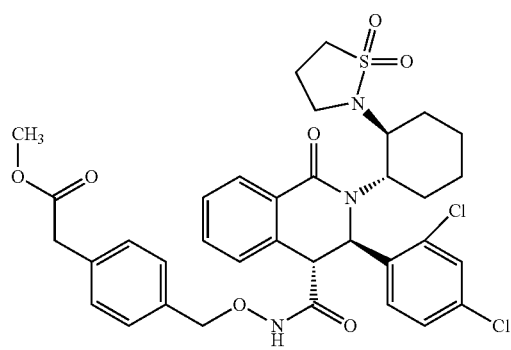 [SMILES: COC(=O)Cc1ccc(CONC(=O)[C@@H]2c3ccccc3C(=O)N([C@H]3CCCC[C@@H]3N3CCCS3(=O)=O)[C@H]2c2ccc(Cl)cc2Cl)cc1] racemic mixture
697 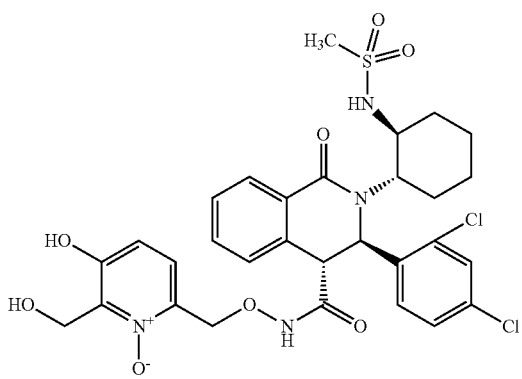 [SMILES: CS(=O)(=O)N[C@H]1CCCC[C@@H]1N1C(=O)c2ccccc2[C@@H](C(=O)NOCc2ccc(O)c(CO)[n+]2[O-])[C@@H]1c1ccc(Cl)cc1Cl] racemic mixture
698 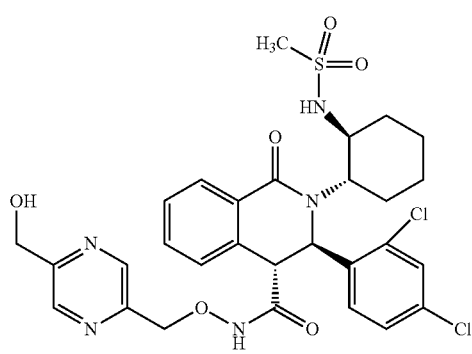 [SMILES: CS(=O)(=O)N[C@H]1CCCC[C@@H]1N1C(=O)c2ccccc2[C@@H](C(=O)NOCc2cnc(CO)cn2)[C@@H]1c1ccc(Cl)cc1Cl]

TABLE 227
| | | |
|---|---|---|
| 699 | 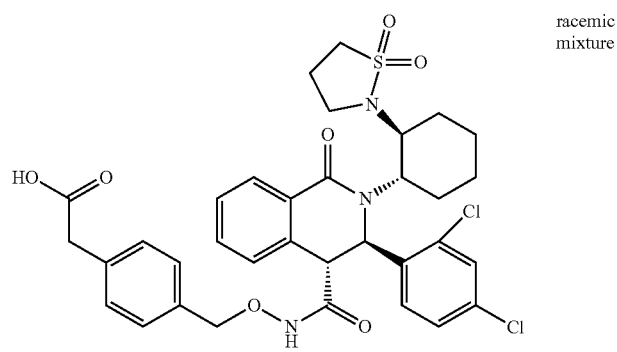 | racemic mixture |
| 700 | 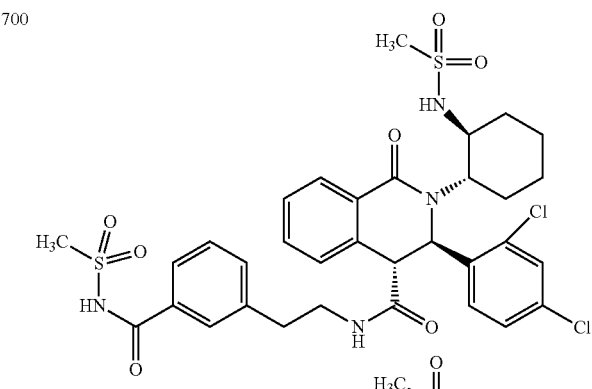 | |
| 701 | 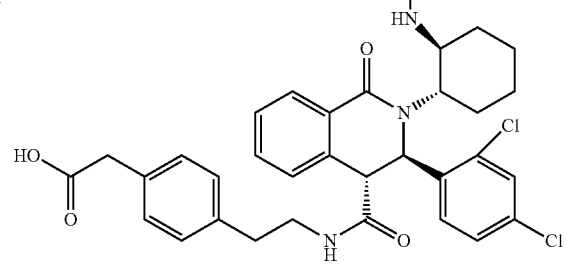 | |
| 702 | 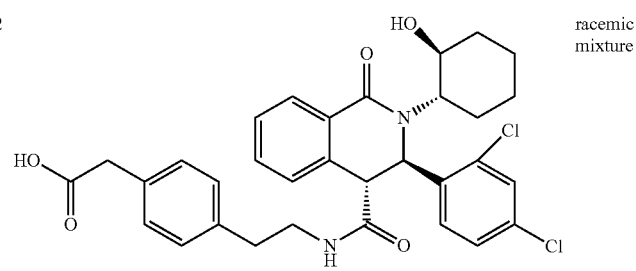 | racemic mixture |
| 703 | 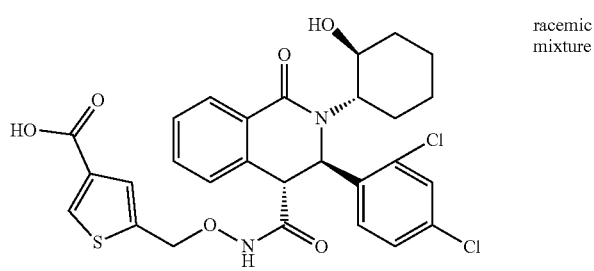 | racemic mixture |

TABLE 228
| 704 | 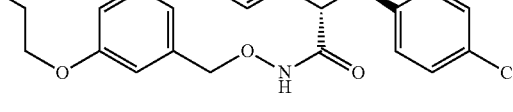 | racemic mixture |
| 705 | 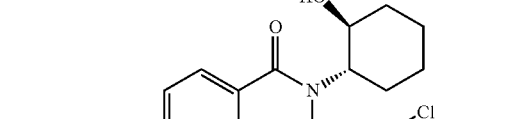 | racemic mixture |
| 706 | 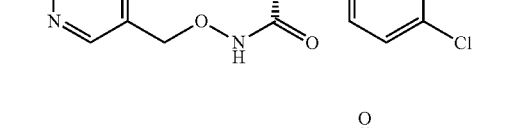 | |
| 707 |  | racemic mixture |
| 708 | 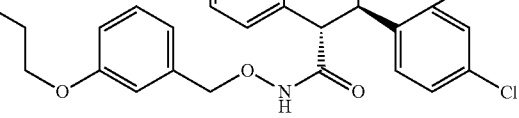 | racemic mixture |

TABLE 229
| | | |
|---|---|---|
| 44 | 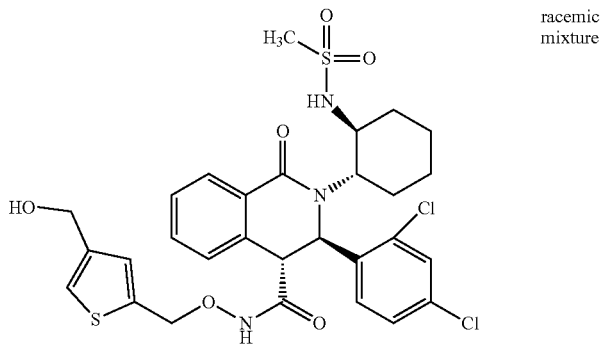 | racemic mixture |
| 709 | 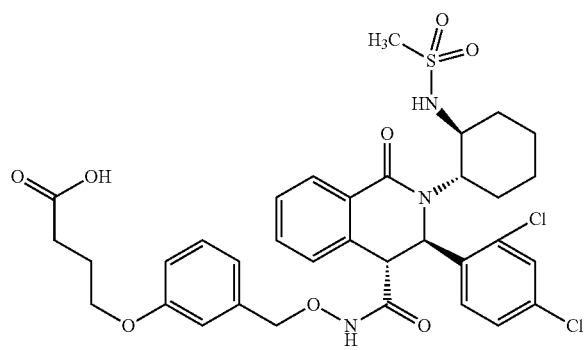 [SMILES: CS(=O)(=O)N[C@H]1CCCC[C@@H]1N1C(=O)c2ccccc2[C@@H](C(=O)NOCc2cccc(OCCCC(=O)O)c2)[C@@H]1c1ccc(Cl)cc1Cl] | |
| 710 | 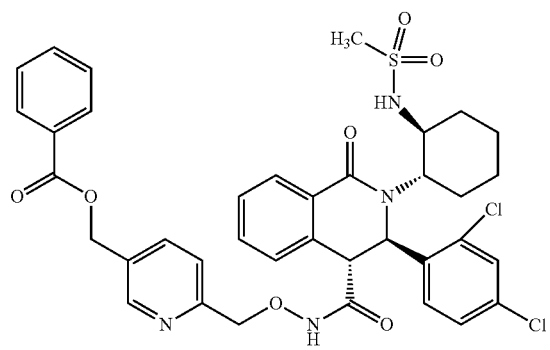 [SMILES: CS(=O)(=O)N[C@H]1CCCC[C@@H]1N1C(=O)c2ccccc2[C@@H](C(=O)NOCc2ccc(COC(=O)c3ccccc3)cn2)[C@@H]1c1ccc(Cl)cc1Cl] | |
| 711 | 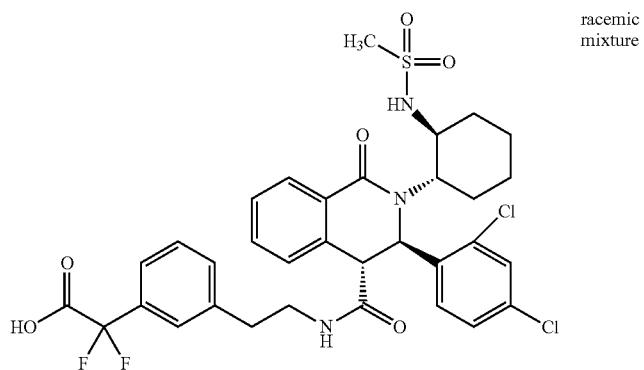 | racemic mixture |

TABLE 230
| | | |
|---|---|---|
| 712 | 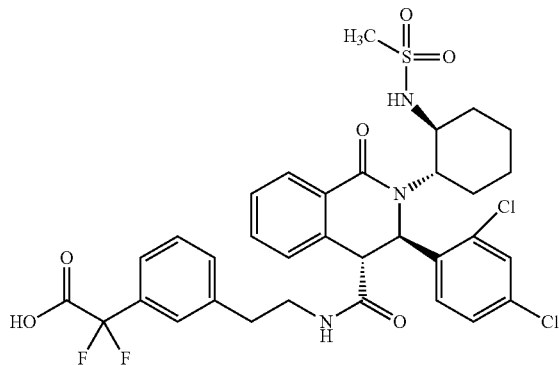 [SMILES: CS(=O)(=O)N[C@H]1CCCC[C@@H]1N1C(=O)c2ccccc2[C@@H](C(=O)NCCc2cccc(C(F)(F)C(=O)O)c2)[C@@H]1c1ccc(Cl)cc1Cl] | |
| 713 | 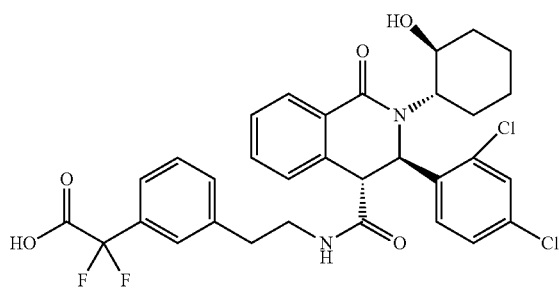 [SMILES: O=C(NCCc1cccc(C(F)(F)C(=O)O)c1)[C@@H]1c2ccccc2C(=O)N([C@H]2CCCC[C@@H]2O)[C@H]1c1ccc(Cl)cc1Cl] | racemic mixture |
| 714 | 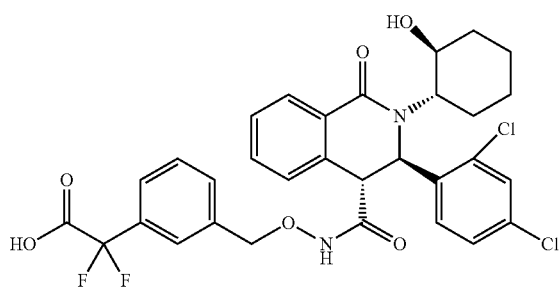 [SMILES: O=C(NOCc1cccc(C(F)(F)C(=O)O)c1)[C@@H]1c2ccccc2C(=O)N([C@H]2CCCC[C@@H]2O)[C@H]1c1ccc(Cl)cc1Cl] | racemic mixture |
| 715 | 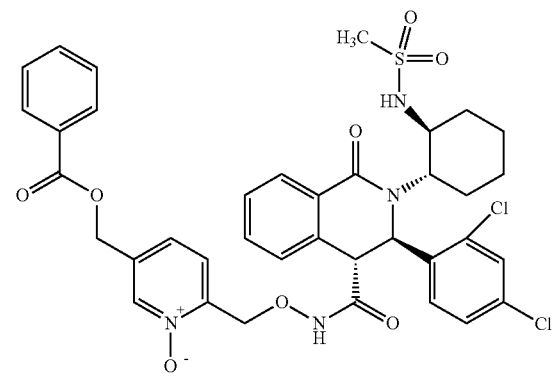 | |

TABLE 231
57 racemic mixture
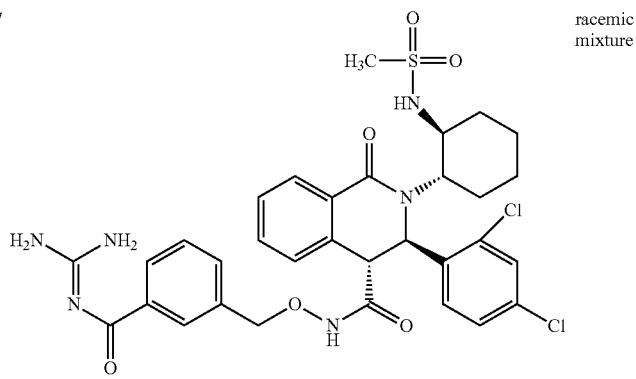
716 racemic mixture
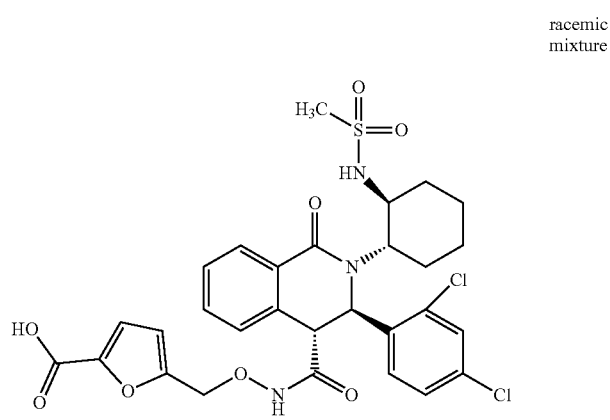
717 racemic mixture
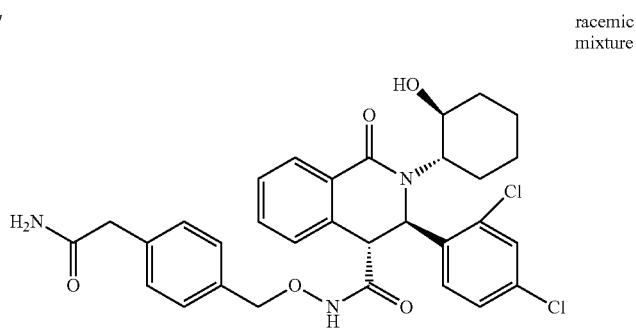
718
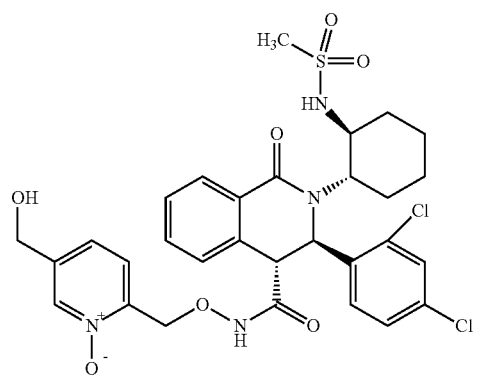

TABLE 232
| | | |
|---|---|---|
| 719 | 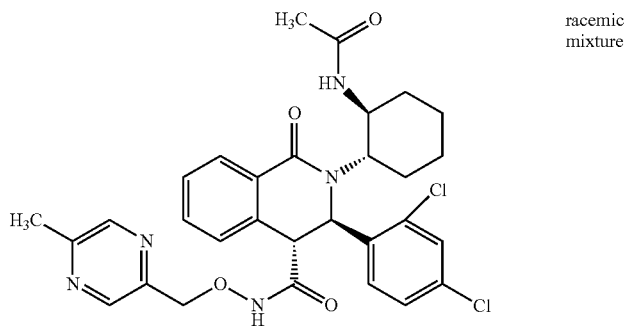 | racemic mixture |
| 720 | 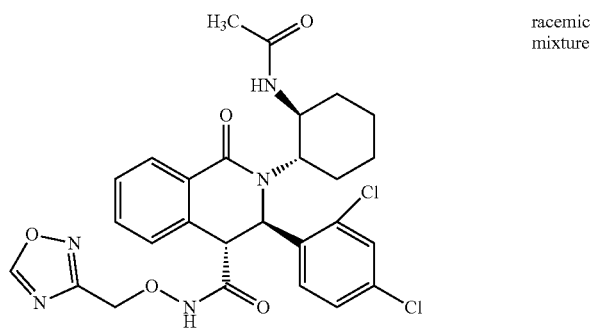 | racemic mixture |
| 721 | 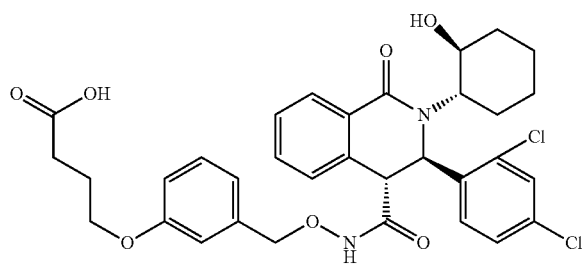 [SMILES: O=C(O)CCCOc1cccc(CONC(=O)[C@@H]2c3ccccc3C(=O)N([C@H]3CCCC[C@@H]3O)[C@H]2c2ccc(Cl)cc2Cl)c1] | |
| 722 | 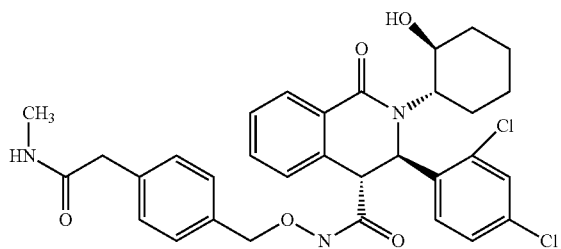 | |
| 723 | 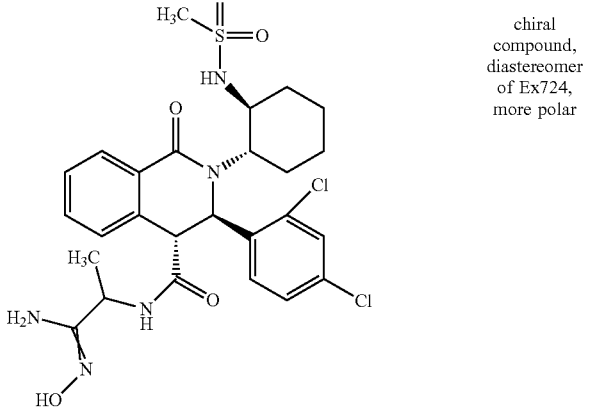 | chiral compound, diastereomer of Ex724, more polar |

TABLE 233
| 724 | 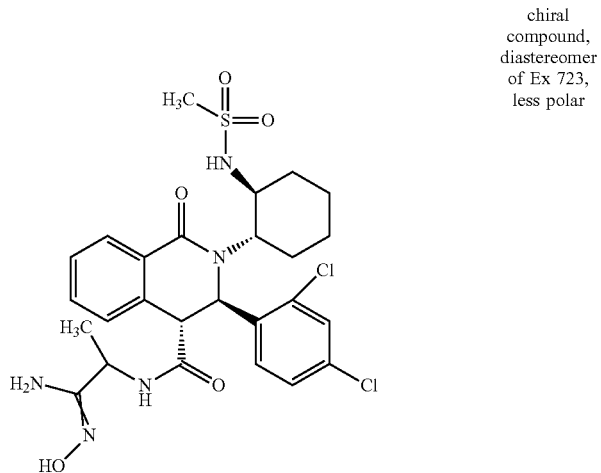 | chiral compound, diastereomer of Ex 723, less polar |
| 725 | 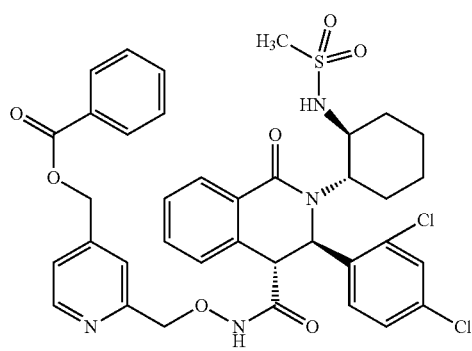 [SMILES: CS(=O)(=O)N[C@H]1CCCC[C@@H]1N1C(=O)c2ccccc2[C@@H](C(=O)NOCc2cc(COC(=O)c3ccccc3)ccn2)[C@@H]1c1ccc(Cl)cc1Cl] | racemic mixture |
| 726 | 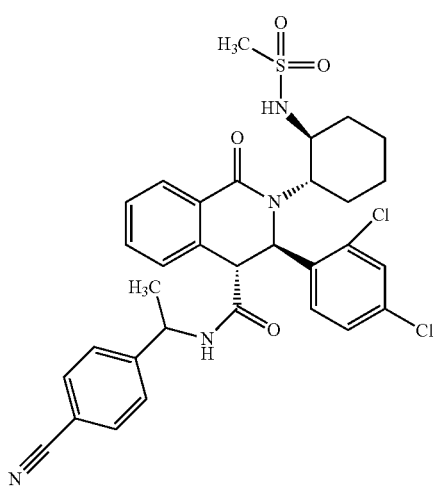 [SMILES: CC(NC(=O)[C@@H]1c2ccccc2C(=O)N([C@H]2CCCC[C@@H]2NS(C)(=O)=O)[C@H]1c1ccc(Cl)cc1Cl)c1ccc(C#N)cc1] | chiral compound, diastereomer of Ex 727, less polar |

TABLE 234
| 727 | 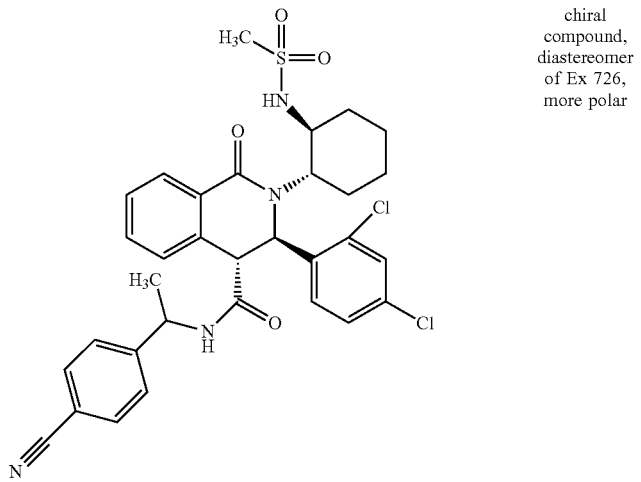 | chiral compound, diastereomer of Ex 726, more polar |
| 728 | 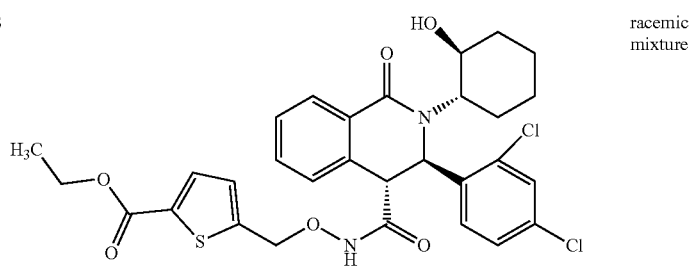 | racemic mixture |
| 729 | 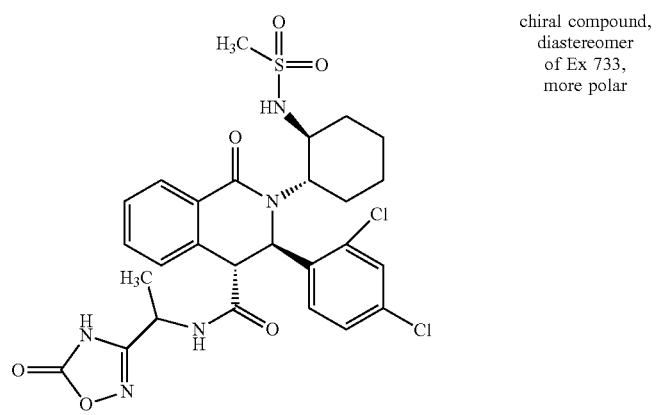 | chiral compound, diastereomer of Ex 733, more polar |
| 730 | 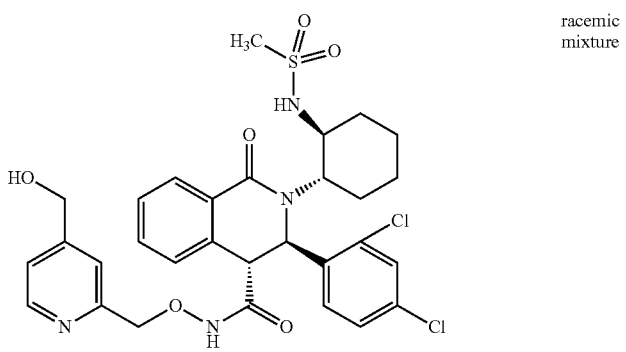 | racemic mixture |

TABLE 235
731 racemic mixture
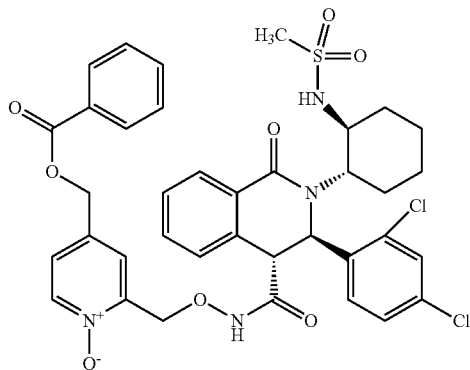 [SMILES: CS(=O)(=O)N[C@H]1CCCC[C@@H]1N1C(=O)c2ccccc2[C@@H](C(=O)NOCc2cc(COC(=O)c3ccccc3)cc[n+]2[O-])[C@@H]1c1ccc(Cl)cc1Cl]
732 racemic mixture
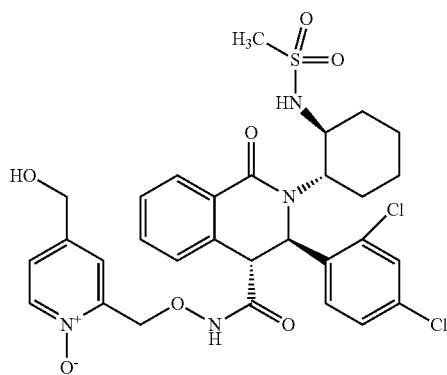 [SMILES: CS(=O)(=O)N[C@H]1CCCC[C@@H]1N1C(=O)c2ccccc2[C@@H](C(=O)NOCc2cc(CO)cc[n+]2[O-])[C@@H]1c1ccc(Cl)cc1Cl]
733 chiral compound, diastereomer of Ex 729, less polar
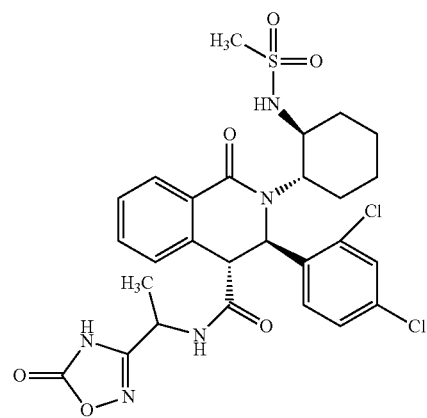 [SMILES: CC(NC(=O)[C@@H]1c2ccccc2C(=O)N([C@H]2CCCC[C@@H]2NS(C)(=O)=O)[C@H]1c1ccc(Cl)cc1Cl)c1noc(=O)[nH]1]

TABLE 236
| | | |
|---|---|---|
| 734 | 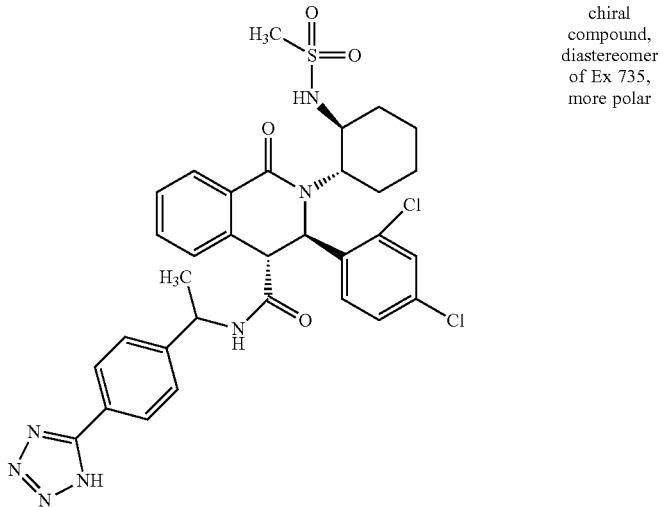 | chiral compound, diastereomer of Ex 735, more polar |
| 735 | 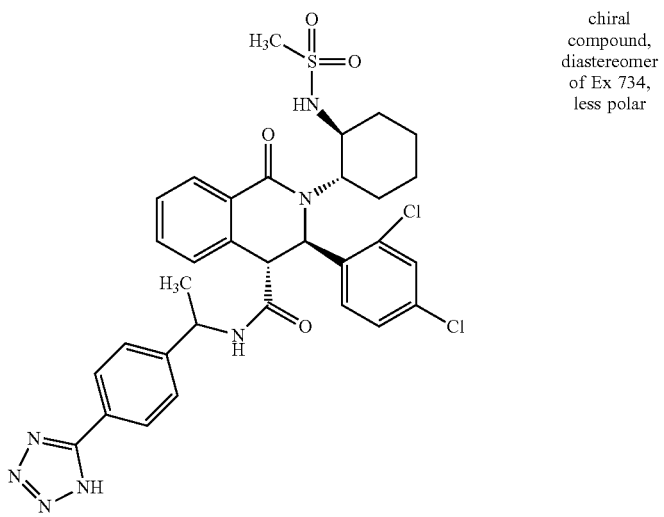 | chiral compound, diastereomer of Ex 734, less polar |
| 736 | 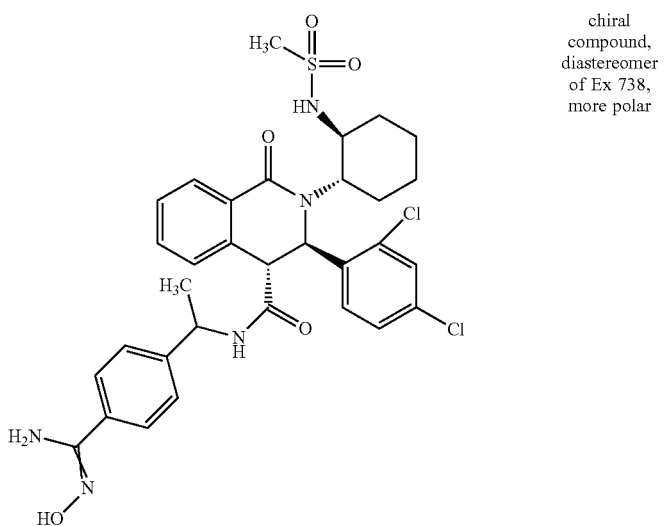 | chiral compound, diastereomer of Ex 738, more polar |

TABLE 237
| | | |
|---|---|---|
| 737 | 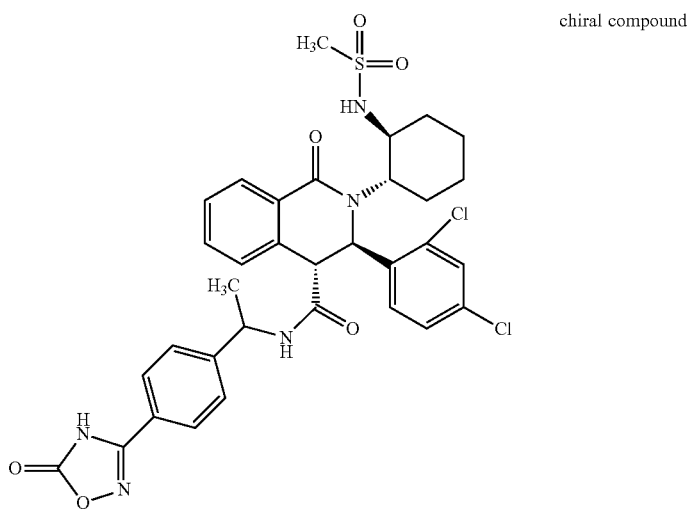 | chiral compound |
| 738 | 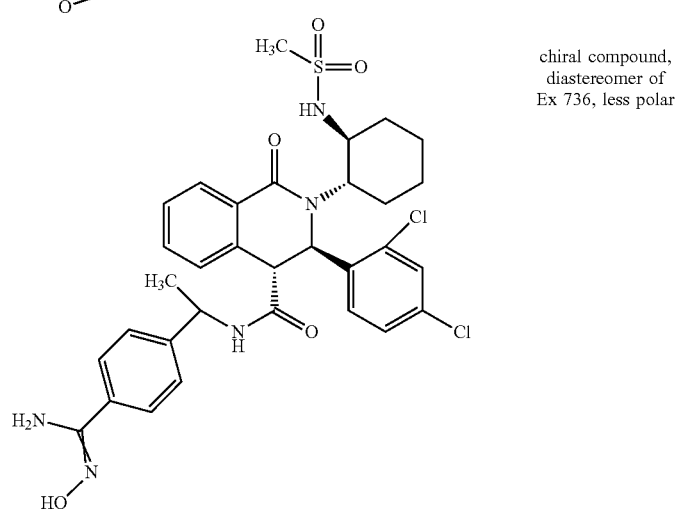 | chiral compound, diastereomer of Ex 736, less polar |
| 739 | 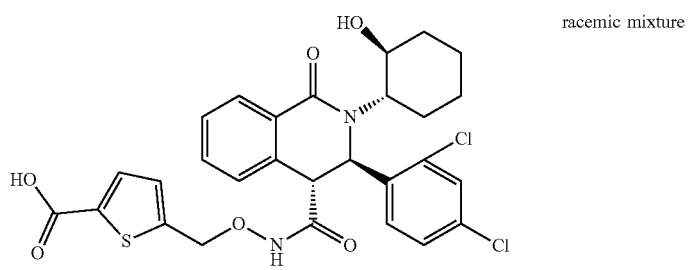 | racemic mixture |
| 740 | 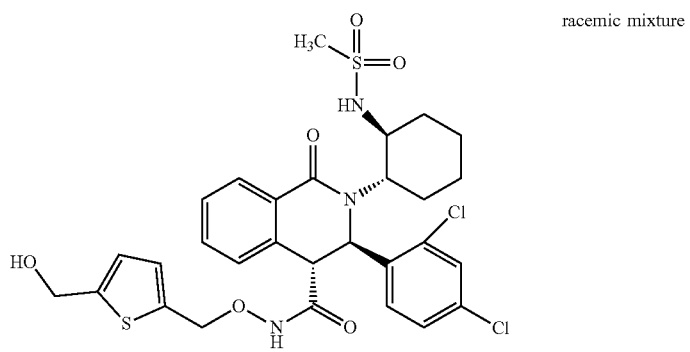 | racemic mixture |

TABLE 238

| | | |
|---|---|---|
| 741 | [structure] | racemic mixture |
| 742 | [structure] | racemic mixture, diastereomer of Ex 743, less polar |
| 743 | [structure] | racemic mixture, diastereomer of Ex 742, more polar |
| 744 | [structure] | racemic mixture, diastereomer of Ex 749, less polar |
| 745 | [structure] | racemic mixture |

TABLE 239
| 746 | 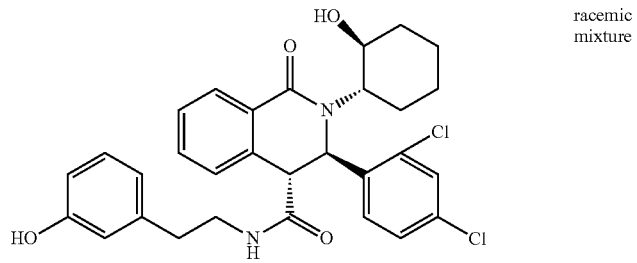 | racemic mixture |
| --- | --- | --- |
| 747 | 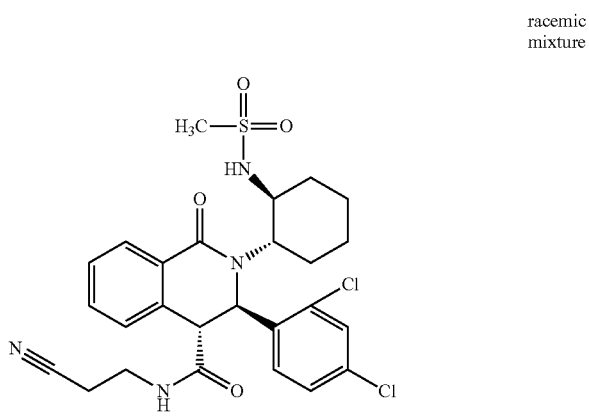 | racemic mixture |
| 748 | 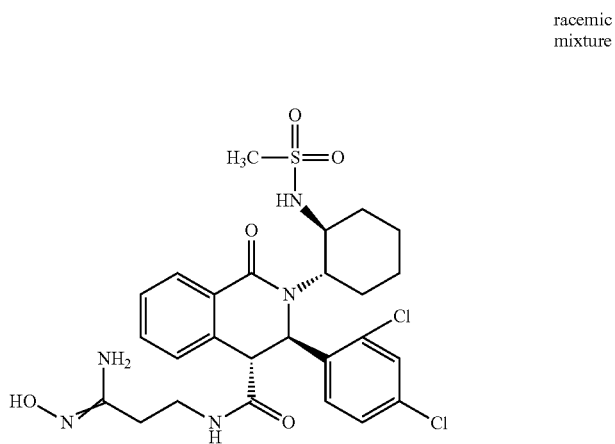 | racemic mixture |
| 59 | 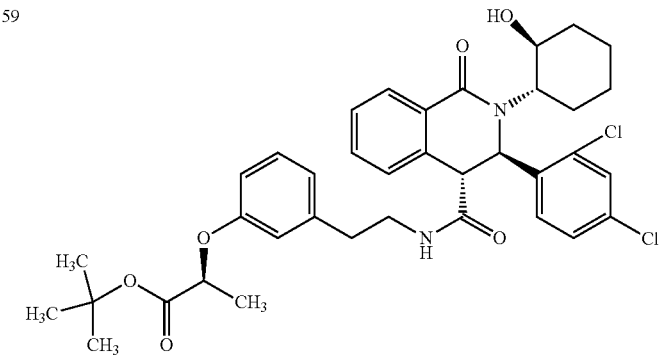 | |

TABLE 240
| | | |
|---|---|---|
| 749 | 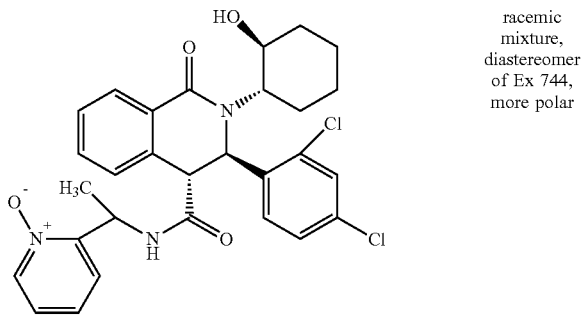 | racemic mixture, diastereomer of Ex 744, more polar |
| 750 | 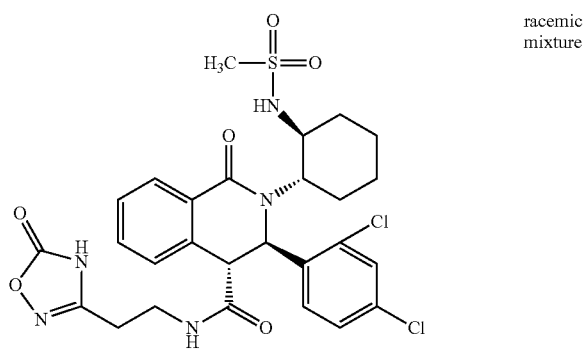 | racemic mixture |
| 751 | 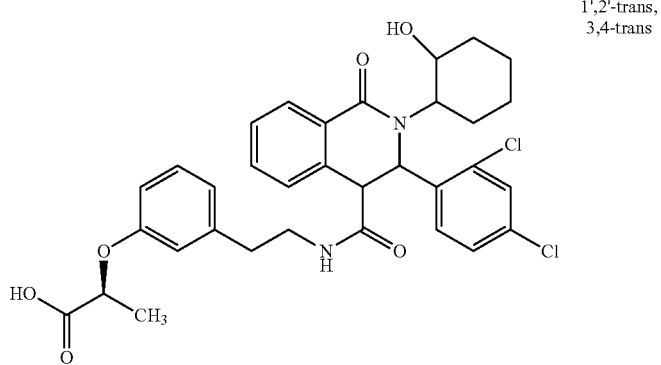 | diastero mixture, 1',2'-trans, 3,4-trans |
| 752 | 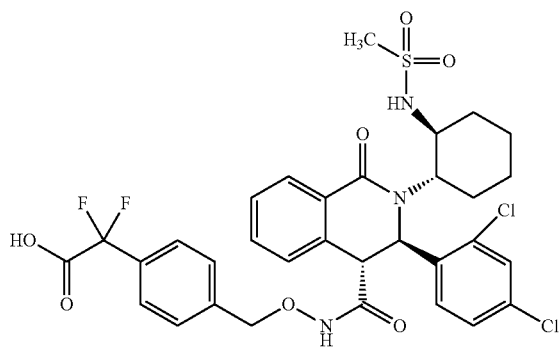 [SMILES: CS(=O)(=O)N[C@H]1CCCC[C@@H]1N1C(=O)c2ccccc2[C@@H](C(=O)NOCc2ccc(C(F)(F)C(=O)O)cc2)[C@@H]1c1ccc(Cl)cc1Cl] | |

TABLE 240-continued
| 753 | 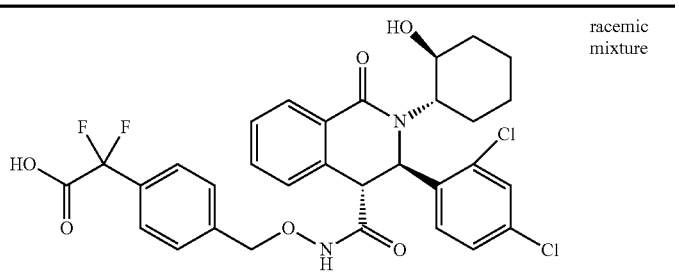 | racemic mixture |
TABLE 241
| 754 | 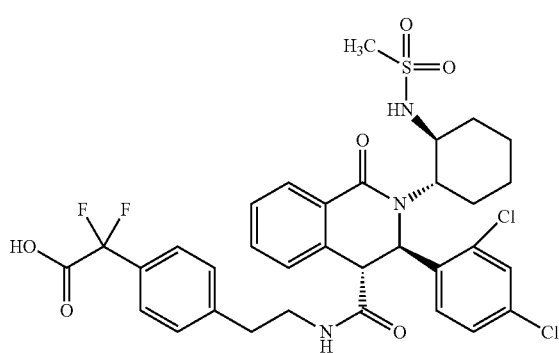 [SMILES: CS(=O)(=O)N[C@H]1CCCC[C@@H]1N1C(=O)c2ccccc2[C@@H](C(=O)NCCc2ccc(C(F)(F)C(=O)O)cc2)[C@@H]1c1ccc(Cl)cc1Cl] | |
| 755 | 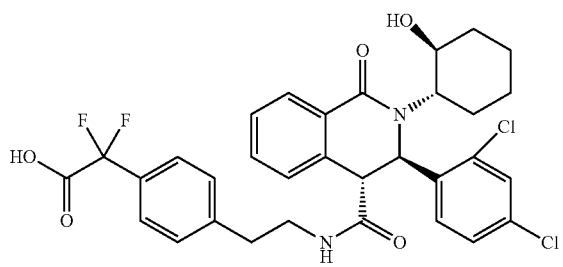 [SMILES: O=C(NCCc1ccc(C(F)(F)C(=O)O)cc1)[C@@H]1c2ccccc2C(=O)N([C@H]2CCCC[C@@H]2O)[C@H]1c1ccc(Cl)cc1Cl] | racemic mixture |
| 756 | 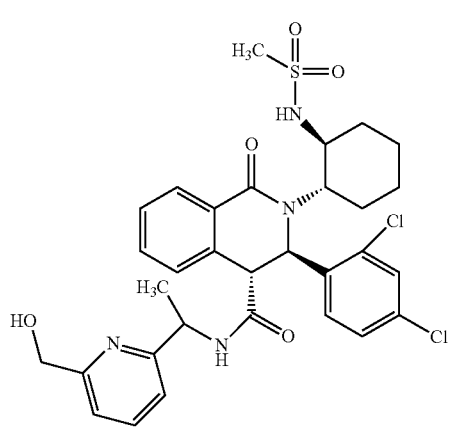 [SMILES: CC(NC(=O)[C@@H]1c2ccccc2C(=O)N([C@H]2CCCC[C@@H]2NS(C)(=O)=O)[C@H]1c1ccc(Cl)cc1Cl)c1cccc(CO)n1] | chiral compound, diastereomer of Ex 757, less polar |

TABLE 241-continued
| 757 | 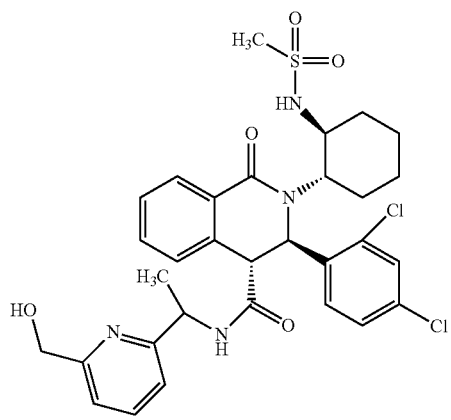 [SMILES: CC(NC(=O)[C@@H]1c2ccccc2C(=O)N([C@H]2CCCC[C@@H]2NS(C)(=O)=O)[C@H]1c1ccc(Cl)cc1Cl)c1cccc(CO)n1] | chiral compound, diastereomer of Ex 756, more polar |
TABLE 242
| 758 | 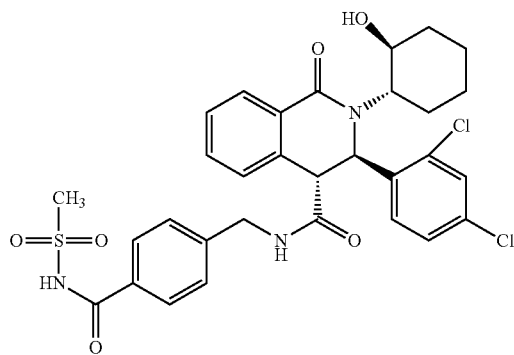 [SMILES: CS(=O)(=O)NC(=O)c1ccc(CNC(=O)[C@@H]2c3ccccc3C(=O)N([C@H]3CCCC[C@@H]3O)[C@H]2c2ccc(Cl)cc2Cl)cc1] | racemic mixture |
| 50 | 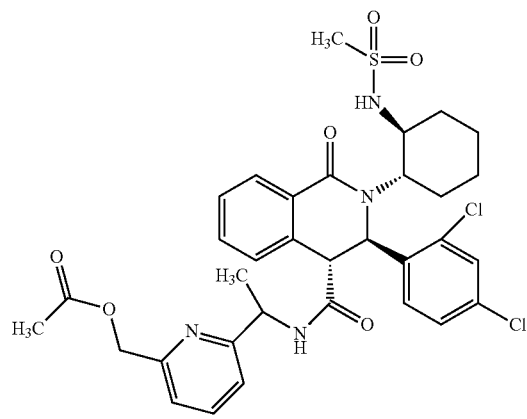 [SMILES: CC(=O)OCc1cccc(C(C)NC(=O)[C@@H]2c3ccccc3C(=O)N([C@H]3CCCC[C@@H]3NS(C)(=O)=O)[C@H]2c2ccc(Cl)cc2Cl)n1] | chiral compound |

TABLE 242-continued
759 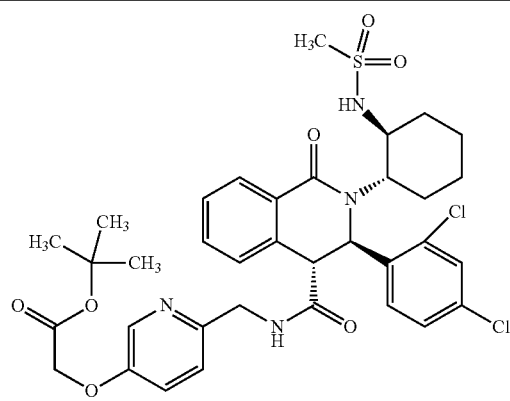
760 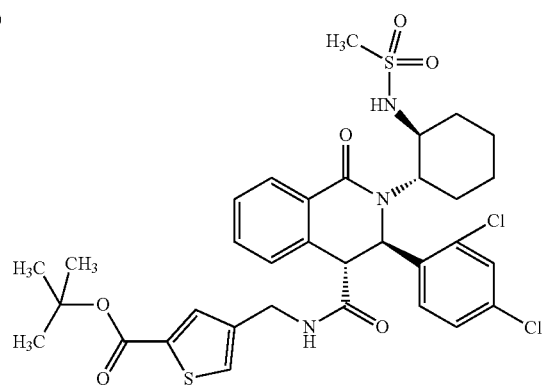
TABLE 243
761 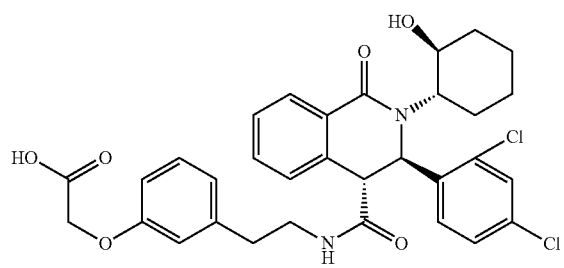 [SMILES: O=C(O)COc1cccc(CCNC(=O)[C@@H]2c3ccccc3C(=O)N([C@H]3CCCC[C@@H]3O)[C@H]2c2ccc(Cl)cc2Cl)c1]
762 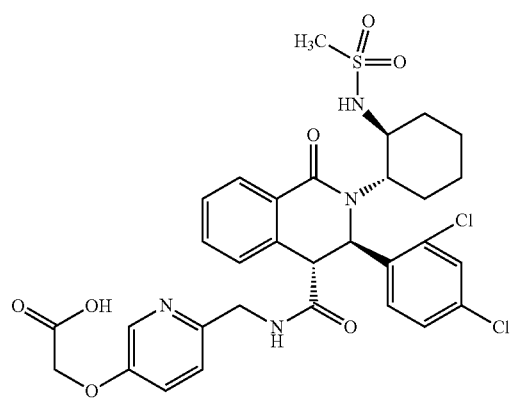
TFA

TABLE 243-continued
| | | |
|---|---|---|
| 763 | 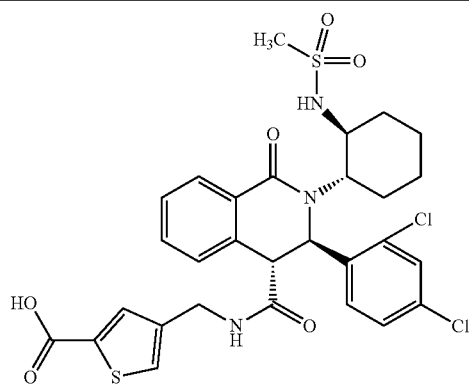 | |
| 764 | 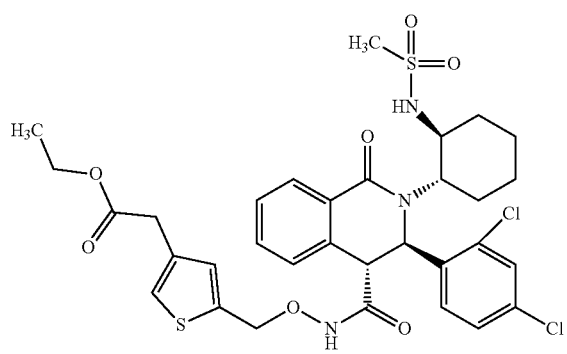 [SMILES: CCOC(=O)Cc1csc(CONC(=O)[C@@H]2c3ccccc3C(=O)N([C@H]3CCCC[C@@H]3NS(C)(=O)=O)[C@H]2c2ccc(Cl)cc2Cl)c1] | racemic mixture |
TABLE 244
| | | |
|---|---|---|
| 765 | 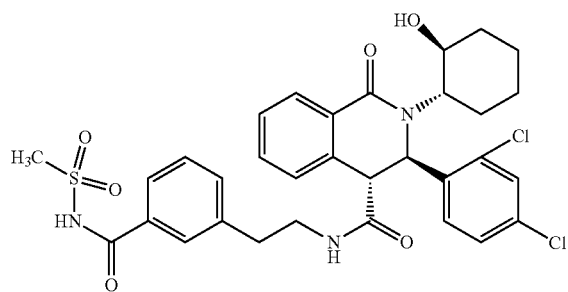 [SMILES: CS(=O)(=O)NC(=O)c1cccc(CCNC(=O)[C@@H]2c3ccccc3C(=O)N([C@H]3CCCC[C@@H]3O)[C@H]2c2ccc(Cl)cc2Cl)c1] | |
| 766 | 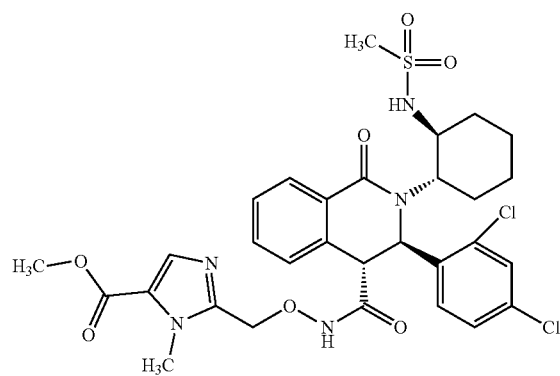 [SMILES: COC(=O)c1cnc(CONC(=O)[C@@H]2c3ccccc3C(=O)N([C@H]3CCCC[C@@H]3NS(C)(=O)=O)[C@H]2c2ccc(Cl)cc2Cl)n1C] | racemic mixture |

TABLE 244-continued
| 767 | 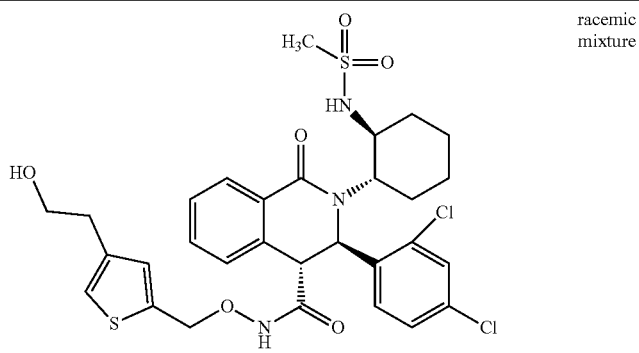 | racemic mixture |
|---|---|---|
| 768 | 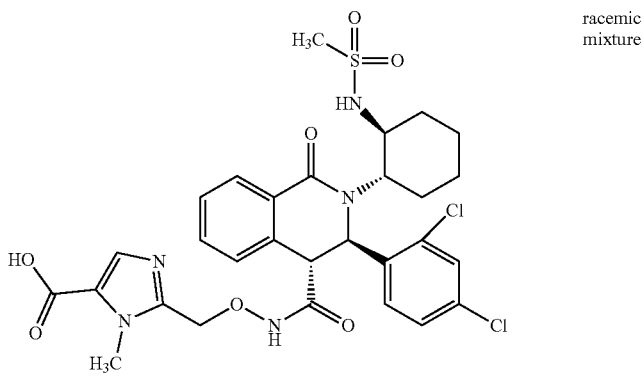 | racemic mixture |
TABLE 245
| 769 | 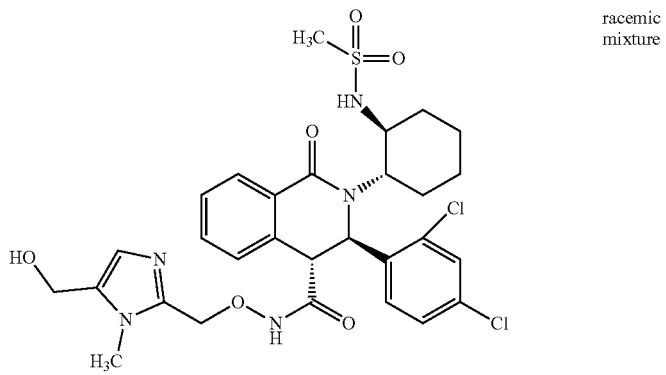 | racemic mixture |
|---|---|---|
| 770 | 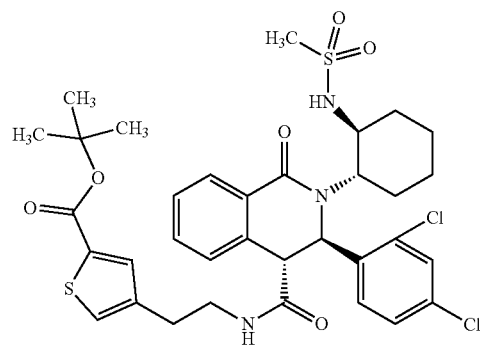 [SMILES: CC(C)(C)OC(=O)c1cc(CCNC(=O)[C@@H]2c3ccccc3C(=O)N([C@H]3CCCC[C@@H]3NS(C)(=O)=O)[C@H]2c2ccc(Cl)cc2Cl)cs1] | |

TABLE 245-continued
| | | |
|---|---|---|
| 771 | 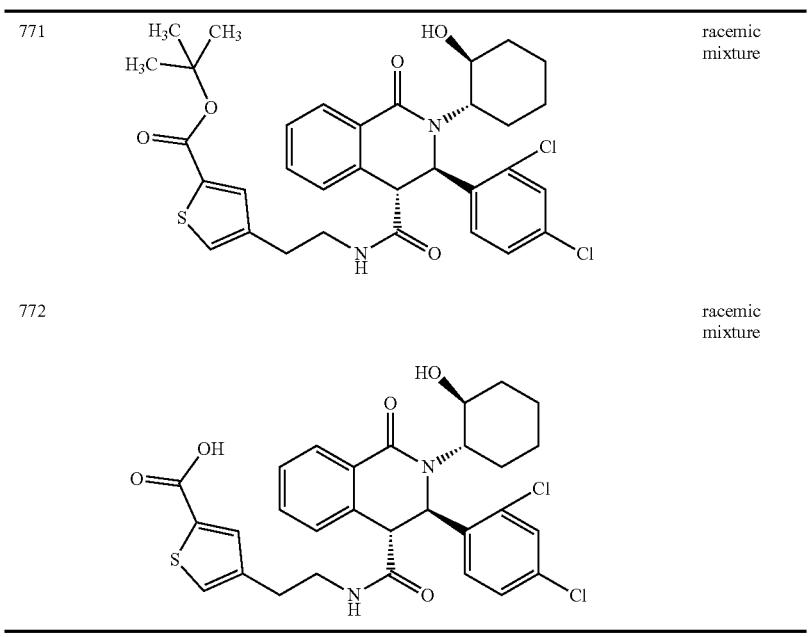 | racemic mixture |
| 772 | | racemic mixture |
TABLE 246
| | | |
|---|---|---|
| 773 | 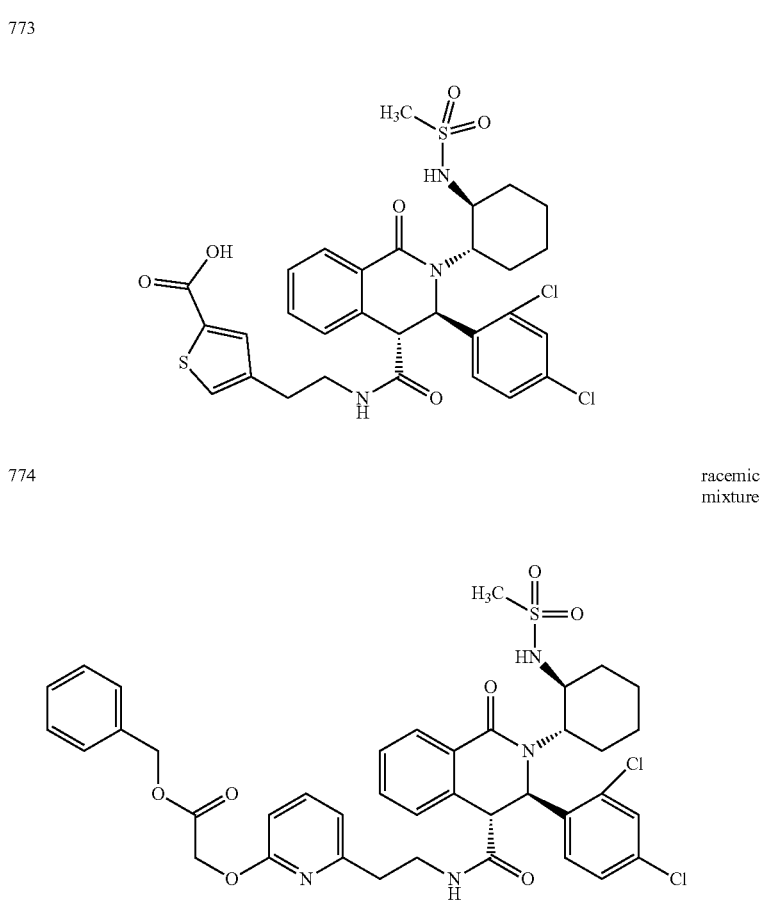 | |
| 774 | | racemic mixture |

TABLE 246-continued
| 775 | 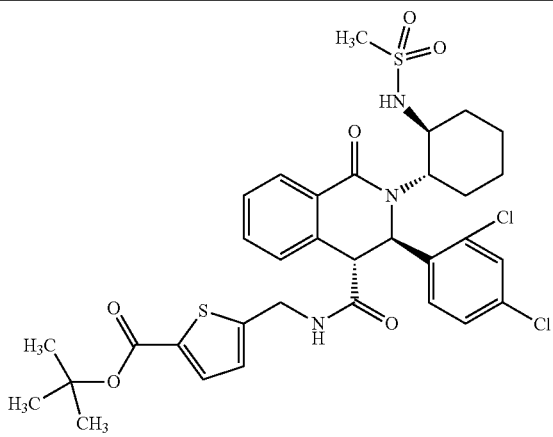 | |
| 776 | 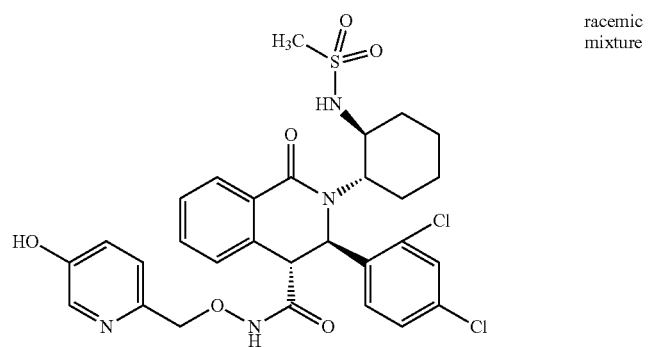 | racemic mixture |
TABLE 247
| 777 | 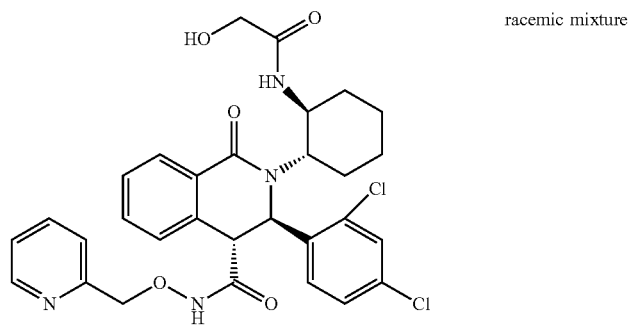 | racemic mixture |
| 48 | 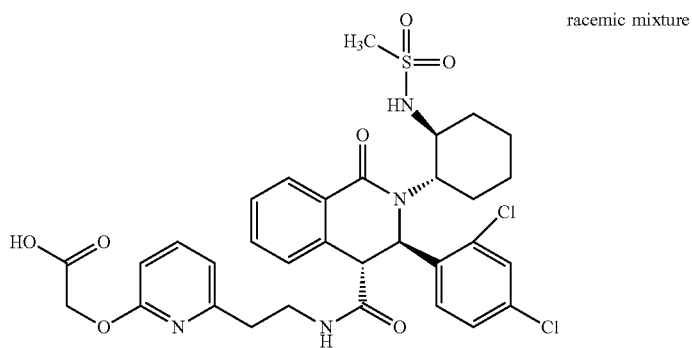 | racemic mixture |

TABLE 247-continued
778
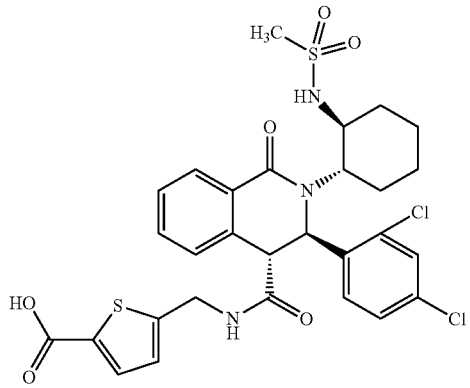 [SMILES: CS(=O)(=O)N[C@H]1CCCC[C@@H]1N1C(=O)c2ccccc2[C@@H](C(=O)NCc2ccc(C(=O)O)s2)[C@@H]1c1ccc(Cl)cc1Cl]
779
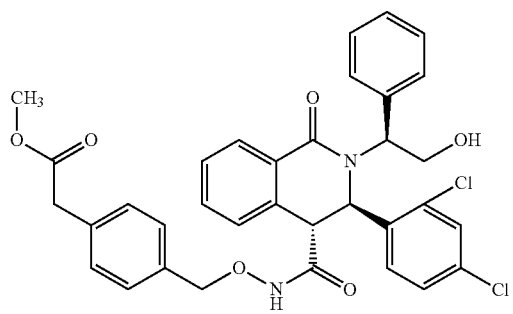 [SMILES: COC(=O)Cc1ccc(CONC(=O)[C@@H]2c3ccccc3C(=O)N([C@H](CO)c3ccccc3)[C@H]2c2ccc(Cl)cc2Cl)cc1]
TABLE 248
780
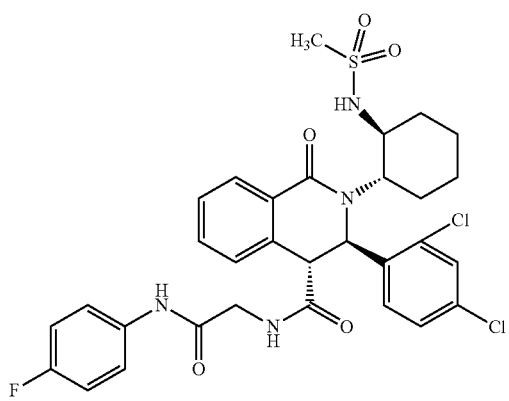 [SMILES: CS(=O)(=O)N[C@H]1CCCC[C@@H]1N1C(=O)c2ccccc2[C@@H](C(=O)NCC(=O)Nc2ccc(F)cc2)[C@@H]1c1ccc(Cl)cc1Cl]
781
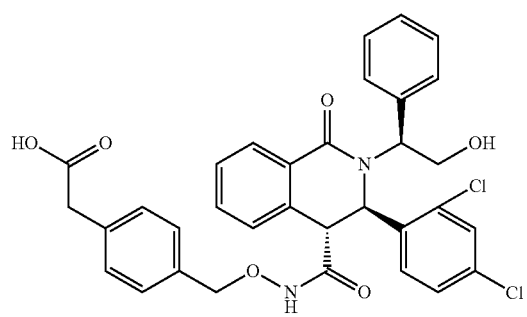

TABLE 248-continued
| 782 | 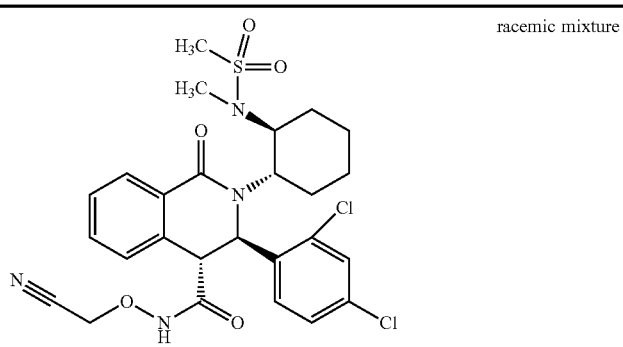 | racemic mixture |
| --- | --- | --- |
| 783 | 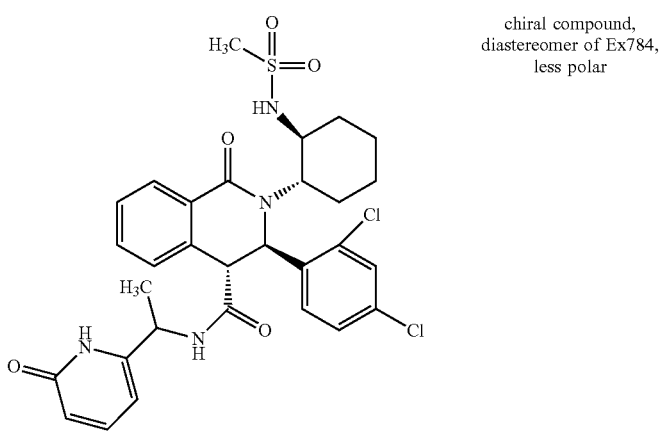 | chiral compound, diastereomer of Ex784, less polar |
TABLE 249
| 784 | 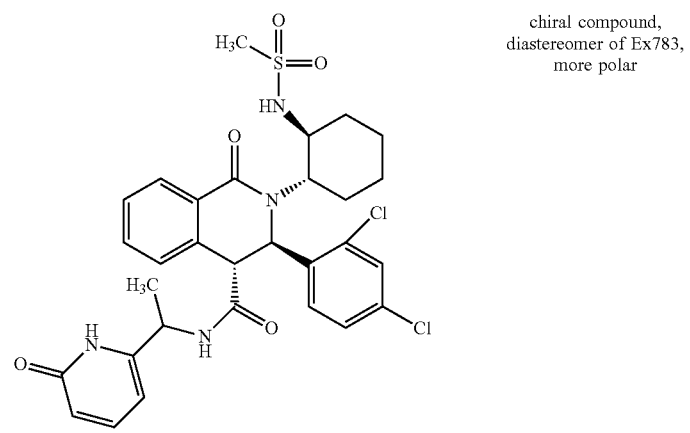 | chiral compound, diastereomer of Ex783, more polar |
| --- | --- | --- |
| 785 | 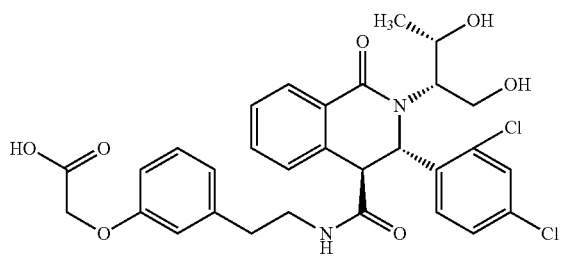 [SMILES: C[C@H](O)[C@H](CO)N1C(=O)c2ccccc2[C@H](C(=O)NCCc2cccc(OCC(=O)O)c2)[C@H]1c1ccc(Cl)cc1Cl] | |

TABLE 249-continued
| 786 | 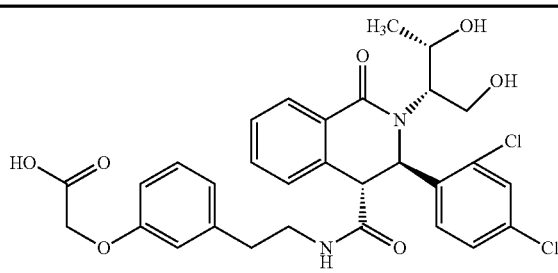 | |
| --- | --- | --- |
| 787 | 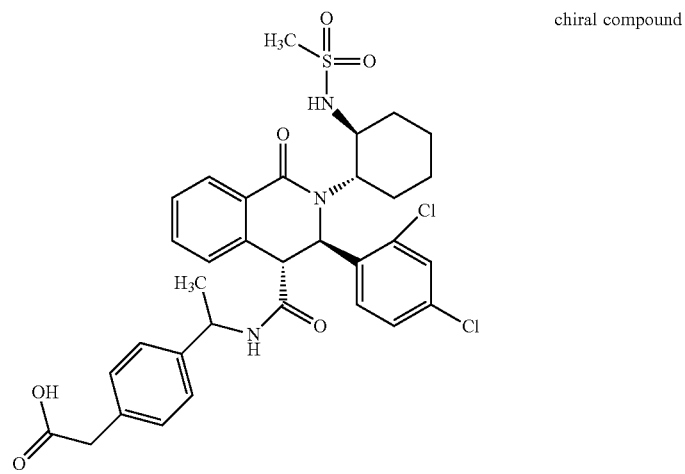 | chiral compound |
TABLE 250
| 788 | 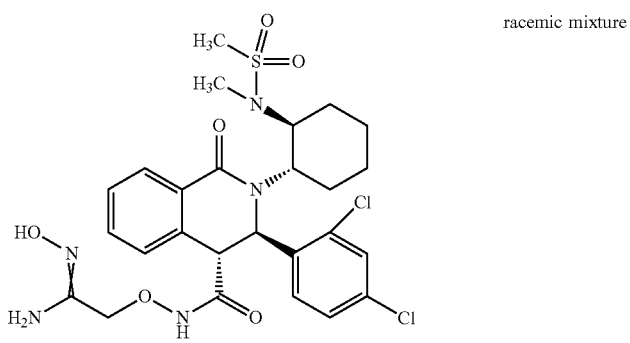 | racemic mixture |
| --- | --- | --- |
| 789 | 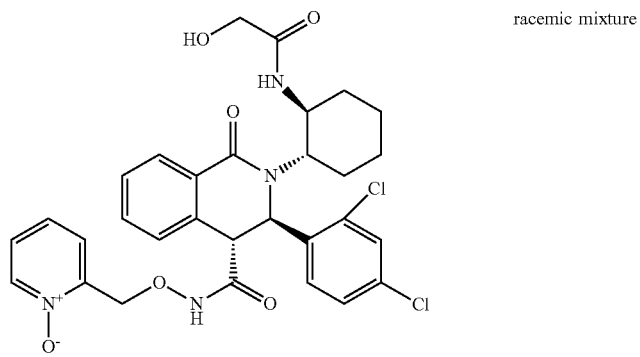 | racemic mixture |

TABLE 250-continued
790
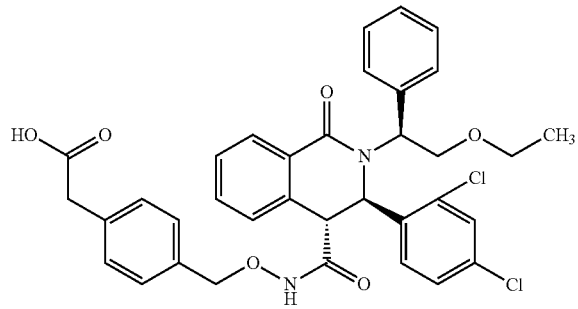 [SMILES: CCOC[C@H](c1ccccc1)N1C(=O)c2ccccc2[C@@H](C(=O)NOCc2ccc(CC(=O)O)cc2)[C@@H]1c1ccc(Cl)cc1Cl]
791
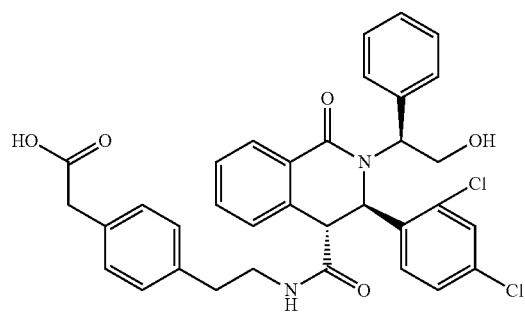 [SMILES: O=C(O)Cc1ccc(CCNC(=O)[C@@H]2c3ccccc3C(=O)N([C@H](CO)c3ccccc3)[C@H]2c2ccc(Cl)cc2Cl)cc1]
792
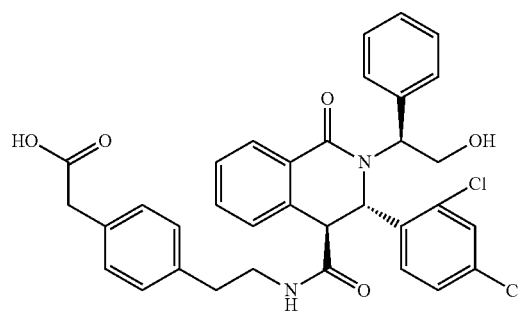
TABLE 251
793 racemic mixture
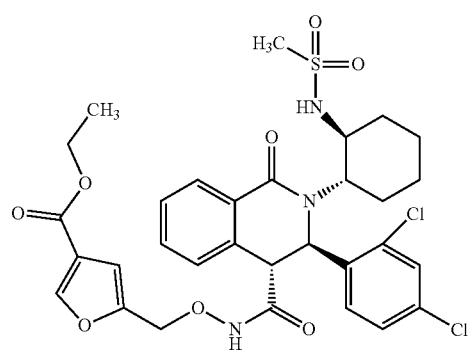 [SMILES: CCOC(=O)c1coc(CONC(=O)[C@@H]2c3ccccc3C(=O)N([C@H]3CCCC[C@@H]3NS(C)(=O)=O)[C@H]2c2ccc(Cl)cc2Cl)c1]

TABLE 251-continued
| 794 | 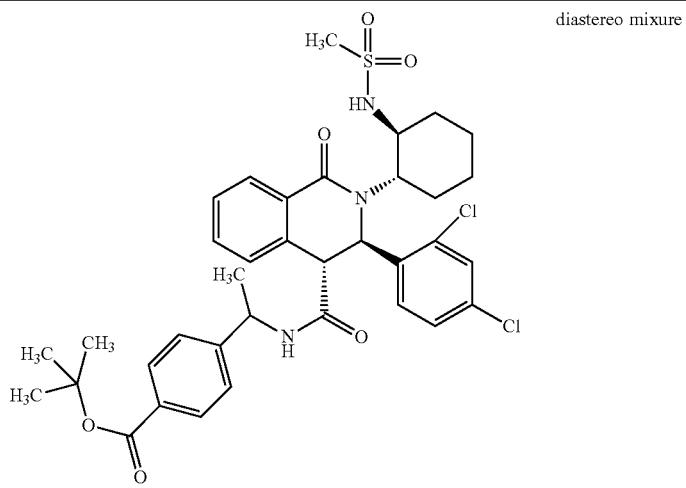 | diastereo mixure |
|---|---|---|
| 795 | 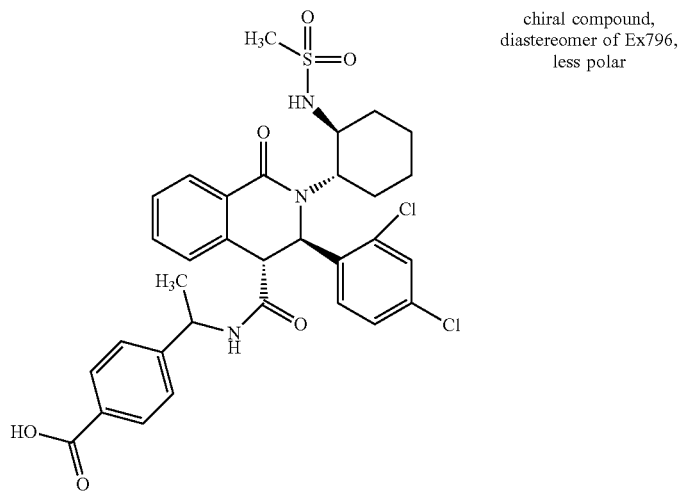 | chiral compound, diastereomer of Ex796, less polar |
TABLE 252
| 796 | 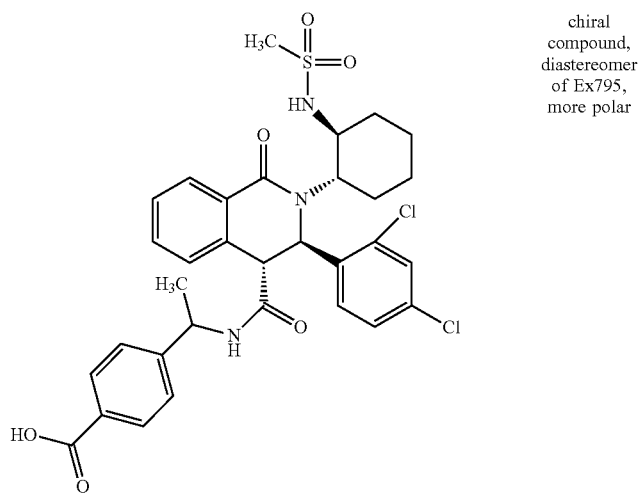 | chiral compound, diastereomer of Ex795, more polar |

TABLE 252-continued
| | | |
|---|---|---|
| 797 | 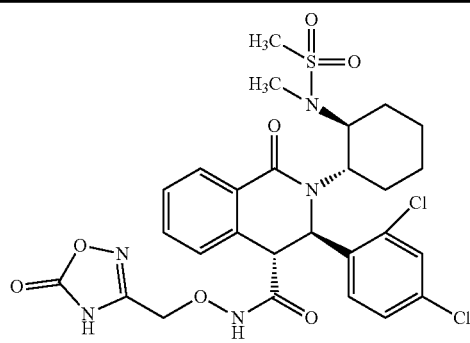 | racemic mixture |
| 798 | 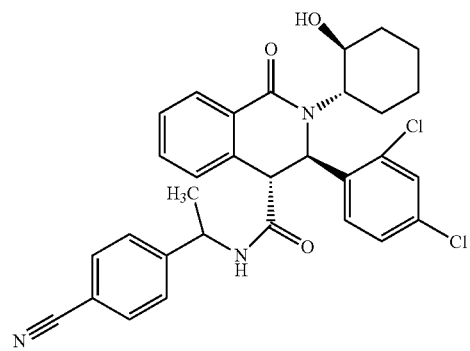 [SMILES: CC(NC(=O)[C@@H]1c2ccccc2C(=O)N([C@H]2CCCC[C@@H]2O)[C@H]1c1ccc(Cl)cc1Cl)c1ccc(C#N)cc1] | chiral compound, diastereomer of Ex799, less polar |
| 799 | 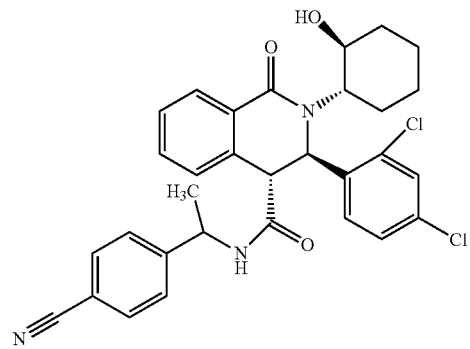 [SMILES: CC(NC(=O)[C@@H]1c2ccccc2C(=O)N([C@H]2CCCC[C@@H]2O)[C@H]1c1ccc(Cl)cc1Cl)c1ccc(C#N)cc1] | chiral compound, diastereomer of Ex798, more polar |
TABLE 253
| | | |
|---|---|---|
| 800 | 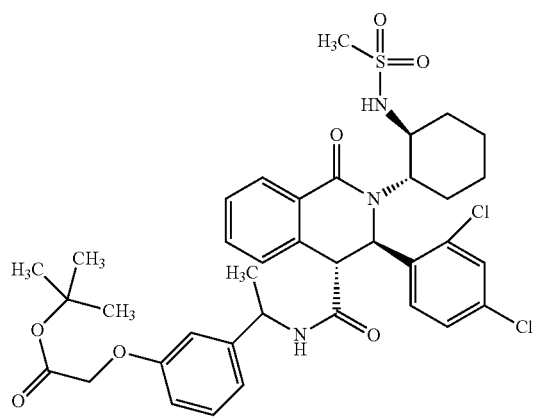 [SMILES: CC(NC(=O)[C@@H]1c2ccccc2C(=O)N([C@H]2CCCC[C@@H]2NS(C)(=O)=O)[C@H]1c1ccc(Cl)cc1Cl)c1cccc(OCC(=O)OC(C)(C)C)c1] | diastereo mixure |

TABLE 253-continued
| 801 | 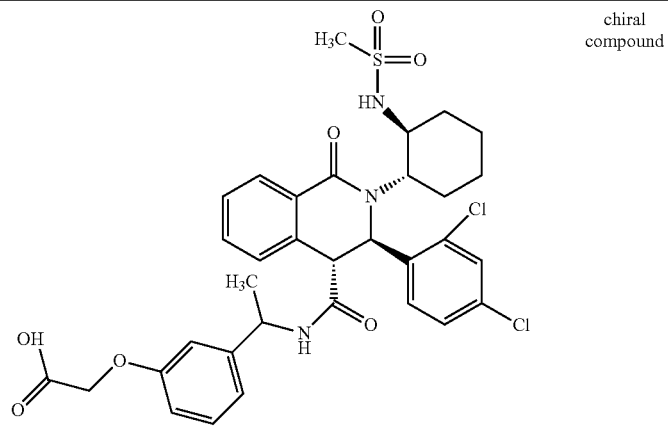 | chiral compound |
| 802 | 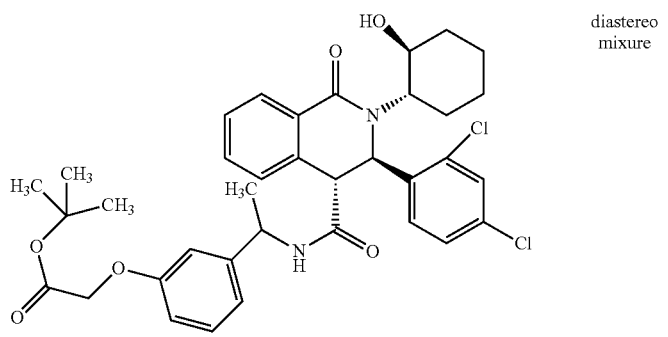 | diastereo mixure |
| 803 | 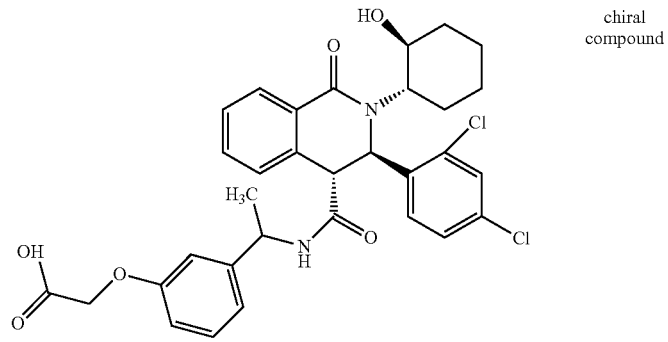 | chiral compound |
TABLE 254
| 804 | 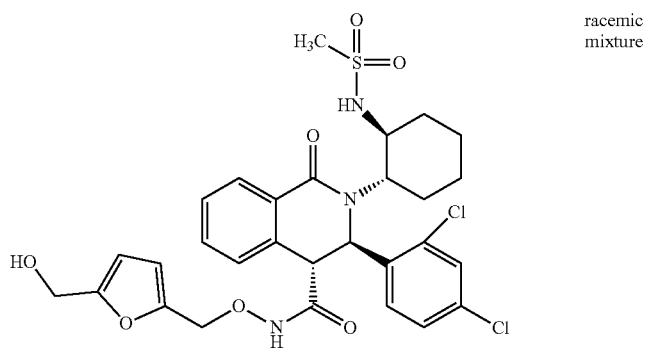 | racemic mixture |

TABLE 254-continued
805 chiral compound
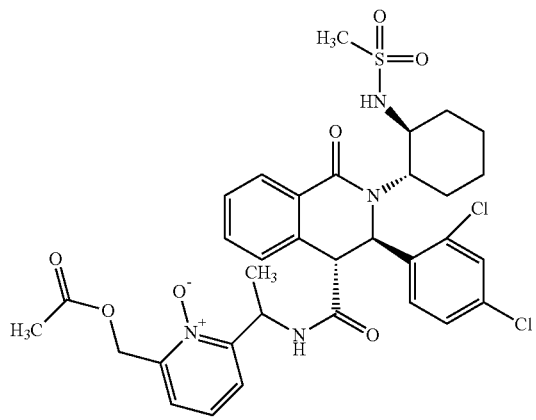
56 chiral compound
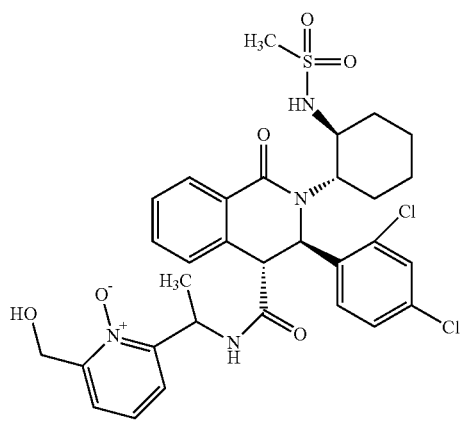
806 racemic mixture
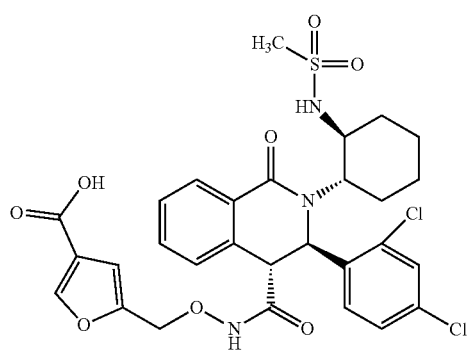 [SMILES: CS(=O)(=O)N[C@H]1CCCC[C@@H]1N1C(=O)c2ccccc2[C@@H](C(=O)NOCc2cc(C(=O)O)co2)[C@@H]1c1ccc(Cl)cc1Cl]

TABLE 255
| 807 | 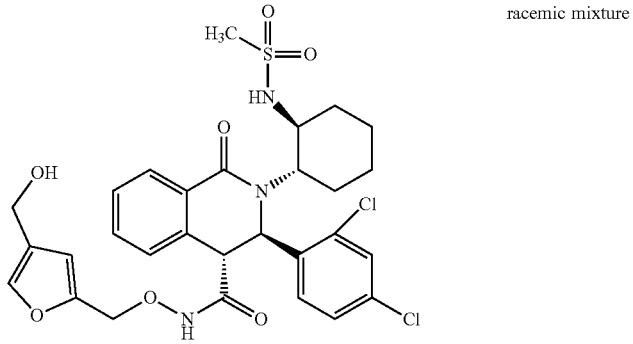 | racemic mixture |
| --- | --- | --- |
| 808 | 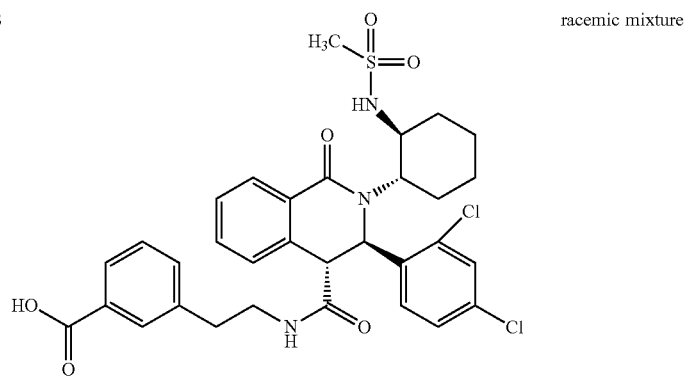 | racemic mixture |
| 809 | 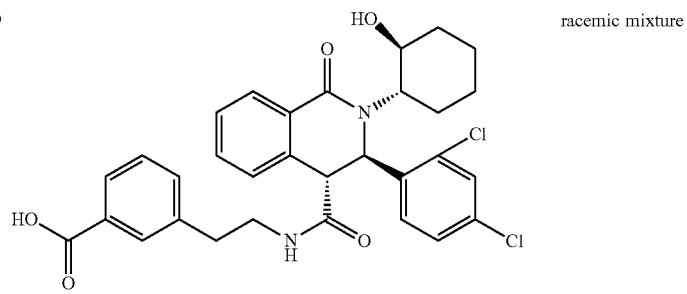 | racemic mixture |
| 810 | 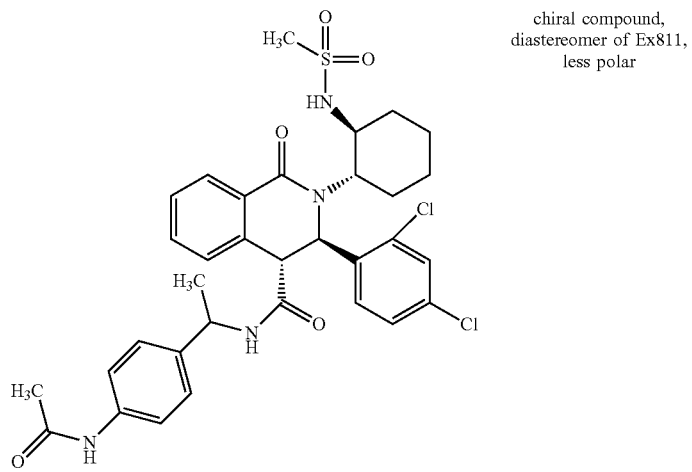 | chiral compound, diastereomer of Ex811, less polar |

TABLE 256
| 811 | 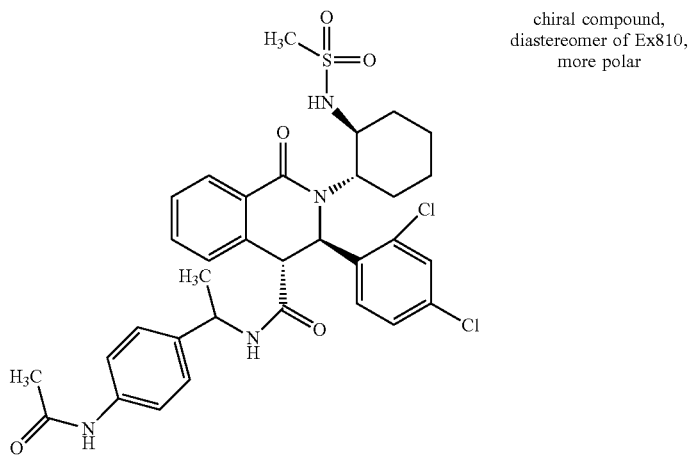 | chiral compound, diastereomer of Ex810, more polar |
| 812 | 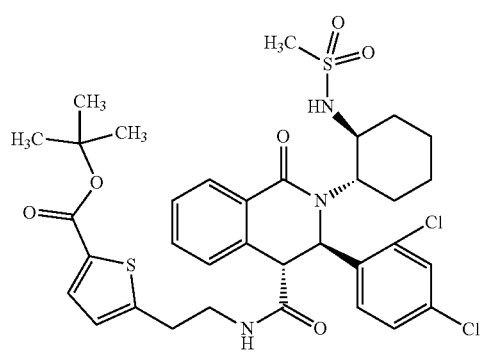 [SMILES: CC(C)(C)OC(=O)c1ccc(CCNC(=O)[C@@H]2c3ccccc3C(=O)N([C@H]3CCCC[C@@H]3NS(C)(=O)=O)[C@H]2c2ccc(Cl)cc2Cl)s1] | |
| 813 | 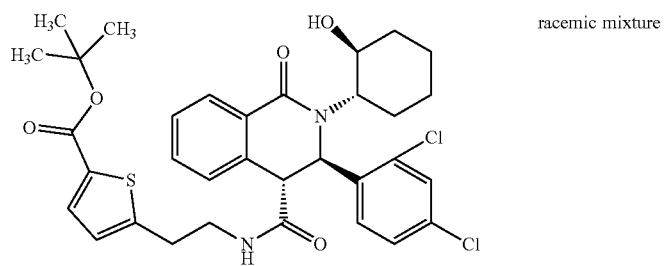 | racemic mixture |
| 814 | 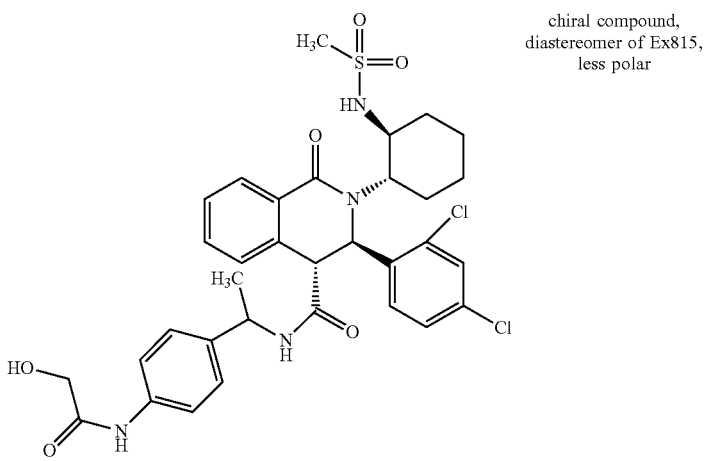 | chiral compound, diastereomer of Ex815, less polar |

TABLE 257
815 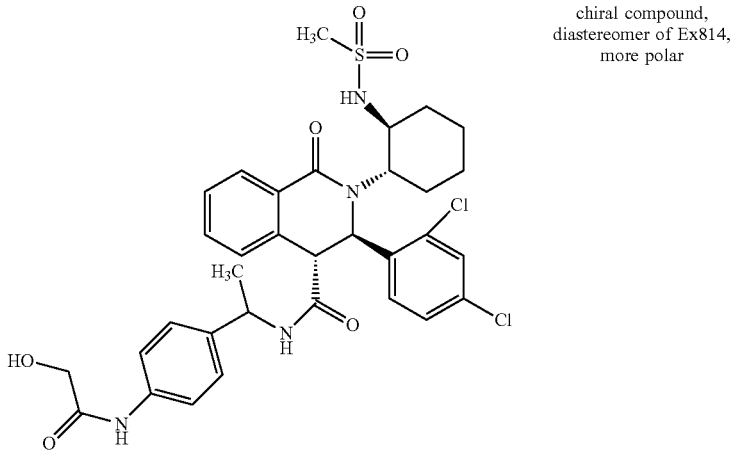 chiral compound, diastereomer of Ex814, more polar
816 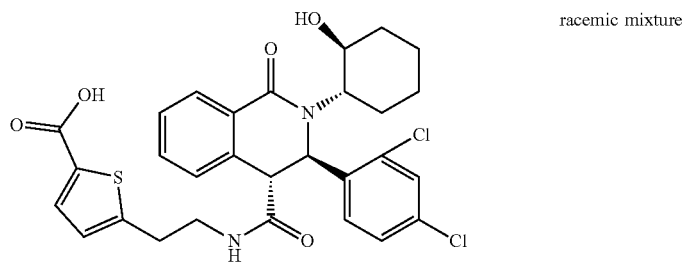 racemic mixture
817 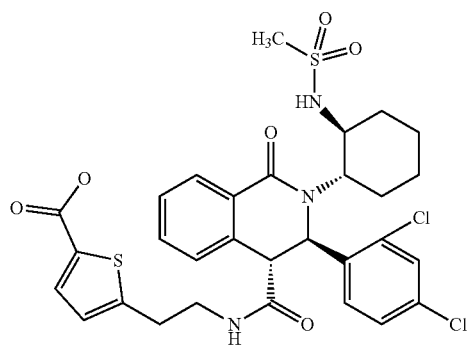 [SMILES: CS(=O)(=O)N[C@H]1CCCC[C@@H]1N1C(=O)c2ccccc2[C@@H](C(=O)NCCc2ccc(C(=O)O)s2)[C@@H]1c1ccc(Cl)cc1Cl]
818 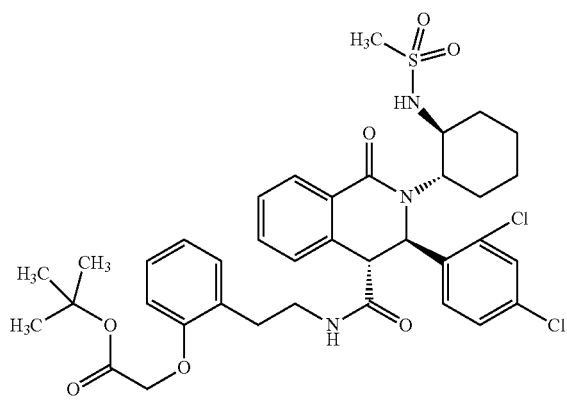 [SMILES: CC(C)(C)OC(=O)COc1ccccc1CCNC(=O)[C@@H]1c2ccccc2C(=O)N([C@H]2CCCC[C@@H]2NS(C)(=O)=O)[C@H]1c1ccc(Cl)cc1Cl]

TABLE 258
819 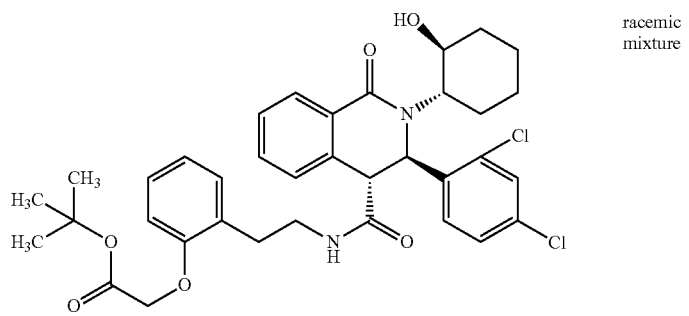 racemic mixture
820 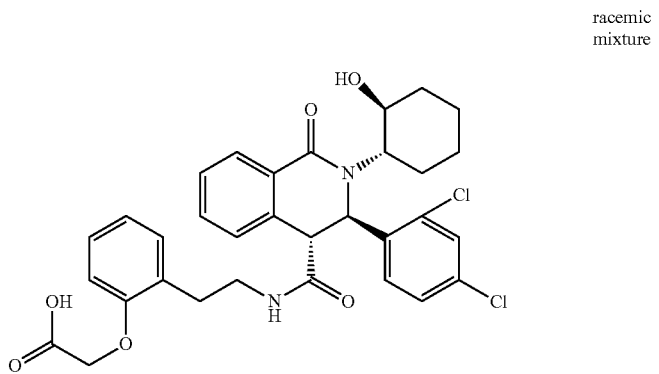 racemic mixture
821 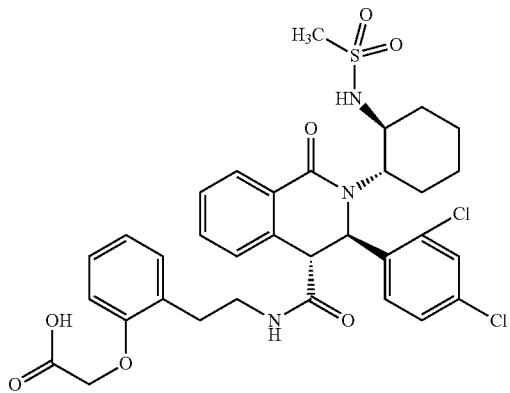 [SMILES: CS(=O)(=O)N[C@H]1CCCC[C@@H]1N1C(=O)c2ccccc2[C@@H](C(=O)NCCc2ccccc2OCC(=O)O)[C@@H]1c1ccc(Cl)cc1Cl]
822 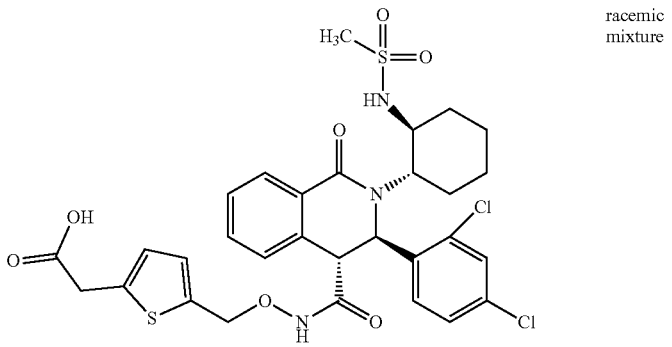 racemic mixture TABLE 259
| 823 | 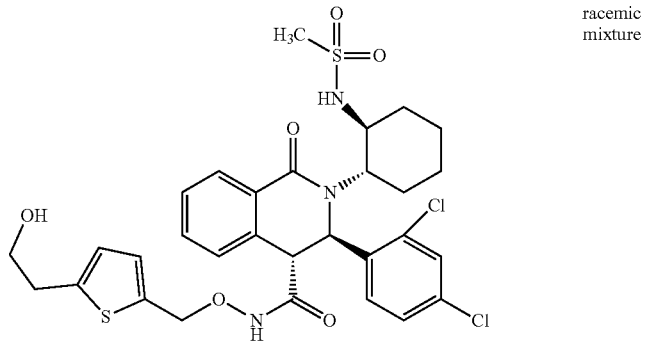 | racemic mixture |
| 824 | 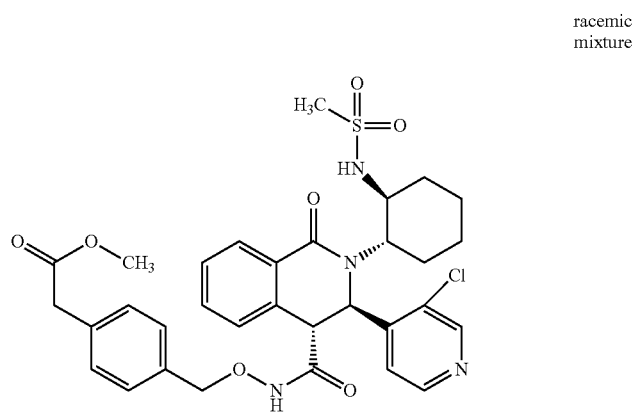 | racemic mixture |
| 825 | 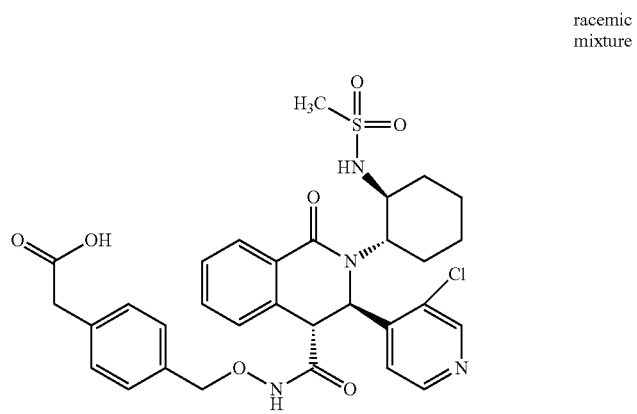 | racemic mixture |
| 826 | 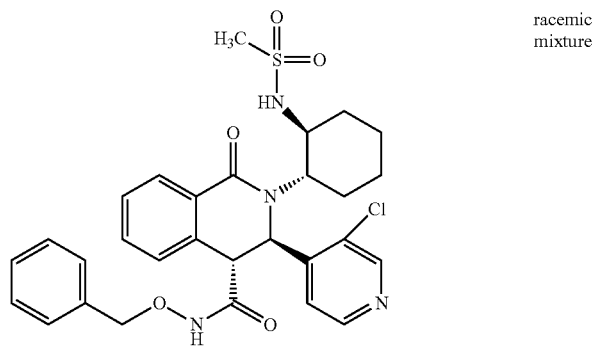 | racemic mixture |

TABLE 260
| 827 | 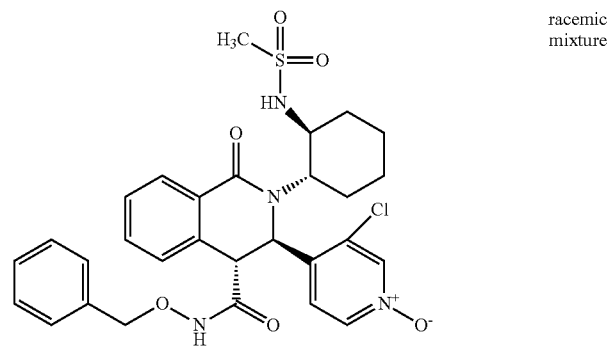 | racemic mixture |
| 828 | 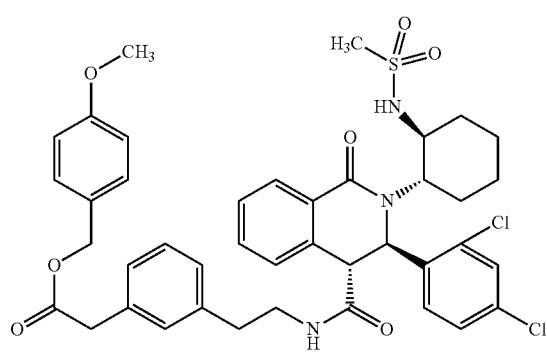 [SMILES: COc1ccc(COC(=O)Cc2cccc(CCNC(=O)[C@@H]3c4ccccc4C(=O)N([C@H]4CCCC[C@@H]4NS(C)(=O)=O)[C@H]3c3ccc(Cl)cc3Cl)c2)cc1] | |
| 829 | 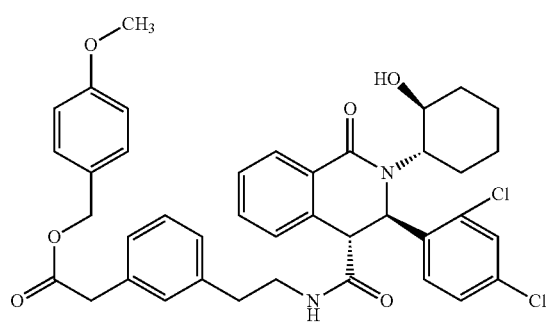 [SMILES: COc1ccc(COC(=O)Cc2cccc(CCNC(=O)[C@@H]3c4ccccc4C(=O)N([C@H]4CCCC[C@@H]4O)[C@H]3c3ccc(Cl)cc3Cl)c2)cc1] | racemic mixture |
| 58 | 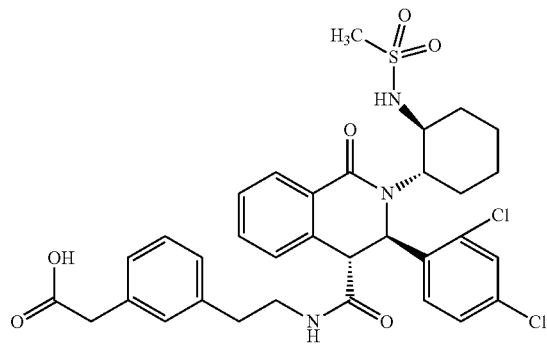 [SMILES: CS(=O)(=O)N[C@H]1CCCC[C@@H]1N1C(=O)c2ccccc2[C@@H](C(=O)NCCc2cccc(CC(=O)O)c2)[C@@H]1c1ccc(Cl)cc1Cl] | |

TABLE 261
| | | |
|---|---|---|
| 830 | 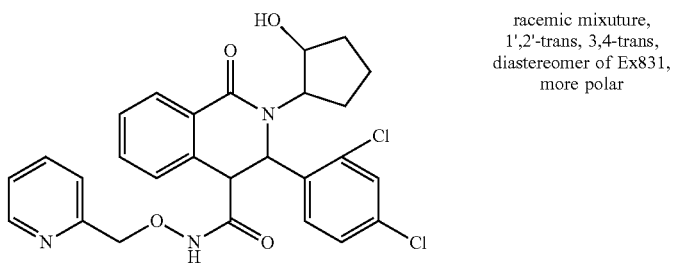 | racemic mixuture, 1',2'-trans, 3,4-trans, diastereomer of Ex831, more polar |
| 831 | 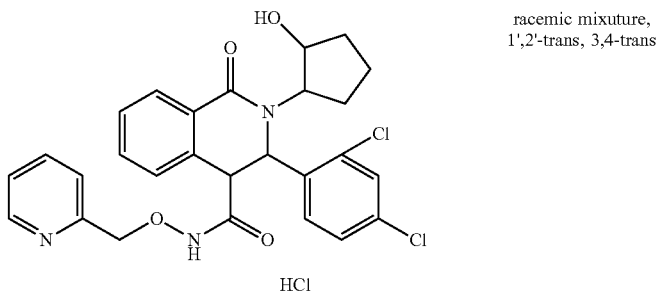 HCl | racemic mixuture, 1',2'-trans, 3,4-trans |
| 832 | 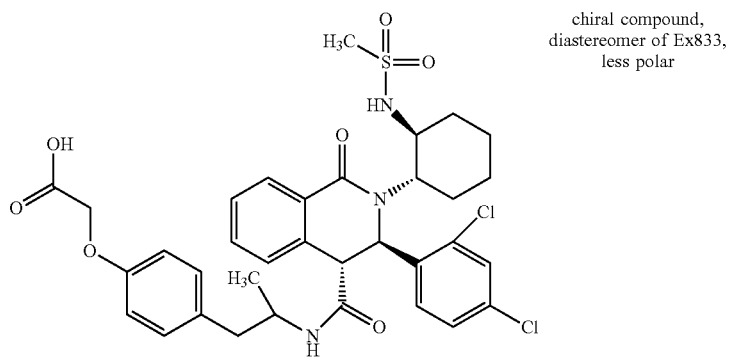 | chiral compound, diastereomer of Ex833, less polar |
| 833 | 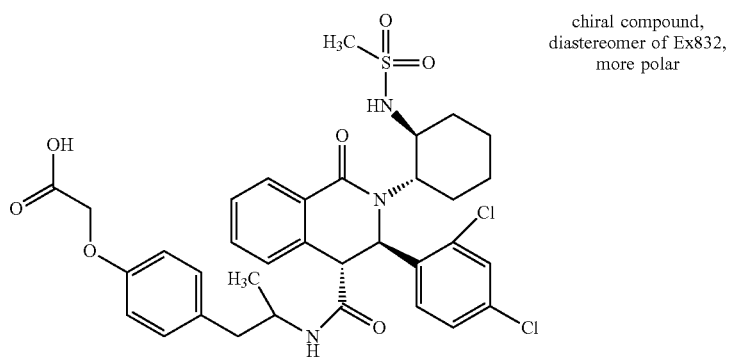 | chiral compound, diastereomer of Ex832, more polar |
| 834 | 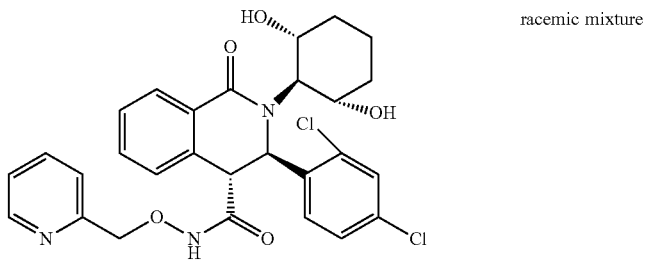 | racemic mixture |

TABLE 262
| 835 | 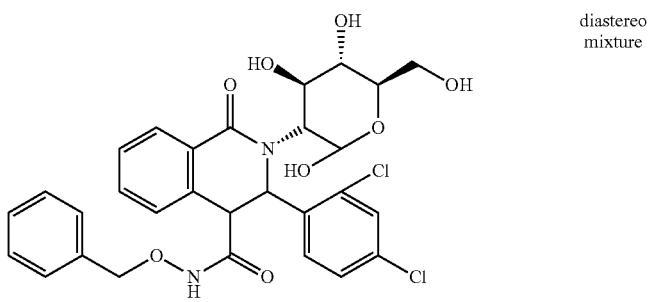 | diastereo mixture |
| 836 | 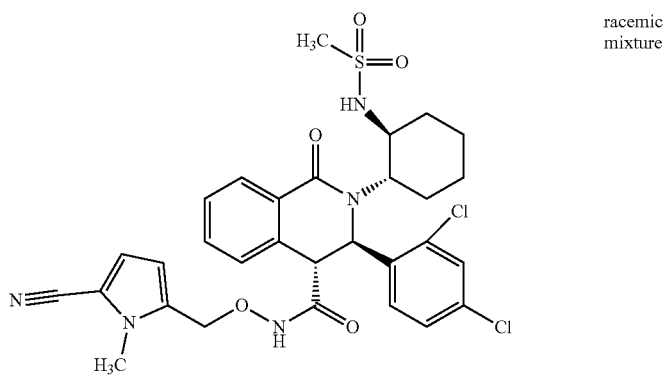 | racemic mixture |
| 837 | 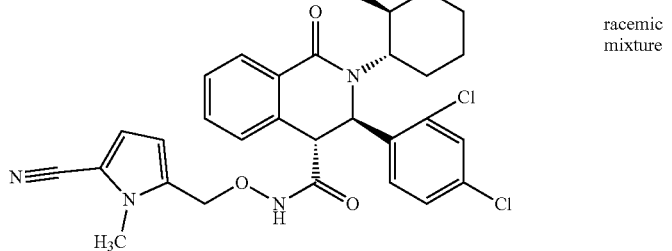 | racemic mixture |
| 838 | 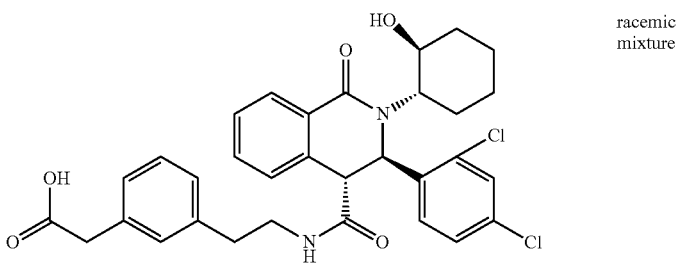 | racemic mixture |
| 839 | 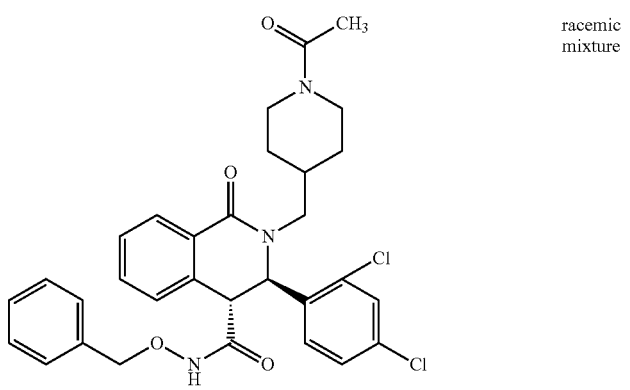 | racemic mixture |

TABLE 263
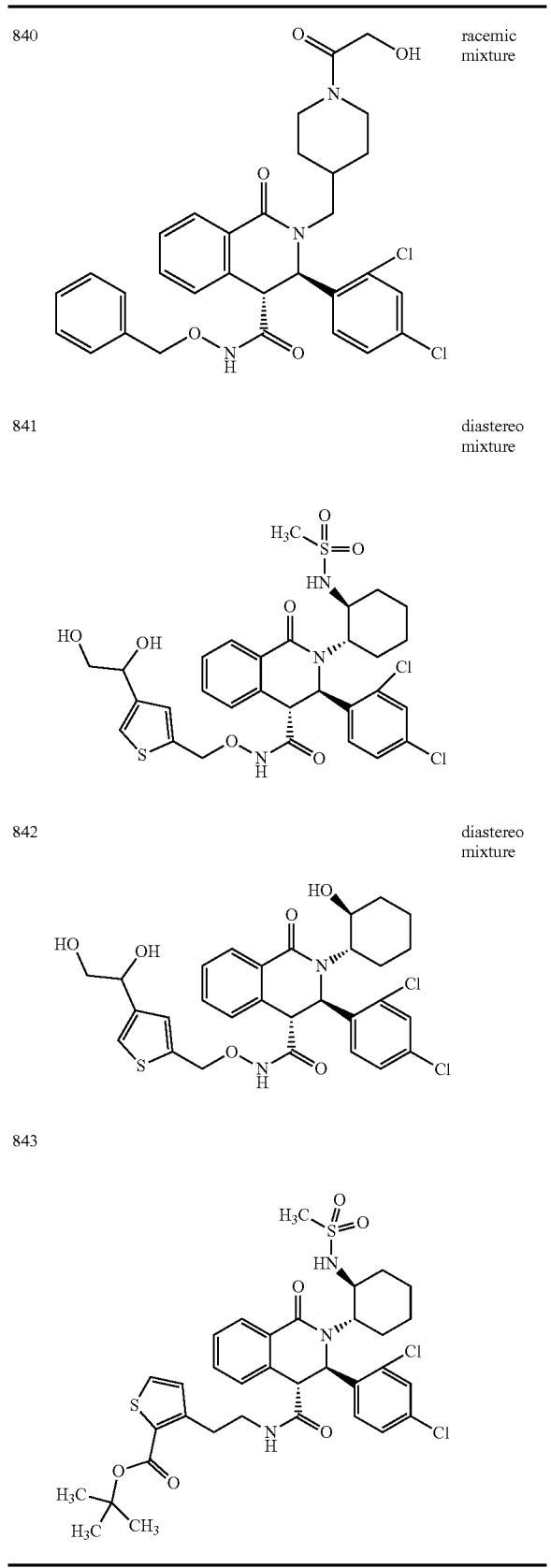
TABLE 264
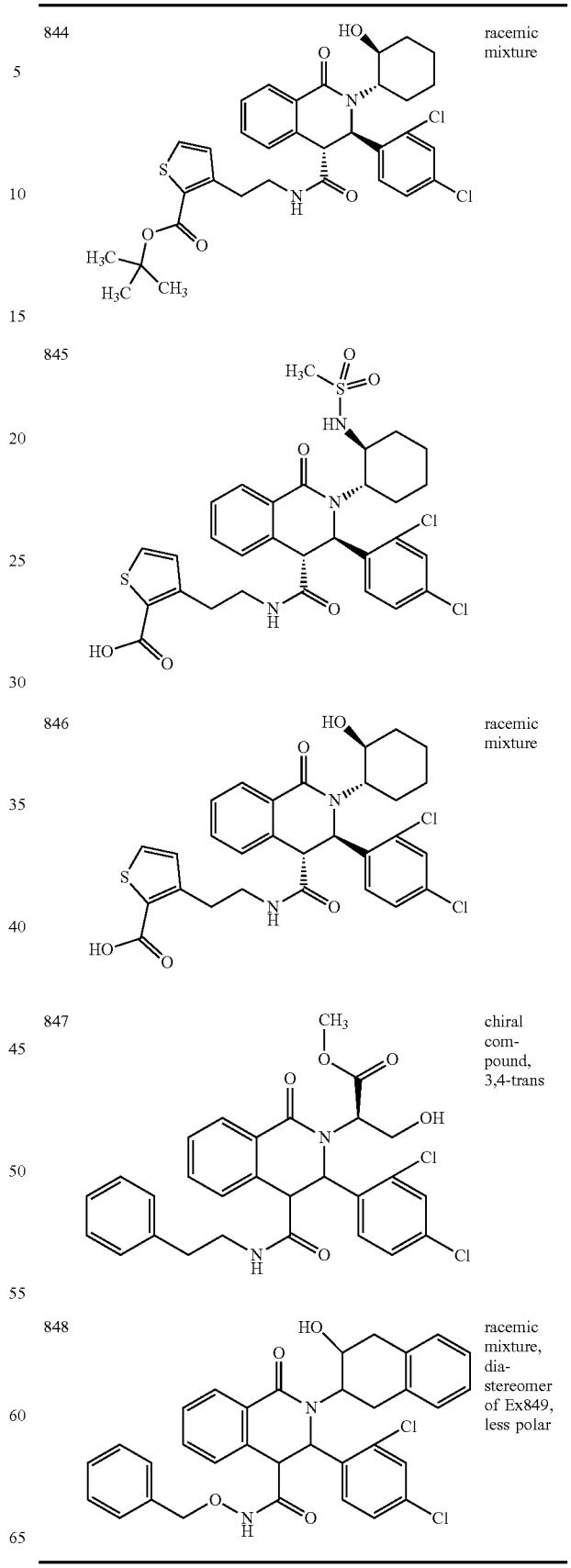

TABLE 265
| | | |
|---|---|---|
| 849 | 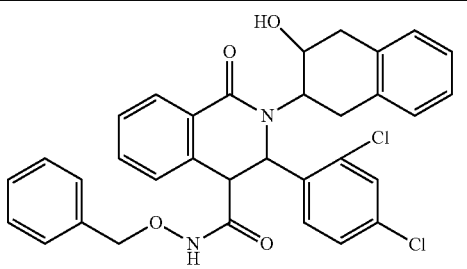 | racemic mixture, diastereomer of Ex848, more polar |
| 850 | 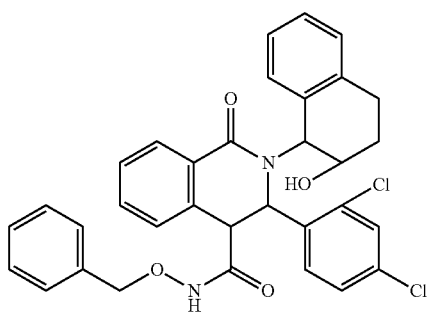 [SMILES: O=C(NOCc1ccccc1)C1c2ccccc2C(=O)N(C2c3ccccc3CCC2O)C1c1ccc(Cl)cc1Cl] | racemic mixture, diastereomer of Ex851, less polar |
| 851 | 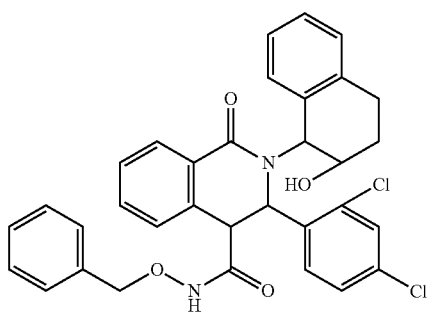 [SMILES: O=C(NOCc1ccccc1)C1c2ccccc2C(=O)N(C2c3ccccc3CCC2O)C1c1ccc(Cl)cc1Cl] | racemic mixture, diastereomer of Ex850, more polar |
| 852 | 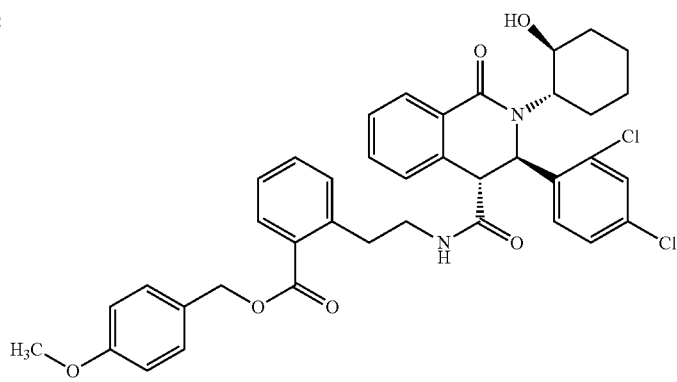 [SMILES: COc1ccc(COC(=O)c2ccccc2CCNC(=O)[C@@H]2c3ccccc3C(=O)N([C@H]3CCCC[C@@H]3O)[C@H]2c2ccc(Cl)cc2Cl)cc1] | |
| 853 | 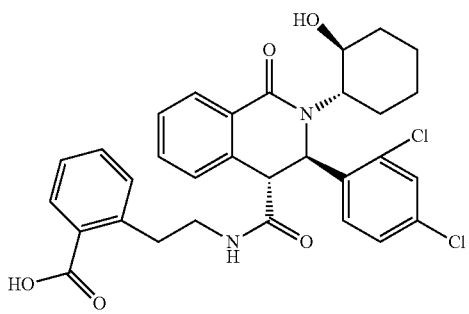 [SMILES: O=C(O)c1ccccc1CCNC(=O)[C@@H]1c2ccccc2C(=O)N([C@H]2CCCC[C@@H]2O)[C@H]1c1ccc(Cl)cc1Cl] | racemic mixture |

TABLE 266
| | | |
|---|---|---|
| 854 | 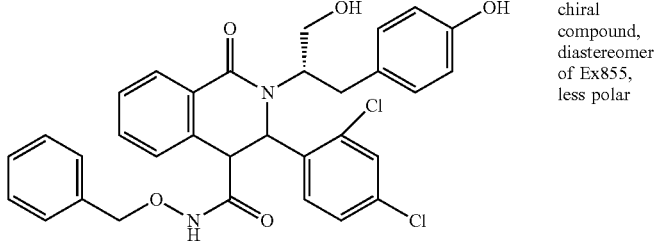 | chiral compound, diastereomer of Ex855, less polar |
| 855 | 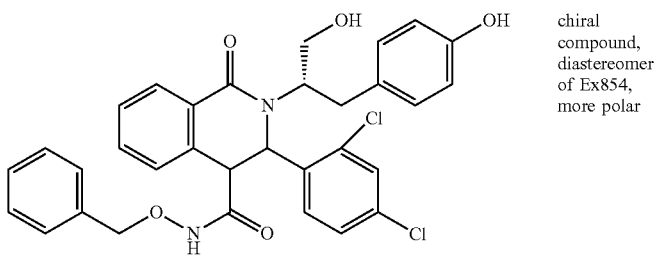 | chiral compound, diastereomer of Ex854, more polar |
| 856 | 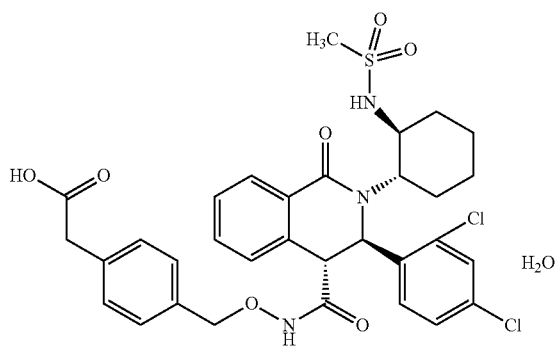 | |
| 857 | 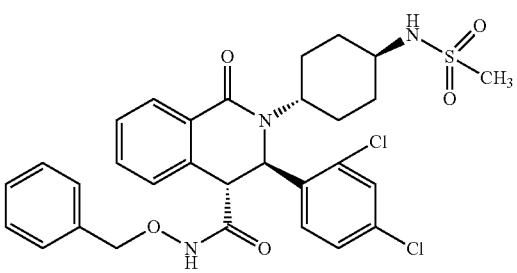 [SMILES: CS(=O)(=O)N[C@H]1CC[C@H](N2C(=O)c3ccccc3[C@@H](C(=O)NOCc3ccccc3)[C@@H]2c2ccc(Cl)cc2Cl)CC1] | racemic mixture |
| 858 | 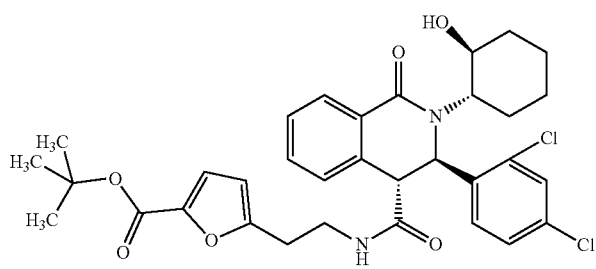 [SMILES: CC(C)(C)OC(=O)c1ccc(CCNC(=O)[C@@H]2c3ccccc3C(=O)N([C@H]3CCCC[C@@H]3O)[C@H]2c2ccc(Cl)cc2Cl)o1] | racemic mixture |

TABLE 267

| | | |
|---|---|---|
| 859 | (structure) | racemic mixture |
| 860 | (structure) | racemic mixture, 1',2'-trans, 3,4-trans |
| 861 | (structure) | racemic mixture, 1',2'-trans, 3,4-trans |
| 862 | (structure) | racemic mixture |
| 863 | (structure) | racemic mixture, 1',2'-trans, 3,4-trans |
| 864 | (structure) | racemic mixture |

TABLE 268

| | | |
|---|---|---|
| 865 | (structure) | racemic mixture, 1',2'-trans, 3,4-trans |
| 866 | (structure) | racemic mixture, diastereomer of Ex872, 1',2'-trans, 3,4-trans |
| 867 | (structure) | racemic mixture, 1',2'-trans, 3,4-trans |
| 868 | (structure) | racemic mixture |
| 869 | (structure) | racemic mixture, 1',2'-trans, 3,4-trans |

TABLE 269
| | | |
|---|---|---|
| 870 | 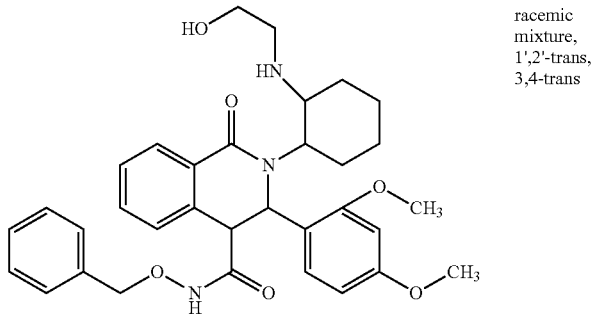 | racemic mixture, 1',2'-trans, 3,4-trans |
| 871 | 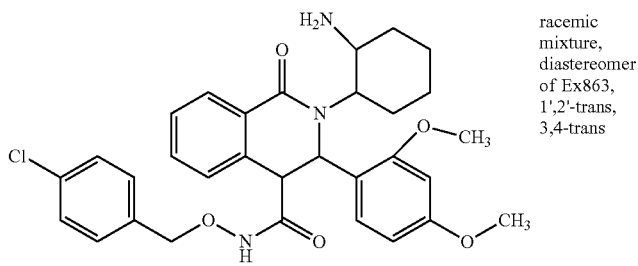 | racemic mixture, diastereomer of Ex863, 1',2'-trans, 3,4-trans |
| 872 | 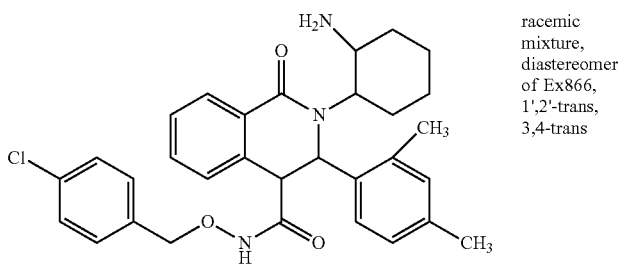 | racemic mixture, diastereomer of Ex866, 1',2'-trans, 3,4-trans |
| 873 | 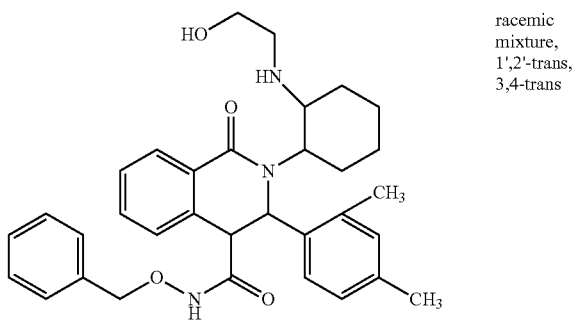 | racemic mixture, 1',2'-trans, 3,4-trans |
| 874 | 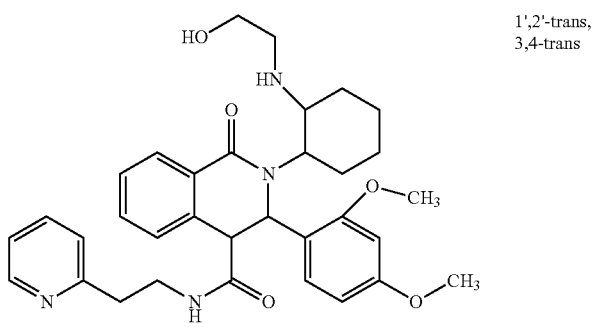 | 1',2'-trans, 3,4-trans |

TABLE 270
| 875 | 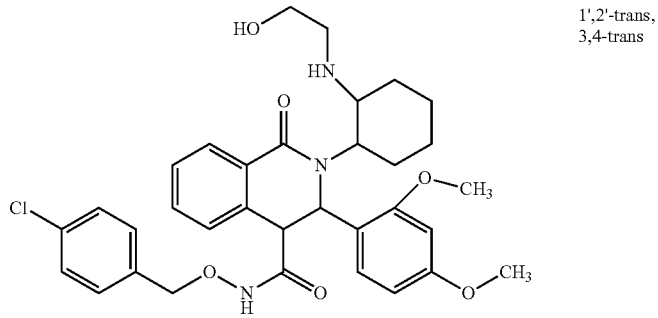 | 1',2'-trans, 3,4-trans |
|---|---|---|
| 876 | 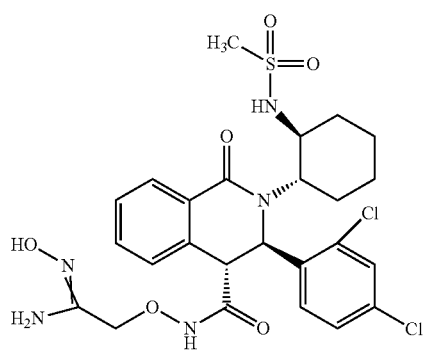 [SMILES: CS(=O)(=O)N[C@H]1CCCC[C@@H]1N1C(=O)c2ccccc2[C@@H](C(=O)NOCC(N)=NO)[C@@H]1c1ccc(Cl)cc1Cl] | |
| 877 | 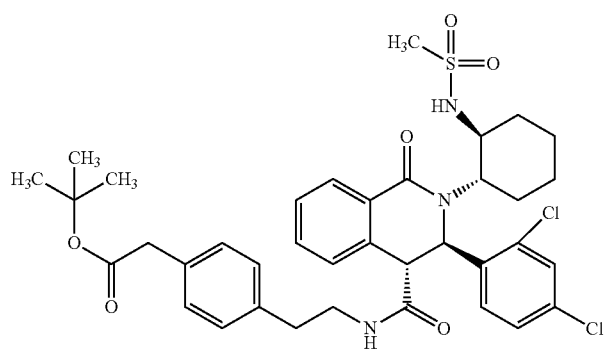 [SMILES: CC(C)(C)OC(=O)Cc1ccc(CCNC(=O)[C@@H]2c3ccccc3C(=O)N([C@H]3CCCC[C@@H]3NS(C)(=O)=O)[C@H]2c2ccc(Cl)cc2Cl)cc1] | |
| 878 | 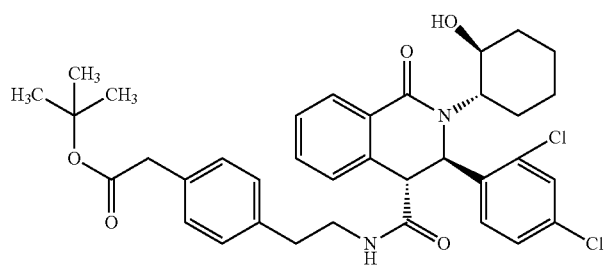 [SMILES: CC(C)(C)OC(=O)Cc1ccc(CCNC(=O)[C@@H]2c3ccccc3C(=O)N([C@H]3CCCC[C@@H]3O)[C@H]2c2ccc(Cl)cc2Cl)cc1] | racemic mixture |

TABLE 271
| 879 | 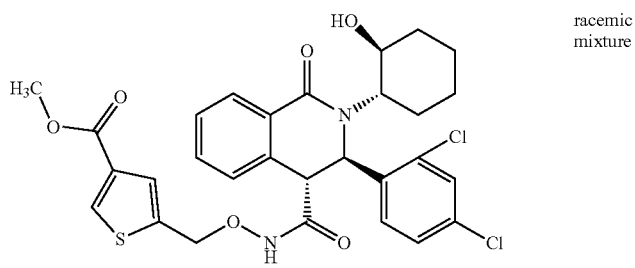 | racemic mixture |
|---|---|---|
| 880 | 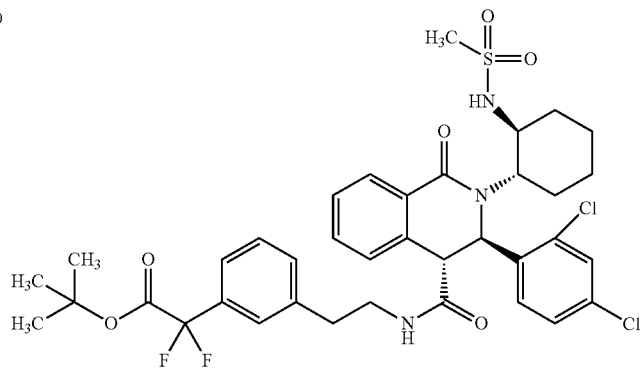 | |
| 881 | 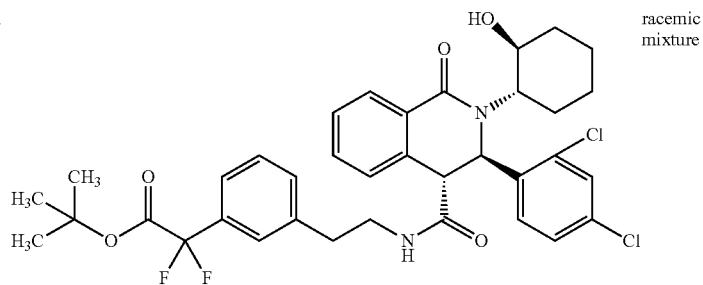 | racemic mixture |
| 882 | 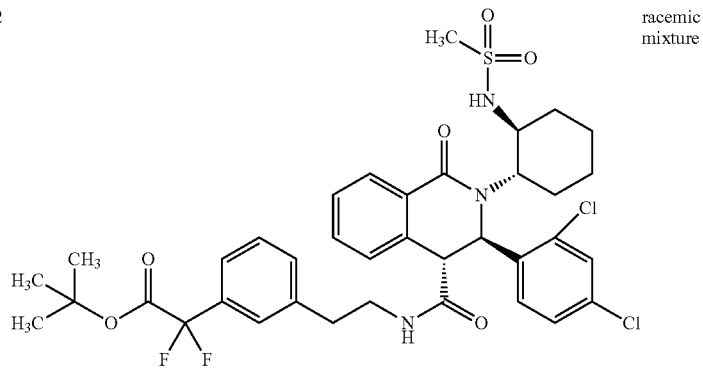 | racemic mixture |
| 883 | 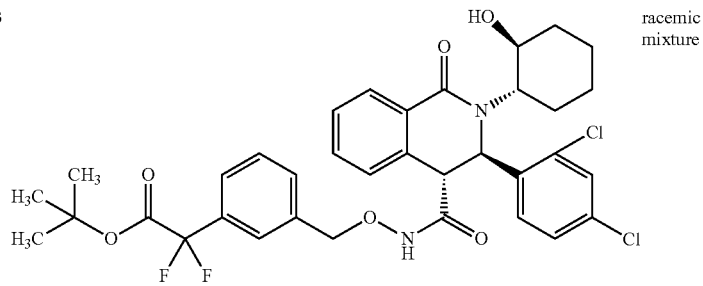 | racemic mixture |

TABLE 272
884 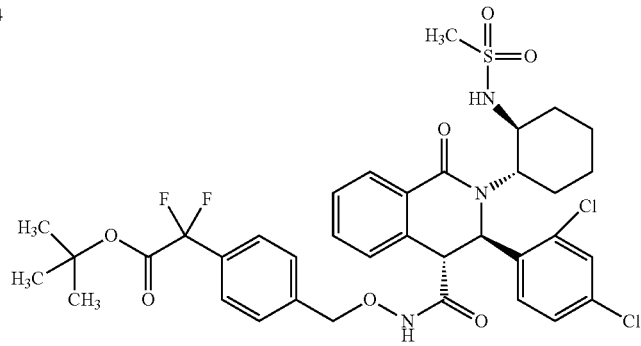
885 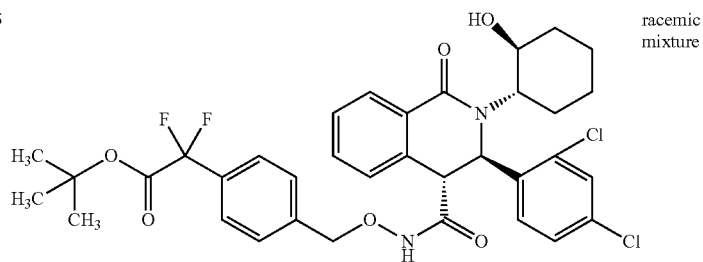
racemic mixture
886 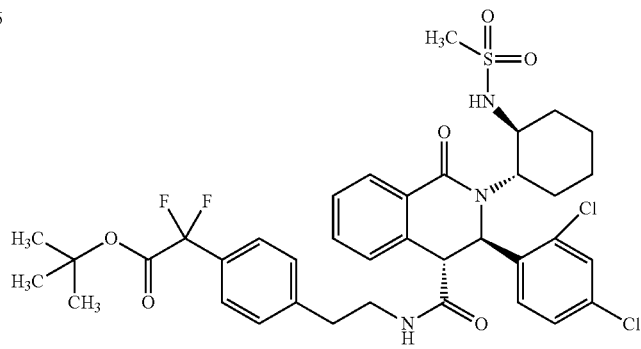
887 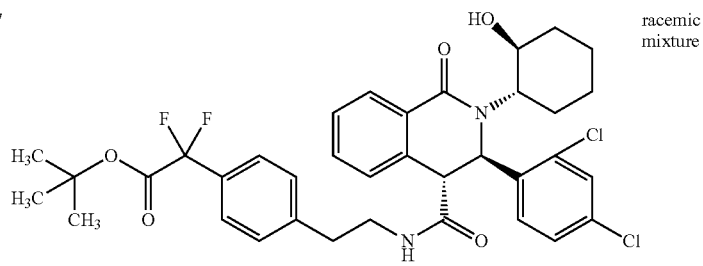
racemic mixture
888 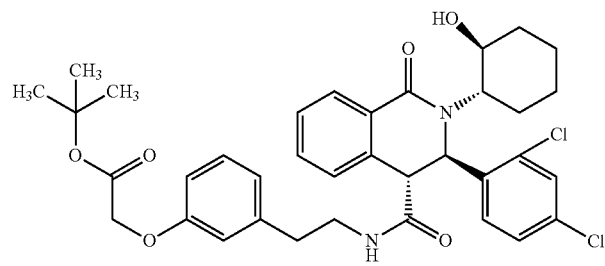 [SMILES: CC(C)(C)OC(=O)COc1cccc(CCNC(=O)[C@@H]2c3ccccc3C(=O)N([C@H]3CCCC[C@@H]3O)[C@H]2c2ccc(Cl)cc2Cl)c1]

TABLE 273
889 racemic mixture
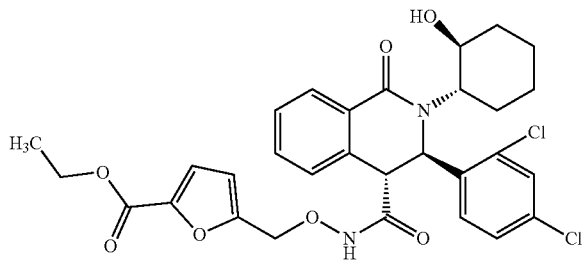 [SMILES: CCOC(=O)c1ccc(CONC(=O)[C@@H]2c3ccccc3C(=O)N([C@H]3CCCC[C@@H]3O)[C@H]2c2ccc(Cl)cc2Cl)o1]
890
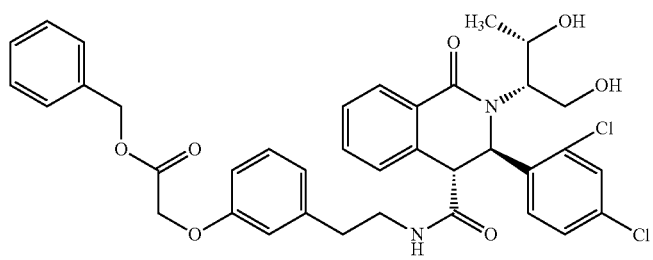 [SMILES: C[C@H](O)[C@H](CO)N1C(=O)c2ccccc2[C@@H](C(=O)NCCc2cccc(OCC(=O)OCc3ccccc3)c2)[C@@H]1c1ccc(Cl)cc1Cl]
891
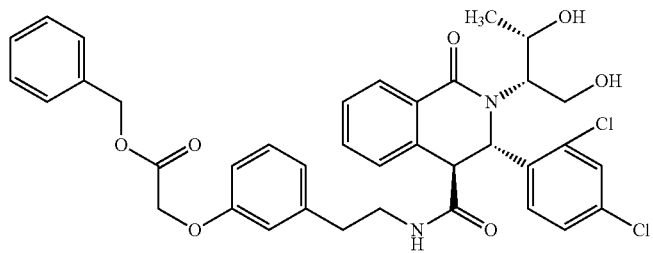 [SMILES: C[C@H](O)[C@H](CO)N1C(=O)c2ccccc2[C@H](C(=O)NCCc2cccc(OCC(=O)OCc3ccccc3)c2)[C@H]1c1ccc(Cl)cc1Cl]
892
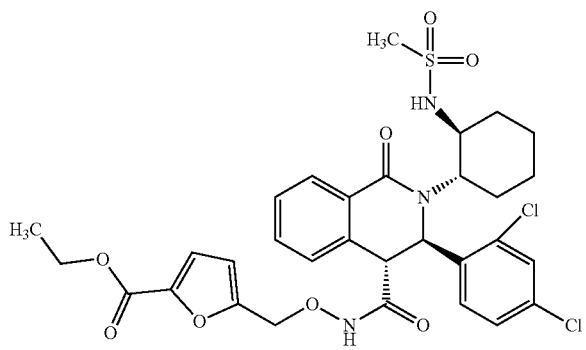 [SMILES: CCOC(=O)c1ccc(CONC(=O)[C@@H]2c3ccccc3C(=O)N([C@H]3CCCC[C@@H]3NS(C)(=O)=O)[C@H]2c2ccc(Cl)cc2Cl)o1]

TABLE 274
| 893 | 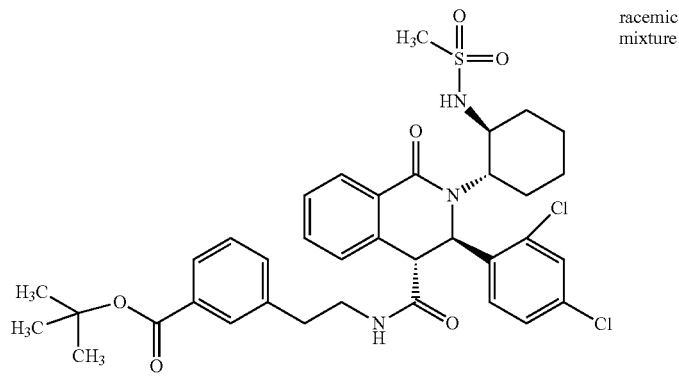 | racemic mixture |
| 894 | 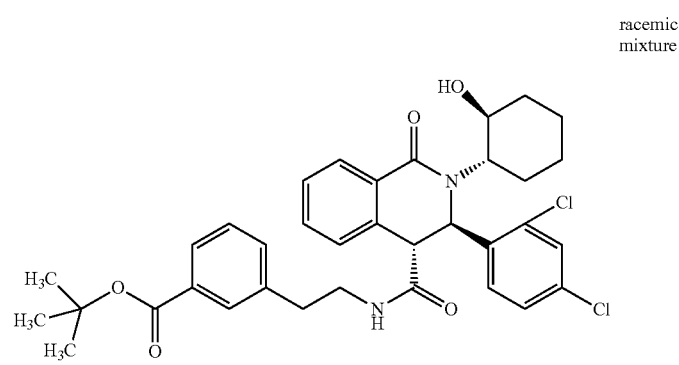 | racemic mixture |
| 895 | 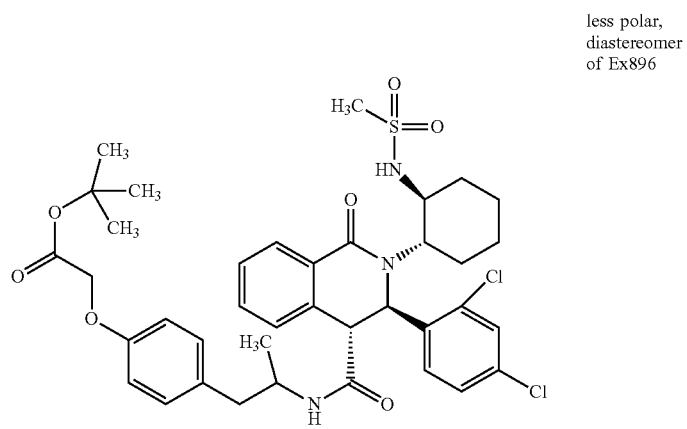 | less polar, diastereomer of Ex896 |
| 896 | 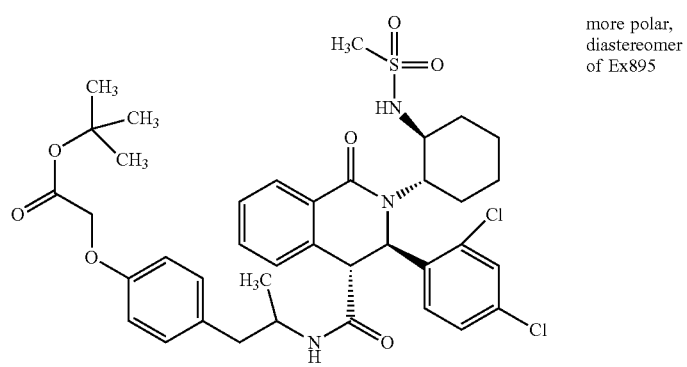 | more polar, diastereomer of Ex895 |

TABLE 275

| | | |
|---|---|---|
| 897 | 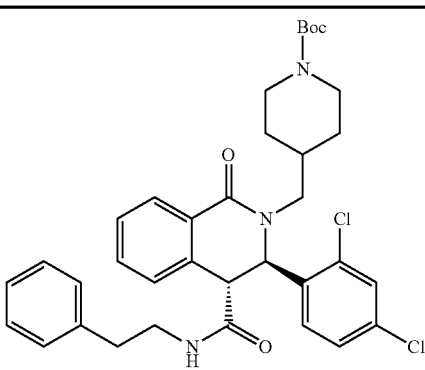 | racemic mixture |
| 898 | 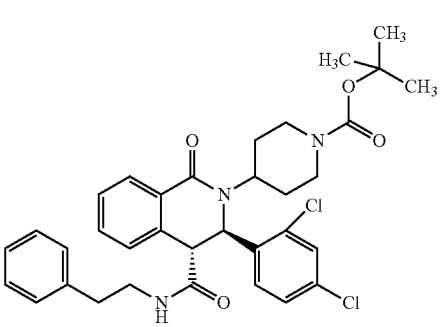 [SMILES: CC(C)(C)OC(=O)N1CCC(N2C(=O)c3ccccc3[C@@H](C(=O)NCCc3ccccc3)[C@@H]2c2ccc(Cl)cc2Cl)CC1] | racemic mixture |
| 899 | 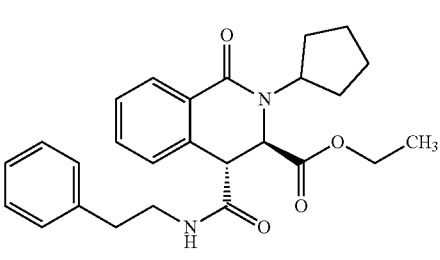 [SMILES: CCOC(=O)[C@H]1[C@H](C(=O)NCCc2ccccc2)c2ccccc2C(=O)N1C1CCCC1] | racemic mixture |

TABLE 276

| Ex | Syn | Data |
|---|---|---|
| 60 | 1 | FAB+: 573 |
| 61 | 1 | FAB+: 574 |
| 62 | 1 | FAB+: 559 |
| 63 | 1 | FAB+: 537 |
| 64 | 3 | FAB+: 590 |
| 65 | 1 | FAB+: 548 |
| 66 | 1 | ESI+: 537 |
| 67 | 1 | FAB+: 537 |
| 68 | 1 | FAB+: 573 |
| 69 | 1 | FAB+: 544 |
| 70 | 1 | FAB+: 519 |
| 71 | 1 | FAB+: 533 |
| 72 | 1 | FAB+: 508 |
| 73 | 1 | FAB+: 523 |
| 74 | 5 | FAB+: 536 |
| 75 | 6 | FAB+: 564 |
| 1 | 1 | FAB+: 507 |
| 76 | 1 | FAB+: 508 |
| 77 | 1 | FAB+: 521 |
| 78 | 1 | FAB+: 525 |
| 3 | 3 | ESI+: 524 |
| 79 | 1 | FAB+: 525 |
| 80 | 1 | FAB+: 503 |
| 81 | 1 | FAB+: 565 |
| 82 | 1 | FAB+: 511 |
| 83 | 1 | FAB+: 467 |
| 84 | 1 | ESI+: 499 |
| 85 | 1 | FAB+: 491 |
| 86 | 1 | FAB+: 539 |

TABLE 276-continued

| Ex | Syn | Data |
|---|---|---|
| 37 | 37 | FAB+: 560 |
| 87 | 1 | FAB+: 533 |
| 88 | 1 | FAB+: 503 |
| 89 | 1 | FAB+: 511 |
| 90 | 1 | FAB+: 525 |
| 91 | 1 | FAB+: 483 |

TABLE 277

| | | |
|---|---|---|
| 92 | 1 | FAB+: 513 |
| 93 | 1 | FAB+: 483 |
| 94 | 1 | FAB+: 548 |
| 95 | 5 | FAB+: 522 |
| 96 | 1 | FAB+: 567 |
| 97 | 1 | FAB+: 538 |
| 98 | 1 | FAB+: 475 |
| 99 | 1 | FAB+: 499 |
| 100 | 1 | FAB+: 491 |
| 101 | 1 | FAB+: 499 |
| 102 | 1 | FAB+: 559 |
| 103 | 6 | FAB+: 550 |
| 104 | 3 | FAB+: 524 |
| 105 | 1 | FAB+: 503 |
| 106 | 1 | FAB+: 499 |
| 107 | 1 | FAB+: 497 |
| 108 | 1 | FAB+: 565 |
| 2 | 2 | FAB+: 507 |
| 109 | 39 | FAB+: 497 |
| 39 | 39 | FAB+: 511 |
| 110 | 1 | FAB+: 391 |
| 111 | 1 | FAB+: 431 |
| 4 | 4 | FAB+: 475 |
| 112 | 1 | FAB+: 573 |
| 113 | 32 | FAB+: 488 |
| 114 | 32 | FAB+: 474 |
| 115 | 38 | FAB+: 407 |
| 116 | 33 | FAB+: 420 |
| 117 | 33 | FAB+: 434 |
| 118 | 1 | FAB+: 573 |
| 119 | 1 | FAB+: 514 |
| 120 | 1 | FAB+: 516 |
| 121 | 1 | FAB+: 529 |
| 122 | 1 | FAB+: 440 |
| 123 | 1 | FAB+: 440 |
| 124 | 1 | FAB+: 440 |

TABLE 278

| | | |
|---|---|---|
| 36 | 36 | FAB+: 456 |
| 125 | 36 | FAB+: 456 |
| 126 | 36 | FAB+: 456 |
| 127 | 1 | FAB+: 497 |
| 38 | 38 | FAB+: 483 |
| 128 | 38 | FAB+: 483 |
| 7 | 7 | FAB+: 393 |
| 129 | 1 | FAB+: 467 |
| 130 | 10 | FAB+: 498 |
| 10 | 10 | FAB+: 604 |
| 131 | 10 | FAB+: 527 |
| 132 | 3 | ESI+: 633 |
| 133 | 3 | ESI+: 617 |
| 134 | 3 | ESI+: 617 |
| 135 | 3 | ESI+: 645 |
| 136 | 3 | ESI+: 617 |
| 137 | 3 | FAB+: 647 |
| 138 | 3 | ESI+: 663 |
| 139 | 3 | ESI+: 647 |
| 140 | 3 | ESI+: 651 |
| 141 | 3 | ESI+: 633 |
| 142 | 3 | ESI+: 633 |
| 143 | 3 | ESI+: 667 |
| 144 | 3 | FAB+: 647 |
| 145 | 3 | ESI+: 655 |

TABLE 278-continued

| | | |
|---|---|---|
| 146 | 3 | ESI+: 631 |
| 147 | 3 | ESI+: 633 |
| | | NMR1: 1.00-1.90 (7 H, m), 2.06-2.23 (1 H, m), 2.92 (3 H, s), 3.25-3.45 (1 H, m), 3.60 (1 H, s), 4.12 (1 H, brs), 4.90-5.06 (2 H, m), 5.21 (1 H, s), 6.39 (1 H, brs), 6.89 (1 H, d, J = 8.4 Hz), 7.04-7.20 (2 H, m), 7.27-7.69 (6 H, m), 7.87-7.97 (1 H, m), 8.29 (1 H, d, J = 6.4 Hz), 11.64 (1 H, brs) |
| 9 | 9 | FAB+: 517 |
| 148 | 11 | FAB+: 580 |
| 149 | 11 | FAB+: 580 |
| 11 | 11 | FAB+: 581 |
| 150 | 1 | ESI−: 635 |
| 151 | 1 | FAB+: 550 |
| 152 | 1 | FAB+: 589 |
| 153 | 1 | FAB+: 582 |
| 154 | 1 | FAB+: 561 |

TABLE 279

| | | |
|---|---|---|
| 155 | 1 | FAB+: 561 |
| 156 | 1 | FAB+: 563 |
| 157 | 1 | FAB+: 563 |
| | | NMR1: 1.19 (3 H, d, J = 6.0 Hz), 3.10-3.40 (2 H, m), 3.54 (1 H, s), 3.99-4.12 (1 H, m), 4.34 (1 H, brs), 4.46-4.58 (1 H, m), 4.80 (2 H, brs), 4.90 (1 H, brs), 5.75 (1 H, s), 6.79 (1 H, d, J = 8.4 Hz), 6.99-7.08 (1 H, m), 7.17 (1 H, d, J = 8.4 Hz), 7.31-7.51 (6 H, m), 7.61 (1 H, s), 7.96-8.09 (1 H, m), 11.63 (1 H, brs) |
| 158 | 1 | FAB+: 523 |
| 159 | 1 | FAB+: 498 |
| 160 | 1 | FAB+: 498 |
| 161 | 1 | FAB+: 555 |
| 162 | 1 | FAB+: 551 |
| 163 | 1 | FAB+: 552 |
| 164 | 1 | FAB+: 538 |
| 165 | 1 | FAB+: 636 |
| 166 | 1 | FAB+: 579 |
| 167 | 1 | FAB+: 482 |
| 168 | 1 | FAB+: 536 |
| 169 | 1 | FAB+: 510 |
| 170 | 1 | FAB+: 540 |
| 171 | 1 | FAB+: 553 |
| 172 | 1 | FAB+: 578 |
| 173 | 1 | FAB+: 552 |
| 174 | 1 | FAB+: 583 |
| 175 | 1 | FAB+: 565 |
| 176 | 1 | FAB+: 579 |
| 177 | 1 | FAB+: 549 |
| 178 | 1 | FAB+: 538 |
| 34 | 34 | FAB+: 647 |
| 179 | 1 | FAB+: 551 |
| 180 | 1 | FAB+: 664 |
| 181 | 1 | FAB+: 555 |
| 182 | 1 | FAB+: 539 |
| 183 | 1 | FAB+: 555 |
| 184 | 1 | FAB+: 540 |
| 185 | 1 | FAB+: 668 |
| 186 | 1 | FAB+: 668 |
| 187 | 1 | FAB+: 547 |
| 188 | 1 | FAB+: 540 |
| 189 | 1 | FAB+: 505 |

TABLE 280

| | | |
|---|---|---|
| 190 | 1 | FAB+: 505 |
| 191 | 1 | FAB+: 499 |
| 192 | 1 | FAB+: 499 |
| 193 | 1 | FAB+: 533 |
| 194 | 1 | FAB+: 528 |
| 195 | 1 | ESI+: 528 |
| 196 | 1 | ESI+: 561 |
| 197 | 1 | ESI+: 559 |
| 198 | 1 | FAB+: 505 |
| 199 | 1 | FAB+: 505 |
| 200 | 1 | FAB+: 594 |

TABLE 280-continued

| | | |
|---|---|---|
| 201 | 1 | FAB+: 594 |
| 202 | 1 | FAB+: 597 |
| 203 | 1 | FAB+: 527 |
| 204 | 1 | ESI+: 534 |
| 205 | 1 | FAB+: 626 |
| 206 | 1 | FAB+: 610 |
| 207 | 1 | FAB+: 610 |
| 208 | 1 | FAB+: 682 |
| 209 | 1 | FAB+: 682 |
| 210 | 1 | FAB+: 539 |
| 211 | 1 | ESI+: 515 |
| 212 | 1 | ESI+: 515 |
| 213 | 1 | FAB+: 533 |
| 214 | 1 | ESI−: 541 |
| 215 | 1 | ESI−: 541 |
| | | NMR1: 1.16 (3 H, d, J = 6.0 Hz), 2.54-2.64 (2 H, m), 3.09-3.38 (4 H, m), 3.77 (1 H, s), 3.99-4.11 (1 H, m), 4.27-4.37 (1 H, m), 4.52 (1 H, brs), 5.13 (1 H, d, J = 4.4 Hz), 5.70 (1 H, s), 6.65 (2 H, d, J = 8.4 Hz), 6.81 (1 H, d, J = 8.4 Hz), 6.94 (2 H, d, J = 8.4 Hz), 7.11-7.24 (2 H, m) 7.36-7.49 (2 H, m), 7.60 (1 H, d, J = 2.0 Hz), 7.95-8.08 (1 H, m), 8.35-8.50 (1 H, m), 9.17 (1 H, s) |
| 216 | 1 | FAB+: 632 |
| 217 | 1 | FAB+: 533 |
| 218 | 1 | FAB+: 538 |
| 219 | 1 | FAB+: 538 |
| | | NMR1: 1.54-1.71 (1 H, m), 1.76-1.90 (1 H, m), 1.96-2.21 (2 H, m), 3.01-3.24 (2 H, m), 3.27-3.40 (1 H, m), 3.55 (1 H, brs), 3.70 (1 H, s), 4.70-4.80 (2 H, m), 5.25 (1 H, s), 7.10-7.18 (1 H, m), 7.22 (1 H, dd, J = 2.4, 8.4 Hz), 7.30-7.47 (7 H, m), 7.52 (1 H, d, J = 8.4 Hz), 7.62 (1 H, d, J = 2.0 Hz), 7.82-7.90 (1 H, m), 11.34 (1 H, s) |

TABLE 281

| | | |
|---|---|---|
| 220 | 1 | FAB+: 610 |
| 221 | 1 | FAB+: 573 |
| 222 | 1 | FAB+: 529 |
| 223 | 1 | ESI−: 527 |
| 224 | 1 | ESI+: 541 |
| 225 | 1 | FAB+: 561 |
| 226 | 1 | FAB+: 616 |
| 227 | 1 | FAB+: 549 |
| 228 | 1 | FAB+: 664 |
| 229 | 1 | FAB+: 679 |
| 230 | 1 | FAB+: 679 |
| 231 | 1 | FAB+: 602 |
| 232 | 1 | ESI+: 680 |
| 233 | 1 | ESI+: 694 |
| 234 | 1 | FAB+: 678 |
| 235 | 1 | ESI+: 674 |
| 236 | 1 | FAB+: 614 |
| 237 | 1 | FAB+: 614 |
| 238 | 1 | FAB+: 693 |
| 239 | 1 | FAB+: 659 |
| 240 | 1 | FAB+: 587 |
| 241 | 1 | FAB+: 694 |
| 242 | 1 | FAB+: 587 |
| 243 | 1 | ESI+: 675 |
| 244 | 1 | FAB+: 670 |
| 245 | 1 | ESI+: 602 |
| 246 | 1 | ESI+: 607 |
| 247 | 1 | ESI+: 672 |
| 248 | R381 | ESI+: 574 |
| 249 | R381 | FAB+: 573 |
| 250 | 1 | FAB+: 567 |
| 251 | 1 | FAB+: 566 |
| 252 | 1 | ESI+: 658 |
| 253 | 1 | ESI+: 658 |
| 254 | 1 | FAB+: 632 |
| 255 | 1 | FAB+: 585 |
| 256 | 1 | FAB+: 584 |
| 257 | 1 | FAB+: 674 |
| 258 | 1 | ESI+: 658 |

TABLE 282

| | | |
|---|---|---|
| 259 | 1 | FAB+: 630 |
| 260 | 1 | FAB+: 639 |
| 261 | 1 | ESI+: 603 |
| 262 | 1 | FAB+: 600 |
| 263 | 1 | FAB+: 607 |
| 264 | 1 | FAB+: 628 |
| 265 | 1 | FAB+: 616 |
| 266 | 1 | FAB+: 616 |
| 267 | 1 | ESI+: 603 |
| 268 | 1 | ESI+: 631 |
| 269 | 1 | FAB+: 629 |
| 270 | 1 | FAB+: 617 |
| 271 | 1 | FAB+: 577 |
| 272 | 1 | FAB+: 554 |
| 273 | 1 | ESI+: 601 |
| 274 | 1 | FAB+: 601 |
| 275 | 1 | FAB+: 577 |
| 276 | 1 | ESI+: 602 |
| 277 | 1 | ESI+: 539 |
| 278 | 1 | ESI+: 539 |
| 279 | 1 | FAB+: 601 |
| 280 | 1 | ESI+: 554 |
| 281 | 1 | FAB+: 624 |
| 282 | 1 | ESI−: 626 |
| 283 | 1 | FAB+: 582 |
| 284 | 1 | ESI+: 593 |
| 285 | 1 | ESI+: 593 |
| 286 | 1 | FAB+: 592 |
| 287 | 1 | FAB+: 592 |
| 288 | 1 | FAB+: 498 |
| 289 | 1 | FAB+: 530 |
| 290 | 1 | FAB+: 530 |
| 291 | 1 | FAB+: 704 |
| 292 | 1 | FAB+: 502 |
| 293 | 1 | FAB+: 529 |
| 294 | 1 | ESI−: 527 |
| 295 | 1 | FAB+: 638 |
| 296 | 1 | FAB+: 630 |
| 297 | 1 | FAB+: 633 |
| 298 | 1 | FAB+: 744 |
| 299 | 1 | FAB+: 746 |

TABLE 283

| | | |
|---|---|---|
| 300 | 1 | ESI+: 718 |
| 301 | 1 | FAB+: 730 |
| 302 | 1 | FAB+: 647 |
| 303 | 1 | ESI+: 633 |
| 304 | 1 | FAB+: 751 |
| 305 | 1 | ESI+: 688 |
| 306 | 1 | ESI+: 647 |
| 307 | 1 | ESI+: 723 |
| 308 | 1 | FAB+: 730 |
| 309 | 1 | FAB+: 652 |
| 310 | 1 | FAB+: 638 |
| 311 | 1 | FAB+: 710 |
| 312 | 1 | ESI+: 849 |
| 313 | 1 | ESI+: 660 |
| 314 | 1 | ESI+: 673 |
| 315 | 1 | FAB+: 647 |
| 316 | 1 | FAB+: 647 |
| 317 | 1 | ESI+: 730 |
| 318 | 1 | ESI+: 656 |
| 319 | 1 | FAB+: 730 |
| 320 | 1 | ESI+: 728 |
| 321 | 1 | ESI+: 618 |
| 322 | 1 | FAB+: 688 |
| 323 | 1 | FAB+: 692 |
| 324 | 1 | FAB+: 704 |
| 325 | 1 | FAB+: 704 |
| 326 | 1 | FAB+: 634 |
| 327 | 1 | FAB+: 702 |
| 328 | 1 | FAB+: 617 |
| 329 | 1 | ESI+: 674 |
| 330 | 1 | FAB+: 680 |
| 331 | 1 | FAB+: 635 |
| 332 | 1 | FAB+: 608 |

TABLE 283-continued

| | | |
|---|---|---|
| 333 | 1 | ESI+: 688 |
| 334 | 1 | FAB+: 622 |
| 335 | 1 | ESI+: 631 |
| 336 | 1 | FAB+: 617 |
| 337 | 1 | FAB+: 617 |
| 338 | 1 | ESI+: 660 |
| 339 | 1 | FAB+: 635 |
| 340 | 1 | ESI+: 622 |

TABLE 284

| | | |
|---|---|---|
| 341 | 1 | FAB+: 647 |
| 342 | 1 | FAB+: 563 |
| 343 | 1 | FAB+: 563 |
| 344 | 1 | FAB+: 635 |
| 345 | 1 | ESI+: 660 |
| 346 | 1 | FAB+: 631 |
| 347 | 1 | ESI+: 622 |
| 348 | 1 | ESI+: 647 |
| 349 | 1 | ESI+: 673 |
| 350 | 1 | ESI+: 606 |
| 351 | 1 | FAB+: 620 |
| 352 | 1 | ESI+: 632 |
| 353 | 1 | FAB+: 619 |
| 354 | 1 | ESI−: 568 |
| 355 | 1 | FAB+: 620 |
| 356 | 1 | FAB+: 642 |
| 357 | 1 | FAB+: 622 |
| 358 | 1 | ESI+: 631 |
| 359 | 1 | ESI+: 680 |
| 360 | 1 | ESI+: 565 |
| 361 | 1 | FAB+: 607 |
| 362 | 1 | ESI+: 591 |
| 363 | 1 | ESI+: 642 |
| 364 | 1 | FAB+: 613 |
| 365 | 1 | ESI+: 651 |
| 366 | 1 | FAB+: 657 |
| 367 | 1 | FAB+: 637 |
| 368 | 1 | FAB+: 631 |
| 369 | 1 | ESI+: 637 |
| 370 | 1 | FAB+: 623 |
| 371 | 1 | FAB+: 631 |
| 372 | 1 | ESI+: 618 |
| 373 | 1 | ESI+: 688 |
| 374 | 1 | FAB+: 631 |
| 375 | 1 | FAB+: 601 |
| 376 | 1 | FAB+: 702 |
| 377 | 1 | FAB+: 601 |
| 378 | 1 | ESI+: 647 |
| 379 | 1 | ESI+: 643 |
| 380 | 1 | FAB+: 654 |
| 381 | 1 | ESI+: 602 |

TABLE 285

| | | |
|---|---|---|
| 382 | 1 | FAB+: 630 |
| 383 | 1 | FAB+: 657 |
| 384 | 1 | FAB+: 587 |
| 385 | 1 | FAB+: 587 |
| 386 | 1 | FAB+: 630 |
| 387 | 1 | FAB+: 630 |
| 388 | 1 | FAB+: 631 |
| 389 | 1 | FAB+: 671 |
| 390 | 1 | ESI+: 679 |
| 391 | 1 | FAB+: 640 |
| 392 | 1 | ESI+: 647 |
| 393 | 1 | FAB+: 608 |
| 394 | 1 | ESI+: 643 |
| 395 | 1 | FAB+: 660 |
| 396 | 1 | ESI+: 602 |
| 397 | 1 | ESI+: 602 |
| 398 | 1 | ESI+: 640 |
| 399 | 1 | ESI+: 641 |
| 400 | 1 | FAB+: 538 |
| 401 | 1 | FAB+: 538 |

TABLE 285-continued

| | | |
|---|---|---|
| | | NMR1: 1.54-1.71 (1 H, m), 1.75-1.89 (1 H, m), 1.97-2.21 (2 H, m), 2.99-3.25 (2 H, m), 3.26-3.41 (1 H, m), 3.55 (1 H, brs), 3.70 (1 H, s), 4.67-4.82 (2 H, m), 5.25 (1 H, s), 7.10-7.18 (1 H, m), 7.22 (1 H, dd, J = 2.4, 8.4 Hz), 7.27-7.40 (7 H, m), 7.52 (1 H, d, J = 8.4 Hz), 7.62 (1 H, d, J = 2.0 Hz), 7.80-7.90 (1 H, m), 11.34 (1 H, s) |
| 402 | 1 | ESI+: 528 |
| 403 | 1 | FAB+: 547 |
| 404 | 1 | ESI+: 528 |
| 405 | 1 | FAB+: 569 |
| 406 | 1 | FAB+: 582 |
| 407 | 1 | FAB+: 529 |
| 408 | 1 | FAB+: 529 |
| 409 | 1 | FAB+: 527 |
| 410 | 1 | FAB+: 539 |
| 411 | 1 | FAB+: 539 |
| 412 | 1 | ESI−: 593 |
| 413 | 1 | FAB+: 540 |
| 414 | 1 | FAB+: 668 |
| 415 | 1 | FAB+: 540 |
| 416 | 1 | FAB+: 592 |
| 417 | 1 | FAB+: 592 |

TABLE 286

| | | |
|---|---|---|
| 418 | 1 | FAB+: 592 |
| 419 | 1 | FAB+: 592 |
| 420 | 1 | FAB+: 537 |
| 421 | 1 | FAB+: 537 |
| 422 | 1 | FAB+: 551 |
| 423 | 1 | FAB+: 540 |
| 424 | 1 | FAB+: 539 |
| 425 | 1 | FAB+: 587 |
| 426 | 1 | FAB+: 575 |
| 427 | 1 | FAB+: 566 |
| 428 | 1 | FAB+: 551 |
| 429 | 1 | FAB+: 530 |
| 430 | 1 | FAB+: 510 |
| 431 | 1 | FAB+: 538 |
| 432 | 1 | FAB+: 508 |
| 433 | 1 | FAB+: 608 |
| 434 | 1 | FAB+: 538 |
| 435 | 1 | FAB+: 601 |
| 436 | 1 | FAB+: 587 |
| 437 | 1 | FAB+: 613 |
| 438 | 1 | FAB+: 674 |
| 439 | 1 | FAB+: 539 |
| 440 | 1 | FAB+: 593 |
| 441 | 1 | FAB+: 500 |
| 442 | 1 | FAB+: 499 |
| 443 | 1 | FAB+: 530 |
| 444 | 1 | FAB+: 540 |
| 445 | 1 | FAB+: 530 |
| 446 | 1 | FAB+: 530 |
| 447 | 1 | FAB+: 530 |
| 448 | 1 | FAB+: 530 |
| 449 | 1 | FAB+: 596 |
| 450 | 1 | FAB+: 540 |
| 451 | 1 | ESI+: 515 |
| 452 | 1 | FAB+: 540 |
| 453 | 1 | FAB+: 596 |
| 454 | 1 | ESI+: 595 |
| 455 | 1 | ESI+: 595 |
| 456 | 1 | ESI+: 595 |
| 457 | 1 | ESI+: 595 |
| 458 | 1 | FAB+: 571 |

TABLE 287

| | | |
|---|---|---|
| 459 | 1 | FAB+: 571 |
| 460 | 1 | FAB+: 538 |
| 461 | 1 | FAB+: 605 |
| 462 | 1 | ESI+: 618 |
| 463 | 1 | ESI+: 606 |
| 464 | 1 | ESI+: 746 |

TABLE 287-continued

| | | |
|---|---|---|
| 465 | 1 | ESI+: 690 |
| 466 | 1 | ESI+: 703 |
| 467 | 1 | ESI+: 692 |
| 468 | 1 | ESI+: 746 |
| 469 | 1 | ESI+: 732 |
| 470 | 1 | ESI+: 718 |
| 471 | 1 | ESI+: 692 |
| 472 | 1 | ESI+: 692 |
| 473 | 1 | FAB+: 642 |
| 474 | 1 | ESI+: 732 |
| 475 | 1 | ESI+: 606 |
| 476 | 1 | ESI+: 746 |
| 477 | 1 | FAB+: 618 |
| 478 | 1 | ESI+: 638 |
| 479 | 1 | ESI+: 692 |
| 480 | 1 | ESI+: 605 |
| 481 | 1 | FAB+: 543 |
| 482 | 1 | ESI+: 557 |
| 483 | 1 | FAB+: 571 |
| 484 | 1 | FAB+: 674 |
| 485 | 1 | ESI+: 674 |
| 486 | 1 | FAB+: 597 |
| 487 | 1 | FAB+: 553 |
| 488 | 1 | FAB+: 597 |
| 489 | 1 | FAB+: 589 |
| 490 | 1 | FAB+: 576 |
| 491 | 1 | FAB+: 567 |
| 492 | 1 | FAB+: 545 |
| 493 | 1 | FAB+: 546 |
| 494 | 1 | ESI−: 567 |
| 495 | 1 | FAB+: 567 |
| 496 | 1 | FAB+: 567 |
| 497 | 1 | FAB+: 607 |
| 498 | 1 | FAB+: 553 |
| 499 | 1 | ESI+: 573 |

TABLE 288

| | | |
|---|---|---|
| 500 | 1 | FAB+: 573 |
| 501 | 1 | ESI+: 592 |
| 502 | 1 | FAB+: 603 |
| 503 | 1 | ESI+: 565 |
| 504 | 1 | FAB+: 565 |
| 505 | 1 | FAB+: 573 |
| 506 | 1 | FAB+: 505 |
| 507 | 1 | ESI+: 557 |
| 32 | 32 | FAB+: 623 |
| 508 | 32 | FAB+: 595 |
| 509 | 32 | ESI+: 659 |
| 510 | 32 | FAB+: 610 |
| 511 | 32 | ESI+: 582 |
| 512 | 32 | ESI+: 596 |
| 513 | 32 | FAB+: 610 |
| 514 | 32 | FAB+: 582 |
| 515 | 32 | FAB+: 596 |
| 33 | 33 | FAB+: 496 |
| 516 | 34 | FAB+: 581 |
| 517 | 34 | FAB+: 567 |
| 518 | 34 | FAB+: 595 |
| 519 | 34 | FAB+: 595 |
| 520 | 34 | FAB+: 611 |
| 521 | 34 | FAB+: 637 |
| 522 | 34 | FAB+: 638 |
| 523 | 34 | FAB+: 650 |
| 524 | 34 | FAB+: 596 |
| 525 | 34 | FAB+: 609 |
| 526 | 34 | ESI−: 627 |
| 35 | 35 | FAB+: 596 |
| 527 | 35 | FAB+: 623 |
| 528 | 4 | ESI+: 674 |
| 529 | 4 | ESI−: 571 |
| | | NMR1: 1.19 (3 H, d, J = 6.0 Hz), 3.12-3.48 (2 H, m), 3.55 (1 H, s), 4.01-4.13 (1 H, m), 4.28-4.38 (1 H, m), 4.47-4.60 (1 H, m), 4.80-4.97 (3 H, m), 5.73 (1 H, s), 6.79 (1 H, d, J = 8.4 Hz), 7.01-7.09 (1 H, m), 7.17 (1 H, dd, J = 2.0, |

TABLE 288-continued

| | | |
|---|---|---|
| | | 8.4 Hz), 7.39-7.69 (5 H, m), 7.91-8.08 (3 H, m), 11.67 (1 H, s), 13.04 (1 H, brs) |
| 530 | 4 | ESI+: 661 |
| 531 | 4 | ESI−: 571 |
| 532 | 4 | FAB+: 644 |

TABLE 289

| | | |
|---|---|---|
| 533 | 4 | ESI+: 666 |
| 534 | 4 | ESI+: 666 |
| 535 | 4 | ESI+: 665 |
| 536 | 4 | ESI+: 645 |
| 537 | 4 | FAB+: 688 |
| 538 | 4 | ESI+: 688 |
| 539 | 4 | ESI+: 690 |
| 540 | 4 | ESI+: 674 |
| 541 | 4 | ESI+: 674 NMR1: 1.00-2.30 (8 H, m), 2.94 (3 H, s), 3.58 (3 H, s), 4.07 (1 H, brs), 4.74 (1 H, d, J = 11.0 Hz), 4.77 (1 H, d, J = 11.0 Hz), 5.18 (1 H, s), 6.36 (1 H, d, J = 6.9 Hz), 6.88 (1 H, d, J = 8.4 Hz), 7.08-7.11 (1 H, m), 7.16 (1 H, d, J = 2.0 Hz), 7.18 (1 H, d, J = 2.0 Hz), 7.26 (2 H, d, J = 8.0 Hz), 7.30 (2 H, d, J = 8.0 Hz), 7.43-7.48 (2 H, m), 7.64 (1 H, d, J = 2.0 Hz) 7.93-7.96 (1 H, m), 11.42 (1 H, s), 12.34 (1 H, brs) |
| 542 | 4 | FAB+: 710 NMR1: 0.48-0.71(1 H, m), 1.01-1.37 (4 H, m), 1.40-1.65 (2 H, m), 2.46-2.59 (1 H, m), 2.78 (3 H, s), 3.15-3.50 (2 H, m), 4.66-4.84 (3 H, m), 5.17 (1 H, s),6.68 (1 H, d, J = 8.4 Hz), 7.02-7.09 (1 H, m), 7.12-7.20 (3 H, m), 7.27-7.40 (2 H, m), 7.46 (1 H, d, J = 0.8 Hz), 7.64 (1 H, d, J = 8.0 Hz), 8.57 (1 H, brs) |
| 543 | 4 | ESI+: 718 |
| 544 | 4 | ESI+: 702 |
| 545 | 4 | ESI−: 702 |
| 546 | 4 | FAB+: 638 |
| 547 | 4 | FAB+: 624 |
| 548 | 4 | ESI+: 702 |
| 549 | 4 | ESI+: 676 |
| 550 | 4 | ESI+: 674 |
| 551 | 4 | ESI+: 640 |
| 552 | 4 | ESI+: 678 |
| 553 | 4 | ESI−: 688 |
| 554 | 4 | ESI+: 690 |
| 555 | 4 | FAB+: 660 |
| 556 | 4 | ESI+: 660 |
| 557 | 4 | ESI+: 666 |
| 558 | 4 | FAB+: 620 |
| 559 | 4 | ESI+: 596 |
| 560 | 4 | ESI+: 660 |
| 561 | 4 | FAB+: 583 |
| 562 | 4 | ESI+: 583 |

TABLE 290

| | | |
|---|---|---|
| 563 | 4 | ESI+: 660 |
| 564 | 4 | ESI+: 660 |
| 565 | 4 | ESI+: 678 |
| 566 | 4 | FAB+: 678 |
| 567 | 4 | ESI+: 690 |
| 568 | 4 | FAB+: 718 |
| 569 | 4 | ESI+: 647 |
| 570 | 4 | ESI+: 678 |
| 571 | 4 | FAB+: 678 |
| 572 | 38 | FAB+: 592 |
| 573 | 39 | ESI+: 569 |
| 574 | 39 | ESI+: 582 |
| 575 | 39 | ESI+: 602 |
| 576 | 39 | FAB+: 565 |
| 577 | 39 | FAB+: 636 |
| 578 | 39 | FAB+: 573 |
| 16 | 16 | FAB+: 579 |
| 15 | 15 | ESI−: 579 |
| 22 | 22 | ESI+: 716 |
| 43 | 43 | FAB+: 680 |
| 29 | 29 | ESI+: 666 |
| 23 | 23 | ESI+: 700 |
| 41 | 41 | FAB+: 624 |
| 579 | 23 | ESI+: 830 |
| 13 | 13 | FAB+: 617 |
| 580 | 13 | FAB+: 609 |
| 581 | 13 | FAB+: 577 |
| 582 | 13 | FAB+: 577 |
| 583 | 13 | FAB+: 618 |
| 14 | 14 | FAB+: 645 |
| 584 | 12 | FAB+: 576 |
| 12 | 12 | FAB+: 616 |
| 585 | 12 | FAB+: 617 |
| 586 | 12 | ESI+: 617 |
| 587 | 12 | FAB+: 608 |
| 588 | 12 | FAB+: 678 |
| 589 | 12 | ESI+: 617 |
| 590 | 12 | FAB+: 615 |
| 591 | 12 | FAB+: 562 |
| 592 | 12 | FAB+: 630 |
| 593 | 12 | FAB+: 616 |

TABLE 291

| | | |
|---|---|---|
| 594 | 12 | FAB+: 608 |
| 595 | 12 | FAB+: 580 |
| 596 | 12 | FAB+: 610 |
| 18 | 18 | ESI+: 684 |
| 597 | 18 | FAB+: 592 |
| 598 | 18 | ESI+: 606 |
| 599 | 18 | ESI+: 606 |
| 600 | 18 | ESI+: 608 |
| 21 | 21 | ESI+: 598 |
| 601 | 21 | ESI+: 674 |
| 20 | 20 | ESI+: 737 |
| 27 | 27 | FAB+: 593 |
| 40 | 40 | ESI−: 568 |
| 602 | 40 | FAB+: 569 |
| 8 | 8 | FAB+: 577 |
| 603 | 6 | FAB+: 566 |
| 604 | 6 | FAB+: 540 |
| 605 | 6 | FAB+: 540 |
| 606 | 6 | FAB+: 524 |
| 6 | 6 | FAB+: 564 |
| 607 | 6 | FAB+: 524 |
| 42 | 42 | ESI+: 648 |
| 31 | 31 | FAB+: 638 |
| 608 | 5 | ESI+: 526 |
| 609 | 5 | ESI+: 484 |
| 610 | 5 | FAB+: 538 |
| 611 | 5 | FAB+: 582 |
| 612 | 5 | ESI+: 510 |
| 613 | 5 | ESI+: 510 |
| 614 | 5 | ESI+: 510 |
| 615 | 5 | ESI+: 510 |
| 616 | 5 | FAB+: 582 |
| 617 | 5 | FAB+: 508 |
| 618 | 5 | FAB+: 508 |
| 619 | 5 | FAB+: 536 |
| 620 | 5 | FAB+: 536 |
| 5 | 5 | FAB+: 482 |
| 621 | 5 | FAB+: 538 |
| 30 | 30 | FAB+: 632 |
| 622 | 30 | ESI+: 648 |
| 623 | 28 | FAB+: 568 |

TABLE 292

| | | |
|---|---|---|
| 28 | 28 | FAB+: 568 |
| 624 | 28 | FAB+: 568 |

TABLE 292-continued

| | | |
|---|---|---|
| 24 | 24 | ESI+: 607 |
| 625 | 19 | ESI+: 632 |
| 626 | 19 | FAB+: 674 |
| 627 | 19 | ESI+: 672 |
| 628 | 19 | ESI+: 688 |
| 629 | 19 | FAB+: 654 |
| 630 | 19 | FAB+: 674 |
| 631 | 19 | ESI+: 690 |
| 632 | 19 | ESI+: 584 |
| 633 | 19 | ESI+: 613 |
| 19 | 19 | ESI+: 690 |
| 634 | 19 | ESI+: 647 |
| 635 | 19 | ESI+: 632 |
| 636 | 19 | FAB+: 690 |
| 25 | 25 | ESI+: 633 |
| 637 | 25 | FAB+: 690 |
| 26 | 26 | FAB+: 526 |
| 17-2 | 17 | FAB+: 568 |
| 17-1 | 17 | FAB+: 550 |
| 638 | 1 | ESI+: 724 |
| 639 | 1 | ESI+: 780 |
| 640 | 53 | ESI+: 650 |
| 53 | 53 | ESI+: 664 |
| 641 | 30 | ESI+: 648 |
| 642 | 1 | ESI+: 662 |
| 45 | 45 | ESI+: 632 |
| 643 | 4 | ESI+: 676 |
| 644 | 1 | ESI+: 623 |
| 645 | 1 | ESI+: 748 |
| 646 | 1 | ESI+: 704 |
| 647 | 1 | ESI+: 688 |
| 648 | 1 4 | FAB+: 676 |
| 649 | 1 4 | ESI+: 690 |
| 650 | 4 | FAB+: 718 |
| 651 | 3 | FAB+: 767 |
| 52 | 52 | ESI+: 663 |

TABLE 293

| | | |
|---|---|---|
| 652 | 19 | ESI+: 648 |
| 653 | 1 19 | FAB+: 611 |
| 654 | 4 | ESI+: 674 |
| 655 | 1 4 | ESI+: 674 |
| 656 | 1 | FAB+: 615 |
| 657 | 1 | FAB+: 615 |
| 51 | 51 | ESI+: 598 |
| 658 | 1 | FAB+: 665 |
| 659 | 3 | ESI+: 631 |
| 660 | 1 | ESI+: 695 |
| 661 | 43 | ESI+: 624 |
| 662 | 41 | ESI+: 680 |
| 663 | 55 | ESI+: 638 |
| 664 | 20 | ESI+: 767 |
| 665 | 6 12 | ESI+: 703 |
| 666 | 4 | ESI+: 651 |
| 667 | 3 | ESI+: 631 |
| 668 | 39 | ESI+: 675 |
| 46 | 46 | FAB+: 660 |
| 669 | 1 | FAB+: 673 |
| 670 | 1 | ESI+: 721 |
| 47 | 47 | ESI+: 624 |
| 671 | 1 | ESI+: 704 |
| 672 | 1 | FAB+: 672 |
| 673 | 1 | ESI+: 731 |
| 674 | 1 19 | ESI+: 710 |
| 675 | 19 | ESI+: 648 |
| 676 | 19 | FAB+: 675 |
| 677 | 1 | ESI+: 695 |
| 678 | 1 | ESI+: 735 |
| 679 | 1 19 | ESI+: 710 |

TABLE 293-continued

| | | |
|---|---|---|
| 680 | 1 19 | ESI+: 688 |
| 681 | P8 P9 1 | ESI−: 675 |

TABLE 294

| | | |
|---|---|---|
| 682 | 1 | FAB+: 658 |
| 683 | 4 | ESI+: 663 |
| 684 | 1 | FAB+: 611 |
| 49 | 49 | FAB+: 689 |
| 685 | 3 | FAB+: 705 |
| 686 | 4 | FAB+: 597 |
| 687 | 1 | FAB+: 633 |
| 688 | 1 | ESI+: 731 |
| 55 | 55 | FAB+: 663 |
| 689 | 1 | FAB+: 703 |
| 690 | 20 | FAB+: 674 |
| 691 | 19 | ESI+: 675 |
| 692 | 1 | ESI+: 744 |
| 693 | 19 | ESI+: 688 |
| 54 | 54 | ESI+: 663 |
| 694 | 3 | FAB+: 719 |
| 695 | 1 | FAB+: 752 |
| 696 | P38 1 | ESI+: 714 |
| 697 | 54 | FAB+: 679 |
| 698 | 52 | ESI+: 648 |
| 699 | 4 | FAB+: 700 |
| 700 | 1 | ESI+: 735<br>NMR1: 0.99-1.85 (8 H, m), 2.10-2.24 (1 H, m), 2.69-2.83 (2 H, m), 2.92 (3 H, s), 3.25-3.45 (5 H, m), 3.73 (1 H, s), 3.95 (1 H, brs), 5.21 (1 H, s), 6.41-6.51 (1 H, m), 6.85 (1 H, d, J = 8.0 Hz), 7.11-7.22 (2 H, m), 7.35-7.48 (4 H, m), 7.64 (1 H, d, J = 2.0 Hz), 7.73-7.81 (2 H, m), 7.88-7.96 (1 H, m), 8.07 (1 H, brs), 12.08 (1 H, brs) |
| 701 | 19 | ESI+: 672<br>NMR1: 0.99-1.87 (8 H, m), 2.11-2.26 (1 H, m), 2.59-2.74 (2 H, m), 2.91 (3 H, s), 3.18-3.40 (2 H, m), 3.51 (2 H, s), 3.75 (1 H, s), 3.93 (1 H, brs), 5.24 (1 H, s), 6.41-6.54 (1 H, m), 6.85 (1 H, d, J = 8.0 Hz), 7.01-7.23 (6 H, m), 7.39-7.48 (2 H, m), 7.65 (1 H, d, J = 2.0 Hz), 7.89-7.98 (1 H, m), 8.08 (1 H, brs), 12.28 (1 H, brs) |
| 702 | 19 | FAB+: 595 |
| 703 | 4 | FAB+: 589 |
| 704 | 1 | ESI+: 669 |
| 705 | 1 | FAB+: 555 |
| 706 | 1 | ESI+: 746 |
| 707 | 1 | FAB+: 531 |
| 708 | 1 | ESI+: 678 |

TABLE 295

| | | |
|---|---|---|
| 44 | 44 | ESI−: 650 |
| 709 | 4 | FAB+: 718<br>NMR1: 1.09 (2 H, t, J = 6.9 Hz), 1.00-2.00 (5 H, m), 2.10-2.25 (1 H, m), 2.40 (2 H, t, J = 7.2 Hz), 2.94 (3 H, s), 3.18-3.50 (3 H, m), 3.57 (1 H, s), 3.98 (1 H, t, J = 6.3 Hz), 4.73 (1 H, d, J = 11.3 Hz), 4.78 (1 H, d J = 11.3 Hz), 5.16 (1 H, s), 6.32-6.38 (1 H, m), 6.85-6.95 (3 H, m), 7.05-7.50 (3 H, m), 7.39-7.48 (2 H, m), 7.63 (1 H, d, J = 2.0 Hz), 7.89-7.98 (1 H, m), 11.39 (1 H, brs) |
| 710 | 1 | ESI+: 751 |
| 711 | 19 | ESI+: 708 |

TABLE 295-continued

| | | |
|---|---|---|
| 712 | 19 | ESI+: 708 |
| | | NMR1: 0.99-1.87 (8 H, m), 2.11-2.26 (1 H, m), 2.59-2.74 (2 H, m), 2.91 (3 H, s), 3.18-3.40 (2 H, m), 3.51 (2 H, s), 3.75 (1 H, s), 3.93 (1 H, brs), 5.24 (1 H, s), 6.41-6.54 (1 H, m), 6.85 (1 H, d, J = 8.0 Hz), 7.01-7.23 (6 H, m), 7.39-7.48 (2 H, m), 7.65 (1 H, d, J = 2.0 Hz), 7.89-7.98 (1 H, m), 8.08 (1 H, brs), 12.28 (1 H, brs) |
| 713 | 19 | ESI+: 631 |
| 714 | 19 | ESI+: 633 |
| 715 | 3 | ESI+: 767 |
| 57 | 57 | ESI+: 701 |
| 716 | 4 | FAB+: 650 |
| 717 | 32 | ESI+: 596 |
| 718 | 52 | ESI+: 663 |
| 719 | 1 | FAB+: 596 |
| 720 | 1 | ESI+: 572 |
| 721 | 4 | ESI+: 641 |
| 722 | 32 | FAB+: 610 |
| 723 | 21 | ESI+: 596 |
| 724 | 21 | FAB+: 596 |
| 725 | 1 | FAB+: 751 |
| 726 | 1 | ESI+: 639 |
| 727 | 1 | ESI+: 639 |
| 728 | P9 P40 1 | ESI+: 617 |
| 729 | 41 | ESI+: 622 |
| 730 | 52 | ESI+: 647 |
| 731 | 3 | FAB+: 767 |
| 732 | 52 | FAB+: 663 |
| 733 | 41 | ESI+: 622 |
| 734 | 18 | ESI+: 682 |
| 735 | 18 | ESI+: 682 |

TABLE 296

| | | |
|---|---|---|
| 736 | 21 | ESI+: 672 |
| 737 | 41 | ESI+: 698 |
| 738 | 21 | ESI+: 672 |
| 739 | 4 | ESI+: 589 |
| 740 | 44 | ESI−: 650 |
| 741 | 1 | ESI+: 782 |
| 742 | 1 | ESI+: 538 |
| 743 | 1 | ESI+: 538 |
| 744 | 3 | ESI+: 554 |
| 745 | 44 | ESI−: 573 |
| 746 | 1 | ESI+: 555 |
| 747 | 1 | ESI+: 563 |
| 748 | 21 | ESI+: 596 |
| 59 | 59 | ESI+: 681 |
| 749 | 3 | ESI+: 554 |
| 750 | 41 | ESI+: 622 |
| 751 | 19 | ESI−: 623 |
| 752 | 19 | FAB+: 710 |
| 753 | 19 | ESI+: 633 |
| 754 | 19 | ESI+: 708 |
| 755 | 19 | ESI+: 631 |
| 756 | 1 | ESI+: 645 |
| 757 | 1 | ESI+: 645 |
| 758 | 1 | ESI+: 644 |
| 50 | 50 | ESI+: 687 |
| 759 | 1 | ESI+: 731 |
| 760 | 1 | ESI+: 706 |
| 761 | 19 | ESI−: 609 |
| 762 | 19 | FAB+: 675 |
| 763 | 19 | ESI+: 650 |
| 764 | 1 | ESI+: 709 |
| 765 | 1 | ESI−: 656 |
| 766 | 1 | ESI+: 678 |
| 767 | 44 | ESI+: 667 |
| 768 | 4 | FAB+: 664 |
| 769 | 44 | ESI+: 650 |
| 770 | 1 | ESI+: 720 |
| 771 | 1 | ESI+: 643 |

TABLE 296-continued

| | | |
|---|---|---|
| 772 | 19 | ESI+: 587 |
| 773 | 19 | ESI+: 664 |
| 774 | 1 | ESI+: 779 |

TABLE 297

| | | |
|---|---|---|
| 775 | 1 | ESI+: 706 |
| 776 | P8 P9 1 | ESI+: 633 |
| 777 | 35 | ESI+: 597 |
| 48 | 48 | ESI+: 689 |
| 778 | 19 | ESI+: 650 |
| 779 | 1 | FAB+: 633 |
| 780 | 1 | ESI+: 661 |
| 781 | 4 | ESI+: 619 |
| 782 | 1 | ESI−: 577 |
| 783 | 1 | ESI+: 631 |
| 784 | 1 | ESI+: 631 |
| 785 | 48 | ESI+: 601 |
| 786 | 48 | ESI+: 601 |
| 787 | 1 19 | ESI+: 672 |
| 788 | 21 | ESI+: 612 |
| 789 | 3 | ESI+: 613 |
| 790 | 4 | ESI+: 647 |
| 791 | 19 | ESI+: 617 |
| 792 | 19 | ESI+: 617 |
| 793 | P9 1 | ESI+: 678 |
| 794 | 1 | ESI+: 714 |
| 795 | 19 | ESI+: 658 |
| 796 | 19 | ESI+: 658 |
| 797 | 41 | ESI+: 638 |
| 798 | 1 | ESI+: 562 |
| 799 | 1 | ESI+: 562 |
| 800 | 1 | FAB+: 744 |
| 801 | 19 | ESI+: 688 |
| 802 | 1 | ESI+: 667 |
| 803 | 19 | ESI+: 611 |
| 804 | 44 | ESI−: 634 |
| 805 | 3 | ESI+: 703 |
| 56 | 56 | ESI: 661 |
| 806 | 4 | ESI+: 650 |
| 807 | 44 | ESI+: 636 |
| 808 | 19 | ESI+: 658 |
| 809 | 19 | ESI+: 581 |

TABLE 298

| | | |
|---|---|---|
| 810 | 1 | ESI+: 671 |
| 811 | 1 | ESI+: 671 |
| 812 | 1 | ESI−: 718 |
| 813 | P23 1 | ESI−: 641 |
| 814 | 1 | ESI+: 687 |
| 815 | 1 | ESI+: 687 |
| 816 | 19 | ESI+: 587 |
| 817 | 19 | ESI+: 664 |
| 818 | P23 1 | ESI+: 744 |
| 819 | 1 | ESI+: 667 |
| 820 | 19 | ESI+: 611 |
| 821 | 19 | ESI+: 688 |
| 822 | P9 1 4 | ESI+: 681 |
| 823 | 1 44 | FAB+: 666 |
| 824 | 1 | ESI+: 655 |
| 825 | 4 | ESI+: 641 |
| 826 | 1 | ESI+: 513 |
| 827 | 36 | ESI+: 599 |
| 828 | 1 | ESI+: 792 |
| 829 | 1 | ESI+: 715 |

TABLE 298-continued

| | | |
|---|---|---|
| 58 | 58 | ESI+: 672 |
| 830 | 1 | ESI+: 526 |
| 831 | 1 | ESI+: 526 |
| 832 | 19 | ESI+: 702 |
| 833 | 19 | ESI+: 702 |
| 834 | 1 | ESI+: 556 |
| 835 | P33 1 | ESI−: 601 |
| 836 | 1 | ESI+: 644 |
| 837 | 1 | ESI+: 567 |
| 838 | 58 | ESI+: 595 |
| 839 | 11 | ESI+: 580 |
| 840 | 35 | ESI+: 596 |
| 841 | 1 | ESI−: 680 |
| 842 | 1 | FAB+: 605 |
| 843 | 1 | ESI+: 721 |

TABLE 299

| | | |
|---|---|---|
| 844 | 1 | ESI+: 643 |
| 845 | 19 | ESI+: 664 |
| 846 | 19 | ESI+: 587 |
| 847 | P33 1 | FAB+: 541 |
| 848 | 1 | FAB+: 587 |
| 849 | 1 | FAB+: 587 |
| 850 | 1 | FAB+: 587 |
| 851 | 1 | FAB+: 587 |
| 852 | 1 | ESI+: 701 |
| 853 | 58 | ESI+: 581 |
| 854 | 1 | FAB+: 591 |
| 855 | 1 | FAB+: 591 |
| 856 | 4 | ESI+: 674<br>NMR1: 1.00-2.30 (8 H, m), 2.94 (3 H, s), 3.58 (3 H, s), 4.07 (1 H, brs), 4.74 (1 H, d, J = 11.0 Hz), 4.77 (1 H, d, J = 11.0 Hz), 5.18 (1 H, s), 6.36 (1 H, d, J = 6.9 Hz), 6.88 (1 H, d, J = 8.4 Hz), 7.08-7.11 (1 H, m), 7.16 (1 H, d, J = 2.0 Hz), 7.18 (1 H, d, J = 2.0 Hz), 7.26 (2 H, d, J = 8.0 Hz), 7.30 (2 H, d, J = 8.0 Hz), 7.43-7.48 (2 H, m), 7.64 (1 H, d, J = 2.0 Hz) 7.93-7.96 (1 H, m), 11.42 (1 H, s), 12.34 (1 H, brs) |
| 857 | 1 | FAB+: 616 |
| 858 | 1 | ESI+: 627 |
| 859 | 19 | ESI+: 571 |
| 860 | 1 | ESI+: 540 |
| 861 | 1 | ESI+: 513 |
| 862 | 1 | ESI+: 545 |
| 863 | 1 | ESI+: 564 |
| 864 | 1 | ESI+: 589 |
| 865 | 1 | ESI+: 537 |
| 866 | 1 | ESI+: 532 |
| 867 | 1 | ESI+: 505 |
| 868 | 1 | ESI+: 616 |
| 869 | 1 | ESI+: 548 |
| 870 | 1 | ESI+: 574 |
| 871 | 1 | FAB+: 564 |
| 872 | 1 | FAB+: 532 |
| 873 | 1 | ESI+: 542 |
| 874 | 1 | ESI+: 573 |
| 875 | 1 | ESI+: 608 |
| 876 | 21 | ESI+: 598 |
| 877 | 1 | FAB+: 728 |

TABLE 300

| | | |
|---|---|---|
| 878 | 1 | FAB+: 651 |
| 879 | 1 | FAB+: 603 |
| 880 | 1 | FAB+: 764 |
| 881 | 1 | FAB+: 687 |
| 882 | 1 | FAB+: 764 |
| 883 | 1 | FAB+: 689 |
| 884 | 1 | ESI+: 766 |

TABLE 300-continued

| | | |
|---|---|---|
| 885 | 1 | ESI+: 689 |
| 886 | 1 | ESI+: 764 |
| 887 | 1 | ESI+: 687 |
| 888 | 1 | ESI−: 665 |
| 889 | 1 | FAB+: 601 |
| 890 | 1 | ESI+: 691 |
| 891 | 1 | ESI+: 691 |
| 892 | P9 1 | ESI+: 678 |
| 893 | 1 | ESI+: 714 |
| 894 | 1 | FAB+: 637 |
| 895 | 1 | FAB+: 758 |
| 896 | 1 | ESI+: 758 |
| 897 | 1 | FAB+: 636 |
| 898 | P33 1 | ESI+: 622 |
| 899 | P33 1 | APCI+: 435 |

TABLE 301

| No | Structure |
|---|---|
| 1 | [chemical structure: methanesulfonamido-cyclohexyl-isoquinolinone with 2,4-dichlorophenyl and 1,2,4-triazine-methyleneoxy-carboxamide] |
| 2 | [chemical structure: methanesulfonamido-cyclohexyl-isoquinolinone with 2,4-dichlorophenyl and 5-hydroxypyrimidin-2-yl-methyleneoxy-carboxamide] |
| 3 | [chemical structure: methanesulfonamido-cyclohexyl-isoquinolinone with 2,4-dichlorophenyl and HOOC-thiophene-ethylamide] |

TABLE 301-continued

| No | Structure |
|----|-----------|
| 4  | 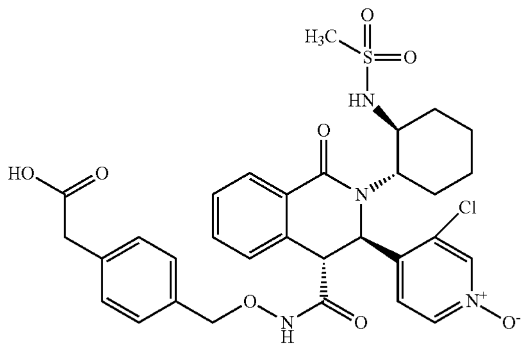 [SMILES: CS(=O)(=O)N[C@H]1CCCC[C@@H]1N1C(=O)c2ccccc2[C@@H](C(=O)NOCc2ccc(CC(=O)O)cc2)[C@@H]1c1cc[n+]([O-])cc1Cl] |

TABLE 302

| 5 | 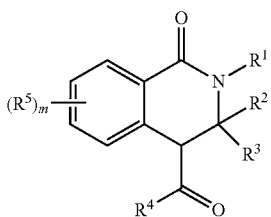 |
|---|---|

INDUSTRIAL APPLICABILITY

The compound (I) of the present invention as described above is useful as a therapeutic agent for the diseases in which BB2 receptors are related, in particular, for IBS since it has an excellent BB2 receptor antagonistic activity, and further, it exhibits excellent efficacy regarding bowel movement disorders.

The invention claimed is:

1. A pharmaceutical composition comprising a compound of formula (I) a pharmaceutically acceptable salt, solvate, or hydrate thereof and a pharmaceutically acceptable excipient, wherein formula (I) is represented by:

in which groups $R^1$-$R^5$ and m are as follows
$R^1$: lower alkylene-OH, lower alkylene-N($R^0$)($R^6$), lower alkylene-CO$_2R^0$, cycloalkyl, cycloalkenyl, aryl, heterocyclic group, -(lower alkylene substituted with —OR$^0$)-aryl or lower alkylene-heterocyclic group, wherein the lower alkylene, cycloalkyl, cycloalkenyl, aryl and heterocyclic group in $R^1$ may each be substituted, $R^0$: the same as or different from each other, each representing —H or lower alkyl,
$R^6$: $R^0$, —C(O)—$R^0$, —CO$_2$-lower alkyl or —S(O)$_2$-lower alkyl,
$R^2$: lower alkyl, lower alkylene-OR$^0$, lower alkylene-aryl, lower alkylene-heterocyclic group, lower alkylene-N($R^0$)CO-aryl, lower alkylene-O-lower alkylene-aryl, —CO$_2R^0$, —C(O)N($R^0$)$_2$, —C(O)N($R^0$)-aryl, —C(O)N($R^0$)-lower alkylene-aryl, or aryl, wherein the aryl and heterocyclic group in $R^2$ may each be substituted,
$R^3$: —H or lower alkyl, or $R^2$ and $R^3$ may be combined to form $C_{2-6}$ alkylene,
$R^4$: —N($R^7$)($R^8$), —N($R^0$)—OH, —N($R^{10}$)—OR$^7$, —N($R^0$)—N($R^0$)($R^7$), —N($R^0$)—S(O)$_2$-aryl, or —N($R^0$)—S(O)$_2$—$R^7$, wherein the aryl in $R^4$ may be substituted,
$R^7$: lower alkyl, halogeno-lower alkyl, lower alkylene-CN, lower alkylene-OR$^0$, lower alkylene-CO$_2R^0$, lower alkylene-C(O)N($R^0$)$_2$, lower alkylene-C(O)N($R^0$)N($R^0$)$_2$, lower alkylene-C(=NH)NH$_2$, lower alkylene-C(=NOH)NH$_2$, heteroaryl, lower alkylene-X-aryl, or lower alkylene-X-heterocyclic group, wherein the lower alkylene, aryl, heteroaryl, and heterocyclic group in $R^7$ may each be substituted,
X: single bond, —O—, —C(O)—, —N($R^0$), —S(O$_p$)—, or *—C(O)N($R^0$)—, wherein * in X represents a bond to lower alkylene,
m: an integer of 0 to 3,
p: an integer of 0 to 2,
$R^8$: —H or lower alkyl, or $R^7$ and $R^8$ may be combined to form lower alkylene-N($R^9$)- lower alkylene, lower alkylene-CH($R^9$)-lower alkylene, lower alkylene-arylene-lower alkylene, or lower alkylene-arylene-C(O)—,
$R^9$: aryl and heteroaryl which may each be substituted,
$R^{10}$: —H, lower alkyl, or —C(O)R$^0$,
$R^5$: lower alkyl, halogeno-lower alkyl, halogen, nitro, —OR$^0$, —O-halogeno-lower alkyl, —N($R^0$)$_2$, —O-lower alkylene-CO$_2R^0$, or —O-lower alkylene-aryl, wherein the aryl in $R^5$ may be substituted, provided that, when $R^4$ is —N($R^7$)($R^8$),
(1) a compound wherein $R^1$ is unsubstituted cyclopentyl and $R^2$ is unsubstituted 2-thienyl;
(2) a compound wherein $R^1$ is unsubstituted cyclohexyl and $R^2$ is 4-methoxyphenyl;
(3) a compound wherein $R^1$ is 4-methoxyphenyl and $R^2$ is 4-methoxyphenyl; and
(4) a compound wherein $R^1$ is (morpholin-4-yl)ethyl and $R^2$ is 4-ethoxyphenyl are excluded, and
further provided that, 2,3-bis(4-chlorophenyl)-N-(2-methoxyethyl)-1-oxo-1,2,3,4-tetrahydroisoquinoline-4-carboxamide,
3-(4-chlorobenzyl)-2-(4-chlorophenyl)-N-(2-methoxyethyl)-1-oxo-1,2,3,4-tetrahydroisoquinoline-4-carboxamide,
3-[3,5-bis(trifluoromethyl)phenyl]-2-cyclopropyl-N-(2-furylmethyl)-1-oxo-1,2,3,4-tetrahydroisoquinoline-4-carboxamide,
3-[3,5-bis(trifluoromethyl)phenyl]-2-cyclopropyl-N-(2-methoxyethyl)-1-oxo-1,2,3,4-tetrahydroisoquinoline-4-carboxamide,
ethyl 3-{3-[3,5-bis(trifluoromethyl)phenyl]-4-[2-(4-methoxyphenyl)ethyl]carbamoyl-1-oxo-3,4-dihydroisoquinolin-2(1H)-yl}propanoate, N-benzyl-3-[3,5-bis(trifluoromethyl)phenyl]-1-oxo-2-(tetrahydrofuran-2-ylmethyl)-1,2,3,4-tetrahydroisoquinoline-4-carboxamide, 3-[3,5-bis(trifluoromethyl)phenyl]-N-(2-methoxyethyl)-2-(2-morpholin-4-ylethyl)-1-oxo-1,2,3,4-tetrahydroisoquinoline-4-carboxamide, 3-[3,5-bis(trifluoromethyl)phenyl]-2-(2-furylmethyl)-N-(2-methoxyethyl)-1-oxo-1,2,3,4-tetrahydroisoquinoline-4-carboxamide, 3-[3,5-bis(trifluoromethyl)phenyl]-N-(2-furylmethyl)-2-(2-morpholin-4-ylethyl)-1-oxo-1,2,3,4-tetrahydroisoquinoline-4-carboxamide, and (4-chlorophenyl)[3-(4-chlorophenyl)-4-[(2-methoxyethyl)carbamoyl]-1-oxo-3-,4-dihydroisoquinolin-2(1H)-yl]acetic acid are excluded.

2. The pharmaceutical composition of claim 1, wherein $R^4$ is —N($R^0$)-lower alkylene-(aryl or heteroaryl, which may each be substituted), or —N($R^0$)—O-lower alkylene-(aryl or heteroaryl, which may each be substituted).

3. The pharmaceutical composition of claim 2, wherein $R^2$ is phenyl which may be substituted with halogen, lower alkyl, or —$OR^0$.

4. The pharmaceutical composition of claim 2, wherein $R^3$ is —H.

5. The pharmaceutical composition of claim 1, wherein the pharmaceutical composition is a solid composition.

6. The pharmaceutical composition of claim 1, wherein the pharmaceutical composition is a liquid composition.

7. The pharmaceutical composition of claim 6, wherein the liquid composition is for parenteral administration.

8. The pharmaceutical composition of claim 6, wherein the liquid composition is for oral administration.

9. A compound of formula (I) a pharmaceutically acceptable salt, solvate, or hydrate thereof and a pharmaceutically acceptable excipient, wherein formula (I) is represented by:

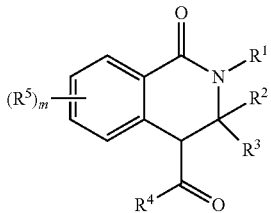

in which groups $R^1$-$R^5$ and m are as follows $R^1$: lower alkylene-OH, lower alkylene-N($R^0$)($R^6$), lower alkylene-$CO_2R^0$, cycloalkyl, cycloalkenyl, aryl, heterocyclic group, -(lower alkylene substituted with —$OR^0$)-aryl or lower alkylene-heterocyclic group, wherein the lower alkylene, cycloalkyl, cycloalkenyl, aryl and heterocyclic group in $R^1$ may each be substituted, $R^0$: the same as or different from each other, each representing —H or lower alkyl, $R^6$: $R^0$, —C(O)—$R^0$, —$CO_2$-lower alkyl or —S(O)$_2$-lower alkyl, $R^2$: lower alkyl, lower alkylene-$OR^0$, lower alkylene-aryl, lower alkylene-heterocyclic group, lower alkylene-N($R^0$)CO-aryl, lower alkylene-O-lower alkylene-aryl, —$CO_2R^0$, —C(O)N($R^0$)$_2$, —C(O)N($R^0$)-aryl, —C(O)N($R^0$)-lower alkylene-aryl, or aryl, wherein the aryl and heterocyclic group in $R^2$ may each be substituted, $R^3$: —H or lower alkyl, or $R^2$ and $R^3$ may be combined to form $C_{2-6}$ alkylene, $R^4$: —N($R^7$)($R^8$), —N($R^0$)—OH, —N($R^{10}$)—$OR^7$, —N($R^0$)—N($R^0$)($R^7$), —N($R^0$)—S(O)$_2$-aryl, or —N($R^0$)—S(O)$_2$—$R^7$, wherein the aryl in $R^4$ may be substituted, $R^7$: lower alkyl, halogeno-lower alkyl, lower alkylene-CN, lower alkylene-$OR^0$, lower alkylene-$CO_2R^0$, lower alkylene-C(O)N($R^0$)$_2$, lower alkylene-C(O)N($R^0$)N($R^0$)$_2$, lower alkylene-C(=NH)NH$_2$, lower alkylene-C(=NOH)NH$_2$, heteroaryl, lower alkylene-X-aryl, or lower alkylene-X-heterocyclic group, wherein the lower alkylene, aryl, heteroaryl, and heterocyclic group in $R^7$ may each be substituted, X: single bond, —O—, —C(O)—, —N($R^0$), —S(O$_p$)—, or *—C(O)N($R^0$)—, wherein * in X represents a bond to lower alkylene, m: an integer of 0 to 3, p: an integer of 0 to 2, $R^8$: —H or lower alkyl, or $R^7$ and $R^8$ may be combined to form lower alkylene-N($R^9$)-lower alkylene, lower alkylene-CH($R^9$)-lower alkylene, lower alkylene-arylene-lower alkylene, or lower alkylene-arylene-C(O)—, $R^9$: aryl and heteroaryl which may each be substituted, $R^{10}$: —H, lower alkyl, or —C(O)$R^0$, $R^5$: lower alkyl, halogeno-lower alkyl, halogen, nitro, —$OR^0$, —O-halogeno-lower alkyl, —N($R^0$)$_2$, —O-lower alkylene-$CO_2R^0$, or —O-lower alkylene-aryl, wherein the aryl in $R^5$ may be substituted, provided that, when $R^4$ is —N($R^7$)($R^8$), (1) a compound wherein $R^1$ is unsubstituted cyclopentyl and $R^2$ is unsubstituted 2-thienyl;

(2) a compound wherein $R^1$ is unsubstituted cyclohexyl and $R^2$ is 4-methoxyphenyl;

(3) a compound wherein $R^1$ is 4-methoxyphenyl and $R^2$ is 4-methoxyphenyl; and (4) a compound wherein $R^1$ is (morpholin-4-yl)ethyl and $R^2$ is 4-ethoxyphenyl are excluded, and further provided that, 2,3-bis(4-chlorophenyl)-N-(2-methoxyethyl)-1-oxo-1,2,3,4-tetrahydroisoquinoline-4-carboxamide, 3-(4-chlorobenzyl)-2-(4-chlorophenyl)-N-(2-methoxyethyl)-1-oxo-1,2,3,4-tetrahydroisoquinoline-4-carboxamide, 3-[3,5-bis(trifluoromethyl)phenyl]-2-cyclopropyl-N-(2-furylmethyl)-1-oxo-1,2,3,4-tetrahydroisoquinoline-4-carboxamide, 3-[3,5-bis(trifluoromethyl)phenyl]-2-cyclopropyl-N-(2-methoxyethyl)-1-oxo-1,2,3,4-tetrahydroisoquinoline-4-carboxamide, ethyl 3-{3-[3,5-bis(trifluoromethyl)phenyl]-4-[2-(4-methoxyphenyl)ethyl]carbamoyl-1-oxo-3,4-dihydroisoquinolin-2(1H)-yl}propanoate, N-benzyl-3-[3,5-bis(trifluoromethyl)phenyl]-1-oxo-2-(tetrahydrofuran-2-ylmethyl)-1,2,3,4-tetrahydroisoquinoline-4-carboxamide, 3-[3,5-bis(trifluoromethyl)phenyl]-N-(2-methoxyethyl)-2-(2-morpholin-4-ylethyl)-1-oxo-1,2,3,4-tetrahydroisoquinoline-4-carboxamide, 3-[3,5-bis(trifluoromethyl)phenyl]-2-(2-furylmethyl)-N-(2-methoxyethyl)-1-oxo-1,2,3,4-tetrahydroisoquinoline-4-carboxamide, 3-[3,5-bis(trifluoromethyl)phenyl]-N-(2-furylmethyl)-2-(2-morpholin-4-ylethyl)-1-oxo-1,2,3,4-tetrahydroisoquinoline-4-carboxamide, and (4-chlorophenyl)[3-(4-chlorophenyl)-4-[(2-methoxyethyl)carbamoyl]-1-oxo-3-,4-dihydroisoquinolin-2(1H)-yl]acetic acid are excluded, wherein one or more atom is isotopically enriched.

10. The compound of claim 9, wherein $R^4$ is —N($R^0$)-lower alkylene-(aryl or heteroaryl, which may each be substituted), or —N($R^0$)—O-lower alkylene-(aryl or heteroaryl, which may each be substituted).

11. The compound of claim 10, wherein $R^1$ is (lower alkylene)-OH or substituted cycloalkyl, wherein said lower alkylene may be substituted with a member selected from the group consisting of —OH and phenyl (which may be substituted with halogen, lower alkyl, or —$OR^0$, and said substituted cycloalkyl is substituted with a member selected from the group consisting of —$OR^0$, —N($R^0$)C(O)$R^0$, —N($R^0$)—C(O)-lower alkylene-$OR^0$, —N($R^0$)S(O)$_2$-lower alkyl and heterocyclic group.

12. The compound of claim 11, wherein $R^2$ is phenyl which may be substituted with halogen, lower alkyl, or —$OR^0$.

13. The compound of claim 9, wherein $R^3$ is —H.

14. The compound of claim 9, wherein the compound of formula (I) is

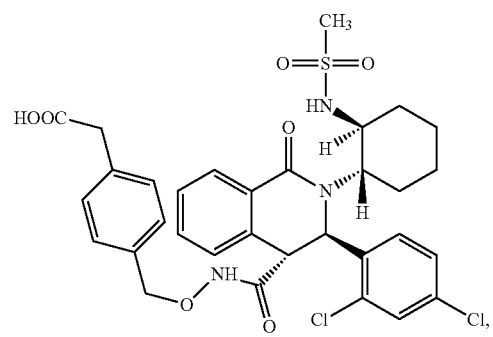 [SMILES: CS(=O)(=O)N[C@H]1CCCC[C@@H]1N1C(=O)c2ccccc2[C@@H](C(=O)NOCc2ccc(CC(=O)O)cc2)[C@@H]1c1ccc(Cl)cc1Cl]

or a pharmaceutically acceptable salt, solvate, or hydrate thereof.

* * * * *